US009212226B2

(12) United States Patent
Blanchetot et al.

(10) Patent No.: US 9,212,226 B2
(45) Date of Patent: Dec. 15, 2015

(54) AMINO ACID SEQUENCES DIRECTED AGAINST CXCR4 AND OTHER GPCRS AND COMPOUNDS COMPRISING THE SAME

(75) Inventors: Christophe Blanchetot, Destelbergen (BE); Martine Smit, Amsterdam (NL); Regorius Leurs, Amsterdam (NL); Sven Jähnichen, Amsterdamn (NL); Michael John Scott Saunders, Brussels (BE); Johannes Joseph Wilhelmus De Haard, Oudelande (NL); Peter Vanlandschoot, Bellem (BE)

(73) Assignee: Ablynx N.V., Zwijnaarde (BE)

( * ) Notice: Subject to any disclaimer, the term of this patent is extended or adjusted under 35 U.S.C. 154(b) by 1347 days.

(21) Appl. No.: 12/992,982

(22) PCT Filed: May 18, 2009

(86) PCT No.: PCT/EP2009/056026
§ 371 (c)(1),
(2), (4) Date: Apr. 5, 2011

(87) PCT Pub. No.: WO2009/138519
PCT Pub. Date: Nov. 19, 2009

(65) Prior Publication Data
US 2011/0206660 A1 Aug. 25, 2011

Related U.S. Application Data

(60) Provisional application No. 61/053,847, filed on May 16, 2008, provisional application No. 61/102,142, filed on Oct. 2, 2008.

(51) Int. Cl.
*A61K 39/395* (2006.01)
*C07K 16/28* (2006.01)
*A61K 39/00* (2006.01)

(52) U.S. Cl.
CPC ....... *C07K 16/2866* (2013.01); *A61K 2039/505* (2013.01); *C07K 2316/96* (2013.01); *C07K 2317/22* (2013.01); *C07K 2317/31* (2013.01); *C07K 2317/92* (2013.01)

(58) Field of Classification Search
CPC .............................. A61K 39/395; C07K 16/00
See application file for complete search history.

(56) References Cited

U.S. PATENT DOCUMENTS

| 8,937,164 B2 | 1/2015 | Descamps et al. |
| 2002/0106739 A1 | 8/2002 | Oakley et al. |
| 2007/0167443 A1 | 7/2007 | Melikian et al. |
| 2010/0062004 A1 | 3/2010 | Adams et al. |
| 2011/0262438 A1 | 10/2011 | Descamps et al. |
| 2013/0130379 A1 | 5/2013 | Adams et al. |
| 2014/0178390 A1 | 6/2014 | Descamps et al. |
| 2014/0228223 A1 | 8/2014 | Descamps et al. |

FOREIGN PATENT DOCUMENTS

| EP | 0 368 684 A1 | 5/1990 |
| EP | 0 542 810 | 5/1993 |
| EP | 1 316 801 A1 | 9/2002 |
| WO | WO 91/01743 A1 | 2/1991 |
| WO | WO 99/50461 A1 | 10/1999 |
| WO | WO 01/45746 A2 | 6/2001 |
| WO | WO 02/076489 A1 | 10/2002 |
| WO | WO03/050531 | * 6/2003 |
| WO | WO 03/050531 A2 | 6/2003 |
| WO | WO03/066830 | * 8/2003 |
| WO | WO 03/066830 A2 | 8/2003 |
| WO | WO 2004/041867 A2 | 5/2004 |
| WO | WO 2004/051268 A1 | 6/2004 |
| WO | WO 2004/064595 A2 | 8/2004 |
| WO | WO 2004/106377 A1 | 12/2004 |
| WO | WO 2005/018629 A1 | 3/2005 |
| WO | WO 2005/019824 | 3/2005 |
| WO | WO 2005/044792 A2 | 5/2005 |
| WO | WO 2006/003388 A2 | 1/2006 |
| WO | WO 2006/030220 A1 | 3/2006 |
| WO | WO 2006/038027 A2 | 4/2006 |
| WO | WO 2006/047417 A2 | 5/2006 |
| WO | WO 2006/089141 A2 | 8/2006 |
| WO | WO 2006/116319 A2 | 11/2006 |
| WO | WO 2007/042289 A2 | 4/2007 |
| WO | WO 2007/051063 A2 | 5/2007 |

(Continued)

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*

(Continued)

*Primary Examiner* — Laura B Goddard
*Assistant Examiner* — Meera Natarajan
(74) *Attorney, Agent, or Firm* — Wolf, Greenfield & Sacks, P.C.

(57) ABSTRACT

The present invention relates to amino acid sequences that are directed against (as defined herein) G-protein coupled receptors (GPCRs) and in particular to CXCR4 and CXCR7, as well as to compounds or constructs, and in particular proteins and polypeptides, that comprise or essentially consist of one or more such amino acid sequences (also referred to herein as "amino acid sequences of the invention", "compounds of the invention", and "polypeptides of the invention", respectively). Furthermore, the invention provides a new method of making amino acid sequences that are directed against transmembrane protein, and in particular for multiple spanning transmembrane proteins for which the native conformation cannot be reproduced in other "in vitro" system (e.g. GPCRs in general).

12 Claims, 15 Drawing Sheets

(56) References Cited

FOREIGN PATENT DOCUMENTS

Figure 1:
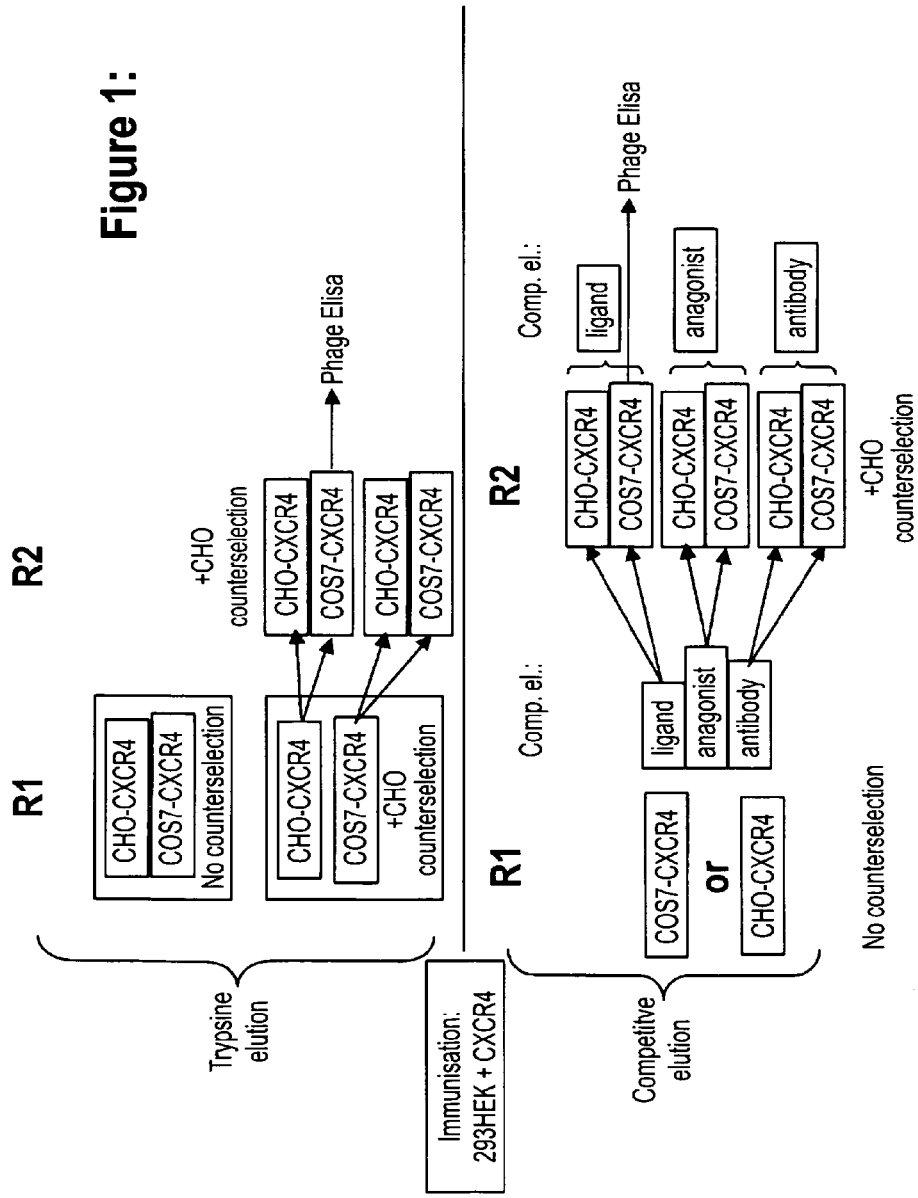

| | | |
|---|---|---|
| WO | WO 2007/118670 A1 | 10/2007 |
| WO | WO 2008/028977 A2 | 3/2008 |
| WO | WO 2008/048519 A2 | 4/2008 |
| WO | WO 2008/068280 A1 | 6/2008 |
| WO | WO 2009/138519 A1 | 11/2009 |
| WO | WO 2010/010119 A1 | 1/2010 |
| WO | WO 2010/043650 A2 | 4/2010 |
| WO | WO 2010/070145 A2 | 6/2010 |
| WO | WO 2010/141986 A1 | 12/2010 |
| WO | WO 2011/117423 A1 | 9/2011 |

OTHER PUBLICATIONS

Lamminmaki et al. (JBC 2001, 276:36687-36694).*
Muyldermans et al. (Reviews in Molecular Biotechnology, vol. 74, p. 277-302, 2001).*
Baribaud et al., Antigenically distinct conformations of CXCR4. J Virol. Oct. 2001;75(19):8957-67.
Carnec et al., Anti-CXCR4 monoclonal antibodies recognizing overlapping epitopes differ significantly in their ability to inhibit entry of human immunodeficiency virus type 1. J Virol. Feb. 2005;79(3):1930-3.
Dimitrov et al., A mechanism of resistance to HIV-1 entry: inefficient interactions of CXCR4 with CD4 and gp120 in macrophages. Virology. Jun. 1999 20;259(1):1-6.
Hoffman et al., A biosensor assay for studying ligand-membrane receptor interactions: binding of antibodies and HIV-1 Env to chemokine receptors. Proc Natl Acad Sci U S A. Oct. 10, 2000;97(21):11215-20.
Hoogenboom et al., Selection-dominant and nonaccessible epitopes on cell-surface receptors revealed by cell-panning with a large phage antibody library. Eur J Biochem. Mar. 1999;260(3):774-84.
Hutchings et al., Therapeutic antibodies directed at G protein-coupled receptors. MAbs. Nov.-Dec. 2010;2(6):594-606. Epub Nov. 1. 2010. Review.
Jähnichen et al., CXCR4 nanobodies (VHH-based single variable domains) potently inhibit chemotaxis and HIV-1 replication and mobilize stem cells. Proc Natl Acad Sci U S A. Nov. 23, 2010;107(47):20565-70. Epub Nov. 8, 2010.
Misumi et al., A novel cyclic peptide immunization strategy for preventing HIV-1/AIDS infection and progression. J Biol Chem. Aug. 22, 2003;278(34):32335-43. Epub May 27, 2003.
Raman et al., Role of chemokines in tumor growth. Cancer Lett. Oct. 28, 2007;256(2):137-65. Epub Jul. 12, 2007. Review.
Sui et al., Identification of CD4 and transferrin receptor antibodies by CXCR4 antibody-guided Pathfinder selection. Eur J Biochem. Nov. 2003;270(22):4497-506.
Vaday et al., CXCR4 and CXCL12 (SDF-1) in prostate cancer: inhibitory effects of human single chain Fv antibodies. Clin Cancer Res. Aug. 15, 2004;10(16):5630-9.
Bednarek et al., Ligands of the melanocortin receptors, 2002-2003 update. Expert Opin Ther Patents. 2004;14(3):327-336.
Binz et al., Engineering novel binding proteins from nonimmunoglobulin domains. Nat Biotechnol. Oct. 2005;23(10):1257-68.
Coutts et al., Localisation of cannabinoid CB(1) receptor immunoreactivity in the guinea pig and rat myenteric plexus. J Comp Neurol. Jul. 8, 2002;448(4):410-22.
Dove Pettit et al., Immunohistochemical localization of the neural cannabinoid receptor in rat brain. J Neurosci Res. Feb. 1, 1998;51(3):391-402.
Gensure et al., Parathyroid hormone and parathyroid hormone-related peptide, and their receptors. Biochem Biophys Res Commun. Mar. 18, 2005;328(3):666-78.
Getting, Targeting melanocortin receptors as potential novel therapeutics. Pharmacol Ther. Jul. 2006;111(1):1-15. Epub Feb. 20, 2006.
Hoogenboom, Selecting and screening recombinant antibody libraries. Nat Biotechnol. Sep. 2005;23(9):1105-16.
Howard et al., Orphan G-protein-coupled receptors and natural ligand discovery. Trends Pharmacol Sci. Mar. 2001;22(3):132-40.
Kim et al., Enhancement of colorectal tumor targeting using a novel biparatopic monoclonal antibody against carcinoembryonic antigen in experimental radioimmunoguided surgery. Int J Cancer. Feb. 1, 2002;97(4):542-7.
Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.
Lieby et al., The clonal analysis of anticardiolipin antibodies in a single patient with primary antiphospholipid syndrome reveals an extreme antibody heterogeneity. Blood. Jun. 15, 2001;97(12):3820-8.
Marinissen et al., G-protein-coupled receptors and signaling networks: emerging paradigms. Trends Pharmacol Sci. Jul. 2001;22(7):368-76.
McIntosh et al., CB1 cannabinoid receptor: cellular regulation and distribution in N18TG2 neuroblastoma cells. Mol Brain Res. Jan. 1998;53(1-2):163-73.
Mitrirattanakul et al., Expression of cannabinoid 1 receptors in rat dorsal root ganglia remains unchanged after spinal nerve ligation. $33^{rd}$ Annual Meeting Soc Neurosci. Nov. 10, 2003;Program No. 483.9. Abstract.
Pacher et al., The endocannabinoid system as an emerging target of pharmacotherapy. Pharmacol Rev. Sep. 2006;58(3):389-462.
Robert et al., Tumor targeting with newly designed biparatopic antibodies directed against two different epitopes of the carcinoembryonic antigen (CEA). Int J Cancer. Apr. 12, 1999;81(2):285-91.
Ulrich et al., DNA and RNA aptamers: from tools for basic research towards therapeutic applications. Comb Chem High Throughput Screen. Sep. 2006;9(8):619-32.
[No Author Listed], Nature Reviews Drug Discovery GPCR Questionnaire Participants. The state of GPCR research in 2004. Nat Rev Drug Discov. Jul. 2004;3(7):575, 577-626.
André et al., Enhancing functional production of G protein-coupled receptors in Pichia pastoris to levels required for structural studies via a single expression screen. Protein Sci. May 2006;15(5):1115-26. Epub Apr. 5, 2006.
Dahmen et al., Expression of olfactory receptors in Xenopus oocytes. J Neurochem. Mar. 1992;58(3):1176-9.
George et al., G-protein-coupled receptor oligomerization and its potential for drug discovery. Nat Rev Drug Discov. Oct. 2002;1(10):808-20.
Halaby et al., The immunoglobulin fold family: sequence analysis and 3D structure comparisons. Protein Eng. Jul. 1999;12(7):563-71.
Hassaine et al., Semliki Forest virus vectors for overexpression of 101 G protein-coupled receptors in mammalian host cells. Protein Expr Purif. Feb. 2006;45(2):343-51. Epub Jul. 11, 2005.
Holliger et al., Engineered antibody fragments and the rise of single domains. Nat Biotechnol. Sep. 2005;23(9):1126-36.
Holt et al., Domain antibodies: proteins for therapy. Trends Biotechnol. Nov. 2003;21(11):484-90.
Houamed et al., Cloning, expression, and gene structure of a G protein-coupled glutamate receptor from rat brain. Science. May 31, 1991;252(5010):1318-21.
Hovius et al., Characterization of a mouse serotonin 5-HT3 receptor purified from mammalian cells. J Neurochem. Feb. 1998;70(2):824-34.
Jacoby et al., the 7 TM G-protein-coupled receptor target family. ChemMedChem. Aug. 2006;1(8):761-82.
Kenakin, Efficacy as a vector: the relative prevalence and paucity of inverse agonism. Mol Pharmacol. Jan. 2004;65(1):2-11.
Kenakin, Principles: receptor theory in pharmacology. Trends Pharmacol Sci. Apr. 2004;25(4):186-92.
Kiefer, In vitro folding of alpha-helical membrane proteins. Biochim Biophys Acta. Feb. 17, 2003;1610(1):57-62.
Lundstrom et al., Structural genomics on membrane proteins: comparison of more than 100 GPCRs in 3 expression systems. J Struct Funct Genomics. Jun. 2006;7(2):77-91. Epub Nov. 22, 2006.
Milligan, Constitutive activity and inverse agonists of G protein-coupled receptors: a current perspective. Mol Pharmacol. Dec. 2003;64(6):1271-6.

(56) References Cited

OTHER PUBLICATIONS

Nicholson et al., Peripheral administration of a melanocortin 4-receptor inverse agonist prevents loss of lean body mass in tumor-bearing mice. J Pharmacol Exp Ther. May 2006;317(2):771-7. Epub Jan. 25, 2006.
Pierce et al., Seven-transmembrane receptors. Nat Rev Mol Cell Biol. Sep. 2002;3(9):639-50.
Rios et al., G-protein-coupled receptor dimerization: modulation of receptor function. Pharmacol Ther. Nov.-Dec. 2001;92(2-3):71-87.
Rosenkilde et al., Virally encoded 7TM receptors. Oncogene. Mar. 26, 2001;20(13):1582-93.
Sadee, Genetic variations in human G protein-coupled receptors: implications for drug therapy. AAPS PharmSci. 2001;3(3):E22.
Schlyer et al., I want a new drug: G-protein-coupled receptors in drug development. Drug Discov Today. Jun. 2006;11(11-12):481-93.
Surgand et al., A chemogenomic analysis of the transmembrane binding cavity of human G-protein-coupled receptors. Proteins. Feb. 1, 2006;62(2):509-38.
Vassilatis et al., The G protein-coupled receptor repertoires of human and mouse. Proc Natl Acad Sci U S A. Apr. 15, 2003;100(8):4903-8. Epub Apr. 4, 2003.
Vilardaga et al., Differential conformational requirements for activation of G proteins and the regulatory proteins arrestin and G protein-coupled receptor kinase in the G protein-coupled receptor for parathyroid hormone (PTH)/PTH-related protein. J Biol Chem. Sep. 7, 2001;276(36):33435-43. Epub May 31 2001.
Ward et al., Binding activities of a repertoire of single immunoglobulin variable domains secreted from *Escherichia coli*. Nature. Oct. 12, 1989;341(6242):544-6.
[No Author Listed], Monoclonal Antibody Anti-CXCR7/RDC1; K0223-3 9C4 Mouse IgG1 [kappa] 100 [mu]g. Jan. 12, 2009.
Balabanian et al., The chemokine SDF-1/CXCL12 binds to and signals through the orphan receptor RDC1 in T lymphocytes. J Biol Chem. Oct. 21, 2005;280(42):35760-6. Epub Aug. 17, 2005.
Burns et al., A novel chemokine receptor for SDF-1 and I-TAC involved in cell survival, cell adhesion, and tumor development. J Exp Med. Sep. 4, 2006;203(9):2201-13. Epub Aug. 28, 2006.
Caldas et al., Humanization of the anti-CD18 antibody 6.7: an unexpected effect of a framework residue in binding to antigen. Mol Immunol. May 2003;39(15):941-52.
Chien et al., Significant structural and functional change of an antigen-binding site by a distant amino acid substitution: proposal of a structural mechanism. Proc Natl Acad Sci U S A. Jul. 1989;86(14):5532-6.
Desmyter et al., Three camelid VHH domains in complex with porcine pancreatic alpha-amylase. Inhibition and versatility of binding topology. J Biol Chem. Jun. 28, 2002;277(26):2364550. Epub Apr. 17, 2002.
GENBANK Submission; NCBI; Accession No. NM_000609.5; Bracci et al.; Mar. 21, 2010. 4 pages.
Giusti et al., Somatic diversification of S107 from an antiphosphocholine to an anti-DNA autoantibody is due to a single base change in its heavy chain variable region. Proc Natl Acad Sci U S A. May 1987;84(9):2926-30.
Güssow et al., Humanization of monoclonal antibodies. Methods Enzymol. 1991;203:99-121.
Hachet-Haas et al., Small neutralizing molecules to inhibit actions of the chemokine CXCL12. J Biol Chem. 2008; 283(34): 23189-99.
Hartmann et al.; A crosstalk between intracellular CXCR7 and CXCR4 involved in rapid CXCL12-triggered integrin activation but not in chemokine-triggered motility of human T lymphocytes and CD34+ cells. J Leukoc Biol. Oct. 2008;84(4):1130-40. Epub Jul. 24, 2008.
Hoffmann et al., Conformational changes in G-protein-coupled receptors-the quest for functionally selective conformations is open. Br J Pharmacol. Mar. 2008;153 Suppl 1:S358-66. Epub Dec. 3, 2007.
Holm et al., Functional mapping and single chain construction of the anti-cytokeratin 8 monoclonal antibody TS1. Mol Immunol. Feb. 2007;44(6):1075-84. Epub Sep. 20, 2006.
Kim et al., Efficient targeting of gastric cancer cells using radiolabeled anti-carcinoembryonic ntigen-specific T84.66 fragments in experimental radioimmunoguided surgery. Anticancer Res. Mar.-Apr. 2006;24(2B):663-70.
Kollmar et al.. CXCR4 and CXCR7 regulate angiogenesis and CT26. WT tumor growth independent from SDF-1. Int J Cancer. Mar. 15, 2010;126(6):1302-15.
Luker et al., Imaging chemokine receptor dimerization with firefly luciferase complementation. FASEB J. Mar. 2009;23(3):823-34. Epub Nov. 10, 2008.
Maksym et al.; The role of stromal-derived factor-1—CXCR7 axis in development and cancer. Eur J Pharmacol. Dec. 25, 2009;625(1-3):31-40. Epub Oct. 14, 2009.
Mariuzza et al., The structural basis of antigen-antibody recognition. Annu Rev Biophys Biophys Chem. 1987;16:139-59.
Miao et al., CXCR7 (RDC1) promotes breast and lung tumor growth in vivo and is expressed on tumor-associated vasculature. Proc Natl Acad Sci USA. Oct. 2, 2007;104(40):15735-40. Epub Sep. 26, 2007.
Michel et al., How reliable are G-protein-coupled receptor antibodies? Naunyn Schmiedebergs Arch Pharmacol. Apr. 2009;379(4):385-8. doi: 10.1007/s00210-009-0395-y. Epub Jan. 27, 2009.
Vosjan et al., Nanobodies targeting the hepatocyte growth factor: potential new drugs for molecular cancer therapy. Mol Cancer Ther. Apr. 2012;11(4):1017-25. Epub Feb. 7, 2012.
Wang et al., The role of CXCR7/RDC1 as a chemokine receptor for CXCL12/SDF-1 in prostate cancer. J Biol Chem. Feb. 15, 2008;283(7):4283-94. Epub Dec. 5, 2007.
Winkler et al., Changing the antigen binding specificity by single point mutations of an anti-p24 (HIV-1) antibody. J Immunol. Oct. 15, 2000;165(8):4505-14.
Zabel et al., Elucidation of CXCR7-mediated signaling events and inhibition of CXCR4-mediated tumor cell transendothelial migration by CXCR7 ligands. J Immunol. Sep. 1, 2009;183(5):3204-11.

\* cited by examiner

Figure 5:
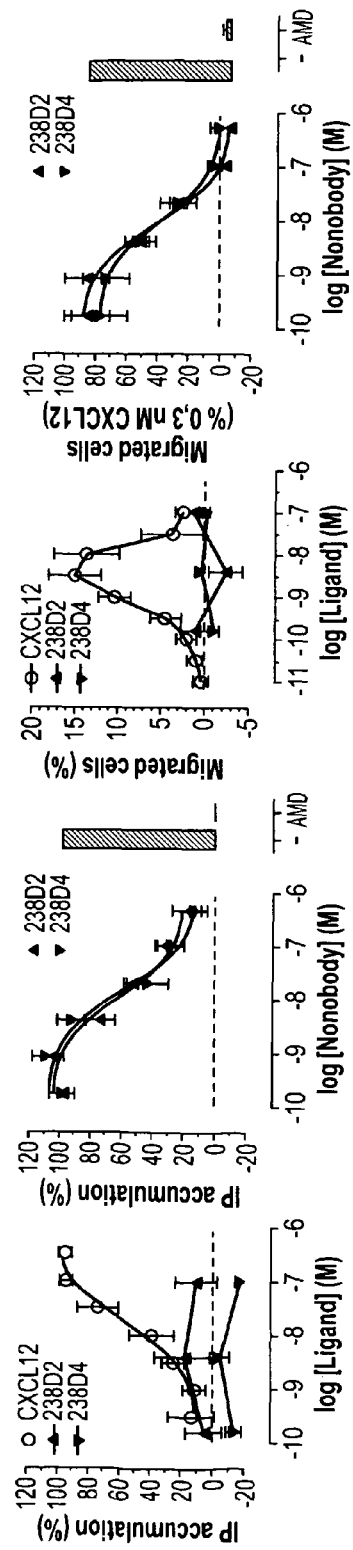
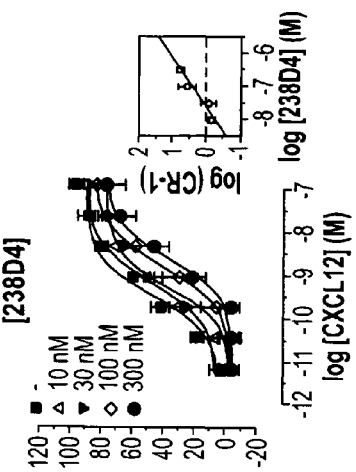
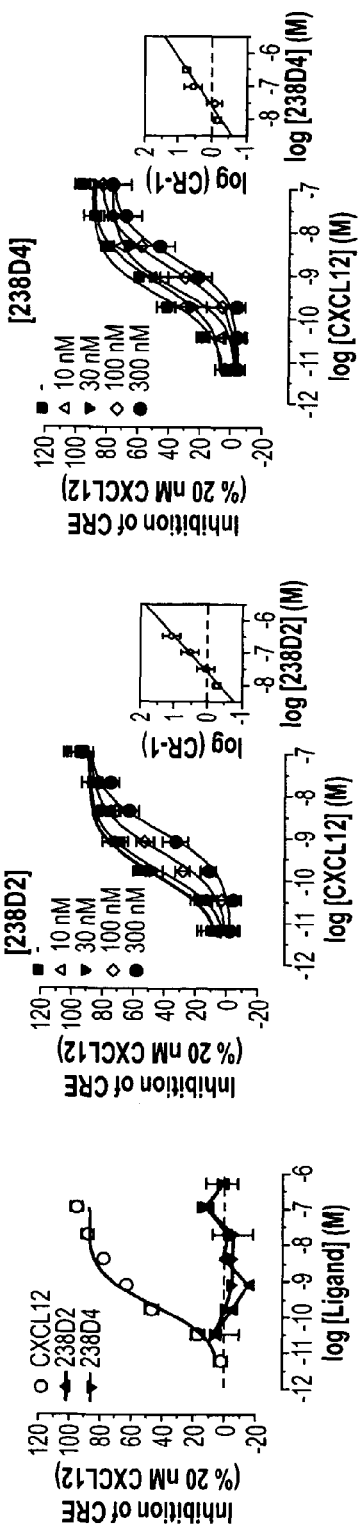

Figure 6:

CXCR4 FAMILY GROUPING

| # | Clone | Family |
|---|---|---|
| 1 | 237B6,A5,D2,D3,E4,F4,G2,G4,xh5, F1,C5,G1 | FAM 1 |
| 2 | 237D4 | |
| 3 | 238B10 | FAM 2 |
| 4 | 238F7 | |
| 5 | 238C5,G2,xH5, C3,D6,E6 | u (4) |
| 6 | 238D4,G3 | FAM 3 |
| | 238C4 | |
| 7 | 238C1,D2 | u (5) |
| 8 | 237B5 | u |
| 9 | 238H2 | u |
| 10 | 238F3 | u |
| 11 | 238D8 | ? |
| 12 | 237F11 | ? |
| 13 | 237A6 | u |
| 14 | xx237C1 | u |
| 15 | 237D1 | u |
| 16 | 237E1 | u |
| 17 | 237G7 | u |

SEQUENCE LISTING

```
<160> NUMBER OF SEQ ID NOS: 267

<210> SEQ ID NO 1
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Pro Phe Ser Xaa Xaa
            20                  25                  30

Xaa Xaa Xaa Trp Phe Arg Gln Ala Pro Gly Lys Gln Arg Asp Ser Val
        35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Arg Cys Tyr Phe Xaa Xaa Xaa Xaa Xaa Trp Gly Gln Gly Thr
            85                  90                  95
```

Gln Val Thr Val Ser Ser
            100

<210> SEQ ID NO 2
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 2

Gln Val Lys Leu Glu Glu Ser Gly Gly Gly Leu Val Gln Ala Gly Gly
1               5                   10                  15

Ser Leu Arg Leu Ser Cys Val Gly Ser Gly Arg Thr Phe Ser Xaa Xaa
            20                  25                  30

Xaa Xaa Xaa Trp Phe Arg Leu Ala Pro Gly Lys Glu Arg Glu Phe Val
        35                  40                  45

Ala Xaa Xaa Xaa Xaa Xaa Arg Phe Thr Ile Ser Arg Asp Thr Ala Ser
    50                  55                  60

Asn Arg Gly Tyr Leu His Met Asn Asn Leu Thr Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 3
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 3

Ala Val Gln Leu Val Asp Ser Gly Gly Gly Leu Val Gln Ala Gly Asp
1               5                   10                  15

Ser Leu Lys Leu Ser Cys Ala Leu Thr Gly Gly Ala Phe Thr Xaa Xaa
            20                  25                  30

Xaa Xaa Xaa Trp Phe Arg Gln Thr Pro Gly Arg Glu Arg Glu Phe Val
        35                  40                  45

Ala Xaa Xaa Xaa Xaa Xaa Arg Phe Thr Ile Ser Arg Asp Asn Ala Lys
    50                  55                  60

```
Asn Met Val Tyr Leu Arg Met Asn Ser Leu Ile Pro Glu Asp Ala Ala
 65                  70                  75                  80

Val Tyr Ser Cys Ala Ala Xaa Xaa Xaa Xaa Xaa Trp Gly Gln Gly Thr
                 85                  90                  95

Leu Val Thr Val Ser Ser
            100

<210> SEQ ID NO 4
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 4

Gln Val Gln Leu Val Glu Ser Gly Gly Gly Leu Val Glu Ala Gly Gly
 1               5                  10                  15

Ser Leu Arg Leu Ser Cys Thr Ala Ser Glu Ser Pro Phe Arg Xaa Xaa
             20                  25                  30

Xaa Xaa Xaa Trp Phe Arg Gln Thr Ser Gly Gln Glu Arg Glu Phe Val
         35                  40                  45

Ala Xaa Xaa Xaa Xaa Xaa Arg Phe Thr Ile Ser Arg Asp Asp Ala Lys
     50                  55                  60

Asn Thr Val Trp Leu His Gly Ser Thr Leu Lys Pro Glu Asp Thr Ala
 65                  70                  75                  80

Val Tyr Tyr Cys Ala Ala Xaa Xaa Xaa Xaa Xaa Trp Gly Gln Gly Thr
                 85                  90                  95

Gln Val Thr Val Ser Ser
            100

<210> SEQ ID NO 5
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 5

Ala Val Gln Leu Val Glu Ser Gly Gly Gly Leu Val Gln Gly Gly Gly
 1               5                  10                  15

Ser Leu Arg Leu Ala Cys Ala Ala Ser Glu Arg Ile Phe Asp Xaa Xaa
```

```
                    20                  25                  30
Xaa Xaa Xaa Trp Tyr Arg Gln Gly Pro Gly Asn Glu Arg Glu Leu Val
            35                  40                  45

Ala Xaa Xaa Xaa Xaa Xaa Arg Phe Thr Ile Ser Met Asp Tyr Thr Lys
    50                  55                  60

Gln Thr Val Tyr Leu His Met Asn Ser Leu Arg Pro Glu Asp Thr Gly
65                  70                  75                  80

Leu Tyr Tyr Cys Lys Ile Xaa Xaa Xaa Xaa Trp Gly Gln Gly Thr
                85                  90                  95

Gln Val Thr Val Ser Ser
            100

<210> SEQ ID NO 6
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 6

Asp Val Lys Phe Val Glu Ser Gly Gly Gly Leu Val Gln Ala Gly Gly
1               5                   10                  15

Ser Leu Arg Leu Ser Cys Val Ala Ser Gly Phe Asn Phe Asp Xaa Xaa
                20                  25                  30

Xaa Xaa Xaa Trp Phe Arg Gln Ala Pro Gly Lys Glu Arg Glu Val
            35                  40                  45

Ala Xaa Xaa Xaa Xaa Xaa Arg Phe Thr Ile Ser Ser Glu Lys Asp Lys
    50                  55                  60

Asn Ser Val Tyr Leu Gln Met Asn Ser Leu Lys Pro Glu Asp Thr Ala
65                  70                  75                  80

Leu Tyr Ile Cys Ala Gly Xaa Xaa Xaa Xaa Xaa Trp Gly Arg Gly Thr
                85                  90                  95

Gln Val Thr Val Ser Ser
            100

<210> SEQ ID NO 7
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid
```

<400> SEQUENCE: 7

Gln Val Arg Leu Ala Glu Ser Gly Gly Gly Leu Val Gln Ser Gly Gly
1               5                   10                  15

Ser Leu Arg Leu Ser Cys Val Ala Ser Gly Ser Thr Tyr Thr Xaa Xaa
            20                  25                  30

Xaa Xaa Xaa Trp Tyr Arg Gln Tyr Pro Gly Lys Gln Arg Ala Leu Val
        35                  40                  45

Ala Xaa Xaa Xaa Xaa Arg Phe Thr Ile Ala Arg Asp Ser Thr Lys
50                  55                  60

Asp Thr Phe Cys Leu Gln Met Asn Asn Leu Lys Pro Glu Asp Thr Ala
65                  70                  75                  80

Val Tyr Tyr Cys Tyr Ala Xaa Xaa Xaa Xaa Xaa Trp Gly Gln Gly Thr
                85                  90                  95

Gln Val Thr Val Ser Ser
            100

<210> SEQ ID NO 8
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Ser Asp Xaa Xaa
            20                  25                  30

Xaa Xaa Xaa Trp Phe Arg Gln Ala Pro Gly Lys Pro Arg Glu Gly Val
        35                  40                  45

Ser Xaa Xaa Xaa Xaa Xaa Arg Phe Thr Ile Ser Thr Asp Asn Ala Lys
50                  55                  60

Asn Thr Val His Leu Leu Met Asn Arg Val Asn Ala Glu Asp Thr Ala
65                  70                  75                  80

Leu Tyr Tyr Cys Ala Val Xaa Xaa Xaa Xaa Xaa Trp Gly Arg Gly Thr
                85                  90                  95

Arg Val Thr Val Ser Ser
            100

<210> SEQ ID NO 9
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:

```
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
        35                  40                  45

Ala Xaa Xaa Xaa Xaa Xaa Arg Phe Thr Ile Ser Gly Asp Asn Ala Lys
    50                  55                  60

Arg Ala Ile Tyr Leu Gln Met Asn Asn Leu Lys Pro Asp Asp Thr Ala
65              70                  75                  80

Val Tyr Tyr Cys Asn Arg Xaa Xaa Xaa Xaa Xaa Trp Gly Gln Gly Thr
                85                  90                  95

Gln Val Thr Val Ser Pro
            100

<210> SEQ ID NO 10
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 10

Gln Val Pro Val Val Glu Ser Gly Gly Gly Leu Val Gln Ala Gly Asp
1               5                   10                  15

Ser Leu Arg Leu Phe Cys Ala Val Pro Ser Phe Thr Ser Thr Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asn Ala Thr Lys
    50                  55                  60

Asn Thr Leu Thr Leu Arg Met Asp Ser Leu Lys Pro Glu Asp Thr Ala
65              70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 11
<211> LENGTH: 102
<212> TYPE: PRT
<213> ORGANISM: Artificial
```

```
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 11

Glu Val Gln Leu Val Glu Ser Gly Gly Gly Leu Val Gln Ala Gly Asp
1               5                   10                  15

Ser Leu Arg Leu Phe Cys Thr Val Ser Gly Gly Thr Ala Ser Xaa Xaa
            20                  25                  30

Xaa Xaa Xaa Trp Phe Arg Gln Ala Pro Gly Glu Lys Arg Glu Phe Val
        35                  40                  45

Ala Xaa Xaa Xaa Xaa Xaa Arg Phe Thr Ile Ala Arg Glu Asn Ala Gly
50                  55                  60

Asn Met Val Tyr Leu Gln Met Asn Asn Leu Lys Pro Asp Asp Thr Ala
65                  70                  75                  80

Leu Tyr Thr Cys Ala Ala Xaa Xaa Xaa Xaa Xaa Trp Gly Arg Gly Thr
                85                  90                  95

Gln Val Thr Val Ser Ser
            100

<210> SEQ ID NO 12
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 12

Ala Val Gln Leu Val Glu Ser Gly Gly Asp Ser Val Gln Pro Gly Asp
1               5                   10                  15

Ser Gln Thr Leu Ser Cys Ala Ala Ser Gly Arg Thr Asn Ser Xaa Xaa
            20                  25                  30

Xaa Xaa Xaa Trp Phe Arg Gln Ala Pro Gly Lys Glu Arg Val Phe Leu
        35                  40                  45

Ala Xaa Xaa Xaa Xaa Xaa Arg Phe Thr Ile Ser Arg Asp Ser Ala Lys
50                  55                  60

Asn Met Met Tyr Leu Gln Met Asn Asn Leu Lys Pro Gln Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
```

<210> SEQ ID NO 13
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 13

Ala Val Gln Leu Val Glu Ser Gly Gly Gly Leu Val Gln Ala Gly Gly
1               5                   10                  15

Ser Leu Arg Leu Ser Cys Val Val Ser Gly Leu Thr Ser Ser Xaa Xaa
            20                  25                  30

Xaa Xaa Xaa Trp Phe Arg Gln Thr Pro Trp Gln Glu Arg Asp Phe Val
        35                  40                  45

Ala Xaa Xaa Xaa Xaa Xaa Arg Phe Thr Ile Ser Arg Asp Asn Tyr Lys
    50                  55                  60

Asp Thr Val Leu Leu Glu Met Asn Phe Leu Lys Pro Glu Asp Thr Ala
65                  70                  75                  80

Ile Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 14
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 14

Ala Val Gln Leu Val Glu Ser Gly Gly Gly Leu Val Gln Ala Gly Ala
1               5                   10                  15

Ser Leu Arg Leu Ser Cys Ala Thr Ser Thr Arg Thr Leu Asp Xaa Xaa
            20                  25                  30

Xaa Xaa Xaa Trp Phe Arg Gln Ala Pro Gly Arg Asp Arg Glu Phe Val
        35                  40                  45

Ala Xaa Xaa Xaa Xaa Xaa Arg Phe Thr Val Ser Arg Asp Ser Ala Glu
    50                  55                  60

```
Asn Thr Val Ala Leu Gln Met Asn Ser Leu Lys Pro Glu Asp Thr Ala
 65                  70                  75                  80

Val Tyr Tyr Cys Ala Ala Xaa Xaa Xaa Xaa Trp Gly Gln Gly Thr
                 85                  90                  95

Arg Val Thr Val Ser Ser
            100

<210> SEQ ID NO 15
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 15

Gln Val Gln Leu Val Glu Ser Gly Gly Gly Leu Val Gln Pro Gly Gly
  1               5                  10                  15

Ser Leu Arg Leu Ser Cys Thr Val Ser Arg Leu Thr Ala His Xaa Xaa
             20                  25                  30

Xaa Xaa Xaa Trp Phe Arg Gln Ala Pro Gly Lys Glu Arg Glu Ala Val
             35                  40                  45

Ser Xaa Xaa Xaa Xaa Xaa Arg Phe Thr Ile Ser Arg Asp Tyr Ala Gly
 50                  55                  60

Asn Thr Ala Phe Leu Gln Met Asp Ser Leu Lys Pro Glu Asp Thr Gly
 65                  70                  75                  80

Val Tyr Tyr Cys Ala Thr Xaa Xaa Xaa Xaa Xaa Trp Gly Gln Gly Thr
                 85                  90                  95

Gln Val Thr Val Ser Ser
            100

<210> SEQ ID NO 16
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 16

Glu Val Gln Leu Val Glu Ser Gly Gly Glu Leu Val Gln Ala Gly Gly
  1               5                  10                  15

Ser Leu Lys Leu Ser Cys Thr Ala Ser Gly Arg Asn Phe Val Xaa Xaa
             20                  25                  30
```

```
Xaa Xaa Xaa Trp Phe Arg Arg Ala Pro Gly Lys Glu Arg Glu Phe Val
        35                  40                  45

Ala Xaa Xaa Xaa Xaa Arg Phe Thr Val Ser Arg Asp Asn Gly Lys
    50                  55                  60

Asn Thr Ala Tyr Leu Arg Met Asn Ser Leu Lys Pro Glu Asp Thr Ala
 65                  70                  75                  80

Asp Tyr Tyr Cys Ala Val Xaa Xaa Xaa Xaa Xaa Leu Gly Ser Gly Thr
                 85                  90                  95

Gln Val Thr Val Ser Ser
            100
```

<210> SEQ ID NO 17
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 17

```
Ala Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Gln Met Asn Ser Leu Lys Pro Glu Asp Thr Ala
 65                  70                  75                  80

Val Tyr Tyr Cys Val Lys Xaa Xaa Xaa Xaa Xaa Gly Ser Gln Gly Thr
                 85                  90                  95

Gln Val Thr Val Ser Ser
            100
```

<210> SEQ ID NO 18
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

```
<400> SEQUENCE: 18

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
                100

<210> SEQ ID NO 19
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 19

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser Xaa Xaa
            20                  25                  30

Xaa Xaa Xaa Trp Val Arg His Thr Pro Gly Lys Ala Glu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Glu Met Asn Ser Leu Ser Pro Glu Asp Thr Ala
65                  70                  75                  80

Met Tyr Tyr Cys Gly Arg Xaa Xaa Xaa Xaa Xaa Arg Ser Lys Gly Ile
                85                  90                  95

Gln Val Thr Val Ser Ser
                100

<210> SEQ ID NO 20
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
```

<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 20

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Tyr Cys Ala Ala Xaa Xaa Xaa Xaa Xaa Arg Gly Gln Gly Thr
                85                  90                  95

Gln Val Thr Val Ser Ser
            100

<210> SEQ ID NO 21
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 21

Asp Val Gln Leu Val Glu Ser Gly Gly Asp Leu Val Gln Pro Gly Gly
1               5                   10                  15

Ser Leu Arg Leu Ser Cys Ala Ala Ser Gly Phe Ser Phe Asp Xaa Xaa
            20                  25                  30

Xaa Xaa Xaa Trp Leu Arg Gln Thr Pro Gly Lys Gly Leu Glu Trp Val
        35                  40                  45

Gly Xaa Xaa Xaa Xaa Xaa Arg Phe Thr Ile Ser Arg Asp Asn Ala Lys
    50                  55                  60

Asn Met Leu Tyr Leu His Leu Asn Asn Leu Lys Ser Glu Asp Thr Ala
65                  70                  75                  80

Val Tyr Tyr Cys Arg Arg Xaa Xaa Xaa Xaa Xaa Leu Gly Gln Gly Thr
                85                  90                  95

Gln Val Thr Val Ser Ser
            100

<210> SEQ ID NO 22
<211> LENGTH: 102
<212> TYPE: PRT
<213> ORGANISM: Artificial
<220> FEATURE:

<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 23
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 23

Gln Val Gln Arg Val Glu Ser Gly Gly Gly Leu Val Gln Ala Gly Gly
1               5                   10                  15

Ser Leu Arg Leu Ser Cys Ala Ala Ser Gly Arg Thr Ser Ser
            20                  25                  30

<210> SEQ ID NO 24
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 24

Gln Val Gln Leu Val Glu Ser Gly Gly Gly Leu Val Gln Thr Gly Asp
1               5                   10                  15

Ser Leu Ser Leu Ser Cys Ser Ala Ser Gly Arg Thr Phe Ser
            20                  25                  30

<210> SEQ ID NO 25
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 25

```
Gln Val Lys Leu Glu Glu Ser Gly Gly Gly Leu Val Gln Ala Gly Asp
1               5                   10                  15

Ser Leu Arg Leu Ser Cys Ala Ala Thr Gly Arg Ala Phe Gly
            20                  25                  30
```

<210> SEQ ID NO 26
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 26

```
Ala Val Gln Leu Val Glu Ser Gly Gly Gly Leu Val Gln Pro Gly Glu
1               5                   10                  15

Ser Leu Gly Leu Ser Cys Val Ala Ser Gly Arg Asp Phe Val
            20                  25                  30
```

<210> SEQ ID NO 27
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 27

```
Glu Val Gln Leu Val Glu Ser Gly Gly Gly Leu Val Gln Ala Gly Gly
1               5                   10                  15

Ser Leu Arg Leu Ser Cys Glu Val Leu Gly Arg Thr Ala Gly
            20                  25                  30
```

<210> SEQ ID NO 28
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 28

```
Gln Val Gln Leu Val Glu Ser Gly Gly Gly Trp Val Gln Pro Gly Gly
1               5                   10                  15

Ser Leu Arg Leu Ser Cys Ala Ala Ser Glu Thr Ile Leu Ser
            20                  25                  30
```

<210> SEQ ID NO 29
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 29

```
Gln Val Gln Leu Val Glu Ser Gly Gly Gly Thr Val Gln Pro Gly Gly
1               5                   10                  15

Ser Leu Asn Leu Ser Cys Val Ala Ser Gly Asn Thr Phe Asn
            20                  25                  30
```

<210> SEQ ID NO 30
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 30

```
Glu Val Gln Leu Val Glu Ser Gly Gly Gly Leu Ala Gln Pro Gly Gly
1               5                   10                  15

Ser Leu Gln Leu Ser Cys Ser Ala Pro Gly Phe Thr Leu Asp
                20                  25                  30

<210> SEQ ID NO 31
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 31

Ala Gln Glu Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn
                20                  25                  30

<210> SEQ ID NO 32
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 32

Val Glu Ser Gly Gly Gly Leu Val Gln Pro Gly Gly Ser Leu Arg Leu
1               5                   10                  15

Ser Cys Ala Ala Ser Gly
                20

<210> SEQ ID NO 33
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 33

Val Asp Ser Gly Gly Gly Leu Val Gln Ala Gly Asp Ser Leu Lys Leu
1               5                   10                  15

Ser Cys Ala Leu Thr Gly
                20

<210> SEQ ID NO 34
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 34

Val Asp Ser Gly Gly Gly Leu Val Gln Ala Gly Asp Ser Leu Arg Leu
1               5                   10                  15

Ser Cys Ala Ala Ser Gly
                20

<210> SEQ ID NO 35
<211> LENGTH: 22
<212> TYPE: PRT
<213> ORGANISM: Artificial
<220> FEATURE:
<223> OTHER INFORMATION: KERE-class Nanobody FW1 sequence
```

```
<400> SEQUENCE: 35

Val Asp Ser Gly Gly Gly Leu Val Glu Ala Gly Gly Ser Leu Arg Leu
1               5                   10                  15

Ser Cys Gln Val Ser Glu
            20

<210> SEQ ID NO 36
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 36

Gln Asp Ser Gly Gly Gly Ser Val Gln Ala Gly Gly Ser Leu Lys Leu
1               5                   10                  15

Ser Cys Ala Ala Ser Gly
            20

<210> SEQ ID NO 37
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 37

Val Gln Ser Gly Gly Arg Leu Val Gln Ala Gly Asp Ser Leu Arg Leu
1               5                   10                  15

Ser Cys Ala Ala Ser Glu
            20

<210> SEQ ID NO 38
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 38

Val Glu Ser Gly Gly Thr Leu Val Gln Ser Gly Asp Ser Leu Lys Leu
1               5                   10                  15

Ser Cys Ala Ser Ser Thr
            20

<210> SEQ ID NO 39
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 39

Met Glu Ser Gly Gly Asp Ser Val Gln Ser Gly Gly Ser Leu Thr Leu
1               5                   10                  15

Ser Cys Val Ala Ser Gly
            20

<210> SEQ ID NO 40
<211> LENGTH: 22
<212> TYPE: PRT
<213> ORGANISM: Artificial
<220> FEATURE:
<223> OTHER INFORMATION: KERE-class Nanobody FW1 sequence
```

<400> SEQUENCE: 40

Gln Ala Ser Gly Gly Gly Leu Val Gln Ala Gly Gly Ser Leu Arg Leu
1               5                   10                  15

Ser Cys Ser Ala Ser Val
            20

<210> SEQ ID NO 41
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 41

Trp Phe Arg Gln Ala Pro Gly Lys Glu Arg Glu Phe Val Ala
1               5                   10

<210> SEQ ID NO 42
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 42

Trp Phe Arg Gln Thr Pro Gly Arg Glu Arg Glu Phe Val Ala
1               5                   10

<210> SEQ ID NO 43
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 43

Trp Tyr Arg Gln Ala Pro Gly Lys Gln Arg Glu Met Val Ala
1               5                   10

<210> SEQ ID NO 44
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 44

Trp Tyr Arg Gln Gly Pro Gly Lys Gln Arg Glu Leu Val Ala
1               5                   10

<210> SEQ ID NO 45
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 45

Trp Ile Arg Gln Ala Pro Gly Lys Glu Arg Glu Gly Val Ser
1               5                   10

<210> SEQ ID NO 46
<211> LENGTH: 14
<212> TYPE: PRT
<213> ORGANISM: Artificial

```
<220> FEATURE:
<223> OTHER INFORMATION: KERE-class Nanobody FW2 sequence

<400> SEQUENCE: 46

Trp Phe Arg Glu Ala Pro Gly Lys Glu Arg Glu Gly Ile Ser
1               5                   10

<210> SEQ ID NO 47
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 47

Trp Tyr Arg Gln Ala Pro Gly Lys Glu Arg Asp Leu Val Ala
1               5                   10

<210> SEQ ID NO 48
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 48

Trp Phe Arg Gln Ala Pro Gly Lys Gln Arg Glu Glu Val Ser
1               5                   10

<210> SEQ ID NO 49
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 49

Trp Phe Arg Gln Pro Pro Gly Lys Val Arg Glu Phe Val Gly
1               5                   10

<210> SEQ ID NO 50
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 50

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Arg Cys Tyr Phe
            20                  25                  30

<210> SEQ ID NO 51
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 51

Arg Phe Ala Ile Ser Arg Asp Asn Asn Lys Asn Thr Gly Tyr Leu Gln
1               5                   10                  15

Met Asn Ser Leu Glu Pro Glu Asp Thr Ala Val Tyr Tyr Cys Ala Ala
            20                  25                  30
```

<210> SEQ ID NO 52
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 52

Arg Phe Thr Val Ala Arg Asn Asn Ala Lys Asn Thr Val Asn Leu Glu
1               5                   10                  15

Met Asn Ser Leu Lys Pro Glu Asp Thr Ala Val Tyr Tyr Cys Ala Ala
            20                  25                  30

<210> SEQ ID NO 53
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 53

Arg Phe Thr Ile Ser Arg Asp Ile Ala Lys Asn Thr Val Asp Leu Leu
1               5                   10                  15

Met Asn Asn Leu Glu Pro Glu Asp Thr Ala Val Tyr Tyr Cys Ala Ala
            20                  25                  30

<210> SEQ ID NO 54
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 54

Arg Leu Thr Ile Ser Arg Asp Asn Ala Val Asp Thr Met Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 55
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 55

Arg Phe Thr Ile Ser Arg Asp Asn Ala Lys Asn Thr Val Tyr Leu Gln
1               5                   10                  15

Met Asp Asn Val Lys Pro Glu Asp Thr Ala Ile Tyr Tyr Cys Ala Ala
            20                  25                  30

<210> SEQ ID NO 56
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 56

Arg Phe Thr Ile Ser Lys Asp Ser Gly Lys Asn Thr Val Tyr Leu Gln
1               5                   10                  15

Met Thr Ser Leu Lys Pro Glu Asp Thr Ala Val Tyr Tyr Cys Ala Thr
            20                  25                  30

```
<210> SEQ ID NO 57
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 57

Arg Phe Thr Ile Ser Arg Asp Ser Ala Lys Asn Met Met Tyr Leu Gln
1               5                   10                  15

Met Asn Asn Leu Lys Pro Gln Asp Thr Ala Val Tyr Tyr Cys Ala Ala
            20                  25                  30

<210> SEQ ID NO 58
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 58

Arg Phe Thr Ile Ser Arg Glu Asn Asp Lys Ser Thr Val Tyr Leu Gln
1               5                   10                  15

Leu Asn Ser Leu Lys Pro Glu Asp Thr Ala Val Tyr Tyr Cys Ala Ala
            20                  25                  30

<210> SEQ ID NO 59
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 59

Arg Phe Thr Ile Ser Arg Asp Tyr Ala Gly Asn Thr Ala Tyr Leu Gln
1               5                   10                  15

Met Asn Ser Leu Lys Pro Glu Asp Thr Gly Val Tyr Tyr Cys Ala Thr
            20                  25                  30

<210> SEQ ID NO 60
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 60

Trp Gly Gln Gly Thr Gln Val Thr Val Ser Ser
1               5                   10

<210> SEQ ID NO 61
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 61

Trp Gly Lys Gly Thr Leu Val Thr Val Ser Ser
1               5                   10

<210> SEQ ID NO 62
<211> LENGTH: 11
<212> TYPE: PRT
```

```
<213> ORGANISM: Artificial
<220> FEATURE:
<223> OTHER INFORMATION: KERE-class Nanobody FW4 sequence

<400> SEQUENCE: 62

Arg Gly Gln Gly Thr Arg Val Thr Val Ser Ser
1               5                   10

<210> SEQ ID NO 63
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 63

Trp Gly Leu Gly Thr Gln Val Thr Ile Ser Ser
1               5                   10

<210> SEQ ID NO 64
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 65
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 65

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30

<210> SEQ ID NO 66
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 66

Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30

<210> SEQ ID NO 67
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 67
```

```
Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 68
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 68

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 69
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 69

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 70
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 70

Glu Glu Ser Gly Gly Gly Leu Ala Gln Pro Gly Gly Ser Leu Arg Leu
1               5                   10                  15

Ser Cys Val Ala Ser Gly
            20

<210> SEQ ID NO 71
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 71

Val Glu Ser Gly Gly Gly Leu Ala Leu Pro Gly Gly Ser Leu Thr Leu
1               5                   10                  15

Ser Cys Val Phe Ser Gly
            20

<210> SEQ ID NO 72
<211> LENGTH: 14
<212> TYPE: PRT
<213> ORGANISM: Artificial
<220> FEATURE:
<223> OTHER INFORMATION: GLEW-class Nanobody FW2 sequence
```

```
<400> SEQUENCE: 72

Trp Val Arg Gln Ala Pro Gly Lys Val Leu Glu Trp Val Ser
1               5                   10

<210> SEQ ID NO 73
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 73

Trp Val Arg Arg Pro Pro Gly Lys Gly Leu Glu Trp Val Ser
1               5                   10

<210> SEQ ID NO 74
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 74

Trp Val Arg Gln Ala Pro Gly Met Gly Leu Glu Trp Val Ser
1               5                   10

<210> SEQ ID NO 75
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 75

Trp Val Arg Gln Ala Pro Gly Lys Glu Pro Glu Trp Val Ser
1               5                   10

<210> SEQ ID NO 76
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 76

Trp Val Arg Gln Ala Pro Gly Lys Asp Gln Glu Trp Val Ser
1               5                   10

<210> SEQ ID NO 77
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 77

Trp Val Arg Gln Ala Pro Gly Lys Ala Glu Glu Trp Val Ser
1               5                   10

<210> SEQ ID NO 78
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 78
```

Trp Val Arg Gln Ala Pro Gly Lys Gly Leu Glu Trp Val Ala
1               5                   10

<210> SEQ ID NO 79
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 79

Trp Val Arg Gln Ala Pro Gly Arg Ala Thr Glu Trp Val Ser
1               5                   10

<210> SEQ ID NO 80
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 80

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Val Lys
            20                  25                  30

<210> SEQ ID NO 81
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 81

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 82
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 82

Arg Phe Thr Ser Ser Arg Asp Asn Ala Lys Ser Thr Leu Tyr Leu Gln
1               5                   10                  15

Met Asn Asp Leu Lys Pro Glu Asp Thr Ala Leu Tyr Tyr Cys Ala Arg
            20                  25                  30

<210> SEQ ID NO 83
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 83

Arg Phe Ile Ile Ser Arg Asp Asn Ala Lys Asn Thr Leu Tyr Leu Gln
1               5                   10                  15

Met Asn Ser Leu Gly Pro Glu Asp Thr Ala Met Tyr Tyr Cys Gln Arg 20                  25                  30

<210> SEQ ID NO 84
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 84

Arg Phe Thr Ala Ser Arg Asp Asn Ala Lys Asn Thr Leu Tyr Leu Gln
1               5                   10                  15

Met Asn Ser Leu Lys Ser Glu Asp Thr Ala Arg Tyr Tyr Cys Ala Arg
            20                  25                  30

<210> SEQ ID NO 85
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 85

Arg Phe Thr Ile Ser Arg Asp Asn Ala Lys Asn Thr Leu Tyr Leu Gln
1               5                   10                  15

Met Asp Asp Leu Gln Ser Glu Asp Thr Ala Met Tyr Tyr Cys Gly Arg
            20                  25                  30

<210> SEQ ID NO 86
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 86

Gly Ser Gln Gly Thr Gln Val Thr Val Ser Ser
1               5                   10

<210> SEQ ID NO 87
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 87

Leu Arg Gly Gly Thr Gln Val Thr Val Ser Ser
1               5                   10

<210> SEQ ID NO 88
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 88

Arg Gly Gln Gly Thr Leu Val Thr Val Ser Ser
1               5                   10

<210> SEQ ID NO 89
<211> LENGTH: 11
<212> TYPE: PRT
<213> ORGANISM: Artificial
<220> FEATURE:

<223> OTHER INFORMATION: GLEW-class Nanobody FW4 sequence

<400> SEQUENCE: 89

Arg Ser Arg Gly Ile Gln Val Thr Val Ser Ser
1               5                   10

<210> SEQ ID NO 90
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 90

Trp Gly Lys Gly Thr Gln Val Thr Val Ser Ser
1               5                   10

<210> SEQ ID NO 91
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 91

Trp Gly Gln Gly Thr Gln Val Thr Val Ser Ser
1               5                   10

<210> SEQ ID NO 92
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 92

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 93
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 93

Gln Val Gln Leu Gln Glu Ser Gly Gly Gly Met Val Gln Pro Gly Gly
1               5                   10                  15

Ser Leu Arg Leu Ser Cys Ala Ala Ser Gly Phe Asp Phe Gly
            20                  25                  30

<210> SEQ ID NO 94
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 94

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys 20                  25                  30

<210> SEQ ID NO 95
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 95

Gln Val Gln Leu Ala Glu Ser Gly Gly Gly Leu Val Gln Pro Gly Gly
1               5                   10                  15

Ser Leu Lys Leu Ser Cys Ala Ala Ser Arg Thr Ile Val Ser
            20                  25                  30

<210> SEQ ID NO 96
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 96

Gln Glu His Leu Val Glu Ser Gly Gly Gly Leu Val Asp Ile Gly Gly
1               5                   10                  15

Ser Leu Arg Leu Ser Cys Ala Ala Ser Glu Arg Ile Phe Ser
            20                  25                  30

<210> SEQ ID NO 97
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 97

Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30

<210> SEQ ID NO 98
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 99
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 99

Glu Val Gln Leu Val Glu Ser Gly Gly Gly Leu Ala Leu Pro Gly Gly
1               5                   10                  15

```
Ser Leu Thr Leu Ser Cys Val Phe Ser Gly Ser Thr Phe Ser
            20                  25                  30

<210> SEQ ID NO 100
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 100

Val Glu Ser Gly Gly Gly Leu Val Gln Ala Gly Gly Ser Leu Arg Leu
1               5                   10                  15

Ser Cys Ala Ala Ser Gly
            20

<210> SEQ ID NO 101
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 101

Ala Glu Ser Gly Gly Gly Leu Val Gln Pro Gly Gly Ser Leu Lys Leu
1               5                   10                  15

Ser Cys Ala Ala Ser Arg
            20

<210> SEQ ID NO 102
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 102

Trp Phe Arg Gln Ala Pro Gly Lys Glu Arg Glu Phe Val Ala
1               5                   10

<210> SEQ ID NO 103
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 103

Trp Val Arg Gln Ala Pro Gly Lys Val Leu Glu Trp Val Ser
1               5                   10

<210> SEQ ID NO 104
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 104

Trp Val Arg Arg Pro Pro Gly Lys Gly Leu Glu Trp Val Ser
1               5                   10

<210> SEQ ID NO 105
<211> LENGTH: 14
<212> TYPE: PRT
<213> ORGANISM: Artificial
```

```
<220> FEATURE:
<223> OTHER INFORMATION: P,R,S 103-class Nanobody FW2 sequence

<400> SEQUENCE: 105

Trp Ile Arg Gln Ala Pro Gly Lys Glu Arg Glu Gly Val Ser
1               5                   10

<210> SEQ ID NO 106
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 106

Trp Val Arg Gln Tyr Pro Gly Lys Glu Pro Glu Trp Val Ser
1               5                   10

<210> SEQ ID NO 107
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 107

Trp Phe Arg Gln Pro Pro Gly Lys Glu His Glu Phe Val Ala
1               5                   10

<210> SEQ ID NO 108
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 108

Trp Tyr Arg Gln Ala Pro Gly Lys Arg Thr Glu Leu Val Ala
1               5                   10

<210> SEQ ID NO 109
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 109

Trp Leu Arg Gln Ala Pro Gly Gln Gly Leu Glu Trp Val Ser
1               5                   10

<210> SEQ ID NO 110
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 110

Trp Leu Arg Gln Thr Pro Gly Lys Gly Leu Glu Trp Val Gly
1               5                   10

<210> SEQ ID NO 111
<211> LENGTH: 14
<212> TYPE: PRT
<213> ORGANISM: Artificial
<220> FEATURE:
```

```
<223> OTHER INFORMATION: P,R,S 103-class Nanobody FW2 sequence

<400> SEQUENCE: 111

Trp Val Arg Gln Ala Pro Gly Lys Ala Glu Glu Phe Val Ser
1               5                   10

<210> SEQ ID NO 112
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 112

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 113
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 113

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 114
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 114

Arg Phe Thr Ile Ser Arg Asp Asn Ala Lys Asn Glu Met Tyr Leu Gln
1               5                   10                  15

Met Asn Asn Leu Lys Thr Glu Asp Thr Gly Val Tyr Trp Cys Gly Ala
            20                  25                  30

<210> SEQ ID NO 115
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 115

Arg Phe Thr Ile Ser Ser Asp Ser Asn Arg Asn Met Ile Tyr Leu Gln
1               5                   10                  15

Met Asn Asn Leu Lys Pro Glu Asp Thr Ala Val Tyr Tyr Cys Ala Ala
            20                  25                  30

<210> SEQ ID NO 116
<211> LENGTH: 32
<212> TYPE: PRT
<213> ORGANISM: Artificial
<220> FEATURE:
<223> OTHER INFORMATION: P,R,S 103-class Nanobody FW3 sequence
```

```
<400> SEQUENCE: 116

Arg Phe Thr Ile Ser Arg Asp Asn Ala Lys Asn Met Leu Tyr Leu His
1               5                   10                  15

Leu Asn Asn Leu Lys Ser Glu Asp Thr Ala Val Tyr Tyr Cys Arg Arg
                20                  25                  30

<210> SEQ ID NO 117
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 117

Arg Phe Thr Ile Ser Arg Asp Asn Ala Lys Lys Thr Val Tyr Leu Arg
1               5                   10                  15

Leu Asn Ser Leu Asn Pro Glu Asp Thr Ala Val Tyr Ser Cys Asn Leu
                20                  25                  30

<210> SEQ ID NO 118
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 118

Arg Phe Lys Ile Ser Arg Asp Asn Ala Lys Lys Thr Leu Tyr Leu Gln
1               5                   10                  15

Met Asn Ser Leu Gly Pro Glu Asp Thr Ala Met Tyr Tyr Cys Gln Arg
                20                  25                  30

<210> SEQ ID NO 119
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 119

Arg Phe Thr Val Ser Arg Asp Asn Gly Lys Asn Thr Ala Tyr Leu Arg
1               5                   10                  15

Met Asn Ser Leu Lys Pro Glu Asp Thr Ala Asp Tyr Tyr Cys Ala Val
                20                  25                  30

<210> SEQ ID NO 120
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 120

Arg Gly Gln Gly Thr Gln Val Thr Val Ser Ser
1               5                   10

<210> SEQ ID NO 121
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 121
```

```
Leu Arg Gly Gly Thr Gln Val Thr Val Ser Ser
1               5                   10

<210> SEQ ID NO 122
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 122

Gly Asn Lys Gly Thr Leu Val Thr Val Ser Ser
1               5                   10

<210> SEQ ID NO 123
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 123

Ser Ser Pro Gly Thr Gln Val Thr Val Ser Ser
1               5                   10

<210> SEQ ID NO 124
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 124

Ser Ser Gln Gly Thr Leu Val Thr Val Ser Ser
1               5                   10

<210> SEQ ID NO 125
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 125

Arg Ser Arg Gly Ile Gln Val Thr Val Ser Ser
1               5                   10

<210> SEQ ID NO 126
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 126

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser
            20                  25                  30

<210> SEQ ID NO 127
<211> LENGTH: 30
<212> TYPE: PRT
<213> ORGANISM: Artificial
<220> FEATURE:
<223> OTHER INFORMATION: Nanobody, Nanobody constructs or fragments
```

```
       thereof

<400> SEQUENCE: 127

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 128
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 128

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser
            20                  25                  30

<210> SEQ ID NO 129
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp
            20                  25                  30

<210> SEQ ID NO 130
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 130

Glu Val Gln Leu Val Glu Ser Gly Gly Gly Phe Val Gln Ala Gly Gly
1               5                   10                  15

Ser Leu Arg Leu Ser Cys Glu Thr Ser Gly Arg Pro Leu Leu
            20                  25                  30

<210> SEQ ID NO 131
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 131

Glu Val Gln Leu Met Glu Ser Gly Gly Gly Leu Val Gln Ala Gly Gly
1               5                   10                  15

Ser Leu Arg Leu Ala Cys Ala Ala Ser Gly Phe Thr Phe Glu
            20                  25                  30
```

```
<210> SEQ ID NO 132
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 132

Glu Val Gln Leu Val Glu Ser Gly Gly Gly Phe Val Gln Ala Gly Gly
1               5                   10                  15

Ser Leu Arg Leu Ser Cys Glu Thr Ser Gly Arg Pro Leu Leu
            20                  25                  30

<210> SEQ ID NO 133
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 133

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser
            20                  25                  30

<210> SEQ ID NO 134
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp
            20                  25                  30

<210> SEQ ID NO 135
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 135

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Thr Tyr Ala
            20                  25                  30

<210> SEQ ID NO 136
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 136

Glu Val Gln Leu Val Glu Ser Gly Gly Gly Leu Val Gln Ala Gly Gly
```

```
                1               5                  10                  15
Ser Leu Arg Leu Ser Cys Ala Ala Ser Gly Ser Ile Phe Ser
                20                  25                  30
```

<210> SEQ ID NO 137
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 137

```
Glu Val Gln Leu Val Glu Ser Gly Gly Gly Leu Ala Gln Pro Gly Gly
1               5                   10                  15
Pro Leu Arg Leu Thr Cys Glu Ala Ser Gly Val Ile Tyr Ser
                20                  25                  30
```

<210> SEQ ID NO 138
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 138

```
Glu Val Gln Leu Val Glu Ser Gly Gly Gly Leu Val Gln Pro Gly Gly
1               5                   10                  15
Ser Leu Arg Leu Ser Cys Glu Val Ser Gly Phe Thr Arg Asp
                20                  25                  30
```

<210> SEQ ID NO 139
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 139

```
Glu Val Gln Leu Val Glu Ser Gly Gly Gly Leu Val Gln Pro Gly Gly
1               5                   10                  15
Ser Leu Arg Leu Ser Cys Ala Ala Ser Ser Phe Ile Gly Asn
                20                  25                  30
```

<210> SEQ ID NO 140
<211> LENGTH: 30
<212> TYPE: PRT
<213> ORGANISM: Artificial
<220> FEATURE:
<223> OTHER INFORMATION: Nanobody, Nanobody constructs or fragments
      thereof

<400> SEQUENCE: 140

```
Glu Val Gln Leu Val Glu Ser Gly Gly Gly Leu Val Gln Ala Gly Gly
1               5                   10                  15
Ser Leu Arg Leu Ser Cys Lys Ala Ser Gly Gly Thr Phe Asn
                20                  25                  30
```

<210> SEQ ID NO 141
<211> LENGTH: 30
<212> TYPE: PRT
<213> ORGANISM: Artificial
<220> FEATURE:

<223> OTHER INFORMATION: Nanobody, Nanobody constructs or fragments
      thereof

<400> SEQUENCE: 141

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Ser
            20                  25                  30

<210> SEQ ID NO 142
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 142

Ser Tyr Ala Met Ser
1               5

<210> SEQ ID NO 143
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 143

Asn Tyr Ala Met Gly
1               5

<210> SEQ ID NO 144
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 144

Ile His Thr Met Ser
1               5

<210> SEQ ID NO 145
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 145

Asp Tyr Ala Met Ser
1               5

<210> SEQ ID NO 146
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 146

Gly Tyr Thr Ile Ala

```
<210> SEQ ID NO 147
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 147

Asp Tyr Ala Ile Gly
1               5

<210> SEQ ID NO 148
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 148

Gly Tyr Thr Ile Ala
1               5

<210> SEQ ID NO 149
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 149

Pro Ser Ala Met Ala
1               5

<210> SEQ ID NO 150
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 150

Asp Tyr Ala Met Ser
1               5

<210> SEQ ID NO 151

<400> SEQUENCE: 151

000

<210> SEQ ID NO 152
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 152

Leu Asn Ala Met Gly
1               5
```

<210> SEQ ID NO 153
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 153

Val Asn Asp Met Gly
1               5

<210> SEQ ID NO 154
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 154

Tyr Tyr Thr Ile Gly
1               5

<210> SEQ ID NO 155
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 155

Tyr His Ala Ile Val
1               5

<210> SEQ ID NO 156
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 156

Asn Tyr Ala Met Gly
1               5

<210> SEQ ID NO 157
<211> LENGTH: 5
<212> TYPE: PRT
<213> ORGANISM: Artificial
<220> FEATURE:
<223> OTHER INFORMATION: Nanobody, Nanobody constructs or fragments
      thereof

<400> SEQUENCE: 157

Ile Asn Ala Met Gly
1               5

<210> SEQ ID NO 158
<211> LENGTH: 14
<212> TYPE: PRT
<213> ORGANISM: Artificial
<220> FEATURE:
<223> OTHER INFORMATION: Nanobody, Nanobody constructs or fragments
      thereof -continued

```
<400> SEQUENCE: 158

Trp Val Arg Gln Ala Pro Gly Lys Gly Leu Glu Trp Val Ser
1               5                   10

<210> SEQ ID NO 159
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 159

Trp Phe Arg Arg Ala Pro Gly Lys Glu Arg Glu Phe Val Ala
1               5                   10

<210> SEQ ID NO 160
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 160

Trp Val Arg Gln Ala Pro Gly Lys Gly Pro Glu Trp Val Ser
1               5                   10

<210> SEQ ID NO 161
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 161

Trp Val Arg Gln Ala Pro Gly Lys Gly Leu Glu Trp Val Ser
1               5                   10

<210> SEQ ID NO 162
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 162

Trp Phe Arg Gln Val Pro Gly Lys Glu Arg Glu Phe Val Ala
1               5                   10

<210> SEQ ID NO 163
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 163

Trp Phe Arg Lys Ala Pro Gly Lys Glu Arg Glu Gly Val Ser
1               5                   10

<210> SEQ ID NO 164
<211> LENGTH: 14
<212> TYPE: PRT
```

<213> ORGANISM: Artificial
<220> FEATURE:
<223> OTHER INFORMATION: Nanobody, Nanobody constructs or fragments
      thereof

<400> SEQUENCE: 164

Trp Phe Arg Gln Val Pro Gly Lys Glu Arg Glu Phe Val Ala
1               5                   10

<210> SEQ ID NO 165
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 165

Trp Tyr Arg Gln Gly Pro Gly Lys Glu Arg Asp Phe Val Ala
1               5                   10

<210> SEQ ID NO 166
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 166

Trp Val Arg Gln Ala Pro Gly Lys Gly Leu Glu Trp Val Ser
1               5                   10

<210> SEQ ID NO 167
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 167

Trp Phe Arg Gln Ala Pro Gly Lys Glu Arg Glu Phe Val Thr
1               5                   10

<210> SEQ ID NO 168
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 168

Trp Tyr Arg Gln Ala Pro Gly Lys Gln Arg Glu Leu Val Ala
1               5                   10

<210> SEQ ID NO 169
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 169

Trp Tyr Arg Gln Ala Pro Gly Lys Gln Arg Glu Leu Val Ala
1               5                   10

<210> SEQ ID NO 170
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 170

Trp Phe Arg Gln Ala Pro Gly Lys Glu Arg Glu Gly Val Ser
1               5                   10

<210> SEQ ID NO 171
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 171

Trp Leu Arg Gln Ala Pro Gly Lys Glu Leu Glu Gly Val Ser
1               5                   10

<210> SEQ ID NO 172
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 172

Trp Phe Arg Arg Ala Pro Gly Lys Glu Arg Glu Phe Val Ala
1               5                   10

<210> SEQ ID NO 173
<211> LENGTH: 14
<212> TYPE: PRT
<213> ORGANISM: Artificial
<220> FEATURE:
<223> OTHER INFORMATION: Nanobody, Nanobody constructs or fragments
      thereof

<400> SEQUENCE: 173

Trp Tyr Arg Gln Ala Pro Gly Lys Gln Arg Glu Leu Val Ala
1               5                   10

<210> SEQ ID NO 174
<211> LENGTH: 17
<212> TYPE: PRT
<213> ORGANISM: Artificial
<220> FEATURE:
<223> OTHER INFORMATION: Nanobody, Nanobody constructs or fragments
      thereof

<400> SEQUENCE: 174

Gly Ile Lys Ser Ser Gly Asp Ser Thr Arg Tyr Ala Gly Ser Val Lys
1               5                   10                  15

Gly

<210> SEQ ID NO 175
<211> LENGTH: 21
<212> TYPE: PRT
<213> ORGANISM: Artificial
<220> FEATURE:

<223> OTHER INFORMATION: Nanobody, Nanobody constructs or fragments
     thereof

<400> SEQUENCE: 175

Ala Ile Thr Arg Ser Gly Val Arg Ser Gly Val Ser Ala Ile Tyr Gly
1               5                   10                  15

Asp Ser Val Lys Asp
            20

<210> SEQ ID NO 176
<211> LENGTH: 17
<212> TYPE: PRT
<213> ORGANISM: Artificial
<220> FEATURE:
<223> OTHER INFORMATION: Nanobody, Nanobody constructs or fragments
     thereof

<400> SEQUENCE: 176

Thr Ile Lys Pro Ser Gly Asp Thr Thr Asn Tyr Ala Asn Ala Val Lys
1               5                   10                  15

Gly

<210> SEQ ID NO 177
<211> LENGTH: 17
<212> TYPE: PRT
<213> ORGANISM: Artificial
<220> FEATURE:
<223> OTHER INFORMATION: Nanobody, Nanobody constructs or fragments
     thereof

<400> SEQUENCE: 177

Ala Ile Ser Trp Asn Gly Gly Ser Thr Asp Tyr Ala Asp Ser Val Lys
1               5                   10                  15

Gly

<210> SEQ ID NO 178
<211> LENGTH: 17
<212> TYPE: PRT
<213> ORGANISM: Artificial
<220> FEATURE:
<223> OTHER INFORMATION: Nanobody, Nanobody constructs or fragments
     thereof

<400> SEQUENCE: 178

Tyr His Arg Trp Ser Asp Gly Ala Asn Leu Tyr Ala Asp Ser Val Lys
1               5                   10                  15

Gly

<210> SEQ ID NO 179
<211> LENGTH: 17
<212> TYPE: PRT
<213> ORGANISM: Artificial
<220> FEATURE:
<223> OTHER INFORMATION: Nanobody, Nanobody constructs or fragments
     thereof

<400> SEQUENCE: 179

Cys Ile Ser Gly Ser Asp Gly Ser Thr Thr Tyr Ala Asp Ser Val Lys
1               5                   10                  15

Gly

<210> SEQ ID NO 180
<211> LENGTH: 17
<212> TYPE: PRT

```
<213> ORGANISM: Artificial
<220> FEATURE:
<223> OTHER INFORMATION: Nanobody, Nanobody constructs or fragments
      thereof

<400> SEQUENCE: 180

Tyr His Arg Trp Ser Asp Gly Ala Asn Leu Tyr Ala Asp Ser Val Lys
1               5                   10                  15

Gly

<210> SEQ ID NO 181
<211> LENGTH: 17
<212> TYPE: PRT
<213> ORGANISM: Artificial
<220> FEATURE:
<223> OTHER INFORMATION: Nanobody, Nanobody constructs or fragments
      thereof

<400> SEQUENCE: 181

Ser Thr Ile Trp Ser Arg Gly Asp Thr Tyr Phe Ala Asp Ser Val Lys
1               5                   10                  15

Gly

<210> SEQ ID NO 182
<211> LENGTH: 17
<212> TYPE: PRT
<213> ORGANISM: Artificial
<220> FEATURE:
<223> OTHER INFORMATION: Nanobody, Nanobody constructs or fragments
      thereof

<400> SEQUENCE: 182

Ala Ile Ser Trp Asn Gly Gly Ser Ala Asp Tyr Ala Asp Ser Val Lys
1               5                   10                  15

Gly

<210> SEQ ID NO 183
<211> LENGTH: 17
<212> TYPE: PRT
<213> ORGANISM: Artificial
<220> FEATURE:
<223> OTHER INFORMATION: Nanobody, Nanobody constructs or fragments
      thereof

<400> SEQUENCE: 183

Thr Ser Arg Leu Ile Thr Asp Asn Ile Ile Tyr Ala Asp Ser Val Lys
1               5                   10                  15

Gly

<210> SEQ ID NO 184
<211> LENGTH: 16
<212> TYPE: PRT
<213> ORGANISM: Artificial
<220> FEATURE:
<223> OTHER INFORMATION: Nanobody, Nanobody constructs or fragments
      thereof

<400> SEQUENCE: 184

Gly Ile Thr Ser Ser Thr Ser Thr Tyr Tyr Ala Asp Ser Val Lys Gly
1               5                   10                  15

<210> SEQ ID NO 185
<211> LENGTH: 16
<212> TYPE: PRT
<213> ORGANISM: Artificial
```

```
<220> FEATURE:
<223> OTHER INFORMATION: Nanobody, Nanobody constructs or fragments
      thereof

<400> SEQUENCE: 185

Val Ile Thr Ser Gly Gly Gly Thr Asn Tyr Val Asp Ser Val Lys Gly
1               5                   10                  15

<210> SEQ ID NO 186
<211> LENGTH: 17
<212> TYPE: PRT
<213> ORGANISM: Artificial
<220> FEATURE:
<223> OTHER INFORMATION: Nanobody, Nanobody constructs or fragments
      thereof

<400> SEQUENCE: 186

Cys Ile Ser Ser Ser Asp Gly Ser Thr Ala Tyr Leu Gly Ser Val Gln
1               5                   10                  15

Gly

<210> SEQ ID NO 187
<211> LENGTH: 17
<212> TYPE: PRT
<213> ORGANISM: Artificial
<220> FEATURE:
<223> OTHER INFORMATION: Nanobody, Nanobody constructs or fragments
      thereof

<400> SEQUENCE: 187

Cys Ile Thr Ser Arg Asp Ser Ile Thr Tyr Tyr Ala Ser Phe Val Lys
1               5                   10                  15

Gly

<210> SEQ ID NO 188
<211> LENGTH: 21
<212> TYPE: PRT
<213> ORGANISM: Artificial
<220> FEATURE:
<223> OTHER INFORMATION: Nanobody, Nanobody constructs or fragments
      thereof

<400> SEQUENCE: 188

Ala Ile Thr Arg Ser Gly Val Arg Ser Gly Val Ser Ala Ile Tyr Gly
1               5                   10                  15

Asp Ser Val Lys Asp
            20

<210> SEQ ID NO 189
<211> LENGTH: 16
<212> TYPE: PRT
<213> ORGANISM: Artificial
<220> FEATURE:
<223> OTHER INFORMATION: Nanobody, Nanobody constructs or fragments
      thereof

<400> SEQUENCE: 189

Ser Ile Thr Ser Gly Gly Ser Thr Val Tyr Ala Asp Ser Val Lys Gly
1               5                   10                  15

<210> SEQ ID NO 190
<211> LENGTH: 32
<212> TYPE: PRT
<213> ORGANISM: Artificial
<220> FEATURE:
<223> OTHER INFORMATION: Nanobody, Nanobody constructs or fragments
``` thereof

<400> SEQUENCE: 190

Arg Phe Thr Ile Ser Arg Asp Asn Ala Lys Asn Met Leu Tyr Leu Gln
1               5                   10                  15

Met Tyr Ser Leu Lys Pro Glu Asp Thr Ala Val Tyr Tyr Cys Ala Lys
            20                  25                  30

<210> SEQ ID NO 191
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 191

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 192
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 192

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 193
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 193

Arg Phe Thr Ile Ser Arg Asp Asn Ala Lys Asn Thr Leu Tyr Leu Gln
1               5                   10                  15

Met Asn Ser Leu Lys Ser Glu Asp Thr Ala Glu Tyr Tyr Cys Ala Arg
            20                  25                  30

<210> SEQ ID NO 194
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 194

Arg Phe Thr Ile Ser Gly His Asn Ala Lys Asn Thr Val Ser Leu Gln
1               5                   10                  15

Met Asn Ser Leu Lys Pro Glu Asp Thr Ala Val Tyr Tyr Cys Ala Ala
            20                  25                  30

```
<210> SEQ ID NO 195
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 195

Arg Phe Thr Ile Ser Thr Asp Asn Ala Lys Asn Thr Val Tyr Leu Glu
1               5                   10                  15

Met Asn Ser Leu Lys Pro Glu Asp Thr Ala Val Tyr Tyr Cys Ala Gln
            20                  25                  30

<210> SEQ ID NO 196
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 196

Arg Phe Thr Ile Ser Gly His Asn Ala Lys Asn Thr Val Ser Leu Gln
1               5                   10                  15

Met Asn Ser Leu Lys Pro Glu Asp Thr Ala Val Tyr Tyr Cys Ala Ala
            20                  25                  30

<210> SEQ ID NO 197
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 197

Arg Phe Thr Ile Ser Arg Asp Thr Ala Asn Tyr Thr Leu Tyr Leu Gln
1               5                   10                  15

Met Asn Asn Leu Lys Pro Glu Asp Thr Ala Val Tyr Tyr Cys Ser Leu
            20                  25                  30

<210> SEQ ID NO 198
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 198

Arg Phe Thr Ile Ser Arg Asp Asn Ala Lys Asn Thr Leu Tyr Leu Gln
1               5                   10                  15

Met Asn Ser Leu Lys Ser Glu Asp Thr Ala Val Tyr Tyr Cys Ala Lys
            20                  25                  30

<210> SEQ ID NO 199
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 199

Arg Phe Thr Leu Thr Arg Asp Asn Gly Lys Asn Thr Val Tyr Leu Gln
```

```
1               5                   10                  15
Met Asp Ser Leu Lys Pro Asp Asp Thr Ala Val Tyr Phe Cys Ala Ala
                20                  25                  30

<210> SEQ ID NO 200
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 200

Arg Phe Thr Ile Ser Arg Asp Asn Thr Lys Asn Thr Val Tyr Leu Gln
1               5                   10                  15
Met Asn Ser Leu Lys Pro Glu Asp Thr Ala Val Tyr Tyr Cys Asn Val
                20                  25                  30

<210> SEQ ID NO 201
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 201

Arg Phe Thr Ile Ser Gly Asp Asn Arg Lys Lys Thr Val Tyr Leu Gln
1               5                   10                  15
Met Asn Ser Leu Lys Pro Glu Asp Thr Ala Val Tyr Tyr Cys Ser Ile
                20                  25                  30

<210> SEQ ID NO 202
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 202

Arg Phe Thr Val Ser Arg Asp Asn Ala Lys Asn Thr Val Tyr Leu Gln
1               5                   10                  15
Met Asn Asn Leu Lys Pro Glu Asp Thr Ala Val Tyr Tyr Cys Ala Leu
                20                  25                  30

<210> SEQ ID NO 203
<211> LENGTH: 32
<212> TYPE: PRT
<213> ORGANISM: Artificial
<220> FEATURE:
<223> OTHER INFORMATION: Nanobody, Nanobody constructs or fragments
      thereof

<400> SEQUENCE: 203

Arg Phe Thr Ile Ser Arg Asp Asp Ala Lys Asn Thr Val Tyr Leu Gln
1               5                   10                  15
Met Asn Asn Leu Lys Pro Glu Asp Thr Ala Val Tyr Tyr Cys Ala Val
                20                  25                  30

<210> SEQ ID NO 204
<211> LENGTH: 32
<212> TYPE: PRT
<213> ORGANISM: Artificial
<220> FEATURE:
```

<223> OTHER INFORMATION: Nanobody, Nanobody constructs or fragments
      thereof

<400> SEQUENCE: 204

Arg Phe Thr Ile Ser Arg Asp Asn Val Lys Asn Thr Leu Tyr Leu Gln
1               5                   10                  15

Met Asn Thr Leu Lys Pro Glu Asp Thr Ala Val Tyr Thr Cys Ala Ala
            20                  25                  30

<210> SEQ ID NO 205
<211> LENGTH: 31
<212> TYPE: PRT
<213> ORGANISM: Artificial
<220> FEATURE:
<223> OTHER INFORMATION: Nanobody, Nanobody constructs or fragments
      thereof

<400> SEQUENCE: 205

Arg Phe Thr Ile Ser Arg Asp Asn Tyr Asn Thr Val Tyr Leu Gln Met
1               5                   10                  15

Asn Ser Leu Lys Pro Glu Asp Thr Ala Val Tyr Tyr Cys Asn Ala
            20                  25                  30

<210> SEQ ID NO 206
<211> LENGTH: 13
<212> TYPE: PRT
<213> ORGANISM: Artificial
<220> FEATURE:
<223> OTHER INFORMATION: Nanobody, Nanobody constructs or fragments
      thereof

<400> SEQUENCE: 206

Ser Arg Val Ser Arg Thr Gly Leu Tyr Thr Tyr Asp Asn
1               5                   10

<210> SEQ ID NO 207
<211> LENGTH: 15
<212> TYPE: PRT
<213> ORGANISM: Artificial
<220> FEATURE:
<223> OTHER INFORMATION: Nanobody, Nanobody constructs or fragments
      thereof

<400> SEQUENCE: 207

Ser Ala Ile Gly Ser Gly Ala Leu Arg Arg Phe Glu Tyr Asp Tyr
1               5                   10                  15

<210> SEQ ID NO 208
<211> LENGTH: 7
<212> TYPE: PRT
<213> ORGANISM: Artificial
<220> FEATURE:
<223> OTHER INFORMATION: Nanobody, Nanobody constructs or fragments
      thereof

<400> SEQUENCE: 208

Asp Tyr Phe Gly Thr Gly Val
1               5

<210> SEQ ID NO 209
<211> LENGTH: 18
<212> TYPE: PRT
<213> ORGANISM: Artificial
<220> FEATURE:
<223> OTHER INFORMATION: Nanobody, Nanobody constructs or fragments
      thereof

```
<400> SEQUENCE: 209

Asp Gln Gly Pro Phe Tyr Ser Gly Thr Tyr Tyr Tyr Thr Arg Gln Tyr
1               5                   10                  15

Gly Tyr

<210> SEQ ID NO 210
<211> LENGTH: 13
<212> TYPE: PRT
<213> ORGANISM: Artificial
<220> FEATURE:
<223> OTHER INFORMATION: Nanobody, Nanobody constructs or fragments
      thereof

<400> SEQUENCE: 210

Ala Arg Met Thr Thr Ser Asn Asp Lys Glu Tyr Leu Tyr
1               5                   10

<210> SEQ ID NO 211
<211> LENGTH: 18
<212> TYPE: PRT
<213> ORGANISM: Artificial
<220> FEATURE:
<223> OTHER INFORMATION: Nanobody, Nanobody constructs or fragments
      thereof

<400> SEQUENCE: 211

Gln Tyr Gly Val Gly Gly Arg Val Val Cys Pro Gly Pro Tyr Glu Tyr
1               5                   10                  15

Asp Val

<210> SEQ ID NO 212
<211> LENGTH: 13
<212> TYPE: PRT
<213> ORGANISM: Artificial
<220> FEATURE:
<223> OTHER INFORMATION: Nanobody, Nanobody constructs or fragments
      thereof

<400> SEQUENCE: 212

Ala Trp Met Thr Thr Ser Asn Asp Lys Glu Tyr Leu Tyr
1               5                   10

<210> SEQ ID NO 213
<211> LENGTH: 10
<212> TYPE: PRT
<213> ORGANISM: Artificial
<220> FEATURE:
<223> OTHER INFORMATION: Nanobody, Nanobody constructs or fragments
      thereof

<400> SEQUENCE: 213

Arg Val Arg Pro Tyr Gly Gln Tyr Asp Tyr
1               5                   10

<210> SEQ ID NO 214
<211> LENGTH: 18
<212> TYPE: PRT
<213> ORGANISM: Artificial
<220> FEATURE:
<223> OTHER INFORMATION: Nanobody, Nanobody constructs or fragments
      thereof

<400> SEQUENCE: 214

Asp Gln Gly Pro Phe Tyr Ser Gly Thr Tyr Tyr Tyr Thr Lys Gly Tyr
1               5                   10                  15
```

Ala Tyr

<210> SEQ ID NO 215
<211> LENGTH: 16
<212> TYPE: PRT
<213> ORGANISM: Artificial
<220> FEATURE:
<223> OTHER INFORMATION: Nanobody, Nanobody constructs or fragments
      thereof

<400> SEQUENCE: 215

Arg Gln Asn Tyr Ser Arg Ser Val Phe Gly Ala Lys Asp Tyr Asp Tyr
1               5                   10                  15

<210> SEQ ID NO 216
<211> LENGTH: 15
<212> TYPE: PRT
<213> ORGANISM: Artificial
<220> FEATURE:
<223> OTHER INFORMATION: Nanobody, Nanobody constructs or fragments
      thereof

<400> SEQUENCE: 216

Asp Cys Pro Asp Tyr Tyr Ser Asp Tyr Glu Cys Pro Leu Glu Asp
1               5                   10                  15

<210> SEQ ID NO 217
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 217

Tyr Tyr Ser Ser Gly Ile Ser Thr Leu Arg Ser
1               5                   10

<210> SEQ ID NO 218
<211> LENGTH: 20
<212> TYPE: PRT
<213> ORGANISM: Artificial
<220> FEATURE:
<223> OTHER INFORMATION: Nanobody, Nanobody constructs or fragments
      thereof

<400> SEQUENCE: 218

Asx Ser Ala Asp Ser Arg Cys Ser Ile Gly Ser Ile Gly Phe Thr Trp
1               5                   10                  15

Leu Tyr Asn Asn
            20

<210> SEQ ID NO 219
<211> LENGTH: 15
<212> TYPE: PRT
<213> ORGANISM: Artificial
<220> FEATURE:
<223> OTHER INFORMATION: Nanobody, Nanobody constructs or fragments
      thereof

<400> SEQUENCE: 219

Asx Thr Ser Met Thr Cys Pro Thr Leu Ile Val Arg Phe Asn Tyr
1               5                   10                  15

<210> SEQ ID NO 220
<211> LENGTH: 15
<212> TYPE: PRT

```
<213> ORGANISM: Artificial
<220> FEATURE:
<223> OTHER INFORMATION: Nanobody, Nanobody constructs or fragments
      thereof

<400> SEQUENCE: 220

Ser Ala Ile Gly Ser Gly Ala Leu Arg Arg Phe Glu Tyr Asp Tyr
1               5                   10                  15

<210> SEQ ID NO 221
<211> LENGTH: 15
<212> TYPE: PRT
<213> ORGANISM: Artificial
<220> FEATURE:
<223> OTHER INFORMATION: Nanobody, Nanobody constructs or fragments
      thereof

<400> SEQUENCE: 221

Asp Gly Val Pro Glu Trp Gly Lys Val Gln Tyr Pro Asp Thr Tyr
1               5                   10                  15

<210> SEQ ID NO 222
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 222

Arg Gly Gln Gly Thr Gln Val Thr Val Ser Ser
1               5                   10

<210> SEQ ID NO 223
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 223

Ser Gly Gln Gly Thr Gln Val Thr Val Ser Ser
1               5                   10

<210> SEQ ID NO 224
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 224

Arg Gly Gln Gly Thr Gln Val Thr Val Ser Ser
1               5                   10

<210> SEQ ID NO 225
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 225

Arg Gly Gln Gly Thr Gln Val Thr Val Ser Ser
1               5                   10
```

<210> SEQ ID NO 226
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 226

Trp Gly Gln Gly Thr Gln Val Thr Val Ser Ser
1               5                   10

<210> SEQ ID NO 227
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 227

Trp Gly Gln Gly Thr Gln Val Thr Val Ser Ser
1               5                   10

<210> SEQ ID NO 228
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 228

Trp Gly Gln Gly Thr Gln Val Thr Val Ser Ser
1               5                   10

<210> SEQ ID NO 229
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 229

Trp Gly Gln Gly Thr Gln Val Thr Val Ser Ser
1               5                   10

<210> SEQ ID NO 230
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 230

Trp Gly Gln Gly Thr Gln Val Thr Val Ser Ser
1               5                   10

<210> SEQ ID NO 231
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 231

Trp Gly Gln Gly Thr Gln Val Thr Val Ser Ser
1               5                   10

<210> SEQ ID NO 232
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 232

Arg Gly Gln Gly Thr Gln Val Thr Val Ser Ser
1               5                   10

<210> SEQ ID NO 233
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 233

Trp Gly Gln Gly Thr Gln Val Thr Val Ser Ser
1               5                   10

<210> SEQ ID NO 234
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 234

Trp Gly Gln Gly Thr Gln Val Thr Val Ser Ser
1               5                   10

<210> SEQ ID NO 235
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 235

Arg Gly Gln Gly Thr Gln Val Thr Val Ser Ser
1               5                   10

<210> SEQ ID NO 236
<211> LENGTH: 11
<212> TYPE: PRT
<213> ORGANISM: Artificial
<220> FEATURE:
<223> OTHER INFORMATION: Nanobody, Nanobody constructs or fragments
      thereof

<400> SEQUENCE: 236

Ser Gly Gln Gly Thr Gln Val Thr Val Ser Ser
1               5                   10

<210> SEQ ID NO 237
<211> LENGTH: 11

```
<212> TYPE: PRT
<213> ORGANISM: Artificial
<220> FEATURE:
<223> OTHER INFORMATION: Nanobody, Nanobody constructs or fragments
      thereof

<400> SEQUENCE: 237

Arg Gly Gln Gly Thr Gln Val Thr Val Ser Ser
1               5                   10

<210> SEQ ID NO 238
<211> LENGTH: 122
<212> TYPE: PRT
<213> ORGANISM: Artificial
<220> FEATURE:
<223> OTHER INFORMATION: Nanobody, Nanobody constructs or fragments
      thereof

<400> SEQUENCE: 238

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Lys Ser Ser Gly Asp Ser Thr Tyr Ala Gly Ser Val
    50                  55                  60

Lys Gly Arg Phe Thr Ile Ser Arg Asp Asn Ala Lys Asn Met Leu Tyr
65                  70                  75                  80

Leu Gln Met Tyr Ser Leu Lys Pro Glu Asp Thr Ala Val Tyr Tyr Cys
                85                  90                  95

Ala Lys Ser Arg Val Ser Arg Thr Gly Leu Tyr Thr Tyr Asp Asn Arg
            100                 105                 110

Gly Gln Gly Thr Gln Val Thr Val Ser Ser
        115                 120

<210> SEQ ID NO 239
<211> LENGTH: 128
<212> TYPE: PRT
<213> ORGANISM: Artificial
<220> FEATURE:
<223> OTHER INFORMATION: Nanobody, Nanobody constructs or fragments
      thereof

<400> SEQUENCE: 239

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Thr Arg Ser Gly Val Arg Ser Gly Val Ser Ala Ile Tyr
    50                  55                  60

Gly Asp Ser Val Lys Asp Arg Phe Thr Ile Ser Arg Asp Asn Ala Lys
65                  70                  75                  80

Asn Thr Leu Tyr Leu Gln Met Asn Ser Leu Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Tyr Ser Gly Gln Gly Thr Gln Val Thr Val Ser Ser
```

<210> SEQ ID NO 240
<211> LENGTH: 116
<212> TYPE: PRT
<213> ORGANISM: Artificial
<220> FEATURE:
<223> OTHER INFORMATION: Nanobody, Nanobody constructs or fragments
     thereof

<400> SEQUENCE: 240

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ile His
            20                  25                  30

Thr Met Ser Trp Val Arg Gln Ala Pro Gly Lys Gly Pro Glu Trp Val
        35                  40                  45

Ser Thr Ile Lys Pro Ser Gly Asp Thr Thr Asn Tyr Ala Asn Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Tyr Phe Gly Thr Gly Val Arg Gly Gln Gly Thr Gln Val
            100                 105                 110

Thr Val Ser Ser
        115

<210> SEQ ID NO 241
<211> LENGTH: 127
<212> TYPE: PRT
<213> ORGANISM: Artificial
<220> FEATURE:
<223> OTHER INFORMATION: Nanobody, Nanobody constructs or fragments
     thereof

<400> SEQUENCE: 241

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Ala Ile Ser Trp Asn Gly Gly Ser Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Glu Tyr Tyr Cys
                85                  90                  95

Ala Arg Asp Gln Gly Pro Phe Tyr Ser Gly Thr Tyr Tyr Tyr Thr Arg
            100                 105                 110

Gln Tyr Gly Tyr Arg Gly Gln Gly Thr Gln Val Thr Val Ser Ser
        115                 120                 125

<210> SEQ ID NO 242
<211> LENGTH: 122
<212> TYPE: PRT
<213> ORGANISM: Artificial
<220> FEATURE:
<223> OTHER INFORMATION: Nanobody, Nanobody constructs or fragments thereof

<400> SEQUENCE: 242

Glu Val Gln Leu Val Glu Ser Gly Gly Gly Phe Val Gln Ala Gly Gly
1               5                   10                  15

Ser Leu Arg Leu Ser Cys Glu Thr Ser Gly Arg Pro Leu Leu Gly Tyr
            20                  25                  30

Thr Ile Ala Trp Phe Arg Gln Val Pro Gly Lys Glu Arg Glu Phe Val
        35                  40                  45

Ala Tyr His Arg Trp Ser Asp Gly Ala Asn Leu Tyr Ala Asp Ser Val
    50                  55                  60

Lys Gly Arg Phe Thr Ile Ser Gly His Asn Ala Lys Asn Thr Val Ser
65                  70                  75                  80

Leu Gln Met Asn Ser Leu Lys Pro Glu Asp Thr Ala Val Tyr Tyr Cys
                85                  90                  95

Ala Ala Ala Arg Met Thr Thr Ser Asn Asp Lys Glu Tyr Leu Tyr Trp
            100                 105                 110

Gly Gln Gly Thr Gln Val Thr Val Ser Ser
        115                 120

<210> SEQ ID NO 243
<211> LENGTH: 127
<212> TYPE: PRT
<213> ORGANISM: Artificial
<220> FEATURE:
<223> OTHER INFORMATION: Nanobody, Nanobody constructs or fragments
      thereof

<400> SEQUENCE: 243

Glu Val Gln Leu Met Glu Ser Gly Gly Gly Leu Val Gln Ala Gly Gly
1               5                   10                  15

Ser Leu Arg Leu Ala Cys Ala Ala Ser Gly Phe Thr Phe Glu Asp Tyr
            20                  25                  30

Ala Ile Gly Trp Phe Arg Lys Ala Pro Gly Lys Glu Arg Glu Gly Val
        35                  40                  45

Ser Cys Ile Ser Gly Ser Asp Gly Ser Thr Thr Tyr Ala Asp Ser Val
    50                  55                  60

Lys Gly Arg Phe Thr Ile Ser Thr Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Ala Gln Gln Tyr Gly Val Gly Arg Val Val Cys Pro Gly Pro Tyr
            100                 105                 110

Glu Tyr Asp Val Trp Gly Gln Gly Thr Gln Val Thr Val Ser Ser
        115                 120                 125

<210> SEQ ID NO 244
<211> LENGTH: 122
<212> TYPE: PRT
<213> ORGANISM: Artificial
<220> FEATURE:
<223> OTHER INFORMATION: Nanobody, Nanobody constructs or fragments
      thereof

<400> SEQUENCE: 244

Glu Val Gln Leu Val Glu Ser Gly Gly Gly Phe Val Gln Ala Gly Gly
1               5                   10                  15

Ser Leu Arg Leu Ser Cys Glu Thr Ser Gly Arg Pro Leu Leu Gly Tyr
            20                  25                  30

```
Thr Ile Ala Trp Phe Arg Gln Val Pro Gly Lys Glu Arg Glu Phe Val
            35                  40                  45

Ala Tyr His Arg Trp Ser Asp Gly Ala Asn Leu Tyr Ala Asp Ser Val
    50                  55                  60

Lys Gly Arg Phe Thr Ile Ser Gly His Asn Ala Lys Asn Thr Val Ser
65                  70                  75                  80

Leu Gln Met Asn Ser Leu Lys Pro Glu Asp Thr Ala Val Tyr Tyr Cys
                85                  90                  95

Ala Ala Ala Trp Met Thr Thr Ser Asn Asp Lys Glu Tyr Leu Tyr Trp
                100                 105                 110

Gly Gln Gly Thr Gln Val Thr Val Ser Ser
            115                 120
```

<210> SEQ ID NO 245
<211> LENGTH: 119
<212> TYPE: PRT
<213> ORGANISM: Artificial
<220> FEATURE:
<223> OTHER INFORMATION: Nanobody, Nanobody constructs or fragments
      thereof

<400> SEQUENCE: 245

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Pro Ser
            20                  25                  30

Ala Met Ala Trp Tyr Arg Gln Gly Pro Gly Lys Glu Arg Asp Phe Val
            35                  40                  45

Ala Ser Thr Ile Trp Ser Arg Gly Asp Thr Tyr Phe Ala Asp Ser Val
    50                  55                  60

Lys Gly Arg Phe Thr Ile Ser Arg Asp Thr Ala Asn Tyr Thr Leu Tyr
65                  70                  75                  80

Leu Gln Met Asn Asn Leu Lys Pro Glu Asp Thr Ala Val Tyr Tyr Cys
                85                  90                  95

Ser Leu Arg Val Arg Pro Tyr Gly Gln Tyr Asp Tyr Trp Gly Gln Gly
                100                 105                 110

Thr Gln Val Thr Val Ser Ser
        115
```

<210> SEQ ID NO 246
<211> LENGTH: 127
<212> TYPE: PRT
<213> ORGANISM: Artificial
<220> FEATURE:
<223> OTHER INFORMATION: Nanobody, Nanobody constructs or fragments
      thereof

<400> SEQUENCE: 246

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
            35                  40                  45

Ser Ala Ile Ser Trp Asn Gly Gly Ser Ala Asp Tyr Ala Asp Ser Val
    50                  55                  60

Lys Gly Arg Phe Thr Ile Ser Arg Asp Asn Ala Lys Asn Thr Leu Tyr
65                  70                  75                  80
```

Leu Gln Met Asn Ser Leu Lys Ser Glu Asp Thr Ala Val Tyr Tyr Cys
                85                  90                  95

Ala Lys Asp Gln Gly Pro Phe Tyr Ser Gly Thr Tyr Tyr Thr Lys
            100                 105                 110

Gly Tyr Ala Tyr Trp Gly Gln Gly Thr Gln Val Thr Val Ser Ser
        115                 120                 125

<210> SEQ ID NO 247
<211> LENGTH: 122
<212> TYPE: PRT
<213> ORGANISM: Artificial
<220> FEATURE:
<223> OTHER INFORMATION: Nanobody, Nanobody constructs or fragments
      thereof

<400> SEQUENCE: 247

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Thr Tyr Ala Met Gly
            20                  25                  30

Trp Phe Arg Gln Ala Pro Gly Lys Glu Arg Glu Phe Val Thr Thr Ser
        35                  40                  45

Arg Leu Ile Thr Asp Asn Ile Ile Tyr Ala Asp Ser Val Lys Gly Arg
    50                  55                  60

Phe Thr Leu Thr Arg Asp Asn Gly Lys Asn Thr Val Tyr Leu Gln Met
65                  70                  75                  80

Asp Ser Leu Lys Pro Asp Asp Thr Ala Val Tyr Phe Cys Ala Ala Arg
                85                  90                  95

Gln Asn Tyr Ser Arg Ser Val Phe Gly Ala Lys Asp Tyr Asp Tyr Trp
            100                 105                 110

Gly Gln Gly Thr Gln Val Thr Val Ser Ser
        115                 120

<210> SEQ ID NO 248
<211> LENGTH: 123
<212> TYPE: PRT
<213> ORGANISM: Artificial
<220> FEATURE:
<223> OTHER INFORMATION: Nanobody, Nanobody constructs or fragments
      thereof

<400> SEQUENCE: 248

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Leu Asn
            20                  25                  30

Ala Met Gly Trp Tyr Arg Gln Ala Pro Gly Lys Gln Arg Glu Leu Val
        35                  40                  45

Ala Gly Ile Thr Ser Ser Thr Ser Thr Tyr Tyr Ala Asp Ser Val Lys
    50                  55                  60

Gly Arg Phe Thr Ile Ser Arg Asp Asn Thr Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Asp Cys Pro Asp Tyr Tyr Ser Asp Tyr Glu Cys Pro Leu Glu Asp
            100                 105                 110

Arg Gly Gln Gly Thr Gln Val Thr Val Ser Ser
        115                 120

<210> SEQ ID NO 249
<211> LENGTH: 119
<212> TYPE: PRT
<213> ORGANISM: Artificial
<220> FEATURE:
<223> OTHER INFORMATION: Nanobody, Nanobody constructs or fragments
      thereof

<400> SEQUENCE: 249

Glu Val Gln Leu Val Glu Ser Gly Gly Gly Leu Ala Gln Pro Gly Gly
1               5                   10                  15

Pro Leu Arg Leu Thr Cys Glu Ala Ser Gly Val Ile Tyr Ser Val Asn
            20                  25                  30

Asp Met Gly Trp Tyr Arg Gln Ala Pro Gly Lys Gln Arg Glu Leu Val
        35                  40                  45

Ala Val Ile Thr Ser Gly Gly Thr Asn Tyr Val Asp Ser Val Lys
    50                  55                  60

Gly Arg Phe Thr Ile Ser Gly Asp Asn Arg Lys Thr Val Tyr Leu
65                  70                  75                  80

Gln Met Asn Ser Leu Lys Pro Glu Asp Thr Ala Val Tyr Tyr Cys Ser
                85                  90                  95

Ile Tyr Tyr Ser Ser Gly Ile Ser Thr Leu Arg Ser Trp Gly Gln Gly
            100                 105                 110

Thr Gln Val Thr Val Ser Ser
        115

<210> SEQ ID NO 250
<211> LENGTH: 129
<212> TYPE: PRT
<213> ORGANISM: Artificial
<220> FEATURE:
<223> OTHER INFORMATION: Nanobody, Nanobody constructs or fragments
      thereof

<400> SEQUENCE: 250

Glu Val Gln Leu Val Glu Ser Gly Gly Gly Leu Val Gln Pro Gly Gly
1               5                   10                  15

Ser Leu Arg Leu Ser Cys Glu Val Ser Gly Phe Thr Arg Asp Tyr Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Asp Gly Ser Thr Ala Tyr Leu Gly Ser Val
    50                  55                  60

Gln Gly Arg Phe Thr Val Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Leu Asx Ser Ala Asp Ser Arg Cys Ser Ile Gly Ser Ile Gly Phe
            100                 105                 110

Thr Trp Leu Tyr Asn Asn Trp Gly Gln Gly Thr Gln Val Thr Val Ser
        115                 120                 125

Ser

<210> SEQ ID NO 251
<211> LENGTH: 124
<212> TYPE: PRT
<213> ORGANISM: Artificial
<220> FEATURE:

<223> OTHER INFORMATION: Nanobody, Nanobody constructs or fragments
      thereof

<400> SEQUENCE: 251

Glu Val Gln Leu Val Glu Ser Gly Gly Gly Leu Val Gln Pro Gly Gly
1               5                   10                  15

Ser Leu Arg Leu Ser Cys Ala Ala Ser Ser Phe Ile Gly Asn Tyr His
            20                  25                  30

Ala Ile Val Trp Leu Arg Gln Ala Pro Gly Lys Glu Leu Glu Gly Val
        35                  40                  45

Ser Cys Ile Thr Ser Arg Asp Ser Ile Thr Tyr Tyr Ala Ser Phe Val
    50                  55                  60

Lys Gly Arg Phe Thr Ile Ser Arg Asp Asp Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Val Asx Thr Ser Met Thr Cys Pro Thr Leu Ile Val Arg Phe Asn
            100                 105                 110

Tyr Arg Gly Gln Gly Thr Gln Val Thr Val Ser Ser
        115                 120

<210> SEQ ID NO 252
<211> LENGTH: 128
<212> TYPE: PRT
<213> ORGANISM: Artificial
<220> FEATURE:
<223> OTHER INFORMATION: Nanobody, Nanobody constructs or fragments
      thereof

<400> SEQUENCE: 252

Glu Val Gln Leu Val Glu Ser Gly Gly Gly Leu Val Gln Ala Gly Gly
1               5                   10                  15

Ser Leu Arg Leu Ser Cys Lys Ala Ser Gly Gly Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Thr Arg Ser Gly Val Arg Ser Gly Val Ser Ala Ile Tyr
    50                  55                  60

Gly Asp Ser Val Lys Asp Arg Phe Thr Ile Ser Arg Asp Asn Val Lys
65                  70                  75                  80

Asn Thr Leu Tyr Leu Gln Met Asn Thr Leu Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Tyr Ser Gly Gln Gly Thr Gln Val Thr Val Ser Ser
        115                 120                 125

<210> SEQ ID NO 253
<211> LENGTH: 122
<212> TYPE: PRT
<213> ORGANISM: Artificial
<220> FEATURE:
<223> OTHER INFORMATION: Nanobody, Nanobody constructs or fragments
      thereof

<400> SEQUENCE: 253

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Ser Ile Asn

```
            20                  25                  30
Ala Met Gly Trp Tyr Arg Gln Ala Pro Gly Lys Gln Arg Glu Leu Val
                35                  40                  45
Ala Ser Ile Thr Ser Gly Gly Ser Thr Val Tyr Ala Asp Ser Val Lys
            50                  55                  60
Gly Arg Phe Thr Ile Ser Arg Asp Asn Tyr Asn Thr Val Tyr Leu Gln
65                  70                  75                  80
Met Asn Ser Leu Lys Pro Glu Asp Thr Ala Val Tyr Tyr Cys Asn Ala
                85                  90                  95
Asp Gly Val Pro Glu Trp Gly Lys Val Gln Tyr Pro Asp Thr Tyr Arg
                100                 105                 110
Gly Gln Gly Thr Gln Val Thr Val Ser Ser
                115                 120

<210> SEQ ID NO 254
<211> LENGTH: 360
<212> TYPE: PRT
<213> ORGANISM: Artificial
<220> FEATURE:
<223> OTHER INFORMATION: Nanobody, Nanobody constructs or fragments
      thereof

<400> SEQUENCE: 254

Met Glu Gly Ile Ser Ser Ile Pro Leu Pro Leu Leu Gln Ile Tyr Thr
1               5                   10                  15
Ser Asp Asn Tyr Thr Glu Glu Met Gly Ser Gly Asp Tyr Asp Ser Met
                20                  25                  30
Lys Glu Pro Cys Phe Arg Glu Asn Ala Asn Phe Asn Lys Ile Phe
                35                  40                  45
Leu Pro Thr Ile Tyr Ser Ile Ile Phe Leu Thr Gly Ile Val Gly Asn
            50                  55                  60
Gly Leu Val Ile Leu Val Met Gly Tyr Gln Lys Lys Leu Arg Ser Met
65                  70                  75                  80
Thr Asp Lys Tyr Arg Leu His Leu Ser Val Ala Asp Leu Leu Phe Val
                85                  90                  95
Ile Thr Leu Pro Phe Trp Ala Val Asp Ala Val Ala Asn Trp Tyr Phe
                100                 105                 110
Gly Asn Phe Leu Cys Lys Ala Val His Val Ile Tyr Thr Val Asn Leu
                115                 120                 125
Tyr Ser Ser Val Leu Ile Leu Ala Phe Ile Ser Leu Asp Arg Tyr Leu
            130                 135                 140
Ala Ile Val His Ala Thr Asn Ser Gln Arg Pro Arg Lys Leu Leu Ala
145                 150                 155                 160
Glu Lys Val Val Tyr Val Gly Val Trp Ile Pro Ala Leu Leu Leu Thr
                165                 170                 175
Ile Pro Asp Phe Ile Phe Ala Asn Val Ser Glu Ala Asp Asp Arg Tyr
                180                 185                 190
Ile Cys Asp Arg Phe Tyr Pro Asn Asp Leu Trp Val Val Phe Gln
                195                 200                 205
Phe Gln His Ile Met Val Gly Leu Ile Leu Pro Gly Ile Val Ile Leu
                210                 215                 220
Ser Cys Tyr Cys Ile Ile Ile Ser Lys Leu Ser His Ser Lys Gly His
225                 230                 235                 240
Gln Lys Arg Lys Ala Leu Lys Thr Thr Val Ile Leu Ile Leu Ala Phe
                245                 250                 255
```

```
Phe Ala Cys Trp Leu Pro Tyr Tyr Ile Gly Ile Ser Ile Asp Ser Phe
                260                 265                 270

Ile Leu Leu Glu Ile Ile Lys Gln Gly Cys Glu Phe Glu Asn Thr Val
275                 280                 285

His Lys Trp Ile Ser Ile Thr Glu Ala Leu Ala Phe Phe His Cys Cys
        290                 295                 300

Leu Asn Pro Ile Leu Tyr Ala Phe Leu Gly Ala Lys Phe Lys Thr Ser
305                 310                 315                 320

Ala Gln His Ala Leu Thr Ser Val Ser Arg Gly Ser Ser Leu Lys Ile
                325                 330                 335

Leu Ser Lys Gly Lys Arg Gly Gly His Ser Ser Val Ser Thr Glu Ser
            340                 345                 350

Glu Ser Ser Ser Phe His Ser Ser
            355                 360

<210> SEQ ID NO 255
<211> LENGTH: 347
<212> TYPE: PRT
<213> ORGANISM: Artificial
<220> FEATURE:
<223> OTHER INFORMATION: Nanobody, Nanobody constructs or fragments
      thereof

<400> SEQUENCE: 255

Ile Tyr Thr Ser Asp Asn Tyr Thr Glu Glu Met Gly Ser Gly Asp Tyr
1               5                   10                  15

Asp Ser Ile Lys Glu Pro Cys Phe Arg Glu Glu Asn Ala His Phe Asn
            20                  25                  30

Arg Ile Phe Leu Pro Thr Ile Tyr Ser Ile Ile Phe Leu Thr Gly Ile
        35                  40                  45

Val Gly Asn Gly Leu Val Ile Leu Val Met Gly Tyr Gln Lys Lys Leu
    50                  55                  60

Arg Ser Met Thr Asp Lys Tyr Arg Leu His Leu Ser Val Ala Asp Leu
65                  70                  75                  80

Leu Phe Val Ile Thr Leu Pro Phe Trp Ala Val Asp Ala Val Ala Asn
                85                  90                  95

Trp Tyr Phe Gly Asn Phe Leu Cys Lys Ala Val His Val Ile Tyr Thr
            100                 105                 110

Val Asn Leu Tyr Ser Ser Val Leu Ile Leu Ala Phe Ile Ser Leu Asp
        115                 120                 125

Arg Tyr Leu Ala Ile Val His Ala Thr Asn Ser Gln Lys Pro Arg Lys
130                 135                 140

Leu Leu Ala Glu Lys Val Val Tyr Val Gly Val Trp Ile Pro Ala Leu
145                 150                 155                 160

Leu Leu Thr Ile Pro Asp Phe Ile Phe Ala Ser Val Ser Glu Ala Asp
                165                 170                 175

Asp Arg Tyr Ile Cys Asp Arg Phe Tyr Pro Asn Asp Leu Trp Val Val
            180                 185                 190

Val Phe Gln Phe Gln His Ile Met Val Gly Leu Ile Leu Pro Gly Ile
        195                 200                 205

Val Ile Leu Ser Cys Tyr Cys Ile Ile Ile Ser Lys Leu Ser His Ser
    210                 215                 220

Lys Gly His Gln Lys Arg Lys Ala Leu Lys Thr Thr Val Ile Leu Ile
225                 230                 235                 240

Leu Ala Phe Phe Ala Cys Trp Leu Pro Tyr Tyr Ile Gly Ile Ser Ile
                245                 250                 255
```

```
Asp Ser Phe Ile Leu Leu Glu Ile Ile Lys Gln Gly Cys Glu Phe Glu
            260                 265                 270

Asn Thr Val His Lys Trp Ile Ser Ile Thr Glu Ala Leu Ala Phe Phe
            275                 280                 285

His Cys Cys Leu Asn Pro Ile Leu Tyr Ala Phe Leu Gly Ala Lys Phe
            290                 295                 300

Lys Thr Ser Ala Gln His Ala Leu Thr Ser Val Ser Arg Gly Ser Ser
305                 310                 315                 320

Leu Lys Ile Leu Ser Lys Gly Lys Arg Gly Gly His Ser Ser Val Ser
            325                 330                 335

Thr Glu Ser Glu Ser Ser Ser Phe His Ser Ser
            340                 345

<210> SEQ ID NO 256
<211> LENGTH: 353
<212> TYPE: PRT
<213> ORGANISM: Artificial
<220> FEATURE:
<223> OTHER INFORMATION: Nanobody, Nanobody constructs or fragments
      thereof

<400> SEQUENCE: 256

Met Glu Glu Leu His Ile Tyr Pro Ser Asp Asn Tyr Thr Glu Glu Asp
1               5                   10                  15

Leu Gly Ser Gly Asp Tyr Asp Ser Met Lys Glu Pro Cys Phe Arg Glu
            20                  25                  30

Glu Asn Ala His Phe Asn Arg Ile Phe Leu Pro Thr Val Tyr Ser Ile
            35                  40                  45

Ile Phe Leu Thr Gly Ile Val Gly Asn Gly Leu Val Ile Leu Val Met
        50                  55                  60

Gly Tyr Gln Lys Lys Leu Arg Ser Met Thr Asp Lys Tyr Arg Leu His
65              70                  75                  80

Leu Ser Val Ala Asp Leu Leu Phe Val Leu Thr Leu Pro Phe Trp Ala
                85                  90                  95

Val Glu Ala Val Ala Asn Trp Tyr Phe Gly Asn Phe Leu Cys Lys Ala
            100                 105                 110

Val His Val Ile Tyr Thr Val Asn Leu Tyr Ser Ser Val Leu Ile Leu
            115                 120                 125

Ala Phe Ile Ser Leu Asp Arg Tyr Leu Ala Ile Val His Ala Thr Asn
        130                 135                 140

Ser Gln Arg Pro Arg Lys Leu Leu Ala Glu Lys Val Val Tyr Val Gly
145                 150                 155                 160

Val Trp Ile Pro Ala Leu Leu Leu Thr Ile Pro Asp Phe Ile Phe Ala
                165                 170                 175

Asn Val Arg Glu Ala Asp Asp Arg Tyr Ile Cys Asp Arg Phe Tyr Pro
            180                 185                 190

Asn Asp Ser Trp Leu Val Val Phe Gln Phe Gln His Ile Met Val Gly
            195                 200                 205

Leu Ile Leu Pro Gly Ile Val Ile Leu Ser Cys Tyr Cys Ile Ile Ile
        210                 215                 220

Ser Lys Leu Ser His Ser Lys Gly Tyr Gln Lys Arg Lys Ala Leu Lys
225                 230                 235                 240

Thr Thr Val Ile Leu Ile Leu Ala Phe Ala Cys Trp Leu Pro Tyr
                245                 250                 255

Tyr Ile Gly Ile Ser Ile Asp Ser Phe Ile Leu Leu Glu Ile Ile Lys
```

```
                260                 265                 270
Gln Gly Cys Glu Phe Glu Lys Thr Val His Lys Trp Ile Ser Ile Thr
            275                 280                 285

Glu Ala Leu Ala Phe Phe His Cys Cys Leu Asn Pro Ile Leu Tyr Ala
        290                 295                 300

Phe Leu Gly Ala Lys Phe Lys Thr Ser Ala Gln His Ala Leu Thr Ser
305                 310                 315                 320

Val Ser Arg Gly Ser Ser Leu Lys Ile Leu Ser Lys Gly Lys Arg Gly
                325                 330                 335

Gly His Ser Ser Val Ser Thr Glu Ser Glu Ser Ser Phe His Ser
            340                 345                 350

Ser

<210> SEQ ID NO 257
<211> LENGTH: 353
<212> TYPE: PRT
<213> ORGANISM: Artificial
<220> FEATURE:
<223> OTHER INFORMATION: Nanobody, Nanobody constructs or fragments
      thereof

<400> SEQUENCE: 257

Met Asp Gly Phe Arg Ile Phe Thr Ser Asp Asn Tyr Thr Glu Asp Asp
1               5                   10                  15

Leu Gly Ser Gly Asp Tyr Asp Ser Ile Lys Glu Pro Cys Phe Arg Glu
            20                  25                  30

Glu Asn Ala His Phe Asn Arg Ile Phe Leu Pro Thr Val Tyr Ser Ile
        35                  40                  45

Ile Phe Leu Thr Gly Ile Val Gly Asn Gly Leu Val Ile Leu Val Met
    50                  55                  60

Gly Tyr Gln Lys Lys Leu Arg Ser Met Thr Asp Lys Tyr Arg Leu His
65                  70                  75                  80

Leu Ser Val Ala Asp Leu Leu Phe Val Leu Thr Leu Pro Phe Trp Ala
                85                  90                  95

Val Asp Ala Val Ala Asn Trp Tyr Phe Gly Lys Phe Leu Cys Lys Ala
            100                 105                 110

Val His Val Ile Tyr Thr Val Asn Leu Tyr Ser Ser Val Leu Ile Leu
        115                 120                 125

Ala Phe Ile Ser Leu Asp Arg Tyr Leu Ala Ile Val His Ala Thr Asn
    130                 135                 140

Ser Gln Arg Pro Arg Lys Leu Leu Ala Glu Lys Val Val Tyr Val Gly
145                 150                 155                 160

Val Trp Ile Pro Ala Leu Leu Leu Thr Ile Pro Asp Phe Ile Phe Ala
                165                 170                 175

Asn Val Arg Glu Gly Asp Gly Arg Tyr Ile Cys Asp Arg Phe Tyr Pro
            180                 185                 190

Asn Asp Leu Trp Leu Val Val Phe Gln Phe Gln His Ile Met Val Gly
        195                 200                 205

Leu Ile Leu Pro Gly Ile Val Ile Leu Ser Cys Tyr Cys Ile Ile Ile
    210                 215                 220

Ser Lys Leu Ser His Ser Lys Gly Tyr Gln Lys Arg Lys Ala Leu Lys
225                 230                 235                 240

Thr Thr Val Ile Leu Ile Leu Ala Phe Phe Ala Cys Trp Leu Pro Tyr
                245                 250                 255

Tyr Ile Gly Ile Ser Ile Asp Ser Phe Ile Leu Leu Glu Ile Ile Gln
```

```
                    260                 265                 270
Gln Gly Cys Glu Phe Glu Ser Thr Val His Lys Trp Ile Ser Ile Thr
            275                 280                 285

Glu Ala Leu Ala Phe Phe His Cys Cys Leu Asn Pro Ile Leu Tyr Ala
            290                 295                 300

Phe Leu Gly Ala Lys Phe Lys Thr Ser Ala Gln His Ala Leu Thr Ser
305                 310                 315                 320

Val Ser Arg Gly Ser Ser Leu Lys Ile Leu Ser Lys Gly Lys Arg Gly
            325                 330                 335

Gly His Ser Ser Val Ser Thr Glu Ser Glu Ser Ser Phe His Ser
            340                 345                 350

Ser

<210> SEQ ID NO 258
<211> LENGTH: 358
<212> TYPE: PRT
<213> ORGANISM: Artificial
<220> FEATURE:
<223> OTHER INFORMATION: Nanobody, Nanobody constructs or fragments
      thereof

<400> SEQUENCE: 258

Met Asp Gly Leu Asp Leu Ser Ser Gly Ile Leu Ile Glu Phe Ala Asp
1               5                   10                  15

Asn Gly Ser Glu Glu Ile Gly Ser Ala Asp Tyr Gly Asp Tyr Gly Glu
            20                  25                  30

Pro Cys Phe Gln His Glu Asn Ala Asp Phe Asn Arg Ile Phe Leu Pro
        35                  40                  45

Thr Ile Tyr Ser Ile Ile Phe Leu Thr Gly Ile Ile Gly Asn Gly Leu
    50                  55                  60

Val Ile Ile Val Met Gly Tyr Gln Lys Lys Gln Arg Ser Met Thr Asp
65                  70                  75                  80

Lys Tyr Arg Leu His Leu Ser Val Ala Asp Leu Leu Phe Val Ile Thr
                85                  90                  95

Leu Pro Phe Trp Ser Val Asp Ala Ala Ile Ser Trp Tyr Phe Gly Asn
            100                 105                 110

Val Leu Cys Lys Ala Val His Val Ile Tyr Thr Val Asn Leu Tyr Ser
        115                 120                 125

Ser Val Leu Ile Leu Ala Phe Ile Ser Leu Asp Arg Tyr Leu Ala Ile
    130                 135                 140

Val His Ala Thr Asn Ser Gln Arg Pro Arg Lys Leu Leu Ala Glu Lys
145                 150                 155                 160

Ile Val Tyr Val Gly Val Trp Leu Pro Ala Val Leu Leu Thr Val Pro
                165                 170                 175

Asp Ile Ile Phe Ala Ser Thr Ser Glu Val Glu Gly Arg Tyr Leu Cys
            180                 185                 190

Asp Arg Met Tyr Pro His Asp Asn Trp Leu Ile Ser Phe Arg Phe Gln
        195                 200                 205

His Ile Leu Val Gly Leu Val Leu Pro Gly Leu Ile Ile Leu Thr Cys
    210                 215                 220

Tyr Cys Ile Ile Ile Ser Lys Leu Ser His Ser Lys Gly His Gln Lys
225                 230                 235                 240

Arg Lys Ala Leu Lys Thr Thr Val Ile Leu Ile Leu Thr Phe Phe Ala
                245                 250                 255

Cys Trp Leu Pro Tyr Tyr Ile Gly Ile Ser Ile Asp Thr Phe Ile Leu
```

```
                        260                 265                 270
Leu Gly Val Ile Arg His Arg Cys Ser Leu Asp Thr Ile Val His Lys
            275                 280                 285

Trp Ile Ser Ile Thr Glu Ala Leu Ala Phe Phe His Cys Cys Leu Asn
            290                 295                 300

Pro Ile Leu Tyr Ala Phe Leu Gly Ala Lys Phe Lys Thr Ser Ala Gln
305                 310                 315                 320

Asn Ala Leu Thr Ser Val Ser Arg Gly Ser Ser Leu Lys Ile Leu Ser
                325                 330                 335

Lys Ser Lys Arg Gly Gly His Ser Ser Val Ser Thr Glu Ser Glu Ser
            340                 345                 350

Ser Ser Phe His Ser Ser
            355

<210> SEQ ID NO 259
<211> LENGTH: 339
<212> TYPE: PRT
<213> ORGANISM: Artificial
<220> FEATURE:
<223> OTHER INFORMATION: Nanobody, Nanobody constructs or fragments
      thereof

<400> SEQUENCE: 259

Thr Ser Asp Asn Tyr Thr Glu Glu Leu Gly Ser Gly Asp Tyr Asp Ser
1               5                   10                  15

Ile Lys Glu Pro Cys Phe Arg Glu Glu Asn Ala His Phe Asn Arg Ile
            20                  25                  30

Phe Leu Pro Thr Ile Tyr Ser Ile Phe Leu Thr Gly Ile Val Gly
        35                  40                  45

Asn Gly Leu Val Ile Leu Val Met Gly Tyr Gln Lys Lys Gln Arg Ser
    50                  55                  60

Met Thr Asp Lys Tyr Arg Leu His Leu Ser Val Ala Asp Leu Leu Phe
65                  70                  75                  80

Val Ile Thr Leu Pro Phe Trp Ala Val Asp Ala Val Ala Asn Trp Tyr
                85                  90                  95

Phe Gly Lys Phe Leu Cys Lys Ala Val His Val Ile Tyr Thr Val Asn
            100                 105                 110

Leu Tyr Ser Ser Val Leu Ile Leu Ala Phe Ile Ser Leu Asp Arg Tyr
        115                 120                 125

Leu Ala Ile Val His Ala Thr Asn Ser Gln Lys Pro Arg Lys Leu Leu
    130                 135                 140

Ala Glu Lys Val Val Tyr Val Gly Val Trp Ile Pro Ala Leu Leu Leu
145                 150                 155                 160

Thr Ile Pro Asp Phe Ile Phe Ala Asn Val Arg Glu Ala Glu Gly Arg
                165                 170                 175

Tyr Ile Cys Asp Arg Phe Tyr Pro Ser Asp Leu Trp Val Val Val Phe
            180                 185                 190

Gln Phe Gln His Ile Met Val Gly Leu Ile Leu Pro Gly Ile Val Ile
        195                 200                 205

Leu Ser Cys Tyr Cys Ile Ile Ile Ser Lys Leu Ser His Ser Lys Gly
    210                 215                 220

His Gln Lys Arg Lys Ala Leu Lys Thr Thr Val Ile Leu Ile Leu Ala
225                 230                 235                 240

Phe Phe Ala Cys Trp Leu Pro Tyr Tyr Ile Gly Ile Ser Ile Asp Ser
                245                 250                 255
```

```
Phe Ile Leu Leu Glu Ile Ile Lys Gln Gly Cys Glu Phe Glu Asn Thr
            260                 265                 270

Val His Lys Trp Ile Ser Ile Thr Glu Ala Leu Ala Phe Phe His Cys
        275                 280                 285

Cys Leu Asn Pro Ile Leu Tyr Ala Phe Leu Gly Ala Lys Phe Lys Thr
        290                 295                 300

Ser Ala Gln His Ala Leu Thr Ser Val Ser Arg Gly Ser Ser Leu Lys
305                 310                 315                 320

Ile Leu Ser Lys Gly Lys Arg Gly Gly His Ser Ser Val Ser Thr Glu
                325                 330                 335

Ser Glu Ser

<210> SEQ ID NO 260
<211> LENGTH: 359
<212> TYPE: PRT
<213> ORGANISM: Artificial
<220> FEATURE:
<223> OTHER INFORMATION: Nanobody, Nanobody constructs or fragments
      thereof

<400> SEQUENCE: 260

Met Glu Pro Ile Ser Val Ser Ile Tyr Thr Ser Asp Asn Tyr Ser Glu
1               5                   10                  15

Glu Val Gly Ser Gly Asp Tyr Asp Ser Asn Lys Glu Pro Cys Phe Arg
            20                  25                  30

Asp Glu Asn Val His Phe Asn Arg Ile Phe Leu Pro Thr Ile Tyr Phe
        35                  40                  45

Ile Ile Phe Leu Thr Gly Ile Val Gly Asn Gly Leu Val Ile Leu Val
    50                  55                  60

Met Gly Tyr Gln Lys Lys Leu Arg Ser Met Thr Asp Lys Tyr Arg Leu
65                  70                  75                  80

His Leu Ser Val Ala Asp Leu Leu Phe Val Ile Thr Leu Pro Phe Trp
                85                  90                  95

Ala Val Asp Ala Met Ala Asp Trp Tyr Phe Gly Lys Phe Leu Cys Lys
            100                 105                 110

Ala Val His Ile Ile Tyr Thr Val Asn Leu Tyr Ser Ser Val Leu Ile
        115                 120                 125

Leu Ala Phe Ile Ser Leu Asp Arg Tyr Leu Ala Ile Val His Ala Thr
    130                 135                 140

Asn Ser Gln Arg Pro Arg Lys Leu Leu Ala Glu Lys Ala Val Tyr Val
145                 150                 155                 160

Gly Val Trp Ile Pro Ala Leu Leu Leu Thr Ile Pro Asp Phe Ile Phe
                165                 170                 175

Ala Asp Val Ser Gln Gly Asp Ile Ser Gln Gly Asp Ala Arg Tyr Ile
            180                 185                 190

Cys Asp Arg Leu Tyr Pro Asp Ser Leu Trp Met Val Val Phe Gln Phe
        195                 200                 205

Gln His Ile Met Val Gly Leu Ile Leu Pro Gly Ile Val Ile Leu Ser
    210                 215                 220

Cys Tyr Cys Ile Ile Ser Lys Leu Ser His Ser Lys Gly His Gln
225                 230                 235                 240

Lys Arg Lys Ala Leu Lys Thr Thr Val Ile Leu Ile Leu Ala Phe Phe
                245                 250                 255

Ala Cys Trp Leu Pro Tyr Tyr Val Gly Ile Ser Ile Asp Ser Phe Ile
            260                 265                 270
```

```
Leu Leu Gly Val Ile Lys Gln Gly Cys Asp Phe Glu Ser Ile Val His
            275                 280                 285

Lys Trp Ile Ser Ile Thr Glu Ala Leu Ala Phe Phe His Cys Cys Leu
        290                 295                 300

Asn Pro Ile Leu Tyr Ala Phe Leu Gly Ala Lys Phe Lys Ser Ser Ala
305                 310                 315                 320

Gln His Ala Leu Asn Ser Met Ser Arg Gly Ser Ser Leu Lys Ile Leu
                325                 330                 335

Ser Lys Gly Lys Arg Gly Gly His Ser Ser Val Ser Thr Glu Ser Glu
            340                 345                 350

Ser Ser Ser Phe His Ser Ser
            355

<210> SEQ ID NO 261
<211> LENGTH: 254
<212> TYPE: PRT
<213> ORGANISM: Artificial
<220> FEATURE:
<223> OTHER INFORMATION: Nanobody, Nanobody constructs or fragments
      thereof

<400> SEQUENCE: 261

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Lys Ser Ser Gly Asp Ser Thr Arg Tyr Ala Gly Ser Val
    50                  55                  60

Lys Gly Arg Phe Thr Ile Ser Arg Asp Asn Ala Lys Asn Met Leu Tyr
65                  70                  75                  80

Leu Gln Met Tyr Ser Leu Lys Pro Glu Asp Thr Ala Val Tyr Tyr Cys
                85                  90                  95

Ala Lys Ser Arg Val Ser Arg Thr Gly Leu Tyr Thr Tyr Asp Asn Arg
            100                 105                 110

Gly Gln Gly Thr Gln Val Thr Val Ser Ser Gly Gly Gly Ser Gly
        115                 120                 125

Gly Gly Gly Ser Glu Val Gln Leu Val Glu Ser Gly Gly Gly Leu Val
    130                 135                 140

Gln Thr Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Gly Ile Lys Ser Ser Gly Asp Ser Thr Arg Tyr
            180                 185                 190

Ala Gly Ser Val Lys Gly Arg Phe Thr Ile Ser Arg Asp Asn Ala Lys
        195                 200                 205

Asn Met Leu Tyr Leu Gln Met Tyr Ser Leu Lys Pro Glu Asp Thr Ala
    210                 215                 220

Val Tyr Tyr Cys Ala Lys Ser Arg Val Ser Arg Thr Gly Leu Tyr Thr
225                 230                 235                 240

Tyr Asp Asn Arg Gly Gln Gly Thr Gln Val Thr Val Ser Ser
                245                 250

<210> SEQ ID NO 262
```

```
<211> LENGTH: 276
<212> TYPE: PRT
<213> ORGANISM: Artificial
<220> FEATURE:
<223> OTHER INFORMATION: Nanobody, Nanobody constructs or fragments
      thereof

<400> SEQUENCE: 262
```

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Thr Arg Ser Gly Val Arg Ser Gly Val Ser Ala Ile Tyr
    50                  55                  60

Gly Asp Ser Val Lys Asp Arg Phe Thr Ile Ser Arg Asp Asn Ala Lys
65                  70                  75                  80

Asn Thr Leu Tyr Leu Gln Met Asn Ser Leu Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Tyr Ser Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Ser Glu Val Gln Leu Met Glu Ser Gly Gly Gly Leu Val
145                 150                 155                 160

Gln Ala Gly Gly Ser Leu Arg Leu Ser Cys Ala Ala Ser Gly Arg Thr
                165                 170                 175

Phe Asn Asn Tyr Ala Met Gly Trp Phe Arg Arg Ala Pro Gly Lys Glu
            180                 185                 190

Arg Glu Phe Val Ala Ala Ile Thr Arg Ser Gly Val Arg Ser Gly Val
        195                 200                 205

Ser Ala Ile Tyr Gly Asp Ser Val Lys Asp Arg Phe Thr Ile Ser Arg
    210                 215                 220

Asp Asn Ala Lys Asn Thr Leu Tyr Leu Gln Met Asn Ser Leu Lys Pro
225                 230                 235                 240

Glu Asp Thr Ala Val Tyr Thr Cys Ala Ala Ser Ala Ile Gly Ser Gly
                245                 250                 255

Ala Leu Arg Arg Phe Glu Tyr Asp Tyr Ser Gly Gln Gly Thr Gln Val
            260                 265                 270

Thr Val Ser Ser
        275

```
<210> SEQ ID NO 263
<211> LENGTH: 265
<212> TYPE: PRT
<213> ORGANISM: Artificial
<220> FEATURE:
<223> OTHER INFORMATION: Nanobody, Nanobody constructs or fragments
      thereof

<400> SEQUENCE: 263
```

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
             35                  40                  45

Ser Gly Ile Lys Ser Ser Gly Asp Ser Thr Arg Tyr Ala Gly Ser Val
         50                  55                  60

Lys Gly Arg Phe Thr Ile Ser Arg Asp Asn Ala Lys Asn Met Leu Tyr
 65                  70                  75                  80

Leu Gln Met Tyr Ser Leu Lys Pro Glu Asp Thr Ala Val Tyr Tyr Cys
                 85                  90                  95

Ala Lys Ser Arg Val Ser Arg Thr Gly Leu Tyr Thr Tyr Asp Asn Arg
             100                 105                 110

Gly Gln Gly Thr Gln Val Thr Val Ser Gly Gly Gly Gly Ser Gly
             115                 120                 125

Gly Gly Gly Ser Gly Gly Gly Ser Glu Val Gln Leu Met Glu Ser
             130                 135                 140

Gly Gly Gly Leu Val Gln Ala Gly Gly Ser Leu Arg Leu Ser Cys Ala
145                 150                 155                 160

Ala Ser Gly Arg Thr Phe Asn Asn Tyr Ala Met Gly Trp Phe Arg Arg
             165                 170                 175

Ala Pro Gly Lys Glu Arg Glu Phe Val Ala Ala Ile Thr Arg Ser Gly
             180                 185                 190

Val Arg Ser Gly Val Ser Ala Ile Tyr Gly Asp Ser Val Lys Asp Arg
             195                 200                 205

Phe Thr Ile Ser Arg Asp Asn Ala Lys Asn Thr Leu Tyr Leu Gln Met
210                 215                 220

Asn Ser Leu Lys Pro Glu Asp Thr Ala Val Tyr Thr Cys Ala Ala Ser
225                 230                 235                 240

Ala Ile Gly Ser Gly Ala Leu Arg Arg Phe Glu Tyr Asp Tyr Ser Gly
             245                 250                 255

Gln Gly Thr Gln Val Thr Val Ser Ser
             260                 265

<210> SEQ ID NO 264
<211> LENGTH: 270
<212> TYPE: PRT
<213> ORGANISM: Artificial
<220> FEATURE:
<223> OTHER INFORMATION: Nanobody, Nanobody constructs or fragments
      thereof

<400> SEQUENCE: 264

Glu Val Gln Leu Val Glu Ser Gly Gly Gly Leu Val Gln Thr Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
             35                  40                  45

Ser Gly Ile Lys Ser Ser Gly Asp Ser Thr Arg Tyr Ala Gly Ser Val
         50                  55                  60

Lys Gly Arg Phe Thr Ile Ser Arg Asp Asn Ala Lys Asn Met Leu Tyr
 65                  70                  75                  80

Leu Gln Met Tyr Ser Leu Lys Pro Glu Asp Thr Ala Val Tyr Tyr Cys
                 85                  90                  95

Ala Lys Ser Arg Val Ser Arg Thr Gly Leu Tyr Thr Tyr Asp Asn Arg
             100                 105                 110

Gly Gln Gly Thr Gln Val Thr Val Ser Ser Gly Gly Gly Gly Ser Gly
```

```
                115                 120                 125
Gly Gly Gly Ser Gly Gly Gly Ser Gly Gly Gly Ser Glu Val
            130                 135                 140

Gln Leu Met Glu Ser Gly Gly Leu Val Gln Ala Gly Gly Ser Leu
145                 150                 155                 160

Arg Leu Ser Cys Ala Ala Ser Gly Arg Thr Phe Asn Asn Tyr Ala Met
                165                 170                 175

Gly Trp Phe Arg Arg Ala Pro Gly Lys Glu Arg Glu Phe Val Ala Ala
                180                 185                 190

Ile Thr Arg Ser Gly Val Arg Ser Gly Val Ser Ala Ile Tyr Gly Asp
                195                 200                 205

Ser Val Lys Asp Arg Phe Thr Ile Ser Arg Asp Asn Ala Lys Asn Thr
            210                 215                 220

Leu Tyr Leu Gln Met Asn Ser Leu Lys Pro Glu Asp Thr Ala Val Tyr
225                 230                 235                 240

Thr Cys Ala Ala Ser Ala Ile Gly Ser Gly Ala Leu Arg Arg Phe Glu
                245                 250                 255

Tyr Asp Tyr Ser Gly Gln Gly Thr Gln Val Thr Val Ser Ser
            260                 265                 270

<210> SEQ ID NO 265
<211> LENGTH: 269
<212> TYPE: PRT
<213> ORGANISM: Artificial
<220> FEATURE:
<223> OTHER INFORMATION: Nanobody, Nanobody constructs or fragments
      thereof

<400> SEQUENCE: 265

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Lys Ser Ser Gly Asp Ser Thr Arg Tyr Ala Gly Ser Val
    50                  55                  60

Lys Gly Arg Phe Thr Ile Ser Arg Asp Asn Ala Lys Asn Met Leu Tyr
65                  70                  75                  80

Leu Gln Met Tyr Ser Leu Lys Pro Glu Asp Thr Ala Val Tyr Tyr Cys
                85                  90                  95

Ala Lys Ser Arg Val Ser Arg Thr Gly Leu Tyr Thr Tyr Asp Asn Arg
            100                 105                 110

Gly Gln Gly Thr Gln Val Thr Val Ser Ser Gly Gly Gly Gly Ser Gly
        115                 120                 125

Gly Gly Gly Ser Gly Gly Gly Ser Gly Gly Gly Ser Glu Val
    130                 135                 140

Gln Leu Met Glu Ser Gly Gly Leu Val Gln Ala Gly Gly Ser Leu
145                 150                 155                 160

Arg Leu Ala Cys Ala Ala Ser Gly Phe Thr Phe Glu Asp Tyr Ala Ile
                165                 170                 175

Gly Trp Phe Arg Lys Ala Pro Gly Lys Glu Arg Glu Gly Val Ser Cys
                180                 185                 190

Ile Ser Gly Ser Asp Gly Ser Thr Thr Tyr Ala Asp Ser Val Lys Gly
            195                 200                 205
```

Arg Phe Thr Ile Ser Thr Asp Asn Ala Lys Asn Thr Val Tyr Leu Glu
    210                 215                 220

Met Asn Ser Leu Lys Pro Glu Asp Thr Ala Val Tyr Tyr Cys Ala Gln
225                 230                 235                 240

Gln Tyr Gly Val Gly Gly Arg Val Val Cys Pro Gly Pro Tyr Glu Tyr
            245                 250                 255

Asp Val Trp Gly Gln Gly Thr Gln Val Thr Val Ser Ser
            260                 265

<210> SEQ ID NO 266
<211> LENGTH: 264
<212> TYPE: PRT
<213> ORGANISM: Artificial
<220> FEATURE:
<223> OTHER INFORMATION: Nanobody, Nanobody constructs or fragments
      thereof

<400> SEQUENCE: 266

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Lys Ser Ser Gly Asp Ser Thr Arg Tyr Ala Gly Ser Val
50                  55                  60

Lys Gly Arg Phe Thr Ile Ser Arg Asp Asn Ala Lys Asn Met Leu Tyr
65                  70                  75                  80

Leu Gln Met Tyr Ser Leu Lys Pro Glu Asp Thr Ala Val Tyr Tyr Cys
                85                  90                  95

Ala Lys Ser Arg Val Ser Arg Thr Gly Leu Tyr Thr Tyr Asp Asn Arg
            100                 105                 110

Gly Gln Gly Thr Gln Val Thr Val Ser Ser Gly Gly Gly Gly Ser Gly
        115                 120                 125

Gly Gly Gly Ser Gly Gly Gly Ser Gly Gly Gly Gly Ser Glu Val
    130                 135                 140

Gln Leu Val Glu Ser Gly Gly Gly Phe Val Gln Ala Gly Gly Ser Leu
145                 150                 155                 160

Arg Leu Ser Cys Glu Thr Ser Gly Arg Pro Leu Leu Gly Tyr Thr Ile
                165                 170                 175

Ala Trp Phe Arg Gln Val Pro Gly Lys Glu Arg Glu Phe Val Ala Tyr
            180                 185                 190

His Arg Trp Ser Asp Gly Ala Asn Leu Tyr Ala Asp Ser Val Lys Gly
        195                 200                 205

Arg Phe Thr Ile Ser Gly His Asn Ala Lys Asn Thr Val Ser Leu Gln
    210                 215                 220

Met Asn Ser Leu Lys Pro Glu Asp Thr Ala Val Tyr Tyr Cys Ala Ala
225                 230                 235                 240

Ala Arg Met Thr Thr Ser Asn Asp Lys Glu Tyr Leu Tyr Trp Gly Gln
                245                 250                 255

Gly Thr Gln Val Thr Val Ser Ser
            260

<210> SEQ ID NO 267
<211> LENGTH: 93
<212> TYPE: PRT
<213> ORGANISM: Artificial

```
<220> FEATURE:
<223> OTHER INFORMATION: Nanobody, Nanobody constructs or fragments
      thereof

<400> SEQUENCE: 267

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90
```

AMINO ACID SEQUENCES DIRECTED AGAINST CXCR4 AND OTHER GPCRS AND COMPOUNDS COMPRISING THE SAME

RELATED APPLICATIONS

This application is a national stage filing under 35 U.S.C. §371 of international application PCT/EP2009/056026, filed May 18, 2009, which was published under PCT Article 21(2) in English, and claims the benefit under 35 U.S.C. §119(e) of U.S. provisional application Ser. No. 61/053,847, filed May 16, 2008, and U.S. provisional application Ser. No. 61/102,142, filed Oct. 2, 2008, the disclosures of which are incorporated by reference herein in their entireties.

The present invention relates to amino acid sequences that are directed against (as defined herein) G-protein coupled receptors (GPCRs) and in particular to CXCR4 and CXCR7, as well as to compounds or constructs, and in particular proteins and polypeptides, that comprise or essentially consist of one or more such amino acid sequences (also referred to herein as "amino acid sequences of the invention", "compounds of the invention", and "polypeptides of the invention", respectively). Furthermore, the invention provides a new method of making amino acid sequences that are directed against transmembrane protein, and in particular for multiple spanning transmembrane proteins for which the native conformation cannot be reproduced in other "in vitro" system (e.g. GPCRs in general).

The invention also relates to nucleic acids encoding such amino acid sequences and polypeptides (also referred to herein as "nucleic acids of the invention" or "nucleotide sequences of the invention"); to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, nucleic acids and/or host cells; and to uses of such amino acid sequences or polypeptides, nucleic acids, host cells and/or compositions, in particular for prophylactic, therapeutic or diagnostic purposes, such as the prophylactic, therapeutic or diagnostic purposes mentioned herein.

Other aspects, embodiments, advantages and applications of the invention will become clear from the further description herein.

GPCRs are a well-known class of receptors. Reference is for example made to the following reviews: Surgand et al., Proteins 62:509-538 (2006); Vassilatis et al., Proc Natl Acad Sci USA 100:4903-4908 (2003) and Pierce et al., Nat Rev Mol Cell Biol 3:639-650 (2002); as well as to for example: George et al., Nat Rev Drug Discov 1:808-820 (2002); Kenakin, Trends Pharmacol Sci 25:186-192 (2002); Rios et al., Pharmacol Ther 92:71-87 (2001); Jacoby et al., ChemMedChem 2006, 1, 760-782; and Schlyer and Horuk, Drug Discovery Today, 11, 11/12. June 2006, 481; and also for example to Rosenkilde, Oncogene (2001), 20, 1582-1593 and Sadee et al., AAPS PharmSci 2001; 3; 1-16; as well as to the further references cited therein.

G-protein-coupled receptors (GPCRs) are the largest class of cell-surface receptors (more than 1000 genes are present in the human genome). They can be activated by a diverse array of stimuli, e.g. hormones, peptides, amino acids, photons of light, and these receptors play a large role in the central nervous system and in the periphery. GPCRs are proteins with 7 transmembrane domains with highly conserved domains.

As half of all known drugs work through G-protein coupled receptors, it is commercially very attractive to select Nanobodies against this protein family. It was estimated that in the year 2000 half of all modern drugs and almost one-quarter of the top 200 best-selling drugs are directed against or modulate GPCR targets (approximately 30 in total). However, due to their architecture of 7 membrane-spanning helices and their strong tendency to aggregate, it's a very challenging target class.

GPCRs can be grouped on the basis of sequence homology into several distinct families. Although all GPCRs have a similar architecture of seven membrane-spanning $\alpha$-helices, the different families within this receptor class show no sequence homology to one another, thus suggesting that the similarity of their transmembrane domain structure might define common functional requirements. Depending on the size of the extracellular domain three families are discriminated.

Members of Family 1 (also called family A or rhodopsin-like family) only have small extracellular loops and the interaction of the ligands occurs with residues within the transmembrane cleft. This is by far the largest group (>90% of the GPCRs) and contains receptors for odorants, small molecules such as catecholamines and amines, (neuro)peptides and glycoprotein hormones. Rhodopsin, which belongs to this family, is the only GPCR for which the structure has been solved.

Family 2 or family B GPCRs are characterized by a relatively long amino terminal extracellular domain involved in ligand-binding. Little is known about the orientation of the transmembrane domains, but it is probably quite different from that of rhodopsin. Ligands for these GPCRs are hormones, such as glucagon, gonadotropin-releasing hormone and parathyroid hormone.

Family 3 members also have a large extracellular domain, which functions like a "Venus fly trap" since it can open and close with the agonist bound inside. Family members are the metabotropic glutamate, the Ca2+-sensing and the $\gamma$-aminobutyric acid (GABA)B receptors.

Traditionally small molecules are used for development of drugs directed against GPCRs, not only because pharmaceutical companies have historical reasons to work with these, but more importantly because of the structural constraints of Family 1 GPCRs, which have the ligand binding site within the transmembrane cleft (Nat Rev Drug Discov. (2004) The state of GPCR research in 2004. Nature Reviews Drug Discovery GPCR Questionnaire Participants 3(7):575, 577-626). For this reason it proved to be difficult or impossible to generate monoclonal antibodies against this target class. The amino acid sequences of the invention (and in particular Nanobodies of the invention) can solve this particular problem by means of their intrinsic property of binding via extended CDR loops into cavities (as further described herein).

Some non-limiting examples of therapeutically relevant GPCRs are for example the following, which are all targets of known drugs that have either been approved or are in clinical development. The text between brackets indicates the desired action of an amino acid sequence, a Nanobody or a polypeptide of the invention (i.e. as agonist or antagonist):

Class A GPCRs
  Muscarinic M1 receptor
  Adrenoceptor
  Histamine receptor
  5-HT GPCR
  Cannabinoid receptor
  Class A hormone protein GPCR
  Chemokine
  Galanin Melanocortin
Neuropeptide Y receptor
Neurotensin receptor
Opioid
Somatostatin
Vasopressin like receptor
Prostanoid receptor
Class B GPCRs
ACTH releasing factor receptor (modulator);
Class C GPCRs
GABA B receptor (agonist);
Metabotropic glutamate receptor
Some other non-limiting examples of therapeutically relevant GPCRs are mentioned in Table C. A more extensive list of human GPCRs is given in Table D.

CXCR4, (a CXC chemokine Receptor), also called fusin, is an alpha-chemokine receptor specific for stromal-derived-factor-1 (SDF-1 also called CXCL12), a molecule endowed with potent chemotactic activity for lymphocytes.

This receptor is one of several chemokine receptors that HIV isolates can use to infect CD4+ T cells. Traditionally, HIV isolates that use CXCR4 are known as T-cell tropic isolates. Typically these viruses are found late in infection. It is unclear whether the emergence of CXCR4-using HIV is a consequence or a cause of immunodeficiency.

CXCR4's ligand SDF-1 is known to be important in hematopoietic stem cell homing to the bone marrow and in hematopoietic stem cell quiescence.

Unusually for chemokines, SDF-1 and CXCR4 are a relatively "monogamous" ligand-receptor pair (other chemokines tend to use several different chemokine receptors in a fairly "promiscuous" manner).

Because the interaction between SDF-1 and CXCR4 plays an important role in holding hematopoietic stem cells in the bone marrow, drugs that block the CXCR4 receptor appear to be capable of "mobilizing" hematopoietic stem cells into the bloodstream as peripheral blood stem cells. Peripheral blood stem cell mobilization is very important in hematopoietic stem cell transplantation (as a recent alternative to transplantation of surgically-harvested bone marrow) and is currently performed using drugs such as G-CSF. G-CSF is a growth factor for neutrophils (a common type of white blood cells), and may act by increasing the activity of neutrophil-derived proteases such as neutrophil elastase in the bone marrow leading to proteolytic degradation of SDF-1.

The polypeptides and compositions of the present invention can generally be used to modulate, and in particular inhibit and/or prevent, GPCRs mediated signalling and/or to modulate the biological pathways in which GPCRs are involved, and/or to modulate the biological mechanisms, responses and effects associated with such signalling or these pathways.

As such, the polypeptides and compositions of the present invention can be used for the prevention and treatment (as defined herein) of GPCR-related diseases and disorders. Generally, "GPCR-related diseases and disorders" can be defined as diseases and disorders that can be prevented and/or treated, respectively, by suitably administering to a subject in need thereof (i.e. having the disease or disorder or at least one symptom thereof and/or at risk of attracting or developing the disease or disorder) of either a polypeptide or composition of the invention (and in particular, of a pharmaceutically active amount thereof) and/or of a known active principle active against GPCRs or a biological pathway or mechanism in which GPCRs is involved (and in particular, of a pharmaceutically active amount thereof). Examples of such GPCR-related diseases and disorders will be clear to the skilled person based on the disclosure herein.

Thus, without being limited thereto, the amino acid sequences and polypeptides of the invention can for example be used to prevent and/or to treat all diseases and disorders that are currently being prevented or treated with active principles that can modulate GPCRs-mediated signalling, such as those mentioned in the prior art cited above. It is also envisaged that the polypeptides of the invention can be used to prevent and/or to treat all diseases and disorders for which treatment with such active principles is currently being developed, has been proposed, or will be proposed or developed in future. In addition, it is envisaged that, because of their favourable properties as further described herein, the polypeptides of the present invention may be used for the prevention and treatment of other diseases and disorders than those for which these known active principles are being used or will be proposed or developed; and/or that the polypeptides of the present invention may provide new methods and regimens for treating the diseases and disorders described herein.

Other applications and uses of the amino acid sequences and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of GPCR-related diseases and disorders and of the further diseases and disorders mentioned herein; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment of GPCR-related diseases and disorders and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide amino acid sequences that are directed against (as defined herein) GPCRs, in particular against GPCRs from a warm-blooded animal, more in particular against GPCRs from a mammal, and especially against human GPCRs; and to provide proteins and polypeptides comprising or essentially consisting of at least one such amino acid sequence.

In particular, it is a specific object of the present invention to provide such amino acid sequences and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such amino acid sequences and such proteins and/or polypeptides that can be used for the prevention, treatment, alleviation and/or diagnosis of one or more diseases, disorders or conditions associated with GPCRs and/or mediated by GPCRs (such as the diseases, disorders and conditions mentioned herein) in a warm-blooded animal, in particular in a mammal, and more in particular in a human being.

It is also a specific object of the invention to provide such amino acid sequences and such proteins and/or polypeptides that can be used in the preparation of pharmaceutical or veterinary compositions for the prevention and/or treatment of one or more diseases, disorders or conditions associated with and/or mediated by GPCRs (such as the diseases, disorders and conditions mentioned herein) in a warm-blooded animal, in particular in a mammal, and more in particular in a human being.

In the invention, generally, these objects are achieved by the use of the amino acid sequences, proteins, polypeptides and compositions that are described herein.

In general, the invention provides amino acid sequences that are directed against (as defined herein) and/or can specifically bind (as defined herein) to GPCRs; as well as compounds and constructs, and in particular proteins and polypeptides, that comprise at least one such amino acid sequence.

More in particular, the invention provides amino acid sequences can bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; as well as compounds and constructs, and in particular proteins and polypeptides, that comprise at least one such amino acid sequence.

In particular, amino acid sequences and polypeptides of the invention are preferably such that they:

bind to GPCRs with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to GPCRs with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to GPCRs with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a monovalent amino acid sequence of the invention (or a polypeptide that contains only one amino acid sequence of the invention) is preferably such that it will bind to GPCRs with an affinity less than 500 nM, preferably less than 200 nM, more preferably less than 10 nM, such as less than 500 pM.

Some preferred IC50 values for binding of the amino acid sequences or polypeptides of the invention to GPCRs will become clear from the further description and examples herein.

For binding to GPCRs, an amino acid sequence of the invention will usually contain within its amino acid sequence one or more amino acid residues or one or more stretches of amino acid residues (i.e. with each "stretch" comprising two or amino acid residues that are adjacent to each other or in close proximity to each other, i.e. in the primary or tertiary structure of the amino acid sequence) via which the amino acid sequence of the invention can bind to GPCRs, which amino acid residues or stretches of amino acid residues thus form the "site" for binding to GPCRs (also referred to herein as the "antigen binding site").

The amino acid sequences provided by the invention are preferably in essentially isolated form (as defined herein), or form part of a protein or polypeptide of the invention (as defined herein), which may comprise or essentially consist of one or more amino acid sequences of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than GPCRs), so as to provide a monovalent, multivalent or multispecific polypeptide of the invention, respectively, all as described herein. Such a protein or polypeptide may also be in essentially isolated form (as defined herein).

The amino acid sequences and polypeptides of the invention as such preferably essentially consist of a single amino acid chain that is not linked via disulphide bridges to any other amino acid sequence or chain (but that may or may not contain one or more intramolecular disulphide bridges. For example, it is known that Nanobodies—as described herein—may sometimes contain a disulphide bridge between CDR3 and CDR1 or FR2). However, it should be noted that one or more amino acid sequences of the invention may be linked to each other and/or to other amino acid sequences (e.g. via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat. Biotechnol. 2005 September; 23(9):1126-36).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, in essentially isolated form (as defined herein).

It will also be clear to the skilled person that for pharmaceutical use, the amino acid sequences of the invention (as well as compounds, constructs and polypeptides comprising the same) are preferably directed against human GPCRs; whereas for veterinary purposes, the amino acid sequences and polypeptides of the invention are preferably directed against GPCRs from the species to be treated, or at least cross-reactive with GPCRs from the species to be treated.

Furthermore, an amino acid sequence of the invention may optionally, and in addition to the at least one binding site for binding against GPCRs, contain one or more further binding sites for binding against other antigens, proteins or targets. The efficacy of the amino acid sequences and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include the expression of the receptors in *Xenopus* oocytes, after which the coupling of many GPCRs to ion channels allows the activation or inhibition of these GPCRs to be monitored in oocytes via voltage clamping techniques. Heterologous GPCRs can be functionally expressed in the oocyte by injecting exogenous, GPCR-encoding mRNA into the oocyte and then allowing the oocyte's endogenous cellular machinery to translate and insert the receptors into the plasma membrane (see, e.g., Houamed et al., Science 252:1318-21, 1991; Dahmen et al., J. Neurochem. 58:1176-79, 1992.) Following functional expression of receptors, the ability of ligands to induce transmembrane conductance changes can be observed via a two-electrode voltage clamp system (Dahmen et al., supra), which can detect either a depolarization or hyperpolarization of the membrane potential.

Other techniques for screening GPCRs will be clear to the skilled person, for example from the handbooks, reviews and prior art cited herein. These include for example the radioligand binding assays, as for example used in Lundstrom et al., J Struct Funct Genomics. 2006 Nov. 22; [Epub ahead of print] and as described in Andre' et al., Protein Sci 5:1115 (2006); Hassaine et al., (2006) Prot Purif Expr 45:343; Nicholson et al. J Pharmacol Exp Ther. 2006 May; 317(2):771-7. [Epub 2006 Jan. 25]. and Vilardaga et al., J Biol. Chem. 2001 Sep. 7; 276(36):33435-43. Epub 2001 May 31, for example using membrane preparations that can be made as described in Hovius et al., (1998) J Neurochem 70:824. Some HTS techniques for screening GPCRs are mentioned in Table 4 of the review by Jacoby et al.

Also, according to the invention, amino acid sequences and polypeptides that are directed against GPCRs from a first species of warm-blooded animal may or may not show cross-reactivity with GPCRs from one or more other species of warm-blooded animal. For example, amino acid sequences and polypeptides directed against human GPCRs may or may not show cross reactivity with GPCRs from one or more other species of primates (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) and/or with GPCRs from one or more species of animals that are often used in animal models for diseases (for example mouse, rat, rabbit, pig or dog), and in particular in animal models for diseases and disorders associated with GPCRs (such as the species and animal models mentioned herein). In this respect, it will be clear to the skilled person that such cross-reactivity, when present, may have advantages from a drug development point of view, since it allows the amino acid sequences and polypeptides against human GPCRs to be tested in such disease models.

More generally, amino acid sequences and polypeptides of the invention that are cross-reactive with GPCRs from multiple species of mammal will usually be advantageous for use in veterinary applications, since it will allow the same amino acid sequence or polypeptide to be used across multiple species. Thus, it is also encompassed within the scope of the invention that amino acid sequences and polypeptides directed against GPCRs from one species of animal (such as amino acid sequences and polypeptides against human GPCRs) can be used in the treatment of another species of animal, as long as the use of the amino acid sequences and/or polypeptides provide the desired effects in the species to be treated.

The present invention is in its broadest sense also not particularly limited to or defined by a specific antigenic determinant, epitope, part, domain, subunit or confirmation (where applicable) of GPCRs against which the amino acid sequences and polypeptides of the invention are directed. For example, amino acid sequences of the invention may be raised by suitably immunizing a mammal (such as a Camelid) with GPCR that has been expressed in a suitable expression system or that has been isolated from a suitable cell or cell fraction. In particular, amino acid sequences of the invention may be raised against GPCRs (or suitable parts or fragments thereof) that have been refolded (for example using the techniques described in the review by Kiefer, Biochim. Biophys. Acta, 1610 (2003), 57-62), and amino acid sequences, Nanobodies and polypeptides that are directed against and/or that have been raised against a refolded GPCR form a further aspect of the invention.

The amino acid sequences and polypeptides of the invention may generally be directed against any desired GPCR, and may in particular be directed against a GPCR that has at least one extracellular loop or domain. Examples of such GPCRs will be clear to the skilled person based on the prior art cited herein According to a specific aspect of the invention, an amino acid sequence or polypeptide of the invention may be directed against (as defined herein) a GPCR that is expressed on the surface of a cell and/or against at least one extracellular region, domain, loop or other extracellular epitope of a GPCR. For example, such amino acid sequences may be raised by suitably immunizing a mammal (such as a Camelid) with a cell or cell fraction that has a GPCR or its surface.

In particular, according to this aspect, an amino acid sequence or polypeptide of the invention is directed against (as defined herein) at least one extracellular region, domain, loop or other extracellular epitope of a GPCR, e.g. human CXCR4 and/or human CXCR7, and is preferably further such that said amino acid sequence or polypeptide of the invention is capable of modulating (as defined herein) said GPCR, e.g. human CXCR4 and/or human CXCR7. More in particular, according to this aspect, an amino acid sequence or polypeptide of the invention is directed against (as defined herein) at least one extracellular region, domain, loop or other extracellular epitope of a GPCR, e.g. human CXCR4 and/or human CXCR7; and is preferably further such that said amino acid sequence or polypeptide of the invention is capable of (fully or partially) blocking said GPCR, e.g. human CXCR4 and/or human CXCR7.

According to this aspect of the invention, the amino acid sequence or polypeptide of the invention may be directed against any suitable extracellular part, region, domain, loop or other extracellular epitope of a GPCR, e.g. human CXCR4 and/or human CXCR7, but is preferably directed against one of the extracellular parts of the transmembrane domains or more preferably against one of the extracellular loops that link the transmembrane domains.

The amino acid sequence of such suitable extracellular parts, regions, domains, loops or epitopes may be derived by Kyte-Doolittle analysis of the amino acid sequence of the pertinent GPCR, e.g. human CXCR4 and/or human CXCR7; by aligning GPCRs belonging to the same (sub)families and identifying the various transmembrane domains and extracellular parts, regions, domain or loops; by TMAP-analysis; or by any suitable combination thereof. The invention also relates to amino acid sequences and (as further defined herein) that are directed against and/or have been raised against such extracellular parts, regions, domains, loops or epitopes (and/or that are directed against and/or have been raised against suitable parts or fragments of such extracellular parts, regions, domains, loops or epitopes and/or against synthetic or semi-synthetic peptides that are derived from or based on such extracellular parts, regions, domains, loops or epitopes).

In particular, amino acid sequences and polypeptides of the invention are preferably such that they:

bind to an extracellular part, region, domain, loop or other extracellular epitope of a GPCR (as described herein) or against a peptide derived therefrom with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to an extracellular part, region, domain, loop or other extracellular epitope of a GPCR (as described herein) or against a peptide derived therefrom with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to an extracellular part, region, domain, loop or other extracellular epitope of a GPCR (as described herein) or against a peptide derived therefrom with a $k_{off}$ rate between $1 s^{-1}$ ($t_{1/2}$=0.69 s) and $10^{-6} s^{-1}$ (providing a near irreversible complex with a $t_{1/2}$ of multiple days), preferably between $10^{-2} s^{-1}$ and $10^{-6} s^{-1}$, more preferably between $10^{-3} s^{-1}$ and $10^{-6} s^{-1}$, such as between $10^{-4} s^{-1}$ and $10^{-6} s^{-1}$.

Preferably, a monovalent amino acid sequence of the invention (or a polypeptide that contains only one amino acid sequence of the invention) is preferably such that it will bind to bind to an extracellular part, region, domain, loop or other extracellular epitope of a GPCR (as described herein) with an affinity less than 500 nM, preferably less than 200 nM, more preferably less than 10 nM, such as less than 500 pM.

Also, according to this aspect, any multivalent or multispecific (as defined herein) polypeptides of the invention may also be suitably directed against two or more different extracellular parts, regions, domains, loops or other extracellular epitopes on the same antigen, for example against two different extracellular loops, against two different extracellular parts of the transmembrane domains or against one extracellular loops and one extracellular loop. Such multivalent or multispecific polypeptides of the invention may also have (or be engineered and/or selected for) increased avidity and/or improved selectivity for the desired GPCR, and/or for any other desired property or combination of desired properties that may be obtained by the use of such multivalent or multispecific polypeptides.

Generally, it is expected that amino acid sequences and polypeptides of the invention that are directed against an extracellular loop or domain of a GPCR (or against a small peptide derived therefrom or based thereon), and/or that have been screened against, selected using and/or raised against an extracellular loop or domain of a GPCR (or against a small peptide derived therefrom or based thereon) will also be able to bind (and in particular, to specifically bind, as defined herein) to such an extracellular loop or domain (or peptide derived therefrom) that forms part of a GPCR (or at least one subunit thereof) that is present on the surface of a cell. Thus, such (peptides derived from) an extracellular loop or domain may find particular use in methods for generating amino acid sequences and polypeptides of the invention (as defined herein); and such methods and uses form further aspects of the invention; as do amino acid sequences, Nanobodies and polypeptides of the invention that are directed against or raised against such an extracellular loop, domain or peptide derived therefrom.

For example, such a method may comprises the following:

a) a step of suitably immunizing a Camelid with a suitable antigen that comprises the desired extracellular part, region, domain, loop or other extracellular epitope(s), or with a suitable peptide derived therefrom or based thereon, such that an immune response against the desired extracellular part, region, domain, loop or other extracellular epitope(s) is raised. The antigen may be any suitable antigen that is capable of raising an immune response against the desired extracellular part, region, domain, loop or other extracellular epitope(s); such as, for example and without limitation, whole cells that are alive and overexpress the desired extracellular part, region, domain, loop or other extracellular epitope(s) on their surface in their native confirmation, cell wall fragments thereof or any other suitable preparation derived from such cells, vesicles that have the desired extracellular part, region, domain, loop or other extracellular epitope(s) on their surface, a subunit or fragment of a subunit of a GPCR, e.g. human CXCR4 and/or human CXCR7, that comprises the desired extracellular part, region, domain, loop or other extracellular epitope(s), or a synthetic or semi-synthetic peptide that comprises and/or is based on (the amino acid sequence of) the desired extracellular part, region, domain, loop or other extracellular epitope(s), more preferably, whole cells (e.g. HEK293) that are alive and overexpress the desired extracellular part, region, domain, loop or other extracellular epitope(s) on their surface in their native confirmation; and b) a step of selection for binding for the desired extracellular part, region, domain, loop or other extracellular epitope(s) using cell membranes preparation of different (than the one using in immunization) and several cell types overexpressing said GPCR, e.g. human CXCR4 and/or human CXCR7. This may for example be performed by selecting from a set, a collection or a library of cells that express heavy chain antibodies on their surface (e.g. B-cells obtained from a suitably immunized Camelid) and using a cell membranes preparation of e.g. a first type of cells such as e.g. CHO for a first round selection and e.g. a second type of cells such as e.g. COS-7 cells for a second round selection, by selecting from a (naïve or immune) library of VHH sequences or Nanobody sequences by using a cell membranes preparation of e.g. a first type of cell such as e.g. CHO for a first round selection and e.g. a second type of cell such as e.g. COS-7 cell for a second round selection, or by selecting from a (naïve or immune) library of nucleic acid sequences that encode VHH sequences or Nanobody sequences by using a cell membranes preparation of e.g. a first type of cell such as e.g. CHO for a first round selection and e.g. a second type of cells such as e.g. COS-7 cell for a second round selection; which may all be performed in a manner known per se; and optionally c) washing only mildly with a buffer such as PBS without detergents; and which method may optionally further comprise one or more other suitable steps known per se, such as, for example and without limitation, a step of affinity maturation, a step of expressing the desired amino acid sequence, a step of screening for binding and/or for activity against the desired antigen (in this case, the GPCR), a step of determining the desired amino acid sequence or nucleotide sequence, a step of introducing one or more humanizing substitutions (e.g. as further described herein), a step of formatting in a suitable multivalent and/or multispecific format, a step of screening for the desired biological and/or physiological properties (i.e. using a suitable assay, such as those described herein); and/or any suitable combination of one or more of such steps, in any suitable order.

Such methods and the amino acid sequences obtained via such methods, as well as proteins and polypeptides comprising or essentially consisting of the same, form further aspects of this invention.

The amino acid sequences, Nanobodies and polypeptides of the invention may also bind to the GPCR at the same site as the endogenous agonist (i.e. at an orthosteric site), so as to activate or increase receptor signalling; or alternatively so as to decrease or inhibit receptor signalling.

The amino acid sequences, Nanobodies and polypeptides of the invention may also bind to the GPCR in such a way that they block of the constitutive activity of the GPCR.

The amino acid sequences, Nanobodies and polypeptides of the invention may also bind to the GPCR in such a way that they mediate allosteric modulation (e.g. bind to the GPCR at an allosteric site). In this way, the amino acid sequences, Nanobodies and polypeptides of the invention may modulation of the receptor function by binding to different regions in the receptor (e.g. at allosteric sites). Reference is for example made to George et al., Nat Rev Drug Discov 1:808-820 (2002); Kenakin, Trends Pharmacol Sci 25:186-192 (2002) and Rios et al., Pharmacol Ther 92:71-87 (2001)).

The amino acid sequences, Nanobodies and polypeptides of the invention may also bind to the GPCR in such a way that they inhibit or enhance the assembly of GPCR functional homodimers or heterodimers.

The amino acid sequences, Nanobodies and polypeptides of the invention may also bind to the GPCR in such a way that they prolong the duration of the GPCR-mediated signalling. The amino acid sequences, Nanobodies and polypeptides of the invention may also enhance receptor signalling by increasing receptor-ligand affinity.

Polypeptides of the invention that are directed against a GPCR and its ligand may also provide for enhanced binding of the ligand to the GPCR by cross-linking the ligand to the orthosteric site; and/or stabilize of the binding of the ligand to the orthosteric site. Thus, a further aspect of the invention relates to a multispecific polypeptide of the invention (as defined herein) that comprises at least one amino acid sequence of the invention (such as a Nanobody) against a GPCR proteinase and at least one binding unit directed against its natural ligand. Such multispecific proteins may further be as described herein.

Also, as will be clear from the further disclosure herein, and depending on the GPCR against which they are directed and their desired (therapeutic) effect, the amino acid sequences, Nanobodies and polypeptides of the invention may act as (full or partial) agonists, (full or partial, and competitive or non-competitive) antagonists or as inverse agonists of the GPCR (and/or of the ligand of the GPCR) and/or of the biological function, pathway, mechanism, effect, signalling or response associated therewith. They may do so in an irreversible but preferably reversible manner.

In a preferred embodiment, the amino acid sequence or polypeptide of the invention is a (full or partial, and competitive or non-competitive) antagonist or an inverse agonist of the GPCR of the invention, more preferably the amino acid sequence or polypeptide of the invention is a Nanobody that is a (full or partial, and competitive or non-competitive) antagonist or an inverse agonist of the GPCR of the invention.

Our results show that nanobodies in monovalent and/or multivalent format, and possibly also the amino acid sequence or polypeptide of the invention, can act as neutral antagonists or inverse agonists on constitutively active GPCR showing the wide applicability of Nanobody platform. A significant number of the top selling GPCR drugs behave as inverse agonists rather than neutral antagonists (Milligan G. (2003). Mol. Pharmacol. 64:1271-1276) and it has been claimed that inverse agonists may have specific therapeutic benefits compared with neutral antagonists for several diseases including cancer (Kenakin T (2004). Mol. Pharmacol. 65:2-11). Furthermore, inverse agonists may be superior over neutral antagonists to inhibit other functions.

In a preferred embodiment, the amino acid sequence or polypeptide of the invention is a "monoclonal" amino acid sequence or polypeptide, by which is meant that at least each of the one or more amino acid sequences directed against the GPCR that are present in said protein or polypeptide (and preferably all of the immunoglobulin sequences that are present in said protein or polypeptide) are "monoclonal" as commonly understood by the skilled person. In this respect, it should however be noted that, as further described herein, the present invention explicitly covers multivalent or multispecific proteins that comprise two or more immunoglobulin sequences (and in particular monoclonal immunoglobulin sequences) that are directed against different parts, regions, domains, loops or epitopes of the same GPCR, and in particular against different extracellular parts, regions, domains, loops or epitopes of the same GPCR.

It is also within the scope of the invention that, where applicable, an amino acid sequence of the invention can bind to two or more antigenic determinants, epitopes, parts, domains, subunits or confirmations of GPCRs. In such a case, the antigenic determinants, epitopes, parts, domains or subunits of GPCRs to which the amino acid sequences and/or polypeptides of the invention bind may be essentially the same (for example, if GPCRs contains repeated structural motifs or occurs in a multimeric form) or may be different (and in the latter case, the amino acid sequences and polypeptides of the invention may bind to such different antigenic determinants, epitopes, parts, domains, subunits of GPCRs with an affinity and/or specificity which may be the same or different). Also, for example, when GPCRs exists in an activated conformation and in an inactive conformation, the amino acid sequences and polypeptides of the invention may bind to either one of these confirmation, or may bind to both these confirmations (i.e. with an affinity and/or specificity which may be the same or different). Also, for example, the amino acid sequences and polypeptides of the invention may bind to a conformation of GPCRs in which it is bound to a pertinent ligand, may bind to a conformation of GPCRs in which it not bound to a pertinent ligand, or may bind to both such conformations (again with an affinity and/or specificity which may be the same or different).

It is also expected that the amino acid sequences and polypeptides of the invention will generally bind to all naturally occurring or synthetic analogs, variants, mutants, alleles, parts and fragments of GPCRs; or at least to those analogs, variants, mutants, alleles, parts and fragments of GPCRs that contain one or more antigenic determinants or epitopes that are essentially the same as the antigenic determinant(s) or epitope(s) to which the amino acid sequences and polypeptides of the invention bind in GPCRs (e.g. in wild-type GPCRs). Again, in such a case, the amino acid sequences and polypeptides of the invention may bind to such analogs, variants, mutants, alleles, parts and fragments with an affinity and/or specificity that are the same as, or that are different from (i.e. higher than or lower than), the affinity and specificity with which the amino acid sequences of the invention bind to (wild-type) GPCRs. It is also included within the scope of the invention that the amino acid sequences and polypeptides of the invention bind to some analogs, variants, mutants, alleles, parts and fragments of GPCRs, but not to others.

When GPCRs exists in a monomeric form and in one or more multimeric forms, it is within the scope of the invention that the amino acid sequences and polypeptides of the invention only bind to GPCRs in monomeric form, only bind to GPCRs in multimeric form, or bind to both the monomeric and the multimeric form. Again, in such a case, the amino acid sequences and polypeptides of the invention may bind to the monomeric form with an affinity and/or specificity that are the same as, or that are different from (i.e. higher than or lower than), the affinity and specificity with which the amino acid sequences of the invention bind to the multimeric form.

Also, when GPCRs can associate with other proteins or polypeptides to form protein complexes (e.g. with multiple subunits), it is within the scope of the invention that the amino acid sequences and polypeptides of the invention bind to GPCRs in its non-associated state, bind to GPCRs in its associated state, or bind to both. In all these cases, the amino acid sequences and polypeptides of the invention may bind to such multimers or associated protein complexes with an affinity and/or specificity that may be the same as or different from (i.e. higher than or lower than) the affinity and/or specificity with which the amino acid sequences and polypeptides of the invention bind to GPCRs in its monomeric and non-associated state.

Also, as will be clear to the skilled person, proteins or polypeptides that contain two or more amino acid sequences directed against GPCRs may bind with higher avidity to GPCRs than the corresponding monomeric amino acid sequence(s). For example, and without limitation, proteins or polypeptides that contain two or more amino acid sequences directed against different epitopes of GPCRs may (and usually will) bind with higher avidity than each of the different monomers, and proteins or polypeptides that contain two or more amino acid sequences directed against GPCRs may (and usually will) bind also with higher avidity to a multimer of GPCRs.

Generally, amino acid sequences and polypeptides of the invention will at least bind to those forms of GPCRs (including monomeric, multimeric and associated forms) that are the most relevant from a biological and/or therapeutic point of view, as will be clear to the skilled person.

It is also within the scope of the invention to use parts, fragments, analogs, mutants, variants, alleles and/or derivatives of the amino acid sequences and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against GPCRs; and more preferably will be capable of specific binding to GPCRs, and even more preferably capable of binding to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

In one specific, but non-limiting aspect of the invention, which will be further described herein, such analogs, mutants, variants, alleles, derivatives have an increased half-life in serum (as further described herein) compared to the amino acid sequence from which they have been derived. For example, an amino acid sequence of the invention may be linked (chemically or otherwise) to one or more groups or moieties that extend the half-life (such as PEG), so as to provide a derivative of an amino acid sequence of the invention with increased half-life.

In one specific, but non-limiting aspect, the amino acid sequence of the invention may be an amino acid sequence that comprises an immunoglobulin fold or may be an amino acid sequence that, under suitable conditions (such as physiological conditions) is capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such an amino acid sequence is capable of specific binding (as defined herein) to GPCRs; and more preferably capable of binding to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such amino acid sequences are preferably such that they comprise an immunoglobulin fold or are capable for forming, under suitable conditions, an immunoglobulin fold.

In particular, but without limitation, the amino acid sequences of the invention may be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein).

The amino acid sequences of the invention may in particular be an immunoglobulin sequence or a suitable fragment thereof, and more in particular be an immunoglobulin variable domain sequence or a suitable fragment thereof, such as light chain variable domain sequence (e.g. a $V_L$-sequence) or a suitable fragment thereof; or a heavy chain variable domain sequence (e.g. a $V_H$-sequence) or a suitable fragment thereof. When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

However, it should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the amino acid sequences of the invention may be naturally occurring amino acid sequences (from any suitable species) or synthetic or semi-synthetic amino acid sequences. In a specific but non-limiting aspect of the invention, the amino acid sequence is a naturally occurring immunoglobulin sequence (from any suitable species) or a synthetic or semi-synthetic immunoglobulin sequence, including but not limited to "humanized" (as defined herein) immunoglobulin sequences (such as partially or fully humanized mouse or rabbit immunoglobulin sequences, and in particular partially or fully humanized $V_{HH}$ sequences or Nanobodies), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Reference is for example made to the standard handbooks, as well as to the further description and prior art mentioned herein.

Similarly, the nucleotide sequences of the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

The amino acid sequence of the invention may in particular be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody™ (as defined herein, and including but not limited to a $V_{HH}$ sequence); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a Nanobody™ (as defined herein) or a suitable fragment thereof. [Note: Nanobody™, Nanobodies™ and Nanoclone™ are trademarks of Ablynx N.V.] Such Nanobodies directed against GPCRs will also be referred to herein as "Nanobodies of the invention".

For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_H3$ class such as DP-47, DP-51 or DP-29), which Nanobodies form a preferred aspect of this invention. It should however be noted that the invention in its broadest sense generally covers any type of Nanobody directed against GPCRs, and for example also covers the Nanobodies belonging to the so-called "$V_H4$ class" (i.e. Nanobodies with a high degree of sequence homology to human germline sequences of the $V_H4$ class such as DP-78), as for example described in the U.S. provisional application 60/792,279 by Ablynx N.V. entitled "DP-78-like Nanobodies" filed on Apr. 14, 2006.

Generally, Nanobodies (in particular $V_{HH}$ sequences and partially humanized Nanobodies) can in particular be characterized by the presence of one or more "Hallmark residues" (as described herein) in one or more of the framework sequences (again as further described herein).

Thus, generally, a Nanobody can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) preferably one or more of the amino acid residues at positions 11, 37, 44, 45, 47, 83, 84, 103, 104 and 108 according to the Kabat numbering are chosen from the Hallmark residues mentioned in Table A-3 below;

and in which:

ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded.

In these Nanobodies, the CDR sequences are generally as further defined herein.

Thus, the invention also relates to such Nanobodies that can bind to (as defined herein) and/or are directed against GPCRs, to suitable fragments thereof, as well as to polypeptides that comprise or essentially consist of one or more of such Nanobodies and/or suitable fragments.

SEQ ID NO's 238 to 253 give the amino acid sequences of a number of $V_{HH}$ sequences that have been raised against human CXCR4 (Table 1).

TABLE 1

Nanobodies directed against human CXCR4 (SEQ ID NO: 254):

| SEQ ID NO: X, where X = Name | Amino acid sequence |
|---|---|
| 238 | 238C1, D2 | EVQLVESGGGLVQTGGSLRLSCAASGFTFSSYAMSWVRQAPGK GLEWVSGIKSSGDSTRYAGSVKGRFTISRDNAKNMLYLQMYSL KPEDTAVYYCAKSRVSRTGLYTYDNRGQGTQVTVSS |
| 239 | 238D4, G3 | EVQLMESGGGLVQAGGSLRLSCAASGRTFNNYAMGWFRRAPKG EREFVAAITRSGVRSGVSAIYGDSVKDRFTISRDNAKNTLYLQ MNSLKPEDTAVYTCAASAIGSGALRRFEYDYSGQGTQVTVSS |
| 240 | 237B5 | KVQLVESGGGLVQPGGSLRLSCAASGFAFSIHTMSWVRQAPGK GPEWVSTIKPSGDTTNYANAVKGRFTISRDNAKNTLYLQMNSL KPEDTAVYYCAKDYFGTVRGQGTQVTVSS |
| 241 | 237B6, A5, D2, D3, E4, F4, G2 G4, xH5 237F1, C5, G1 | EVQLVESGGGLVQPGGSLRLSCAASGFTFDDYAMSWVRQAPGK GLEWVSAISWNGGSTDYADSVKGRFTISRDNAKNTLYLQMNSL KSEDTAEYYCARDQGPFYSGTYYYTRQYGYRGQGTQVTVSS |
| 242 | 238B10 | EVQLVESGGGFVQAGGSLRLSCETSGRPLLGYTIAWFRQVPGK EREFVAYHRWSDGANLYADSVKGRFTISGHNAKNTVSLQMNSL KPEDTAVYYCAAARMTTSNDKEYLYWGQGTQVTVSS |
| 243 | 238C5, G2, xH5, 238C3, D6, E6 | EVQLMESGGGLVQAGGSLRLACAASGFTFEDYAIGWFRKAPGK EREGVSCISGSDGSTTYADSVKGRFTISTDNAKNTVYLEMNSL KPEDTAVYYCAQQYGVGGRVVCPGPYEYDVWGQGTQVTVSS |
| 244 | 238F7 | EVQLVESGGGFVQAGGSLRLSCETSGRPLLGYTIAWFRQVPGK EREFVAYHRWSDGANLYADSVKGRFTISGHNAKNTVSLQMNSL KPEDTAVYYCAAAWMTTSNDKEYLYWGQGTQVTVSS |
| 245 | 238H2 | EVQLVESGGGLVQAGGSLRLSCAASGLTFSPSAMAWYRQGPGK ERDFVASTIWSRGDTYFADSVKGRFTISRDTANYTLYLQMNNL KPEDTAVYYCSLRVRPYGQYDYWGQGTQVTVSS |
| 246 | 237D4 | EVQLVESGGGLVQPGGSLRLSCAASGFTFDDYAMSWVRQAPGK GLEWVSAISWNGGSADYADSVKGRFTISRDNAKNTLYLQMNSL KSEDTAVYYCAKDQGPFYSGTYYYTKGYAYWGQGTQVTVSS |
| 247 | 238F3 | EVQLVESGGGLAQAGGSLRLSCAASGRTYAMGWFRQAPGKERE FVTTSRLITDNIIYADSVKGRFTLTRDNGKNTVYLQMDSLKPD DTAVYFCAARQNYSRSVFGAKDYDYWGQGTQVTVSS |
| 248 | 237A6 | EVQLVESGGGLVQAGGSLRLSCAASGSIFSLNAMGWYRQAPGK QRELVAGITSSTSTYYADSVKGRFTISRDNTKNTVYLQMNSLK PEDTAVYYCNVDCPDYYSDYECPLEDRGQGTQVTVSS |
| 249 | 237D1 | EVQLVESGGGLAQPGGPLRLTCEASGVIYSVNDMGWYRQAPGK QRELVAVITSGGGTNYVDSVKGRFTISGDNRKKTVYLQMNSLK PEDTAVYYCSIYYSSGISTLRSWGQGTQVTVSS |
| 250 | 237-E1 | EVQLVESGGGLVQPGGSLRLSCEVSGFTRDYYTIGWFRQAPGK EREGVSCISSSDGSTAYLGSVQGRFTVSRDNAKNTVYLQMNNL KPEDTAVYYCALBSADSRCSIGSIGFTWLYNNWGQGTQVTVSS |
| 251 | 237G7 | EVQLVESGGGLVQPGGSLRLSCAASSFIGNYHAIVWLRQAPGK ELEGVSCITSRDSITYYASFVKGRFTISRDDAKNTVYLQMNNL KPEDTAVYYCAVBTSMTCPTLIVRFNYRGQGTQVTVSS |
| 252 | 238C4 | EVQLVESGGGLVQAGGSLRLSCKASGGTFNNYAMGWFRRAPGK EREFVAAITRSGVRSGVSAIYGDSVKDRFTISRDNVKNTLYLQ MNTLKPEDTAVYTCAASAIGSGALRRFEYDYSGQGTQVTVSS |
| 253 | 237C1 | EVQLVESGGGLVQAGGSLRLSCAASGFFSINAMGWYRQAPGK QRELVASITSGGSTVYADSVKGRFTISRDNYNTVYLQMNSLKP EDTAVYYCNADGVPEWGKVQYPDTYRGQGTQVTVSS |

TABLE 1.1

CDRs of Nanobodies directed against human CXCR4 (SEQ ID NO: 254):

| SEQ ID NO: X, where X = | Name | Amino acid sequence |
|---|---|---|
| 142 | CDR1 of 238C1, D2 | SYAMS |
| 143 | CDR1 of 238D4, G3 | NYAMG |
| 144 | CDR1 of 237B5 | IHTMS |
| 145 | CDR1 of 237B6, A5, D2, D3, E4, F4, G2, G4, xH5, 237F1, C5, G1 | DYAMS |
| 146 | CDR1 of 238B10 | GYTIA |
| 147 | CDR1 of 238C5, G2, xH5, 238C3, D6, E6 | DYAIG |
| 148 | CDR1 of 238F7 | GYTIA |
| 149 | CDR1 of 238H2 | PSAMA |
| 150 | CDR1 of 237D4 | DYAMS |
| 151 | CDR1 of 238F3 | MG |
| 152 | CDR1 of 237A6 | LNAMG |
| 153 | CDR1 of 237D1 | VNDMG |
| 154 | CDR1 of 237E1 | YYTIG |
| 155 | CDR1 of 237G7 | YHAIV |
| 156 | CDR1 of 238C4 | NYAMG |
| 157 | CDR1 of 237C1 | INAMG |
| 174 | CDR2 of 238C1, D2 | GIKSSGDSTRYAGSVKG |
| 175 | CDR2 of 238D4, G3 | AITRSGVRSGVSAIYGDSVKD |
| 176 | CDR2 of 237B5 | TIKPSGDTTNYANAVKG |
| 177 | CDR2 of 237B6, A5, D2, D3, E4, F4, G2, G4, xH5, 237F1, C5, G1 | AISWNGGSTDYADSVKG |
| 178 | CDR2 of 238B10 | YHRWSDGANLYADSVKG |
| 179 | CDR2 of 238C5, G2, xH5, 238C3, D6, E6 | CISGSDGSTTYADSVKG |
| 180 | CDR2 of 238F7 | YHRWSDGANLYADSVKG |
| 181 | CDR2 of 238H2 | STIWSRGDTYFADSVKG |
| 182 | CDR2 of 237D4 | AISWNGGSADYADSVKG |
| 183 | CDR2 of 238F3 | TSRLITDNIIYADSVKG |
| 184 | CDR2 of 237A6 | GITSSTSTYYADSVKG |
| 185 | CDR2 of 237D1 | VITSGGGTNYVDSVKG |
| 186 | CDR2 of 237E1 | CISSSDGSTAYLGSVQG |
| 187 | CDR2 of 237G7 | CITSRDSITYYASFVKG |
| 188 | CDR2 of 238C4 | AITRSGVRSGVSAIYGDSVKD |
| 189 | CDR2 of 237C1 | SITSGGSTVYADSVKG |
| 206 | CDR3 of 238C1, D2 | SRVSRTGLYTYDN |
| 207 | CDR3 of 238D4, G3 | SAIGSGALRRFEYDY |
| 208 | CDR3 of 237B5 | DYFGTGV |
| 209 | CDR3 of 237B6, A5, D2, D3, E4, F4, G2, G4, xH5, 237F1, C5, G1 | DQGPFYSGTYYYTRQYGY |
| 210 | CDR3 of 238B10 | ARMTTSNDKEYLY |
| 211 | CDR3 of 238C5, G2, xH5, 238C3, D6, E6 | QYGVGGRVVCPGPYEYDV |
| 212 | CDR3 of 238F7 | AWMTTSNDKEYLY |
| 213 | CDR3 of 238H2 | RVRPYGQYDY |
| 214 | CDR3 of 237D4 | DQGPFYSGTYYYTKGYAY |
| 215 | CDR3 of 238F3 | RQNYSRSVFGAKDYDY |
| 216 | CDR3 of 237A6 | DCPDYYSDYECPLED |
| 217 | CDR3 of 237D1 | YYSSGISTLRS |
| 218 | CDR3 of 237E1 | BSADSRCSIGSIGFTWLYNN |
| 219 | CDR3 of 237G7 | BTSMTCPTLIVRFNY |
| 220 | CDR3 of 238C4 | SAIGSGALRRFEYDY |
| 221 | CDR3 of 237C1 | DGVPEWGKVQYPDTY |

It is expected that amino acid sequences, Nanobodies and polypeptides of the invention of the invention directed against human CXCR7 (and in particular antagonists), as well as compositions comprising the same, may find particular use in the prevention and treatment of for example wound healing, AIDS and cancer.

Accordingly, some particularly preferred Nanobodies of the invention are Nanobodies which can bind (as further defined herein) to and/or are directed against to human CXCR4 and which:

i) have 80% amino acid identity with at least one of the amino acid sequences of SEQ ID NO's: 238 to 253, more preferably SEQ ID NO: 238 and SEQ ID NO: 239, in which for the purposes of determining the degree of amino acid identity, the amino acid residues that form the CDR sequences are disregarded. In this respect, reference is also made to Table A-1, which lists the framework 1 sequences (SEQ ID NO's: 126 to 141), framework 2 sequences (SEQ ID NO's: 158 to 173), framework 3 sequences (SEQ ID NO's: 190 to 205) and framework 4 sequences (SEQ ID NO's: 222 to 237) of the Nanobodies of SEQ ID NO's: 238 to 253, more preferably SEQ ID NO: 238 and SEQ ID NO: 239 (with respect to the amino acid residues at positions 1 to 4 and 27 to 30 of the framework 1 sequences, reference is also made to the comments made below. Thus, for determining the degree of amino acid identity, these residues are preferably disregarded);

and in which:

ii) preferably one or more of the amino acid residues at positions 11, 37, 44, 45, 47, 83, 84, 103, 104 and 108 according to the Kabat numbering are chosen from the Hallmark residues mentioned in Table A-3 below.

In these Nanobodies, the CDR sequences are generally as further defined herein.

Again, such Nanobodies may be derived in any suitable manner and from any suitable source, and may for example be naturally occurring $V_{HH}$ sequences (i.e. from a suitable species of Camelid) or synthetic or semi-synthetic amino acid sequences, including but not limited to "humanized" (as defined herein) Nanobodies, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a Nanobody comprises a $V_{HH}$ sequence, said Nanobody may be suitably humanized, as further described herein, so as to provide one or more further (partially or fully) humanized Nanobodies of the invention. Similarly, when a Nanobody comprises a synthetic or semi-synthetic sequence (such as a partially humanized sequence), said Nanobody may optionally be further suitably humanized, again as described herein, again so as to provide one or more further (partially or fully) humanized Nanobodies of the invention.

In particular, humanized Nanobodies may be amino acid sequences that are as generally defined for Nanobodies in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Some particularly preferred humanized Nanobodies of the invention are humanized variants of the Nanobodies of SEQ ID NO's: 238 to 253, more preferably SEQ ID NO: 238 and SEQ ID NO: 239.

Thus, some other preferred Nanobodies of the invention are Nanobodies which can bind (as further defined herein) to human CXCR4 and which:

i) are a humanized variant of one of the amino acid sequences of SEQ ID NO's: 238 to 253, more preferably SEQ ID NO: 238 and SEQ ID NO: 239; and/or ii) have 80% amino acid identity with at least one of the amino acid sequences of SEQ ID NO's: 238 to 253, more preferably SEQ ID NO: 238 and SEQ ID NO: 239, in which for the purposes of determining the degree of amino acid identity, the amino acid residues that form the CDR sequences are disregarded;

and in which:

i) preferably one or more of the amino acid residues at positions 11, 37, 44, 45, 47, 83, 84, 103, 104 and 108 according to the Kabat numbering are chosen from the Hallmark residues mentioned in Table A-3 below.

According to another specific aspect of the invention, the invention provides a number of stretches of amino acid residues (i.e. small peptides) that are particularly suited for binding to GPCRs. These stretches of amino acid residues may be present in, and/or may be corporated into, an amino acid sequence of the invention, in particular in such a way that they form (part of) the antigen binding site of an amino acid sequence of the invention. As these stretches of amino acid residues were first generated as CDR sequences of heavy chain antibodies or $V_{HH}$ sequences that were raised against GPCRs (or may be based on and/or derived from such CDR sequences, as further described herein), they will also generally be referred to herein as "CDR sequences" (i.e. as CDR1 sequences, CDR2 sequences and CDR3 sequences, respectively). It should however be noted that the invention in its broadest sense is not limited to a specific structural role or function that these stretches of amino acid residues may have in an amino acid sequence of the invention, as long as these stretches of amino acid residues allow the amino acid sequence of the invention to bind to GPCRs. Thus, generally, the invention in its broadest sense comprises any amino acid sequence that is capable of binding to GPCRs and that comprises one or more CDR sequences as described herein, and in particular a suitable combination of two or more such CDR sequences, that are suitably linked to each other via one or more further amino acid sequences, such that the entire amino acid sequence forms a binding domain and/or binding unit that is capable of binding to GPCRs. It should however also be noted that the presence of only one such CDR sequence in an amino acid sequence of the invention may by itself already be sufficient to provide an amino acid sequence of the invention that is capable of binding to GPCRs; reference is for example again made to the so-called "Expedite fragments" described in WO 03/050531.

Thus, in another specific, but non-limiting aspect, the amino acid sequence of the invention may be an amino acid sequence that comprises at least one amino acid sequence that is chosen from the group consisting of the CDR1 sequences, CDR2 sequences and CDR3 sequences that are described herein (or any suitable combination thereof). In particular, an amino acid sequence of the invention may be an amino acid sequence that comprises at least one antigen binding site, wherein said antigen binding site comprises at least one amino acid sequence that is chosen from the group consisting of the CDR1 sequences, CDR2 sequences and CDR3 sequences that are described herein (or any suitable combination thereof).

Generally, in this aspect of the invention, the amino acid sequence of the invention may be any amino acid sequence that comprises at least one stretch of amino acid residues, in which said stretch of amino acid residues has an amino acid sequence that corresponds to the sequence of at least one of the CDR sequences described herein. Such an amino acid sequence may or may not comprise an immunoglobulin fold. For example, and without limitation, such an amino acid sequence may be a suitable fragment of an immunoglobulin sequence that comprises at least one such CDR sequence, but that is not large enough to form a (complete) immunoglobulin fold (reference is for example again made to the "Expedite fragments" described in WO 03/050531). Alternatively, such an amino acid sequence may be a suitable "protein scaffold" that comprises least one stretch of amino acid residues that corresponds to such a CDR sequence (i.e. as part of its antigen binding site). Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al. Comb Chem High Throughput Screen 2006 9(8):619-32).

Again, any amino acid sequence of the invention that comprises one or more of these CDR sequences is preferably such that it can specifically bind (as defined herein) to GPCRs, and more in particular such that it can bind to GPCRs with an affinity (suitably measured and/or expressed as a $K_D$-value (actual or apparent), a $K_A$-value (actual or apparent), a $K_{on}$-rate and/or a $k_{off}$-rate, or alternatively as an $IC_{50}$ value, as further described herein), that is as defined herein.

More in particular, the amino acid sequences according to this aspect of the invention may be any amino acid sequence that comprises at least one antigen binding site, wherein said antigen binding site comprises at least two amino acid sequences that are chosen from the group consisting of the CDR1 sequences described herein, the CDR2 sequences described herein and the CDR3 sequences described herein, such that (i) when the first amino acid sequence is chosen from the CDR1 sequences described herein, the second amino acid sequence is chosen from the CDR2 sequences described herein or the CDR3 sequences described herein; (ii) when the first amino acid sequence is chosen from the CDR2 sequences described herein, the second amino acid sequence is chosen from the CDR1 sequences described herein or the CDR3 sequences described herein; or (iii) when the first amino acid sequence is chosen from the CDR3 sequences described herein, the second amino acid sequence is chosen from the CDR1 sequences described herein or the CDR3 sequences described herein.

Even more in particular, the amino acid sequences of the invention may be amino acid sequences that comprise at least one antigen binding site, wherein said antigen binding site comprises at least three amino acid sequences that are chosen from the group consisting of the CDR1 sequences described herein, the CDR2 sequences described herein and the CDR3 sequences described herein, such that the first amino acid sequence is chosen from the CDR1 sequences described herein, the second amino acid sequence is chosen from the CDR2 sequences described herein, and the third amino acid sequence is chosen from the CDR3 sequences described herein. Preferred combinations of CDR1, CDR2 and CDR3 sequences will become clear from the further description herein. As will be clear to the skilled person, such an amino acid sequence is preferably an immunoglobulin sequence (as further described herein), but it may for example also be any other amino acid sequence that comprises a suitable scaffold for presenting said CDR sequences.

Thus, in one specific, but non-limiting aspect, the invention relates to an amino acid sequence directed against GPCRs, that comprises one or more stretches of amino acid residues chosen from the group consisting of:
a) the amino acid sequences of SEQ ID NO's: 142 to 157, more preferably 142 to 143;
b) amino acid sequences that have at least 80% amino acid identity with at least one of the amino acid sequences of SEQ ID NO's: 142 to 157, more preferably 142 to 143;
c) amino acid sequences that have 3, 2, or 1 amino acid difference with at least one of the amino acid sequences of SEQ ID NO's: 142 to 157, more preferably 142 to 143;
d) the amino acid sequences of SEQ ID NO's: 174 to 189, more preferably 174 to 175;
e) amino acid sequences that have at least 80% amino acid identity with at least one of the amino acid sequences of SEQ ID NO's: 174 to 189, more preferably 174 to 175;
f) amino acid sequences that have 3, 2, or 1 amino acid difference with at least one of the amino acid sequences of SEQ ID NO's: 174 to 189, more preferably 174 to 175;
g) the amino acid sequences of SEQ ID NO's: 206 to 221, more preferably 206 to 207;
h) amino acid sequences that have at least 80% amino acid identity with at least one of the amino acid sequences of SEQ ID NO's: 206 to 221, more preferably 206 to 207;
i) amino acid sequences that have 3, 2, or 1 amino acid difference with at least one of the amino acid sequences of SEQ ID NO's: 206 to 221, more preferably 206 to 207;
or any suitable combination thereof.

When an amino acid sequence of the invention contains one or more amino acid sequences according to b) and/or c):
i) any amino acid substitution in such an amino acid sequence according to b) and/or c) is preferably, and compared to the corresponding amino acid sequence according to a), a conservative amino acid substitution, (as defined herein);
and/or
ii) the amino acid sequence according to b) and/or c) preferably only contains amino acid substitutions, and no amino acid deletions or insertions, compared to the corresponding amino acid sequence according to a);
and/or
iii) the amino acid sequence according to b) and/or c) may be an amino acid sequence that is derived from an amino acid sequence according to a) by means of affinity maturation using one or more techniques of affinity maturation known per se.

Similarly, when an amino acid sequence of the invention contains one or more amino acid sequences according to e) and/or f):
i) any amino acid substitution in such an amino acid sequence according to e) and/or f) is preferably, and compared to the corresponding amino acid sequence according to d), a conservative amino acid substitution, (as defined herein);
and/or
ii) the amino acid sequence according to e) and/or f) preferably only contains amino acid substitutions, and no amino acid deletions or insertions, compared to the corresponding amino acid sequence according to d);
and/or
iii) the amino acid sequence according to e) and/or f) may be an amino acid sequence that is derived from an amino acid sequence according to d) by means of affinity maturation using one or more techniques of affinity maturation known per se.

Also, similarly, when an amino acid sequence of the invention contains one or more amino acid sequences according to h) and/or i):

i) any amino acid substitution in such an amino acid sequence according to h) and/or i) is preferably, and compared to the corresponding amino acid sequence according to g), a conservative amino acid substitution, (as defined herein); and/or ii) the amino acid sequence according to h) and/or i) preferably only contains amino acid substitutions, and no amino acid deletions or insertions, compared to the corresponding amino acid sequence according to g); and/or iii) the amino acid sequence according to h) and/or i) may be an amino acid sequence that is derived from an amino acid sequence according to g) by means of affinity maturation using one or more techniques of affinity maturation known per se.

It should be understood that the last preceding paragraphs also generally apply to any amino acid sequences of the invention that comprise one or more amino acid sequences according to b), c), e), f), h) or i), respectively.

In this specific aspect, the amino acid sequence preferably comprises one or more stretches of amino acid residues chosen from the group consisting of:

i) the amino acid sequences of SEQ ID NO's: 142 to 157, more preferably 142 to 143;

ii) the amino acid sequences of SEQ ID NO's: 174 to 189, more preferably 174 to 175; and iii) the amino acid sequences of SEQ ID NO's: 206 to 221, more preferably 206 to 207;

or any suitable combination thereof.

Also, preferably, in such an amino acid sequence, at least one of said stretches of amino acid residues forms part of the antigen binding site for binding against GPCRs.

In a more specific, but again non-limiting aspect, the invention relates to an amino acid sequence directed against GPCRs, that comprises two or more stretches of amino acid residues chosen from the group consisting of:

a) the amino acid sequences of SEQ ID NO's: 142 to 157, more preferably 142 to 143;

b) amino acid sequences that have at least 80% amino acid identity with at least one of the amino acid sequences of SEQ ID NO's: 142 to 157, more preferably 142 to 143;

c) amino acid sequences that have 3, 2, or 1 amino acid difference with at least one of the amino acid sequences of SEQ ID NO's: 142 to 157, more preferably 142 to 143;

d) the amino acid sequences of SEQ ID NO's: 174 to 189, more preferably 174 to 175;

e) amino acid sequences that have at least 80% amino acid identity with at least one of the amino acid sequences of SEQ ID NO's: 174 to 189, more preferably 174 to 175;

f) amino acid sequences that have 3, 2, or 1 amino acid difference with at least one of the amino acid sequences of SEQ ID NO's: 174 to 189, more preferably 174 to 175;

g) the amino acid sequences of SEQ ID NO's: 206 to 221, more preferably 206 to 207;

h) amino acid sequences that have at least 80% amino acid identity with at least one of the amino acid sequences of SEQ ID NO's: 206 to 221, more preferably 206 to 207;

i) amino acid sequences that have 3, 2, or 1 amino acid difference with at least one of the amino acid sequences of SEQ ID NO's: 206 to 221, more preferably 206 to 207;

such that (i) when the first stretch of amino acid residues corresponds to one of the amino acid sequences according to a), b) or c), the second stretch of amino acid residues corresponds to one of the amino acid sequences according to d), e), f), g), h) or i); (ii) when the first stretch of amino acid residues corresponds to one of the amino acid sequences according to d), e) or f), the second stretch of amino acid residues corresponds to one of the amino acid sequences according to a), b), c), g), h) or i); or (iii) when the first stretch of amino acid residues corresponds to one of the amino acid sequences according to g), h) or i), the second stretch of amino acid residues corresponds to one of the amino acid sequences according to a), b), c), d), e) or f).

In this specific aspect, the amino acid sequence preferably comprises two or more stretches of amino acid residues chosen from the group consisting of:

i) the amino acid sequences of SEQ ID NO's: 142 to 157, more preferably 142 to 143;

ii) the amino acid sequences of SEQ ID NO's: 174 to 189, more preferably 174 to 175; and iii) the amino acid sequences of SEQ ID NO's: 206 to 221, more preferably 206 to 207;

such that, (i) when the first stretch of amino acid residues corresponds to one of the amino acid sequences of SEQ ID NO's: 142 to 157, more preferably 142 to 143, the second stretch of amino acid residues corresponds to one of the amino acid sequences of SEQ ID NO's: 174 to 189, more preferably 174 to 175 or of SEQ ID NO's: 206 to 221, more preferably 206 to 207; (ii) when the first stretch of amino acid residues corresponds to one of the amino acid sequences of SEQ ID NO's: 174 to 189, more preferably 174 to 175, the second stretch of amino acid residues corresponds to one of the amino acid sequences of SEQ ID NO's: 142 to 157, more preferably 142 to 143 or of SEQ ID NO's: 206 to 221, more preferably 206 to 207; or (iii) when the first stretch of amino acid residues corresponds to one of the amino acid sequences of SEQ ID NO's: 206 to 221, more preferably 206 to 207, the second stretch of amino acid residues corresponds to one of the amino acid sequences of SEQ ID NO's: 142 to 157, more preferably 142 to 143 or of SEQ ID NO's: 174 to 189, more preferably 174 to 175.

Also, in such an amino acid sequence, the at least two stretches of amino acid residues again preferably form part of the antigen binding site for binding against GPCRs.

In an even more specific, but non-limiting aspect, the invention relates to an amino acid sequence directed against GPCRs, that comprises three or more stretches of amino acid residues, in which the first stretch of amino acid residues is chosen from the group consisting of:

a) the amino acid sequences of SEQ ID NO's: 142 to 157, more preferably 142 to 143;

b) amino acid sequences that have at least 80% amino acid identity with at least one of the amino acid sequences of SEQ ID NO's: 142 to 157, more preferably 142 to 143;

c) amino acid sequences that have 3, 2, or 1 amino acid difference with at least one of the amino acid sequences of SEQ ID NO's: 142 to 157, more preferably 142 to 143;

the second stretch of amino acid residues is chosen from the group consisting of:

d) the amino acid sequences of SEQ ID NO's: 174 to 189, more preferably 174 to 175;

e) amino acid sequences that have at least 80% amino acid identity with at least one of the amino acid sequences of SEQ ID NO's: 174 to 189, more preferably 174 to 175;

f) amino acid sequences that have 3, 2, or 1 amino acid difference with at least one of the amino acid sequences of SEQ ID NO's: 174 to 189, more preferably 174 to 175;

and the third stretch of amino acid residues is chosen from the group consisting of:

g) the amino acid sequences of SEQ ID NO's: 206 to 221, more preferably 206 to 207;

h) amino acid sequences that have at least 80% amino acid identity with at least one of the amino acid sequences of SEQ ID NO's: 206 to 221, more preferably 206 to 207;
i) amino acid sequences that have 3, 2, or 1 amino acid difference with at least one of the amino acid sequences of SEQ ID NO's: 206 to 221, more preferably 206 to 207.

Preferably, in this specific aspect, the first stretch of amino acid residues is chosen from the group consisting of the amino acid sequences of SEQ ID NO's: 142 to 157, more preferably 142 to 143; the second stretch of amino acid residues is chosen from the group consisting of the amino acid sequences of SEQ ID NO's: 174 to 189, more preferably 174 to 175; and the third stretch of amino acid residues is chosen from the group consisting of the amino acid sequences of SEQ ID NO's: 206 to 221, more preferably 206 to 207.

Again, preferably, in such an amino acid sequence, the at least three stretches of amino acid residues forms part of the antigen binding site for binding against GPCRs.

Preferred combinations of such stretches of amino acid sequences will become clear from the further disclosure herein.

Preferably, in such amino acid sequences the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 238 to 253, more preferably SEQ ID NO: 238 and SEQ ID NO: 239. This degree of amino acid identity can for example be determined by determining the degree of amino acid identity (in a manner described herein) between said amino acid sequence and one or more of the sequences of SEQ ID NO's: 238 to 253, more preferably SEQ ID NO: 238 and SEQ ID NO: 239, in which the amino acid residues that form the framework regions are disregarded. Also, such amino acid sequences of the invention can be as further described herein.

Also, such amino acid sequences are preferably such that they can specifically bind (as defined herein) to GPCRs; and more in particular bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

When the amino acid sequence of the invention essentially consists of 4 framework regions (FR1 to FR4, respectively) and 3 complementarity determining regions (CDR1 to CDR3, respectively), the amino acid sequence of the invention is preferably such that:

CDR1 is chosen from the group consisting of:
a) the amino acid sequences of SEQ ID NO's: 142 to 157, more preferably 142 to 143;
b) amino acid sequences that have at least 80% amino acid identity with at least one of the amino acid sequences of SEQ ID NO's: 142 to 157, more preferably 142 to 143;
c) amino acid sequences that have 3, 2, or 1 amino acid difference with at least one of the amino acid sequences of SEQ ID NO's: 142 to 157, more preferably 142 to 143;
and/or
CDR2 is chosen from the group consisting of:
d) the amino acid sequences of SEQ ID NO's: 174 to 189, more preferably 174 to 175;
e) amino acid sequences that have at least 80% amino acid identity with at least one of the amino acid sequences of SEQ ID NO's: 174 to 189, more preferably 174 to 175;
f) amino acid sequences that have 3, 2, or 1 amino acid difference with at least one of the amino acid sequences of SEQ ID NO's: 174 to 189, more preferably 174 to 175;
and/or
CDR3 is chosen from the group consisting of:
g) the amino acid sequences of SEQ ID NO's: 206 to 221, more preferably 206 to 207;
h) amino acid sequences that have at least 80% amino acid identity with at least one of the amino acid sequences of SEQ ID NO's: 206 to 221, more preferably 206 to 207;
i) amino acid sequences that have 3, 2, or 1 amino acid difference with at least one of the amino acid sequences of SEQ ID NO's: 206 to 221, more preferably 206 to 207.

In particular, such an amino acid sequence of the invention may be such that CDR1 is chosen from the group consisting of the amino acid sequences of SEQ ID NO's: 142 to 157, more preferably 142 to 143; and/or CDR2 is chosen from the group consisting of the amino acid sequences of SEQ ID NO's: 174 to 189, more preferably 174 to 175; and/or CDR3 is chosen from the group consisting of the amino acid sequences of SEQ ID NO's: 206 to 221, more preferably 206 to 207.

In particular, when the amino acid sequence of the invention essentially consists of 4 framework regions (FR1 to FR4, respectively) and 3 complementarity determining regions (CDR1 to CDR3, respectively), the amino acid sequence of the invention is preferably such that:

CDR1 is chosen from the group consisting of:
a) the amino acid sequences of SEQ ID NO's: 142 to 157, more preferably 142 to 143;
b) amino acid sequences that have at least 80% amino acid identity with at least one of the amino acid sequences of SEQ ID NO's: 142 to 157, more preferably 142 to 143;
c) amino acid sequences that have 3, 2, or 1 amino acid difference with at least one of the amino acid sequences of SEQ ID NO's: 142 to 157, more preferably 142 to 143;
and
CDR2 is chosen from the group consisting of:
d) the amino acid sequences of SEQ ID NO's: 174 to 189, more preferably 174 to 175;
e) amino acid sequences that have at least 80% amino acid identity with at least one of the amino acid sequences of SEQ ID NO's: 174 to 189, more preferably 174 to 175;
f) amino acid sequences that have 3, 2, or 1 amino acid difference with at least one of the amino acid sequences of SEQ ID NO's: 174 to 189, more preferably 174 to 175;
and
CDR3 is chosen from the group consisting of:
g) the amino acid sequences of SEQ ID NO's: 206 to 221, more preferably 206 to 207;
h) amino acid sequences that have at least 80% amino acid identity with at least one of the amino acid sequences of SEQ ID NO's: 206 to 221, more preferably 206 to 207;
i) amino acid sequences that have 3, 2, or 1 amino acid difference with at least one of the amino acid sequences of SEQ ID NO's: 206 to 221, more preferably 206 to 207; or any suitable fragment of such an amino acid sequence In particular, such an amino acid sequence of the invention may be such that CDR1 is chosen from the group consisting of the amino acid sequences of SEQ ID NO's: 142 to 157, more preferably 142 to 143; and CDR2 is chosen from the group consisting of the amino acid sequences of SEQ ID NO's: 174 to 189, more preferably 174 to 175; and CDR3 is chosen from the group consisting of the amino acid sequences of SEQ ID NO's: 206 to 221, more preferably 206 to 207.

Again, preferred combinations of CDR sequences will become clear from the further description herein.

Also, such amino acid sequences are preferably such that they can specifically bind (as defined herein) to GPCRs; and more in particular bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In one preferred, but non-limiting aspect, the invention relates to an amino acid sequence that essentially consists of 4 framework regions (FR1 to FR4, respectively) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 238 to 253, more preferably SEQ ID NO: 238 and SEQ ID NO: 239. This degree of amino acid identity can for example be determined by determining the degree of amino acid identity (in a manner described herein) between said amino acid sequence and one or more of the sequences of SEQ ID NO's: 238 to 253, more preferably SEQ ID NO: 238 and SEQ ID NO: 239, in which the amino acid residues that form the framework regions are disregarded. Such amino acid sequences of the invention can be as further described herein.

In an even more specific, but non-limiting aspect, the invention relates to an amino acid sequence directed against human CXCR4 able to block CXCL12/SDF1-dependent activation of human CXCR4 (such as a Nanobody of the invention, as further described herein), that comprises one or more stretches of amino acid residues chosen from the group consisting of:
a) the amino acid sequences of SEQ ID NO's: 142 to 143;
b) amino acid sequences that have at least 80% amino acid identity with at least one of the amino acid sequences of SEQ ID NO's: 142 to 143;
c) amino acid sequences that have 3, 2, or 1 amino acid difference with at least one of the amino acid sequences of SEQ ID NO's: 142 to 143;
d) the amino acid sequences of SEQ ID NO's: 174 to 175;
e) amino acid sequences that have at least 80% amino acid identity with at least one of the amino acid sequences of SEQ ID NO's: 174 to 175;
f) amino acid sequences that have 3, 2, or 1 amino acid difference with at least one of the amino acid sequences of SEQ ID NO's: 174 to 175;
g) the amino acid sequences of SEQ ID NO's: 206 to 207;
h) amino acid sequences that have at least 80% amino acid identity with at least one of the amino acid sequences of SEQ ID NO's: 206 to 207;
i) amino acid sequences that have 3, 2, or 1 amino acid difference with at least one of the amino acid sequences of SEQ ID NO's: 206 to 207;
or any suitable combination thereof.

When an amino acid sequence of the invention contains one or more amino acid sequences according to b) and/or c):
i) any amino acid substitution in such an amino acid sequence according to b) and/or c) is preferably, and compared to the corresponding amino acid sequence according to a), a conservative amino acid substitution, (as defined herein); and/or
ii) the amino acid sequence according to b) and/or c) preferably only contains amino acid substitutions, and no amino acid deletions or insertions, compared to the corresponding amino acid sequence according to a); and/or
iii) the amino acid sequence according to b) and/or c) may be an amino acid sequence that is derived from an amino acid sequence according to a) by means of affinity maturation using one or more techniques of affinity maturation known per se.

Similarly, when an amino acid sequence of the invention contains one or more amino acid sequences according to e) and/or f):
i) any amino acid substitution in such an amino acid sequence according to e) and/or f) is preferably, and compared to the corresponding amino acid sequence according to d), a conservative amino acid substitution, (as defined herein); and/or
ii) the amino acid sequence according to e) and/or f) preferably only contains amino acid substitutions, and no amino acid deletions or insertions, compared to the corresponding amino acid sequence according to d); and/or
iii) the amino acid sequence according to e) and/or f) may be an amino acid sequence that is derived from an amino acid sequence according to d) by means of affinity maturation using one or more techniques of affinity maturation known per se.

Also, similarly, when an amino acid sequence of the invention contains one or more amino acid sequences according to h) and/or i):
i) any amino acid substitution in such an amino acid sequence according to h) and/or i) is preferably, and compared to the corresponding amino acid sequence according to g), a conservative amino acid substitution, (as defined herein); and/or
ii) the amino acid sequence according to h) and/or i) preferably only contains amino acid substitutions, and no amino acid deletions or insertions, compared to the corresponding amino acid sequence according to g); and/or
iii) the amino acid sequence according to h) and/or i) may be an amino acid sequence that is derived from an amino acid sequence according to g) by means of affinity maturation using one or more techniques of affinity maturation known per se.

It should be understood that the last preceding paragraphs also generally apply to any amino acid sequences of the invention that comprise one or more amino acid sequences according to b), c), e), f), h) or i), respectively.

In this specific aspect, the amino acid sequence preferably comprises one or more stretches of amino acid residues chosen from the group consisting of:
a) the amino acid sequences of SEQ ID NO's: 142 to 143;
b) the amino acid sequences of SEQ ID NO's: 174 to 175; and
c) the amino acid sequences of SEQ ID NO's: 206 to 207;
or any suitable combination thereof.

Also, preferably, in such an amino acid sequence, at least one of said stretches of amino acid residues forms part of the antigen binding site for binding against HUMAN CXCR4.

In a more specific, but again non-limiting aspect, the invention relates to an amino acid sequence directed against human CXCR4, that comprises two or more stretches of amino acid residues chosen from the group consisting of:
a) the amino acid sequences of SEQ ID NO's: 142 to 143;
b) amino acid sequences that have at least 80% amino acid identity with at least one of the amino acid sequences of SEQ ID NO's: 142 to 143;
c) amino acid sequences that have 3, 2, or 1 amino acid difference with at least one of the amino acid sequences of SEQ ID NO's: 142 to 143;
d) the amino acid sequences of SEQ ID NO's: 174 to 175;

e) amino acid sequences that have at least 80% amino acid identity with at least one of the amino acid sequences of SEQ ID NO's: 174 to 175;
f) amino acid sequences that have 3, 2, or 1 amino acid difference with at least one of the amino acid sequences of SEQ ID NO's: 174 to 175;
g) the amino acid sequences of SEQ ID NO's: 206 to 207;
h) amino acid sequences that have at least 80% amino acid identity with at least one of the amino acid sequences of SEQ ID NO's: 206 to 207;
i) amino acid sequences that have 3, 2, or 1 amino acid difference with at least one of the amino acid sequences of SEQ ID NO's: 206 to 207;
such that (i) when the first stretch of amino acid residues corresponds to one of the amino acid sequences according to a), b) or c), the second stretch of amino acid residues corresponds to one of the amino acid sequences according to d), e), f), g), h) or i); (ii) when the first stretch of amino acid residues corresponds to one of the amino acid sequences according to d), e) or f), the second stretch of amino acid residues corresponds to one of the amino acid sequences according to a), b), c), g), h) or i); or (iii) when the first stretch of amino acid residues corresponds to one of the amino acid sequences according to g), h) or i), the second stretch of amino acid residues corresponds to one of the amino acid sequences according to a), b), c), d), e) or f).

In this specific aspect, the amino acid sequence preferably comprises two or more stretches of amino acid residues chosen from the group consisting of:
a) the amino acid sequences of SEQ ID NO's: 142 to 143;
b) the amino acid sequences of SEQ ID NO's: 174 to 175; and
c) the amino acid sequences of SEQ ID NO's: 206 to 207;
such that, (i) when the first stretch of amino acid residues corresponds to one of the amino acid sequences of SEQ ID NO's: 142 to 143, the second stretch of amino acid residues corresponds to one of the amino acid sequences of SEQ ID NO's: 174 to 175 or of SEQ ID NO's: 206 to 207; (ii) when the first stretch of amino acid residues corresponds to one of the amino acid sequences of SEQ ID NO's: 174 to 175, the second stretch of amino acid residues corresponds to one of the amino acid sequences of SEQ ID NO's: 142 to 143 or of SEQ ID NO's: 206 to 207; or (iii) when the first stretch of amino acid residues corresponds to one of the amino acid sequences of SEQ ID NO's: 206 to 207, the second stretch of amino acid residues corresponds to one of the amino acid sequences of SEQ ID NO's: 142 to 143 or of SEQ ID NO's: 174 to 175.

Also, in such an amino acid sequence, the at least two stretches of amino acid residues again preferably form part of the antigen binding site for binding against human CXCR4.

In an even more specific, but non-limiting aspect, the invention relates to an amino acid sequence directed against human CXCR4, that and/or CDR2 is chosen from the group consisting of:
d) the amino acid sequences of SEQ ID NO's: 174 to 175;
e) amino acid sequences that have at least 80% amino acid identity with at least one of the amino acid sequences of SEQ ID NO's: 174 to 175;
f) amino acid sequences that have 3, 2, or 1 amino acid difference with at least one of the amino acid sequences of SEQ ID NO's: 174 to 175;

and/or

CDR3 is chosen from the group consisting of:
g) the amino acid sequences of SEQ ID NO's: 206 to 207;
h) amino acid sequences that have at least 80% amino acid identity with at least one of the amino acid sequences of SEQ ID NO's: 206 to 207;
i) amino acid sequences that have 3, 2, or 1 amino acid difference with at least one of the amino acid sequences of SEQ ID NO's: 206 to 207.

In particular, such an amino acid sequence of the invention may be such that CDR1 is chosen from the group consisting of the amino acid sequences of SEQ ID NO's: 142 to 143; and/or CDR2 is chosen from the group consisting of the amino acid sequences of SEQ ID NO's: 174 to 175; and/or CDR3 is chosen from the group consisting of the amino acid sequences of SEQ ID NO's: 206 to 207.

In particular, when the amino acid sequence of the invention essentially consists of 4 framework regions (FR1 to FR4, respectively) and 3 complementarity determining regions (CDR1 to CDR3, respectively), the amino acid sequence of the invention is preferably such that:

CDR1 is chosen from the group consisting of:
a) the amino acid sequences of SEQ ID NO's: 142 to 143;
b) amino acid sequences that have at least 80% amino acid identity with at least one of the amino acid sequences of SEQ ID NO's: 142 to 143;
c) amino acid sequences that have 3, 2, or 1 amino acid difference with at least one of the amino acid sequences of SEQ ID NO's: 142 to 143;

and

CDR2 is chosen from the group consisting of:
d) the amino acid sequences of SEQ ID NO's: 174 to 175;
e) amino acid sequences that have at least 80% amino acid identity with at least one of the amino acid sequences of SEQ ID NO's: 174 to 175;
f) amino acid sequences that have 3, 2, or 1 amino acid difference with at least one of the amino acid sequences of SEQ ID NO's: 174 to 175;

and

CDR3 is chosen from the group consisting of:
g) the amino acid sequences of SEQ ID NO's: 206 to 207;
h) amino acid sequences that have at least 80% amino acid identity with at least one of the amino acid sequences of SEQ ID NO's: 206 to 207;
i) amino acid sequences that have 3, 2, or 1 amino acid difference with at least one of the amino acid sequences of SEQ ID NO's: 206 to 207; or any suitable fragment of such an amino acid sequence In particular, such an amino acid sequence of the invention may be such that CDR1 is chosen from the group consisting of the amino acid sequences of SEQ ID NO's: 142 to 143; and CDR2 is chosen from the group consisting of the amino acid sequences of SEQ ID NO's: 174 to 175; and CDR3 is chosen from the group consisting of the amino acid sequences of SEQ ID NO's: 206 to 207.

Again, preferred combinations of CDR sequences will become clear from the further description herein.

Also, such amino acid sequences are preferably such that they can specifically bind (as defined herein) to human CXCR4; and more in particular bind to human CXCR4 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In one preferred, but non-limiting aspect, the invention relates to an amino acid sequence that essentially consists of 4 framework regions (FR1 to FR4, respectively) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 238 to 239. This degree of amino acid identity can for example be determined by determining the degree of amino acid identity (in a manner described herein) between said amino acid sequence and one or more of the sequences of SEQ ID NO's: 238 to 239, in which the amino acid residues that form the framework regions are disregarded. Such amino acid sequences of the invention can be as further described herein.

In such an amino acid sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences are preferably such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a Nanobody™ (including but not limited to $V_{HH}$ sequence). Again, suitable framework sequences will be clear to the skilled person, for example on the basis the standard handbooks and the further disclosure and prior art mentioned herein.

In particular, the framework sequences present in the amino acid sequences of the invention may contain one or more of Hallmark residues (as defined herein), such that the amino acid sequence of the invention is a Nanobody™. Some preferred, but non-limiting examples of (suitable combinations of) such framework sequences will become clear from the further disclosure herein.

Again, as generally described herein for the amino acid sequences of the invention, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived). Such fragments may also again be such that they comprise or can form an immunoglobulin fold, or alternatively be such that they do not comprise or cannot form an immunoglobulin fold.

In one specific aspect, such a fragment comprises a single CDR sequence as described herein (and in particular a CDR3 sequence), that is flanked on each side by (part of) a framework sequence (and in particular, part of the framework sequence(s) that, in the immunoglobulin sequence from which the fragment is derived, are adjacent to said CDR sequence. For example, a CDR3 sequence may be preceded by (part of) a FR3 sequence and followed by (part of) a FR4 sequence). Such a fragment may also contain a disulphide bridge, and in particular a disulphide bridge that links the two framework regions that precede and follow the CDR sequence, respectively (for the purpose of forming such a disulphide bridge, cysteine residues that naturally occur in said framework regions may be used, or alternatively cysteine residues may be synthetically added to or introduced into said framework regions). For a further description of these "Expedite fragments", reference is again made to WO 03/050531, as well as to as well as to the US provisional application of Ablynx N.V. entitled "Peptides capable of binding to serum proteins" of Ablynx N.V. (inventors: Revets, Hilde Adi Pierrette; Kolkman, Joost Alexander; and Hoogenboom, Hendricus Renerus Jacobus Mattheus) filed on Dec. 5, 2006

In another aspect, the invention relates to a compound or construct, and in particular a protein or polypeptide (also referred to herein as a "compound of the invention" or "polypeptide of the invention", respectively) that comprises or essentially consists of one or more amino acid sequences of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence of the invention (and/or to the compound or construct in which it is present) and may or may not modify the properties of the amino acid sequence of the invention.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more amino acid sequences of the invention so as to provide a "derivative" of an amino acid sequence or polypeptide of the invention, as further described herein.

The polypeptides of the invention comprise or essentially consist of at least one Nanobody of the invention. Some preferred, but non-limiting examples of polypeptides of the invention are given in SEQ ID NO's: 261 to 264, more preferably SEQ ID NO's 263 to 264.

TABLE 2

Preferred polypeptide or compound sequences (also referred herein as a sequence with a particular name or SEQ ID NO: X, wherein X is a number referring to the relevant amino acid sequence):

| Amino Acid Sequence | Clone name | SEQ ID NO: |
|---|---|---|
| EVQLVESGGGLVQTGGSLRLSCAASGFTFSS YAMSWVRQAPGKGLEWVSGIKSSGDSTRYAG SVKGRFTISRDNAKNMLYLQMYSLKPEDTAV YYCAKSRVSRTGLYTYDNRGQGTQVTVSSGG GGSGGGGSEVQLVESGGGLVQTGGSLRLSCA ASGFTFSSYAMSWVRQAPGKGLEWVSGIKSS GDSTRYAGSVKGRFTISRDNAKNMLYLQMYS LKPEDTAVYYCAKSRVSRTGLYTYDNRGQGT QVTVSS | 238D2-10GS-238D2 | 261 |
| EVQLMESGGGLVQAGGSLRLSCAASGRTFNN YAMGWFRRAPGKEREFVAAITRSGVRSGVSA IYGDSVKDRFTISRDNAKNTLYLQMNSLKPE DTAVYTCAASAIGSGALRRFEYDYSGQGTQV TVSSGGGGSGGGGSGGGGSGGGGSEVQLMES GGGLVQAGGSLRLSCAASGRTFNNYAMGWFR RAPGKEREFVAAITRSGVRSGVSAIYGDSVK DRFTISRDNAKNTLYLQMNSLKPEDTAVYTC AASAIGSGALRRFEYDYSGQGTQVTVSS | 238D4-20GS-238D4 | 262 |
| EVQLVESGGGLVQTGGSLRLSCAASGFTFSS YAMSWVRQAPGKGLEWVSGIKSSGDSTRYAG SVKGRFTISRDNAKNMLYLQMYSLKPEDTAV YYCAKSRVSRTGLYTYDNRGQGTQVTVSSGG GGSGGGGSGGGGSEVQLMESGGGLVQAGGSL LSCAASGRTFNNYAMGWFRRAPGKEREFVAA IRTSGVRSGVSAIYGDSVKDRFTISRDNAK NTLYLQMNSLKPEDTAVYTCAASAIGSGALR RFEYDYSGQGTQVTVSS | 238D2-15GS-238D4 | 263 |
| EVQLVESGGGLVQTGGSLRLSCAASGFTFSS YAMSWVRQAPGKGLEWVSGIKSSGDSTRYAG SVKGRFTISRDNAKNMLYLQMYSLKPEDTAV YYCAKSRVSRTGLYTYDNRGQGTQVTVSSGG GGSGGGGSGGGGSGGGGSEVQLMESGGGLVQ GGSLRLSCAASGRTFNNYAMGWFRRAPGKER AEFVAAITRSGVRSGVSAIYGDSVKDRFTIS RDNAKNTLYLQMNSLKPEDTAVYTCAASAIG SGALRRFEYDYSGQGTQVTVSS | 238D2-20GS-238D4 | 264 |

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are amino acid sequences.

In the compounds or constructs described above, the one or more amino acid sequences of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion (protein) or fusion (polypeptide).

The compounds or polypeptides of the invention can generally be prepared by a method which comprises at least one step of suitably linking the one or more amino acid sequences of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted amino acid sequences form a further aspect of the invention.

In one specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise amino acid sequences or polypeptides of the invention that have been chemically modified to increase the half-life thereof (for example, by means of pegylation); amino acid sequences of the invention that comprise at least one additional binding site for binding to a serum protein (such as serum albumin); or polypeptides of the invention that comprise at least one amino acid sequence of the invention that is linked to at least one moiety (and in particular at least one amino acid sequence) that increases the half-life of the amino acid sequence of the invention. Examples of polypeptides of the invention that comprise such half-life extending moieties or amino acid sequences will become clear to the skilled person based on the further disclosure herein; and for example include, without limitation, polypeptides in which the one or more amino acid sequences of the invention are suitable linked to one or more serum proteins or fragments thereof (such as (human) serum albumin or suitable fragments thereof) or to one or more binding units that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more amino acid sequences of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006.

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention relates to a nucleic acid that encodes an amino acid sequence of the invention or a polypeptide of the invention (or a suitable fragment thereof). Such a nucleic acid will also be referred to herein as a "nucleic acid of the invention" and may for example be in the form of a genetic construct, as further described herein.

In another aspect, the invention relates to a host or host cell that expresses (or that under suitable circumstances is capable of expressing) an amino acid sequence of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention, at least one polypeptide of the invention (or a suitable fragment thereof) and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention also relates to the use of an amino acid sequence, Nanobody or polypeptide of the invention, or of a composition comprising the same, in (methods or compositions for) modulating a GPCR, either in vitro (e.g. in an in vitro or cellular assay) or in vivo (e.g. in an a single cell or in a multicellular organism, and in particular in a mammal, and more in particular in a human being, such as in a human being that is at risk of or suffers from a GPCR related disease or disorder).

The invention also relates to methods for modulating a GPCR, either in vitro (e.g. in an in vitro or cellular assay) or in vivo (e.g. in an a single cell or multicellular organism, and in particular in a mammal, and more in particular in a human being, such as in a human being that is at risk of or suffers from a GPCR related disease or disorder), which method comprises at least the step of contacting a GPCR with at least one amino acid sequence, Nanobody or polypeptide of the invention, or with a composition comprising the same, in a manner and in an amount suitable to modulate a GPCR, with at least one amino acid sequence, Nanobody or polypeptide of the invention.

The invention also relates to the use of an one amino acid sequence, Nanobody or polypeptide of the invention in the preparation of a composition (such as, without limitation, a pharmaceutical composition or preparation as further described herein) for modulating a GPCR, either in vitro (e.g. in an in vitro or cellular assay) or in vivo (e.g. in an a single cell or multicellular organism, and in particular in a mammal, and more in particular in a human being, such as in a human being that is at risk of or suffers from a GPCR related disease or disorder).

In the context of the present invention, "modulating" or "to modulate" generally means either reducing or inhibiting the activity of, or alternatively increasing the activity of, a GPCR, as measured using a suitable in vitro, cellular or in vivo assay (such as those mentioned herein). In particular, "modulating" or "to modulate" may mean either reducing or inhibiting the activity of, or alternatively increasing the activity of, a GPCR, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of a GPCR in the same assay under the same conditions but without the presence of the amino acid sequence, Nanobody or polypeptide of the invention.

As will be clear to the skilled person, "modulating" may also involve effecting a change (which may either be an increase or a decrease) in affinity, avidity, specificity and/or selectivity of a GPCR for one or more of its targets, ligands or substrates; and/or effecting a change (which may either be an increase or a decrease) in the sensitivity of a GPCR for one or more conditions in the medium or surroundings in which a GPCR is present (such as pH, ion strength, the presence of co-factors, etc.), compared to the same conditions but without the presence of the amino acid sequence, Nanobody or polypeptide of the invention. As will be clear to the skilled person, this may again be determined in any suitable manner and/or using any suitable assay known per se, such as the assays described herein or in the prior art cited herein.

"Modulating" may also mean effecting a change (i.e. an activity as an agonist, as an antagonist or as a reverse agonist, respectively, depending on the GPCR and the desired biological or physiological effect) with respect to one or more biological or physiological mechanisms, effects, responses, functions, pathways or activities in which a GPCR (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, such as the assays described herein or in the prior art cited herein. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the amino acid sequence, Nanobody or polypeptide of the invention.

Modulating may for example involve allosteric modulation (see for example George et al., Nat Rev Drug Discov 1:808-820 (2002); Kenakin, Trends Pharmacol Sci 25:186-192 (2002) and Rios et al., Pharmacol Ther 92:71-87 (2001)) and/or reducing or inhibiting the binding of a GPCR to one of its substrates or ligands and/or competing with a natural ligand, substrate for binding to a GPCR. Modulating may also involve activating a GPCR or the mechanism or pathway in which it is involved. Modulating may be reversible or irreversible, but for pharmaceutical and pharmacological purposes will usually be in a reversible manner.

The invention further relates to methods for preparing or generating the amino acid sequences, polypeptides, nucleic acids, host cells, products and compositions described herein. Some preferred but non-limiting examples of such methods will become clear from the further description herein.

Generally, these methods may comprise the steps of:

a) providing a set, collection or library of amino acid sequences; and b) screening said set, collection or library of amino acid sequences for amino acid sequences that can bind to and/or have affinity for GPCRs; and c) isolating the amino acid sequence(s) that can bind to and/or have affinity for GPCRs.

In particular, in step b) of such a method, the set, collection or library may be screened for amino acid sequences that can bind to and/or have affinity for GPCRs that are expressed on the surface of a suitable cell; for amino acid sequences that can bind to and/or have affinity for an extracellular part, region, domain, loop or other extracellular epitope of a GPCR (as described herein); and/or for amino acid sequences that can bind to and/or have affinity for a peptide that has been derived from or based on the amino acid sequence of an extracellular part, region, domain, loop or other extracellular epitope of a GPCR. This can be performed using methods and techniques known per se, for example those mentioned herein.

In such a method, the set, collection or library of amino acid sequences may be any suitable set, collection or library of amino acid sequences. For example, the set, collection or library of amino acid sequences may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of amino acid sequences may be a set, collection or library of heavy chain variable domains (such as $V_H$ domains or $V_{HH}$ domains) or of light chain variable domains. For example, the set, collection or library of amino acid sequences may be a set, collection or library of domain antibodies or single domain antibodies, or may be a set, collection or library of amino acid sequences that are capable of functioning as a domain antibody or single domain antibody.

In a preferred aspect of this method, the set, collection or library of amino acid sequences may be an immune set, collection or library of immunoglobulin sequences, for example derived from a mammal that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s), or a suitable peptide derived therefrom. Alternatively, as mentioned herein, the set, collection or library of amino acid sequences may be an immune set, collection or library of immunoglobulin sequences, for example derived from a mammal that has been suitably immunized with a refolded GPCR or with a cell, or cell fraction or preparation derived from a cell that has a GPCR on its surface.

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In another aspect, the method for generating amino acid sequences comprises at least the steps of:
a) providing a collection or sample of cells expressing amino acid sequences;
b) screening said collection or sample of cells for cells that express an amino acid sequence that can bind to and/or have affinity for GPCRs;
and
c) either (i) isolating said amino acid sequence; or (ii) isolating from said cell a nucleic acid sequence that encodes said amino acid sequence, followed by expressing said amino acid sequence.

In particular, in step b) of such a method, the set, collection or library may be screened for cells that express amino acid sequences that can bind to and/or have affinity for GPCRs that are expressed on the surface of a suitable cell; for cells that express amino acid sequences that can bind to and/or have affinity for an extracellular part, region, domain, loop or other extracellular epitope of a GPCR (as described herein); and/or for cells that express amino acid sequences that can bind to and/or have affinity for a peptide that has been derived from or based on the amino acid sequence of an extracellular part, region, domain, loop or other extracellular epitope of a GPCR. This can be performed using methods and techniques known per se, for example those mentioned herein.

For example, when the desired amino acid sequence is an immunoglobulin sequence, the collection or sample of cells may for example be a collection or sample of B-cells. Also, in this method, the sample of cells may be derived from a mammal that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s), or a suitable peptide derived therefrom. Alternatively, as mentioned herein, the sample of cells may be derived from a mammal that has been suitably immunized with a refolded GPCR or with a cell, or cell fraction or preparation derived from a cell that has a GPCR on its surface.

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820 (2001).

In another aspect, the method for generating an amino acid sequence directed against GPCRs may comprise at least the steps of:
a) providing a set, collection or library of nucleic acid sequences encoding amino acid sequences;
b) screening said set, collection or library of nucleic acid sequences for nucleic acid sequences that encode an amino acid sequence that can bind to and/or has affinity for GPCRs;
and
c) isolating said nucleic acid sequence, followed by expressing said amino acid sequence.

In particular, in step b) of such a method, the set, collection or library may be screened for nucleotide sequences that encode amino acid sequences that can bind to and/or have affinity for GPCRs that are expressed on the surface of a suitable cell; for nucleotide sequences that encode amino acid sequences that can bind to and/or have affinity for an extracellular part, region, domain, loop or other extracellular epitope of a GPCR (as described herein); and/or for nucleotide sequences that encode amino acid sequences that can bind to and/or have affinity for a peptide that has been derived from or based on the amino acid sequence of an extracellular part, region, domain, loop or other extracellular epitope of a GPCR. This can be performed using methods and techniques known per se, for example those mentioned herein.

In such a method, the set, collection or library of nucleic acid sequences encoding amino acid sequences may for example be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

Also, in such a method, the set, collection or library of nucleic acid sequences may encode a set, collection or library of heavy chain variable domains (such as $V_H$ domains or $V_{HH}$ domains) or of light chain variable domains. For example, the set, collection or library of nucleic acid sequences may encode a set, collection or library of domain antibodies or single domain antibodies, or a set, collection or library of amino acid sequences that are capable of functioning as a domain antibody or single domain antibody.

In a preferred aspect of this method, the set, collection or library of amino acid sequences may be an immune set, collection or library of nucleic acid sequences, for example derived from a mammal that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s), or a suitable peptide derived therefrom. Alternatively, as mentioned herein, the set, collection or library of nucleic acid sequences may be an immune set, collection or library derived from a mammal that has been suitably immunized with a refolded GPCR or with a cell, or cell fraction or preparation derived from a cell that has a GPCR on its surface.

The set, collection or library of nucleic acid sequences may for example encode an immune set, collection or library of heavy chain variable domains or of light chain variable domains. In one specific aspect, the set, collection or library of nucleotide sequences may encode a set, collection or library of $V_{HH}$ sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The invention also relates to amino acid sequences that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more amino acid sequences of the invention may be suitably humanized (or alternatively camelized); and/or the amino acid sequence(s) thus obtained may be linked to each other or to one or more other suitable amino acid sequences (optionally via one or more suitable linkers) so as to provide a polypeptide of the invention. Also, a nucleic acid sequence encoding an amino acid sequence of the invention may be suitably humanized (or alternatively camelized) and suitably expressed; and/or one or more nucleic acid sequences encoding an amino acid sequence of the invention may be linked to each other or to one or more nucleic acid sequences that encode other suitable amino acid sequences (optionally via nucleotide sequences that encode one or more suitable linkers), after which the nucleotide sequence thus obtained may be suitably expressed so as to provide a polypeptide of the invention.

The invention further relates to applications and uses of the amino acid sequences, polypeptides, nucleic acids, host cells, products and compositions described herein, as well as to methods for the prevention and/or treatment for diseases and disorders associated with GPCRs. Some preferred but non-limiting applications and uses will become clear from the further description herein. For example, as mentioned herein, it is expected that amino acid sequences, Nanobodies and polypeptides of the invention that are directed against olfactory GPCRs can find use as artificial flavourings or even perfumes. The amino acid sequences, Nanobodies and polypeptides of the invention may also find use as markers for detecting cells that express the GPCRs against which they are directed, for example in vitro (e.g. using Western blot, immunoprecipitation or immunofluorescence techniques) or in vivo (e.g. using suitable imaging techniques). The amino acid sequences, Nanobodies and polypeptides of the invention may also find use in affinity purification techniques for (cells expressing) the GPCRs against which they are directed.

Other aspects, embodiments, advantages and applications of the invention will also become clear from the further description herein, in which the invention will be described and discussed in more detail with reference to the Nanobodies of the invention and polypeptides of the invention comprising the same, which form some of the preferred aspects of the invention.

As will become clear from the further description herein, Nanobodies generally offer certain advantages (outlined herein) compared to "dAb's" or similar (single) domain antibodies or immunoglobulin sequences, which advantages are also provided by the Nanobodies of the invention. However, it will be clear to the skilled person that the more general aspects of the teaching below can also be applied (either directly or analogously) to other amino acid sequences of the invention.

FIGURES

FIG. 1: Schematic representation of the selection procedure.

Figure 2:
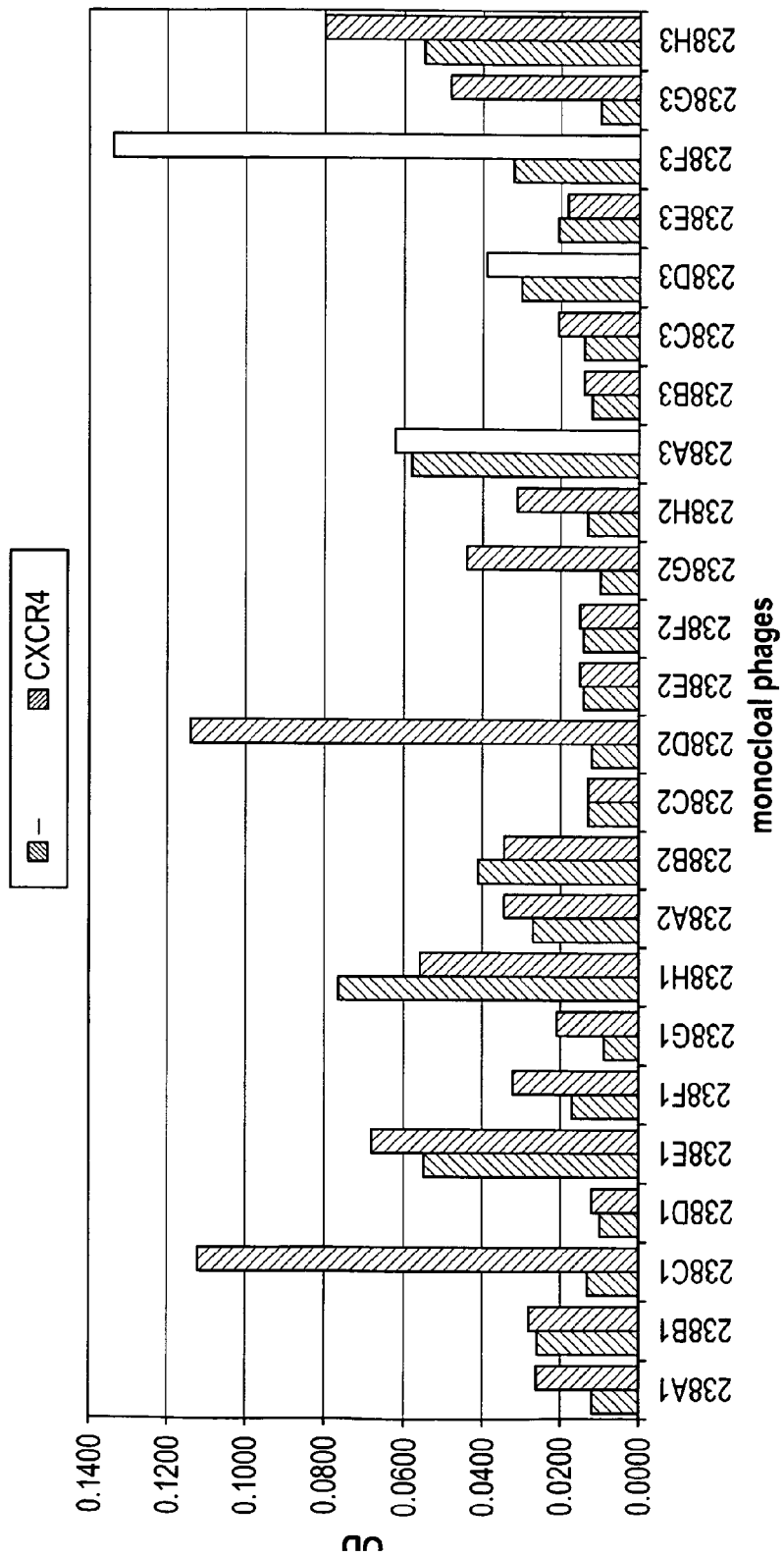

FIG. 2. Results from Phage ELISA (as described in example 1.5). Showed that 238C1, 238D2, 238F3 have high specificity toward CXCR4 expressing membrane compared to non-expressing membrane (−).

Figure 3:
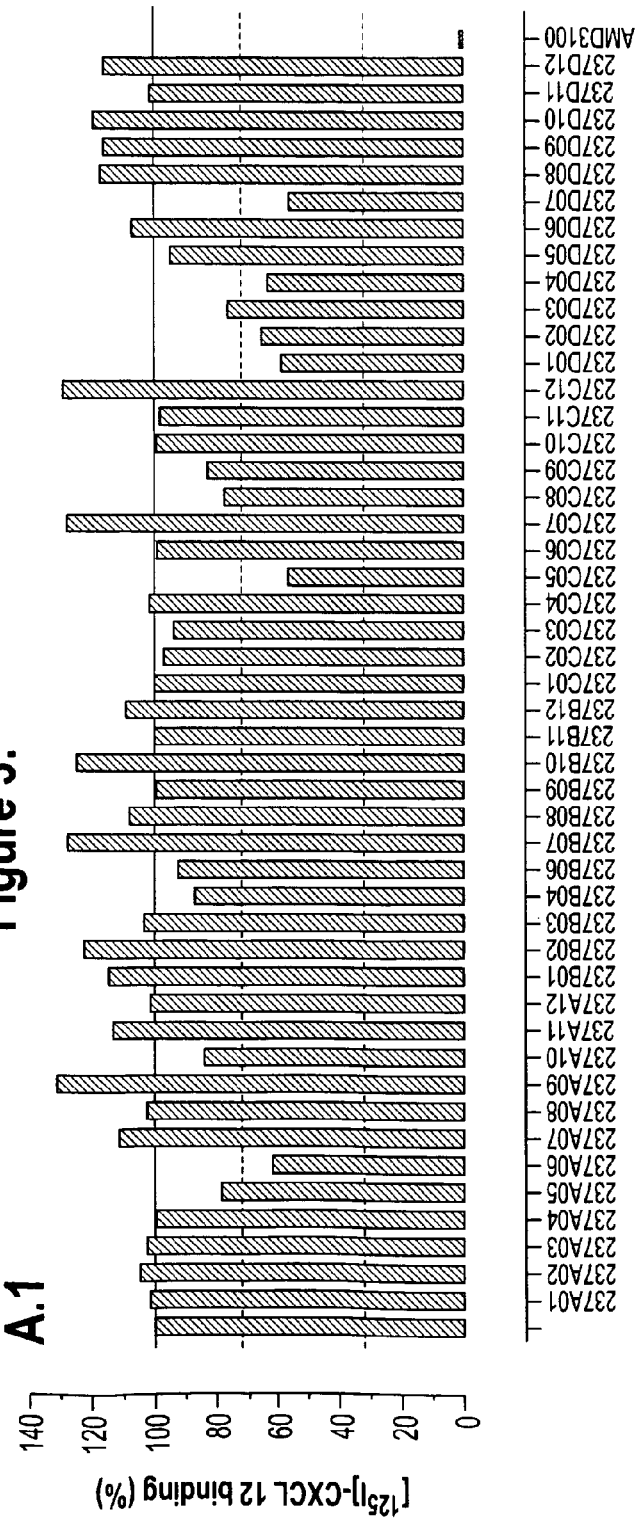
Figure 3:
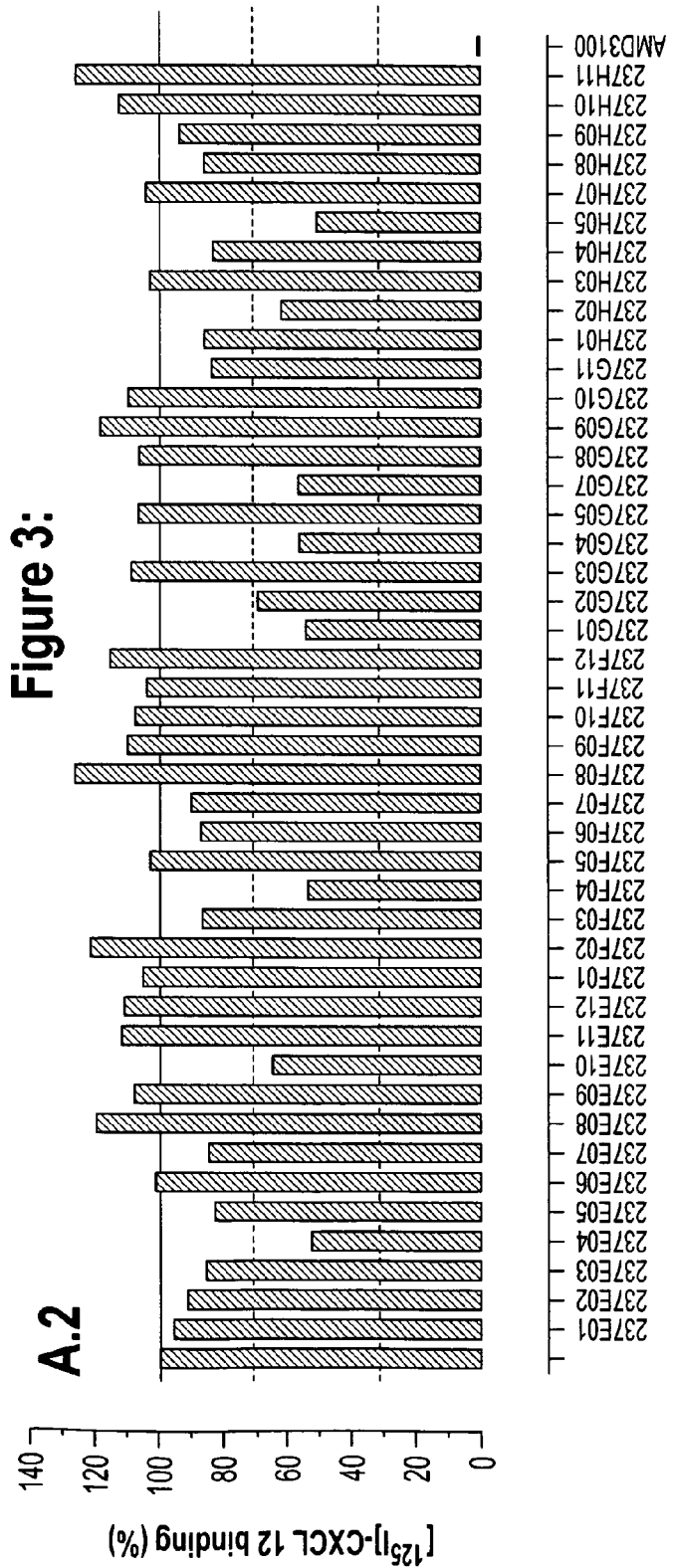
Figure 3:
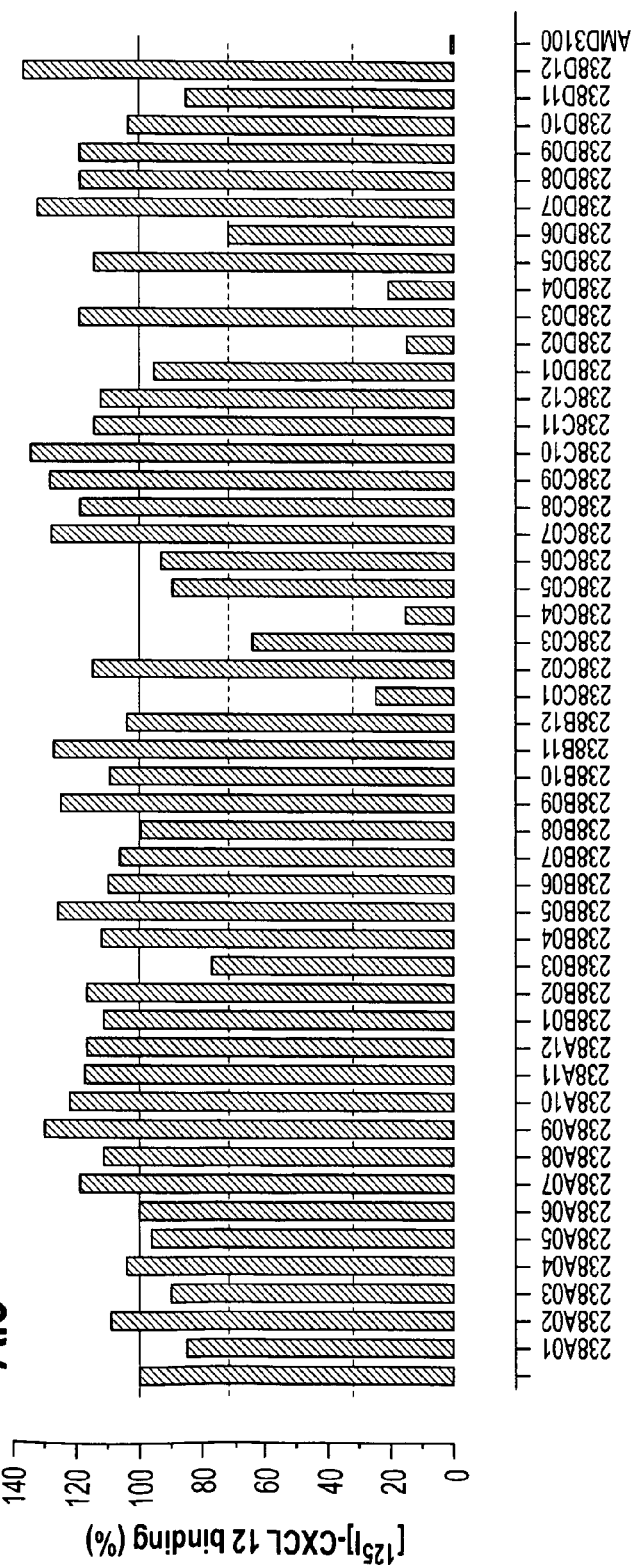
Figure 3:
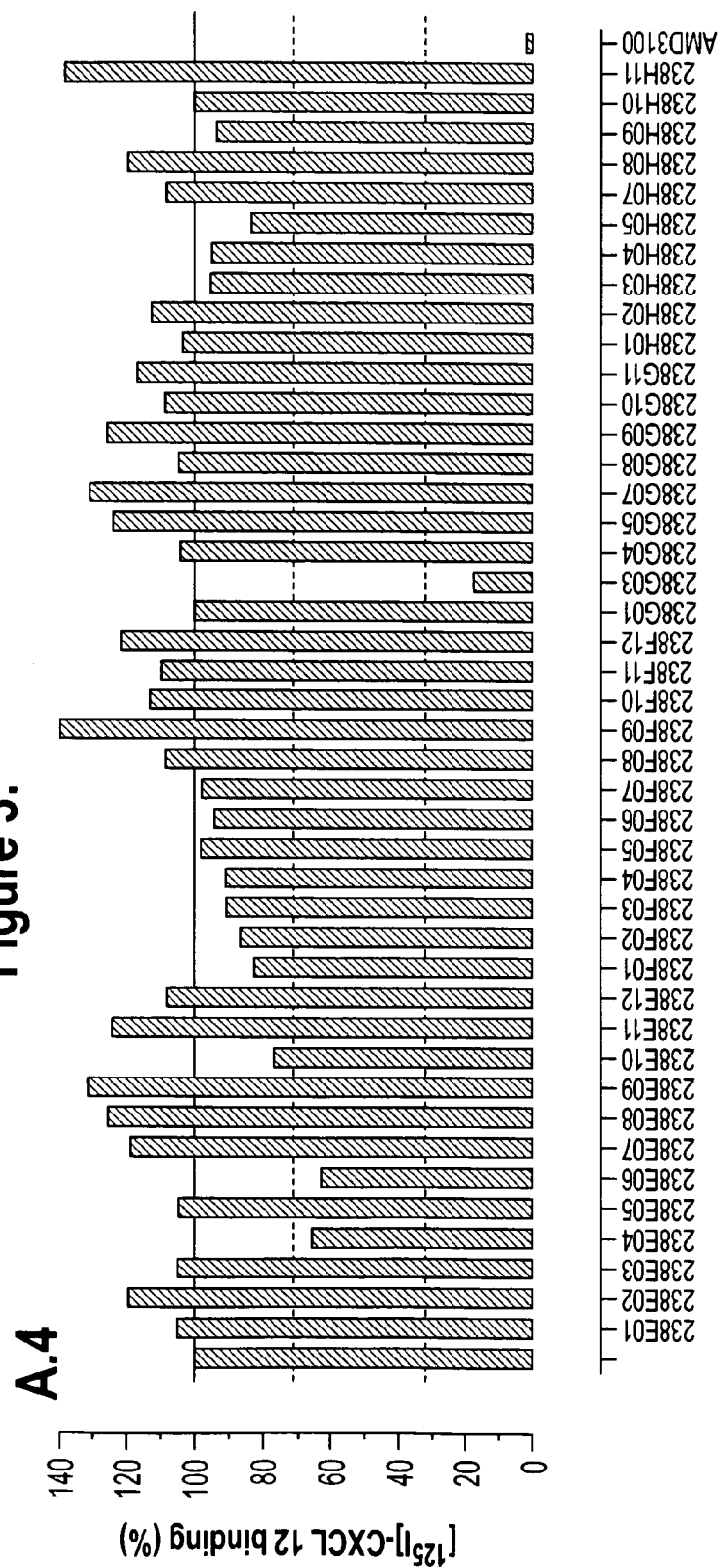
Figure 3:
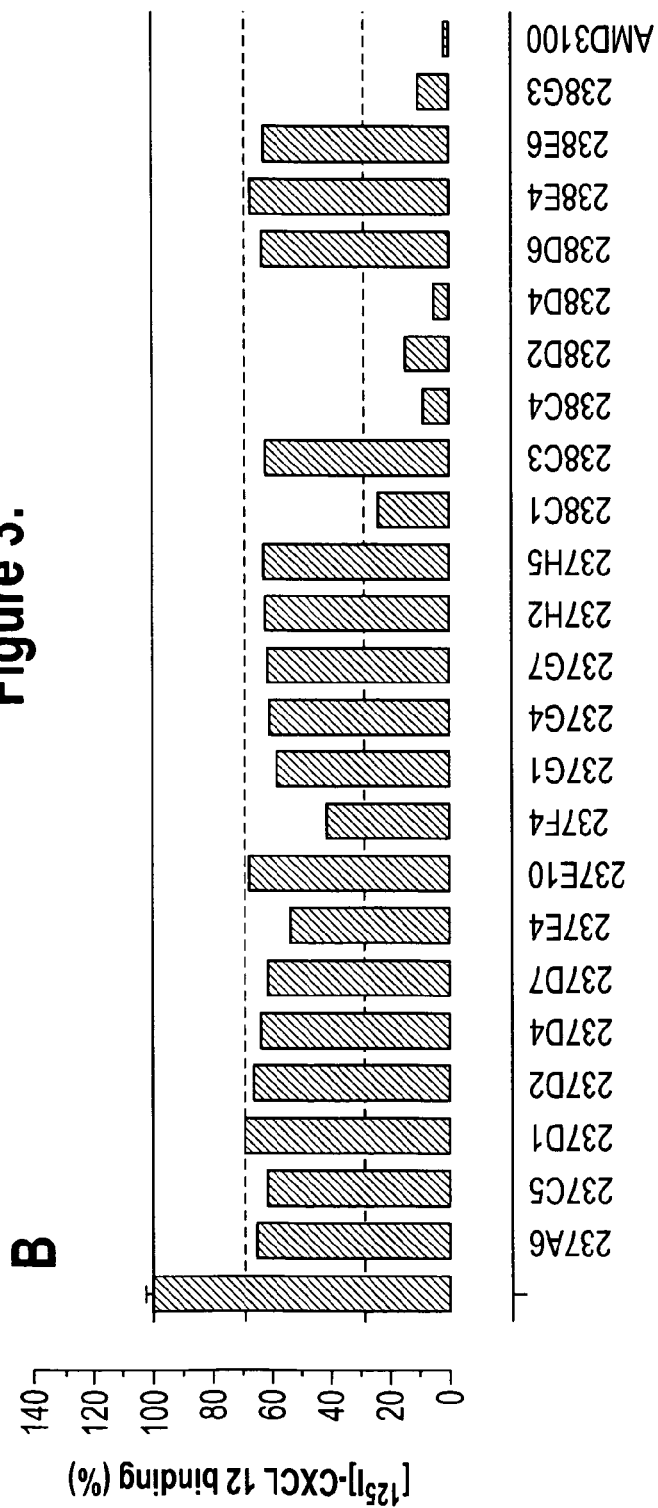

FIG. 3. Primary and secondary screen of Nanobody clones binding to CXCR4. [$^{125}$I]-CXCL12 competition binding experiments were directly performed with periplasma fractions (1:10) on cell membranes from HEK293T cells transiently expressing CXCR4. All primary hits (A) were confirmed in a second screen (B). Control experiments with AMD3100 (3 µM) or vehicle (−) were performed to show full and no displacement, respectively.

Figure 4:
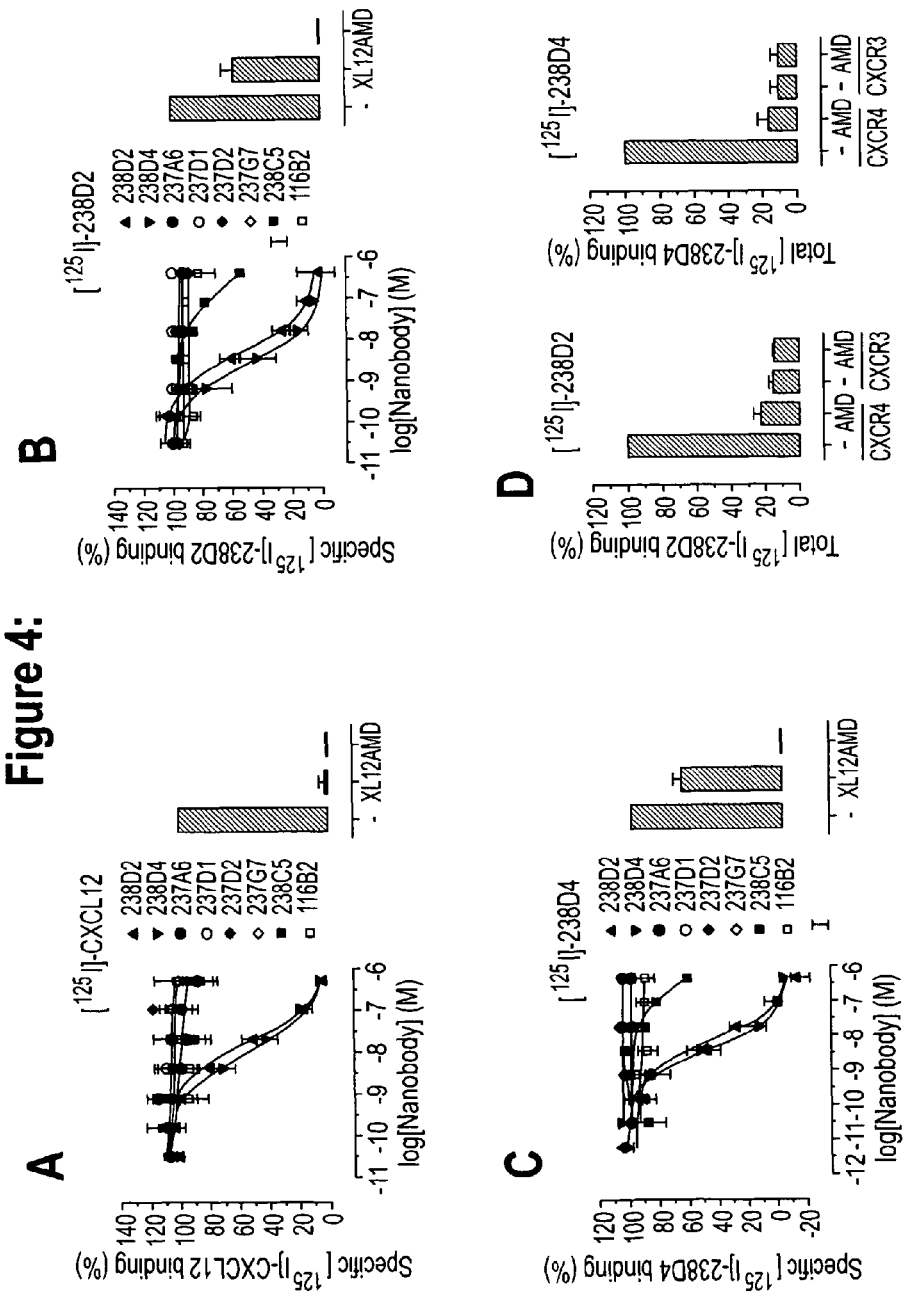

FIG. 4: Competition binding of monovalent Nanobodies and reference ligands to CXCR4. A-C) Competition binding experiments with [$^{125}$I]-CXCL12, [$^{125}$I]-238D2 or [$^{125}$I]-238D4 as radioligand were performed on cell membranes from HEK293T cells transiently expressing CXCR4. Control displacement experiments with AMD3100 (3 µM; AMD), CXCL12 (30 nM; XL12) or vehicle (−) were performed. Data are shown as means±S.E.M. (n=2-6). D) Total binding (vehicle; −) and competition binding experiments (3 µM AMD3100; AMD) with [$^{125}$I]-238D2 or [$^{125}$I]-238D4 as radioligand were performed on cell membranes from HEK293T cells transiently expressing CXCR4 or CXCR3. Data are shown as means±S.E.M. (n=3).

FIG. 5: The monovalent antibodies 238D2 and 238D4 are potent CXCR4 antagonists. A) Inositol phosphate (IP) accumulation experiments were performed in HEK293T cells transiently expressing CXCR4 and Gα$_{qi5}$. Agonism experiments (left graph) show no intrinsic activity for 238D2 and 238D4. Antagonism experiments (right graph) were performed in the presence of CXCL12 (30 nM) following 1 h pre-incubation with 238D2 or 238D4. Control experiments with vehicle (−) or AMD3100 (3 µM; AMD) were performed. Data are shown as means±S.E.M. (n=4). B) Reporter gene experiments were performed in HEK293T cells transiently transfected with pCRE/β-galactosidase and a plasmid encoding CXCR4. No agonist activity for 238D2 and 238D4 was observed (left graph). Data are shown as means±S.E.M. (n=3). Experiments showing competitive antagonism of the CXCL12-induced reporter gene activation were performed by establishing concentration response curves for CXCL12 in the presence of increasing concentrations of 238D2 or 238D4 (right graphs). Schild regression analysis graphs are embedded. Data are shown as means±S.E.M. (n=4-6). C) Chemotaxis experiments using ChemoTx™ plates were performed with Jurkat cells endogenously expressing CXCR4. Agonism experiments (left graph) show migration of Jurkat cells from the upper compartment towards CXCL12 but not towards 238D2 and 238D4 in the lower compartment of the chemotaxis plate. Experiments showing the inhibition of migration towards CXCL12 (0.3 nM) were performed in the presence of 238D2 or 238D4 in both compartments. Control experiments with AMD3100 (3 µM; AMD) were performed. Data are shown as means±S.E.M. (n=4).

FIG. 6: Monoclonals were sequenced and grouped based on their similarity to form families (more than 2 sequences).

The clones on the same lane are 100% identical. U=unique sequences non related to each others.

Figure 7:
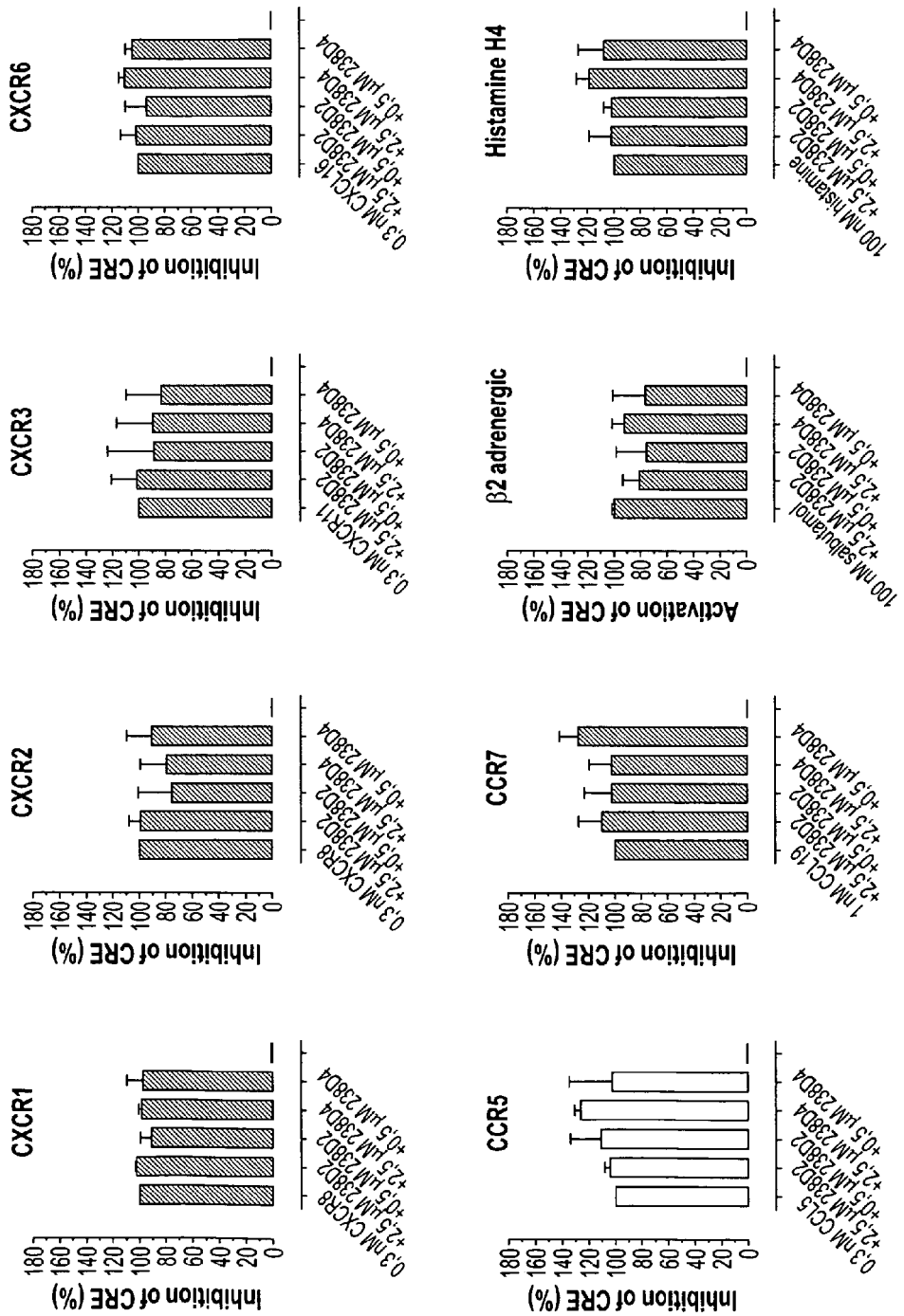

FIG. 7: The monovalent Nanobodies 238D2 and 238D4 do not act as agonists or antagonists on chemokine CCR5, CCR7, CXCR1, CXCR2, CXCR3, CXCR6, $\beta_2$ adrenergic and histamine $H_4$ receptors. The selectivity screen was performed with two concentrations of 238D2 and 238D4 in the presence of a $EC_{50}$-$EC_{80}$ of an agonist and in the absence (for the investigation of $\beta_2$ adrenoceptors) or the presence of forskolin (3 µM; for the investigation of all other receptors) on HEK293T cells transiently transfected with cDNA encoding the mentioned receptors (or mock for the investigation of endogenously expressed $\beta_2$ adrenoceptors) using the CRE/$\beta$-galactosidase reporter gene assay. Data are shown as means±S.E.M. (n=2-3).

Figure 8:
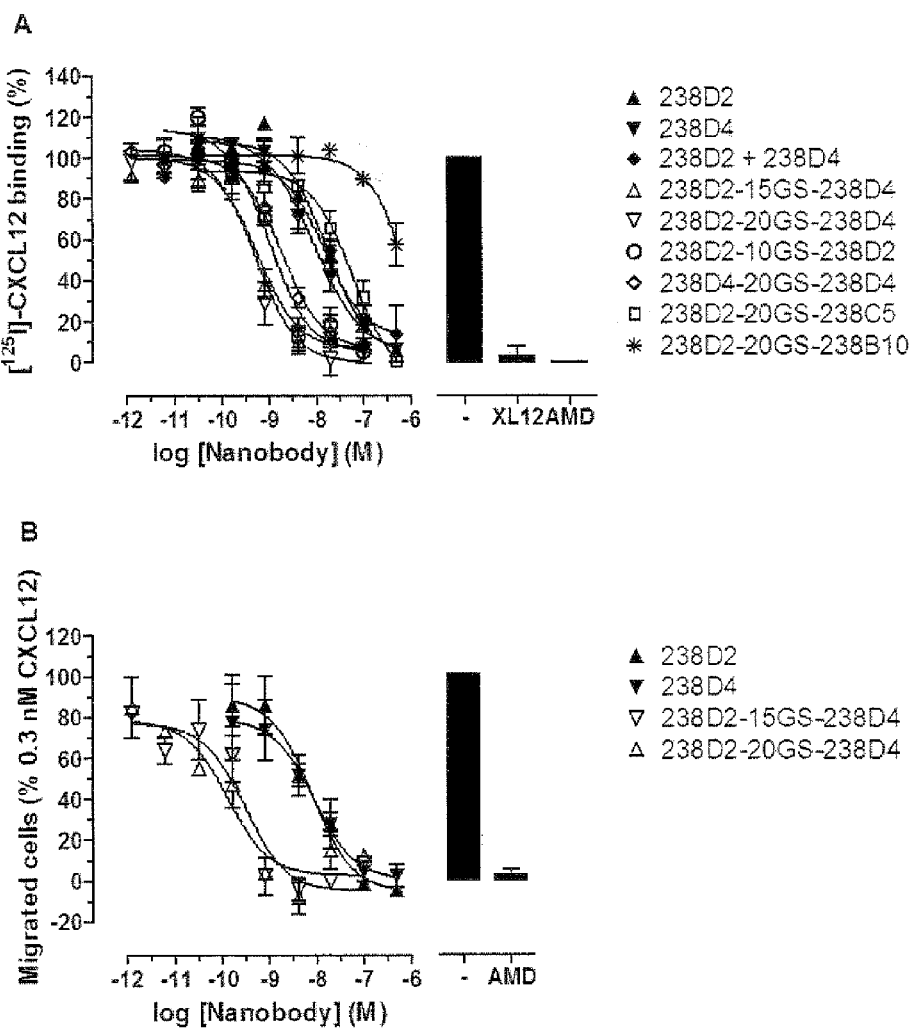

FIG. 8: Bivalent Nanobodies show increased affinity and inhibitory potency compared to their monovalent counterparts. A) Competition binding experiments with [$^{125}$I]-CXCL12 were performed on cell membranes from HEK293T cells transiently expressing CXCR4. Control displacement experiments with AMD3100 (3 µM; AMD), CXCL12 (30 nM; XL12) or vehicle (−) were performed. Data are shown as means±S.E.M. (n=2-6). B) Chemotaxis experiments using ChemoTx™ plates were performed with Jurkat cells endogenously expressing CXCR4. Experiments showing the inhibition of migration towards CXCL12 (0.3 nM) in the lower compartment were performed in the presence of Nanobodies in both compartments. Control experiments with AMD3100 (3 µM; AMD) were performed. Data are shown as means±S.E.M. (n=3-4).

Figure 9:
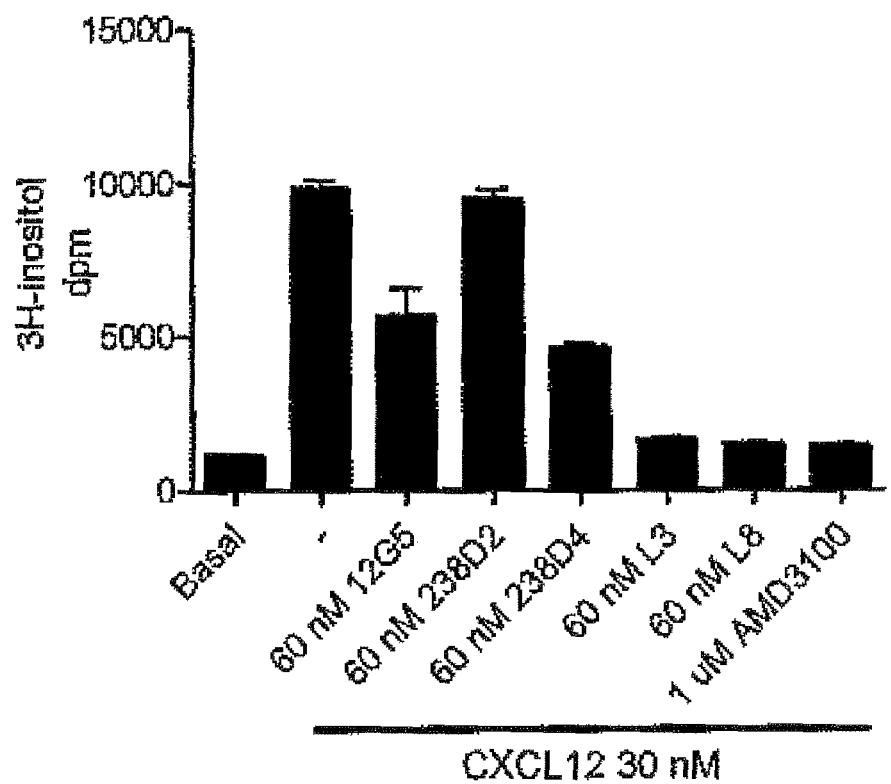

FIG. 9: Bivalent nanobodies inhibit CXCR4-mediated signalings. CXCL12-induced inositol phosphate accumulation in cells transfected with CXCR4 and the chimeric G$\alpha$qi5 protein is inhibited by monovalent and bivalent nanobodies. Bivalent nanobodies present a more potent inhibition.

Figure 10:
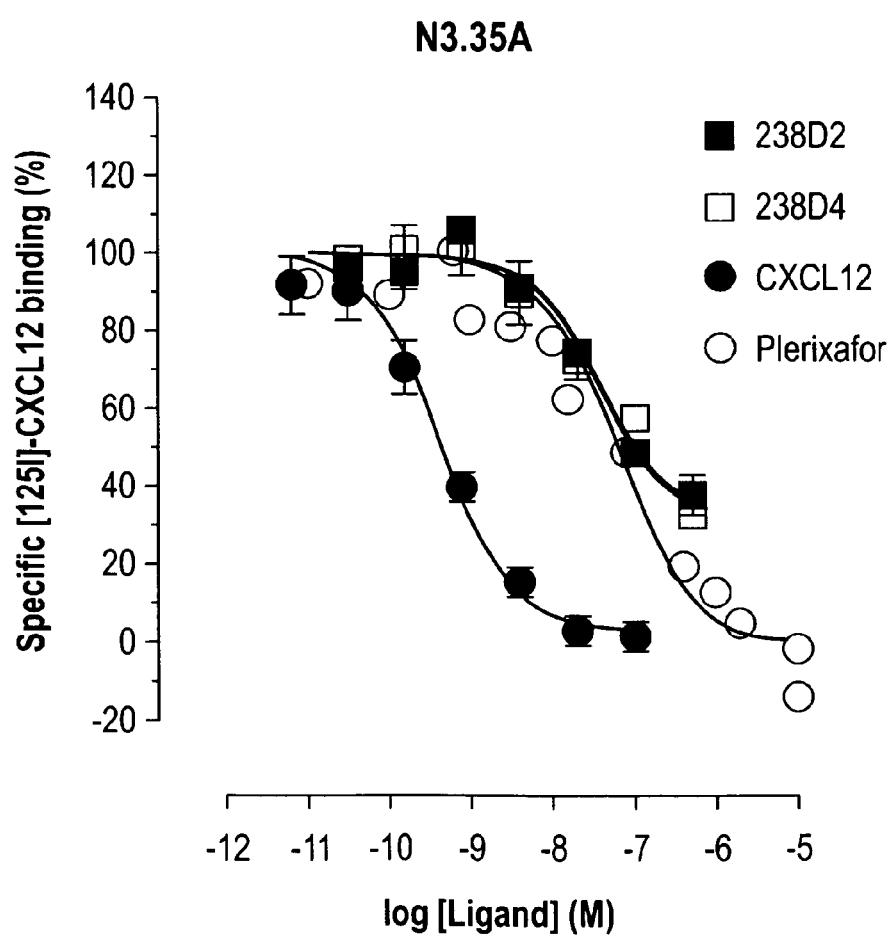

FIG. 10: 238D2 and 238D4 displace [125I]-CXCL12 from the constitutively active CXCR4 mutant N119A. Control experiments with CXCL12 and plerixafor were performed (n=3).

Figure 11:
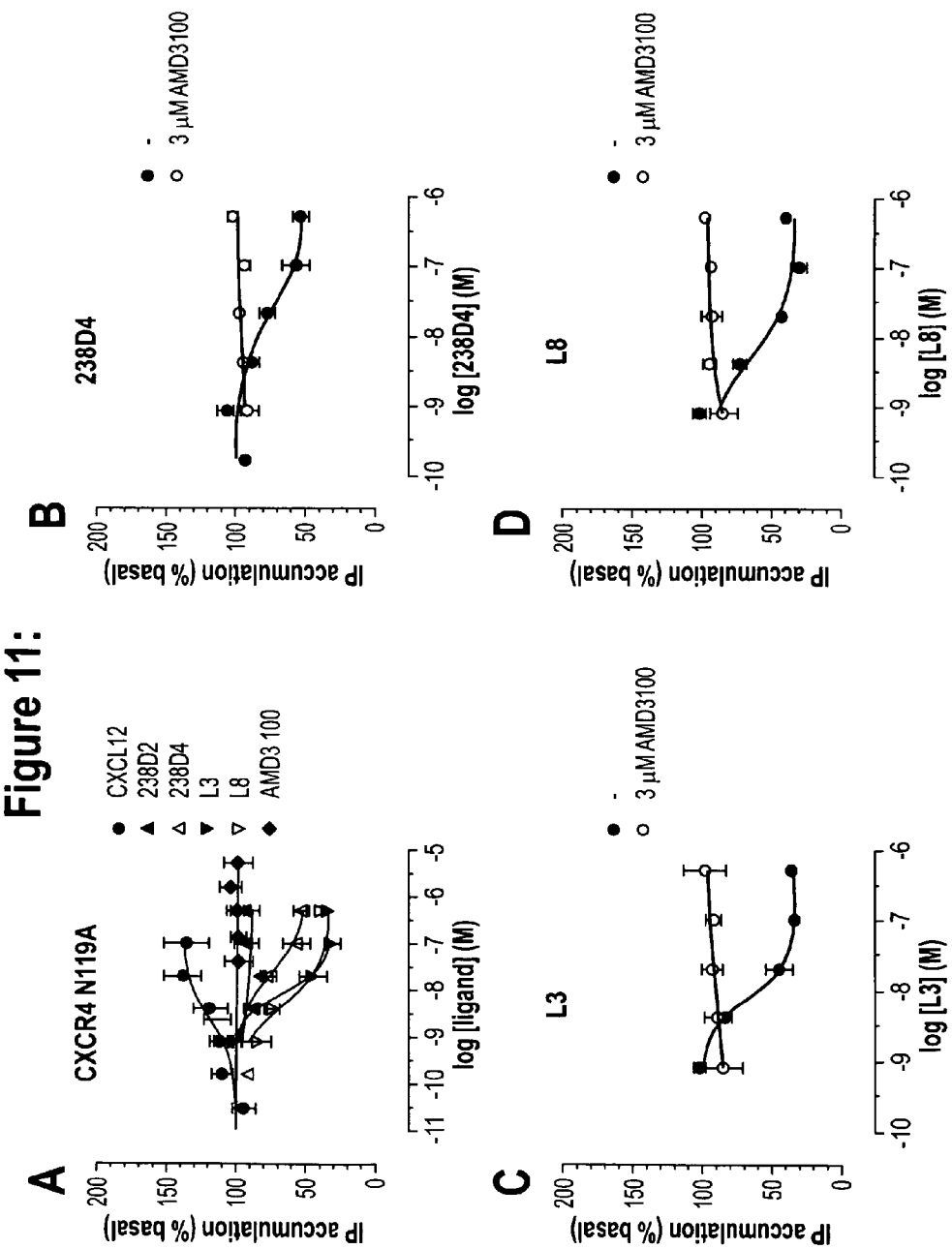

FIG. 11: The nanobodies 238D4, L3 and L8 are inverse antagonists whereas 238D2 behaves as an neutral antagonist at the constitutively active CXCR4 mutant N119A. A) Ligand-mediated alteration of the basal inositol phosphate accumulation by nanobodies and reference ligands (n=3-5). B-D) Inhibiton of the inverse antagonistic effects of 238D4, L3 and L8 by the neutral antagonist plerixafor (AMD3100) (n=2).

DETAILED DESCRIPTION OF THE INVENTION

G protein-coupled receptors (GPCRs), also known as seven transmembrane receptors, 7™ receptors, heptahelical receptors, and G protein linked receptors (GPLR), are a protein family of transmembrane receptors that transduce an extracellular signal (ligand binding) into an intracellular signal (G protein activation). GPCRs are integral membrane proteins that possess seven membrane-spanning domains or transmembrane helices. The extracellular parts of the receptor can be glycosylated. These extracellular loops also contain two highly conserved cysteine residues which build disulfide bonds to stabilize the receptor structure.

The GPCRs form the largest and most diverse group of transmembrane proteins involved in signal transduction (Howard et al., Trends Pharmacol. Sci. 22:132-40, 2001). GPCRs are involved in various cellular and biological functions, such as stimulus-response pathways (from intercellular communication to physiological senses), including, for example, embryogenesis, neurotransmitter release, neurosensation (e.g., 15 chemosensory functions such as taste and smell) (Mombaerts, Science 286:707-711, 1999), neuronal axon pathfinding (Mombaerts et al., Cell 87:675, 1996; Mombaerts et al., Cold Spring Harbor Symp. Quant. Biol. 56:135, 1996), leukocyte targeting to sites of inflammation (Tager et al., J. Exp. Med., 192:439-46, 2000), and cell survival, proliferation, and differentiation. (Ryan et al., J. Biol. Chem. 273:13613-24, 1998).

The complexity of the GPCR repertoire surpasses that of the immunoglobulin and T cell receptor genes combined, with members of the GPCR superfamily estimated at as many as 2,000, or more than 1.5% of the human genome. Further, members of the GPCR superfamily are the direct or indirect target of more than 50% of the current pharmaceutical drugs used clinically in humans.

The diversity of functions is matched by the wide range of ligands recognized by members of the family, from photons (rhodopsin, the archetypal GPCR) to small molecules (in the case of the histamine receptors) to proteins (for example, chemokine receptors). For an overview of the human GPCR family and ligands of human GPCRs reference is made to FIG. 1 in the US application 2002/0106739.

GPCRs can be grouped into 4 classes based on structural homology and functional similarity: Class A (rhodopsin-like), Class B (secretin-like), Class C (metabotropic/pheromone), and Class D (Fungal pheromone), of which Class A receptors, Class B receptors, and receptors with virtually non-existent carboxyl-terminal tails form the major classes. GPCRs can be classified accordingly based on their interactions with an affinity for rat,8-arrestin-2 in HEK-293 cells and may be predicted based on the amino acid residues in their carboxyl-terminal tail and the length of their carboxyl-terminal tail. A Class B receptor is a GPCR that has one or more sites of phosphorylation (e.g., clusters of phosphorylation sites) properly positioned in its carboxyl-terminal tail such that it does recruit rat 8-arrestin-2 to endosomes in HEK-293 cells under conditions as described in U.S. Pat. No. 5,891, 646, Oakley, et al., Journal of Biological Chemistry, Vol 275, No. 22, pp 17201-17210, Jun. 2, 2000, and Oakley et al., Journal of Biological Chemistry, Vol. 276, No. 22, pp 19452-19460, 2001. A Class A receptor is a GPCR that does not have one or more sites of phosphorylation (e.g., clusters of phosphorylation sites) properly positioned in its carboxyl-terminal tail such that it does not recruit rat p-arrestin-2 to endosomes in HEK-293 cells under conditions as described above for Class B receptors. Receptors with virtually non existent carboxyl-terminal tails include, for example, olfactory and taste receptors.

Some examples of the biological and physiological roles of GPCRs include:
   the visual sense: the opsins use a photo isomerization reaction to translate electromagnetic radiation into cellular signals. Rhodopsin, for example, uses the conversion of 11-cis-retinal to all-trans-retinal for this purpose.
   the sense of smell: receptors of the olfactory epithelium bind odorants (olfactory receptors) and pheromones (vomeronasal receptors)
   behavioral and mood regulation: receptors in the mammalian brain bind several different neurotransmitters, including serotonin, dopamine, GABA and glutamate.
   regulation of immune system activity and inflammation: chemokine receptors bind ligands that mediate intercellular communication between cells of the immune system; receptors such as histamine receptors bind inflammatory mediators and engage target cell types in the inflammatory response autonomic nervous system transmission: both the sympathetic and parasympathetic nervous systems are regulated by GPCR pathways. These systems are responsible for control of many automatic functions of the body such as blood pressure, heart rate and digestive processes.

Generally, for GPCRs reference is made to the standard handbooks, such as the G Protein Coupled Receptors Handbook, L. Devi (Ed.), Humana Press, 2005, as well as to the available databases, such as GPCRDB (see for example http://www.gpcr.org/7tm/htmls/entries.html).

Thus, generally, as used herein, the term "G-protein coupled receptor" (or "GPCR") refers to a receptor that, when expressed by a cell, associates with a G-protein (e.g., a protein composed of cc, P and y subunits and which hydrolyzes GTP). Preferably, the GPCR is a "seven transmembrane segment receptor" (or "7 TMS receptor"), which refers to a protein that structurally comprises seven hydrophobic transmembrane spanning regions.

Some non-limiting examples of GPCRs include, but are not limited to:

GPCRs that are known targets for pharmaceuticals (either small molecules or biologicals) that are currently on the market or in clinical development (for example, those mentioned herein);

the luteinizing hormone releasing hormone (LHRH) (also known as gonadotropin releasing hormone, GnRH) receptor, the MI muscarinic receptor and the D2-adrenergic receptor;

opioid receptors, endothelin receptors, angiotensin receptors, neuropeptide Y receptors and serotonin K receptors;

GPCRs that couple to (i.e., associates with) a Gq/1 I G-protein, such as LHRH (=GnRH), acetylcholine (ml, 3 and 5 subtypes), MI muscarinic, adenosine 1, CC-adrenergic (alA, alB and a I C subtypes), angiotensin (AT I A subtype), bombesin (BB I and B132 subtypes), bradykinin (132 subtype), C5a, cholycystokinin (CCKa and CCKb subtypes), endothelin (Eta and Etb subtypes), glutamate (mGlul, 5 subtypes), 5HT (2A, B and C subtypes), histamine (H I subtype), neurotensin, neurokinin (NK2, 3 subtypes), oxytocin, thyrotropin releasing hormone (TRIJ), thyroid stimulating hormone (TSH), thromoboxane A2 and vasopressin (V I a subtypes);

GPCRs that couple to a Gs G-protein, such as the following receptors: P2-adrenergic, cardiac P-adrenergic, histamine (H2 subtype), thyrotropin, growth hormone releasing factor, adrenocorticotropic hormone (ACTH), 5HT4, follicle stimulating hormone (FSH), thyroid stimulating hormone (TSH), GLP-1, glucagon, domamine5 (D5), doparnine1 (DI), calcitonin, adenosine-2p (A2p), vasopressin2, vasoactive intestinal polypeptide and parathyroid hormone;

GPCRs that couple to a Gi G-protein, such as the following receptors: 5HT (I A, I B, I D and I F subtypes), mGlutamineR (2, 3 subtypes), dopamine4 (D4), dopamine-2 (D2) cannabinoid, adenosine3 (A3), somatostatin (4, 3 subtypes), t-opioid, 6-opioid, K-Opioid, neuropeptide Y (1, 2 subtypes);

The GPCRs mentioned in US 2002/0106739;

The GPCRs listed in Table 1 of Lundstrom et al., J. Struct. Funct. Genomics, 2006 Nov. 22; [Epub ahead of print]

GPCRs that are so-called "orphan" receptors, i.e. a GPCR that is structurally similar to other GPCRs but for which the natural ligand is not yet known;

The GPCRs mentioned in Table C;

The GPCRs mentioned in Table D.

Other GPCRs will be clear to the skilled person, for example from the standard handbooks, such as the G Protein Coupled Receptors Handbook, L. Devi (Ed.), Humana Press, 2005; as well as from the standard databases, such as GPCRDB (see for example http://www.gpcr.org/7tm/htmls/entries.html).

In the present description, examples and aspects:

a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, $10^{th}$ Ed. Blackwell Publishing, UK (2001); and Janeway et al., "Immunobiology" (6th Ed.), Garland Science Publishing/Churchill Livingstone, N.Y. (2005), as well as to the general background art cited herein;

b) GPCR receptor molecule exists in a conformational equilibrium between active and inactive biophysical states. The binding of ligands to the receptor may shift the equilibrium toward the active receptor states. Four types of ligands exist: agonists are ligands that shift the equilibrium in favour of active states; inverse agonists or antagonists are ligands that shift the equilibrium in favour of inactive states; and neutral antagonists are ligands that do not affect the equilibrium. As used herein, an "antagonist" is a ligand which competitively binds to the receptor at the same site as an agonist, but does not activate an intracellular response initiated by an active form of a receptor, and thereby inhibits the intracellular response induced by an agonist, by at least 10%, preferably 15-25%, more preferably 25-50% and most preferably, 50-100%, as compared to the intracellular response in the presence of an agonist and in the absence of an antagonist. As used herein, an "agonist" refers to a ligand that activates an intracellular response when it binds to the GDP. An agonist according to the invention may increase the intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc . . . ), as compared to the intracellular response in the absence of agonist. As used herein, an "inverse agonist" refers to a ligand which decreases a constitutive activity of a cell surface receptor when it binds to a receptor but does not competitively bind to the receptor at the same site as an agonist. An inverse agonist according to the invention may decrease the constitutive intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc), as compared to the intracellular response in the absence of inverse agonist. As used herein, an "inverse antagonist" refers to a ligand which decreases a constitutive activity of a cell surface receptor when it binds to a receptor and competitively binds to the receptor at the same site as an agonist. An inverse antagonist according to the invention may decrease the constitutive intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc . . . ), as compared to the intracellular response in the absence of inverse antagonist. Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

c) Amino acid residues will be indicated according to the standard three-letter or one-letter amino acid code, as mentioned in Table A-2;

TABLE A-2 one-letter and three-letter amino acid code

| | | | |
|---|---|---|---|
| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, uncharged (at pH 6.0-7.0) | Glycine[2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged (at pH 6.0-7.0) | Lysine | Lys | K |
| | Arginine | Arg | R |
| | Histidine[4] | His | H |
| | Aspartate | Asp | D |
| | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residue can generally be considered essentially uncharged at a pH of about 6.5.

d) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;

e) For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Nad. Acad. Sci. USA 81: 140-144, 1984; Kyte & Doolittle; J. Molec. Biol. 157: 105-132, 198 1, and Goldman et al., Ann Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

f) Amino acid sequences and nucleic acid sequences are said to be "exactly the same" if they have 100% sequence identity (as defined herein) over their entire length;

g) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

h) When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the firstmentioned nucleotide sequence or amino acid sequence, respectively, but more usually this generally means that the firstmentioned nucleotide sequence or amino acid sequence comprises within its sequence a stretch of nucleotides or amino acid residues, respectively, that has the same nucleotide sequence or amino acid sequence, respectively, as the latter sequence, irrespective of how the firstmentioned sequence has actually been generated or obtained (which may for example be by any suitable method described herein). By means of a non-limiting example, when a Nanobody of the invention is said to comprise a CDR sequence, this may mean that said CDR sequence has been incorporated into the Nanobody of the invention, but more usually this generally means that the Nanobody of the invention contains within its sequence a stretch of amino acid residues with the same amino acid sequence as said CDR sequence, irrespective of how said Nanobody of the invention has been generated or obtained. It should also be noted that when the latter amino acid sequence has a specific biological or structural function, it preferably has essentially the same, a similar or an equivalent biological or structural function in the firstmentioned amino acid sequence (in other words, the firstmentioned amino acid sequence is preferably such that the latter sequence is capable of performing essentially the same, a similar or an equivalent biological or structural function). For example, when a Nanobody of the invention is said to comprise a CDR sequence or framework sequence, respectively, the CDR sequence and framework are preferably capable, in said Nanobody, of functioning as a CDR sequence or framework sequence, respectively. Also, when a nucleotide sequence is said to comprise another nucleotide sequence, the firstmentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the firstmentioned, larger nucleotide sequence).

i) A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis;

j) The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein);

k) The term "antigenic determinant" refers to the epitope on the antigen recognized by the antigen-binding molecule (such as a Nanobody or a polypeptide of the invention) and more in particular by the antigen-binding site of said molecule. The terms "antigenic determinant" and "epitope" may also be used interchangeably herein.

l) An amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

m) The term "specificity" refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship $[K_D=1/K_A]$.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation of second). The on-rate $k_{on}$ has units $M^{-1} s^{-1}$. The on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ $s^{-1}$ (near irreversible complex with a $t_{1/2}$ of multiple days) to 1 $s^{-1}$ ($t_{1/2}$=0.69 s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance. Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref} \ll K_{D\ ref}, K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

n) The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

o) As further described herein, the total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein;

p) The amino acid residues of a Nanobody are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of $V_H$ domains, which methods can also be applied in an analogous manner to $V_{HH}$ domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to $V_{HH}$ domains by Riechmann and Muyldermans will be followed, unless indicated otherwise; and q) The Figures, Sequence Listing and the Experimental Part/ Examples are only given to further illustrate the invention and should not be interpreted or construed as limiting the scope of the invention and/or of the appended aspects in any way, unless explicitly indicated otherwise herein.

For a general description of heavy chain antibodies and the variable domains thereof, reference is inter alia made to the prior art cited herein, to the review article by Muyldermans in Reviews in Molecular Biotechnology 74 (2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference.

In accordance with the terminology used in the art (see the above references), the variable domains present in naturally occurring heavy chain antibodies will also be referred to as "$V_{HH}$ domains", in order to distinguish them from the heavy chain variable domains that are present in conventional 4-chain antibodies (which will be referred to hereinbelow as "$V_H$ domains") and from the light chain variable domains that are present in conventional 4-chain antibodies (which will be referred to hereinbelow as "$V_L$ domains").

As mentioned in the prior art referred to above, $V_{HH}$ domains have a number of unique structural characteristics and functional properties which make isolated $V_{HH}$ domains (as well as Nanobodies based thereon, which share these structural characteristics and functional properties with the naturally occurring $V_{HH}$ domains) and proteins containing the same highly advantageous for use as functional antigen-binding domains or proteins. In particular, and without being limited thereto, $V_{HH}$ domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a $V_H$ domain covalently linked to a $V_L$ domain).

Because of these unique properties, the use of $V_{HH}$ domains and Nanobodies as single antigen-binding proteins or as antigen binding domains (i.e. as part of a larger protein or polypeptide) offers a number of significant advantages over the use of conventional $V_H$ and $V_L$ domains, scFv's or conventional antibody fragments (such as Fab- or F(ab')$_2$- fragments):

only a single domain is required to bind an antigen with high affinity and with high selectivity, so that there is no need to have two separate domains present, nor to assure that these two domains are present in the right spatial conformation and configuration (i.e. through the use of especially designed linkers, as with scFv's);

$V_{HH}$ domains and Nanobodies can be expressed from a single gene and require no post-translational folding or modifications;

$V_{HH}$ domains and Nanobodies can easily be engineered into multivalent and multispecific formats (as further discussed herein);

$V_{HH}$ domains and Nanobodies are highly soluble and do not have a tendency to aggregate (as with the mouse-derived "dAb's" described by Ward et al., Nature, Vol. 341, 1989, p. 544);

$V_{HH}$ domains and Nanobodies are highly stable to heat, pH, proteases and other denaturing agents or conditions (see for example Ewert et al, supra);

$V_{HH}$ domains and Nanobodies are easy and relatively cheap to prepare, even on a scale required for production. For example, $V_{HH}$ domains, Nanobodies and proteins/polypeptides containing the same can be produced using microbial fermentation (e.g. as further described below) and do not require the use of mammalian expression systems, as with for example conventional antibody fragments;

$V_{HH}$ domains and Nanobodies are relatively small (approximately 15 kDa, or 10 times smaller than a conventional IgG) compared to conventional 4-chain antibodies and antigen-binding fragments thereof, and therefore show high(er) penetration into tissues (including but not limited to solid tumors and other dense tissues) than such conventional 4-chain antibodies and antigen binding fragments thereof;

$V_{HH}$ domains and Nanobodies can show so-called cavity-binding properties (inter alia due to their extended CDR3 loop, compared to conventional $V_H$ domains) and can therefore also access targets and epitopes not accessible to conventional 4-chain antibodies and antigen-binding fragments thereof. For example, it has been shown that $V_{HH}$ domains and Nanobodies can inhibit enzymes (see for example WO 97/49805; Transue et al., Proteins 1998 Sep. 1; 32(4): 515-22; Lauwereys et al., EMBO J. 1998 Jul. 1; 17(13): 3512-20).

In a specific and preferred aspect, the invention provides Nanobodies against GPCRs, and in particular Nanobodies against GPCRs from a warm-blooded animal, and more in particular Nanobodies against GPCRs from a mammal, and especially Nanobodies against human GPCRs; as well as proteins and/or polypeptides comprising at least one such Nanobody.

In particular, the invention provides Nanobodies against GPCRs, and proteins and/or polypeptides comprising the same, that have improved therapeutic and/or pharmacological properties and/or other advantageous properties (such as, for example, improved ease of preparation and/or reduced costs of goods), compared to conventional antibodies against GPCRs or fragments thereof, compared to constructs that could be based on such conventional antibodies or antibody fragments (such as Fab' fragments, F(ab')2 fragments, ScFv constructs, "diabodies" and other multispecific constructs (see for example the review by Holliger and Hudson, Nat. Biotechnol. 2005 September; 23(9):1126-36)), and also compared to the so-called "dAb's" or similar (single) domain antibodies that may be derived from variable domains of conventional antibodies. These improved and advantageous properties will become clear from the further description herein, and for example include, without limitation, one or more of:

increased affinity and/or avidity for GPCRs, either in a monovalent format, in a multivalent format (for example in a bivalent format) and/or in a multispecific format (for example one of the multispecific formats described hereinbelow);

increased potentcy for specific properties such as e.g. ability to increase inverse antagonistic effect by coupling, formatting e.g. an inverse antagonist with an antagonist (see experimantel part);

better suitability for formatting in a multivalent format (for example in a bivalent format);

better suitability for formatting in a multispecific format (for example one of the multispecific formats described hereinbelow);

improved suitability or susceptibility for "humanizing" substitutions (as defined herein); less immunogenicity, either in a monovalent format, in a multivalent format (for example in a bivalent format) and/or in a multispecific format (for example one of the multispecific formats described hereinbelow);

increased stability, either in a monovalent format, in a multivalent format (for example in a bivalent format) and/or in a multispecific format (for example one of the multispecific formats described hereinbelow);

increased specificity towards GPCRs, either in a monovalent format, in a multivalent format (for example in a bivalent format) and/or in a multispecific format (for example one of the multispecific formats described hereinbelow);

decreased or where desired increased cross-reactivity with GPCRs from different species;

and/or one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described hereinbelow).

As generally described herein for the amino acid sequences of the invention, the Nanobodies of the invention are preferably in essentially isolated form (as defined herein), or form part of a protein or polypeptide of the invention (as defined herein), which may comprise or essentially consist of one or more Nanobodies of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than GPCRs), so as to provide a monovalent, multivalent or multispecific polypeptide of the invention, respectively, all as described herein. In particular, such a protein or polypeptide may comprise or essentially consist of one or more Nanobodies of the invention and optionally one or more (other) Nanobodies (i.e. directed against other targets than GPCRs), all optionally linked via one or more suitable linkers, so as to provide a monovalent, multivalent or multispecific Nanobody construct, respectively, as further described herein. Such proteins or polypeptides may also be in essentially isolated form (as defined herein).

In a Nanobody of the invention, the binding site for binding against GPCRs is preferably formed by the CDR sequences. Optionally, a Nanobody of the invention may also, and in addition to the at least one binding site for binding against GPCRs, contain one or more further binding sites for binding against other antigens, proteins or targets. For methods and positions for introducing such second binding sites, reference is for example made to Keck and Huston, Biophysical Journal, 71, October 1996, 2002-2011; EP 0 640 130; WO 06/07260 and the US provisional application by Ablynx N.V. entitled "Immunoglobulin domains with multiple binding sites" filed on Nov. 27, 2006.

As generally described herein for the amino acid sequences of the invention, when a Nanobody of the invention (or a polypeptide of the invention comprising the same) is intended for administration to a subject (for example for therapeutic and/or diagnostic purposes as described herein), it is preferably directed against human GPCRs; whereas for veterinary purposes, it is preferably directed against GPCRs from the species to be treated. Also, as with the amino acid sequences of the invention, a Nanobody of the invention may or may not be cross-reactive (i.e. directed against GPCRs from two or more species of mammal, such as against human GPCRs and GPCRs from at least one of the species of mammal mentioned herein).

Also, again as generally described herein for the amino acid sequences of the invention, the Nanobodies of the invention may generally be directed against any antigenic determinant, epitope, part, domain, subunit or confirmation (where applicable) of GPCRs. However, it is generally assumed and preferred that the Nanobodies of the invention (and polypeptides comprising the same) are directed against and/or have been raised against at least one extracellular region, domain, loop or other extracellular epitope of a GPCR (or a suitable peptide derived therefrom).

As already described herein, the amino acid sequence and structure of a Nanobody can be considered—without however being limited thereto—to be comprised of four framework regions or "FR's" (or sometimes also referred to as "FW's"), which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Some preferred framework sequences and CDR's (and combinations thereof) that are present in the Nanobodies of the invention are as described herein. Other suitable CDR sequences can be obtained by the methods described herein.

According to a non-limiting but preferred aspect of the invention, (the CDR sequences present in) the Nanobodies of the invention are such that:

the Nanobodies can bind to GPCRs with a dissociation constant ($K_D$) of $10^{-5}$ to $10^{12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that:

the Nanobodies can bind to GPCRs with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5 M^{-1}s^{-1}$ and $10^7$ $M^{-1}s^{-1}$;

and/or such that they:

the Nanobodies can bind to GPCRs with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ s$^{-1}$ and $10^{-6}$ s$^{-1}$, more preferably between $10^{-3}$ s$^{-1}$ and $10^{-6}$ s$^{-1}$, such as between $10^{-4}$ s$^{-1}$ and $10^{-6}$ s$^{-1}$.

Preferably, (the CDR sequences present in) the Nanobodies of the invention are such that: a monovalent Nanobody of the invention (or a polypeptide that contains only one Nanobody of the invention) is preferably such that it will bind to GPCRs with an affinity less than 500 nM, preferably less than 200 nM, more preferably less than 10 nM, such as less than 500 pM.

The affinity of the Nanobody of the invention against GPCRs can be determined in a manner known per se, for example using the general techniques for measuring $K_D$, $K_A$, $k_{off}$ or $k_{on}$ mentioned herein, as well as some of the specific assays described herein.

Some preferred IC50 values for binding of the Nanobodies of the invention (and of polypeptides comprising the same) to GPCRs will become clear from the further description and examples herein.

In a preferred but non-limiting aspect, the invention relates to a Nanobody (as defined herein) against GPCRs, which consists of 4 framework regions (FR1 to FR4 respectively) and 3 complementary determining regions (CDR1 to CDR3 respectively), in which:

CDR1 is chosen from the group consisting of:
a) the amino acid sequences of SEQ ID NO's: 142 to 157, more preferably 142 to 143;
b) amino acid sequences that have at least 80% amino acid identity with at least one of the amino acid sequences of SEQ ID NO's: 142 to 157, more preferably 142 to 143;
c) amino acid sequences that have 3, 2, or 1 amino acid difference with at least one of the amino acid sequences of SEQ ID NO's: 142 to 157, more preferably 142 to 143;
and/or
CDR2 is chosen from the group consisting of:
d) the amino acid sequences of SEQ ID NO's: 174 to 189, more preferably 174 to 175;
e) amino acid sequences that have at least 80% amino acid identity with at least one of the amino acid sequences of SEQ ID NO's: 174 to 189, more preferably 174 to 175;
f) amino acid sequences that have 3, 2, or 1 amino acid difference with at least one of the amino acid sequences of SEQ ID NO's: 174 to 189, more preferably 174 to 175;
and/or
CDR3 is chosen from the group consisting of:
g) the amino acid sequences of SEQ ID NO's: 206 to 221, more preferably 206 to 207;
h) amino acid sequences that have at least 80% amino acid identity with at least one of the amino acid sequences of SEQ ID NO's: 206 to 221, more preferably 206 to 207;
i) amino acid sequences that have 3, 2, or 1 amino acid difference with at least one of the amino acid sequences of SEQ ID NO's: 206 to 221, more preferably 206 to 207;
or any suitable fragment of such an amino acid sequence.

In particular, according to this preferred but non-limiting aspect, the invention relates to a Nanobody (as defined herein) against human CXCR4, which consists of 4 framework regions (FR1 to FR4 respectively) and 3 complementarity determining regions (CDR1 to CDR3 respectively), in which:

CDR1 is chosen from the group consisting of:
a) the amino acid sequences of SEQ ID NO's: 142 to 157, more preferably 142 to 143;
b) amino acid sequences that have at least 80% amino acid identity with at least one of the amino acid sequences of SEQ ID NO's: 142 to 157, more preferably 142 to 143;
c) amino acid sequences that have 3, 2, or 1 amino acid difference with at least one of the amino acid sequences of SEQ ID NO's: 142 to 157, more preferably 142 to 143;
and
CDR2 is chosen from the group consisting of:
d) the amino acid sequences of SEQ ID NO's: 174 to 189, more preferably 174 to 175;
e) amino acid sequences that have at least 80% amino acid identity with at least one of the amino acid sequences of SEQ ID NO's: 174 to 189, more preferably 174 to 175;
f) amino acid sequences that have 3, 2, or 1 amino acid difference with at least one of the amino acid sequences of SEQ ID NO's: 174 to 189, more preferably 174 to 175;
and
CDR3 is chosen from the group consisting of:
g) the amino acid sequences of SEQ ID NO's: 206 to 221, more preferably 206 to 207;
h) amino acid sequences that have at least 80% amino acid identity with at least one of the amino acid sequences of SEQ ID NO's: 206 to 221, more preferably 206 to 207;
i) amino acid sequences that have 3, 2, or 1 amino acid difference with at least one of the amino acid sequences of SEQ ID NO's: 206 to 221, more preferably 206 to 207;
or any suitable fragment of such an amino acid sequences.

As generally mentioned herein for the amino acid sequences of the invention, when a Nanobody of the invention contains one or more CDR1 sequences according to b) and/or c):
i) any amino acid substitution in such a CDR according to b) and/or c) is preferably, and compared to the corresponding CDR according to a), a conservative amino acid substitution (as defined herein);
and/or
ii) the CDR according to b) and/or c) preferably only contains amino acid substitutions, and no amino acid deletions or insertions, compared to the corresponding CDR according to a);
and/or
iii) the CDR according to b) and/or c) may be a CDR that is derived from a CDR according to a) by means of affinity maturation using one or more techniques of affinity maturation known per se.

Similarly, when a Nanobody of the invention contains one or more CDR2 sequences according to e) and/or f):
i) any amino acid substitution in such a CDR according to e) and/or f) is preferably, and compared to the corresponding CDR according to d), a conservative amino acid substitution (as defined herein);
and/or
ii) the CDR according to e) and/or f) preferably only contains amino acid substitutions, and no amino acid deletions or insertions, compared to the corresponding CDR according to d);
and/or
iii) the CDR according to e) and/or f) may be a CDR that is derived from a CDR according to d) by means of affinity maturation using one or more techniques of affinity maturation known per se.

Also, similarly, when a Nanobody of the invention contains one or more CDR3 sequences according to h) and/or i):
i) any amino acid substitution in such a CDR according to h) and/or i) is preferably, and compared to the corresponding CDR according to g), a conservative amino acid substitution (as defined herein);

and/or ii) the CDR according to h) and/or i) preferably only contains amino acid substitutions, and no amino acid deletions or insertions, compared to the corresponding CDR according to g);

and/or iii) the CDR according to h) and/or i) may be a CDR that is derived from a CDR according to g) by means of affinity maturation using one or more techniques of affinity maturation known per se.

It should be understood that the last three paragraphs generally apply to any Nanobody of the invention that comprises one or more CDR1 sequences, CDR2 sequences and/or CDR3 sequences according to b), c), e), f), h) or i), respectively.

Of the Nanobodies of the invention, Nanobodies comprising one or more of the CDR's explicitly listed above are particularly preferred; Nanobodies comprising two or more of the CDR's explicitly listed above are more particularly preferred; and Nanobodies comprising three of the CDR's explicitly listed above are most particularly preferred.

Some particularly preferred, but non-limiting combinations of CDR sequences, as well as preferred combinations of CDR sequences and framework sequences, are mentioned in Table A-1 below, which lists the CDR sequences and framework sequences that are present in a number of preferred (but non-limiting) Nanobodies of the invention. As will be clear to the skilled person, a combination of CDR1, CDR2 and CDR3 sequences that occur in the same clone (i.e. CDR1, CDR2 and CDR3 sequences that are mentioned on the same line in Table A-1) will usually be preferred (although the invention in its broadest sense is not limited thereto, and also comprises other suitable combinations of the CDR sequences mentioned in Table A-1). Also, a combination of CDR sequences and framework sequences that occur in the same clone (i.e. CDR sequences and framework sequences that are mentioned on the same line in Table A-1) will usually be preferred (although the invention in its broadest sense is not limited thereto, and also comprises other suitable combinations of the CDR sequences and framework sequences mentioned in Table A-1, as well as combinations of such CDR sequences and other suitable framework sequences, e.g. as further described herein).

Also, in the Nanobodies of the invention that comprise the combinations of CDR's mentioned in Table A-1, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which:

i) any amino acid substitution in such a CDR is preferably, and compared to the corresponding CDR sequence mentioned in Table A-1, a conservative amino acid substitution (as defined herein);

and/or ii) any such CDR sequence preferably only contains amino acid substitutions, and no amino acid deletions or insertions, compared to the corresponding CDR sequence mentioned in Table A-1;

and/or iii) any such CDR sequence is a CDR that is derived by means of a technique for affinity maturation known per se, and in particular starting from the corresponding CDR sequence mentioned in Table A-1.

However, as will be clear to the skilled person, the (combinations of) CDR sequences, as well as (the combinations of) CDR sequences and framework sequences mentioned in Table A-1 will generally be preferred.

TABLE A-1

| | | | | CDR's and framework sequences of Nanobodies against human CXCR4 | | | |
|---|---|---|---|---|---|---|---|
| SEQ FR1 | SEQ CDR1 | SEQ FR2 | SEQ CDR2 | SEQ FR3 | | SEQ CDR3 | SEQ FR4 |
| 126 EVQLVESGG GLVQTGGSL RLSCAASGF TFS | 142 SYAMS | 158 WVRQAPG KGLEWVS | 174 GIKSSGDSTRY AGSVKG | 190 RFTISRDNAKNML YLQMYSLKPEDTA VYYCAK | | 206 SRVSRT GLYTYD N | 222 RGQGTQ VTVSS |
| 127 EVQLMESGG GLVQAGGSL RLSCAASGR TFN | 143 NYAMG | 158 WFRRAPG KEREFVA | 175 AITRSGVRSGV SAIYGDSVKD | 191 RFTISRDNAKNTL YLQMNSLKPEDTA VYTCAA | | 207 SAIGSG ALRRFE YDY | 223 SGQGTQ VTVSS |
| 128 KVQLVESGG GLVQPGGSL RLSCAASGF AFS | 144 IHTMS | 160 WVRQAPG KGPEWVS | 176 TIKPSGDTTNY ANAVKG | 192 RFTISRDNAKNTL YLQMNSLKPEDTA VYYCAK | | 208 DYFGTG V | 224 RGQGTQ VTVSS |
| 129 EVQLVESGG GLVQPGGSL RLSCAASGF TFD | 145 DYAMS | 161 WVRQAPG KGLEWVS | 177 AISWNGGSTDY ADSVKG | 193 RFTISRDNAKNTL YLQMNSLKSEDTA EYYCAR | | 209 DQGPFY SGTYYY TRQYGY | 225 RGQGTQ VTVSS |
| 130 EVQLVESGG GFVQAGGSL RLSCETSGR PLL | 146 GYTIA | 162 WFRQVPG KEREFVA | 178 YHRWSDGANLY ADSVKG | 194 RFTISGHNAKNTV SLQMNSLKPEDTA VYYCAA | | 210 ARMTTS NDKEYL Y | 226 WGQGTQ VTVSS |
| 131 EVQLMESGG GLVQAGGSL RLACAASGF TFE | 147 DYAIG | 163 WFRKAPG KEREGVS | 179 CISGSDGSTTY ADSVKG | 195 RFTISTDNAKNTV YLEMNSLKPEDTA VYYCAQ | | 211 QYGVGG RVVCPG PYEYDV | 227 WGQGTQ VTVSS |

TABLE A-1-continued

CDR's and framework sequences of Nanobodies against human CXCR4

| SEQFR1 | SEQCDR1 | SEQFR2 | SEQCDR2 | SEQFR3 | SEQCDR3 | SEQFR4 |
|---|---|---|---|---|---|---|
| 132 EVQLVESGG GFVQAGGSL RLSCETSGR PLL | 148 GYTIA | 164 WFRQVPG KEREFVA | 180 YHRWSDGANLY ADSVKG | 196 RFTISGHNAKNTV SLQMNSLKPEDTA VYYCAA | 212 AWMTTS NDKEYL Y | 228 WGQGTQ VTVSS |
| 133 EVQLVESGG GLVQAGGSL RLSCAASGL TFS | 149 PSAMA | 165 WYRQGP GKERDFV | 181 STIWSRGDTYF ADSVKG | 197 RFTISRDTANYTL YLQMNNLKPEDTA VA | 213 RVRPYG QYDY YYCSL | 229 WGQGTQ VTVSS |
| 134 EVQLVESGG GLVQPGGSL RLSCAASGF TFD | 150 DYAMS | 166 WVRQAPG KGLEWVS | 182 AISWNGGSADY ADSVKG | 198 RFTISRDNAKNTL YLQMNSLKSEDTA VYYCAK | 214 DQGPFY SGTYYY TKGYAY | 230 WGQGTQ VTVSS |
| 135 EVQLVESGG GLAQAGGSL RLSCAASGR TYA | 151 MG | 167 WFRQAPG KEREFVT | 183 TSRLITDNIIY ADSVKG | 199 RFTLTRDNGKNTV YLQMDSLKPDDTA VYFCAA | 215 RQNYSR SVFGAK DYDY | 231 WGQGTQ VTVSS |
| 136 EVQLVESGG GLVQAGGSL RLSCAASGS IFS | 152 LNAMG | 168 WYRQAPG KQRELVA | 184 GITSSTSTYYA DSVKG | 200 RFTISRDNTKNTV YLQMNSLKPEDTA VYYCNV | 216 DCPDYY SDYECP LED | 232 RGQGTQ VTVSS |
| 137 EVQLVESGG GLAQPGGPL RLTCEASGV IYS | 153 VNDMG | 169 WYRQAPG KQRELVA | 185 VITSGGGTNYV DSVKG | 201 RFTISGDNRKKTV YLQMNSLKPEDTA VYYCSI | 217 YYSSGIS VTVSS TLRS | 233 WGQGTQ VTVSS |
| 138 EVQLVESGG GLVQPGGSL RLSCEVSGF TRD | 154 YYTIG | 170 WFRQAPG KEREGVS | 186 CISSSDGSTAY LGSVQG | 202 RFTVSRDNAKNTV YLQMNNLKPEDTA VYYCAL | 218 BSADSR CSIGSIG FTWLYN N | 234 WGQGTQ VTVSS |
| 139 EVQLVESGG GLVQPGGSL RLSCAASSF IGN | 155 YHAIV | 171 WLRQAPG KELEGVS | 187 CITSRDSITYY ASFVKG | 203 RFTISRDDAKNTV YLQMNNLKPEDTA VYYCAV | 219 BTSMTC PTLIVRF NY | 235 RGQGTQ VTVSS |
| 140 EVQLVESGG GLVQAGGSL RLSCKASGG TFN | 156 NYAMG | 172 WFRRAPG KEREFVA | 188 AITRSGVRSGV AIYGDSVKD | 204 RFTISRDNVKNTL YLQMNTLKPEDTA VYTCAA | 220 SAIGSGA LRRFEY DY | 236 SGQGTQ VTVSS |
| 141 EVQLVESGG GLVQAGGSL RLSCAASGS FFS | 157 INAMG | 173 WYRQAPG KQRELVA | 189 SITSGGSTVYA DSVKG | 205 RFTISRDNYNTVY LQMNSLKPEDTAV YYCNA | 221 DGVPEW GKVQYP DTY | 237 RGQGTQ VTVSS |

Thus, in the Nanobodies of the invention, at least one of the CDR1, CDR2 and CDR3 sequences present is suitably chosen from the group consisting of the CDR1, CDR2 and CDR3 sequences, respectively, listed in Table A-1; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table A-1; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table A-1.

In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein), and a CDR3 sequence is chosen from suitable CDR3 sequence (i.e. as defined herein), respectively. More in particular, the CDR sequences are preferably chosen such that the Nanobodies of the invention bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In particular, in the Nanobodies of the invention, at least the CDR3 sequence present is suitably chosen from the group consisting of the CDR3 sequences listed in Table A-1 or from the group of CDR3 sequences that have at least 80%, preferably at least 90%, more preferably at least 95%, even more preferably at least 99% sequence identity with at least one of the CDR3 sequences listed in Table A-1; and/or from the group consisting of the CDR3 sequences that have 3, 2 or only 1 amino acid difference(s) with at least one of the CDR3 sequences listed in Table A-1.

Preferably, in the Nanobodies of the invention, at least two of the CDR1, CDR2 and CDR3 sequences present are suitably chosen from the group consisting of the CDR1, CDR2 and CDR3 sequences, respectively, listed in Table A-1 or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table A-1; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table A-1.

In particular, in the Nanobodies of the invention, at least the CDR3 sequence present is suitably chosen from the group consisting of the CDR3 sequences listed in Table A-1 or from the group of CDR3 sequences that have at least 80%, preferably at least 90%, more preferably at least 95%, even more preferably at least 99% sequence identity with at least one of the CDR3 sequences listed in Table A-1, respectively; and at least one of the CDR1 and CDR2 sequences present is suitably chosen from the group consisting of the CDR1 and CDR2 sequences, respectively, listed in Table A-1 or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table A-1; and/or from the group consisting of the CDR1 and CDR2 sequences, respectively, that have 3, 2 or only 1 amino acid difference(s) with at least one of the CDR1 and CDR2 sequences, respectively, listed in Table A-1.

Most preferably, in the Nanobodies of the invention, all three CDR1, CDR2 and CDR3 sequences present are suitably chosen from the group consisting of the CDR1, CDR2 and CDR3 sequences, respectively, listed in Table A-1 or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table A-1; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table A-1.

Even more preferably, in the Nanobodies of the invention, at least one of the CDR1, CDR2 and CDR3 sequences present is suitably chosen from the group consisting of the CDR1, CDR2 and CDR3 sequences, respectively, listed in Table A-1. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table A-1; and/or from the group consisting of the CDR sequences that have 3, 2 or only 1 amino acid difference(s) with at least one of the corresponding sequences, respectively, listed in Table A-1.

In particular, in the Nanobodies of the invention, at least the CDR3 sequence present is suitably chosen from the group consisting of the CDR3 listed in Table A-1. Preferably, in this aspect, at least one and preferably both of the CDR1 and CDR2 sequences present are suitably chosen from the groups of CDR1 and CDR2 sequences, respectively, that have at least 80%, preferably at least 90%, more preferably at least 95%, even more preferably at least 99% sequence identity with the CDR1 and CDR2 sequences, respectively, listed in Table A-1; and/or from the group consisting of the CDR1 and CDR2 sequences, respectively, that have 3, 2 or only 1 amino acid difference(s) with at least one of the CDR1 and CDR2 sequences, respectively, listed in Table A-1.

Even more preferably, in the Nanobodies of the invention, at least two of the CDR1, CDR2 and CDR3 sequences present are suitably chosen from the group consisting of the CDR1, CDR2 and CDR3 sequences, respectively, listed in Table A-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table A-1; and/or from the group consisting of CDR sequences that have 3, 2 or only 1 amino acid difference(s) with at least one of the corresponding sequences listed in Table A-1.

In particular, in the Nanobodies of the invention, at least the CDR3 sequence is suitably chosen from the group consisting of the CDR3 sequences listed in Table A-1, and either the CDR1 sequence or the CDR2 sequence is suitably chosen from the group consisting of the CDR1 and CDR2 sequences, respectively, listed in Table A-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table A-1; and/or from the group consisting of CDR sequences that have 3, 2 or only 1 amino acid difference(s) with the corresponding CDR sequences listed in Table A-1.

Even more preferably, in the Nanobodies of the invention, all three CDR1, CDR2 and CDR3 sequences present are suitably chosen from the group consisting of the CDR1, CDR2 and CDR3 sequences, respectively, listed in Table A-1.

Also, generally, the combinations of CDR's listed in Table A-1 (i.e. those mentioned on the same line in Table A-1) are preferred. Thus, it is generally preferred that, when a CDR in a Nanobody of the invention is a CDR sequence mentioned in Table A-1 or is suitably chosen from the group of CDR sequences that have at least 80%, preferably at least 90%, more preferably at least 95%, even more preferably at least 99% sequence identity with a CDR sequence listed in Table A-1; and/or from the group consisting of CDR sequences that have 3, 2 or only 1 amino acid difference(s) with a CDR sequence listed in Table A-1, that at least one and preferably both of the other CDR's are suitably chosen from the CDR sequences that belong to the same combination in Table A-1 (i.e. mentioned on the same line in Table A-1) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table A-1.

Thus, by means of non-limiting examples, a Nanobody of the invention can for example comprise a CDR1 sequence that has more than 80% sequence identity with one of the CDR1 sequences mentioned in Table A-1, a CDR2 sequence that has 3, 2 or 1 amino acid difference with one of the CDR2 sequences mentioned in Table A-1 (but belonging to a different combination), and a CDR3 sequence.

Some preferred Nanobodies of the invention may for example comprise: (1) a CDR1 sequence that has more than 80% sequence identity with one of the CDR1 sequences mentioned in Table A-1; a CDR2 sequence that has 3, 2 or 1 amino acid difference with one of the CDR2 sequences mentioned in Table A-1 (but belonging to a different combination); and a CDR3 sequence that has more than 80% sequence identity with one of the CDR3 sequences mentioned in Table A-1 (but belonging to a different combination); or (2) a CDR1 sequence that has more than 80% sequence identity with one of the CDR1 sequences mentioned in Table A-1; a CDR2 sequence, and one of the CDR3 sequences listed in Table A-1; or (3) a CDR1 sequence; a CDR2 sequence that has more than 80% sequence identity with one of the CDR2 sequence listed in Table A-1; and a CDR3 sequence that has 3, 2 or 1 amino acid differences with the CDR3 sequence mentioned in Table A-1 that belongs to the same combination as the CDR2 sequence.

Some particularly preferred Nanobodies of the invention may for example comprise: (1) a CDR1 sequence that has more than 80% sequence identity with one of the CDR1 sequences mentioned in Table A-1; a CDR2 sequence that has 3, 2 or 1 amino acid difference with the CDR2 sequence mentioned in Table A-1 that belongs to the same combination; and a CDR3 sequence that has more than 80% sequence identity with the CDR3 sequence mentioned in Table A-1 that belongs to the same combination; (2) a CDR1 sequence; a CDR 2 listed in Table A-1 and a CDR3 sequence listed in Table A-1 (in which the CDR2 sequence and CDR3 sequence may belong to different combinations).

Some even more preferred Nanobodies of the invention may for example comprise: (1) a CDR1 sequence that has more than 80% sequence identity with one of the CDR1 sequences mentioned in Table A-1; the CDR2 sequence listed in Table A-1 that belongs to the same combination; and a CDR3 sequence mentioned in Table A-1 that belongs to a different combination; or (2) a CDR1 sequence mentioned in Table A-1; a CDR2 sequence that has 3, 2 or 1 amino acid differences with the CDR2 sequence mentioned in Table A-1 that belongs to the same combination; and a CDR3 sequence that has more than 80% sequence identity with the CDR3 sequence listed in Table A-1 that belongs to the same or a different combination.

Particularly preferred Nanobodies of the invention may for example comprise a CDR1 sequence mentioned in Table A-1, a CDR2 sequence that has more than 80% sequence identity with the CDR2 sequence mentioned in Table A-1 that belongs to the same combination; and the CDR3 sequence mentioned in Table A-1 that belongs to the same combination.

In the most preferred Nanobodies of the invention, the CDR1, CDR2 and CDR3 sequences present are suitably chosen from one of the combinations of CDR1, CDR2 and CDR3 sequences, respectively, listed in Table A-1.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a Nanobody in which the CDR sequences (as defined herein) have more than 80%, preferably more than 90%, more preferably more than 95%, such as 99% or more sequence identity (as defined herein) with the CDR sequences of at least one of the amino acid sequences of SEQ ID NO's: 238 to 253, more preferably SEQ ID NO: 238 and SEQ ID NO: 239.

Generally, Nanobodies with the above CDR sequences may be as further described herein, and preferably have framework sequences that are also as further described herein. Thus, for example and as mentioned herein, such Nanobodies may be naturally occurring Nanobodies (from any suitable species), naturally occurring $V_{HH}$ sequences (i.e. from a suitable species of Camelid) or synthetic or semi-synthetic amino acid sequences or Nanobodies, including but not limited to partially humanized Nanobodies or $V_{HH}$ sequences, fully humanized Nanobodies or $V_{HH}$ sequences, camelized heavy chain variable domain sequences, as well as Nanobodies that have been obtained by the techniques mentioned herein.

Thus, in one specific, but non-limiting aspect, the invention relates to a humanized Nanobody, which consists of 4 framework regions (FR1 to FR4 respectively) and 3 complementarity determining regions (CDR1 to CDR3 respectively), in which CDR1 to CDR3 are as defined herein and in which said humanized Nanobody comprises at least one humanizing substitution (as defined herein), and in particular at least one humanizing substitution in at least one of its framework sequences (as defined herein).

In another preferred, but non-limiting aspect, the invention relates to a Nanobody in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 238 to 253, more preferably SEQ ID NO: 238 and SEQ ID NO: 239. This degree of amino acid identity can for example be determined by determining the degree of amino acid identity (in a manner described herein) between said Nanobody and one or more of the sequences of SEQ ID NO's: 238 to 253, more preferably SEQ ID NO: 238 and SEQ ID NO: 239, in which the amino acid residues that form the framework regions are disregarded. Such Nanobodies can be as further described herein.

In another preferred, but non-limiting aspect, the invention relates to a Nanobody with an amino acid sequence that is chosen from the group consisting of SEQ ID NO's: 238 to 253, more preferably SEQ ID NO: 238 and SEQ ID NO: 239 or from the group consisting of from amino acid sequences that have more than 80%, preferably more than 90%, more preferably more than 95%, such as 99% or more sequence identity (as defined herein) with at least one of the amino acid sequences of SEQ ID NO's: 238 to 253, more preferably SEQ ID NO: 238 and SEQ ID NO: 239.

Another preferred, but non-limiting aspect of the invention relates to humanized variants of the Nanobodies of SEQ ID NO's: 238 to 253, more preferably SEQ ID NO: 238 and SEQ ID NO: 239, that comprise, compared to the corresponding native $V_{HH}$ sequence, at least one humanizing substitution (as defined herein), and in particular at least one humanizing substitution in at least one of its framework sequences (as defined herein).

The polypeptides of the invention comprise or essentially consist of at least one Nanobody of the invention. Thus in another preferred, but non-limiting aspect, the invention relates to a polypeptide comprise or essentially consist of at least one Nanobody that is chosen from the group consisting of SEQ ID NO's: 238 to 253, more preferably SEQ ID NO: 238 and SEQ ID NO: 239 or from the group consisting of from amino acid sequences that have more than 80%, preferably more than 90%, more preferably more than 95%, such as 99% or more sequence identity (as defined herein) with at least one of the amino acid sequences of SEQ ID NO's: 238 to 253, more preferably SEQ ID NO: 238 and SEQ ID NO: 239. Thus in another preferred, but non-limiting aspect, the invention relates to a polypeptide comprise or essentially consist of amino acid sequences of SEQ ID NO's: 261 to 264, more preferably SEQ ID NO: 263 to 264.

It will be clear to the skilled person that the Nanobodies that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" Nanobodies of the invention will generally be preferred, and polypeptides that comprise or essentially consist of one or more "more preferred" Nanobodies of the invention will generally be more preferred, etc.

Generally, proteins or polypeptides that comprise or essentially consist of a single Nanobody (such as a single Nanobody of the invention) will be referred to herein as "monovalent" proteins or polypeptides or as "monovalent constructs". Proteins and polypeptides that comprise or essentially consist of two or more Nanobodies (such as at least two Nanobodies of the invention or at least one Nanobody of the invention and at least one other Nanobody) will be referred to herein as "multivalent" proteins or polypeptides or as "multivalent constructs", and these may provide certain advantages compared to the corresponding monovalent Nanobodies of the invention. Some non-limiting examples of such multivalent constructs will become clear from the further description herein.

According to one specific, but non-limiting aspect, a polypeptide of the invention comprises or essentially consists of at least two Nanobodies of the invention, such as two or three Nanobodies of the invention. As further described herein, such multivalent constructs can provide certain advantages compared to a protein or polypeptide comprising or essentially consisting of a single Nanobody of the invention, such as a much improved avidity for GPCRs. Such multivalent constructs will be clear to the skilled person based on the disclosure herein, and e.g. are polypeptides that comprise or essentially consist of amino acid sequences of SEQ ID NO: 261 to 262.

According to another specific, but non-limiting aspect, a polypeptide of the invention comprises or essentially consists of at least one Nanobody of the invention and at least one other binding unit (i.e. directed against another epitope, antigen, target, protein or polypeptide), which is preferably also a Nanobody. Such proteins or polypeptides are also referred to herein as "multispecific" proteins or polypeptides or as 'multispecific constructs", and these may provide certain advantages compared to the corresponding monovalent Nanobodies of the invention (as will become clear from the further discussion herein of some preferred, but-nonlimiting multispecific constructs). Such multispecific constructs will be clear to the skilled person based on the disclosure herein, and e.g. are polypeptides that comprise or essentially consist of amino acid sequences of SEQ ID NO: 263 to 264.

According to yet another specific, but non-limiting aspect, a polypeptide of the invention comprises or essentially consists of at least one Nanobody of the invention, optionally one or more further Nanobodies, and at least one other amino acid sequence (such as a protein or polypeptide) that confers at least one desired property to the Nanobody of the invention and/or to the resulting fusion protein. Again, such fusion proteins may provide certain advantages compared to the corresponding monovalent Nanobodies of the invention. Some non-limiting examples of such amino acid sequences and of such fusion constructs will become clear from the further description herein.

It is also possible to combine two or more of the above aspects, for example to provide a trivalent bispecific construct comprising two Nanobodies of the invention and one other Nanobody, and optionally one or more other amino acid sequences. Further non-limiting examples of such constructs, as well as some constructs that are particularly preferred within the context of the present invention, will become clear from the further description herein. In the above constructs, the one or more Nanobodies and/or other amino acid sequences may be directly linked to each other and/or suitably linked to each other via one or more linker sequences. Some suitable but non-limiting examples of such linkers will become clear from the further description herein.

In one specific aspect of the invention, a Nanobody of the invention or a compound, construct or polypeptide of the invention comprising at least one Nanobody of the invention may have an increased half-life, compared to the corresponding amino acid sequence of the invention. Some preferred, but non-limiting examples of such Nanobodies, compounds and polypeptides will become clear to the skilled person based on the further disclosure herein, and for example comprise Nanobodies sequences or polypeptides of the invention that have been chemically modified to increase the half-life thereof (for example, by means of pegylation); amino acid sequences of the invention that comprise at least one additional binding site for binding to a serum protein (such as serum albumin. Reference is for example made to the US provisional application by Ablynx N.V. entitled "Immunoglobulin domains with multiple binding sites" filed on Nov. 27, 2006); or polypeptides of the invention that comprise at least one Nanobody of the invention that is linked to at least one moiety (and in particular at least one amino acid sequence) that increases the half-life of the Nanobody of the invention. Examples of polypeptides of the invention that comprise such half-life extending moieties or amino acid sequences will become clear to the skilled person based on the further disclosure herein; and for example include, without limitation, polypeptides in which the one or more Nanobodies of the invention are suitable linked to one or more serum proteins or fragments thereof (such as serum albumin or suitable fragments thereof) or to one or more binding units that can bind to serum proteins (such as, for example, Nanobodies or (single) domain antibodies that can bind to serum proteins such as serum albumin, serum immunoglobulins such as IgG, or transferrin); polypeptides in which a Nanobody of the invention is linked to an Fc portion (such as a human Fc) or a suitable part or fragment thereof; or polypeptides in which the one or more Nanobodies of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006.

Again, as will be clear to the skilled person, such Nanobodies, compounds, constructs or polypeptides may contain one or more additional groups, residues, moieties or binding units, such as one or more further amino acid sequences and in particular one or more additional Nanobodies (i.e. not directed against GPCRs), so as to provide a tri- of multispecific Nanobody construct.

Generally, the Nanobodies of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the Nanobodies, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such Nanobodies, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another one aspect of the invention, a polypeptide of the invention comprises one or more (such as two or preferably one) Nanobodies of the invention linked (optionally via one or more suitable linker sequences) to one or more (such as two and preferably one) amino acid sequences that allow the resulting polypeptide of the invention to cross the blood brain barrier. In particular, said one or more amino acid sequences that allow the resulting polypeptides of the invention to cross the blood brain barrier may be one or more (such as two and preferably one) Nanobodies, such as the Nanobodies described in WO 02/057445, of which FC44 (SEQ ID NO: 189 of WO 06/040153) and FC5 (SEQ ID NO: 190 of WO 06/040154) are preferred examples.

In particular, polypeptides comprising one or more Nanobodies of the invention are preferably such that they:
  bind to GPCRs with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
and/or such that they:
  bind to GPCRs with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;
and/or such that they:
  bind to GPCRs with a $k_{off}$-rate between $1$ $s^{-1}$ ($t_{1/2}$=0.69 s) and $10^{-6}$ $s^{-1}$ (providing a near irreversible complex with a $t_{1/2}$ of multiple days), preferably between $10^{-2}s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a polypeptide that contains only one amino acid sequence of the invention is preferably such that it will bind to GPCRs with an affinity less than 500 nM, preferably less than 200 nM, more preferably less than 10 nM, such as less than 500 μM. In this respect, it will be clear to the skilled person that a polypeptide that contains two or more Nanobodies of the invention may bind to GPCRs with an increased avidity, compared to a polypeptide that contains only one amino acid sequence of the invention.

Some preferred $IC_{50}$ values for binding of the amino acid sequences or polypeptides of the invention to GPCRs will become clear from the further description and examples herein.

Another aspect of this invention relates to a nucleic acid that encodes a Nanobody of the invention or a polypeptide of the invention comprising the same. Again, as generally described herein for the nucleic acids of the invention, such a nucleic acid may be in the form of a genetic construct, as defined herein.

In another aspect, the invention relates to host or host cell that expresses or that is capable of expressing a Nanobody of the invention and/or a polypeptide of the invention comprising the same; and/or that contains a nucleic acid of the invention. Some preferred but non-limiting examples of such hosts or host cells will become clear from the further description herein.

Another aspect of the invention relates to a product or composition containing or comprising at least one Nanobody of the invention, at least one polypeptide of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention further relates to methods for preparing or generating the Nanobodies, polypeptides, nucleic acids, host cells, products and compositions described herein. Some preferred but non-limiting examples of such methods will become clear from the further description herein.

The invention further relates to applications and uses of the Nanobodies, polypeptides, nucleic acids, host cells, products and compositions described herein, as well as to methods for the prevention and/or treatment for diseases and disorders associated with GPCRs. Some preferred but non-limiting applications and uses will become clear from the further description herein.

Other aspects, embodiments, advantages and applications of the invention will also become clear from the further description hereinbelow.

Generally, it should be noted that the term Nanobody as used herein in its broadest sense is not limited to a specific biological source or to a specific method of preparation. For example, as will be discussed in more detail below, the Nanobodies of the invention can generally be obtained: (1) by isolating the $V_{HH}$ domain of a naturally occurring heavy chain antibody; (2) by expression of a nucleotide sequence encoding a naturally occurring $V_{HH}$ domain; (3) by "humanization" (as described herein) of a naturally occurring $V_{HH}$ domain or by expression of a nucleic acid encoding a such humanized $V_{HH}$ domain; (4) by "camelization" (as described herein) of a naturally occurring $V_H$ domain from any animal species, and in particular a from species of mammal, such as from a human being, or by expression of a nucleic acid encoding such a camelized $V_H$ domain; (5) by "camelisation" of a "domain antibody" or "Dab" as described by Ward et al (supra), or by expression of a nucleic acid encoding such a camelized $V_H$ domain; (6) by using synthetic or semi-synthetic techniques for preparing proteins, polypeptides or other amino acid sequences known per se; (7) by preparing a nucleic acid encoding a Nanobody using techniques for nucleic acid synthesis known per se, followed by expression of the nucleic acid thus obtained; and/or (8) by any combination of one or more of the foregoing. Suitable methods and techniques for performing the foregoing will be clear to the skilled person based on the disclosure herein and for example include the methods and techniques described in more detail herein.

One preferred class of Nanobodies corresponds to the $V_{HH}$ domains of naturally occurring heavy chain antibodies directed against GPCRs. As further described herein, such $V_{HH}$ sequences can generally be generated or obtained by suitably immunizing a species of Camelid with GPCRs (i.e. so as to raise an immune response and/or heavy chain antibodies directed against GPCRs), by obtaining a suitable biological sample from said Camelid (such as a blood sample, serum sample or sample of B-cells), and by generating $V_{HH}$ sequences directed against GPCRs, starting from said sample, using any suitable technique known per se. Such techniques will be clear to the skilled person and/or are further described herein.

Alternatively, such naturally occurring $V_{HH}$ domains against GPCRs, can be obtained from naïve libraries of Camelid $V_{HH}$ sequences, for example by screening such a library using GPCRs, or at least one part, fragment, antigenic determinant or epitope thereof using one or more screening techniques known per se. Such libraries and techniques are for example described in WO 99/37681, WO 01/90190, WO 03/025020 and WO 03/035694.

Alternatively, improved synthetic or semi-synthetic libraries derived from naïve $V_{HH}$ libraries may be used, such as $V_{HH}$ libraries obtained from naïve $V_{HH}$ libraries by techniques such as random mutagenesis and/or CDR shuffling, as for example described in WO 00/43507.

Thus, in another aspect, the invention relates to a method for generating Nanobodies, that are directed against GPCRs. In one aspect, said method at least comprises the steps of:
a) providing a set, collection or library of Nanobody sequences; and
b) screening said set, collection or library of Nanobody sequences for Nanobody sequences that can bind to and/or have affinity for GPCRs; and
c) isolating the amino acid sequence(s) that can bind to and/or have affinity for GPCRs.

In such a method, the set, collection or library of Nanobody sequences may be a naïve set, collection or library of Nanobody sequences; a synthetic or semi-synthetic set, collection or library of Nanobody sequences; and/or a set, collection or library of Nanobody sequences that have been subjected to affinity maturation.

In a preferred aspect of this method, the set, collection or library of Nanobody sequences may be an immune set, collection or library of Nanobody sequences, and in particular an immune set, collection or library of $V_{HH}$ sequences, that have been derived from a species of Camelid that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of Nanobody or $V_{HH}$ sequences may be displayed on a phage, phagemid, ribosome or suitable micro-organism (such as yeast), such as to facilitate screening. Suitable methods, techniques and host organisms for displaying and screening (a set, collection or library of) Nanobody sequences will be clear to the person skilled in the art, for example on the basis of the further disclosure herein. Reference is also made to WO 03/054016 and to the review by Hoogenboom in Nature Biotechnology, 23, 9, 1105-1116 (2005).

In another aspect, the method for generating Nanobody sequences comprises at least the steps of:
a) providing a collection or sample of cells derived from a species of Camelid that express immunoglobulin sequences;
b) screening said collection or sample of cells for (i) cells that express an immunoglobulin sequence that can bind to and/or have affinity for GPCRs; and (ii) cells that express heavy chain antibodies, in which substeps (i) and (ii) can be performed essentially as a single screening step or in any suitable order as two separate screening steps, so as to provide at least one cell that expresses a heavy chain antibody that can bind to and/or has affinity for GPCRs; and
c) either (i) isolating from said cell the $V_{HH}$ sequence present in said heavy chain antibody; or (ii) isolating from said cell a nucleic acid sequence that encodes the $V_{HH}$ sequence present in said heavy chain antibody, followed by expressing said $V_{HH}$ domain.

In another aspect, the method for generating Nanobody sequences directed against a GPCR, e.g. human CXCR4 or human CXCR7, comprises at least the steps of:
a. a step of suitably immunizing a Camelid with a suitable antigen that comprises the desired extracellular part, region, domain, loop or other extracellular epitope(s), or with a suitable peptide derived therefrom or based thereon, such that an immune response against the desired extracellular part, region, domain, loop or other extracellular epitope(s) is raised. The antigen may be any suitable antigen that is capable of raising an immune response against the desired extracellular part, region, domain, loop or other extracellular epitope(s); such as, for example and without limitation, whole cells that are alive and overexpress the desired extracellular part, region, domain, loop or other extracellular epitope(s) on their surface in their native confirmation, cell wall fragments thereof or any other suitable preparation derived from such cells, vesicles that have the desired extracellular part, region, domain, loop or other extracellular epitope(s) on their surface, a subunit or fragment of a subunit of a GPCR, e.g. human CXCR4 and/or human CXCR7, that comprises the desired extracellular part, region, domain, loop or other extracellular epitope(s), or a synthetic or semi-synthetic peptide that comprises and/or is based on (the amino acid sequence of) the desired extracellular part, region, domain, loop or other extracellular epitope(s), more preferably, whole cells (e.g. HEK293) that are alive and overexpress the desired extracellular part, region, domain, loop or other extracellular epitope(s) on their surface in their native confirmation; and
b. a step of selection for binding for the desired extracellular part, region, domain, loop or other extracellular epitope(s) using cell membranes preparation of different (than the one using in immunization) and several cell types overexpressing said GPCR, e.g. human CXCR4 and/or human CXCR7. This may for example be performed by selecting from a set, a collection or a library of cells that express heavy chain antibodies on their surface (e.g. B-cells obtained from a suitably immunized Camelid) and using a cell membranes preparation of e.g. a first type of cells such as e.g. CHO for a first round selection and e.g. a second type of cells such as e.g. COS-7 cells for a second round selection, by selecting from a (naïve or immune) library of $V_{HH}$ sequences or Nanobody sequences by using a cell membranes preparation of e.g. a first type of cell such as e.g. CHO for a first round selection and e.g. a second type of cell such as e.g. COS-7 cell for a second round selection, or by selecting from a (naïve or immune) library of nucleic acid sequences that encode VHH sequences or Nanobody sequences by using a cell membranes preparation of e.g. a first type of cell such as e.g. CHO for a first round selection and e.g. a second type of cells such as e.g. COS-7 cell for a second round selection; which may all be performed in a manner known per se; and optionally c. washing only mildly with a buffer such as PBS without detergents; and which method may optionally further comprise one or more other suitable steps known per se, such as, for example and without limitation, a step of affinity maturation, a step of expressing the desired amino acid sequence, a step of screening for binding and/or for activity against the desired antigen (in this case, the GPCR), a step of determining the desired amino acid sequence or nucleotide sequence, a step of introducing one or more humanizing substitutions (e.g. as further described herein), a step of formatting in a suitable multivalent and/or multispecific format, a step of screening for the desired biological and/or physiological properties (i.e. using a suitable assay, such as those described herein); and/or any suitable combination of one or more of such steps, in any suitable order.

In another aspect, the method for generating Nanobody sequences directed against a transmembranal protein comprises at least the steps of:

a. a step of suitably immunizing a Camelid with a suitable antigen that comprises the desired extracellular part, region, domain, loop or other extracellular epitope(s), or with a suitable peptide derived therefrom or based thereon, such that an immune response against the desired extracellular part, region, domain, loop or other extracellular epitope(s) is raised. The antigen may be any suitable antigen that is capable of raising an immune response against the desired extracellular part, region, domain, loop or other extracellular epitope(s); such as, for example and without limitation, whole cells that are alive and overexpress the desired extracellular part, region, domain, loop or other extracellular epitope(s) on their surface in their native confirmation, cell wall fragments thereof or any other suitable preparation derived from such cells, vesicles that have the desired extracellular part, region, domain, loop or other extracellular epitope(s) on their surface, a subunit or fragment of a subunit of a transmembrane protein, in particular multiple spanning transmembrane protein for which the native conformation cannot be reproduced in other "in vitro" system (at least at time of filing of this application), that comprises the desired extracellular part, region, domain, loop or other extracellular epitope(s), or a synthetic or semi-synthetic peptide that comprises and/or is based on (the amino acid sequence of) the desired extracellular part, region, domain, loop or other extracellular epitope(s), more preferably, whole cells (e.g. HEK293) that are alive and overexpress the desired extracellular part, region, domain, loop or other extracellular epitope(s) on their surface in their native confirmation; and b. a step of selection for binding for the desired extracellular part, region, domain, loop or other extracellular epitope(s) using cell membranes preparation of different (than the one using in immunization) and several cell types overexpressing said transmembrane protein, in particular multiple spanning transmembrane protein for which the native conformation cannot be reproduced in other "in vitro" system (at least at time of filing of this application). This may for example be performed by selecting from a set, a collection or a library of cells that express heavy chain antibodies on their surface (e.g. B-cells obtained from a suitably immunized Camelid) and using a cell membranes preparation of e.g. a first type of cells such as e.g. CHO for a first round selection and e.g. a second type of cells such as e.g. COS-7 cells for a second round selection, by selecting from a (naïve or immune) library of VHH sequences or Nanobody sequences by using a cell membranes preparation of e.g. a first type of cell such as e.g. CHO for a first round selection and e.g. a second type of cell such as e.g. COS-7 cell for a second round selection, or by selecting from a (naïve or immune) library of nucleic acid sequences that encode VHH sequences or Nanobody sequences by using a cell membranes preparation of e.g. a first type of cell such as e.g. CHO for a first round selection and e.g. a second type of cells such as e.g. COS-7 cell for a second round selection; which may all be performed in a manner known per se; and optionally c. washing only mildly with a buffer such as PBS without detergents; and which method may optionally further comprise one or more other suitable steps known per se, such as, for example and without limitation, a step of affinity maturation, a step of expressing the desired amino acid sequence, a step of screening for binding and/or for activity against the desired antigen (in this case, the transmembrane protein), a step of determining the desired amino acid sequence or nucleotide sequence, a step of introducing one or more humanizing substitutions (e.g. as further described herein), a step of formatting in a suitable multivalent and/or multispecific format, a step of screening for the desired biological and/or physiological properties (i.e. using a suitable assay, such as those described herein); and/or any suitable combination of one or more of such steps, in any suitable order.

In the method according to this aspect, the collection or sample of cells may for example be a collection or sample of B-cells.

Also, in this method, the sample of cells may be derived from a Camelid that has been suitably immunized with GPCRs or a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820. Particular reference is made to the so-called "Nanoclone™" technique described in International application WO 06/079372 by Ablynx N.V.

In another aspect, the method for generating an amino acid sequence directed against GPCRs may comprise at least the steps of:

a) providing a set, collection or library of nucleic acid sequences encoding heavy chain antibodies or Nanobody sequences;

b) screening said set, collection or library of nucleic acid sequences for nucleic acid sequences that encode a heavy chain antibody or a Nanobody sequence that can bind to and/or has affinity for GPCRs; and c) isolating said nucleic acid sequence, followed by expressing the $V_{HH}$ sequence present in said heavy chain antibody or by expressing said Nanobody sequence, respectively.

In such a method, the set, collection or library of nucleic acid sequences encoding heavy chain antibodies or Nanobody sequences may for example be a set, collection or library of nucleic acid sequences encoding a naïve set, collection or library of heavy chain antibodies or $V_{HH}$ sequences; a set, collection or library of nucleic acid sequences encoding a synthetic or semi-synthetic set, collection or library of Nanobody sequences; and/or a set, collection or library of nucleic acid sequences encoding a set, collection or library of Nanobody sequences that have been subjected to affinity maturation.

In a preferred aspect of this method, the set, collection or library of amino acid sequences may be an immune set, collection or library of nucleic acid sequences encoding heavy chain antibodies or $V_{HH}$ sequences derived from a Camelid that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to WO 03/054016 and to the review by Hoogenboom in Nature Biotechnology, 23, 9, 1105-1116 (2005).

As will be clear to the skilled person, the screening step of the methods described herein can also be performed as a selection step. Accordingly the term "screening" as used in the present description can comprise selection, screening or any suitable combination of selection and/or screening techniques. Also, when a set, collection or library of sequences is used, it may contain any suitable number of sequences, such as 1, 2, 3 or about 5, 10, 50, 100, 500, 1000, 5000, $10^4$, $10^5$, $10^6$, $10^7$, $10^8$ or more sequences.

Also, one or more or all of the sequences in the above set, collection or library of amino acid sequences may be obtained or defined by rational, or semi-empirical approaches such as computer modelling techniques or biostatics or datamining techniques.

Furthermore, such a set, collection or library can comprise one, two or more sequences that are variants from one another (e.g. with designed point mutations or with randomized positions), compromise multiple sequences derived from a diverse set of naturally diversified sequences (e.g. an immune library)), or any other source of diverse sequences (as described for example in Hoogenboom et al, Nat Biotechnol 23:1105, 2005 and Binz et al, Nat Biotechnol 2005, 23:1247). Such set, collection or library of sequences can be displayed on the surface of a phage particle, a ribosome, a bacterium, a yeast cell, a mammalian cell, and linked to the nucleotide sequence encoding the amino acid sequence within these carriers. This makes such set, collection or library amenable to selection procedures to isolate the desired amino acid sequences of the invention. More generally, when a sequence is displayed on a suitable host or host cell, it is also possible (and customary) to first isolate from said host or host cell a nucleotide sequence that encodes the desired sequence, and then to obtain the desired sequence by suitably expressing said nucleotide sequence in a suitable host organism. Again, this can be performed in any suitable manner known per se, as will be clear to the skilled person.

Yet another technique for obtaining $V_{HH}$ sequences or Nanobody sequences directed against GPCRs involves suitably immunizing a transgenic mammal that is capable of expressing heavy chain antibodies (i.e. so as to raise an immune response and/or heavy chain antibodies directed against GPCRs), obtaining a suitable biological sample from said transgenic mammal that contains (nucleic acid sequences encoding) said $V_{HH}$ sequences or Nanobody sequences (such as a blood sample, serum sample or sample of B-cells), and then generating $V_{HH}$ sequences directed against GPCRs, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

The invention also relates to the $V_{HH}$ sequences or Nanobody sequences that are obtained by the above methods, or alternatively by a method that comprises the one of the above methods and in addition at least the steps of determining the nucleotide sequence or amino acid sequence of said $V_{HH}$ sequence or Nanobody sequence; and of expressing or synthesizing said $V_{HH}$ sequence or Nanobody sequence in a manner known per se, such as by expression in a suitable host cell or host organism or by chemical synthesis.

As mentioned herein, a particularly preferred class of Nanobodies of the invention comprises Nanobodies with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized Nanobodies of the invention can be obtained in any suitable manner known per se (i.e. as indicated under points (1)-(8) above) and thus are not strictly limited to polypeptides that have been obtained using a polypeptide that comprises a naturally occurring $V_{HH}$ domain as a starting material.

Another particularly preferred class of Nanobodies of the invention comprises Nanobodies with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). Preferably, the $V_H$ sequence that is used as a starting material or starting point for generating or designing the camelized Nanobody is preferably a $V_H$ sequence from a mammal, more preferably the $V_H$ sequence of a human being, such as a $V_H3$ sequence. However, it should be noted that such camelized Nanobodies of the invention can be obtained in any suitable manner known per se (i.e. as indicated under points (1)-(8) above) and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" Nanobody of the invention, respectively. This nucleic acid can then be expressed in a manner known per se, so as to provide the desired Nanobody of the invention. Alternatively, based on the amino acid sequence of a naturally occurring $V_{HH}$ domain or $V_H$ domain, respectively, the amino acid sequence of the desired humanized or camelized Nanobody of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized Nanobody of the invention, respectively, can be designed and then synthesized de novo using techniques for nucleic acid synthesis known per se, after which the nucleic acid thus obtained can be expressed in a manner known per se, so as to provide the desired Nanobody of the invention.

Other suitable methods and techniques for obtaining the Nanobodies of the invention and/or nucleic acids encoding the same, starting from naturally occurring $V_H$ sequences or preferably $V_{HH}$ sequences, will be clear from the skilled person, and may for example comprise combining one or more parts of one or more naturally occurring $V_H$ sequences (such as one or more FR sequences and/or CDR sequences), one or more parts of one or more naturally occurring $V_{HH}$ sequences (such as one or more FR sequences or CDR sequences), and/or one or more synthetic or semi-synthetic sequences, in a suitable manner, so as to provide a Nanobody of the invention or a nucleotide sequence or nucleic acid encoding the same (which may then be suitably expressed). Nucleotide sequences encoding framework sequences of $V_{HH}$ sequences or Nanobodies will be clear to the skilled person based on the disclosure herein and/or the further prior art cited herein (and/or may alternatively be obtained by PCR starting from the nucleotide sequences obtained using the methods described herein) and may be suitably combined with nucleotide sequences that encode the desired CDR's (for example, by PCR assembly using overlapping primers), so as to provide a nucleic acid encoding a Nanobody of the invention.

As mentioned herein, Nanobodies may in particular be characterized by the presence of one or more "Hallmark residues" (as described herein) in one or more of the framework sequences.

Thus, according to one preferred, but non-limiting aspect of the invention, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 45 according to the Kabat numbering is a charged amino acid (as defined herein) or a cysteine residue, and position 44 is preferably an E;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure
FR1-CDR1-FR2-CDR2-FR3-CDR3-4
in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q;
and/or in which:
b) the amino acid residue at position 45 according to the Kabat numbering is a charged amino acid or a cysteine and the amino acid residue at position 44 according to the Kabat numbering is preferably E;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, according to a preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which a) the amino acid residue at position 108 according to the Kabat numbering is Q;

and/or in which:

b) the amino acid residue at position 44 according to the Kabat numbering is E and in which the amino acid residue at position 45 according to the Kabat numbering is an R;

and/or in which:

c) the amino acid residue at position 103 according to the Kabat numbering is chosen from the group consisting of P, R and S, and is in particular chosen from the group consisting of R and S;

and in which:

d) CDR1, CDR2 and CDR3 are as defined herein, and are preferably as defined according to one of the preferred aspects herein, and are more preferably as defined according to one of the more preferred aspects herein.

In particular, a Nanobody against GPCRs according to the invention may have the structure:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which a) the amino acid residue at position 108 according to the Kabat numbering is Q;

and/or in which:

b) the amino acid residue at position 44 according to the Kabat numbering is E and in which the amino acid residue at position 45 according to the Kabat numbering is an R;

and/or in which:

c) the amino acid residue at position 103 according to the Kabat numbering is chosen from the group consisting of P, R and S, and is in particular chosen from the group consisting of R and S;

and in which:

d) CDR1, CDR2 and CDR3 are as defined herein, and are preferably as defined according to one of the preferred aspects herein, and are more preferably as defined according to one of the more preferred aspects herein.

In particular, according to one preferred, but non-limiting aspect of the invention, a Nanobody can generally be defined as a polypeptide comprising an amino acid sequence that is comprised of four framework regions/sequences interrupted by three complementarity determining regions/sequences, in which;

a-1) the amino acid residue at position 44 according to the Kabat numbering is chosen from the group consisting of A, G, E, D, G, Q, R, S, L; and is preferably chosen from the group consisting of G, E or Q; and a-2) the amino acid residue at position 45 according to the Kabat numbering is chosen from the group consisting of L, R or C; and is preferably chosen from the group consisting of L or R; and a-3) the amino acid residue at position 103 according to the Kabat numbering is chosen from the group consisting of W, R or S; and is preferably W or R, and is most preferably W;

a-4) the amino acid residue at position 108 according to the Kabat numbering is Q;

or in which:

b-1) the amino acid residue at position 44 according to the Kabat numbering is chosen from the group consisting of E and Q; and b-2) the amino acid residue at position 45 according to the Kabat numbering is R; and b-3) the amino acid residue at position 103 according to the Kabat numbering is chosen from the group consisting of W, R and S; and is preferably W;

b-4) the amino acid residue at position 108 according to the Kabat numbering is chosen from the group consisting of Q and L; and is preferably Q;

or in which:

c-1) the amino acid residue at position 44 according to the Kabat numbering is chosen from the group consisting of A, G, E, D, Q, R, S and L; and is preferably chosen from the group consisting of G, E and Q; and c-2) the amino acid residue at position 45 according to the Kabat numbering is chosen from the group consisting of L, R and C; and is preferably chosen from the group consisting of L and R; and c-3) the amino acid residue at position 103 according to the Kabat numbering is chosen from the group consisting of P, R and S; and is in particular chosen from the group consisting of R and S; and c-4) the amino acid residue at position 108 according to the Kabat numbering is chosen from the group consisting of Q and L; is preferably Q;

and in which d) CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

a-1) the amino acid residue at position 44 according to the Kabat numbering is chosen from the group consisting of A, G, E, D, G, Q, R, S, L; and is preferably chosen from the group consisting of G, E or Q;

and in which:

a-2) the amino acid residue at position 45 according to the Kabat numbering is chosen from the group consisting of L, R or C; and is preferably chosen from the group consisting of L or R;

and in which:

a-3) the amino acid residue at position 103 according to the Kabat numbering is chosen from the group consisting of W, R or S; and is preferably W or R, and is most preferably W;

and in which a-4) the amino acid residue at position 108 according to the Kabat numbering is Q; and in which:

d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

b-1) the amino acid residue at position 44 according to the Kabat numbering is chosen from the group consisting of E and Q;

and in which:

b-2) the amino acid residue at position 45 according to the Kabat numbering is R;

and in which:

b-3) the amino acid residue at position 103 according to the Kabat numbering is chosen from the group consisting of W, R and S; and is preferably W;

and in which:

b-4) the amino acid residue at position 108 according to the Kabat numbering is chosen from the group consisting of Q and L; and is preferably Q;

and in which:

d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

c-1) the amino acid residue at position 44 according to the Kabat numbering is chosen from the group consisting of A, G, E, D, Q, R, S and L; and is preferably chosen from the group consisting of G, E and Q;

and in which:

c-2) the amino acid residue at position 45 according to the Kabat numbering is chosen from the group consisting of L, R and C; and is preferably chosen from the group consisting of L and R;

and in which:

c-3) the amino acid residue at position 103 according to the Kabat numbering is chosen from the group consisting of P, R and S; and is in particular chosen from the group consisting of R and S;

and in which:

c-4) the amino acid residue at position 108 according to the Kabat numbering is chosen from the group consisting of Q and L; is preferably Q;

and in which:

d) CDR1, CDR2 and CDR3 are as defined herein, and are preferably as defined according to one of the preferred aspects herein, and are more preferably as defined according to one of the more preferred aspects herein.

Two particularly preferred, but non-limiting groups of the Nanobodies of the invention are those according to a) above; according to (a-1) to (a-4) above; according to b) above; according to (b-1) to (b-4) above; according to (c) above; and/or according to (c-1) to (c-4) above, in which either:

i) the amino acid residues at positions 44-47 according to the Kabat numbering form the sequence GLEW (or a GLEW-like sequence as described herein) and the amino acid residue at position 108 is Q;

or in which:

ii) the amino acid residues at positions 43-46 according to the Kabat numbering form the sequence KERE or KQRE (or a KERE-like sequence as described) and the amino acid residue at position 108 is Q or L, and is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 44-47 according to the Kabat numbering form the sequence GLEW (or a GLEW-like sequence as defined herein) and the amino acid residue at position 108 is Q;

and in which:

ii) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 43-46 according to the Kabat numbering form the sequence KERE or KQRE (or a KERE-like sequence) and the amino acid residue at position 108 is Q or L, and is preferably Q;

and in which:

ii) CDR1, CDR2 and CDR3 are as defined herein, and are preferably as defined according to one of the preferred aspects herein, and are more preferably as defined according to one of the more preferred aspects herein.

In the Nanobodies of the invention in which the amino acid residues at positions 43-46 according to the Kabat numbering form the sequence KERE or KQRE, the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, I, L, V or F, and is most preferably V.

Thus, without being limited hereto in any way, on the basis of the amino acid residues present on the positions mentioned above, the Nanobodies of the invention can generally be classified on the basis of the following three groups:

i) The "GLEW-group": Nanobodies with the amino acid sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table A-3 below;

ii) The "KERE-group": Nanobodies with the amino acid sequence KERE or KQRE (or another KERE-like sequence) at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103;

iii) The "103 P, R, S-group": Nanobodies with a P, R or S at position 103. These Nanobodies can have either the amino acid sequence GLEW at positions 44-47 according to the Kabat numbering or the amino acid sequence KERE or KQRE at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Also, where appropriate, Nanobodies may belong to (i.e. have characteristics of) two or more of these classes. For example, one specifically preferred group of Nanobodies has GLEW or a GLEW-like sequence at positions 44-47; P, R or S (and in particular R) at position 103; and Q at position 108 (which may be humanized to L).

More generally, it should be noted that the definitions referred to above describe and apply to Nanobodies in the form of a native (i.e. non-humanized) $V_{HH}$ sequence, and that humanized variants of these Nanobodies may contain other amino acid residues than those indicated above (i.e. one or more humanizing substitutions as defined herein). For example, and without limitation, in some humanized Nanobodies of the GLEW-group or the 103 P, R, S-group, Q at position 108 may be humanized to 108L. As already mentioned herein, other humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Thus, in another preferred, but non-limiting aspect, a Nanobody of the invention may be a Nanobody belonging to the GLEW-group (as defined herein), and in which CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may be a Nanobody belonging to the KERE-group (as defined herein), and CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may be a Nanobody belonging to the 103 P, R, S-group (as defined herein), and in which CDR1, CDR2 and CDR3 are as defined herein, and are preferably as defined according to one of the preferred aspects herein, and are more preferably as defined according to one of the more preferred aspects herein.

Also, more generally and in addition to the 108Q, 43E/44R and 103 P,R,S residues mentioned above, the Nanobodies of the invention can contain, at one or more positions that in a conventional $V_H$ domain would form (part of) the $V_H/V_L$ interface, one or more amino acid residues that are more highly charged than the amino acid residues that naturally occur at the same position(s) in the corresponding naturally occurring $V_H$ sequence, and in particular one or more charged amino acid residues (as mentioned in Table A-2). Such substitutions include, but are not limited to, the GLEW-like sequences mentioned in Table A-3 below; as well as the substitutions that are described in the International Application WO 00/29004 for so-called "microbodies", e.g. so as to obtain a Nanobody with Q at position 108 in combination with KLEW at positions 44-47. Other possible substitutions at these positions will be clear to the skilled person based upon the disclosure herein.

In one aspect of the Nanobodies of the invention, the amino acid residue at position 83 is chosen from the group consisting of L, M, S, V and W; and is preferably L.

Also, in one aspect of the Nanobodies of the invention, the amino acid residue at position 83 is chosen from the group consisting of R, K, N, E, G, I, T and Q; and is most preferably either K or E (for Nanobodies corresponding to naturally occurring $V_{HH}$ domains) or R (for "humanized" Nanobodies, as described herein). The amino acid residue at position 84 is chosen from the group consisting of P, A, R, S, D T, and V in one aspect, and is most preferably P (for Nanobodies corresponding to naturally occurring $V_{HH}$ domains) or R (for "humanized" Nanobodies, as described herein).

Furthermore, in one aspect of the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human $V_H$ domain, $V_H3$, are summarized in Table A-3.

Some especially preferred but non-limiting combinations of these Hallmark Residues as occur in naturally occurring $V_{HH}$ domains are mentioned in Table A-4. For comparison, the corresponding amino acid residues of the human $V_H3$ called DP-47 have been indicated in italics.

TABLE A-3

Hallmark Residues in Nanobodies

| Position | Human $V_H3$ | Hallmark Residues |
|---|---|---|
| 11 | L, V; predominantly L | L, M, S, V, W; preferably L |
| 37 | V, I, F; usually V | $F^{(1)}$, Y, H, I, L or V; preferably $F^{(1)}$ or Y |
| 44[8] | G | $G^{(2)}$, $E^{(3)}$, A, D, Q, R, S, L; preferably $G^{(2)}$, $E^{(3)}$ or Q; most preferably $G^{(2)}$ or $E^{(3)}$. |
| 45[8] | L | $L^{(2)}$, $R^{(3)}$, C, I, L, P, Q, V; preferably $L^{(2)}$ or $R^{(3)}$ |
| 47[8] | W, Y | $W^{(2)}$, $L^{(1)}$ or $F^{(1)}$, A, G, I, M, R, S, V or Y; preferably $W^{(2)}$, $L^{(1)}$, $F^{(1)}$ or R |
| 83 | R or K; usually R | R, $K^{(5)}$, N, $E^{(5)}$, G, I, M, Q or T; preferably K or R; most preferably K |
| 84 | A, T, D; predominantly A | $P^{(5)}$, A, L, R, S, T, D, V; preferably P |
| 103 | W | $W^{(4)}$, $P^{(6)}$, $R^{(6)}$, S; preferably W |
| 104 | G | G or D; preferably G |
| 108 | L, M or T; predominantly L | Q, $L^{(7)}$ or R; preferably Q or $L^{(7)}$ |

Notes:
[1] In particular, but not exclusively, in combination with KERE or KQRE at positions 43-46.
[2] Usually as GLEW at positions 44-47.
[3] Usually as KERE or KQRE at positions 43-46, e.g. as KEREL, KEREF, KQREL, KQREF or KEREG at positions 43-47. Alternatively, also sequences such as TERE (for example TEREL), KECE (for example KECEL or KECER), RERE (for example REREG), QERE (for example QEREG), KGRE (for example KGREG), KDRE (for example KDREV) are possible. Some other possible, but less preferred sequences include for example DECKL and NVCEL.
[4] With both GLEW at positions 44-47 and KERE or KQRE at positions 43-46.
[5] Often as KP or EP at positions 83-84 of naturally occurring $V_{HH}$ domains.
[6] In particular, but not exclusively, in combination with GLEW at positions 44-47.
[7] With the proviso that when positions 44-47 are GLEW, position 108 is always Q in (non-humanized) $V_{HH}$ sequences that also contain a W at 103.
[8] The GLEW group also contains GLEW-like sequences at positions 44-47, such as for example GVEW, EPEW, GLER, DQEW, DLEW, GIEW, ELEW, GPEW, EWLP, GPER, GLER and ELEW.

TABLE A-4

Some preferred but non-limiting combinations of Hallmark Residues in naturally occurring Nanobodies. For humanization of these combinations, reference is made to the specification.

|  | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
|  | L | F | E | R | F | E | P | W | G | Q |
|  | L | F | E | R | F | K | P | W | G | Q |
|  | L | Y | Q | R | L | K | P | W | G | Q |
|  | L | F | L | R | V | K | P | Q | G | Q |
|  | L | F | Q | R | L | K | P | W | G | Q |
|  | L | F | E | R | F | K | P | W | G | Q |
| "GLEW" group | L | V | G | L | W | K | S | W | G | Q |
|  | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables A-5 to A-8 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering by Chothia (supra) that the residues at these positions already form part of CDR1.)

In Tables A-5-A-8, some of the non-limiting residues that can be present at each position of a human $V_H 3$ domain have also been mentioned. Again, for each position, the amino acid residue that most frequently occurs at each position of a naturally occurring human $V_H 3$ domain is indicated in bold; and other preferred amino acid residues have been underlined.

For reference only, Tables A-5-A-8 also contain data on the $V_{HH}$ entropy ("$V_{HH}$ Ent.") and $V_{HH}$ variability ("$V_{HH}$ Var.") at each amino acid position for a representative sample of 1118 $V_{HH}$ sequences (data kindly provided by David Lutje Hulsing and Prof. Theo Verrips of Utrecht University). The values for the $V_{HH}$ entropy and the $V_{HH}$ variability provide a measure for the variability and degree of conservation of amino acid residues between the 1118 $V_{HH}$ sequences analyzed: low values (i.e. <1, such as <0.5) indicate that an amino acid residue is highly conserved between the $V_{HH}$ sequences (i.e. little variability). For example, the G at position 8 and the G at position 9 have values for the $V_{HH}$ entropy of 0.1 and 0 respectively, indicating that these residues are highly conserved and have little variability (and in case of position 9 is G in all 1118 sequences analysed), whereas for residues that form part of the CDR's generally values of 1.5 or more are found (data not shown). Note that (1) the amino acid residues listed in the second column of Tables A-5-A-8 are based on a bigger sample than the 1118 $V_{HH}$ sequences that were analysed for determining the $V_{HH}$ entropy and $V_{HH}$ variability referred to in the last two columns; and (2) the data represented below support the hypothesis that the amino acid residues at positions 27-30 and maybe even also at positions 93 and 94 already form part of the CDR's (although the invention is not limited to any specific hypothesis or explanation, and as mentioned above, herein the numbering according to Kabat is used). For a general explanation of sequence entropy, sequence variability and the methodology for determining the same, see Oliveira et al., PROTEINS: Structure, Function and Genetics, 52: 544-552 (2003).

TABLE A-5

Non-limiting examples of amino acid residues in FR1 (for the footnotes, see the footnotes to Table A-3)

| | Amino acid residue(s): | | $V_{HH}$ | $V_{HH}$ |
|---|---|---|---|---|
| Pos. | Human $V_H 3$ | Camelid $V_{HH}$'s | Ent. | Var. |
| 1 | E, Q | Q, A, E | — | — |
| 2 | V | V | 0.2 | 1 |
| 3 | Q | Q, K | 0.3 | 2 |
| 4 | L | L | 0.1 | 1 |
| 5 | V, L | Q, E, L, V | 0.8 | 3 |
| 6 | E | E, D, Q, A | 0.8 | 4 |
| 7 | S, T | S, F | 0.3 | 2 |
| 8 | G, R | G | 0.1 | 1 |
| 9 | G | G | 0 | 1 |
| 10 | G, V | G, D, R | 0.3 | 2 |
| 11 | Hallmark residue: L, M, S, V, W; preferably L | | 0.8 | 2 |
| 12 | V, I | V, A | 0.2 | 2 |
| 13 | Q, K, R | Q, E, K, P, R | 0.4 | 4 |
| 14 | P | A, Q, A, G, P, S, T, V | 1 | 5 |
| 15 | G | G | 0 | 1 |
| 16 | G, R | G, A, E, D | 0.4 | 3 |
| 17 | S | S, F | 0.5 | 2 |
| 18 | L | L, V | 0.1 | 1 |
| 19 | R, K | R, K, L, N, S, T | 0.6 | 4 |
| 20 | L | L, F, I, V | 0.5 | 4 |
| 21 | S | S, A, F, T | 0.2 | 3 |
| 22 | C | C | 0 | 1 |
| 23 | A, T | A, D, E, P, S, T, V | 1.3 | 5 |
| 24 | A | A, I, L, S, T, V | 1 | 6 |
| 25 | S | S, A, F, P, T | 0.5 | 5 |
| 26 | G | G, A, D, E, R, S, T, V | 0.7 | 7 |
| 27 | F | S, F, R, L, P, G, N, | 2.3 | 13 |
| 28 | T | N, T, E, D, S, I, R, A, G, R, F, Y | 1.7 | 11 |
| 29 | F, V | F, L, D, S, I, G, V, A | 1.9 | 11 |
| 30 | S, D, G | N, S, E, G, A, D, M, T | 1.8 | 11 |

TABLE A-6

Non-limiting examples of amino acid residues in FR2 (for the footnotes, see the footnotes to Table A-3)

| | Amino acid residue(s): | | $V_{HH}$ | $V_{HH}$ |
|---|---|---|---|---|
| Pos. | Human $V_H 3$ | Camelid $V_{HH}$'s | Ent. | Var. |
| 36 | W | W | 0.1 | 1 |
| 37 | Hallmark residue: F$^{(1)}$, H, I, L, Y or V, preferably F$^{(1)}$ or Y | | 1.1 | 6 |
| 38 | R | R | 0.2 | 1 |
| 39 | Q | Q, H, P, R | 0.3 | 2 |
| 40 | A | A, F, G, L, P, T, V | 0.9 | 7 |
| 41 | P, S, T | P, A, L, S | 0.4 | 3 |
| 42 | G | G, E | 0.2 | 2 |
| 43 | K | K, D, E, N, Q, R, T, V | 0.7 | 6 |
| 44 | Hallmark residue: G$^{(2)}$, E$^{(3)}$, A, D, Q, R, S, L; preferably G$^{(2)}$, E$^{(3)}$ or Q; most preferably G$^{(2)}$ or E$^{(3)}$ | | 1.3 | 5 |
| 45 | Hallmark residue: L$^{(2)}$, R$^{(3)}$, C, I, L, P, Q, V; preferably L$^{(2)}$ or R$^{(3)}$ | | 0.6 | 4 |
| 46 | E, V | E, D, K, Q, V | 0.4 | 2 |
| 47 | Hallmark residue: W$^{(2)}$, L$^{(1)}$ or F$^{(1)}$, A, G, I, M, R, S, V or Y; preferably W$^{(2)}$, L$^{(1)}$, F$^{(1)}$ or R | | 1.9 | 9 |
| 48 | V | V, I, L | 0.4 | 3 |
| 49 | S, A, G | A, S, G, T, V | 0.8 | 3 |

TABLE A-7

Non-limiting examples of amino acid residues in FR3
(for the footnotes, see the footnotes to Table A-3)

| | Amino acid residue(s): | | $V_{HH}$ | $V_{HH}$ |
|---|---|---|---|---|
| Pos. | Human $V_H3$ | Camelid $V_{HH}$'s | Ent. | Var. |
| 66 | R | R | 0.1 | 1 |
| 67 | F | F, L, V | 0.1 | 1 |
| 68 | T | T, A, N, S | 0.5 | 4 |
| 69 | I | I, L, M, V | 0.4 | 4 |
| 70 | S | S, A, F, T | 0.3 | 4 |
| 71 | R | R, G, H, I, L, K, Q, S, T, W | 1.2 | 8 |
| 72 | D, E | D, E, G, N, V | 0.5 | 4 |
| 73 | N, D, G | N, A, D, F, I, K, L, R, S, T, V, Y | 1.2 | 9 |
| 74 | A, S | A, D, G, N, P, S, T, V | 1 | 7 |
| 75 | K | K, A, E, K, L, N, Q, R | 0.9 | 6 |
| 76 | N, S | N, D, K, R, S, T, Y | 0.9 | 6 |
| 77 | S, T, I | T, A, E, I, M, P, S | 0.8 | 5 |
| 78 | L, A | V, L, A, F, G, I, M | 1.2 | 5 |
| 79 | Y, H | Y, A, D, F, H, N, S, T | 1 | 7 |
| 80 | L | L, F, V | 0.1 | 1 |
| 81 | Q | Q, E, I, L, R, T | 0.6 | 5 |
| 82 | M | M, I, L, V | 0.2 | 2 |
| 82a | N, G | N, D, G, H, S, T | 0.8 | 4 |
| 82b | S | S, N, D, G, R, T | 1 | 6 |
| 82c | L | L, P, V | 0.1 | 2 |
| 83 | | Hallmark residue: R, K[(5)], N, E[(5)], G, I, M, Q or T; preferably K or R; most preferably K | 0.9 | 7 |
| 84 | | Hallmark residue: P[(5)], A, D, L, R, S, T, V; preferably P | 0.7 | 6 |
| 85 | E, G | E, D, G, Q | 0.5 | 3 |
| 86 | D | D | 0 | 1 |
| 87 | T, M | T, A, S | 0.2 | 3 |
| 88 | A | A, G, S | 0.3 | 2 |
| 89 | V, L | V, A, D, I, L, M, N, R, T | 1.4 | 6 |
| 90 | Y | Y, F | 0 | 1 |
| 91 | Y, H | Y, D, F, H, L, S, T, V | 0.6 | 4 |
| 92 | C | C | 0 | 1 |
| 93 | A, K, T | A, N, G, H, K, N, R, S, T, V, Y | 1.4 | 10 |
| 94 | K, R, T | A, V, C, F, G, I, K, L, R, S or T | 1.6 | 9 |

TABLE A-8

Non-limiting examples of amino acid residues in FR4
(for the footnotes, see the footnotes to Table A-3)

| | Amino acid residue(s): | | $V_{HH}$ | $V_{HH}$ |
|---|---|---|---|---|
| Pos. | Human $V_H3$ | Camelid $V_{HH}$'s | Ent. | Var. |
| 103 | | Hallmark residue: W[(4)], P[(6)], R[(6)], S; preferably W | 0.4 | 2 |
| 104 | | Hallmark residue: G or D; preferably G | 0.1 | 1 |
| 105 | Q, R | Q, E, K, P, R | 0.6 | 4 |
| 106 | G | G | 0.1 | 1 |
| 107 | T | T, A, I | 0.3 | 2 |
| 108 | | Hallmark residue: Q, L[(7)] or R; preferably Q or L[(7)] | 0.4 | 3 |
| 109 | V | V | 0.1 | 1 |
| 110 | T | T, I, A | 0.2 | 1 |
| 111 | V | V, A, I | 0.3 | 2 |
| 112 | S | S, F | 0.3 | 1 |
| 113 | S | S, A, L, P, T | 0.4 | 3 |

Thus, in another preferred, but not limiting aspect, a Nanobody of the invention can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) one or more of the amino acid residues at positions 11, 37, 44, 45, 47, 83, 84, 103, 104 and 108 according to the Kabat numbering are chosen from the Hallmark residues mentioned in Table A-3;

and in which:

ii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In particular, a Nanobody of the invention can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) (preferably) one or more of the amino acid residues at positions 11, 37, 44, 45, 47, 83, 84, 103, 104 and 108 according to the Kabat numbering are chosen from the Hallmark residues mentioned in Table A-3 (it being understood that $V_{HH}$ sequences will contain one or more Hallmark residues; and that partially humanized Nanobodies will usually, and preferably, [still] contain one or more Hallmark residues [although it is also within the scope of the invention to provide—where suitable in accordance with the invention—partially humanized Nanobodies in which all Hallmark residues, but not one or more of the other amino acid residues, have been humanized]; and that in fully humanized Nanobodies, where suitable in accordance with the invention, all amino acid residues at the positions of the Hallmark residues will be amino acid residues that occur in a human $V_H3$ sequence. As will be clear to the skilled person based on the disclosure herein that such $V_{HH}$ sequences, such partially humanized Nanobodies with at least one Hallmark residue, such partially humanized Nanobodies without Hallmark residues and such fully humanized Nanobodies all form aspects of this invention);

and in which:

ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded;

and in which:

iii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

TABLE A-9

Representative amino acid sequences for Nanobodies of the KERE, GLEW and P, R, S 103 group.
The CDR's are indicated with XXXX

| | | |
|---|---|---|
| KERE sequence no. 1 | SEQ ID NO: 1 | EVQLVESGGGLVQPGGSLRLSCAASGIPFSXXXXXXWFRQAPGKQRDSVAXXXXXXRFTI SRDNAKNTVYLQMNSLKPEDTAVYRCYFXXXXXXWGQGTQVTVSS |
| KERE sequence no. 2 | SEQ ID NO: 2 | QVKLEESGGGLVQAGGSLRLSCVGSGRTFSXXXXXXWFRLAPGKEREFVAXXXXXXRFTI SRDTASNRGYLHMNNLTPEDTAVYYCAAXXXXXXWGQGTQVTVSS |
| KERE sequence no. 3 | SEQ ID NO: 3 | AVQLVDSGGGLVQAGDSLKLSCALTGGAFTXXXXXXWFRQTPGREREFVAXXXXXXRFTI SRDNAKNMVYLRMNSLIPEDAAVYSCAAXXXXXXWGQGTLVTVSS |
| KERE sequence no. 4 | SEQ ID NO: 4 | QVQLVESGGGLVEAGGSLRLSCTASESPFRXXXXXXWFRQTSGQEREFVAXXXXXXRFTI SRDDAKNTVWLHGSTLKPEDTAVYYCAAXXXXXXWGQGTQVTVSS |
| KERE sequence no. 5 | SEQ ID NO: 5 | AVQLVESGGGLVQGGGSLRLACAASERIFDXXXXXXWYRQGPGNERELVAXXXXXXRFTI SMDYTKQTVYLHMNSLRPEDTGLYYCKIXXXXXXWGQGTQVTVSS |
| KERE sequence no. 6 | SEQ ID NO: 6 | DVKFVESGGGLVQAGGSLRLSCVASGFNFDXXXXXXWFRQAPGKEREEVAXXXXXXRFTI SSEKDKNSVYLQMNSLKPEDTALYICAGXXXXXXWGRGTQVTVSS |
| KERE sequence no. 7 | SEQ ID NO: 7 | QVRLAESGGGLVQSGGSLRLSCVASGSTYTXXXXXXWYRQYPGKQRALVAXXXXXXRFTI ARDSTKDTFCLQMNNLKPEDTAVYYCYAXXXXXXWGQGTQVTVSS |
| KERE sequence no. 8 | SEQ ID NO: 8 | EVQLVESGGGLVQAGGSLRLSCAASGFTSDXXXXXXWFRQAPGKPREGVSXXXXXXRFTI STDNAKNTVHLLMNRVNAEDTALYYCAVXXXXXXWGRGTRVTVSS |
| KERE sequence no. 9 | SEQ ID NO: 9 | QVQLVESGGGLVQPGGSLRLSCQASGDISTXXXXXXWYRQVPGKLREFVAXXXXXXRFTI SGDNAKRAIYLQMNNLKPDDTAVYYCNRXXXXXXWGQGTQVTVSP |
| KERE sequence no. 10 | SEQ ID NO: 10 | QVPWESGGGLVQAGDSLRLFCAVPSFTSTXXXXXXWFRQAPGKEREFVAXXXXXXRFTI SRNATKNTLTLRMDSLKPEDTAVYYCAAXXXXXXWGQGTQVTVSS |
| KERE sequence no. 11 | SEQ ID NO: 11 | EVQLVESGGGLVQAGDSLRLFCTVSGGTASXXXXXXWFRQAPGEKREFVAXXXXXXRFTI ARENAGNMVYLQMNNLKPDDTALYTCAAXXXXXXWGRGTQVTVSS |
| KERE sequence no. 12 | SEQ ID NO: 12 | AVQLVESGGDSVQPGDSQTLSCAASGRTNSXXXXXXWFRQAPGKERVFLAXXXXXXRFTI SRDSAKNMMYLQMNNLKPQDTAVYYCAAXXXXXXWGQGTQVTVSS |
| KERE sequence no. 13 | SEQ ID NO: 13 | AVQLVESGGGLVQAGGSLRLSCWSGLTSSXXXXXXWFRQTPWQERDFVAXXXXXXRFTIS RDNYKDTVLLEMNFLKPEDTAIYYCAAXXXXXXWGQGTQVTVSS |
| KERE sequence no. 14 | SEQ ID NO: 14 | AVQLVESGGGLVQAGASLRLSCATSTRTLDXXXXXXWFRQAPGRDREFVAXXXXXXRFTV SRDSAENTVALQMNSLKPEDTAVYYCAAXXXXXXWGQGTRVTVSS |
| KERE sequence no. 15 | SEQ ID NO: 15 | QVQLVESGGGLVQPGGSLRLSCTVSRLTAHXXXXXXWFRQAPGKEREAVSXXXXXXRFTI SRDYAGNTAFLQMDSLKPEDTGVYYCATXXXXXXWGQGTQVTVSS |
| KERE sequence no. 16 | SEQ ID NO: 16 | EVQLVESGGELVQAGGSLKLSCTASGRNFVXXXXXXWFRRAPGKEREFVAXXXXXXRFTV SRDNGKNTAYLRMNSLKPEDTADYYCAVXXXXXXLGSGTQVTVSS |
| GLEW sequence no. 1 | SEQ ID NO: 17 | AVQLVESGGGLVQPGGSLRLSCAASGFTFSXXXXXXWVRQAPGKVLEWVSXXXXXXRFTI SRDNAKNTLYLQMNSLKPEDTAVYYCVKXXXXXXGSQGTQVTVSS |
| GLEW sequence no. 2 | SEQ ID NO: 18 | EVQLVESGGGLVQPGGSLRLSCVCVSSGCTXXXXXXWVRQAPGKAEEWVSXXXXXXRFKI SRDNAKKTLYLQMNSLGPEDTAMYYCQRXXXXXXRGQGTQVTVSS |
| GLEW sequence no. 3 | SEQ ID NO: 19 | EVQLVESGGGLALPGGSLTLSCVFSGSTFSXXXXXXWVRHTPGKAEEWVSXXXXXXRFTI SRDNAKNTLYLEMNSLSPEDTAMYYCGRXXXXXXRSKGIQVTVSS |
| P, R, S 103 sequence no. 1 | SEQ ID NO: 20 | AVQLVESGGGLVQAGGSLRLSCAASGRTFSXXXXXXWFRQAPGKEREFVAXXXXXXRFTI SRDNAKNTVYLQ MNSLKPEDTAVYYCAAXXXXXXRGQGTQVTVSS |
| P, R, S 103 sequence no. 2 | SEQ ID NO: 21 | DVQLVESGGDLVQPGGSLRLSCAASGFSFDXXXXXXWLRQTPGKGLEVVVGXXXXXXRFT ISRDNAKNMLYLHLNNLKSEDTAVYYCRRXXXXXXLGQGTQVTVSS |
| P, R, S 103 sequence no. 3 | SEQ ID NO: 22 | EVQLVESGGGLVQPGGSLRLSCVCVSSGCTXXXXXXWVRQAPGKAEEWVSXXXXXXRFKI SRDNAKKTLYLQMNSLGPEDTAMYYCQRXXXXXXRGQGTQVTVSS |

In particular, a Nanobody of the invention of the KERE group can be an amino acid sequence with the (general) structure

FR1-CDR1-FR2-CDR2-FR3-CDR3-FR4 in which:

i) the amino acid residue at position 45 according to the Kabat numbering is a charged amino acid (as defined herein) or a cysteine residue, and position 44 is preferably an E;

and in which:

ii) FR1 is an amino acid sequence that has at least 80% amino acid identity with at least one of the following amino acid sequences:

TABLE A-10

Representative FW1 sequences for Nanobodies of the KERE-group.

| | | |
|---|---|---|
| KERE FW1 sequence no. 1 | SEQ ID NO: 23 | QVQRVESGGGLVQAGGSLRLSCAASGRTSS |
| KERE FW1 sequence no. 2 | SEQ ID NO: 24 | QVQLVESGGGLVQTGDSLSLSCSASGRTFS |
| KERE FW1 sequence no. 3 | SEQ ID NO: 25 | QVKLEESGGGLVQAGDSLRLSCAATGRAFG |
| KERE FW1 sequence no. 4 | SEQ ID NO: 26 | AVQLVESGGGLVQPGESLGLSCVASGRDFV |
| KERE FW1 sequence no. 5 | SEQ ID NO: 27 | EVQLVESGGGLVQAGGSLRLSCEVLGRTAG |
| KERE FW1 sequence no. 6 | SEQ ID NO: 28 | QVQLVESGGGWVQPGGSLRLSCAASETILS |
| KERE FW1 sequence no. 7 | SEQ ID NO: 29 | QVQLVESGGGTVQPGGSLNLSCVASGNTFN |
| KERE FW1 sequence no. 8 | SEQ ID NO: 30 | EVQLVESGGGLAQPGGSLQLSCSAPGFTLD |
| KERE FW1 sequence no. 9 | SEQ ID NO: 31 | AQELEESGGGLVQAGGSLRLSCAASGRTFN | and in which:

iii) FR2 is an amino acid sequence that has at least 80% amino acid identity with at least one of the following amino acid sequences:

TABLE A-11

Representative FW2 sequences for Nanobodies of the KERE-group.

| | | |
|---|---|---|
| KERE FW2 sequence no. 1 | SEQ ID NO: 41 | WFRQAPGKEREFVA |
| KERE FW2 sequence no. 2 | SEQ ID NO: 42 | WFRQTPGREREFVA |
| KERE FW2 sequence no. 3 | SEQ ID NO: 43 | WYRQAPGKQREMVA |
| KERE FW2 sequence no. 4 | SEQ ID NO: 44 | WYRQGPGKQRELVA |

TABLE A-11-continued

Representative FW2 sequences for Nanobodies of the KERE-group.

| | | |
|---|---|---|
| KERE FW2 sequence no. 5 | SEQ ID NO: 45 | WIRQAPGKEREGVS |
| KERE FW2 sequence no. 6 | SEQ ID NO: 46 | WFREAPGKEREGIS |
| KERE FW2 sequence no. 7 | SEQ ID NO: 47 | WYRQAPGKERDLVA |
| KERE FW2 sequence no. 8 | SEQ ID NO: 48 | WFRQAPGKQREEVS |
| KERE FW2 sequence no. 9 | SEQ ID NO: 49 | WFRQPPGKVREFVG | and in which:

iv) FR3 is an amino acid sequence that has at least 80% amino acid identity with at least one of the following amino acid sequences:

TABLE A-12

Representative FW3 sequences for Nanobodies of the KERE-group.

| | | |
|---|---|---|
| KERE FW3 sequence no. 1 | SEQ ID NO: 50 | RFTISRDNAKNTVYLQMNSLKPEDTAVYRCYF |
| KERE FW3 sequence no. 2 | SEQ ID NO: 51 | RFAISRDNNKNTGYLQMNSLEPEDTAVYYCAA |
| KERE FW3 sequence no. 3 | SEQ ID NO: 52 | RFTVARNNAKNTVNLEMNSLKPEDTAVYYCAA |
| KERE FW3 sequence no. 4 | SEQ ID NO: 53 | RFTISRDIAKNTVDLLMNNLEPEDTAVYYCAA |
| KERE FW3 sequence no. 5 | SEQ ID NO: 54 | RLTISRDNAVDTMYLQMNSLKPEDTAVYYCAA |
| KERE FW3 sequence no. 6 | SEQ ID NO: 55 | RFTISRDNAKNTVYLQMDNVKPEDTAIYYCAA |
| KERE FW3 sequence no. 7 | SEQ ID NO: 56 | RFTISKDSGKNTVYLQMTSLKPEDTAVYYCAT |
| KERE FW3 sequence no. 8 | SEQ ID NO: 57 | RFTISRDSAKNMMYLQMNNLKPQDTAVYYCAA |
| KERE FW3 sequence no. 9 | SEQ ID NO: 58 | RFTISRENDKSTVYLQLNSLKPEDTAVYYCAA |
| KERE FW3 sequence no. 10 | SEQ ID NO: 59 | RFTISRDYAGNTAYLQMNSLKPEDTGVYYCAT | and in which:

v) FR4 is an amino acid sequence that has at least 80% amino acid identity with at least one of the following amino acid sequences:

TABLE A-13

Representative FW4 sequences for Nanobodies of the KERE-group.

| | | |
|---|---|---|
| KERE FW4 sequence no. 1 | SEQ ID NO: 60 | WGQGTQVTVSS |
| KERE FW4 sequence no. 2 | SEQ ID NO: 61 | WGKGTLVTVSS |
| KERE FW4 sequence no. 3 | SEQ ID NO: 62 | RGQGTRVTVSS |
| KERE FW4 sequence no. 4 | SEQ ID NO: 63 | WGLGTQVTISS | and in which:

vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

Also, the above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

With regard to framework 1, it will be clear to the skilled person that, when an amino acid sequence as outlined above is generated by expression of a nucleotide sequence, the first four amino acid sequences (i.e. amino acid residues 1-4 according to the Kabat numbering) may often be determined by the primer(s) that have been used to generate said nucleic acid. Thus, for determining the degree of amino acid identity, the first four amino acid residues are preferably disregarded.

Also, with regard to framework 1, and although amino acid positions 27 to 30 are according to the Kabat numbering considered to be part of the framework regions (and not the CDR's), it has been found by analysis of a database of more than 1000 $V_{HH}$ sequences that the positions 27 to 30 have a variability (expressed in terms of $V_{HH}$ entropy and $V_{HH}$ variability—see Tables A-5 to A-8) that is much greater than the variability on positions 1 to 26. Because of this, for determining the degree of amino acid identity, the amino acid residues at positions 27 to 30 are preferably also disregarded.

In view of this, a Nanobody of the KERE class may be an amino acid sequence that is comprised of four framework regions/sequences interrupted by three complementarity determining regions/sequences, in which:

i) the amino acid residue at position 45 according to the Kabat numbering is a charged amino acid (as defined herein) or a cysteine residue, and position 44 is preferably an E;

and in which:

ii) FR1 is an amino acid sequence that, on positions 5 to 26 of the Kabat numbering, has at least 80% amino acid identity with at least one of the following amino acid sequences:

TABLE A-14

Representative FW1 sequences (amino acid residues 5 to 26) for Nanobodies of the KERE-group.

| | | |
|---|---|---|
| KERE FW1 sequence no. 10 | SEQ ID NO: 32 | VESGGGLVQPGGSLRLSCAASG |
| KERE FW1 sequence no. 11 | SEQ ID NO: 33 | VDSGGGLVQAGDSLKLSCALTG |
| KERE FW1 sequence no. 12 | SEQ ID NO: 34 | VDSGGGLVQAGDSLRLSCAASG |
| KERE FW1 sequence no. 13 | SEQ ID NO: 35 | VDSGGGLVEAGGSLRLSCQVSE |
| KERE FW1 sequence no. 14 | SEQ ID NO: 36 | QDSGGGSVQAGGSLKLSCAASG |
| KERE FW1 sequence no. 15 | SEQ ID NO: 37 | VQSGGRLVQAGDSLRLSCAASE |
| KERE FW1 sequence no. 16 | SEQ ID NO: 38 | VESGGTLVQSGDSLKLSCASST |
| KERE FW1 sequence no. 17 | SEQ ID NO: 39 | MESGGDSVQSGGSLTLSCVASG |
| KERE FW1 sequence no. 18 | SEQ ID NO: 40 | QASGGGLVQAGGSLRLSCSASV | and in which:

iii) FR2, FR3 and FR4 are as mentioned herein for FR2, FR3 and FR4 of Nanobodies of the KERE-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

A Nanobody of the GLEW class may be an amino acid sequence that is comprised of four framework regions/sequences interrupted by three complementarity determining regions/sequences, in which i) preferably, when the Nanobody of the GLEW-class is a non-humanized Nanobody, the amino acid residue in position 108 is Q;
ii) FR1 is an amino acid sequence that has at least 80% amino acid identity with at least one of the following amino acid sequences:

TABLE A-15

Representative FW1 sequences for Nanobodies of the GLEW-group.

| | | |
|---|---|---|
| GLEW FW1 sequence no. 1 | SEQ ID NO: 64 | QVQLVESGGGLVQPGGSLRLSCAASGFTFS |
| GLEW FW1 sequence no. 2 | SEQ ID NO: 65 | EVHLVESGGGLVRPGGSLRLSCAAFGFIFK |
| GLEW FW1 sequence no. 3 | SEQ ID NO: 66 | QVKLEESGGGLAQPGGSLRLSCVASGFTFS |
| GLEW FW1 sequence no. 4 | SEQ ID NO: 67 | EVQLVESGGGLVQPGGSLRLSCVCVSSGCT |
| GLEW FW1 sequence no. 5 | SEQ ID NO: 68 | EVQLVESGGGLALPGGSLTLSCVFSGSTFS | and in which:
iii) FR2 is an amino acid sequence that has at least 80% amino acid identity with at least one of the following amino acid sequences:

TABLE A-16

Representative FW2 sequences for Nanobodies of the GLEW-group.

| | | |
|---|---|---|
| GLEW FW2 sequence no. 1 | SEQ ID NO: 72 | WVRQAPGKVLEWVS |
| GLEW FW2 sequence no. 2 | SEQ ID NO: 73 | WVRRPPGKGLEWVS |
| GLEW FW2 sequence no. 3 | SEQ ID NO: 74 | WVRQAPGMGLEWVS |
| GLEW FW2 sequence no. 4 | SEQ ID NO: 75 | WVRQAPGKEPEWVS |
| GLEW FW2 sequence no. 5 | SEQ ID NO: 76 | WVRQAPGKDQEWVS |
| GLEW FW2 sequence no. 6 | SEQ ID NO: 77 | WVRQAPGKAEEWVS |
| GLEW FW2 sequence no. 7 | SEQ ID NO: 78 | WVRQAPGKGLEWVA |
| GLEW FW2 sequence no. 8 | SEQ ID NO: 79 | WVRQAPGRATEWVS | and in which:
iv) FR3 is an amino acid sequence that has at least 80% amino acid identity with at least one of the following amino acid sequences:

TABLE A-17

Representative FW3 sequences for Nanobodies of the GLEW-group.

| | | |
|---|---|---|
| GLEW FW3 sequence no. 1 | SEQ ID NO: 80 | RFTISRDNAKNTLYLQMNSLKPEDTAVYYCVK |
| GLEW FW3 sequence no. 2 | SEQ ID NO: 81 | RFTISRDNARNTLYLQMDSLIPEDTALYYCAR |
| GLEW FW3 sequence no. 3 | SEQ ID NO: 82 | RFTSSRDNAKSTLYLQMNDLKPEDTALYYCAR |
| GLEW FW3 sequence no. 4 | SEQ ID NO: 83 | RFIISRDNAKNTLYLQMNSLGPEDTAMYYCQR |
| GLEW FW3 sequence no. 5 | SEQ ID NO: 84 | RFTASRDNAKNTLYLQMNSLKSEDTARYYCAR |
| GLEW FW3 sequence no. 6 | SEQ ID NO: 85 | RFTISRDNAKNTLYLQMDDLQSEDTAMYYCGR | and in which:
v) FR4 is an amino acid sequence that has at least 80% amino acid identity with at least one of the following amino acid sequences:

TABLE A-18

Representative FW4 sequences for Nanobodies of the GLEW-group.

| | | |
|---|---|---|
| GLEW FW4 sequence no. 1 | SEQ ID NO: 86 | GSQGTQVTVSS |
| GLEW FW4 sequence no. 2 | SEQ ID NO: 87 | LRGGTQVTVSS |
| GLEW FW4 sequence no. 3 | SEQ ID NO: 88 | RGQGTLVTVSS |
| GLEW FW4 sequence no. 4 | SEQ ID NO: 89 | RSRGIQVTVSS |
| GLEW FW4 sequence no. 5 | SEQ ID NO: 90 | WGKGTQVTVSS |
| GLEW FW4 sequence no. 6 | SEQ ID NO: 91 | WGQGTQVTVSS | and in which:
vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are V$_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the GLEW class may be an amino acid sequence that is comprised of four framework regions/sequences interrupted by three complementarity determining regions/sequences, in which:
i) preferably, when the Nanobody of the GLEW-class is a non-humanized Nanobody, the amino acid residue in position 108 is Q;

and in which:
ii) FR1 is an amino acid sequence that, on positions 5 to 26 of the Kabat numbering, has at least 80% amino acid identity with at least one of the following amino acid sequences:

TABLE A-19

Representative FW1 sequences (amino acid residues 5 to 26) for Nanobodies of the KERE-group.

| | | |
|---|---|---|
| GLEW FW1 sequence no. 6 | SEQ ID NO: 69 | VESGGGLVQPGGSLRLSCAASG |
| GLEW FW1 sequence no. 7 | SEQ ID NO: 70 | EESGGGLAQPGGSLRLSCVASG |
| GLEW FW1 sequence no. 8 | SEQ ID NO: 71 | VESGGGLALPGGSLTLSCVFSG | and in which:

iii) FR2, FR3 and FR4 are as mentioned herein for FR2, FR3 and FR4 of Nanobodies of the GLEW-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein. In the above Nanobodies, one or more of the further Hallmark residues are preferably as described herein (for example, when they are $V_{HH}$ sequences or partially humanized Nanobodies).

A Nanobody of the P, R, S 103 class may be an amino acid sequence that is comprised of four framework regions/sequences interrupted by three complementarity determining regions/sequences, in which i) the amino acid residue at position 103 according to the Kabat numbering is different from W;

and in which:

ii) preferably the amino acid residue at position 103 according to the Kabat numbering is P, R or S, and more preferably R;

and in which:

iii) FR1 is an amino acid sequence that has at least 80% amino acid identity with at least one of the following amino acid sequences:

TABLE A-20

Representative FW1 sequences for Nanobodies of the P, R, S 103-group.

| | | |
|---|---|---|
| P, R, S 103 FW1 sequence no. 1 | SEQ ID NO: 92 | AVQLVESGGGLVQAGGSLRLSCAASGRTFS |
| P, R, S 103 FW1 sequence no. 2 | SEQ ID NO: 93 | QVQLQESGGGMVQPGGSLRLSCAASGFDFG |
| P, R, S 103 FW1 sequence no. 3 | SEQ ID NO: 94 | EVHLVESGGGLVRPGGSLRLSCAAFGFIFK |
| P, R, S 103 FW1 sequence no. 4 | SEQ ID NO: 95 | QVQLAESGGGLVQPGGSLKLSCAASRTIVS |
| P, R, S 103 FW1 sequence no. 5 | SEQ ID NO: 96 | QEHLVESGGGLVDIGGSLRLSCAASERIFS |
| P, R, S 103 FW1 sequence no. 6 | SEQ ID NO: 97 | QVKLEESGGGLAQPGGSLRLSCVASGFTFS |
| P, R, S 103 FW1 sequence no. 7 | SEQ ID NO: 98 | EVQLVESGGGLVQPGGSLRLSCVCVSSGCT |
| P, R, S 103 FW1 sequence no. 8 | SEQ ID NO: 99 | EVQLVESGGGLALPGGSLTLSCVFSGSTFS | and in which iv) FR2 is an amino acid sequence that has at least 80% amino acid identity with at least one of the following amino acid sequences:

TABLE A-21

Representative FW2 sequences for Nanobodies of the P, R, S 103-group.

| | | |
|---|---|---|
| P, R, S 103 FW2 sequence no. 1 | SEQ ID NO: 102 | WFRQAPGKEREFVA |
| P, R, S 103 FW2 sequence no. 2 | SEQ ID NO: 103 | WVRQAPGKVLEWVS |
| P, R, S 103 FW2 sequence no. 3 | SEQ ID NO: 104 | WVRRPPGKGLEWVS |
| P, R, S 103 FW2 sequence no. 4 | SEQ ID NO: 105 | WIRQAPGKEREGVS |
| P, R, S 103 FW2 sequence no. 5 | SEQ ID NO: 106 | WVRQYPGKEPEWVS |
| P, R, S 103 FW2 sequence no. 6 | SEQ ID NO: 107 | WFRQPPGKEHEFVA |
| P, R, S 103 FW2 sequence no. 7 | SEQ ID NO: 108 | WYRQAPGKRTELVA |
| P, R, S 103 FW2 sequence no. 8 | SEQ ID NO: 109 | WLRQAPGQGLEWVS |
| P, R, S 103 FW2 sequence no. 9 | SEQ ID NO: 110 | WLRQTPGKGLEWVG |
| P, R, S 103 FW2 sequence no. 10 | SEQ ID NO: 111 | WVRQAPGKAEEFVS | and in which:

v) FR3 is an amino acid sequence that has at least 80% amino acid identity with at least one of the following amino acid sequences:

TABLE A-22

Representative FW3 sequences for Nanobodies of the P, R, S 103-group.

| | | |
|---|---|---|
| P, R, S 103 FW3 sequence no. 1 | SEQ ID NO: 112 | RFTISRDNAKNTVYLQMNSLKPEDTAVYYCAA |
| P, R, S 103 FW3 sequence no. 2 | SEQ ID NO: 113 | RFTISRDNARNTLYLQMDSLIPEDTALYYCAR |
| P, R, S 103 FW3 sequence no. 3 | SEQ ID NO: 114 | RFTISRDNAKNEMYLQMNNLKTEDTGVYWCGA |
| P, R, S 103 FW3 sequence no. 4 | SEQ ID NO: 115 | RFTISSDSNRNMIYLQMNNLKPEDTAVYYCAA |
| P, R, S 103 FW3 sequence no. 5 | SEQ ID NO: 116 | RFTISRDNAKNMLYLHLNNLKSEDTAVYYCRR |
| P, R, S 103 FW3 sequence no. 6 | SEQ ID NO: 117 | RFTISRDNAKKTVYLRLNSLNPEDTAVYSCNL |
| P, R, S 103 FW3 sequence no. 7 | SEQ ID NO: 118 | RFKISRDNAKKTLYLQMNSLGPEDTAMYYCQR |
| P, R, S 103 FW3 sequence no. 8 | SEQ ID NO: 119 | RFTVSRDNGKNTAYLRMNSLKPEDTADYYCAV | and in which:

vi) FR4 is an amino acid sequence that has at least 80% amino acid identity with at least one of the following amino acid sequences:

TABLE A-23

Representative FW4 sequences for Nanobodies of the P, R, S 103-group.

| | | |
|---|---|---|
| P, R, S 103 FW4 sequence no. 1 | SEQ ID NO: 120 | RGQGTQVTVSS |
| P, R, S 103 FW4 sequence no. 2 | SEQ ID NO: 121 | LRGGTQVTVSS |
| P, R, S 103 FW4 sequence no. 3 | SEQ ID NO: 122 | GNKGTLVTVSS |
| P, R, S 103 FW4 sequence no. 4 | SEQ ID NO: 123 | SSPGTQVTVSS |
| P, R, S 103 FW4 sequence no. 5 | SEQ ID NO: 124 | SSQGTLVTVSS |
| P, R, S 103 FW4 sequence no. 6 | SEQ ID NO: 125 | RSRGIQVTVSS | and in which:

vii) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are V$_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the P,R,S 103 class may be an amino acid sequence that is comprised of four framework regions/sequences interrupted by three complementarity determining regions/sequences, in which:

i) the amino acid residue at position 103 according to the Kabat numbering is different from W;

and in which:

ii) preferably the amino acid residue at position 103 according to the Kabat numbering is P, R or S, and more preferably R;

and in which:

iii) FR1 is an amino acid sequence that, on positions 5 to 26 of the Kabat numbering, has at least 80% amino acid identity with at least one of the following amino acid sequences:

TABLE A-24

Representative FW1 sequences (amino acid residues 5 to 26) for Nanobodies of the P, R, S 103-group.

| | | |
|---|---|---|
| P, R, S 103 FW1 sequence no. 9 | SEQ ID NO: 100 | VESGGGLVQAGGSLRLSCAASG |
| P, R, S 103 FW1 sequence no. 10 | SEQ ID NO: 101 | AESGGGLVQPGGSLKLSCAASR | and in which:

iv) FR2, FR3 and FR4 are as mentioned herein for FR2, FR3 and FR4 of Nanobodies of the P,R,S 103 class;

and in which:

v) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In the above Nanobodies, one or more of the further Hallmark residues are preferably as described herein (for example, when they are $V_{HH}$ sequences or partially humanized Nanobodies).

In another preferred, but non-limiting aspect, the invention relates to a Nanobody as described above, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 238 to 253, more preferably SEQ ID NO: 238 and SEQ ID NO: 239. This degree of amino acid identity can for example be determined by determining the degree of amino acid identity (in a manner described herein) between said Nanobody and one or more of the sequences of SEQ ID NO's: 238 to 253, more preferably SEQ ID NO: 238 and SEQ ID NO: 239, in which the amino acid residues that form the framework regions are disregarded. Such Nanobodies can be as further described herein.

As already mentioned herein, another preferred but non-limiting aspect of the invention relates to a Nanobody with an amino acid sequence that is chosen from the group consisting of SEQ ID NO's: 238 to 253, more preferably SEQ ID NO: 238 and SEQ ID NO: 239 or from the group consisting of from amino acid sequences that have more than 80%, preferably more than 90%, more preferably more than 95%, such as 99% or more sequence identity (as defined herein) with at least one of the amino acid sequences of SEQ ID NO's: 238 to 253, more preferably SEQ ID NO: 238 and SEQ ID NO: 239.

Also, in the above Nanobodies:

i) any amino acid substitution (when it is not a humanizing substitution as defined herein) is preferably, and compared to the corresponding amino acid sequence of SEQ ID NO's: 238 to 253, more preferably SEQ ID NO: 238 and SEQ ID NO: 239, a conservative amino acid substitution, (as defined herein);

and/or:

ii) its amino acid sequence preferably contains either only amino acid substitutions, or otherwise preferably no more than 5, preferably no more than 3, and more preferably only 1 or 2 amino acid deletions or insertions, compared to the corresponding amino acid sequence of SEQ ID NO's: 238 to 253, more preferably SEQ ID NO: 238 and SEQ ID NO: 239;

and/or iii) the CDR's may be CDR's that are derived by means of affinity maturation, for example starting from the CDR's of to the corresponding amino acid sequence of SEQ ID NO's: 238 to 253, more preferably SEQ ID NO: 238 and SEQ ID NO: 239.

Preferably, the CDR sequences and FR sequences in the Nanobodies of the invention are such that the Nanobodies of the invention (and polypeptides of the invention comprising the same):

bind to GPCRs with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to GPCRs with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to GPCRs with a $k_{off}$ rate between $1$ $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, CDR sequences and FR sequences present in the Nanobodies of the invention are such that the Nanobodies of the invention will bind to GPCRs with an affinity less than 500 nM, preferably less than 200 nM, more preferably less than 10 nM, such as less than 500 pM.

According to one non-limiting aspect of the invention, a Nanobody may be as defined herein, but with the proviso that it has at least "one amino acid difference" (as defined herein) in at least one of the framework regions compared to the corresponding framework region of a naturally occurring human $V_H$ domain, and in particular compared to the corresponding framework region of DP-47. More specifically, according to one non-limiting aspect of the invention, a Nanobody may be as defined herein, but with the proviso that it has at least "one amino acid difference" (as defined herein) at least one of the Hallmark residues (including those at positions 108, 103 and/or 45) compared to the corresponding framework region of a naturally occurring human $V_H$ domain, and in particular compared to the corresponding framework region of DP-47. Usually, a Nanobody will have at least one such amino acid difference with a naturally occurring $V_H$ domain in at least one of FR2 and/or FR4, and in particular at least one of the Hallmark residues in FR2 and/or FR4 (again, including those at positions 108, 103 and/or 45).

Also, a humanized Nanobody of the invention may be as defined herein, but with the proviso that it has at least "one amino acid difference" (as defined herein) in at least one of the framework regions compared to the corresponding framework region of a naturally occurring $V_{HH}$ domain. More specifically, according to one non-limiting aspect of the invention, a humanized Nanobody may be as defined herein, but with the proviso that it has at least "one amino acid difference" (as defined herein) at least one of the Hallmark residues (including those at positions 108, 103 and/or 45) compared to the corresponding framework region of a naturally occurring $V_{HH}$ domain. Usually, a humanized Nanobody will have at least one such amino acid difference with a naturally occurring $V_{HH}$ domain in at least one of FR2 and/or FR4, and in particular at least one of the Hallmark residues in FR2 and/or FR4 (again, including those at positions 108, 103 and/or 45).

As will be clear from the disclosure herein, it is also within the scope of the invention to use natural or synthetic analogs, mutants, variants, alleles, homologs and orthologs (herein collectively referred to as "analogs") of the Nanobodies of the invention as defined herein, and in particular analogs of the Nanobodies of SEQ ID NO's 238 to 253, more preferably SEQ ID NO: 238 and SEQ ID NO: 239. Thus, according to one aspect of the invention, the term "Nanobody of the invention" in its broadest sense also covers such analogs.

Generally, in such analogs, one or more amino acid residues may have been replaced, deleted and/or added, compared to the Nanobodies of the invention as defined herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanizing substitutions as described herein).

By means of non-limiting examples, a substitution may for example be a conservative substitution (as described herein) and/or an amino acid residue may be replaced by another amino acid residue that naturally occurs at the same position in another $V_{HH}$ domain (see Tables A-5 to A-8 for some non-limiting examples of such substitutions), although the invention is generally not limited thereto. Thus, any one or more substitutions, deletions or insertions, or any combination thereof, that either improve the properties of the Nanobody of the invention or that at least do not detract too much from the desired properties or from the balance or combination of desired properties of the Nanobody of the invention (i.e. to the extent that the Nanobody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the Nanobodies thus obtained.

For example, and depending on the host organism used to express the Nanobody or polypeptide of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5 to A-8 above, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions.

The analogs are preferably such that they can bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

The analogs are preferably also such that they retain the favourable properties the Nanobodies, as described herein.

Also, according to one preferred aspect, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference (as defined herein), with one of the Nanobodies of SEQ ID NOs: 238 to 253, more preferably SEQ ID NO: 238 and SEQ ID NO: 239.

Also, the framework sequences and CDR's of the analogs are preferably such that they are in accordance with the preferred aspects defined herein. More generally, as described herein, the analogs will have (a) a Q at position 108; and/or (b) a charged amino acid or a cysteine residue at position 45 and preferably an E at position 44, and more preferably E at position 44 and R at position 45; and/or (c) P, R or S at position 103.

One preferred class of analogs of the Nanobodies of the invention comprise Nanobodies that have been humanized (i.e. compared to the sequence of a naturally occurring Nanobody of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, for example from the Tables herein, from the possible humanizing substitutions mentioned in the background art cited herein, and/or from a comparison between the sequence of a Nanobody and the sequence of a naturally occurring human $V_H$ domain.

The humanizing substitutions should be chosen such that the resulting humanized Nanobodies still retain the favourable properties of Nanobodies as defined herein, and more preferably such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies thus obtained.

Generally, as a result of humanization, the Nanobodies of the invention may become more "human-like", while still retaining the favorable properties of the Nanobodies of the invention as described herein. As a result, such humanized Nanobodies may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_{HH}$ domains on the other hand.

The Nanobodies of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies of the "P,R,S-103 group" or the "KERE group" is Q108 into L108. Nanobodies of the "GLEW class" may also be humanized by a Q108 into L108 substitution, provided at least one of the other Hallmark residues contains a camelid (camelizing) substitution (as defined herein). For example, as mentioned above, one particularly preferred class of humanized Nanobodies has GLEW or a GLEW-like sequence at positions 44-47; P, R or S (and in particular R) at position 103, and an L at position 108.

The humanized and other analogs, and nucleic acid sequences encoding the same, can be provided in any manner known per se. For example, the analogs can be obtained by providing a nucleic acid that encodes a naturally occurring $V_{HH}$ domain, changing the codons for the one or more amino acid residues that are to be substituted into the codons for the corresponding desired amino acid residues (e.g. by site-directed mutagenesis or by PCR using suitable mismatch primers), expressing the nucleic acid/nucleotide sequence thus obtained in a suitable host or expression system; and optionally isolating and/or purifying the analog thus obtained to provide said analog in essentially isolated form (e.g. as further described herein). This can generally be performed using methods and techniques known per se, which will be clear to the skilled person, for example from the handbooks and references cited herein, the background art cited herein and/or from the further description herein. Alternatively, a nucleic acid encoding the desired analog can be synthesized in a manner known per se (for example using an automated apparatus for synthesizing nucleic acid sequences with a predefined amino acid sequence) and can then be expressed as described herein. Yet another technique may involve combining one or more naturally occurring and/or synthetic nucleic acid sequences each encoding a part of the desired analog, and then expressing the combined nucleic acid sequence as described herein. Also, the analogs can be provided using chemical synthesis of the pertinent amino acid sequence using techniques for peptide synthesis known per se, such as those mentioned herein.

In this respect, it will be also be clear to the skilled person that the Nanobodies of the invention (including their analogs) can be designed and/or prepared starting from human $V_H$ sequences (i.e. amino acid sequences or the corresponding nucleotide sequences), such as for example from human $V_H3$ sequences such as DP-47, DP-51 or DP-29, i.e. by introducing one or more camelizing substitutions (i.e. changing one or more amino acid residues in the amino acid sequence of said human $V_H$ domain into the amino acid residues that occur at the corresponding position in a $V_{HH}$ domain), so as to provide the sequence of a Nanobody of the invention and/or so as to confer the favourable properties of a Nanobody to the sequence thus obtained. Again, this can generally be performed using the various methods and techniques referred to in the previous paragraph, using an amino acid sequence and/or nucleotide sequence for a human $V_H$ domain as a starting point.

Some preferred, but non-limiting camelizing substitutions can be derived from Tables A-5-A-8. It will also be clear that camelizing substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelizing substitutions that already confer at least some the desired properties, and then to introduce further camelizing substitutions that either further improve said properties and/or confer additional favourable properties. Again, the skilled person will generally be able to determine and select suitable camelizing substitutions or suitable combinations of camelizing substitutions, based on the disclosure herein and optionally after a limited degree of routine experimentation, which may for example involve introducing a limited number of possible camelizing substitutions and determining whether the favourable properties of Nanobodies are obtained or improved (i.e. compared to the original $V_H$ domain). Generally, however, such camelizing substitutions are preferably such that the resulting an amino acid sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelizing substitutions. More preferably, the camelizing substitutions are such that they result in a Nanobody of the invention and/or in an analog thereof (as defined herein), such as in a humanized analog and/or preferably in an analog that is as defined in the preceding paragraphs.

As will also be clear from the disclosure herein, it is also within the scope of the invention to use parts or fragments, or combinations of two or more parts or fragments, of the Nanobodies of the invention as defined herein, and in particular parts or fragments of the Nanobodies of SEQ ID NO's: 238 to 253, more preferably SEQ ID NO: 238 and SEQ ID NO: 239. Thus, according to one aspect of the invention, the term "Nanobody of the invention" in its broadest sense also covers such parts or fragments.

Generally, such parts or fragments of the Nanobodies of the invention (including analogs thereof) have amino acid sequences in which, compared to the amino acid sequence of the corresponding full length Nanobody of the invention (or analog thereof), one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length Nanobody of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting aspect, such a part or fragment comprises at least CDR3, such as FR3, CDR3 and FR4 of the corresponding full length Nanobody of the invention, i.e. as for example described in the International application WO 03/050531 (Lasters et al.).

As already mentioned above, it is also possible to combine two or more of such parts or fragments (i.e. from the same or different Nanobodies of the invention), i.e. to provide an analog (as defined herein) and/or to provide further parts or fragments (as defined herein) of a Nanobody of the invention. It is for example also possible to combine one or more parts or fragments of a Nanobody of the invention with one or more parts or fragments of a human $V_H$ domain.

According to one preferred aspect, the parts or fragments have a degree of sequence identity of at least 50%, preferably at least 60%, more preferably at least 70%, even more preferably at least 80%, such as at least 90%, 95% or 99% or more with one of the Nanobodies of SEQ ID NOs 238 to 253, more preferably SEQ ID NO: 238 and SEQ ID NO: 239.

The parts and fragments, and nucleic acid sequences encoding the same, can be provided and optionally combined in any manner known per se. For example, such parts or fragments can be obtained by inserting a stop codon in a nucleic acid that encodes a full-sized Nanobody of the invention, and then expressing the nucleic acid thus obtained in a manner known per se (e.g. as described herein). Alternatively, nucleic acids encoding such parts or fragments can be obtained by suitably restricting a nucleic acid that encodes a full-sized Nanobody of the invention or by synthesizing such a nucleic acid in a manner known per se. Parts or fragments may also be provided using techniques for peptide synthesis known per se.

The invention in its broadest sense also comprises derivatives of the Nanobodies of the invention. Such derivatives can generally be obtained by modification, and in particular by chemical and/or biological (e.g. enzymatical) modification, of the Nanobodies of the invention and/or of one or more of the amino acid residues that form the Nanobodies of the invention.

Examples of such modifications, as well as examples of amino acid residues within the Nanobody sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the Nanobody of the invention, and in particular of one or more functional groups, residues or moieties that confer one or more desired properties or functionalities to the Nanobody of the invention. Example of such functional groups will be clear to the skilled person.

For example, such modification may comprise the introduction (e.g. by covalent binding or in any other suitable manner) of one or more functional groups that increase the half-life, the solubility and/or the absorption of the Nanobody of the invention, that reduce the immunogenicity and/or the toxicity of the Nanobody of the invention, that eliminate or attenuate any undesirable side effects of the Nanobody of the invention, and/or that confer other advantageous properties to and/or reduce the undesired properties of the Nanobodies and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a Nanobody of the invention, a Nanobody of the invention may be modified so as to suitably introduce one or more cysteine residues for attachment of PEG, or an amino acid sequence comprising one or more cysteine residues for attachment of PEG may be fused to the N- and/or C-terminus of a Nanobody of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the Nanobody or polypeptide of the invention.

Yet another modification may comprise the introduction of one or more detectable labels or other signal-generating groups or moieties, depending on the intended use of the labelled Nanobody. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metal chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the Nanobody of the invention to another protein, polypeptide or chemical compound that is bound to the other half of the binding pair, i.e. through formation of the binding pair. For example, a Nanobody of the invention may be conjugated to biotin, and linked to another protein, polypeptide, compound or carrier conjugated to avidin or streptavidin. For example, such a conjugated Nanobody may be used as a reporter, for example in a diagnostic system where a detectable signal-producing agent is conjugated to avidin or streptavidin. Such binding pairs may for example also be used to bind the Nanobody of the invention to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the Nanobody of the invention.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a toxin or to a toxic residue or moiety. Examples of toxic moieties, compounds or residues which can be linked to a Nanobody of the invention to provide—for example—a cytotoxic compound will be clear to the skilled person and can for example be found in the prior art cited above and/or in the further description herein. One example is the so-called ADEPT™ technology described in WO 03/055527.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

As mentioned above, the invention also relates to proteins or polypeptides that essentially consist of or comprise at least one Nanobody of the invention. By "essentially consist of" is meant that the amino acid sequence of the polypeptide of the invention either is exactly the same as the amino acid sequence of a Nanobody of the invention or corresponds to the amino acid sequence of a Nanobody of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence of the Nanobody.

Said amino acid residues may or may not change, alter or otherwise influence the (biological) properties of the Nanobody and may or may not add further functionality to the Nanobody. For example, such amino acid residues:

can comprise an N-terminal Met residue, for example as result of expression in a heterologous host cell or host organism.

may form a signal sequence or leader sequence that directs secretion of the Nanobody from a host cell upon synthesis. Suitable secretory leader peptides will be clear to the skilled person, and may be as further described herein. Usually, such a leader sequence will be linked to the N-terminus of the Nanobody, although the invention in its broadest sense is not limited thereto;

may form a sequence or signal that allows the Nanobody to be directed towards and/or to penetrate or enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such amino acid sequences will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousselle, J. Pharmacol. Exp. Ther., 296, 124-131 (2001), and the membrane translocator sequence described by Zhao et al., Apoptosis, 8, 631-637 (2003). C-terminal and N-terminal amino acid sequences for intracellular targeting of antibody fragments are for example described by Cardinale et al., Methods, 34, 171 (2004). Other suitable techniques for intracellular targeting involve the expression and/or use of so-called "intrabodies" comprising a Nanobody of the invention, as mentioned below;

may form a "tag", for example an amino acid sequence or residue that allows or facilitates the purification of the Nanobody, for example using affinity techniques directed against said sequence or residue. Thereafter, said sequence or residue may be removed (e.g. by chemical or enzymatical cleavage) to provide the Nanobody sequence (for this purpose, the tag may optionally be linked to the Nanobody sequence via a cleavable linker sequence or contain a cleavable motif). Some preferred, but non-limiting examples of such residues are multiple histidine residues, glutathione residues and a myc-tag (see for example SEQ ID NO:31 of WO 06/12282).

may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the Nanobodies of the invention.

According to another aspect, a polypeptide of the invention comprises a Nanobody of the invention, which is fused at its amino terminal end, at its carboxy terminal end, or both at its amino terminal end and at its carboxy terminal end to at least one further amino acid sequence, i.e. so as to provide a fusion protein comprising said Nanobody of the invention and the one or more further amino acid sequences. Such a fusion will also be referred to herein as a "Nanobody fusion".

The one or more further amino acid sequence may be any suitable and/or desired amino acid sequences. The further amino acid sequences may or may not change, alter or otherwise influence the (biological) properties of the Nanobody, and may or may not add further functionality to the Nanobody or the polypeptide of the invention. Preferably, the further amino acid sequence is such that it confers one or more desired properties or functionalities to the Nanobody or the polypeptide of the invention.

For example, the further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the Nanobody of the invention is directed, or a different protein, polypeptide, antigen, antigenic determinant or epitope).

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005), For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the Nanobody of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In particular, it has been described in the art that linking fragments of immunoglobulins (such as $V_H$ domains) to serum albumin or to fragments thereof can be used to increase the half-life. Reference is for made to WO 00/27435 and WO 01/077137). According to the invention, the Nanobody of the invention is preferably either directly linked to serum albumin (or to a suitable fragment thereof) or via a suitable linker, and in particular via a suitable peptide linked so that the polypeptide of the invention can be expressed as a genetic fusion (protein). According to one specific aspect, the Nanobody of the invention may be linked to a fragment of serum albumin that at least comprises the domain III of serum albumin or part thereof. Reference is for example made to the U.S. provisional application 60/788,256 of Ablynx N.V. entitled "Albumin derived amino acid sequence, use thereof for increasing the half-life of therapeutic proteins and of other therapeutic proteins and entities, and constructs comprising the same" filed on Mar. 31, 2006.

Alternatively, the further amino acid sequence may provide a second binding site or binding unit that is directed against a serum protein (such as, for example, human serum albumin or another serum protein such as IgG), so as to provide increased half-life in serum. Such amino acid sequences for example include the Nanobodies described below, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to the following the U.S. provisional applications 60/843,349, 60/850,774, 60/850,775 by Ablynx N.V. mentioned herein US provisional application of Ablynx N.V. entitled "Peptides capable of binding to serum proteins" filed on Dec. 5, 2006 (also mentioned herein).

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example the U.S. provisional application 60/843,349 by Ablynx N.V. entitled "Serum albumin binding proteins with long half-lives" filed on Sep. 8, 2006); amino acid sequences against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*), reference is again made to the U.S. provisional application 60/843,349); amino acid sequences that can bind to serum albumin in a pH independent manner (see for example the U.S. provisional application 60/850,774 by Ablynx N.V. entitled "Amino acid sequences that bind to serum proteins in a manner that is essentially independent of the pH, compounds comprising the same, and uses thereof", filed on Oct. 11, 2006) and/or amino acid sequences that are conditional binders (see for example the U.S. provisional application 60/850,775 by Ablynx N.V. entitled "Amino acid sequences that bind to a desired molecule in a conditional manner", filed on Oct. 11, 2006).

According to another aspect, the one or more further amino acid sequences may comprise one or more parts, fragments or domains of conventional 4-chain antibodies (and in particular human antibodies) and/or of heavy chain antibodies. For example, although usually less preferred, a Nanobody of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

The at least one Nanobody may also be linked to one or more (preferably human) $C_H1$, $C_H2$ and/or $C_H3$ domains, optionally via a linker sequence. For instance, a Nanobody linked to a suitable $C_H1$ domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by a Nanobody of the invention. Also, two Nanobodies could be linked to a $C_H3$ domain (optionally via a linker) to provide a construct with increased half-life in vivo.

According to one specific aspect of a polypeptide of the invention, one or more Nanobodies of the invention may be linked to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG, from IgE or from another human Ig. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the Nanobodies of the invention so as to provide an effector function will be clear to the skilled person, and may be chosen on the basis of the desired effector function(s). Reference is for example made to WO 04/058820, WO 99/42077 and WO 05/017148, as well as the review by Holliger and Hudson, supra. Coupling of a Nanobody of the invention to an Fc portion may also lead to an increased half-life, compared to the corresponding Nanobody of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more Nanobodies and one or more constant domains with increased half-life in vivo will be clear to the skilled person, and may for example comprise two Nanobodies linked to a $C_H3$ domain, optionally via a linker sequence. Generally, any fusion protein or derivatives with increased half-life will preferably have a molecular weight of more than 50 kD, the cut-off value for renal absorption.

The further amino acid sequences may also form a signal sequence or leader sequence that directs secretion of the Nanobody or the polypeptide of the invention from a host cell upon synthesis (for example to provide a pre-, pro- or preproform of the polypeptide of the invention, depending on the host cell used to express the polypeptide of the invention).

The further amino acid sequence may also form a sequence or signal that allows the Nanobody or polypeptide of the invention to be directed towards and/or to penetrate or enter into specific organs, tissues, cells, or parts or compartments of cells, and/or that allows the Nanobody or polypeptide of the invention to penetrate or cross a biological barrier such as a cell membrane, a cell layer such as a layer of epithelial cells, a tumor including solid tumors, or the blood-brain-barrier. Suitable examples of such amino acid sequences will be clear to the skilled person, and for example include, but are not limited to, the "Peptrans" vectors mentioned above, the sequences described by Cardinale et al. and the amino acid sequences and antibody fragments known per se that can be used to express or produce the Nanobodies and polypeptides of the invention as so-called "intrabodies", for example as described in WO 94/02610, WO 95/22618, U.S. Pat. No. 7,004,940, WO 03/014960, WO 99/07414; WO 05/01690; EP 1 512 696; and in Cattaneo, A. & Biocca, S. (1997) Intracellular Antibodies: Development and Applications. Landes and Springer-Verlag; and in Kontermann, Methods 34, (2004), 163-170, and the further references described therein.

For some applications, in particular for those applications in which it is intended to kill a cell that expresses the target against which the Nanobodies of the invention are directed (e.g. in the treatment of cancer), or to reduce or slow the growth and/or proliferation of such a cell, the Nanobodies of the invention may also be linked to a (cyto)toxic protein or polypeptide. Examples of such toxic proteins and polypeptides which can be linked to a Nanobody of the invention to provide—for example—a cytotoxic polypeptide of the invention will be clear to the skilled person and can for example be found in the prior art cited above and/or in the further description herein. One example is the so-called ADEPT™ technology described in WO 03/055527.

According to one preferred, but non-limiting aspect, said one or more further amino acid sequences comprise at least one further Nanobody, so as to provide a polypeptide of the invention that comprises at least two, such as three, four, five or more Nanobodies, in which said Nanobodies may optionally be linked via one or more linker sequences (as defined herein). Polypeptides of the invention that comprise two or more Nanobodies, of which at least one is a Nanobody of the invention, will also be referred to herein as "multivalent" polypeptides of the invention, and the Nanobodies present in such polypeptides will also be referred to herein as being in a "multivalent format". For example a "bivalent" polypeptide of the invention comprises two Nanobodies, optionally linked via a linker sequence, whereas a "trivalent" polypeptide of the invention comprises three Nanobodies, optionally linked via two linker sequences; etc.; in which at least one of the Nanobodies present in the polypeptide, and up to all of the Nanobodies present in the polypeptide, is/are a Nanobody of the invention.

In a multivalent polypeptide of the invention, the two or more Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof.

For example, a bivalent polypeptide of the invention may comprise (a) two identical Nanobodies; (b) a first Nanobody directed against a first antigenic determinant of a protein or antigen and a second Nanobody directed against the same antigenic determinant of said protein or antigen which is different from the first Nanobody; (c) a first Nanobody directed against a first antigenic determinant of a protein or antigen and a second Nanobody directed against another antigenic determinant of said protein or antigen (e.g. an inverse antagonistic CXCR4 Nanobody and an antagonistic CXCR4 Nanobody); or (d) a first Nanobody directed against a first protein or antigen and a second Nanobody directed against a second protein or antigen (i.e. different from said first antigen) (e.g. CXCR4 Nanobody that has inverse antagonistic properties and CXCR7 Nanobody that has antagonistic properties or vice versa). Similarly, a trivalent polypeptide of the invention may, for example and without being limited thereto, comprise (a) three identical Nanobodies; (b) two identical Nanobody against a first antigenic determinant of an antigen and a third Nanobody directed against a different antigenic determinant of the same antigen; (c) two identical Nanobody against a first antigenic determinant of an antigen and a third Nanobody directed against a second antigen different from said first antigen; (d) a first Nanobody directed against a first antigenic determinant of a first antigen, a second Nanobody directed against a second antigenic determinant of said first antigen and a third Nanobody directed against a second antigen different from said first antigen; or (e) a first Nanobody directed against a first antigen, a second Nanobody directed against a second antigen different from said first antigen, and a third Nanobody directed against a third antigen different from said first and second antigen.

Polypeptides of the invention that contain at least two Nanobodies, in which at least one Nanobody is directed against a first antigen (i.e. against GPCRs,) and at least one Nanobody is directed against a second antigen (i.e. different from GPCRs,), will also be referred to as "multispecific" polypeptides of the invention, and the Nanobodies present in such polypeptides will also be referred to herein as being in a "multispecific format". Thus, for example, a "bispecific" polypeptide of the invention is a polypeptide that comprises at least one Nanobody directed against a first antigen (i.e. GPCRs,) and at least one further Nanobody directed against a second antigen (i.e. different from GPCRs,), whereas a "trispecific" polypeptide of the invention is a polypeptide that comprises at least one Nanobody directed against a first antigen (i.e. GPCRs,), at least one further Nanobody directed against a second antigen (i.e. different from GPCRs,) and at least one further Nanobody directed against a third antigen (i.e. different from both GPCRs, and the second antigen); etc.

Accordingly, in its simplest form, a bispecific polypeptide of the invention is a bivalent polypeptide of the invention (as defined herein), comprising a first Nanobody directed against GPCRs, and a second Nanobody directed against a second antigen, in which said first and second Nanobody may optionally be linked via a linker sequence (as defined herein); whereas a trispecific polypeptide of the invention in its simplest form is a trivalent polypeptide of the invention (as defined herein), comprising a first Nanobody directed against GPCRs, a second Nanobody directed against a second antigen and a third Nanobody directed against a third antigen, in which said first, second and third Nanobody may optionally be linked via one or more, and in particular one and more, in particular two, linker sequences.

However, as will be clear from the description hereinabove, the invention is not limited thereto, in the sense that a multispecific polypeptide of the invention may comprise at least one Nanobody against GPCRs, and any number of Nanobodies directed against one or more antigens different from GPCRs.

Furthermore, although it is encompassed within the scope of the invention that the specific order or arrangement of the various Nanobodies in the polypeptides of the invention may have some influence on the properties of the final polypeptide of the invention (including but not limited to the affinity, specificity, potency, functionality or avidity for GPCRs, or against the one or more other antigens), said order or arrangement is usually not critical and may be suitably chosen by the skilled person, optionally after some limited routine experiments based on the disclosure herein. Thus, when reference is made to a specific multivalent or multispecific polypeptide of the invention, it should be noted that this encompasses any order or arrangements of the relevant Nanobodies, unless explicitly indicated otherwise.

Moreover, it is also within the scope of the invention that the polypeptides of the invention contain two or more Nanobodies and one or more further amino acid sequences (as mentioned herein).

The present invention also relates to bispecific immunoglobulin sequences and in general to bispecific ligands wherein said bispecific immunoglobulin sequences and/or ligands are i) specific and/or have affinity for an epitope that upon binding is capable to provoke an inverse antagonistic effect; and said bispecific immunoglobulin sequences and/or ligands are ii) specific and/or have affinity for an epitope that upon binding is capable to provoke an antagonistic effect. It has surprisingly been found that linking a neutral antagonist with an inverse antagonist leds to an improved inverse antagonist behavior (baseline levels were unexpectedly further reduced compared to inverse antagonist alone).

Wherein the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies. In one embodiment of the invention, the immunoglobulin sequences are light chain variable domain sequences (e.g. a $V_L$-sequence), or heavy chain variable domain sequences (e.g. a $V_H$-sequence); more specifically, the immunoglobulin sequences can be heavy chain variable domain sequences that are derived from a conventional four-chain antibody or heavy chain variable domain sequences that are derived from a heavy chain antibody. According to the invention, the immunoglobulin sequences can be domain antibodies, or amino acid sequences that are suitable for use as domain antibodies, single domain antibodies, or amino acid sequences that are suitable for use as single domain antibodies, "dAbs", or amino acid sequences that are suitable for use as dAbs, or Nanobodies, including but not limited to $V_{HH}$ sequences, and preferably are Nanobodies.

Four types of ligands exist for a GPCR: agonists are ligands that shift the equilibrium in favour of active states; inverse agonists or inverse antagonist are ligands that shift the equilibrium in favour of inactive states; and neutral antagonists are ligands that do not affect the equilibrium. As used herein, "ligand" refers to a moiety that is capable of associating or binding to a receptor. According to the method of the invention, a ligand and a receptor have a binding constant that is sufficiently strong to allow detection of binding by an assay method that is appropriate for detection of a ligand binding to a receptor (e.g. a second messenger assay to detect an increase or decrease in the production of a second messenger in response to ligand binding to the receptor, a binding assay to measure protein-ligand binding or an immunoassay to measure antibody-antigen interactions). A ligand according to the invention includes any nucleotide, antibody, antigen, enzyme, peptide, polypeptide, small molecule or nucleic acid capable of binding to the receptor. According to the method of the invention, a ligand and receptor specifically bind to each other (e.g. via covalent or hydrogen bonding or via an interaction between, for example, a protein and a ligand, an antibody and an antigen or protein subunits). For multivalent and multispecific polypeptides containing one or more $V_{HH}$ domains and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the applications by Ablynx N.V. referred to herein.

One preferred, but non-limiting example of a multispecific polypeptide of the invention comprises at least one Nanobody of the invention and at least one Nanobody that provides for an increased half-life. Such Nanobodies may for example be Nanobodies that are directed against a serum protein, and in particular a human serum protein, such as human serum albumin, thyroxine-binding protein, (human) transferrin, fibrinogen, an immunoglobulin such as IgG, IgE or IgM, or against one of the serum proteins listed in WO 04/003019. Of these, Nanobodies that can bind to serum albumin (and in particular human serum albumin) or to IgG (and in particular human IgG, see for example Nanobody VH-1 described in the review by Muyldermans, supra) are particularly preferred (although for example, for experiments in mice or primates, Nanobodies against or cross-reactive with mouse serum albumin (MSA) or serum albumin from said primate, respectively, can be used. However, for pharmaceutical use, Nanobodies against human serum albumin or human IgG will usually be preferred). Nanobodies that provide for increased half-life and that can be used in the polypeptides of the invention include the Nanobodies directed against serum albumin that are described in WO 04/041865, in WO 06/122787 and in the further patent applications by Ablynx N.V., such as those mentioned above.

For example, the some preferred Nanobodies that provide for increased half-life for use in the present invention include Nanobodies that can bind to amino acid residues on (human) serum albumin that are not involved in binding of serum albumin to FcRn (see for example WO 06/0122787); Nanobodies that are capable of binding to amino acid residues on serum albumin that do not form part of domain III of serum albumin (see for example WO 06/0122787); Nanobodies that have or can provide an increased half-life (see for example the U.S. provisional application 60/843,349 by Ablynx N.V mentioned herein); Nanobodies against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) (see for example the U.S. provisional application 60/843,349 by Ablynx N.V); Nanobodies that can bind to serum albumin in a pH independent manner (see for example the U.S. provisional application 60/850,774 by Ablynx N.V. mentioned herein) and/or Nanobodies that are conditional binders (see for example the U.S. provisional application 60/850,775 by Ablynx N.V.).

Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred.

According to a specific, but non-limiting aspect of the invention, the polypeptides of the invention contain, besides the one or more Nanobodies of the invention, at least one Nanobody against human serum albumin.

Generally, any polypeptides of the invention with increased half-life that contain one or more Nanobodies of the invention, and any derivatives of Nanobodies of the invention or of such polypeptides that have an increased half-life, preferably have a half-life that is at least 1.5 times, preferably at least 2 times, such as at least 5 times, for example at least 10 times or more than 20 times, greater than the half-life of the corresponding Nanobody of the invention per se. For example, such a derivative or polypeptides with increased half-life may have a half-life that is increased with more than 1 hours, preferably more than 2 hours, more preferably more than 6 hours, such as more than 12 hours, or even more than 24, 48 or 72 hours, compared to the corresponding Nanobody of the invention per se.

In a preferred, but non-limiting aspect of the invention, such derivatives or polypeptides may exhibit a serum half-life in human of at least about 12 hours, preferably at least 24 hours, more preferably at least 48 hours, even more preferably at least 72 hours or more. For example, such derivatives or polypeptides may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

According to one aspect of the invention the polypeptides are capable of binding to one or more molecules which can increase the half-life of the polypeptide in vivo.

The polypeptides of the invention are stabilised in vivo and their half-life increased by binding to molecules which resist degradation and/or clearance or sequestration. Typically, such molecules are naturally occurring proteins which themselves have a long half-life in vivo.

Another preferred, but non-limiting example of a multispecific polypeptide of the invention comprises at least one Nanobody of the invention and at least one Nanobody that directs the polypeptide of the invention towards, and/or that allows the polypeptide of the invention to penetrate or to enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such Nanobodies include Nanobodies that are directed towards specific cell-surface proteins, markers or epitopes of the desired organ, tissue or cell (for example cell-surface markers associated with tumor cells), and the single-domain brain targeting antibody fragments described in WO 02/057445 and WO 06/040153, of which FC44 (SEQ ID NO: 189 of WO 06/040153) and FC5 (SEQ ID NO: 190 of WO 06/040154) are preferred examples.

In the polypeptides of the invention, the one or more Nanobodies and the one or more polypeptides may be directly linked to each other (as for example described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each Nanobody by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678).

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for GPCRs, or for one or more of the other antigens. Based on the disclosure herein, the skilled person will be able to determine the optimal linker(s) for use in a specific polypeptide of the invention, optionally after some limited routine experiments.

For example, in multivalent polypeptides of the invention that comprise Nanobodies directed against a multimeric antigen (such as a multimeric receptor or other protein), the length and flexibility of the linker are preferably such that it allows each Nanobody of the invention present in the polypeptide to bind to the antigenic determinant on each of the subunits of the multimer. Similarly, in a multispecific polypeptide of the invention that comprises Nanobodies directed against two or more different antigenic determinants on the same antigen (for example against different epitopes of an antigen and/or against different subunits of a multimeric receptor, channel or protein), the length and flexibility of the linker are preferably such that it allows each Nanobody to bind to its intended antigenic determinant. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the Nanobodies of the invention). For example, linkers containing one or more charged amino acid residues (see Table A-2 above) can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three of more Nanobodies, it is possible to link them by use of a linker with three or more "arms", which each "arm" being linked to a Nanobody, so as to provide a "star-shaped" construct. It is also possible, although usually less preferred, to use circular constructs.

The invention also comprises derivatives of the polypeptides of the invention, which may be essentially analogous to the derivatives of the Nanobodies of the invention, i.e. as described herein.

The invention also comprises proteins or polypeptides that "essentially consist" of a polypeptide of the invention (in which the wording "essentially consist of" has essentially the same meaning as indicated hereinabove).

According to one aspect of the invention, the polypeptide of the invention is in essentially isolated from, as defined herein.

The amino acid sequences, Nanobodies, polypeptides and nucleic acids of the invention can be prepared in a manner known per se, as will be clear to the skilled person from the further description herein. For example, the Nanobodies and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, polypeptides and nucleic acids include the methods and techniques described herein.

As will be clear to the skilled person, one particularly useful method for preparing an amino acid sequence, Nanobody and/or a polypeptide of the invention generally comprises the steps of:
i) the expression, in a suitable host cell or host organism (also referred to herein as a "host of the invention") or in another suitable expression system of a nucleic acid that encodes said amino acid sequence, Nanobody or polypeptide of the invention (also referred to herein as a "nucleic acid of the invention"), optionally followed by:
ii) isolating and/or purifying the amino acid sequence, Nanobody or polypeptide of the invention thus obtained.

In particular, such a method may comprise the steps of:
i) cultivating and/or maintaining a host of the invention under conditions that are such that said host of the invention expresses and/or produces at least one amino acid sequence, Nanobody and/or polypeptide of the invention; optionally followed by:
ii) isolating and/or purifying the amino acid sequence, Nanobody or polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of GPCRs as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises
i) at least one nucleic acid of the invention; operably connected to
ii) one or more regulatory elements, such as a promoter and optionally a suitable terminator;
and optionally also
iii) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 7,207,410, U.S. Pat. No. 5,693,492 and EP 1 085 089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the amino acid sequence, Nanobody or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;

a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;

a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;

an amphibian cell or cell line, such as *Xenopus* oocytes;

an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;

a plant or plant cell, for example in tobacco plants; and/or a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The amino acid sequences, Nanobodies and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-)introduced into the body of the patient. All this can be performed using gene therapy vectors, techniques and delivery systems which are well known to the skilled person, and for example described in Culver, K. W., "Gene Therapy", 1994, p. xii, Mary Ann Liebert, Inc., Publishers, New York, N.Y.); Giordano, Nature F Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91; (1998), 30-36; Verma, Gene Ther. 5 (1998), 692-699; Nabel, Ann N.Y. Acad. Sci.: 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580,859; U.S. Pat. No. 5589,5466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the Nanobodies in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino acid sequences, Nanobodies and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori.*

Furthermore, the amino acid sequences, Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical (i.e. GMP grade) expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, Nanobody or polypeptide to be obtained.

Thus, according to one non-limiting aspect of the invention, the amino acid sequence, Nanobody or polypeptide of the invention is glycosylated. According to another non-limiting aspect of the invention, the amino acid sequence, Nanobody or polypeptide of the invention is non-glycosylated.

According to one preferred, but non-limiting aspect of the invention, the amino acid sequence, Nanobody or polypeptide of the invention is produced in a bacterial cell, in particular a bacterial cell suitable for large scale pharmaceutical production, such as cells of the strains mentioned above.

According to another preferred, but non-limiting aspect of the invention, the amino acid sequence, Nanobody or polypeptide of the invention is produced in a yeast cell, in particular a yeast cell suitable for large scale pharmaceutical production, such as cells of the species mentioned above.

According to yet another preferred, but non-limiting aspect of the invention, the amino acid sequence, Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, Nanobodies and the polypeptides of the invention, the amino acid sequences, Nanobodies and polypeptides of the invention can be produced either intracellularly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic host cells are used, extracellular production is usually preferred since this considerably facilitates the further isolation and downstream processing of the Nanobodies and proteins obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular an amino acid sequence, Nanobody or a polypeptide of the invention, can be used.

Thus, according to one non-limiting aspect of the invention, the amino acid sequence, Nanobody or polypeptide of the invention is an amino acid sequence, Nanobody or polypeptide that has been produced intracellularly and that has been isolated from the host cell, and in particular from a bacterial cell or from an inclusion body in a bacterial cell. According to another non-limiting aspect of the invention, the amino acid sequence, Nanobody or polypeptide of the invention is an amino acid sequence, Nanobody or polypeptide that has been produced extracellularly, and that has been isolated from the medium in which the host cell is cultivated.

Some preferred, but non-limiting promoters for use with these host cells include, for expression in *E. coli*: lac promoter (and derivatives thereof such as the lacUV5 promoter); arabinose promoter; left- (PL) and rightward (PR) promoter of phage lambda; promoter of the trp operon; hybrid lac/trp promoters (tac and trc); T7 promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1,10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);

for expression in *Pichia pastoris*: the AOX1 promoter (alcohol oxidase I);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α(hEF-1α) promoter from human, chimpanzee, mouse or rat; the SV40 early promoter; HIV-1 long terminal repeat promoter; β-actin promoter;

Some preferred, but non-limiting vectors for use with these host cells include:

vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUC-Tag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and *Pichia* expression vectors (Invitrogen);

vectors for expression in insect cells: pBlueBacII (Invitrogen) and other baculovirus vectors vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:

for use in bacterial cells such as *E. coli*: PelB, Bla, OmpA, OmpC, OmpF, OmpT, StII, PhoA, PhoE, MalE, Lpp, LamB, and the like; TAT signal peptide, hemolysin C-terminal secretion signal;

for use in yeast: α-mating factor prepro-sequence, phosphatase (pho1), invertase (Suc), etc.;

for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence, Nanobody or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) amino acid sequence, Nanobody or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence, Nanobody or polypeptide of the invention may (first) be generated in an immature form (as mentioned above), which may then be subjected to post-translational modification, depending on the host cell/host organism used. Also, the amino acid sequence, Nanobody or polypeptide of the invention may be glycosylated, again depending on the host cell/host organism used.

The amino acid sequence, Nanobody or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody or polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one Nanobody of the invention or at least one polypeptide of the invention and at least one suitable carrier, diluent or excipient (i.e. suitable for pharmaceutical use), and optionally one or more further active substances.

Generally, the amino acid sequences, Nanobodies and polypeptides of the invention can be formulated and administered in any suitable manner known per se, for which reference is for example made to the general background art cited above (and in particular to WO 04/041862, WO 04/041863, WO 04/041865 and WO 04/041867) as well as to the standard handbooks, such as Remington's Pharmaceutical Sciences, 18$^{th}$ Ed., Mack Publishing Company, USA (1990) or Remington, the Science and Practice of Pharmacy, 21st Edition, Lippincott Williams and Wilkins (2005).

For example, the amino acid sequences, Nanobodies and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The amino acid sequences, Nanobodies and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, Nanobody or polypeptide of the invention can additionally be transfected with tissue specific promoters to target specific organs, tissue, grafts, tumors, or cells and can additionally be transfected with signal and stabilization sequences for subcellularly localized expression.

Thus, the amino acid sequences, Nanobodies and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, Nanobody or polypeptide of the invention. Their percentage in the compositions and preparations may, of course, be varied and may conveniently be between about 2 to about 60% of the weight of a given unit dosage form. The amount of the amino acid sequence, Nanobody or polypeptide of the invention in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino acid sequences, Nanobodies and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies and polypeptides of the invention may also be administered intravenously or intraperitoneally by infusion or injection. Solutions of the amino acid sequences, Nanobodies and polypeptides of the invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the amino acid sequences, Nanobodies and polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the amino acid sequences, Nanobodies and polypeptides of the invention may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the amino acid sequences, Nanobodies and polypeptides of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the amino acid sequences, Nanobodies and polypeptides of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the amino acid sequences, Nanobodies and polypeptides of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the amino acid sequences, Nanobodies and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the amino acid sequences, Nanobodies and polypeptides of the invention required for use in treatment will vary not only with the particular amino acid sequence, Nanobody or polypeptide selected but also with the route of administration, the nature of the condition being treated and the age and condition of the patient and will be ultimately at the discretion of the attendant physician or clinician. Also the dosage of the amino acid sequences, Nanobodies and polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one GPCR-related diseases and disorders, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with GPCRs, with its biological or pharmacological activity, and/or with the biological pathways or signalling in which GPCRs is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, the invention relates to a method for the prevention and/or treatment of at least one disease or disorder that can be treated by modulating GPCRs, its biological or pharmacological activity, and/or the biological pathways or signalling in which GPCRs is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, said pharmaceutically effective amount may be an amount that is sufficient to modulate GPCRs, its biological or pharmacological activity, and/or the biological pathways or signalling in which GPCRs is involved; and/or an amount that provides a level of the amino acid sequence of the invention, of a Nanobody of the invention, of a polypeptide of the invention in the circulation that is sufficient to modulate GPCRs, its biological or pharmacological activity, and/or the biological pathways or signalling in which GPCRs is involved.

The invention furthermore relates to a method for the prevention and/or treatment of at least one disease or disorder that can be prevented and/or treated by administering an amino acid sequence of the invention, a Nanobody of the invention or a polypeptide of the invention to a patient, said method comprising administering, to a subject in need thereof, a pharmaceutically active amount of an amino acid sequence of the invention, of a Nanobody of the invention, of a polypeptide of the invention, and/or of a pharmaceutical composition comprising the same.

More in particular, the invention relates to a method for the prevention and/or treatment of at least one disease or disorder chosen from the group consisting of the diseases and disorders listed herein, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In another aspect, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a Nanobody of the invention, of a polypeptide of the invention, and/or of a pharmaceutical composition comprising the same.

In the above methods, the amino acid sequences, Nanobodies and/or polypeptides of the invention and/or the compositions comprising the same can be administered in any suitable manner, depending on the specific pharmaceutical formulation or composition to be used. Thus, the amino acid sequences, Nanobodies and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The amino acid sequences, Nanobodies and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, Nanobody or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, Nanobodies and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific amino acid sequence, Nanobody and polypeptide of the invention to be used, the specific route of administration and the specific pharmaceutical formulation or composition used, the amino acid sequences, Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, Nanobody or polypeptide of the invention will be used. It is however within the scope of the invention to use two or more amino acid sequences, Nanobodies and/or polypeptides of the invention in combination.

The Nanobodies, amino acid sequences and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, Nanobodies and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, Nanobody or polypeptide of the invention in the preparation of a pharmaceutical composition for prevention and/or treatment of at least one GPCR-related diseases and disorders; and/or for use in one or more of the methods of treatment mentioned herein.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention also relates to the use of an amino acid sequence, Nanobody or polypeptide of the invention in the preparation of a pharmaceutical composition for the prevention and/or treatment of at least one disease or disorder that can be prevented and/or treated by administering an amino acid sequence, Nanobody or polypeptide of the invention to a patient.

More in particular, the invention relates to the use of an amino acid sequence, Nanobody or polypeptide of the invention in the preparation of a pharmaceutical composition for the prevention and/or treatment of GPCR-related diseases and disorders, and in particular for the prevention and treatment of one or more of the diseases and disorders listed herein.

Again, in such a pharmaceutical composition, the one or more amino acid sequences, Nanobodies or polypeptides of the invention may also be suitably combined with one or more other active principles, such as those mentioned herein.

Finally, although the use of the Nanobodies of the invention (as defined herein) and of the polypeptides of the invention is much preferred, it will be clear that on the basis of the description herein, the skilled person will also be able to design and/or generate, in an analogous manner, other amino acid sequences and in particular (single) domain antibodies against GPCRs, as well as polypeptides comprising such (single) domain antibodies.

For example, it will also be clear to the skilled person that it may be possible to "graft" one or more of the CDR's mentioned above for the Nanobodies of the invention onto such (single) domain antibodies or other protein scaffolds, including but not limited to human scaffolds or non-immunoglobulin scaffolds. Suitable scaffolds and techniques for such CDR grafting will be clear to the skilled person and are well known in the art, see for example U.S. Pat. No. 7,180, 370, WO 01/27160, EP 0 605 522, EP 0 460 167, U.S. Pat. No. 7,054,297, Nicaise et al., Protein Science (2004), 13:1882-1891; Ewert et al., Methods, 2004 October; 34(2):184-199; Kettleborough et al., Protein Eng. 1991 October; 4(7): 773-783; O'Brien and Jones, Methods Mol. Biol. 2003:207:81-100; Skerra, J. Mol. Recognit. 2000:13:167-187, and Saerens et al., J. Mol. Biol. 2005 Sep. 23; 352(3):597-607, and the further references cited therein. For example, techniques known per se for grafting mouse or rat CDR's onto human frameworks and scaffolds can be used in an analogous manner to provide chimeric proteins comprising one or more of the CDR's of the Nanobodies of the invention and one or more human framework regions or sequences.

It should also be noted that, when the Nanobodies of the inventions contain one or more other CDR sequences than the preferred CDR sequences mentioned above, these CDR sequences can be obtained in any manner known per se, for example from Nanobodies (preferred), $V_H$ domains from conventional antibodies (and in particular from human antibodies), heavy chain antibodies, conventional 4-chain antibodies (such as conventional human 4-chain antibodies) or other immunoglobulin sequences directed against GPCRs. Such immunoglobulin sequences directed against GPCRs can be generated in any manner known per se, as will be clear to the skilled person, i.e. by immunization with GPCRs or by screening a suitable library of immunoglobulin sequences with GPCRs, or any suitable combination thereof. Optionally, this may be followed by techniques such as random or site-directed mutagenesis and/or other techniques for affinity maturation known per se. Suitable techniques for generating such immunoglobulin sequences will be clear to the skilled person, and for example include the screening techniques reviewed by Hoogenboom, Nature Biotechnology, 23, 9, 1105-1116 (2005) Other techniques for generating immunoglobulins against a specified target include for example the Nanoclone technology (as for example described in the published US patent application 2006-0211088), so-called SLAM technology (as for example described in the European patent application 0 542 810), the use of transgenic mice expressing human immunoglobulins or the well-known hybridoma techniques (see for example Larrick et al, Biotechnology, Vol. 7, 1989, p. 934). All these techniques can be used to generate immunoglobulins against GPCRs, and the CDR's of such immunoglobulins can be used in the Nanobodies of the invention, i.e. as outlined above. For example, the sequence of such a CDR can be determined, synthesized and/or isolated, and inserted into the sequence of a Nanobody of the invention (e.g. so as to replace the corresponding native CDR), all using techniques known per se such as those described herein, or Nanobodies of the invention containing such CDR's (or nucleic acids encoding the same) can be synthesized de novo, again using the techniques mentioned herein.

Further uses of the amino acid sequences, Nanobodies, polypeptides, nucleic acids, genetic constructs and hosts and host cells of the invention will be clear to the skilled person based on the disclosure herein. For example, and without limitation, the amino acid sequences of the invention can be linked to a suitable carrier or solid support so as to provide a medium than can be used in a manner known per se to purify GPCRs from compositions and preparations comprising the same. Derivatives of the amino acid sequences of the invention that comprise a suitable detectable label can also be used as markers to determine (qualitatively or quantitatively) the presence of GPCRs in a composition or preparation or as a marker to selectively detect the presence of GPCRs on the surface of a cell or tissue (for example, in combination with suitable cell sorting techniques).

The invention will now be further described by means of the following non-limiting experimental part:

EXPERIMENTAL PART

Example 1

Generation of CXCR4 Nanobodies

Methods:
Cell Culture and Transfection—
HEK293T cells were maintained at 37° C. in a humidified 5% $CO_2$, 95% air atmosphere in Dulbecco's modified Eagle's medium (DMEM) containing 2 mM L-glutamine, 50 IU/ml penicillin, 50 µg/ml streptomycin, and 10% (v/v) fetal calf serum. Jurkat cells were cultured in a humidified 5% $CO_2$, 95% air atmosphere in a 1:1 mixture of Dulbecco's modified Eagle's medium (DMEM) and Ham's F12 medium containing 2 mM L-glutamine, 50 IU/ml penicillin, 50 µg/ml streptomycin, and 10% (v/v) fetal calf serum. HEK293T cells were transiently transfected with a constant amount of total DNA using linear 25 kDa polyethyleneimine (Polysciences, Warrington, Pa.) as carrier as previously described (Verzijl et al., Noncompetitive Antagonism and Inverse Agonism as Mechanism of Action of Nonpeptidergic Antagonists at Primate and Rodent CXCR3 Chemokine Receptors. Journal of Pharmacology and Experimental Therapeutics (2008) 325 (2):544-55). cDNA encoding chemokine receptors CCR5, CCR7, CXCR1, CXCR2, CXCR3 and CXCR7 are obtained from cdna.org (Missouri S&T cDNA Resource Center, Rolla, Mo.) were amplified by PCR and cloned into an expression vector.

$[^{125}I]$-Labelling—
Radiolabeling of Nanobodies with $^{125}I$ was performed using the Iodo-gen method (Pierce, Rockford, Ill.) according to the manufacturer's protocol. $^{125}I$-labeled Nanobodies was separated from free iodine (>99%) using a Sephadex G-25 gel filtration column (Amersham Biosciences, Piscataway, N.J.). Iodine incorporation and specific activity were controlled via precipitation of the protein with trichloroacetic acid. myo-[2-$^3$H]-inositol (10-20 Ci/mmol) and [$^{125}$I]-labeled CXCL12 (2,200 Ci/mmol) were obtained from PerkinElmer Life and Analytical Sciences (Boston, Mass.).

Competition Binding Assays—
Membranes from HEK293T cells transiently expressing CXCR3 or CXCR4 were prepared 48 h after transfection as follows. Cells were washed and scraped from the cell culture dishes with ice-cold PBS containing 1 mm EDTA. The scraped cells were pelleted at 1500×g for 10 min at 4° C. The pellet was washed and then resuspended in ice-cold membrane buffer (15 mM Tris, pH 7.5, 1 mM EGTA, 0.3 mM EDTA, and 2 mM $MgCl_2$). The cell suspension was homogenized by 10 strokes at 1200 rpm using a Teflon-glass homogenizer and rotor and further subjected to three freeze-thaw cycles using liquid nitrogen. Membranes were separated by centrifugation at 40,000 g for 25 min at 4° C. The membrane pellet was washed and resuspended in ice-cold Tris-sucrose buffer (20 mM Tris, pH 7.4, and 250 mM sucrose) and frozen in liquid nitrogen. The total protein was determined using a Bradford assay (Bio-Rad).

Periplasmas (1:10) or ligands were pre-incubated with membranes in binding buffer (50 mM HEPES (pH 7.4), 1 mM $CaCl_2$, 5 mM $MgCl_2$, 100 mM NaCl, 0.5% bovine serum albumin) supplemented with 0.5% BSA for 1 h at 22° C. before the addition of [$^{125}$I]-CXCL12 (40 pM) or [$^{125}$I]-238D2 (3 nM) or [$^{125}$I]-238D4 (3 nM) for additional 2 h at 22° C. The non-specific binding was determined in the presence of AMD3100 (3 µM). Membranes were then harvested over polyethylenimine (0.5%)-treated Whatman GF/C filter plates and washed three times with ice cold binding buffer containing 500 mM NaCl. Plates were counted by liquid scintillation.

Inositol Phosphate Accumulation Assay—
24 hours post transfection with pcDNA3.1-CXCR4 and pcDNA1-HA-mG {alpha} qi5 (see Verzijl et al, 2008 supra), 250.000 cells were seeded into 24-wells plates and labelled overnight using inositol-free minimal essential medium supplemented with 1 µCi myo-[2-$^3$H]-inositol. The next day, the cells were washed once to remove not incorporated myo-[2-$^3$H]-inositol. In antagonist experiments, the cells were pre-incubated with test compounds at 37° C. in assay medium (20 mM HEPES, 140 mM NaCl, 5 mM KCl, 1 mM $MgSO_4$, 1 mM $CaCl_2$, 10 mM glucose and 0.05% (w/v) bovine serum albumin, pH 7.4) for 1 h before stimulation with LiCl (10 mM) and CXCL12 (30 nM) for further 2 h at 37° C. In agonist experiments, the cells were directly stimulated with test compounds and LiCl (10 mM) in assay buffer for 2 h at 37° C. The stimulation was stopped by aspirating the stimulation medium and adding ice-cold 10 mM formic acid. The accumulated inositol phosphates were isolated by anion exchange chromatography and counted by liquid scintillation.

CRE Reporter Gene Assay—
HEK239T cells were transfected with pCRE/β-galactosidase (Chen W, Shields T S, Stork P J S, Cone R D (1995) Anal Biochem 226:349-354) and plasmids (pcDEF$_3$ or pcDNA3.1) encoding the indicated receptors. 40,000 transfected cells per well were seeded into 96 well plates and grown in DMEM supplemented with 10% fetal calf serum. The medium was replaced 32 h after transfection by serum-free DMEM supplemented with 0.5% bovine serum albumin and ligands as indicated. Following 16 h of ligand incubation, the medium was removed, the cells were lysed in 100 µl of assay buffer (100 mM sodium phosphate buffer at pH 8.0, 4 mM 2-nitrophenol-β-D-pyranoside, 0.5% Triton X-100, 2 mM $MgSO_4$, 0.1 mM MnCl$_2$, and 40 mM β-mercaptoethanol) and incubated at room temperature. The β-galactosidase activity was determined by the measurement of absorption at 420 nm with a PowerwaveX340 plate reader (Bio-Tek Instruments Inc., Winooski, Vt.) after incubation with the assay buffer when the OD$_{420}$ value for forskolin (3 μM) controls reached 0.4-0.6.

Chemotaxis Assay—

The chemotactic responsiveness of Jurkat 3D cells was assessed using ChemoTx™ plates (Receptor Technologies Ltd., Oxon, UK) in which a upper cell-containing compartment is separated from a lower chemoattractant-containing compartment by a polyvinylpyrollidone-free polycarbonate filter with 5-μm pores. Cells were harvested, washed and resuspended in RPMI containing 0.5% bovine serum albumin and then loaded to 150,000 cells per well in a volume of 25 μl into the upper compartment of the chemotaxis chamber. To stimulate cells migrating through the membrane, CXCL12 and/or test compounds were loaded in a final volume of 31 μl at indicated concentrations into the lower compartment (agonist experiments). For the characterization of antagonistic properties, AMD3100 or test compounds were loaded to the lower CXCL12 (300 μM) containing compartment and additionally pre-incubated with the cells in the upper compartment. The chemotaxis chambers were incubated at 37° C., 100% humidity, and 5% CO$_2$ for 4 h. The number of cells migrating into each lower compartment was determined by fluorescence measurement at 535 nm following incubation with calcein AM and calibration with 0 to 50,000 Jurkat 3D cells per well.

HIV-1 Infection Assays—

The CXCR4-using (X4) HIV-1 molecular clone NL4.3 was obtained from the National Institutes of Health NIAID AIDS Reagent program (Bethesda, Md.), the CCR5-using (R5) HIV-1 strain BaL was obtained from the Medical Research Council AIDS reagent project (Herts, UK). The dual-tropic (R5/X4) HIV-1 HE strain was initially isolated from a patient at the University Hospital in Leuven, and had been routinely cultured in MT-4 cells (Pauwels R, Andries K, Desmyter J, Schols D, Kukla M J, Breslin H J, Raeymaeckers A, Van Gelder J, Woestenborghs R, Heykants J. Potent and selective inhibition of HIV-1 replication in vitro by a novel series of TIBO derivatives. Nature 1990; 343:470-474). The MT-4 cells were seeded out in 96-well plate and the U87 cells in 24-well plates. The test compounds were added at different concentrations together with HIV-1 and the plates were maintained at 37° C. in 10% CO$_2$. Cytopathic effect induced by the virus was monitored by daily microscopic evaluation of the virus-infected cell cultures. At day 4-5 after infection, when strong cytopathic effect was observed in the positive control (i.e., untreated HIV-infected cells), the cell viability was assessed via the in situ reduction of the tetrazolium compound MTS, using the CellTiter 96® AQ$_{ueous}$ One Solution Cell Proliferation Assay (Promega, Madison, Wis.). The absorbance was then measured spectrophotometrically at 490 nm with a 96-well plate reader (Molecular Devices, Sunnyvale, Calif.) and compared with four cell control replicates (cells without virus and drugs) and four virus control wells (virus-infected cells without drugs). The 50% inhibitory concentration (IC$_{50}$, i.e. the drug concentration that inhibits HIV-induced cell death by 50%), was calculated for each compound from the dose-response curve. The CC$_{50}$ or 50% cytotoxic concentration of each of the compounds was determined from the reduction of viability of uninfected cells exposed to the agents, as measured by the MTS method described above.

Peripheral blood mononuclear cells (PBMCs) from healthy donors were isolated by density centrifugation (Lymphoprep; Nycomed Pharma, AS Diagnostics, Oslo, Norway) and stimulated with phytohemagglutinin (PHA) (Sigma Chemical Co., Bornem Belgium) for 3 days. The activated cells (PHA-stimulated blasts) were washed with PBS and viral infections were performed as described previously (Schols D, Struyf S, Van Damme J, Este J A, Henson G, De Clercq E. Inhibition of T-tropic HIV strains by selective antagonization of the chemokine receptor CXCR4. J Exp Med 1997; 186: 1383-1388). At 8-10 days after the start of the infection, viral p24 Ag was detected in the culture supernatant by an enzyme-linked immunosorbent assay (Perkin Elmer, Brussels, Belgium).

Data Analysis and Presentation—

Data are presented as mean±S.E.M. from n independent experiments. Concentration response curves (E/[A] curves) were fitted to the Hill equation using an iterative, least-squares method (GraphPad Prism 4.0, GraphPad Software, San Diego, Calif.) to provide maximal inhibitory effects (I$_{max}$), half maximal effective (EC$_{50}$) or inhibitory concentrations (IC$_{50}$). Competition binding affinities and functional antagonist affinities (pK$_i$) were calculated using the Cheng and Prusoff equation pK$_i$=IC$_{50}$/(1+[agonist]/EC$_{50}$) (Cheng & Prusoff, 1973). Antagonist affinities were optionally expressed as pK$_B$ values using the method of Arunlakshana and Schild (1959) based on the equation pK$_B$=−log [antagonist]+log(CR−1) where CR represents the ratio of the agonist EC$_{50}$ in the presence and the absence of an antagonist.

Results were compared using Student's t-test or one way analysis of variance followed by Bonferroni corrected t-test for stepwise comparison, when multiple comparison was made. P values<0.05 were considered to be significant.

Sequence Targets:

Synonyms: CXCR-4/Stromal cell-derived factor 1 receptor (SDF-1 receptor)/Fusin/Leukocyte-derived seven transmembrane domain receptor (LESTR)/LCR1/FB22/NPYRL/HM89/CD184 antigen Human CXCR4 was used for selection:

TABLE B-1

HOMOLOGY AGAINST HUMAN SEQUENCE:
95% WITH MACACA, 92% PIG, 93% DOG, 91% RABBIT, 88% MOUSE, 80% CHICK

| Amino acid sequence | Clone name | SEQ ID NO: |
|---|---|---|
| MEGISSIPLPLLQIYTSDNYTEEMGSGDYDSMKEP CFREENANFNKIFLPTIYSIIFLTGIVGNGLVILVMG YQKKLRSMTDKYRLHLSVADLLFVITLPFWAVD AVANWYFGNFLCKAVHVIYTVNLYSSVLILAFIS LDRYLAIVHATNSQRPRKLLAEKVVYVGVWIPAL LLTIPDFIFANVSEADDRYICDRFYPNDLWVVFQ FQHIMVGLILPGIVILSCYCIIISKLSHSKGHQKRKA | HUMAN gi\|3059120\|emb\|CAA12166.1\| CXCR4 [Homo sapiens] | 254 |

TABLE B-1-continued

HOMOLOGY AGAINST HUMAN SEQUENCE:
95% WITH MACACA, 92% PIG, 93% DOG, 91% RABBIT,
88% MOUSE, 80% CHICK

| Amino acid sequence | Clone name | SEQ ID NO: |
| --- | --- | --- |
| LKTTVILILAFFACWLPYYIGISIDSFILLEIIKQGCE FENTVHKWISITEALAFFHCCLNPILYAFLGAKFK TSAQHALTSVSRGSSLKILSKGKRGGHSSVSTESE SSSFHSS | | |
| IYTSDNYTEEMGSGDYDSIKEPCFREENAHFNRIF LPTIYSIIFLTGIVGNGLVILVMGYQKKLRSMTDK YRLHLSVADLLFVITLPFWAVDAVANWYFGNFL CKAVHVIYTVNLYSSVLILAFISLDRYLAIVHATN SQKPRKLLAEKVVYVGVWIPALLLTIPDFIFASVS EADDRYICDRFYPNDLWVVVFQFQHIMVGLILPG IVILSCYCIIISKLSHSKGHQKRKALKTTVILILAFF ACWLPYYIGISIDSFILLEIIKQGCEFENTVHKWISI TEALAFFHCCLNPILYAFLGAKFKTSAQHALTSVS RGSSLKILSKGKRGGHSSVSTESESSSFHSS | MACACA6 gi\|9587708\|gb\|AAF8 9346.1\|AF172226_1 chemokine receptor CXCR4 [Macaca nemestrina] | 255 |
| MEELHIYPSDNYTEEDLGSGDYDSMKEPCFREEN AHFNRIFLPTVYSIIFLTGIVGNGLVILVMGYQKKL RSMTDKYRLHLSVADLLFVLTLPFWAVEAVANW YFGNFLCKAVHVIYTVNLYSSVLILAFISLDRYLAI VHATNSQRPRKLLAEKVVYVGVWIPALLLTIPDFI FANVREADDRYICDRFYPNDSWLVVFQFQHIMV GLILPGIVILSCYCIIISKLSHSKGYQKRKALKTTVI LILAFFACWLPYYIGISIDSFILLEIIKQGCEFEKTV HKWISITEALAFFHCCLNPILYAFLGAKFKTSAQH ALTSVSRGSSLKILSKGKRGGHSSVSTESESSSFHS S | DOG gi\|114149257\|sp\|Q3LSL 6.1\|CXCR4_CANFA C-X-C chemokine receptor type 4 (CXC-R4) (CXCR-4) (CD184 antigen) | 256 |
| MDGFRIFTSDNYTEDDLGSGDYDSIKEPCFREENA HFNRIFLPTVYSIIFLTGIVGNGLVILVMGYQKKLR SMTDKYRLHLSVADLLFVLTLPFWAVDAVANW YFGKFLCKAVHVIYTVNLYSSVLILAFISLDRYLAI VHATNSQRPRKLLAEKVVYVGVWIPALLLTIPDFI FANVREGDGRYICDRFYPNDLWLVVFQFQHIMV GLILPGIVILSCYCIIISKLSHSKGYQKRKALKTTVI LILAFFACWLPYYIGISIDSFILLEIIQQGCEFESTVH KWISITEALAFFHCCLNPILYAFLGAKFKTSAQHA LTSVSRGSSLKILSKGKRGGHSSVSTESESSSFHSS | PIG gi\|71493324\|gb\|AAZ 32767.1\| CXCR4 [Sus scrofa] | 257 |
| MDGLDLSSGILIEFADNGSEEIGSADYGDYGEPCF QHENADFNRIFLPTIYSIIFLTGIIGNGLVIIVMGYQ KKQRSMTDKYRLHLSVADLLFVITLPFWSVDAAI SWYFGNVLCKAVHVIYTVNLYSSVLILAFISLDRY LAIVHATNSQRPRKLLAEKIVYVGVWLPAVLLTV PDIIFASTSEVEGRYLCDRMYPHDNWLISFRFQHI LVGLVLPGLIILTCYCIIISKLSHSKGHQKRKALKT TVILILTFFACWLPYYIGISIDTFILLGVIRHRCSLD TIVHKWISITEALAFFHCCLNPILYAFLGAKFTSA QNALTSVSRGSSLKILSKSKRGGHSSVSTESESSSF HSS | CHICK gi\|9954428\|gb\|AAG0 9054.1\|AF294794_1 chemokine receptor CXCR4 [Gallus gallus] | 258 |
| TSDNYTEELGSGDYDSIKEPCFREENAHFNRIFLP TIYSIIFLTGIVGNGLVILVMGYQKKQRSMTDKYR LHLSVADLLFVITLPFWAVDAVANWYFGKFLCK AVHVIYTVNLYSSVLILAFISLDRYLAIVHATNSQ KPRKLLAEKVVYVGVWIPALLLTIPDFIFANVREA EGRYICDRFYPSDLWVVVFQFQHIMVGLILPGIVI LSCYCIIISKLSHSKGHQKRKALKTTVILILAFFAC WLPYYIGISIDSFILLEIIKQGCEFENTVHKWISITE ALAFFHCCLNPILYAFLGAKFKTSAQHALTSVSR GSSLKILSKGKRGGHSSVSTESES | RABBIT gi\|161177115\|gb\|ABX59 689.1\| chemokine receptor CXCR4 [Oryctolagus cuniculus] | 259 |
| MEPISVSIYTSDNYSEEVGSGDYDSNKEPCFRDEN VHFNRIFLPTIYFIIFLTGIVGNGLVILVMGYQKKL RSMTDKYRLHLSVADLLFVITLPFWAVDAMADW YFGKFLCKAVHIIYTVNLYSSVLILAFISLDRYLAI VHATNSQRPRKLLAEKAVYVGVWIPALLLTIPDFI FADVSQGDISQGDDRYICDRLYPDSLWMVVFQF QHIMVGLILPGIVILSCYCIIISKLSHSKGHQKRKA LKTTVILILAFFACWLPYYIGISIDSFILLGVIKQG CDFESIVHKWISITEALAFFHCCLNPILYAFLGAKF | MOUSE1 gi\|2494970\|sp\|P7065 8.2/CXCR4 MOUSE C-X-C chemokine receptor type 4 (CXC-R4) (CXCR-4) (Stromal cell-derived factor 1 receptor) (SDF-1 | 260 |

TABLE B-1-continued

HOMOLOGY AGAINST HUMAN SEQUENCE:
95% WITH MACACA, 92% PIG, 93% DOG, 91% RABBIT,
88% MOUSE, 80% CHICK

| Amino acid sequence | Clone name | SEQ ID NO: |
|---|---|---|
| KSSAQHALNSMSRGSSLKILSKGKRGGHSSVSTES ESSSFHSS | receptor) (Fusin) (Leukocyte-derived seven transmembrane domain receptor) (LESTR) (Pre-B-cell-derived chemokine receptor) (PB-CKR) (CD184 antigen) | |

Sequences:

TABLE B-1.1

SEQUENCES SELECTED NANOBODIES:

| Amino Acid Sequence | Clone name | SEQ ID NO: |
|---|---|---|
| EVQLVESGGGLVQTGGSLRLSCAASGFTFSSYAM SWVRQAPGKGLEWVSGIKSSGDSTRYAGSVKGR FTISRDNAKNMLYLQMYSLKPEDTAVYYCAKSR VSRTGLYTYDNRGQGTQVTVSS | 238C1, D2 or 238D2 | 238 |
| EVQLMESGGGLVQAGGSLRLSCAASGRTFNNYA MGWFRRAPGKEREFVAAITRSGVRSGVSAIYGDS VKDRFTISRDNAKNTLYLQMNSLKPEDTAVYTC AASAIGSGALRRFEYDYSGQGTQVTVSS | 238D4, G3 or 238D4 | 239 |
| KVQLVESGGGLVQPGGSLRLSCAASGFAFSIHTM SWVRQAPGKGPEWVSTIKPSGDTTNYANAVKGR FTISRDNAKNTLYLQMNSLKPEDTAVYYCAKDY FGTGVRGQGTQVTVSS | 237B5 | 240 |
| EVQLVESGGGLVQPGGSLRLSCAASGFTFDDYA MSWVRQAPGKGLEWVSAISWNGGSTDYADSVK GRFTISRDNAKNTLYLQMNSLKSEDTAEYYCARD QGPFYSGTYYYTRQYGYRGQGTQVTVSS | 237B6, A5, D2, D3, E4, F4, G2, G4, xH5, 237F 1, C5, G1 | 241 |
| EVQLVESGGGFVQAGGSLRLSCETSGRPLLGYTI AWFRQVPGKEREFVAYHRWSDGANLYADSVKG RFTISGHNAKNTVSLQMNSLKPEDTAVYYCAAA RMTTSNDKEYLYWGQGTQVTVSS | 238B10 | 242 |
| EVQLVESGGGFVQAGGSLRLSCETSGRPLLGYTI AWFRQVPGKEREFVAYHRWSDGANLYADSVKG RFTISGHNAKNTVSLQMNSLKPEDTAVYYCAAA WMTTSNDKEYLYWGQGTQVTVSS | 238F7 | 244 |
| EVQLVESGGGLVQAGGSLRLSCAASGLTFSPSAM AWYRQGPGKERDFVASTIWSRGDTYFADSVKGR FTISRDTANYTLYLQMNNLKPEDTAVYYCSLRVR PYGQYDYWGQGTQVTVSS | 238H2 | 245 |
| EVQLVESGGGLVQPGGSLRLSCAASGFTFDDYA MSWVRQAPGKGLEWVSAISWNGGSADYADSVK GRFTISRDNAKNTLYLQMNSLKSEDTAVYYCAK DQGPFYSGTYYYTKGYAYWGQGTQVTVSS | 237D4 | 246 |
| EVQLVESGGGLAQAGGSLRLSCAASGRTYAMG WFRQAPGKEREFVTTSRLITDNIIYADSVKGRFTL TRDNGKNTVYLQMDSLKPDDTAVYFCAARQNY SRSVFGAKDYDYWGQGTQVTVSS | 238F3 | 247 |
| EVQLVESGGGLVQAGGSLRLSCAASGSIFSLNAM GWYRQAPGKQRELVAGITSSTSTYYADSVKGRFT ISRDNTKNTVYLQMNSLKPEDTAVYYCNVDCPD YYSDYECPLEDRGQGTQVTVSS | 237A6 | 248 |

TABLE B-1.1-continued

SEQUENCES SELECTED NANOBODIES:

| Amino Acid Sequence | Clone name | SEQ ID NO: |
|---|---|---|
| EVQLVESGGGLAQPGGPLRLTCEASGVIYSVNDM GWYRQAPGKQRELVAVITSGGGTNYVDSVKGRF TISGDNRKKTVYLQMNSLKPEDTAVYYCSIYYSS GISTLRSWGQGTQVTVSS | 237D1 | 249 |
| EVQLVESGGGLVQPGGSLRLSCEVSGFTRDYYTI GWFRQAPGKEREGVSCISSSDGSTAYLGSVQGRF TVSRDNAKNTVYLQMNNLKPEDTAVYYCALBSA DSRCSIGSIGFTWLYNNWGQGTQVTVSS | 237E1 | 250 |
| EVQLVESGGGLVQPGGSLRLSCAASSFIGNYHAIV WLRQAPGKELEGVSCITSRDSITYYASFVKGRFTI SRDDAKNTVYLQMNNLKPEDTAVYYCAVBTSM TCPTLIVRFNYRGQGTQVTVSS | 237G7 | 251 |
| EVQLVESGGGLVQAGGSLRLSCKASGGTFNNYA MGWFRRAPGKEREFVAAITRSGVRSGVSAIYGDS VKDRFTISRDNVKNTLYLQMNTLKPEDTAVYTC AASAIGSGALRRFEYDYSGQGTQVTVSS | 238C4 | 252 |
| EVQLVESGGGLVQAGGSLRLSCAASGSFFSINAM GWYRQAPGKQRELVASITSGGSTVYADSVKGRF TISRDNYNTVYLQMNSLKPEDTAVYYCNADGVP EWGKVQYPDTYRGQGTQVTVSS | 237C1 | 253 |
| EVQLMESGGGLVQAGGSLRLACAASGFTFEDYAI GWFRKAPGKEREGVSCISGSDGSTTYADSVKGRF TISTDNAKNTVYLEMNSLKPEDTAVYYCAQQYG VGGRVVCPGPYEYDVWGQGTQVTVSS | 238C5, G2, xH5, 238C 3, D6, E6 | 243 |

Example 1.1

Immunizations

For immunization, HEK293 cells (human embryonic kidney) transiently expressing human CXCR4 were used as "antigen".

Two llamas were immunized according to standard protocols with 6 boosts of a cells (1*10E7 cells) at day 0, 7, 21, 32, 43 and 56. Blood were collected from these animals at 4 and 8 days after the 6$^{th}$ boost.

Example 1.2

Library Construction

Peripheral blood mononuclear cells were prepared from blood samples using Ficoll-Hypaque according to the manufacturer's instructions. Next, total RNA extracted was extracted from these cells as well as from the lymph node bow cells and used as starting material for RT-PCR to amplify Nanobody encoding gene fragments. These fragments were cloned into phagemid vector pAX50. Phage was prepared according to standard methods (see for example the prior art and applications filed by applicant cited herein) and stored at 4° C. for further use, making phage library 217 and 218.

Example 1.3

Selections Using 2 Rounds of Trypsine Elution

To identify Nanobodies recognizing CXCR4, phage libraries (217, 218) were used in a phage display selection.

Because hCXCR4 is an integral transmembrane protein, it is essential to conserve the native conformation of hCXCR4. Therefore, the phage display selection was done on cell membranes preparation of CHO and COST cells overexpressing hCXCR4. Membranes was coated onto Maxisorp plate overnight at 4 C (10 ug in 100 ul PBS).

The next day, after blocking in 4% milk-PBS 1 hour, phages from the libraries were incubated with the coated membrane in the presence (and in parallel without) of 1% milk-PBS and CHO-membrane preparation expressing a non-relevant GPCR. After 2 hours incubation, the plates were washed extensively with PBS. After washing, bound phages were eluted using trypsin (1 ug/ml) for 15 min at RT.

Phages were rescued and reamplified in TG1 as usual giving R1 polyclonal phages.

Those R1 phages were used for a second round of selection like the first round with the only difference that phages selected on CHO-CXCR4 membrane in the first round were also used on COS7-CXCR4 membrane and reverse. This unique strategy allows the depletion on non-CXCR4 specific phages. After 2 hours incubation, the plates were washed extensively with PBS and bound phages were eluted using trypsin (1 ug/ml) for 15 min at RT.

Output of R2 selections were analyzed for enrichment factor (phage present in eluate relative to controls). Based on these parameters the best selections were chosen for further analysis. The polyclonal output was rescued in TG1 individual TG1 colonies were picked and grown in 96 deep well plates (1 ml volume) to produce monoclonal phages (addition of helper phage) or monoclonal (addition of IPTG) to make periplasm fraction. Periplasmic extracts (volume: ~90 ul) were prepared according to standard methods (see for example the prior art and applications filed by applicant cited herein).

A schematic representation of the selection can be found in FIG. 1.

Abbreviations: CHO-CXCR4: membrane of CHO (Chinese Hamster Ovary) cells transiently transfected with human CXCR4; COST-CXCR4: membrane of COST (Monkey cells) cells transiently transfected with human CXCR4; R1 is first round of selection; R2 is the second round of selection; Counterselection means that the selection was done in the presence of CHO-membrane (non expressing CXCR4); ligand is CXCL12/SDF1 (3 ug in 100 ul PBS), antagonist is AMD3100 (50 uM), antibody is 12G5 (5 ug in 100 ul PBS).

Example 1.4

Selections Using 2 Rounds of Specific (Competitive) Elution

An alternative to the non-specific trypsin elution is to use specific CXCR4 binding compound to elute (compete out) the phages binding to the site of the compound binding. In this case, 2.5 ug of membrane preparation was coated overnight at 4 C in 100 ul PBS and elution was done for 30 min at RT with an excess of:
  CXCL12/SDF1 (3 ug in 100 ul PBS), the natural ligand for CXCR4,
  AMD3100 (50 uM), a know chemical antagonist (from Sigma Aldrich)
  12G5 (5 ug in 100 ul PBS), a known neutralizing antibody (from R&D System).
Eluted phages were rescued and reamplified in TG1 as usual giving R1 polyclonal phages. Those R1 phages were used for a second round of selection like the first round with the only difference that phages selected on CHO-CXCR4 membrane in the first round were also used on COS7-CXCR4 membrane and reverse. This unique strategy allows the depletion on non-CXCR4 specific phages (membrane specific). After 2 hours incubation, the plates were washed extensively with PBS and bound phages were eluted as the first round. This way, 2 rounds of CXCL12/SDF1 was done as well as 2 rounds of AMD3100.

Output of R2 selections were analyzed for enrichment factor (phage present in eluate relative to controls). Based on these parameters the best selections were chosen for further analysis. The polyclonal output was rescued in TG1 individual TG1 colonies were picked and grown in 96 deep well plates (1 ml volume) to produce monoclonal phages (addition of helper phage) or monoclonal (addition of IPTG) to make periplasm fraction. Periplasmic extracts (volume: ~90 ul) were prepared according to standard methods (see for example the prior art and applications filed by applicant cited herein).

Example 1.5

Screening for Binding

In order to determine binding specificity of the Nanobodies, 15 ul of the produced phage were tested in an Phage ELISA binding assay.

In short, 2 ug in 100 ul PBS of membrane expressing either CXCR4 (CHO-CXCR4) or a non relevant GPCR(CHO) were coated directly on Maxisorp microtiter plates (Nunc) overnight at 4 C. Free binding sites were blocked using 4% Marvel in PBS for 1 h. Next, 15 ul of monoclonal phages was added in 100 ul 1% Marvel PBS for 2 hours. After incubation and a extensive PBS washing step, phage binding was revealed using an anti-M13-HRPO antibody. Binding specificity (binding to CHO-CXCR4) was determined based on OD values compared to controls (binding to CHO).

An example is shown in FIG. 2.

Example 1.6

Screening of CXCR4-Binding Nanobodies by Displacement of [$^{125}$I]-CXCL12

180 clones were analyzed and their periplasma fractions were screened using a CXCR4 competition binding assay. In a primary screen with membranes from HEK293T cells transiently expressing CXCR4, approximately 13% of the clones were found to compete with the radiolabeled endogenous CXCR4 ligand [$^{125}$I]-CXCL12 for binding to CXCR4 and produce an inhibition of specific [$^{125}$I]-CXCL12 binding of at least 30% (FIG. 3). A total amount of five clones (approximately 3%) strongly inhibit specific [$^{125}$I]-CXCL12 binding by more than 70%. No inhibition was observed for control phages expressing Nanobodies directed against membrane proteins different from CXCR4. All primary hits were confirmed in a second screen (FIG. 3b) and therefore the $V_H$H-encoding DNA of CXCL12-displacing Nanobody-producing clones were sequenced. Sequencing analysis results in seven pools of identical or highly similar clones strongly (2 pools) or partially (5 pools) displacing [$^{125}$I]-CXCL12 (Table B-2). Nanobodies representing these pools, namely 237A6, 237D1, 237D2, 237G7, 238C5, 238D2 and 238D4 were purified and further pharmacologically analyzed.

Characterization of Nanobody Binding to CXCR4—

Following purification, receptor binding characteristics for 237A6, 237D1, 237D2, 237G7, 238C5, 238D2 and 238D4 were investigated on cell membranes from transiently CXCR4 expressing HEK293T cells. The Nanobodies 238D2 and 238D4 fully displace all specifically bound [$^{125}$I]-CXCL12 and show affinities to CXCR4 in the low nanomolar range (Table 2). All other Nanobodies were unable to displace [$^{125}$I]-CXCL12 even at the highest test concentration of 0.5 µM (237A6, 237D1, 237D2, 237G7 and 238C5) (FIG. 4A; Table B-3).

In order to further investigate the binding properties of the two potently [$^{125}$I]-CXCL12-displacing Nanobodies 238D2 and 238D4 to CXCR4, we generated $^{125}$I-labeled Nanobodies for competition binding studies. Both, [$^{125}$I]-238D2 and [$^{125}$I]-238D4 selectively bind to membranes from HEK293T cells transiently expressing CXCR4 compared to those expressing CXCR3 (FIG. 4D). Both Nanobodies compete for binding to CXCR4 as shown by the full displacement of [$^{125}$I]-238D2 by 238D4 and by the full inhibition of [$^{125}$I]-238D4 binding by 238D2 (FIGS. 4B, 4C). Furthermore, the small molecule ligand AMD3100 displaces [$^{125}$I]-238D2 and [$^{125}$I]-238D4 with affinities comparable to those obtained against [$^{125}$I]-CXCL12 (Table B-3) indicating that also AMD3100 compete with the Nanobodies 238D2 and 238D4 for the same receptor. The monoclonal antibody 12G5 that has previously been reported to label a certain subpopulation of CXCR4 (J. Virol. Baribaud et al. 75 (19): 8957) potently but incompletely displace specifically bound [$^{125}$I]-CXCL12, [$^{125}$I]-238D2 and [$^{125}$I]-238D4 from CXCR4. 237A6, 237D1, 237D2 and 237G7 were unable to inhibit binding of [$^{125}$I]-238D2 or [$^{125}$I]-238D4 to CXCR4. 238C5 displaces [$^{125}$I]-238D2 and [$^{125}$I]-238D4 but not [$^{125}$I]-CXCL12 at high concentrations (≥100 nM) indicating that this Nanobody binds to the receptor as a low affinity allosteric CXCR4 ligand (FIGS. 4B, 4C).

TABLE B-2

Screening and sequencing of Nanobody clones displacing [$^{125}$I]-CXCL12. Binding efficiency was determined by competition binding with [$^{125}$I]-CXCL12 on membranes from HEK293T cells transiently expressing CXCR4.

| Pool | Clones | Binding[a] |
|---|---|---|
| 237A6 | 237A6 | + |
| 237D1 | 237D1 | + |
| 237D2 | 237B6, 237C1, 237C5, 237D2, 237D4, 237E4, 237F4, 237H1, 237G1 237G4, 237H5 | −/+ |
| 237G7 | 237G7 | + |
| 238C5 | 238C5, 238D6, 238E6 | + |
| 238D2 | 238C1, 238D2 | ++ |
| 238D4 | 238C4, 238D4, 238G3 | ++ |

[a]− = 0-29%; + = 30-69%; ++ = 70-100%.

TABLE B-3

Receptor affinity (pK$_i$) and maximal displacement of [$^{125}$I]-CXCL12, [$^{125}$I]-238D2 and [$^{125}$I]-238D4 for monovalent Nanobodies and CXCR4 reference ligands. The experiments were performed on membranes from HEK293T cells transiently expressing CXCR4. Data were shown as means ± S.E.M. The number of experiments is given as n.

| | [$^{125}$I]-CXCL12 | | | [$^{125}$I]-238D2 | | | [$^{125}$I]-238D4 | | |
|---|---|---|---|---|---|---|---|---|---|
| | Displacem. (%) | pK$_i$ | n | Displacem. (%) | pK$_i$ | n | Displacem. (%) | pK$_i$ | n |
| 238D2 | 93 ± 5 | 8.01 ± 0.12 | 6 | 97 ± 6 | 8.41 ± 0.11 | 4 | 105 ± 4 | 8.23 ± 0.23 | 4 |
| 238D4 | 99 ± 5 | 8.22 ± 0.16 | 6 | 101 ± 1 | 8.80 ± 0.23 | 4 | 103 ± 1 | 8.55 ± 0.09 | 4 |
| 237A6 | 0[a] | <6.3 | 4 | 0[a] | <6.3 | 2 | 0[a] | <6.3 | 2 |
| 237D1 | 0[a] | <6.3 | 3 | 0[a] | <6.3 | 2 | 0[a] | <6.3 | 2 |
| 237D2 | 0[a] | <6.3 | 4 | 0[a] | <6.3 | 2 | 0[a] | <6.3 | 2 |
| 237G7 | 0[a] | <6.3 | 4 | 0[a] | <6.3 | 2 | 0[a] | <6.3 | 2 |
| 238C5 | 0[a] | <6.3 | 4 | 45 ± 5[b] | <7.0 | 3 | 38 ± 4[b] | <7.0 | 3 |
| 116B2 | 0[a] | <6.3 | 2 | 0[a] | <6.3 | 2 | 0[a] | <6.3 | 2 |
| CXCL12 | 105 ± 2 | 9.84 ± 0.13 | 3 | 98 ± 8 | 7.46 ± 0.17 | 4 | 93 ± 2 | 7.45 ± 0.12 | 4 |
| AMD3100 | 94 ± 2 | 7.41 ± 0.28 | 3 | 102 ± 1 | 7.74 ± 0.19 | 4 | 99 ± 4 | 7.34 ± 0.16 | 4 |
| 12G5 | 54 ± 5[c] | 9.19 ± 0.19 | 3 | 89 ± 2[c] | 9.65 ± 0.17 | 4 | 90 ± 1[c] | 9.31 ± 0.16 | 4 |

[a]No significant displacement at 0.5 µM.
[b]Maximum not reached at the highest test concentration of 0.5 µM, displacement at 0.5 µM.
[c]Significantly different from 100%.

Example 1.7

Inhibition of CXCR4-Mediated Signal Transduction

In an effort to functionally characterize the Nanobodies 238D2 and 238D4, we measured their ability to activate G-protein signaling or to inhibit the CXCL12-induced G-protein signaling in HEK293T cells transiently co-transfected with cDNAs encoding CXCR4 and Gα$_{qi5}$. This assay is based upon the use of the chimeric Gα$_{qi5}$-protein that contains of a Gα$_q$ backbone with the 5 C-terminal amino acids replaced by those from Gα$_i$. The chimeric G-protein is activated by CXCR4 like a Gα$_i$ subunit but transduces signals like Gα$_q$ proteins (Coward, P., et al., Chimeric G Proteins Allow a High-Throughput Signaling Assay of G1-Coupled Receptors, Analytical Biochemistry (1999) 270: 242-248). Thus, the activation of Gα$_{qi5}$ can be quantified by the measurement of accumulated inositol phosphates. CXCL12 stimulates inositol phosphate accumulation with a pEC$_{50}$ of 7.89±0.21 (n=4). No agonist activity was observed for the Nanobodies 238D2 or 238D4 up to a concentration of 100 nM. However, 238D2 and 238D4 fully inhibited the CXCL12-induced accumulation of inositol phosphates in a concentration-dependent manner (FIG. 5 A).

In addition, we investigated the ability of the Nanobodies 238D2 and 238D4 to inhibit the CXCL12-induced activation at a later step of signal transduction in HEK293T cells transiently transfected with pcDNA3.1-CXCR4 and a β-galactosidase reporter gene under the control of a cAMP response element (CRE). Stimulation of G$_i$-protein-coupled receptors like CXCR4 may result in an inhibition the forskolin-induced activation of CRE. Indeed, CXCL12 potently inhibited the forskolin (3 µM)-induced activation of the CRE-dependent transcription of β-galactosidase with a pEC$_{50}$ of 9.78±0.09 (n=11), whereas the Nanobodies 238D2 and 238D4 did not show any agonist activity in the absence of CXCL12 (FIG. 5B). However, both Nanobodies inhibited the CXCL12 response by parallel rightward-shifts of the concentration response curves of CXCL12 without affecting its maximal effect upon increasing Nanobody concentrations. Schild analysis showed linearity between log(CR−1) and −log [Nanobody](M) with slopes of 0.91±0.20 and 0.71±0.17 (not significantly different from unity) for both 238D2 and 238D4, respectively (FIG. 5B). These results indicate competitive antagonism of the CXCL12-induced activation of signal transduction for both Nanobodies. Based on the Schild plot data, pK$_B$ values of 7.64±0.16 and 7.70±0.16 were calculated for 238D2 and 238D4, respectively.

In order to demonstrate the specificity of the Nanobodies for CXCR4, we also investigated the effects of 238D2 and 238D4 on other chemokine and non-chemokine receptor signaling by using the CRE/β-galactosidase reporter gene. Sub maximally effective agonist concentrations (50-80% E$_{max}$) in the absence or the presence of 3 µM forskolin were used to stimulate the cells. The Nanobodies 238D2 and 238D4 even in concentrations up to 2.5 do not alter the agonist-induced inhibition of the forskolin (3 µM)-induced activation of CRE in HEK293T cells transiently transfected with cDNA encoding CXCR1, CXCR2, CXCR3, CXCR6, CCR5, CCR7 or histamine H4 receptors, respectively (FIG. 7). Furthermore, 238D2 and 238D4 (2.5 µM) did not inhibit the activation of endogenously expressed β$_2$-adrenoceptors by the β$_2$-adrenoceptor agonist salbutamol (100 nM). These results demonstrate an over 100-fold selectivity of 238D2 and 238D4 for CXCR4 over all other receptors tested.

The chemoattractant or anti-chemoattractant effects of CXCL12 and the Nanobodies were investigated in Jurkat leukaemia T cells endogenously expressing CXCR4.

CXCL12 induced migration of Jurkat cells with a typical bell-shaped profile with a $pEC_{50}$ of 9.41±0.26 (n=5) for the first phase of the concentration response curve. 238D2 and 238D4 were unable to induce any significant migration of Jurkat cells by themselves (FIG. 5C). In contrast, both 238D2 and 238D4 concentration-dependently inhibited the migration of Jurkat cells towards 300 pM CXCL12 (FIG. 5C).

TABLE B-4

Maximal inhibition ($I_{max}$) and functional inhibitory potency ($pK_i$ or $pIC_{50}$) of the Nanobodies 238D2 and 238D4. Data were shown as means ± S.E.M. The number of experiments is given as n.

| | 238D2 | | | 238D4 | | |
|---|---|---|---|---|---|---|
| | $I_{max}$ (%) | $pK_i$ $pIC_{50}$ | or n | $I_{max}$ (%) | $pK_i$ $pIC_{50}$ | or n |
| IP accumulation | | | | | | |
| HEK293T-CXCR4-$G\alpha_{qi5}$/30 nM CXCL12 CRE activation | 86 ± 12 | 8.51 ± 0.11 | 4 | 90 ± 5 | 8.39 ± 0.24 | 4 |
| HEK293T-CXCR4-CREbgal/0.01-100 nM CXCL12 Chemotaxis | 104 ± 5$^a$ | 7.64 ± 0.16$^b$ | 4 | 90 ± 15$^a$ | 7.70 ± 0.16$^b$ | 6 |
| Jurkat/0.3 nM CXCL12 | 106 ± 2 | 8.33 ± 0.16 | 4 | 101 ± 4 | 8.31 ± 0.22 | 4 |

Example 2

Generation of Nanobodies Directed Against Human CXCR7

Same approach as for Nanobodies directed against human CXCR4. In particular, the method using at least the following steps:
a) immunization with whole living cell (e.g. HEK293) over-expressing human CXCR7.
b) Immunization and selection using different cell types (e.g. HEK293 for immunization, CHO-membrane enriched for human CXCR7 for 1$^{st}$ round selection, COS7 membranes enriched for human CXCR7 for 2$^{nd}$ round selection)
c) Optionally, washing with mild buffer, e.g. PBS (without detergents).

Reference is also made to the human protein sequence of CXCR7 that can e.g. be found in the Swissprot database under "P25106"

Example 3

Examples of HIV Assays

Example 3.1

Single-Round Pseudovirus Neutralization Assay

Reference is made to James M. Binley,[1,†] Terri Wrin,[2] Bette Korber,[3] Michael B. Zwick,[1] Meng Wang,[1] Colombe Chappey,[2] Gabriela Stiegler,[4] Renate Kunert,[4] Susan Zolla-Pazner,[5] Hermann Katinger,[4] Christos J. Petropoulos,[2] and Dennis R. Burton Comprehensive Cross-Clade Neutralization Analysis of a Panel of Anti-Human Immunodeficiency Virus Type 1 Monoclonal Antibodies Journal of Virology, December 2004, p. 13232-13252, Vol. 78, No. 23.

A recombinant-virus assay involving a single round of virus infection is used to measure neutralization. Recombinant luciferase pseudoviruses are incubated for 1 h at 37° C. with 10 serial fourfold dilutions of MAbs or heat-inactivated plasma, usually starting from 50 µg/ml (MAbs) or a 1:20 dilution (plasma). In a variant protocol, virus is incubated with antibody for 18 h before the mixture is added to target cells. U87 cells expressing CD4 plus the CCR5 and CXCR4 coreceptors are inoculated with virus-antibody (Ab) dilutions in the absence of added cations. Virus stocks are screened to ensure that they were functional and yielded a high luciferase reporter light signal in target cell lysates. Input virus used in each experiment is not standardized. Virus infectivity is determined 72 h postinoculation by measuring the amount of luciferase activity expressed in infected cells. Neutralizing activity is reported as the concentration or dilution of each MAb or plasma required to confer 50% ($IC_{50}$) or 90% ($IC_{90}$) inhibition of infection (percent inhibition={1−[luciferase+Ab/luciferase−Ab]}×100). To eliminate nonspecific neutralization, the criterion for genuine neutralization is that the titer must be at least 2.5-fold higher against HIV-1 than it is against the amphotropic control MuLV. Due to the large size of this study, each individual virus-Ab combination is in general tested only once. To ensure that the results are reproducible, the control viruses JR-CSF (R5-tropic) and NL4-3 (X4-tropic) are run at least six times in all assays. The reproducibility of the assay within and between runs is assessed by looking at these controls.

Example 3.2

GHOST Assay

Reference is made to Steyaert et al., 2007 Inhibition of replication of primary HIV-1 isolates in huPBL-NOD/Scid mice by antibodies from HIV-1 infected patients. Antiviral Res. 2007 August; 75(2):129-38. Epub 2007 Mar. 6. Human plasma and purified immunoglobulins are screened for neutralizing activity with a highly sensitive GHOST cell based assay (Donners et al., 2003). These cells are derived from human osteosarcoma cells and are transfected with the gene coding for human CD4, one of the HIV co-receptors (CCR5 or CXCR4) and green fluorescent protein under the control of the HIV-2 LTR promoter. The number of infected cells is measured by FACS. Plasma samples are diluted 1/20 and purified IgGs to a concentration of 500 ug/ml. The format of the neutralization assay is 24/24/48 where 24/x/x is the time in hours during which antibody and virus are pre-incubated, x/24/x is the time in hours during which cells are exposed to these mixtures and x/x/48 is the time in hours between the start of viral inoculation and the FACS analysis. The percentage neutralization is calculated as 100−[(# infected cells of tested sample/# infected cells of seronegative control)×100].

Example 3.3

PBMC Assay

Reference is made to Beirnaert et al., 2000. Virus neutralization assays are carried out as described previously with some minor modifications [Nyambi et al., 1996]. Briefly, culture supernatant of virus infected PBMCs (50 TCID50/well) and twofold serial dilutions (1/10-1/1,280) of heat-inactivated serum (30 min at 56° C.) are mixed in a 96-well tray and incubated for 1 hr at 37° C. in a 5% $CO_2$ atmosphere. In each experiment, an HIV (−) serum is assayed in the same conditions as the sample sera, to serve as a negative control. Subsequently, 7.5×104/well PHA stimulated, IL-2 maintained PBMCs are added. After 2 hr incubation, the cells are washed three times and incubated in RPMI 1640 medium supplemented with 20 U/ml IL-2, 15% FCS, 0.03% L-Glutamine, 2 mg/ml polybrene, 5 mg/ml hydrocortisone and antibiotics. For every neutralization experiment, the virus is titrated again to compare the infectivity of the virus stock in different donor PBMCs. If the virus titer differed from the input virus titer by more than a factor 3, the neutralization experiment is considered invalid. Viral replication is assessed after 7 days using a non-commercial antigen capture ELISA that captures antigen of HIV-1 belonging to Group M as well as to Group O [Beirnaert et al., 1998, Identification and characterization of sera from HIV-infected individuals with broad cross-neutralizing activity against group M (env clade A-H) and group O primary HIV-1 isolates. J Med. Virol. 2000 September; 62(1):14-24]. Fifty-percent inhibitory doses (ID50) are defined as the reciprocal of the highest serum dilution that produced 50% reduction in absorbance value in the antigen capture assay compared to the negative serum control. Serum neutralizing titers of <1/10 are considered negative. Sera are assayed in duplicate and tests are carried out at least three times.

Example 3.4

HIV In Vivo Neutralization Models

Example 3.4.1

Hu-PBL (NOD/SCID)

Reference in made to: Gauduin, M. C., Parren, P. W., Weir, R., Barbas, C. F., Burton, D. R., Koup, R. A., 1997. Passive immunization with a human monoclonal antibody protects hu-PBL-SCID mice against challenge by primary isolates of HIV-1. Nat. Med. 3, 1389-1393, Steyaert et al., 2007.

To assess virus-inhibiting activity in vivo, human polyclonal immunoglobulins are administered to huPBL-NOD/Scid mice 6 days after reconstitution and 1 day before viral challenge. All injections are given intraperitoneally (i.p.). Each experimental group may consist of four mice. The minimal viral inoculum needed to infect all mice is determined in preliminary titrations. The chimeric mice that survived the graft-versus-host reaction (82%) are sacrificed 14 days after challenge and viral load is measured in their plasma using COBAS Amplicor HIV-1 Monitor™ version 1.5 (Roche) according manufacturer's instructions. Due to the limited availability of mouse plasma, these may be diluted 1/100 and therefore the lower limit of detection of this assay is about 3.70 log equiv/ml.

Example 3.4.2

SHIV Macaque Model

For antibody infusions, vaginal challenge, and blood and mucosal collections, macaques are lightly anesthetized with ketamine HCl. A SHIV89.9PD challenge stock is grown and titrated in rhesus PBMC. Antibodies are infused intravenously 24 h prior to virus challenge. Vaginal SHIV challenge is done by gently introducing 1 ml of a 1:5 dilution of virus stock (600 TCID50) into the vaginal canal of macaques using a 1-ml syringe. Macaques are kept in a prone position for at least 15 min post challenge. Thirty days prior to vaginal challenge, macaques may have received 30 mg of medroxyprogesterone acetate (Depo-Provera, Upjohn, Kalamazoo, Mich.) by intramuscular injection. Recent titration experiments in progesterone treated macaques demonstrated that the monkeys are exposed to 10-50 animal infectious doses of SHIV89.6PD. After vaginal challenge, monkeys are followed clinically and by routine hematology, lymphocyte subset, and blood chemistry measurements. Inguinal lymph node biopsies for viral co-culture and PCR for viral DNA are done on all monkeys at 3 weeks post-virus challenge.

Example 4

Optimization of the Functional Nanobody Profile Directed Against hCXCR4

Example 4.1

Generation of Bivalent Nanobodies

In order to improve the functional inhibitory profile by engineering, a series of bivalent Nanobodies on the basis of 238D2 and 238D4 were generated (Table B-5).

TABLE B-5

Sequences of selected bivalent Nanobodies

| Amino Acid Sequence | Clone name | SEQ ID NO: |
|---|---|---|
| EVQLVESGGGLVQTGGSLRLSCAASGFTFSSYAM SWVRQAPGKGLEWVSGIKSSGDSTRYAGSVKGR FTISRDNAKNMLYLQMYSLKPEDTAVYYCAKSR VSRTGLYTYDNRGQGTQVTVSSGGGGSGGGGSE VQLVESGGGLVQTGGSLRLSCAASGFTFSSYAMS WVRQAPGKGLEWVSGIKSSGDSTRYAGSVKGRF TISRDNAKNMLYLQMYSLKPEDTAVYYCAKSRV SRTGLYTYDNRGQGTQVTVSS | 238D2-10GS-238D2 | 261 |
| EVQLMESGGGLVQAGGSLRLSCAASGRTFNNYA MGWFRRAPGKEREFVAAITRSGVRSGVSAIYGDS VKDRFTISRDNAKNTLYLQMNSLKPEDTAVYTC | 238D4-20GS-238D4 | 262 |

TABLE B-5-continued

Sequences of selected bivalent Nanobodies

| Amino Acid Sequence | Clone name | SEQ ID NO: |
|---|---|---|
| AASAIGSGALRRFEYDYSGQGTQVTVSSGGGGSG GGGSGGGSGGGGSEVQLMESGGGLVQAGGSLR LSCAASGRTFNNYAMGWFRRAPGKEREFVAAIT RSGVRSGVSAIYGDSVKDRFTISRDNAKNTLYLQ MNSLKPEDTAVYTCAASAIGSGALRRFEYDYSGQ GTQVTVSS | | |
| EVQLVESGGGLVQTGGSLRLSCAASGFTFSSYAM SWVRQAPGKGLEWVSGIKSSGDSTRYAGSVKGR FTISRDNAKNMLYLQMYSLKPEDTAVYYCAKSR VSRTGLYTYDNRGQGTQVTVSSGGGGSGGGGSG GGGSEVQLMESGGGLVQAGGSLRLSCAASGRTF NNYAMGWFRRAPGKEREFVAAITRSGVRSGVSAI YGDSVKDRFTISRDNAKNTLYLQMNSLKPEDTA VYTCAASAIGSGALRRFEYDYSGQGTQVTVSS | 238D2-15GS-238D4 | 263 |
| EVQLVESGGGLVQTGGSLRLSCAASGFTFSSYAM SWVRQAPGKGLEWVSGIKSSGDSTRYAGSVKGR FTISRDNAKNMLYLQMYSLKPEDTAVYYCAKSR VSRTGLYTYDNRGQGTQVTVSSGGGGSGGGGSG GGGSGGGGSEVQLMESGGGLVQAGGSLRLSCAA SGRTFNNYAMGWFRRAPGKEREFVAAITRSGVR SGVSAIYGDSVKDRFTISRDNAKNTLYLQMNSLK PEDTAVYTCAASAIGSGALRRFEYDYSGQGTQVT VSS | 238D2-20GS-238D4 | 264 |
| EVQLVESGGGLVQTGGSLRLSCAASGFTFSSYAM SWVRQAPGKGLEWVSGIKSSGDSTRYAGSVKGR FTISRDNAKNMLYLQMYSLKPEDTAVYYCAKSR VSRTGLYTYDNRGQGTQVTVSSGGGGSGGGGSG GGGSGGGGSEVQLMESGGGLVQAGGSLRLACAA SGFTFEDYAIGWFRKAPGKEREGVSCISGSDGSTT YADSVKGRFTISTDNAKNTVYLEMNSLKPEDTAV YYCAQQYGVGGRVVCPGPYEYDVWGQGTQVTV SS | 238D2-20GS-238C5 | 265 |
| EVQLVESGGGLVQTGGSLRLSCAASGFTFSSYAM SWVRQAPGKGLEWVSGIKSSGDSTRYAGSVKGR FTISRDNAKNMLYLQMYSLKPEDTAVYYCAKSR VSRTGLYTYDNRGQGTQVTVSSGGGGSGGGGSG GGGSGGGGSEVQLVESGGGFVQAGGSLRLSCETS GRPLLGYTIAWFRQVPGKEREFVAYHRWSDGAN LYADSVKGRFTISGHNAKNTVSLQMNSLKPEDTA VYYCAAARMTTSNDKEYLYWGQGTQVTVSS | 238D2-20GS-238B10 | 266 |

Example 4.2

Potency of Bivalent Nanobodies

Recombinant linking of 238D2 to 238D2 and 238D4 to 238D4 using amino acid linkers with repetitive GGGGS sequences of different sizes result in a 14 and 4.4-fold increase in affinity to CXCR4, respectively (Table B-6, Table B-6). A significant increase in apparent affinity was also observed when 238D2 was linked to 238D4. In case of the obtained heterobivalent Nanobody 238D2-20GS-238D4, the affinity to CXCR4 was increased by 27 and 17-fold over the respective monovalent counterparts 238D2 and 238D4. Alteration in the linker size between 15 amino acids and 20 amino acids does not show any influence in respect to the receptor affinity. However, linking of 238D2 to the inactive Nanobody 238B10 or to the low affinity Nanobody 238C5 did not result in an increase but even lowers the receptor affinity. These results exclude the possibility that the linker increases the receptor affinity by its own. Furthermore, competition in binding between 238D2 and 238D4 (FIGS. 4B,4C) and lacking increase of [125I]-CXCL12 displacement potency by equi-molar mixing of 238D2 and 238D4 argues against a positive cooperative effect due to allosteric binding on the same receptor molecule.

TABLE B-6

Receptor affinity (pK$_i$), relative potency and maximal displacement of [125I]-CXCL12 by bivalent Nanobodies in comparison to their monovalent counterparts. The experiments were performed on membranes from HEK293T cells transiently expressing CXCR4. Data were shown as means ± S.E.M. The number of experiments is given as n.

| Alternative Name | Clone name (see table B-5) | Displacem. (%) | pK$_i$ | Rel. potency | n |
|---|---|---|---|---|---|
| L9 | 238D2-10GS-238D2 | 95 ± 5 | 9.16 ± 0.08 | 14[a] | 3 |
| L13 | 238D4-20GS-238D4 | 96 ± 5 | 8.85 ± 0.08 | 4.4[b] | 4 |
| L3 | 238D2-15GS-238D4 | 92 ± 6 | 9.45 ± 0.09 | 28[a]/17[b] | 3 |
| L8 | 238D2-20GS-238D4 | 103 ± 4 | 9.44 ± 0.07 | 27[a]/17[b] | 3 |
| L6 | 238D2-20GS-238C5 | 110 ± 2 | 7.35 ± 0.07 | 0.18[a] | 2 |

TABLE B-6-continued

Receptor affinity ($pK_i$), relative potency and maximal displacement of [$^{125}$I]-CXCL12 by bivalent Nanobodies in comparison to their monovalent counterparts. The experiments were performed on membranes from HEK293T cells transiently expressing CXCR4. Data were shown as means ± S.E.M. The number of experiments is given as n.

| Alternative Name | Clone name (see table B-5) | Displacem. (%) | $pK_i$ | Rel. potency | n |
|---|---|---|---|---|---|
| L10 | 238D2-20GS-238B10 | 43 ± 11[c] | <7.00 | <0.1[a] | 2 |
|  | 238D2 + 238D4 (1:1) | 92 ± 11 | 8.00 ± 0.36 | 1.0[a]/0.6[b] | 3 |

[a]Potency relative to those of monovalent 238D2.
[b]Potency relative to those of monovalent 238D4.
[c]Maximum not reached at the highest test concentration of 0.5 µM, displacement at 0.5 µM.

TABLE B-7

Chemotaxis
Maximal inhibition ($I_{max}$) and functional inhibitory potency ($pK_i$ or $pIC_{50}$) of the compound 238D2-15GS-238D4 and compound 238D2-20GS-238D4. Data were shown as means ± S.E.M. The number of experiments is given as n.

|  | 238D2-15GS-238D4 | | | 238D2-20GS-238D4 | | |
|---|---|---|---|---|---|---|
| Chemotaxis | $I_{max}$ (%) | $pK_i$ or $pIC_{50}$ | n | $I_{max}$ (%) | $pK_i$ or $pIC_{50}$ | n |
| Jurkat/0.3 nM CXCL12 | 107 ± 5 | 9.86 ± 0.04 | 3 | 100 ± 4 | 10.19 ± 0.27 | 3 |

The most potent bivalent Nanobodies 238D2-15GS-238D4 and 238D2-20GS-238D4 were further functionally characterized. Both, 238D2-15GS-238D4 and 238D2-20GS-238D4 fully antagonized the chemoattractant effects of CXCL12 in subnanomolar concentrations ($pK_i$=9.86±0.04 and 10.19±0.27, respectively; n=3). In conclusion, linking of the Nanobodies 238D2 and 238D4 to a single chain molecule result in a significant increase of anti-chemotactic potency via blocking of CXCR4 by even one to two orders of magnitude (see Table B-7 but also Table B-4).

Example 4.3

Comparison Effectivity 12G5 Vs Monovalent 238D2, 238D4 and Bivalent Nanobodies

In membrane binding experiments 12G5 seems only to displace 50% of 125I-CXCL12. We were therefore interested to test whether 12G5 effectively inhibits CXCR4 function.
Inositol Phosphate Measurement 12G5 has been tested as a full curve (n=2) and single point (10 nM) on hCXCR4/Gαqi5; cells were stimulated with 30 nM CXCL12.

Methods: On day 1, HEK293T cells were plated out at a density of 2 million cells/dish. On day 2, these cells were transfected with 2.5 µg CXCR4 DNA and 2.5 µg Gαqi5, using the PEI method. Cells were plated out the next day in poly-L-lysine coated 24 well plates (500 µl/well) and labeled after 4-6 hours with 2 µCi/ml 3H-inositol in inositol-free medium. On day 4, cells were pre-stimulated with either nanobodies, 12G5 or 1 µM AMD3100 in Rosenkilde buffer for 2 hours at 37° C. After this pre-stimulation, both 30 nM CXCL12 (or buffer for basal signaling) and 10 mM LiCl were added to each well (final concentrations), followed by a final 2 hour incubation at 37° C. After this final incubation, the reaction was stopped by aspiration of stimulation medium and addition of 10 mM formic acid (FIG. 9).

Example 5

Mode of Action of Nanobodies

Example 5.1

CXCR4-Specific Nanobodies Behave as Neutral Antagonists or Inverse Antagonists on Constitutively Active Mutants of CXCR4

The CXCR4-specific monovalent nanobodies 238D2 and 238D4 as well as their bivalent fusion products L3 and L8 were investigated on the constitutively active CXCR4 mutant N119A (equivalent to N3.35A in the Ballestros-Weinstein numbering of class A GPCRs). Mutants of N119 have previously been identified by Peiper and co-workers as the only mutants which have been selected from a CXCR4 random mutagenesis library using a yeast reporter gene assay for constitutively active mutants (CAMs) (Zhang W. B., Navenot J. M., Haribabu B., Tamamura H., Hiramatu K., Omagari A., Pei G., Manfredi J. P., Fujii N., Broach J. R., Peiper S. C. (2002). A point mutation that confers constitutive activity to CXCR4 reveals that T140 is an inverse agonist and that AMD3100 and ALX40-4C are weak partial agonists. J. Biol. Chem. 277:24515-24521.). Despite of the large number of CAMs for other class A GPCRs and further efforts to generate additional CAMs for CXCR4 (Berchiche et al., 2007), the N119 mutants of CXCR4 remain the only known CAMs for this receptors. Both monovalent nanobodies investigated, 238D2 and 238D4, were able to bind to CXCR4 (N119A). Their binding affinities were somewhat less compared to the wild type receptor. Due to the reduced affinity, no plateau was reached at the highest nanobody test concentration of 2 µM (FIG. 10).

Methods: Preparation of membranes and competition binding experiments with [125I]-CXCL12 (40 µM) were performed as described before for wild type CXCR4 (vide supra). The functional profile of monovalent nanobodies 238D2 and 238D4 as well as the bivalent constructs L3 and L8 on CXCR4 (N119A) were investigated by measurement of the ligand-induced alteration of the basal inositol phosphate accumulation. HEK293T cells transiently expressing CXCR4 (N119A) show a 3-8 times higher basal rate of inositol phosphate accumulation compared to wild type CXCR4 or mock (which are virtually at the same level). The ability of CXCL12 to further stimulate the mutant receptor is reduced (0.4 fold over basal) compared to wild type (FIG. 11A). 238D4, L3 and L8 behave as partial inverse agonists at this mutant and reduce the constitutively increased basal signalling of CXCR4 (N119A) by 49, 64, and 65%, respectively (FIG. 11A). The nanobody-induced reduction of basal inositol phosphate accumulation was antagonized by the selective neutral CXCR4 antagonist plerixafor confirming that the observed inverse antagonistic effects are mediated via CXCR4 (N119A) (FIG. 11B-D). Neither significant agonistic nor inverse antagonistic activity were observed for 238D2 and plerixafor (FIG. 11A) although these ligands clearly bind to the mutant receptor (vide supra).

Our results show that nanobodies can act as neutral antagonists or inverse antagonists on constitutively active CXCR4 mutants. A significant number of the top selling GPCR drugs behave as inverse antagonists rather than neutral antagonists (Milligan G. (2003). Constitutive activity and inverse agonists of G protein-coupled receptors: a current perspective.

Mol. Pharmacol. 64:1271-1276) and it has been claimed that inverse agonists may have specific therapeutic benefits compared with neutral antagonists for several diseases including cancer (Kenakin T. (2004). Efficacy as a vector: the relative prevalence and paucity of inverse agonism. Mol. Pharmacol. 65:2-11). Despite of the novelty of our observation that CXCR4-specific nanobodies may behave as inverse antagonists, the physiological relevance of inverse CXCR4 agonism is not clear. As we could not detect any significant basal activity of CXCR4 (wt) compared to mock in the inositol phosphate accumulation assay, it is impossible to detect any inverse agonism at least in this assay. Furthermore, the most obvious function of CXCR4 is the chemotactic recruitment of stem cells to the bone marrow. The chemotaxis is mediated by an asymmetric activation of cell surface receptors to let cells migrate towards a chemoattractant gradient. Thus, chemotaxis is strictly depended on a chemoattractant ligand. However, inverse antagonists may be superior over neutral antagonists to inhibit other functions of CXCR4 like chemokinesis or promotion of tumour growth.

Example 6

Potential Uses of a Nanobody or Nanobody Construct Directed Against CXCR4

Immune deficiency disorders
WHIM syndrome: Wart, Hypogammaglobulinemia, Infection and Myelokathexis syndrome
Cancers:
  Hematopoietic cancers: CLL, AML, ALL, MM, Non-Hodgkin lymphoma
  Solid tumors: breast cancer, lung cancer, brain tumors . . .
  Stromal chemoresistance of tumors
  leukemia and other cancers
  Stem cell mobilization
  Disrupting adhesive stromal interactions that confer tumor cell survival and drug resistance
  Mobilizing tumor cells form tissue sites and making them better accessible to conventional therapy
  Blocking of migration and dissemination of tumor cells (metastasis)
  Blocking or paracrine growth and survival signals
  Blocking pro-angiogenesis effects of SDF-1
Inflammatory diseases
RA, asthma, pulmonary fibrosis, SLE
Stem cell recruitment to injured tissues (heart, brain)
Neuro-inflammatory diseases
MS, stroke, HIV-associated dementia
Infectious diseases
HIV/AIDS, West Nile Virus encephalitis Example 7

Table C of Non-Limiting List of Some Therapeutically Relevant GPCRs (and Desired Action of an Amino Acid Sequence, a Nanobody or a Polypeptide of the Invention)

Class A GPCRs
  Acetylcholine receptor (agonist),
  Muscarinic receptor (agonist),
  Muscarinic M1 receptor (agonist),
  Muscarinic M2 receptor (agonist),
  Muscarinic M3 receptor (agonist),
  Muscarinic M4 receptor (agonist),
  Muscarinic M5 receptor (agonist)
  Muscarinic receptor (partial agonist)
  Adrenoceptor (agonist),
  Alpha adrenoceptor (agonist),
  Alpha 1 adrenoceptor (agonist),
  Alpha 1A adrenoceptor (agonist),
  Alpha 1B adrenoceptor (agonist)
  Alpha 1D adrenoceptor (agonist)
  Alpha 2 adrenoceptor (agonist),
  Alpha 2A adrenoceptor (agonist),
  Alpha 2B adrenoceptor (agonist),
  Alpha 2C adrenoceptor (agonist),
  Alpha 2 adrenoceptor (partial agonist)
  Alpha 3 adrenoceptor (agonist),
  Beta adrenoceptor (agonist),
  Beta 1 adrenoceptor (agonist),
  Beta 2 adrenoceptor (agonist),
  Beta 3 adrenoceptor (agonist),
  Dopamine receptor (agonist),
  Dopamine D5 receptor (agonist)
  Dopamine D1 receptor (agonist),
  Dopamine D2 receptor (agonist),
  Dopamine D3 receptor (agonist),
  Dopamine D4 receptor (agonist),
  Histamine receptor (agonist),
  Histamine H1 receptor (agonist),
  Histamine H2 receptor (agonist),
  Histamine H3 receptor (agonist),
  Histamine H4 receptor (agonist),
  5-HT GPCR (agonist),
  5-HT 1 (agonist),
  5-HT 2 (agonist),
  5-HT 4 (agonist),
  5-HT 5a (agonist),
  5-HT 5b (agonist)
  5-HT 6 (agonist),
  5-HT 7 (agonist),
  Trace amine-associated receptor (agonist),
  Trace amine-associated receptor-1 (agonist),
  Trace amine-associated receptor-2 (agonist)
  Trace amine-associated receptor-3 (agonist)
  Trace amine-associated receptor-4 (agonist)
  Trace amine-associated receptor-5 (agonist)
  Trace amine-associated receptor-6 (agonist)
  Trace amine-associated receptor-7 (agonist)
  Trace amine-associated receptor-8 (agonist)
  Trace amine-associated receptor-9 (agonist)
  Apelin receptor (agonist),
  Cannabinoid receptor (agonist),
  Cannabinoid CB1 receptor (agonist),
  Cannabinoid CB2 receptor (agonist),
  Lysosphingolipid receptor (agonist),
  Sphingosine-1-phosphate receptor-1 (agonist),
  Lysophosphatidate-1 receptor (agonist)
  Sphingosine-1-phosphate receptor-3 (agonist),
  Lysophosphatidate-2 receptor (agonist)
  Sphingosine-1-phosphate receptor-2 (agonist)
  Sphingosine-1-phosphate receptor-4 (agonist),
  Lysophosphatidate-3 receptor (agonist)
  Sphingosine-1-phosphate receptor-5 (agonist)
  Class A hormone protein GPCR (agonist),
  FSH (agonist),
  Luteinizing hormone receptor (agonist),
  TSH (agonist),
  Leukotriene (agonist),
  Leukotriene BLT receptor (agonist),
  Cysteinyl leukotriene receptor (agonist), Melatonin (agonist),
Melatonin MT1 (agonist),
Melatonin MT2 (agonist),
Melatonin MT3 (agonist)
Class A nucleotide like GPCR (agonist),
Adenosine receptor (agonist),
P2Y receptor (agonist),
Class A orphan GPCR (agonist),
Ghrelin (agonist),
Class A peptide GPCR (agonist),
Angiotensin receptor (agonist),
Angiotensin I receptor (agonist),
Angiotensin II receptor (agonist),
Bombesin receptor (agonist),
Bombesin BB1 receptor (agonist)
Bombesin BB2 receptor (agonist)
Bombesin bb3 receptor (agonist),
Gastrin releasing peptide ligand,
Neuromedin B ligand
Neuromedin C ligand
Bradykinin receptor (agonist),
Bradykinin B1 receptor (agonist),
Bradykinin B2 receptor (agonist),
C3a receptor (agonist),
C5a (agonist),
CCK receptor (agonist),
CCK 1 receptor (agonist),
CCK 2 receptor (agonist),
Gastrin (agonist),
Chemokine (agonist),
CC chemokine receptor (agonist),
CCR1 chemokine (agonist),
CCR2 chemokine (agonist),
CCR3 chemokine (agonist),
CCR4 chemokine (agonist),
CCR5 chemokine (agonist),
CCR6 chemokine (agonist),
CCR7 chemokine (agonist)
CCR8 chemokine (agonist),
CCR9 chemokine (agonist)
CCR10 chemokine (agonist),
CCR11 chemokine (agonist)
CX3C chemokine receptor (agonist),
CX3CR1 chemokine (agonist),
XCR1 chemokine (agonist)
CXC chemokine receptor (agonist),
CXCR1 chemokine (agonist)
CXCR3 chemokine (agonist),
CXCR4 chemokine (agonist),
CXCR5 chemokine (agonist)
Adrenomedullin receptor (agonist),
Endothelin (agonist),
Endothelin ET-A (agonist),
Endothelin ET-B (agonist),
Galanin (agonist),
Galanin GAL1 (agonist),
Galanin GAL2 (agonist),
Galanin GAL3 (agonist)
IL-9 (agonist),
KiSS-1 receptor (agonist),
Melanin concentrating hormone (agonist),
MCH receptor-1 (agonist)
MCH receptor-2 (agonist)
Melanocortin (agonist),
Melanocortin MC1 (agonist),
ACTH receptor (agonist),
Melanocortin MC3 (agonist),
Melanocortin MC4 (agonist),
Melanocortin MC5 (agonist),
NK (agonist),
NK1 (agonist),
NK2 (agonist)
NK3 (agonist), Drugs: 1
Neuropeptide Y receptor (agonist),
Neuropeptide Y1 receptor (agonist)
Neuropeptide Y2 receptor (agonist),
Neuropeptide Y4 receptor (agonist),
Neuropeptide Y5 receptor (agonist),
Neuropeptide Y6 receptor (agonist)
Neurotensin receptor (agonist),
Neurotensin NTS1 (agonist),
Neurotensin NTS2 (agonist)
Orexin & neuropeptide FF receptor (agonist),
Orexin (agonist),
Opioid (agonist),
Delta opioid (agonist),
Kappa opioid (agonist),
Mu opioid (agonist),
ORL1 receptor (agonist),
Opioid (partial agonist)
Sigma opioid (agonist),
Orexin & neuropeptide FF receptor (agonist),
Neuropeptide FF receptor (agonist),
Neuropeptide FF1 receptor (agonist)
Neuropeptide FF2 receptor (agonist),
Orexin (agonist),
Orexin-1 (agonist)
Orexin-2 (agonist)
Protease-activated receptor (agonist),
Protease-activated receptor-1 (agonist),
Protease-activated receptor-2 (agonist),
Protease-activated receptor-3 (agonist)
Protease-activated receptor-4 (agonist)
Prokineticin receptor (agonist),
Prokineticin receptor-1 (agonist),
Prokineticin receptor-2 (agonist),
Somatostatin (agonist),
Somatostatin 1 (agonist),
Somatostatin 2 (agonist),
Somatostatin 3 (agonist),
Somatostatin 4 (agonist),
Somatostatin 5 (agonist),
Urotensin II (agonist),
Vasopressin like receptor (agonist),
Oxytocin (agonist),
Vasopressin (agonist),
Vasopressin V1 (agonist),
Vasopressin V2 (agonist),
Prostanoid receptor (agonist),
DP prostanoid (agonist),
PGD2 (agonist),
EP1 prostanoid (agonist),
PGE2 (agonist),
EP2 prostanoid (agonist),
PGE2 (agonist),
EP3 prostanoid (agonist),
PGE2 (agonist),
EP4 prostanoid (agonist),
PGE2 (agonist),
FP prostanoid (agonist),
PGF2 alpha (agonist),
IP prostanoid (agonist),
Prostacyclin (agonist),
Prostanoid receptor (partial agonist)

TP prostanoid (agonist),
Thromboxane A2 (agonist)
Succinate receptor 1 (agonist)
TRH (agonist),
TRH1 (agonist)
TRH2 (agonist)
Vomeronasal type-1 receptor (agonist)
Vomeronasal type-1 receptor-1 (agonist)
Vomeronasal type-1 receptor-2 (agonist)
Vomeronasal type-1 receptor-3 (agonist)
Vomeronasal type-1 receptor-4 (agonist)
Vomeronasal type-1 receptor-5 (agonist)
Apelin receptor (modulator),
Cannabinoid receptor (modulator),
Chemokine receptor-like 1 (modulator),
Lysosphingolipid receptor (modulator),
Class A hormone protein GPCR (modulator),
Leukotriene receptor (modulator),
Melatonin receptor (modulator),
Class A nucleotide like GPCR (modulator),
Class A orphan GPCR (modulator),
PAF receptor (modulator),
Class A peptide GPCR (modulator),
Prostanoid receptor (modulator),
Succinate receptor 1 (modulator)
TRH receptor (modulator),
Vomeronasal type-1 receptor (modulator),
Class B GPCRs
  G-protein coupled receptor-3 (modulator),
  G-protein coupled receptor-3 (agonist)
  G-protein coupled receptor-3 (antagonist),
  G-protein coupled receptor-6 (modulator),
  G-protein coupled receptor-6 (agonist)
  G-protein coupled receptor-6 (antagonist),
  G-protein coupled receptor-12 (modulator),
  G-protein coupled receptor-12 (agonist)
  G-protein coupled receptor-12 (antagonist),
  G-protein coupled receptor-14 (modulator)
  G-protein coupled receptor-14 (agonist)
  G-protein coupled receptor-14 (antagonist)
  Class B GPCR (agonist),
  CRF-1 receptor (agonist)
  CRF-2 receptor (agonist),
  Calcitonin receptor (modulator),
  Calcitonin (agonist),
  Calcitonin (antagonist),
  ACTH releasing factor receptor (modulator),
  CRF-1 receptor (modulator),
  CRF-1 receptor (agonist)
  CRF-1 receptor (antagonist),
  CRF-2 receptor (modulator),
  CRF-2 receptor (agonist),
  CRF-2 receptor (antagonist),
  ACTH releasing factor (agonist),
  CRF-1 receptor (agonist)
  CRF-2 receptor (agonist),
  ACTH releasing factor (antagonist),
  CRF-1 receptor (antagonist),
  CRF-2 receptor (antagonist),
  Glucagon-like peptide receptor (modulator),
  Glucagon-like peptide 1 receptor (modulator),
  Glucagon-like peptide 2 receptor (modulator),
  Glucagon-like peptide (agonist),
  Glucagon-like peptide (antagonist),
  Glucagon receptor (modulator),
  Glucagon (agonist),
  Glucagon (antagonist),
  GHRH receptor (modulator),
  GHRH (agonist),
  Growth hormone releasing factor (antagonist),
  PACAP type I receptor (modulator),
  PACAP type I receptor (agonist),
  PACAP type I receptor (antagonist)
  PTH receptor (modulator),
  PTH-1 receptor (modulator)
  PTH-2 receptor (modulator)
  PTH (agonist),
  PTH (antagonist),
  Secretin receptor (modulator),
  Secretin (agonist),
  Secretin (antagonist)
  VIP receptor (modulator),
  VIP-1 receptor (modulator),
  VIP-2 receptor (modulator),
  VIP (agonist),
  VIP (antagonist),
Class C GPCRs
  Class C GPCR (modulator),
  Class C GPCR (agonist),
  GABA B receptor (agonist),
  Metabotropic glutamate receptor (agonist),
  Metabotropic glutamate receptor 1 (agonist),
  Metabotropic glutamate receptor 2 (agonist),
  Metabotropic glutamate receptor 3 (agonist),
  Metabotropic glutamate receptor 4 (agonist),
  Metabotropic glutamate receptor 5 (agonist),
  Metabotropic glutamate receptor 6 (agonist)
  Metabotropic glutamate receptor 7 (agonist)
  Metabotropic glutamate receptor 8 (agonist)

TABLE D non-limiting list human GPCRs

| | | | | |
|---|---|---|---|---|
| 5HT1A_HUMAN | (P08908) | HTR1A | Serotonin type 1 | Homo sapiens (Human) |
| 5HT1B_HUMAN | (P28222) | HTR1B | Serotonin type 1 | Homo sapiens (Human) |
| 5HT1D_HUMAN | (P28221) | HTR1D | Serotonin type 1 | Homo sapiens (Human) |
| 5HT1E_HUMAN | (P28566) | HTR1E | Serotonin type 1 | Homo sapiens (Human) |
| 5HT1F_HUMAN | (P30939) | HTR1F | Serotonin type 1 | Homo sapiens (Human) |
| 5HT2A_HUMAN | (P28223) | HTR2A | Serotonin type 2 | Homo sapiens (Human) |
| 5HT2B_HUMAN | (P41595) | HTR2B | Serotonin type 2 | Homo sapiens (Human) |
| 5HT2C_HUMAN | (P28335) | HTR2C | Serotonin type 2 | Homo sapiens (Human) |
| 5HT4R_HUMAN | (Q13639) | HTR4 | Serotonin type 4 | Homo sapiens (Human) |
| 5HT5A_HUMAN | (P47898) | HTR5A | Serotonin type 5 | Homo sapiens (Human) |
| 5HT6R_HUMAN | (P50406) | HTR6 | Serotonin type 6 | Homo sapiens (Human) |
| 5HT7R_HUMAN | (P34969) | HTR7 | Serotonin type 7 | Homo sapiens (Human) |
| AA1R_HUMAN | (P30542) | ADORA1 | Adenosine type 1 | Homo sapiens (Human) |
| AA2AR_HUMAN | (P29274) | ADORA2A | Adenosine type 2 | Homo sapiens (Human) |
| AA2BR_HUMAN | (P29275) | ADORA2B | Adenosine type 2 | Homo sapiens (Human) |

TABLE D-continued non-limiting list human GPCRs

| | | | | |
|---|---|---|---|---|
| AA3R_HUMAN | (P33765) | ADORA3 | Adenosine type 3 | *Homo sapiens* (Human) |
| ACM1_HUMAN | (P11229) | CHRM1 | Musc. acetylcholine Vertebrate type 1 | *Homo sapiens* (Human) |
| ACM2_HUMAN | (P08172) | CHRM2 | Musc. acetylcholine Vertebrate type 2 | *Homo sapiens* (Human) |
| ACM3_HUMAN | (P20309) | CHRM3 | Musc. acetylcholine Vertebrate type 3 | *Homo sapiens* (Human) |
| ACM4_HUMAN | (P08173) | CHRM4 | Musc. acetylcholine Vertebrate type 4 | *Homo sapiens* (Human) |
| ACM5_HUMAN | (P08912) | CHRM5 | Musc. acetylcholine Vertebrate type 5 | *Homo sapiens* (Human) |
| ACTHR_HUMAN | (Q01718) | MC2R | Adrenocorticotropic hormone | *Homo sapiens* (Human) |
| ADA1A_HUMAN | (P35348) | ADRA1A | Alpha Adrenoceptors type 1 | *Homo sapiens* (Human) |
| ADA1B_HUMAN | (P35368) | ADRA1B | Alpha Adrenoceptors type 1 | *Homo sapiens* (Human) |
| ADA1D_HUMAN | (P25100) | ADRA1D | Alpha Adrenoceptors type 1 | *Homo sapiens* (Human) |
| ADA2A_HUMAN | (P08913) | ADRA2A | Alpha Adrenoceptors type 2 | *Homo sapiens* (Human) |
| ADA2B_HUMAN | (P18089) | ADRA2B | Alpha Adrenoceptors type 2 | *Homo sapiens* (Human) |
| ADA2C_HUMAN | (P18825) | ADRA2C | Alpha Adrenoceptors type 2 | *Homo sapiens* (Human) |
| ADMR_HUMAN | (O15218) | ADMR | Adrenomedullin (G10D) | *Homo sapiens* (Human) |
| ADRB1_HUMAN | (P08588) | ADRB1 | Beta Adrenoceptors type 1 | *Homo sapiens* (Human) |
| ADRB2_HUMAN | (P07550) | ADRB2 | Beta Adrenoceptors type 2 | *Homo sapiens* (Human) |
| ADRB3_HUMAN | (P13945) | ADRB3 | Beta Adrenoceptors type 3 | *Homo sapiens* (Human) |
| AGTR1_HUMAN | (P30556) | AGTR1 | Angiotensin type 1 | *Homo sapiens* (Human) |
| AGTR2_HUMAN | (P50052) | AGTR2 | Angiotensin type 2 | *Homo sapiens* (Human) |
| APJ_HUMAN | (P35414) | AGTRL1 | APJ like | *Homo sapiens* (Human) |
| BAI1_HUMAN | (O14514) | BAI1 | Brain-specific angiogenesis inhibitor (BAI) | *Homo sapiens* (Human) |
| BAI2_HUMAN | (O60241) | BAI2 | Brain-specific angiogenesis inhibitor (BAI) | *Homo sapiens* (Human) |
| BAI3_HUMAN | (O60242) | BAI3 | Brain-specific angiogenesis inhibitor (BAI) | *Homo sapiens* (Human) |
| BKRB1_HUMAN | (P46663) | BDKRB1 | Bradykinin | *Homo sapiens* (Human) |
| BKRB2_HUMAN | (P30411) | BDKRB2 | Bradykinin | *Homo sapiens* (Human) |
| BRS3_HUMAN | (P32247) | BRS3 | Bombesin | *Homo sapiens* (Human) |
| C3AR_HUMAN | (Q16581) | C3AR1 | C5a anaphylatoxin | *Homo sapiens* (Human) |
| C5ARL_HUMAN | (Q9P296) | GPR77 | C5a anaphylatoxin | *Homo sapiens* (Human) |
| C5AR_HUMAN | (P21730) | C5AR1 | C5a anaphylatoxin | *Homo sapiens* (Human) |
| CALCR_HUMAN | (P30988) | CALCR | Calcitonin | *Homo sapiens* (Human) |
| CALRL_HUMAN | (Q16602) | CALCRL | Calcitonin | *Homo sapiens* (Human) |
| CASR_HUMAN | (P41180) | CASR | Extracellular calcium-sensing | *Homo sapiens* (Human) |
| CCBP2_HUMAN | (O00590) | CCBP2 | C-C Chemokine type X | *Homo sapiens* (Human) |
| CCKAR_HUMAN | (P32238) | CCKAR | CCK type A | *Homo sapiens* (Human) |
| CCR10_HUMAN | (P46092) | CCR10 | C-C Chemokine type 10 | *Homo sapiens* (Human) |
| CCR1_HUMAN | (P32246) | CCR1 | C-C Chemokine type 1 | *Homo sapiens* (Human) |
| CCR2_HUMAN | (P41597) | CCR2 | C-C Chemokine type 2 | *Homo sapiens* (Human) |
| CCR3_HUMAN | (P51677) | CCR3 | C-C Chemokine type 3 | *Homo sapiens* (Human) |
| CCR4_HUMAN | (P51679) | CCR4 | C-C Chemokine type 4 | *Homo sapiens* (Human) |
| CCR5_HUMAN | (P51681) | CCR5 | C-C Chemokine type 5 | *Homo sapiens* (Human) |
| CCR6_HUMAN | (P51684) | CCR6 | C-C Chemokine type 6 | *Homo sapiens* (Human) |
| CCR7_HUMAN | (P32248) | CCR7 | C-C Chemokine type 7 | *Homo sapiens* (Human) |
| CCR8_HUMAN | (P51685) | CCR8 | C-C Chemokine type 8 | *Homo sapiens* (Human) |
| CCR9_HUMAN | (P51686) | CCR9 | C-C Chemokine type 9 | *Homo sapiens* (Human) |
| CCRL1_HUMAN | (Q9NPB9) | CCRL1 | C-C Chemokine type 11 | *Homo sapiens* (Human) |
| CD97_HUMAN | (P48960) | CD97 | EMR1 | *Homo sapiens* (Human) |
| CELR1_HUMAN | (Q9NYQ6) | CELSR1 | Cadherin EGF LAG (CELSR) | *Homo sapiens* (Human) |
| CELR2_HUMAN | (Q9HCU4) | CELSR2 | Cadherin EGF LAG (CELSR) | *Homo sapiens* (Human) |
| CELR3_HUMAN | (Q9NYQ7) | CELSR3 | Cadherin EGF LAG (CELSR) | *Homo sapiens* (Human) |
| CLTR1_HUMAN | (Q9Y271) | CYSLTR1 | Cysteinyl leukotriene | *Homo sapiens* (Human) |
| CLTR2_HUMAN | (Q9NS75) | CYSLTR2 | Cysteinyl leukotriene | *Homo sapiens* (Human) |
| CML1_HUMAN | (Q99788) | CMKLR1 | Chemokine receptor-like 1 | *Homo sapiens* (Human) |
| CML2_HUMAN | (Q99527) | GPR30 | Chemokine receptor-like 2 | *Homo sapiens* (Human) |
| CNR1_HUMAN | (P21554) | CNR1 | Cannabinoid | *Homo sapiens* (Human) |
| CNR2_HUMAN | (P34972) | CNR2 | Cannabinoid | *Homo sapiens* (Human) |
| CRFR1_HUMAN | (P34998) | CRHR1 | Corticotropin releasing factor | *Homo sapiens* (Human) |
| CRFR2_HUMAN | (Q13324) | CRHR2 | Corticotropin releasing factor | *Homo sapiens* (Human) |
| CX3C1_HUMAN | (P49238) | CX3CR1 | C—X3—C Chemokine | *Homo sapiens* (Human) |
| CXCR1_HUMAN | (P25024) | IL8RA | Interleukin-8 type A | *Homo sapiens* (Human) |
| CXCR3_HUMAN | (P49682) | CXCR3 | C—X—C Chemokine type 3 | *Homo sapiens* (Human) |
| CXCR4_HUMAN | (P61073) | CXCR4 | C—X—C Chemokine type 4 | *Homo sapiens* (Human) |
| CXCR5_HUMAN | (P32302) | BLR1 | C—X—C Chemokine type 5 | *Homo sapiens* (Human) |
| CXCR6_HUMAN | (O00574) | CXCR6 | C—X—C Chemokine type 6 (Bonzo) | *Homo sapiens* (Human) |
| DRD1_HUMAN | (P21728) | DRD1 | Dopamine Vertebrate type 1 | *Homo sapiens* (Human) |
| DRD2_HUMAN | (P14416) | DRD2 | Dopamine Vertebrate type 2 | *Homo sapiens* (Human) |
| DRD3_HUMAN | (P35462) | DRD3 | Dopamine Vertebrate type 3 | *Homo sapiens* (Human) |
| DRD4_HUMAN | (P21917) | DRD4 | Dopamine Vertebrate type 4 | *Homo sapiens* (Human) |
| DRD5_HUMAN | (P21918) | DRD5 | Dopamine Vertebrate type 1 | *Homo sapiens* (Human) |
| DUFFY_HUMAN | (Q16570) | DARC | Duffy antigen | *Homo sapiens* (Human) |
| EBI2_HUMAN | (P32249) | EBI2 | EBV-induced | *Homo sapiens* (Human) |
| EDG1_HUMAN | (P21453) | EDG1 | Sphingosine 1-phosphate Edg-1 | *Homo sapiens* (Human) |
| EDG2_HUMAN | (Q92633) | EDG2 | Lysophosphatidic acid Edg-2 | *Homo sapiens* (Human) |
| EDG3_HUMAN | (Q99500) | EDG3 | Sphingosine 1-phosphate Edg-3 | *Homo sapiens* (Human) |
| EDG4_HUMAN | (Q9HBW0) | EDG4 | Lysophosphatidic acid Edg-4 | *Homo sapiens* (Human) |
| EDG5_HUMAN | (O95136) | EDG5 | Sphingosine 1-phosphate Edg-5 | *Homo sapiens* (Human) |
| EDG6_HUMAN | (O95977) | EDG6 | Sphingosine 1-phosphate Edg-6 | *Homo sapiens* (Human) |
| EDG7_HUMAN | (Q9UBY5) | EDG7 | Lysophosphatidic acid Edg-7 | *Homo sapiens* (Human) |
| EDG8_HUMAN | (Q9H228) | EDG8 | Sphingosine 1-phosphate Edg-8 | *Homo sapiens* (Human) |

TABLE D-continued non-limiting list human GPCRs

| | | | | |
|---|---|---|---|---|
| EDNRA_HUMAN | (P25101) | EDNRA | Endothelin | *Homo sapiens* (Human) |
| EDNRB_HUMAN | (P24530) | EDNRB | Endothelin | *Homo sapiens* (Human) |
| ELTD1_HUMAN | (Q9HBW9) | ELTD1 | ETL receptors | *Homo sapiens* (Human) |
| EMR1_HUMAN | (Q14246) | EMR1 | EMR1 | *Homo sapiens* (Human) |
| EMR2_HUMAN | (Q9UHX3) | EMR2 | EMR1 | *Homo sapiens* (Human) |
| EMR3_HUMAN | (Q9BY15) | EMR3 | EMR1 | *Homo sapiens* (Human) |
| EMR4_HUMAN | (Q86SQ3) | EMR4 | fragments | *Homo sapiens* (Human) |
| ETBR2_HUMAN | (O60883) | GPR37L1 | GPR37/endothelin B-like | *Homo sapiens* (Human) |
| FFAR1_HUMAN | (O14842) | FFAR1 | Free fatty acid receptor (GP40, GP41, GP43) | *Homo sapiens* (Human) |
| FFAR2_HUMAN | (O15552) | FFAR2 | Free fatty acid receptor (GP40, GP41, GP43) | *Homo sapiens* (Human) |
| FFAR3_HUMAN | (O14843) | FFAR3 | Free fatty acid receptor (GP40, GP41, GP43) | *Homo sapiens* (Human) |
| FPR1_HUMAN | (P21462) | FPR1 | Fmet-leu-phe | *Homo sapiens* (Human) |
| FPRL1_HUMAN | (P25090) | FPRL1 | Fmet-leu-phe | *Homo sapiens* (Human) |
| FPRL2_HUMAN | (P25089) | FPRL2 | Fmet-leu-phe | *Homo sapiens* (Human) |
| FSHR_HUMAN | (P23945) | FSHR | Follicle stimulating hormone | *Homo sapiens* (Human) |
| FZD10_HUMAN | (Q9ULW2) | FZD10 | frizzled Group A (Fz 1&2&4&5&7-9) | *Homo sapiens* (Human) |
| FZD1_HUMAN | (Q9UP38) | FZD1 | frizzled Group A (Fz 1&2&4&5&7-9) | *Homo sapiens* (Human) |
| FZD2_HUMAN | (Q14332) | FZD2 | frizzled Group A (Fz 1&2&4&5&7-9) | *Homo sapiens* (Human) |
| FZD3_HUMAN | (Q9NPG1) | FZD3 | frizzled Group B (Fz 3 & 6) | *Homo sapiens* (Human) |
| FZD4_HUMAN | (Q9ULV1) | FZD4 | frizzled Group A (Fz 1&2&4&5&7-9) | *Homo sapiens* (Human) |
| FZD5_HUMAN | (Q13467) | FZD5 | frizzled Group A (Fz 1&2&4&5&7-9) | *Homo sapiens* (Human) |
| FZD6_HUMAN | (O60353) | FZD6 | frizzled Group B (Fz 3 & 6) | *Homo sapiens* (Human) |
| FZD7_HUMAN | (O75084) | FZD7 | frizzled Group A (Fz 1&2&4&5&7-9) | *Homo sapiens* (Human) |
| FZD8_HUMAN | (Q9H461) | FZD8 | frizzled Group A (Fz 1&2&4&5&7-9) | *Homo sapiens* (Human) |
| FZD9_HUMAN | (O00144) | FZD9 | frizzled Group A (Fz 1&2&4&5&7-9) | *Homo sapiens* (Human) |
| G109A_HUMAN | (Q8TDS4) | GPR109A | Putative/unclassified Class A GPCRs | *Homo sapiens* (Human) |
| G109B_HUMAN | (P49019) | GPR109B | Putative/unclassified Class A GPCRs | *Homo sapiens* (Human) |
| GABR1_HUMAN | (Q9UBS5) | GABBR1 | GABA-B subtype 1 | *Homo sapiens* (Human) |
| GABR2_HUMAN | (O75899) | GABBR2 | GABA-B subtype 2 | *Homo sapiens* (Human) |
| GALR1_HUMAN | (P47211) | GALR1 | Galanin | *Homo sapiens* (Human) |
| GALR2_HUMAN | (O43603) | GALR2 | Galanin | *Homo sapiens* (Human) |
| GALR3_HUMAN | (O60755) | GALR3 | Galanin | *Homo sapiens* (Human) |
| GASR_HUMAN | (P32239) | CCKBR | CCK type B | *Homo sapiens* (Human) |
| GHRHR_HUMAN | (Q02643) | GHRHR | Growth hormone-releasing hormone | *Homo sapiens* (Human) |
| GHSR_HUMAN | (Q92847) | GHSR | Growth hormone secretagogue | *Homo sapiens* (Human) |
| GIPR_HUMAN | (P48546) | GIPR | Gastric inhibitory peptide | *Homo sapiens* (Human) |
| GLP1R_HUMAN | (P43220) | GLP1R | Glucagon | *Homo sapiens* (Human) |
| GLP2R_HUMAN | (O95838) | GLP2R | Glucagon | *Homo sapiens* (Human) |
| GLR_HUMAN | (P47871) | GCGR | Glucagon | *Homo sapiens* (Human) |
| GNRHR_HUMAN | (P30968) | GNRHR | Gonadotropin-releasing hormone type I | *Homo sapiens* (Human) |
| GNRR2_HUMAN | (Q96P88) | GNRHR2 | Gonadotropin-releasing hormone type II | *Homo sapiens* (Human) |
| GP101_HUMAN | (Q96P66) | GPR101 | Putative/unclassified Class A GPCRs | *Homo sapiens* (Human) |
| GP107_HUMAN | (Q5VW38) | GPR107 | Putative/unclassified other | *Homo sapiens* (Human) |
| GP110_HUMAN | (Q5T601) | GPR110 | Putative/unclassified Class B GPCRs | *Homo sapiens* (Human) |
| GP111_HUMAN | (Q8IZF7) | GPR111 | Putative/unclassified Class B GPCRs | *Homo sapiens* (Human) |
| GP112_HUMAN | (Q8IZF6) | GPR112 | Putative/unclassified Class B GPCRs | *Homo sapiens* (Human) |
| GP113_HUMAN | (Q8IZF5) | GPR113 | Putative/unclassified Class B GPCRs | *Homo sapiens* (Human) |
| GP114_HUMAN | (Q8IZF4) | GPR114 | Putative/unclassified Class B GPCRs | *Homo sapiens* (Human) |
| GP115_HUMAN | (Q8IZF3) | GPR115 | Putative/unclassified Class B GPCRs | *Homo sapiens* (Human) |
| GP116_HUMAN | (Q8IZF2) | GPR116 | Putative/unclassified Class B GPCRs | *Homo sapiens* (Human) |
| GP119_HUMAN | (Q8TDV5) | GPR119 | Putative/unclassified Class A GPCRs | *Homo sapiens* (Human) |
| GP120_HUMAN | (Q5NUL3) | GPR120 | Putative/unclassified Class A GPCRs | *Homo sapiens* (Human) |
| GP123_HUMAN | (Q86SQ6) | GPR123 | Putative/unclassified Class B GPCRs | *Homo sapiens* (Human) |
| GP124_HUMAN | (Q96PE1) | GPR124 | Putative/unclassified Class B GPCRs | *Homo sapiens* (Human) |
| GP125_HUMAN | (Q8IWK6) | GPR125 | Putative/unclassified Class B GPCRs | *Homo sapiens* (Human) |
| GP126_HUMAN | (Q86SQ4) | GPR126 | Putative/unclassified Class B GPCRs | *Homo sapiens* (Human) |
| GP128_HUMAN | (Q96K78) | GPR128 | Putative/unclassified Class B GPCRs | *Homo sapiens* (Human) |
| GP132_HUMAN | (Q9UNW8) | GPR132 | Putative/unclassified Class A GPCRs | *Homo sapiens* (Human) |
| GP133_HUMAN | (Q6QNK2) | GPR133 | Putative/unclassified Class B GPCRs | *Homo sapiens* (Human) |
| GP135_HUMAN | (Q8IZ08) | GPR135 | Putative/unclassified Class A GPCRs | *Homo sapiens* (Human) |
| GP139_HUMAN | (Q6DWJ6) | GPR139 | Putative/unclassified Class A GPCRs | *Homo sapiens* (Human) |
| GP141_HUMAN | (Q7Z602) | GPR141 | Putative/unclassified Class A GPCRs | *Homo sapiens* (Human) |
| GP142_HUMAN | (Q7Z601) | GPR142 | Putative/unclassified Class A GPCRs | *Homo sapiens* (Human) |
| GP143_HUMAN | (P51810) | GPR143 | Ocular albinism proteins | *Homo sapiens* (Human) |
| GP144_HUMAN | (Q7Z7M1) | GPR144 | Putative/unclassified Class B GPCRs | *Homo sapiens* (Human) |
| GP146_HUMAN | (Q96CH1) | GPR146 | Putative/unclassified Class A GPCRs | *Homo sapiens* (Human) |
| GP148_HUMAN | (Q8TDV2) | GPR148 | Putative/unclassified Class A GPCRs | *Homo sapiens* (Human) |
| GP149_HUMAN | (Q86SP6) | GPR149 | Putative/unclassified Class A GPCRs | *Homo sapiens* (Human) |
| GP150_HUMAN | (Q8NGU9) | GPR150 | Putative/unclassified Class A GPCRs | *Homo sapiens* (Human) |
| GP151_HUMAN | (Q8TDV0) | GPR151 | Putative/unclassified Class A GPCRs | *Homo sapiens* (Human) |
| GP152_HUMAN | (Q8TDT2) | GPR152 | Putative/unclassified Class A GPCRs | *Homo sapiens* (Human) |
| GP153_HUMAN | (Q6NV75) | GPR153 | Putative/unclassified Class A GPCRs | *Homo sapiens* (Human) |
| GP154_HUMAN | (Q6W5P4) | GPR154 | Putative/unclassified Class A GPCRs | *Homo sapiens* (Human) |
| GP155_HUMAN | (Q7Z3F1) | GPR155 | Putative/unclassified other | *Homo sapiens* (Human) |
| GP156_HUMAN | (Q8NFN8) | GPR156 | GABA-B like | *Homo sapiens* (Human) |
| GP157_HUMAN | (Q5UAW9) | GPR157 | Putative/unclassified Class B GPCRs | *Homo sapiens* (Human) |
| GP158_HUMAN | (Q5T848) | GPR158 | Putative/unclassified Class C GPCRs | *Homo sapiens* (Human) |
| GP160_HUMAN | (Q9UJ42) | GPR160 | Putative/unclassified Class A GPCRs | *Homo sapiens* (Human) |

TABLE D-continued non-limiting list human GPCRs

| | | | | |
|---|---|---|---|---|
| GP161_HUMAN | (Q8N6U8) | GPR161 | Putative/unclassified Class A GPCRs | *Homo sapiens* (Human) |
| GP162_HUMAN | (Q16538) | GPR162 | Putative/unclassified Class A GPCRs | *Homo sapiens* (Human) |
| GP171_HUMAN | (O14626) | GPR171 | Putative/unclassified Class A GPCRs | *Homo sapiens* (Human) |
| GP173_HUMAN | (Q9NS66) | GPR173 | SREB | *Homo sapiens* (Human) |
| GP174_HUMAN | (Q9BXC1) | GPR174 | Purinoceptor P2RY5,8,9,10 GPR35,92,174 | *Homo sapiens* (Human) |
| GP175_HUMAN | (Q86W33) | GPR175 | Putative/unclassified other | *Homo sapiens* (Human) |
| GP176_HUMAN | (Q14439) | GPR176 | Putative/unclassified Class A GPCRs | *Homo sapiens* (Human) |
| GP179_HUMAN | (Q6PRD1) | GPR179 | Putative/unclassified Class C GPCRs | *Homo sapiens* (Human) |
| GPBAR_HUMAN | (Q8TDU6) | GPBAR1 | G-protein coupled bile acid receptor | *Homo sapiens* (Human) |
| GPC5B_HUMAN | (Q9NZH0) | GPRC5B | Orphan GPRC5 | *Homo sapiens* (Human) |
| GPC5C_HUMAN | (Q9NQ84) | GPRC5C | Orphan GPRC5 | *Homo sapiens* (Human) |
| GPC5D_HUMAN | (Q9NZD1) | GPRC5D | Orphan GPRC5 | *Homo sapiens* (Human) |
| GPC6A_HUMAN | (Q5T6X5) | GPRC6A | Orphan GPCR6 | *Homo sapiens* (Human) |
| GPR12_HUMAN | (P47775) | GPR12 | GPR | *Homo sapiens* (Human) |
| GPR15_HUMAN | (P49685) | GPR15 | GPR | *Homo sapiens* (Human) |
| GPR17_HUMAN | (Q13304) | GPR17 | GPR | *Homo sapiens* (Human) |
| GPR18_HUMAN | (Q14330) | GPR18 | Putative/unclassified Class A GPCRs | *Homo sapiens* (Human) |
| GPR19_HUMAN | (Q15760) | GPR19 | GPR | *Homo sapiens* (Human) |
| GPR1_HUMAN | (P46091) | GPR1 | GPR | *Homo sapiens* (Human) |
| GPR20_HUMAN | (Q99678) | GPR20 | GPR | *Homo sapiens* (Human) |
| GPR21_HUMAN | (Q99679) | GPR21 | GPR | *Homo sapiens* (Human) |
| GPR22_HUMAN | (Q99680) | GPR22 | GPR | *Homo sapiens* (Human) |
| GPR25_HUMAN | (O00155) | GPR25 | GPR | *Homo sapiens* (Human) |
| GPR26_HUMAN | (Q8NDV2) | GPR26 | Putative/unclassified Class A GPCRs | *Homo sapiens* (Human) |
| GPR27_HUMAN | (Q9NS67) | GPR27 | SREB | *Homo sapiens* (Human) |
| GPR31_HUMAN | (O00270) | GPR31 | GPR | *Homo sapiens* (Human) |
| GPR32_HUMAN | (O75388) | GPR32 | Chemokine receptor-like 1 | *Homo sapiens* (Human) |
| GPR33_HUMAN | (Q49SQ1) | GPR33 | Chemokine receptor-like 1 | *Homo sapiens* (Human) |
| GPR34_HUMAN | (Q9UPC5) | GPR34 | Putative/unclassified Class A GPCRs | *Homo sapiens* (Human) |
| GPR35_HUMAN | (Q9HC97) | GPR35 | Purinoceptor P2RY5,8,9,10 GPR35,92,174 | *Homo sapiens* (Human) |
| GPR37_HUMAN | (O15354) | GPR37 | GPR37/endothelin B-like | *Homo sapiens* (Human) |
| GPR39_HUMAN | (O43194) | GPR39 | Putative/unclassified Class A GPCRs | *Homo sapiens* (Human) |
| GPR3_HUMAN | (P46089) | GPR3 | GPR | *Homo sapiens* (Human) |
| GPR42_HUMAN | (O15529) | GPR42 | Free fatty acid receptor (GP40, GP41, GP43) | *Homo sapiens* (Human) |
| GPR44_HUMAN | (Q9Y5Y4) | GPR44 | Chemokine receptor-like 1 | *Homo sapiens* (Human) |
| GPR45_HUMAN | (Q9Y5Y3) | GPR45 | GPR45 like | *Homo sapiens* (Human) |
| GPR4_HUMAN | (P46093) | GPR4 | GPR | *Homo sapiens* (Human) |
| GPR52_HUMAN | (Q9Y2T5) | GPR52 | GPR | *Homo sapiens* (Human) |
| GPR55_HUMAN | (Q9Y2T6) | GPR55 | Putative/unclassified Class A GPCRs | *Homo sapiens* (Human) |
| GPR56_HUMAN | (Q9Y653) | GPR56 | Putative/unclassified Class B GPCRs | *Homo sapiens* (Human) |
| GPR61_HUMAN | (Q9BZJ8) | GPR61 | Putative/unclassified Class A GPCRs | *Homo sapiens* (Human) |
| GPR62_HUMAN | (Q9BZJ7) | GPR62 | Putative/unclassified Class A GPCRs | *Homo sapiens* (Human) |
| GPR63_HUMAN | (Q9BZJ6) | GPR63 | GPR45 like | *Homo sapiens* (Human) |
| GPR64_HUMAN | (Q8IZP9) | GPR64 | Putative/unclassified Class B GPCRs | *Homo sapiens* (Human) |
| GPR6_HUMAN | (P46095) | GPR6 | GPR | *Homo sapiens* (Human) |
| GPR75_HUMAN | (O95800) | GPR75 | Putative/unclassified Class A GPCRs | *Homo sapiens* (Human) |
| GPR78_HUMAN | (Q96P69) | GPR78 | Putative/unclassified Class A GPCRs | *Homo sapiens* (Human) |
| GPR81_HUMAN | (Q9BXC0) | GPR81 | Putative/unclassified Class A GPCRs | *Homo sapiens* (Human) |
| GPR82_HUMAN | (Q96P67) | GPR82 | Putative/unclassified Class A GPCRs | *Homo sapiens* (Human) |
| GPR83_HUMAN | (Q9NYM4) | GPR83 | Neuropeptide Y other | *Homo sapiens* (Human) |
| GPR84_HUMAN | (Q9NQS5) | GPR84 | Putative/unclassified Class A GPCRs | *Homo sapiens* (Human) |
| GPR85_HUMAN | (P60893) | GPR85 | SREB | *Homo sapiens* (Human) |
| GPR87_HUMAN | (Q9BY21) | GPR87 | Purinoceptor P2RY12-14 GPR87 (UDP-Glucose) | *Homo sapiens* (Human) |
| GPR88_HUMAN | (Q9GZN0) | GPR88 | Putative/unclassified Class A GPCRs | *Homo sapiens* (Human) |
| GPR92_HUMAN | (Q9H1C0) | GPR92 | Purinoceptor P2RY5,8,9,10 GPR35,92,174 | *Homo sapiens* (Human) |
| GPR97_HUMAN | (Q86Y34) | GPR97 | Putative/unclassified Class B GPCRs | *Homo sapiens* (Human) |
| GRPR_HUMAN | (P30550) | GRPR | Bombesin | *Homo sapiens* (Human) |
| HRH1_HUMAN | (P35367) | HRH1 | Histamine type 1 | *Homo sapiens* (Human) |
| HRH2_HUMAN | (P25021) | HRH2 | Histamine type 2 | *Homo sapiens* (Human) |
| HRH3_HUMAN | (Q9Y5N1) | HRH3 | Histamine type 3 | *Homo sapiens* (Human) |
| HRH4_HUMAN | (Q9H3N8) | HRH4 | Histamine type 4 | *Homo sapiens* (Human) |
| KISSR_HUMAN | (Q969F8) | KISS1R | Kiss receptor (GPR54) | *Homo sapiens* (Human) |
| LGR4_HUMAN | (Q9BXB1) | LGR4 | LGR like (hormone receptors) | *Homo sapiens* (Human) |
| LGR5_HUMAN | (O75473) | LGR5 | LGR like (hormone receptors) | *Homo sapiens* (Human) |
| LGR6_HUMAN | (Q9HBX8) | LGR6 | LGR like (hormone receptors) | *Homo sapiens* (Human) |
| LGR8_HUMAN | (Q8WXD0) | LGR8 | LGR like (hormone receptors) | *Homo sapiens* (Human) |
| LPHN1_HUMAN | (O94910) | LPHN1 | Latrophilin type 1 | *Homo sapiens* (Human) |
| LPHN2_HUMAN | (O95490) | LPHN2 | Latrophilin type 2 | *Homo sapiens* (Human) |
| LPHN3_HUMAN | (Q9HAR2) | LPHN3 | Latrophilin type 3 | *Homo sapiens* (Human) |
| LSHR_HUMAN | (P22888) | LHCGR | Lutropin-choriogonadotropic hormone | *Homo sapiens* (Human) |
| LT4R1_HUMAN | (Q15722) | LTB4R | Leukotriene B4 receptor BLT1 | *Homo sapiens* (Human) |
| LT4R2_HUMAN | (Q9NPC1) | LTB4R2 | Leukotriene B4 receptor BLT2 | *Homo sapiens* (Human) |
| MAS1L_HUMAN | (P35410) | MAS1L | Mas proto-oncogene & Mas-related (MRGs) | *Homo sapiens* (Human) |
| MASS1_HUMAN | (Q8WXG9) | MASS1 | Very large G-protein coupled receptor | *Homo sapiens* (Human) |
| MAS_HUMAN | (P04201) | MAS1 | Mas proto-oncogene & Mas-related (MRGs) | *Homo sapiens* (Human) |

TABLE D-continued

| non-limiting list human GPCRs ||||||
|---|---|---|---|---|---|
| MC3R_HUMAN | (P41968) | MC3R | Melanocortin hormone | Homo sapiens (Human) |
| MC4R_HUMAN | (P32245) | MC4R | Melanocortin hormone | Homo sapiens (Human) |
| MC5R_HUMAN | (P33032) | MC5R | Melanocortin hormone | Homo sapiens (Human) |
| MCHR1_HUMAN | (Q99705) | MCHR1 | Melanin-concentrating hormone receptors | Homo sapiens (Human) |
| MCHR2_HUMAN | (Q969V1) | MCHR2 | Melanin-concentrating hormone receptors | Homo sapiens (Human) |
| MGR1_HUMAN | (Q13255) | GRM1 | Metabotropic glutamate group I | Homo sapiens (Human) |
| MGR2_HUMAN | (Q14416) | GRM2 | Metabotropic glutamate group II | Homo sapiens (Human) |
| MGR3_HUMAN | (Q14832) | GRM3 | Metabotropic glutamate group II | Homo sapiens (Human) |
| MGR4_HUMAN | (Q14833) | GRM4 | Metabotropic glutamate group III | Homo sapiens (Human) |
| MGR5_HUMAN | (P41594) | GRM5 | Metabotropic glutamate group I | Homo sapiens (Human) |
| MGR6_HUMAN | (O15303) | GRM6 | Metabotropic glutamate group III | Homo sapiens (Human) |
| MGR7_HUMAN | (Q14831) | GRM7 | Metabotropic glutamate group III | Homo sapiens (Human) |
| MGR8_HUMAN | (O00222) | GRM8 | Metabotropic glutamate group III | Homo sapiens (Human) |
| MRGRD_HUMAN | (Q8TDS7) | MRGPRD | Mas proto-oncogene & Mas-related (MRGs) | Homo sapiens (Human) |
| MRGRE_HUMAN | (Q86SM8) | MRGPRE | fragments | Homo sapiens (Human) |
| MRGRF_HUMAN | (Q96AM1) | MRGPRF | Putative/unclassified Class A GPCRs | Homo sapiens (Human) |
| MRGRG_HUMAN | (Q86SM5) | MRGPRG | fragments | Homo sapiens (Human) |
| MRGX1_HUMAN | (Q96LB2) | MRGPRX1 | Mas proto-oncogene & Mas-related (MRGs) | Homo sapiens (Human) |
| MRGX2_HUMAN | (Q96LB1) | MRGPRX2 | Mas proto-oncogene & Mas-related (MRGs) | Homo sapiens (Human) |
| MRGX3_HUMAN | (Q96LB0) | MRGPRX3 | Mas proto-oncogene & Mas-related (MRGs) | Homo sapiens (Human) |
| MRGX4_HUMAN | (Q96LA9) | MRGPRX4 | Mas proto-oncogene & Mas-related (MRGs) | Homo sapiens (Human) |
| MSHR_HUMAN | (Q01726) | MC1R | Melanocyte stimulating hormone | Homo sapiens (Human) |
| MTLR_HUMAN | (O43193) | MLNR | Growth hormone secretagogue like | Homo sapiens (Human) |
| MTR1A_HUMAN | (P48039) | MTNR1A | Melatonin | Homo sapiens (Human) |
| MTR1B_HUMAN | (P49286) | MTNR1B | Melatonin | Homo sapiens (Human) |
| MTR1L_HUMAN | (Q13585) | GPR50 | Melatonin | Homo sapiens (Human) |
| NK1R_HUMAN | (P25103) | TACR1 | Substance P (NK1) | Homo sapiens (Human) |
| NK2R_HUMAN | (P21452) | TACR2 | Substance K (NK2) | Homo sapiens (Human) |
| NK3R_HUMAN | (P29371) | TACR3 | Neuromedin K (NK3) | Homo sapiens (Human) |
| NMBR_HUMAN | (P28336) | NMBR | Bombesin | Homo sapiens (Human) |
| NMUR1_HUMAN | (Q9HB89) | NMUR1 | Neuromedin U | Homo sapiens (Human) |
| NMUR2_HUMAN | (Q9GZQ4) | NMUR2 | Neuromedin U | Homo sapiens (Human) |
| NPBW1_HUMAN | (P48145) | NPBWR1 | GPR | Homo sapiens (Human) |
| NPBW2_HUMAN | (P48146) | NPBWR2 | GPR | Homo sapiens (Human) |
| NPFF1_HUMAN | (Q9GZQ6) | NPFFR1 | Neuropeptide FF | Homo sapiens (Human) |
| NPFF2_HUMAN | (Q9Y5X5) | NPFFR2 | Neuropeptide FF | Homo sapiens (Human) |
| NPY1R_HUMAN | (P25929) | NPY1R | Neuropeptide Y type 1 | Homo sapiens (Human) |
| NPY2R_HUMAN | (P49146) | NPY2R | Neuropeptide Y type 2 | Homo sapiens (Human) |
| NPY4R_HUMAN | (P50391) | PPYR1 | Neuropeptide Y type 4 | Homo sapiens (Human) |
| NPY5R_HUMAN | (Q15761) | NPY5R | Neuropeptide Y type 5 | Homo sapiens (Human) |
| NTR1_HUMAN | (P30989) | NTSR1 | Neurotensin | Homo sapiens (Human) |
| NTR2_HUMAN | (O95665) | NTSR2 | Neurotensin | Homo sapiens (Human) |
| O00325_HUMAN | (O00325) | PTGER3 | Prostaglandin E2 subtype EP3 | Homo sapiens (Human) |
| O00421_HUMAN | (O00421) | ccr6 | C-C Chemokine other | Homo sapiens (Human) |
| O10A1_HUMAN | (O95223) | OR10A1 | fragments | Homo sapiens (Human) |
| O10A3_HUMAN | (P58181) | OR10A3 | Olfactory II fam 10/MOR263-269 | Homo sapiens (Human) |
| O10A4_HUMAN | (Q9H209) | OR10A4 | Olfactory II fam 10/MOR263-269 | Homo sapiens (Human) |
| O10A5_HUMAN | (Q9H207) | OR10A5 | Olfactory II fam 10/MOR263-269 | Homo sapiens (Human) |
| O10A6_HUMAN | (Q8NH74) | OR10A6 | Olfactory II fam 10/MOR263-269 | Homo sapiens (Human) |
| O10A7_HUMAN | (Q8NGE5) | OR10A7 | Olfactory II fam 10/MOR263-269 | Homo sapiens (Human) |
| O10AD_HUMAN | (Q8NGE0) | OR10AD1 | Olfactory II fam 10/MOR263-269 | Homo sapiens (Human) |
| O10AG_HUMAN | (Q8NH19) | OR10AG1 | Olfactory II fam 10/MOR263-269 | Homo sapiens (Human) |
| O10C1_HUMAN | (Q96KK4) | OR10C1 | Olfactory II fam 10/MOR263-269 | Homo sapiens (Human) |
| O10D4_HUMAN | (Q8NGN7) | OR10D4 | Olfactory II fam 10/MOR263-269 | Homo sapiens (Human) |
| O10G2_HUMAN | (Q8NGC3) | OR10G2 | Olfactory II fam 10/MOR263-269 | Homo sapiens (Human) |
| O10G3_HUMAN | (Q8NGC4) | OR10G3 | Olfactory II fam 10/MOR263-269 | Homo sapiens (Human) |
| O10G4_HUMAN | (Q8NGN3) | OR10G4 | Olfactory II fam 10/MOR263-269 | Homo sapiens (Human) |
| O10G6_HUMAN | (Q8NH81) | OR10G6 | Olfactory II fam 10/MOR263-269 | Homo sapiens (Human) |
| O10G7_HUMAN | (Q8NGN6) | OR10G7 | Olfactory II fam 10/MOR263-269 | Homo sapiens (Human) |
| O10G8_HUMAN | (Q8NGN5) | OR10G8 | Olfactory II fam 10/MOR263-269 | Homo sapiens (Human) |
| O10G9_HUMAN | (Q8NGN4) | OR10G9 | Olfactory II fam 10/MOR263-269 | Homo sapiens (Human) |
| O10H1_HUMAN | (Q9Y4A9) | OR10H1 | Olfactory II fam 10/MOR263-269 | Homo sapiens (Human) |
| O10H2_HUMAN | (O60403) | OR10H2 | Olfactory II fam 10/MOR263-269 | Homo sapiens (Human) |
| O10H3_HUMAN | (O60404) | OR10H3 | Olfactory II fam 10/MOR263-269 | Homo sapiens (Human) |
| O10H4_HUMAN | (Q8NGA5) | OR10H4 | Olfactory II fam 10/MOR263-269 | Homo sapiens (Human) |
| O10H5_HUMAN | (Q8NGA6) | OR10H5 | Olfactory II fam 10/MOR263-269 | Homo sapiens (Human) |
| O10J1_HUMAN | (P30954) | OR10J1 | Olfactory II fam 10/MOR263-269 | Homo sapiens (Human) |
| O10J3_HUMAN | (Q5JRS4) | OR10J3 | Olfactory II fam 10/MOR263-269 | Homo sapiens (Human) |
| O10J5_HUMAN | (Q8NHC4) | OR10J5 | Olfactory II fam 10/MOR263-269 | Homo sapiens (Human) |
| O10J6_HUMAN | (Q8NGY7) | OR10J6 | Olfactory II fam 10/MOR263-269 | Homo sapiens (Human) |
| O10K1_HUMAN | (Q8NGX5) | OR10K1 | Olfactory II fam 10/MOR263-269 | Homo sapiens (Human) |

TABLE D-continued non-limiting list human GPCRs

| | | | | |
|---|---|---|---|---|
| O10K2_HUMAN | (Q6IF99) | OR10K2 | Olfactory II fam 10/MOR263-269 | *Homo sapiens* (Human) |
| O10P1_HUMAN | (Q8NGE3) | OR10P1 | Olfactory II fam 10/MOR263-269 | *Homo sapiens* (Human) |
| O10Q1_HUMAN | (Q8NGQ4) | OR10Q1 | Olfactory II fam 10/MOR263-269 | *Homo sapiens* (Human) |
| O10R2_HUMAN | (Q8NGX6) | OR10R2 | Olfactory II fam 10/MOR263-269 | *Homo sapiens* (Human) |
| O10S1_HUMAN | (Q8NGN2) | OR10S1 | Olfactory II fam 10/MOR263-269 | *Homo sapiens* (Human) |
| O10T2_HUMAN | (Q8NGX3) | OR10T2 | Olfactory II fam 10/MOR263-269 | *Homo sapiens* (Human) |
| O10V1_HUMAN | (Q8NGI7) | OR10V1 | Olfactory II fam 10/MOR263-269 | *Homo sapiens* (Human) |
| O10W1_HUMAN | (Q8NGF6) | OR10W1 | Olfactory II fam 10/MOR263-269 | *Homo sapiens* (Human) |
| O10X1_HUMAN | (Q8NGY0) | OR10X1 | Olfactory II fam 10/MOR263-269 | *Homo sapiens* (Human) |
| O10Z1_HUMAN | (Q8NGY1) | OR10Z1 | Olfactory II fam 10/MOR263-269 | *Homo sapiens* (Human) |
| O11A1_HUMAN | (Q9GZK7) | OR11A1 | Olfactory II fam 11/MOR106,121-122 | *Homo sapiens* (Human) |
| O11G2_HUMAN | (Q8NGC1) | OR11G2 | Olfactory II fam 11/MOR106,121-122 | *Homo sapiens* (Human) |
| O11H1_HUMAN | (Q8NG94) | OR11H1 | Olfactory II fam 11/MOR106,121-122 | *Homo sapiens* (Human) |
| O11H4_HUMAN | (Q8NGC9) | OR11H4 | Olfactory II fam 11/MOR106,121-122 | *Homo sapiens* (Human) |
| O11H6_HUMAN | (Q8NGC7) | OR11H6 | Olfactory II fam 11/MOR106,121-122 | *Homo sapiens* (Human) |
| O11L1_HUMAN | (Q8NGX0) | OR11L1 | Olfactory II fam 11/MOR106,121-122 | *Homo sapiens* (Human) |
| O12D2_HUMAN | (P58182) | OR12D2 | Olfactory II fam 12/MOR250 | *Homo sapiens* (Human) |
| O12D3_HUMAN | (Q9UGF7) | OR12D3 | Olfactory II fam 12/MOR250 | *Homo sapiens* (Human) |
| O13A1_HUMAN | (Q8NGR1) | OR13A1 | Olfactory II fam 13/MOR253 | *Homo sapiens* (Human) |
| O13C2_HUMAN | (Q8NGS9) | OR13C2 | Olfactory II fam 13/MOR253 | *Homo sapiens* (Human) |
| O13C3_HUMAN | (Q8NGS6) | OR13C3 | Olfactory II fam 13/MOR253 | *Homo sapiens* (Human) |
| O13C4_HUMAN | (Q8NGS5) | OR13C4 | Olfactory II fam 13/MOR253 | *Homo sapiens* (Human) |
| O13C5_HUMAN | (Q8NGS8) | OR13C5 | Olfactory II fam 13/MOR253 | *Homo sapiens* (Human) |
| O13C8_HUMAN | (Q8NGS7) | OR13C8 | Olfactory II fam 13/MOR253 | *Homo sapiens* (Human) |
| O13C9_HUMAN | (Q8NGT0) | OR13C9 | Olfactory II fam 13/MOR253 | *Homo sapiens* (Human) |
| O13D1_HUMAN | (Q8NGV5) | OR13D1 | Olfactory II fam 13/MOR253 | *Homo sapiens* (Human) |
| O13F1_HUMAN | (Q8NGS4) | OR13F1 | Olfactory II fam 13/MOR253 | *Homo sapiens* (Human) |
| O13G1_HUMAN | (Q8NGZ3) | OR13G1 | Olfactory II fam 13/MOR253 | *Homo sapiens* (Human) |
| O13H1_HUMAN | (Q8NG92) | OR13H1 | Olfactory II fam 13/MOR253 | *Homo sapiens* (Human) |
| O13J1_HUMAN | (Q8NGT2) | OR13J1 | Olfactory II fam 13/MOR253 | *Homo sapiens* (Human) |
| O14694_HUMAN | (O14694) | CCR5 | fragments | *Homo sapiens* (Human) |
| O2A12_HUMAN | (Q8NGT7) | OR2A12 | Olfactory II fam 2/MOR256-262,270-285 | *Homo sapiens* (Human) |
| O2A14_HUMAN | (Q96R47) | OR2A14 | Olfactory II fam 2/MOR256-262,270-285 | *Homo sapiens* (Human) |
| O2A42_HUMAN | (Q8NGT9) | OR2A42 | Olfactory II fam 2/MOR256-262,270-285 | *Homo sapiens* (Human) |
| O2AE1_HUMAN | (Q8NHA4) | OR2AE1 | Olfactory II fam 2/MOR256-262,270-285 | *Homo sapiens* (Human) |
| O2AG1_HUMAN | (Q9H205) | OR2AG1 | Olfactory II fam 2/MOR256-262,270-285 | *Homo sapiens* (Human) |
| O2AJ1_HUMAN | (Q8NGZ0) | OR2AJ1 | Olfactory II fam 2/MOR256-262,270-285 | *Homo sapiens* (Human) |
| O2AK2_HUMAN | (Q8NG84) | OR2AK2 | Olfactory II fam 2/MOR256-262,270-285 | *Homo sapiens* (Human) |
| O2AP1_HUMAN | (Q8NGE2) | OR2AP1 | Olfactory II fam 6/MOR103-105,107-119 | *Homo sapiens* (Human) |
| O2T10_HUMAN | (Q8NGZ9) | OR2T10 | Olfactory II fam 2/MOR256-262,270-285 | *Homo sapiens* (Human) |
| O2T11_HUMAN | (Q8NH01) | OR2T11 | Olfactory II fam 2/MOR256-262,270-285 | *Homo sapiens* (Human) |
| O2T12_HUMAN | (Q8NG77) | OR2T12 | Olfactory II fam 2/MOR256-262,270-285 | *Homo sapiens* (Human) |
| O2T27_HUMAN | (Q8NH04) | OR2T27 | Olfactory II fam 2/MOR256-262,270-285 | *Homo sapiens* (Human) |
| O2T29_HUMAN | (Q8NH02) | OR2T29 | Olfactory II fam 2/MOR256-262,270-285 | *Homo sapiens* (Human) |
| O2T33_HUMAN | (Q8NG76) | OR2T33 | Olfactory II fam 2/MOR256-262,270-285 | *Homo sapiens* (Human) |
| O2T34_HUMAN | (Q8NGX1) | OR2T34 | Olfactory II fam 2/MOR256-262,270-285 | *Homo sapiens* (Human) |
| O2T35_HUMAN | (Q8NGX2) | OR2T35 | Olfactory II fam 2/MOR256-262,270-285 | *Homo sapiens* (Human) |
| O43192_HUMAN | (O43192) | | Vasopressin type 2 | *Homo sapiens* (Human) |
| O43200_HUMAN | (O43200) | TSHR | fragments | *Homo sapiens* (Human) |
| O43624_HUMAN | (O43624) | OLFR 42A | fragments | *Homo sapiens* (Human) |
| O43625_HUMAN | (O43625) | OLFR 42A | fragments | *Homo sapiens* (Human) |
| O43626_HUMAN | (O43626) | OLFR 42B | fragments | *Homo sapiens* (Human) |
| O43627_HUMAN | (O43627) | OR2H5P | fragments | *Homo sapiens* (Human) |
| O43789_HUMAN | (O43789) | | fragments | *Homo sapiens* (Human) |
| O43871_HUMAN | (O43871) | OR16-36 | fragments | *Homo sapiens* (Human) |
| O43872_HUMAN | (O43872) | OR16-37 | fragments | *Homo sapiens* (Human) |
| O43873_HUMAN | (O43873) | OR16-88 | fragments | *Homo sapiens* (Human) |
| O43874_HUMAN | (O43874) | OR16-89 | fragments | *Homo sapiens* (Human) |
| O43875_HUMAN | (O43875) | OR16-90 | fragments | *Homo sapiens* (Human) |
| O43876_HUMAN | (O43876) | OR17-130 | fragments | *Homo sapiens* (Human) |
| O43878_HUMAN | (O43878) | OR17-137 | fragments | *Homo sapiens* (Human) |
| O43879_HUMAN | (O43879) | OR17-15 | fragments | *Homo sapiens* (Human) |

TABLE D-continued non-limiting list human GPCRs

| | | | | |
|---|---|---|---|---|
| O43880_HUMAN | (O43880) | OR17-16 | fragments | *Homo sapiens* (Human) |
| O43886_HUMAN | (O43886) | OR7-139 | fragments | *Homo sapiens* (Human) |
| O43887_HUMAN | (O43887) | OR7-140 | fragments | *Homo sapiens* (Human) |
| O43898_HUMAN | (O43898) | | GPR45 like | *Homo sapiens* (Human) |
| O4A15_HUMAN | (Q8NGL6) | OR4A15 | Olfactory II fam 4/MOR225-248 | *Homo sapiens* (Human) |
| O4A16_HUMAN | (Q8NH70) | OR4A16 | Olfactory II fam 4/MOR225-248 | *Homo sapiens* (Human) |
| O4A47_HUMAN | (Q6IF82) | OR4A47 | Olfactory II fam 4/MOR225-248 | *Homo sapiens* (Human) |
| O4F15_HUMAN | (Q8NGB8) | OR4F15 | Olfactory II fam 4/MOR225-248 | *Homo sapiens* (Human) |
| O4F17_HUMAN | (Q8NGA8) | OR4F17 | Olfactory II fam 4/MOR225-248 | *Homo sapiens* (Human) |
| O4F29_HUMAN | (Q6IEY1) | OR4F29 | Olfactory II fam 4/MOR225-248 | *Homo sapiens* (Human) |
| O51A2_HUMAN | (Q8NGJ7) | OR51A2 | Olfactory I fam 51-52/MOR1-42 | *Homo sapiens* (Human) |
| O51A4_HUMAN | (Q8NGJ6) | OR51A4 | Olfactory I fam 51-52/MOR1-42 | *Homo sapiens* (Human) |
| O51A7_HUMAN | (Q8NH64) | OR51A7 | Olfactory I fam 51-52/MOR1-42 | *Homo sapiens* (Human) |
| O51B2_HUMAN | (Q9Y5P1) | OR51B2 | Olfactory I fam 51-52/MOR1-42 | *Homo sapiens* (Human) |
| O51B4_HUMAN | (Q9Y5P0) | OR51B4 | Olfactory I fam 51-52/MOR1-42 | *Homo sapiens* (Human) |
| O51B5_HUMAN | (Q9H339) | OR51B5 | Olfactory I fam 51-52/MOR1-42 | *Homo sapiens* (Human) |
| O51B6_HUMAN | (Q9H340) | OR51B6 | Olfactory I fam 51-52/MOR1-42 | *Homo sapiens* (Human) |
| O51D1_HUMAN | (Q8NGF3) | OR51D1 | Olfactory I fam 51-52/MOR1-42 | *Homo sapiens* (Human) |
| O51E1_HUMAN | (Q8TCB6) | OR51E1 | Olfactory I fam 51-52/MOR1-42 | *Homo sapiens* (Human) |
| O51E2_HUMAN | (Q9H255) | OR51E2 | Olfactory I fam 51-52/MOR1-42 | *Homo sapiens* (Human) |
| O51F1_HUMAN | (Q8NH61) | OR51F2 | Olfactory I fam 51-52/MOR1-42 | *Homo sapiens* (Human) |
| O51G1_HUMAN | (Q8NGK1) | OR51G1 | Olfactory I fam 51-52/MOR1-42 | *Homo sapiens* (Human) |
| O51G2_HUMAN | (Q8NGK0) | OR51G2 | Olfactory I fam 51-52/MOR1-42 | *Homo sapiens* (Human) |
| O51H1_HUMAN | (Q8NH63) | OR51H1 | Olfactory I fam 51-52/MOR1-42 | *Homo sapiens* (Human) |
| O51I1_HUMAN | (Q9H343) | OR51I1 | Olfactory I fam 51-52/MOR1-42 | *Homo sapiens* (Human) |
| O51I2_HUMAN | (Q9H344) | OR51I2 | Olfactory I fam 51-52/MOR1-42 | *Homo sapiens* (Human) |
| O51L1_HUMAN | (Q8NGJ5) | OR51L1 | Olfactory I fam 51-52/MOR1-42 | *Homo sapiens* (Human) |
| O51M1_HUMAN | (Q9H341) | OR51M1 | Olfactory I fam 51-52/MOR1-42 | *Homo sapiens* (Human) |
| O51Q1_HUMAN | (Q8NH59) | OR51Q1 | Olfactory I fam 51-52/MOR1-42 | *Homo sapiens* (Human) |
| O51S1_HUMAN | (Q8NGJ8) | OR51S1 | Olfactory I fam 51-52/MOR1-42 | *Homo sapiens* (Human) |
| O51T1_HUMAN | (Q8NGJ9) | OR51T1 | Olfactory I fam 51-52/MOR1-42 | *Homo sapiens* (Human) |
| O51V1_HUMAN | (Q9H2C8) | OR51V1 | Olfactory I fam 51-52/MOR1-42 | *Homo sapiens* (Human) |
| O52A1_HUMAN | (Q9UKL2) | OR52A1 | Olfactory I fam 51-52/MOR1-42 | *Homo sapiens* (Human) |
| O52A5_HUMAN | (Q9H2C5) | OR52A5 | Olfactory I fam 51-52/MOR1-42 | *Homo sapiens* (Human) |
| O52B2_HUMAN | (Q96RD2) | OR52B2 | Olfactory I fam 51-52/MOR1-42 | *Homo sapiens* (Human) |
| O52B4_HUMAN | (Q8NGK2) | OR52B4 | Olfactory I fam 51-52/MOR1-42 | *Homo sapiens* (Human) |
| O52B6_HUMAN | (Q8NGF0) | OR52B6 | Olfactory I fam 51-52/MOR1-42 | *Homo sapiens* (Human) |
| O52D1_HUMAN | (Q9H346) | OR52D1 | Olfactory I fam 51-52/MOR1-42 | *Homo sapiens* (Human) |
| O52E1_HUMAN | (Q8NGJ3) | OR52E1 | Olfactory I fam 51-52/MOR1-42 | *Homo sapiens* (Human) |
| O52E2_HUMAN | (Q8NGJ4) | OR52E2 | Olfactory I fam 51-52/MOR1-42 | *Homo sapiens* (Human) |
| O52E4_HUMAN | (Q8NGH9) | OR52E4 | Olfactory I fam 51-52/MOR1-42 | *Homo sapiens* (Human) |
| O52E5_HUMAN | (Q8NH55) | OR52E5 | Olfactory I fam 51-52/MOR1-42 | *Homo sapiens* (Human) |
| O52E6_HUMAN | (Q96RD3) | OR52E6 | Olfactory I fam 51-52/MOR1-42 | *Homo sapiens* (Human) |
| O52E8_HUMAN | (Q6IFG1) | OR52E8 | Olfactory I fam 51-52/MOR1-42 | *Homo sapiens* (Human) |
| O52H1_HUMAN | (Q8NGJ2) | OR52H1 | Olfactory I fam 51-52/MOR1-42 | *Homo sapiens* (Human) |
| O52I1_HUMAN | (Q8NGK6) | OR52I1 | Olfactory I fam 51-52/MOR1-42 | *Homo sapiens* (Human) |
| O52I2_HUMAN | (Q8NH67) | OR52I2 | Olfactory I fam 51-52/MOR1-42 | *Homo sapiens* (Human) |
| O52J3_HUMAN | (Q8NH60) | OR52J3 | Olfactory I fam 51-52/MOR1-42 | *Homo sapiens* (Human) |
| O52K1_HUMAN | (Q8NGK4) | OR52K1 | Olfactory I fam 51-52/MOR1-42 | *Homo sapiens* (Human) |
| O52K2_HUMAN | (Q8NGK3) | OR52K2 | Olfactory I fam 51-52/MOR1-42 | *Homo sapiens* (Human) |
| O52L1_HUMAN | (Q8NGH7) | OR52L1 | Olfactory I fam 51-52/MOR1-42 | *Homo sapiens* (Human) |
| O52L2_HUMAN | (Q8NGH6) | OR52L2 | Olfactory I fam 51-52/MOR1-42 | *Homo sapiens* (Human) |
| O52M1_HUMAN | (Q8NGK5) | OR52M1 | Olfactory I fam 51-52/MOR1-42 | *Homo sapiens* (Human) |
| O52N1_HUMAN | (Q8NH53) | OR52N1 | Olfactory I fam 51-52/MOR1-42 | *Homo sapiens* (Human) |
| O52N2_HUMAN | (Q8NGI0) | OR52N2 | Olfactory I fam 51-52/MOR1-42 | *Homo sapiens* (Human) |
| O52N4_HUMAN | (Q8NGI2) | OR52N4 | Olfactory I fam 51-52/MOR1-42 | *Homo sapiens* (Human) |
| O52N5_HUMAN | (Q8NH56) | OR52N5 | Olfactory I fam 51-52/MOR1-42 | *Homo sapiens* (Human) |
| O52P1_HUMAN | (Q8NH57) | OR52P1 | Olfactory I fam 51-52/MOR1-42 | *Homo sapiens* (Human) |
| O52R1_HUMAN | (Q8NGF1) | OR52R1 | Olfactory I fam 51-52/MOR1-42 | *Homo sapiens* (Human) |
| O52W1_HUMAN | (Q6IF63) | OR52W1 | Olfactory I fam 51-52/MOR1-42 | *Homo sapiens* (Human) |
| O56A1_HUMAN | (Q8NGH5) | OR56A1 | Olfactory I fam 51-52/MOR1-42 | *Homo sapiens* (Human) |
| O56A3_HUMAN | (Q8NH54) | OR56A3 | Olfactory I fam 51-52/MOR1-42 | *Homo sapiens* (Human) |
| O56A4_HUMAN | (Q8NGH8) | OR56A4 | Olfactory I fam 51-52/MOR1-42 | *Homo sapiens* (Human) |
| O56B1_HUMAN | (Q8NGI3) | OR56B1 | Olfactory I fam 51-52/MOR1-42 | *Homo sapiens* (Human) |
| O56B2_HUMAN | (Q8NGI1) | OR56B2P | Olfactory I fam 51-52/MOR1-42 | *Homo sapiens* (Human) |
| O56B4_HUMAN | (Q8NH76) | OR56B4 | Olfactory I fam 51-52/MOR1-42 | *Homo sapiens* (Human) |
| O5AC2_HUMAN | (Q9NZP5) | OR5AC2 | Olfactory II fam 5/MOR172-224,249,254 | *Homo sapiens* (Human) |
| O5AK2_HUMAN | (Q8NH90) | OR5AK2 | Olfactory II fam 5/MOR172-224,249,254 | *Homo sapiens* (Human) |
| O5AK3_HUMAN | (Q8NH89) | OR5AK3 | Olfactory II fam 5/MOR172-224,249,254 | *Homo sapiens* (Human) |
| O5AN1_HUMAN | (Q8NGI8) | OR5AN1 | Olfactory II fam 5/MOR172-224,249,254 | *Homo sapiens* (Human) |
| O5AP2_HUMAN | (Q8NGF4) | OR5AP2 | Olfactory II fam 5/MOR172-224,249,254 | *Homo sapiens* (Human) |
| O5AR1_HUMAN | (Q8NGP9) | OR5AR1 | Olfactory II fam 5/MOR172-224,249,254 | *Homo sapiens* (Human) |

TABLE D-continued non-limiting list human GPCRs

| | | | | |
|---|---|---|---|---|
| O5AS1_HUMAN | (Q8N127) | OR5AS1 | Olfactory II fam 5/MOR172-224,249,254 | *Homo sapiens* (Human) |
| O5AT1_HUMAN | (Q8NHC5) | OR5AT1 | Olfactory II fam 5/MOR172-224,249,254 | *Homo sapiens* (Human) |
| O5AU1_HUMAN | (Q8NGC0) | OR5AU1 | Olfactory II fam 5/MOR172-224,249,254 | *Homo sapiens* (Human) |
| O5AV1_HUMAN | (Q8NHC6) | OR5AV1P | Olfactory II fam 5/MOR172-224,249,254 | *Homo sapiens* (Human) |
| O5AY1_HUMAN | (Q8NGZ2) | OR5AY1 | Olfactory II fam 5/MOR172-224,249,254 | *Homo sapiens* (Human) |
| O5BF1_HUMAN | (Q8NHC7) | OR5BF1 | Olfactory II fam 5/MOR172-224,249,254 | *Homo sapiens* (Human) |
| O60411_HUMAN | (O60411) | | fragments | *Homo sapiens* (Human) |
| O75228_HUMAN | (O75228) | TBXA2R | Thromboxane | *Homo sapiens* (Human) |
| O75307_HUMAN | (O75307) | CCRL2 | C-C Chemokine other | *Homo sapiens* (Human) |
| O75824_HUMAN | (O75824) | CCKBR | fragments | *Homo sapiens* (Human) |
| O95220_HUMAN | (O95220) | OR5D3 | fragments | *Homo sapiens* (Human) |
| O95499_HUMAN | (O95499) | olfr89 | Olfactory II fam 2/MOR256-262,270-285 | *Homo sapiens* (Human) |
| O95950_HUMAN | (O95950) | | fragments | *Homo sapiens* (Human) |
| OPN3_HUMAN | (Q9H1Y3) | OPN3 | Rhodopsin Other | *Homo sapiens* (Human) |
| OPN4_HUMAN | (Q9UHM6) | OPN4 | Rhodopsin Other | *Homo sapiens* (Human) |
| OPN5_HUMAN | (Q6U736) | OPN5 | Rhodopsin Other | *Homo sapiens* (Human) |
| OPRD_HUMAN | (P41143) | OPRD1 | Opioid type D | *Homo sapiens* (Human) |
| OPRK_HUMAN | (P41145) | OPRK1 | Opioid type K | *Homo sapiens* (Human) |
| OPRM_HUMAN | (P35372) | OPRM1 | Opioid type M | *Homo sapiens* (Human) |
| OPRX_HUMAN | (P41146) | OPRL1 | Opioid type X | *Homo sapiens* (Human) |
| OPSB_HUMAN | (P03999) | OPN1SW | Rhodopsin Vertebrate type 3 | *Homo sapiens* (Human) |
| OPSD_HUMAN | (P08100) | RHO | Rhodopsin Vertebrate type 1 | *Homo sapiens* (Human) |
| OPSG_HUMAN | (P04001) | OPN1MW | Rhodopsin Vertebrate type 2 | *Homo sapiens* (Human) |
| OPSR_HUMAN | (P04000) | OPN1LW | Rhodopsin Vertebrate type 2 | *Homo sapiens* (Human) |
| OPSX_HUMAN | (O14718) | RRH | Rhodopsin Other | *Homo sapiens* (Human) |
| OR1A1_HUMAN | (Q9P1Q5) | OR1A1 | Olfactory II fam 1/MOR125-138,156 | *Homo sapiens* (Human) |
| OR1A2_HUMAN | (Q9Y585) | OR1A2 | Olfactory II fam 1/MOR125-138,156 | *Homo sapiens* (Human) |
| OR1B1_HUMAN | (Q8NGR6) | OR1B1 | Olfactory II fam 1/MOR125-138,156 | *Homo sapiens* (Human) |
| OR1C1_HUMAN | (Q15619) | OR1C1 | Olfactory II fam 1/MOR125-138,156 | *Homo sapiens* (Human) |
| OR1D2_HUMAN | (P34982) | OR1D2 | Olfactory II fam 1/MOR125-138,156 | *Homo sapiens* (Human) |
| OR1D4_HUMAN | (P47884) | OR1D4 | Olfactory II fam 1/MOR125-138,156 | *Homo sapiens* (Human) |
| OR1D5_HUMAN | (P58170) | OR1D5 | Olfactory II fam 1/MOR125-138,156 | *Homo sapiens* (Human) |
| OR1E1_HUMAN | (P30953) | OR1E1 | Olfactory II fam 1/MOR125-138,156 | *Homo sapiens* (Human) |
| OR1E2_HUMAN | (P47887) | OR1E2 | Olfactory II fam 1/MOR125-138,156 | *Homo sapiens* (Human) |
| OR1F1_HUMAN | (O43749) | OR1F1 | Olfactory II fam 1/MOR125-138,156 | *Homo sapiens* (Human) |
| OR1F2_HUMAN | (Q96R84) | OR1F2 | Olfactory II fam 1/MOR125-138,156 | *Homo sapiens* (Human) |
| OR1FC_HUMAN | (Q8NHA8) | OR1F12P | Olfactory II fam 1/MOR125-138,156 | *Homo sapiens* (Human) |
| OR1G1_HUMAN | (P47890) | OR1G1 | Olfactory II fam 1/MOR125-138,156 | *Homo sapiens* (Human) |
| OR1I1_HUMAN | (O60431) | OR1I1 | Olfactory II fam 1/MOR125-138,156 | *Homo sapiens* (Human) |
| OR1J1_HUMAN | (Q8NGS3) | OR1J1 | Olfactory II fam 1/MOR125-138,156 | *Homo sapiens* (Human) |
| OR1J2_HUMAN | (Q8NGS2) | OR1J2 | Olfactory II fam 1/MOR125-138,156 | *Homo sapiens* (Human) |
| OR1J4_HUMAN | (Q8NGS1) | OR1J4 | Olfactory II fam 1/MOR125-138,156 | *Homo sapiens* (Human) |
| OR1K1_HUMAN | (Q8NGR3) | OR1K1 | Olfactory II fam 1/MOR125-138,156 | *Homo sapiens* (Human) |
| OR1L1_HUMAN | (Q8NH94) | OR1L1 | Olfactory II fam 1/MOR125-138,156 | *Homo sapiens* (Human) |
| OR1L3_HUMAN | (Q8NH93) | OR1L3 | Olfactory II fam 1/MOR125-138,156 | *Homo sapiens* (Human) |
| OR1L4_HUMAN | (Q8NGR5) | OR1L4 | Olfactory II fam 1/MOR125-138,156 | *Homo sapiens* (Human) |
| OR1L6_HUMAN | (Q8NGR2) | OR1L6 | Olfactory II fam 1/MOR125-138,156 | *Homo sapiens* (Human) |
| OR1L8_HUMAN | (Q8NGR8) | OR1L8 | Olfactory II fam 1/MOR125-138,156 | *Homo sapiens* (Human) |
| OR1M1_HUMAN | (Q8NGA1) | OR1M1 | Olfactory II fam 1/MOR125-138,156 | *Homo sapiens* (Human) |
| OR1N1_HUMAN | (Q8NGS0) | OR1N1 | Olfactory II fam 1/MOR125-138,156 | *Homo sapiens* (Human) |
| OR1N2_HUMAN | (Q8NGR9) | OR1N2 | Olfactory II fam 1/MOR125-138,156 | *Homo sapiens* (Human) |
| OR1Q1_HUMAN | (Q15612) | OR1Q1 | Olfactory II fam 1/MOR125-138,156 | *Homo sapiens* (Human) |
| OR1S1_HUMAN | (Q8NH92) | OR1S1 | Olfactory II fam 1/MOR125-138,156 | *Homo sapiens* (Human) |
| OR1S2_HUMAN | (Q8NGQ3) | OR1S2 | Olfactory II fam 1/MOR125-138,156 | *Homo sapiens* (Human) |
| OR2A2_HUMAN | (Q6IF42) | OR2A2 | Olfactory II fam 2/MOR256-262,270-285 | *Homo sapiens* (Human) |
| OR2A4_HUMAN | (O95047) | OR2A4 | Olfactory II fam 2/MOR256-262,270-285 | *Homo sapiens* (Human) |
| OR2A5_HUMAN | (Q96R48) | OR2A5 | Olfactory II fam 2/MOR256-262,270-285 | *Homo sapiens* (Human) |
| OR2A7_HUMAN | (Q96R45) | OR2A7 | Olfactory II fam 2/MOR256-262,270-285 | *Homo sapiens* (Human) |
| OR2B2_HUMAN | (Q9GZK3) | OR2B2 | Olfactory II fam 2/MOR256-262,270-285 | *Homo sapiens* (Human) |
| OR2B3_HUMAN | (O76000) | OR2B3 | Olfactory II fam 2/MOR256-262,270-285 | *Homo sapiens* (Human) |
| OR2B6_HUMAN | (P58173) | OR2B6 | Olfactory II fam 2/MOR256-262,270-285 | *Homo sapiens* (Human) |
| OR2B8_HUMAN | (P59922) | OR2B8 | Olfactory II fam 2/MOR256-262,270-285 | *Homo sapiens* (Human) |
| OR2BB_HUMAN | (Q5JQS5) | OR2B11 | Olfactory II fam 2/MOR256-262,270-285 | *Homo sapiens* (Human) |
| OR2C1_HUMAN | (O95371) | OR2C1 | Olfactory II fam 2/MOR256-262,270-285 | *Homo sapiens* (Human) |
| OR2C3_HUMAN | (Q8N628) | OR2C3 | Olfactory II fam 2/MOR256-262,270-285 | *Homo sapiens* (Human) |
| OR2D2_HUMAN | (Q9H210) | OR2D2 | Olfactory II fam 2/MOR256-262,270-285 | *Homo sapiens* (Human) |

TABLE D-continued

| | | | non-limiting list human GPCRs | |
|---|---|---|---|---|
| OR2D3_HUMAN | (Q8NGH3) | OR2D3 | Olfactory II fam 2/MOR256-262,270-285 | *Homo sapiens* (Human) |
| OR2F1_HUMAN | (Q13607) | OR2F1 | Olfactory II fam 2/MOR256-262,270-285 | *Homo sapiens* (Human) |
| OR2F2_HUMAN | (O95006) | OR2F2 | Olfactory II fam 2/MOR256-262,270-285 | *Homo sapiens* (Human) |
| OR2G2_HUMAN | (Q8NGZ5) | OR2G2 | Olfactory II fam 2/MOR256-262,270-285 | *Homo sapiens* (Human) |
| OR2G3_HUMAN | (Q8NGZ4) | OR2G3 | Olfactory II fam 2/MOR256-262,270-285 | *Homo sapiens* (Human) |
| OR2G6_HUMAN | (Q5TZ20) | OR2G6 | Olfactory II fam 2/MOR256-262,270-285 | *Homo sapiens* (Human) |
| OR2H1_HUMAN | (Q9GZK4) | OR2H1 | Olfactory II fam 2/MOR256-262,270-285 | *Homo sapiens* (Human) |
| OR2H2_HUMAN | (O95918) | OR2H2 | Olfactory II fam 2/MOR256-262,270-285 | *Homo sapiens* (Human) |
| OR2I1_HUMAN | (Q8NGU4) | OR2I1P | Olfactory II fam 2/MOR256-262,270-285 | *Homo sapiens* (Human) |
| OR2J1_HUMAN | (Q9GZK6) | OR2J1 | Olfactory II fam 2/MOR256-262,270-285 | *Homo sapiens* (Human) |
| OR2J2_HUMAN | (O76002) | OR2J2 | Olfactory II fam 2/MOR256-262,270-285 | *Homo sapiens* (Human) |
| OR2J3_HUMAN | (O76001) | OR2J3 | Olfactory II fam 2/MOR256-262,270-285 | *Homo sapiens* (Human) |
| OR2K1_HUMAN | (Q8NGT1) | OR2K2 | Olfactory II fam 13/MOR253 | *Homo sapiens* (Human) |
| OR2L2_HUMAN | (Q8NH16) | OR2L2 | Olfactory II fam 2/MOR256-262,270-285 | *Homo sapiens* (Human) |
| OR2L3_HUMAN | (Q8NG85) | OR2L3 | Olfactory II fam 2/MOR256-262,270-285 | *Homo sapiens* (Human) |
| OR2L5_HUMAN | (Q8NG80) | OR2L5 | Olfactory II fam 2/MOR256-262,270-285 | *Homo sapiens* (Human) |
| OR2L8_HUMAN | (Q8NGY9) | OR2L8 | Olfactory II fam 2/MOR256-262,270-285 | *Homo sapiens* (Human) |
| OR2LD_HUMAN | (Q8N349) | OR2L13 | Olfactory II fam 2/MOR256-262,270-285 | *Homo sapiens* (Human) |
| OR2M2_HUMAN | (Q96R28) | OR2M2 | Olfactory II fam 2/MOR256-262,270-285 | *Homo sapiens* (Human) |
| OR2M3_HUMAN | (Q8NG83) | OR2M3 | Olfactory II fam 2/MOR256-262,270-285 | *Homo sapiens* (Human) |
| OR2M4_HUMAN | (Q96R27) | OR2M4 | Olfactory II fam 2/MOR256-262,270-285 | *Homo sapiens* (Human) |
| OR2M7_HUMAN | (Q8NG81) | OR2M7 | Olfactory II fam 2/MOR256-262,270-285 | *Homo sapiens* (Human) |
| OR2S1_HUMAN | (Q9NQN1) | OR2S2 | Olfactory II fam 13/MOR253 | *Homo sapiens* (Human) |
| OR2T1_HUMAN | (O43869) | OR2T1 | Olfactory II fam 2/MOR256-262,270-285 | *Homo sapiens* (Human) |
| OR2T2_HUMAN | (Q6IF00) | OR2T2 | Olfactory II fam 2/MOR256-262,270-285 | *Homo sapiens* (Human) |
| OR2T3_HUMAN | (Q8NH03) | OR2T3 | Olfactory II fam 2/MOR256-262,270-285 | *Homo sapiens* (Human) |
| OR2T4_HUMAN | (Q8NH00) | OR2T4 | Olfactory II fam 2/MOR256-262,270-285 | *Homo sapiens* (Human) |
| OR2T5_HUMAN | (Q6IEZ7) | OR2T5 | Olfactory II fam 2/MOR256-262,270-285 | *Homo sapiens* (Human) |
| OR2T6_HUMAN | (Q8NHC8) | OR2T6 | Olfactory II fam 2/MOR256-262,270-285 | *Homo sapiens* (Human) |
| OR2V2_HUMAN | (Q96R30) | OR2V2 | Olfactory II fam 2/MOR256-262,270-285 | *Homo sapiens* (Human) |
| OR2W1_HUMAN | (Q9Y3N9) | OR2W1 | Olfactory II fam 2/MOR256-262,270-285 | *Homo sapiens* (Human) |
| OR2W3_HUMAN | (Q7Z3T1) | OR2W3 | Olfactory II fam 2/MOR256-262,270-285 | *Homo sapiens* (Human) |
| OR2Y1_HUMAN | (Q8NGV0) | OR2Y1 | Olfactory II fam 2/MOR256-262,270-285 | *Homo sapiens* (Human) |
| OR2Z1_HUMAN | (Q8NG97) | OR2Z1 | Olfactory II fam 2/MOR256-262,270-285 | *Homo sapiens* (Human) |
| OR3A1_HUMAN | (P47881) | OR3A1 | Olfactory II fam 3/MOR255 | *Homo sapiens* (Human) |
| OR3A2_HUMAN | (P47893) | OR3A2 | Olfactory II fam 3/MOR255 | *Homo sapiens* (Human) |
| OR3A3_HUMAN | (P47888) | OR3A3 | Olfactory II fam 3/MOR255 | *Homo sapiens* (Human) |
| OR3A4_HUMAN | (P47883) | OR3A4 | Olfactory II fam 3/MOR255 | *Homo sapiens* (Human) |
| OR4A4_HUMAN | (Q8NGN8) | OR4A4 | Olfactory II fam 4/MOR225-248 | *Homo sapiens* (Human) |
| OR4A5_HUMAN | (Q8NH83) | OR4A5 | Olfactory II fam 4/MOR225-248 | *Homo sapiens* (Human) |
| OR4B1_HUMAN | (Q8NGF8) | OR4B1 | Olfactory II fam 4/MOR225-248 | *Homo sapiens* (Human) |
| OR4C3_HUMAN | (Q8NH37) | OR4C3 | Olfactory II fam 4/MOR225-248 | *Homo sapiens* (Human) |
| OR4C5_HUMAN | (Q8NGB2) | OR4C5 | Olfactory II fam 4/MOR225-248 | *Homo sapiens* (Human) |
| OR4C6_HUMAN | (Q8NH72) | OR4C6 | Olfactory II fam 4/MOR225-248 | *Homo sapiens* (Human) |
| OR4CB_HUMAN | (Q6IEV9) | OR4C11 | Olfactory II fam 4/MOR225-248 | *Homo sapiens* (Human) |
| OR4CC_HUMAN | (Q96R67) | OR4C12 | Olfactory II fam 4/MOR225-248 | *Homo sapiens* (Human) |
| OR4CD_HUMAN | (Q8NGP0) | OR4C13 | Olfactory II fam 4/MOR225-248 | *Homo sapiens* (Human) |
| OR4CF_HUMAN | (Q8NGM1) | OR4C15 | Olfactory II fam 4/MOR225-248 | *Homo sapiens* (Human) |
| OR4CG_HUMAN | (Q8NGL9) | OR4C16 | Olfactory II fam 4/MOR225-248 | *Homo sapiens* (Human) |
| OR4D1_HUMAN | (Q15615) | OR4D1 | Olfactory II fam 4/MOR225-248 | *Homo sapiens* (Human) |
| OR4D2_HUMAN | (P58180) | OR4D2 | Olfactory II fam 4/MOR225-248 | *Homo sapiens* (Human) |
| OR4D5_HUMAN | (Q8NGN0) | OR4D5 | Olfactory II fam 4/MOR225-248 | *Homo sapiens* (Human) |
| OR4D6_HUMAN | (Q8NGJ1) | OR4D6 | Olfactory II fam 4/MOR225-248 | *Homo sapiens* (Human) |
| OR4D9_HUMAN | (Q8NGE8) | OR4D9 | Olfactory II fam 4/MOR225-248 | *Homo sapiens* (Human) |
| OR4DA_HUMAN | (Q8NGI6) | OR4D10 | Olfactory II fam 4/MOR225-248 | *Homo sapiens* (Human) |

TABLE D-continued

| | | | non-limiting list human GPCRs | |
|---|---|---|---|---|
| OR4DB_HUMAN | (Q8NGI4) | OR4D11 | Olfactory II fam 4/MOR225-248 | *Homo sapiens* (Human) |
| OR4E2_HUMAN | (Q8NGC2) | OR4E2 | Olfactory II fam 4/MOR225-248 | *Homo sapiens* (Human) |
| OR4F3_HUMAN | (O95013) | OR4F3 | Olfactory II fam 4/MOR225-248 | *Homo sapiens* (Human) |
| OR4F4_HUMAN | (Q96R69) | OR4F4 | Olfactory II fam 4/MOR225-248 | *Homo sapiens* (Human) |
| OR4F5_HUMAN | (Q8NH21) | OR4F5 | Olfactory II fam 4/MOR225-248 | *Homo sapiens* (Human) |
| OR4F6_HUMAN | (Q8NGB9) | OR4F6 | Olfactory II fam 4/MOR225-248 | *Homo sapiens* (Human) |
| OR4K1_HUMAN | (Q8NGD4) | OR4K1 | Olfactory II fam 4/MOR225-248 | *Homo sapiens* (Human) |
| OR4K2_HUMAN | (Q8NGD2) | OR4K2 | Olfactory II fam 4/MOR225-248 | *Homo sapiens* (Human) |
| OR4K3_HUMAN | (Q96R72) | OR4K3 | Olfactory II fam 4/MOR225-248 | *Homo sapiens* (Human) |
| OR4K5_HUMAN | (Q8NGD3) | OR4K5 | Olfactory II fam 4/MOR225-248 | *Homo sapiens* (Human) |
| OR4KD_HUMAN | (Q8NH42) | OR4K13 | Olfactory II fam 4/MOR225-248 | *Homo sapiens* (Human) |
| OR4KE_HUMAN | (Q8NGD5) | OR4K14 | Olfactory II fam 4/MOR225-248 | *Homo sapiens* (Human) |
| OR4KF_HUMAN | (Q8NH41) | OR4K15 | Olfactory II fam 4/MOR225-248 | *Homo sapiens* (Human) |
| OR4KH_HUMAN | (Q8NGC6) | OR4K17 | Olfactory II fam 4/MOR225-248 | *Homo sapiens* (Human) |
| OR4L1_HUMAN | (Q8NH43) | OR4L1 | Olfactory II fam 4/MOR225-248 | *Homo sapiens* (Human) |
| OR4M1_HUMAN | (Q8NGD0) | OR4M1 | Olfactory II fam 4/MOR225-248 | *Homo sapiens* (Human) |
| OR4M2_HUMAN | (Q8NGB6) | OR4M2 | Olfactory II fam 4/MOR225-248 | *Homo sapiens* (Human) |
| OR4N2_HUMAN | (Q8NGD1) | OR4N2 | Olfactory II fam 4/MOR225-248 | *Homo sapiens* (Human) |
| OR4N4_HUMAN | (Q8N0Y3) | OR4N4 | Olfactory II fam 4/MOR225-248 | *Homo sapiens* (Human) |
| OR4N5_HUMAN | (Q8IXE1) | OR4N5 | Olfactory II fam 4/MOR225-248 | *Homo sapiens* (Human) |
| OR4P4_HUMAN | (Q8NGL7) | OR4P4 | Olfactory II fam 4/MOR225-248 | *Homo sapiens* (Human) |
| OR4Q3_HUMAN | (Q8NH05) | OR4Q3 | Olfactory II fam 4/MOR225-248 | *Homo sapiens* (Human) |
| OR4S1_HUMAN | (Q8NGB4) | OR4S1 | Olfactory II fam 4/MOR225-248 | *Homo sapiens* (Human) |
| OR4S2_HUMAN | (Q8NH73) | OR4S2 | Olfactory II fam 4/MOR225-248 | *Homo sapiens* (Human) |
| OR4X1_HUMAN | (Q8NH49) | OR4X1 | Olfactory II fam 4/MOR225-248 | *Homo sapiens* (Human) |
| OR4X2_HUMAN | (Q8NGF9) | OR4X2 | Olfactory II fam 4/MOR225-248 | *Homo sapiens* (Human) |
| OR5A1_HUMAN | (Q8NGJ0) | OR5A1 | Olfactory II fam 5/MOR172-224,249,254 | *Homo sapiens* (Human) |
| OR5A2_HUMAN | (Q8NGI9) | OR5A2 | Olfactory II fam 5/MOR172-224,249,254 | *Homo sapiens* (Human) |
| OR5B2_HUMAN | (Q96R09) | OR5B2 | Olfactory II fam 5/MOR172-224,249,254 | *Homo sapiens* (Human) |
| OR5B3_HUMAN | (Q8NH48) | OR5B3 | Olfactory II fam 5/MOR172-224,249,254 | *Homo sapiens* (Human) |
| OR5BC_HUMAN | (Q96R08) | OR5B12 | Olfactory II fam 5/MOR172-224,249,254 | *Homo sapiens* (Human) |
| OR5BH_HUMAN | (Q8NGF7) | OR5B17 | Olfactory II fam 5/MOR172-224,249,254 | *Homo sapiens* (Human) |
| OR5C1_HUMAN | (Q8NGR4) | OR5C1 | Olfactory II fam 5/MOR172-224,249,254 | *Homo sapiens* (Human) |
| OR5DD_HUMAN | (Q8NGL4) | OR5D13 | Olfactory II fam 5/MOR172-224,249,254 | *Homo sapiens* (Human) |
| OR5DE_HUMAN | (Q8NGL3) | OR5D14 | Olfactory II fam 5/MOR172-224,249,254 | *Homo sapiens* (Human) |
| OR5DG_HUMAN | (Q8NGK9) | OR5D16 | Olfactory II fam 5/MOR172-224,249,254 | *Homo sapiens* (Human) |
| OR5DI_HUMAN | (Q8NGL1) | OR5D18 | Olfactory II fam 5/MOR172-224,249,254 | *Homo sapiens* (Human) |
| OR5F1_HUMAN | (O95221) | OR5F1 | Olfactory II fam 5/MOR172-224,249,254 | *Homo sapiens* (Human) |
| OR5H2_HUMAN | (Q8NGV7) | OR5H2 | Olfactory II fam 5/MOR172-224,249,254 | *Homo sapiens* (Human) |
| OR5H6_HUMAN | (Q8NGV6) | OR5H6 | Olfactory II fam 5/MOR172-224,249,254 | *Homo sapiens* (Human) |
| OR5I1_HUMAN | (Q13606) | OR5I1 | Olfactory II fam 5/MOR172-224,249,254 | *Homo sapiens* (Human) |
| OR5J2_HUMAN | (Q8NH18) | OR5J2 | Olfactory II fam 5/MOR172-224,249,254 | *Homo sapiens* (Human) |
| OR5K1_HUMAN | (Q8NHB7) | OR5K1 | Olfactory II fam 5/MOR172-224,249,254 | *Homo sapiens* (Human) |
| OR5K2_HUMAN | (Q8NHB8) | OR5K2 | Olfactory II fam 5/MOR172-224,249,254 | *Homo sapiens* (Human) |
| OR5L1_HUMAN | (Q8NGL2) | OR5L1 | Olfactory II fam 5/MOR172-224,249,254 | *Homo sapiens* (Human) |
| OR5L2_HUMAN | (Q8NGL0) | OR5L2 | Olfactory II fam 5/MOR172-224,249,254 | *Homo sapiens* (Human) |
| OR5M1_HUMAN | (Q8NGP8) | OR5M1 | Olfactory II fam 5/MOR172-224,249,254 | *Homo sapiens* (Human) |
| OR5M3_HUMAN | (Q8NGP4) | OR5M3 | Olfactory II fam 5/MOR172-224,249,254 | *Homo sapiens* (Human) |
| OR5M8_HUMAN | (Q8NGP6) | OR5M8 | Olfactory II fam 5/MOR172-224,249,254 | *Homo sapiens* (Human) |
| OR5M9_HUMAN | (Q8NGP3) | OR5M9 | Olfactory II fam 5/MOR172-224,249,254 | *Homo sapiens* (Human) |
| OR5MA_HUMAN | (Q6IEU7) | OR5M10 | Olfactory II fam 5/MOR172-224,249,254 | *Homo sapiens* (Human) |
| OR5MB_HUMAN | (Q96RB7) | OR5M11 | Olfactory II fam 5/MOR172-224,249,254 | *Homo sapiens* (Human) |
| OR5P2_HUMAN | (Q8WZ92) | OR5P2 | Olfactory II fam 5/MOR172-224,249,254 | *Homo sapiens* (Human) |
| OR5P3_HUMAN | (Q8WZ94) | OR5P3 | Olfactory II fam 5/MOR172-224,249,254 | *Homo sapiens* (Human) |
| OR5R1_HUMAN | (Q8NH85) | OR5R1 | Olfactory II fam 8/MOR161-171 | *Homo sapiens* (Human) |
| OR5T1_HUMAN | (Q8NG75) | OR5T1 | Olfactory II fam 5/MOR172-224,249,254 | *Homo sapiens* (Human) |

TABLE D-continued

| non-limiting list human GPCRs | | | | |
|---|---|---|---|---|
| OR5T2_HUMAN | (Q8NGG2) | OR5T2 | Olfactory II fam 5/MOR172-224,249,254 | *Homo sapiens* (Human) |
| OR5T3_HUMAN | (Q8NGG3) | OR5T3 | Olfactory II fam 5/MOR172-224,249,254 | *Homo sapiens* (Human) |
| OR5U1_HUMAN | (Q9UGF5) | OR5U1 | Olfactory II fam 5/MOR172-224,249,254 | *Homo sapiens* (Human) |
| OR5V1_HUMAN | (Q9UGF6) | OR5V1 | Olfactory II fam 5/MOR172-224,249,254 | *Homo sapiens* (Human) |
| OR5W2_HUMAN | (Q8NH69) | OR5W2 | Olfactory II fam 5/MOR172-224,249,254 | *Homo sapiens* (Human) |
| OR6A2_HUMAN | (O95222) | OR6A2 | Olfactory II fam 6/MOR103-105,107-119 | *Homo sapiens* (Human) |
| OR6B1_HUMAN | (O95007) | OR6B1 | Olfactory II fam 6/MOR103-105,107-119 | *Homo sapiens* (Human) |
| OR6B2_HUMAN | (Q6IFH4) | OR6B2 | Olfactory II fam 6/MOR103-105,107-119 | *Homo sapiens* (Human) |
| OR6B3_HUMAN | (Q8NGW1) | OR6B3 | Olfactory II fam 6/MOR103-105,107-119 | *Homo sapiens* (Human) |
| OR6C1_HUMAN | (Q96RD1) | OR6C1 | Olfactory II fam 6/MOR103-105,107-119 | *Homo sapiens* (Human) |
| OR6C2_HUMAN | (Q9NZP2) | OR6C2 | Olfactory II fam 6/MOR103-105,107-119 | *Homo sapiens* (Human) |
| OR6C3_HUMAN | (Q9NZP0) | OR6C3 | Olfactory II fam 6/MOR103-105,107-119 | *Homo sapiens* (Human) |
| OR6C4_HUMAN | (Q8NGE1) | OR6C4 | Olfactory II fam 6/MOR103-105,107-119 | *Homo sapiens* (Human) |
| OR6F1_HUMAN | (Q8NGZ6) | OR6F1 | Olfactory II fam 6/MOR103-105,107-119 | *Homo sapiens* (Human) |
| OR6J1_HUMAN | (Q8NGC5) | OR6J1 | Olfactory II fam 6/MOR103-105,107-119 | *Homo sapiens* (Human) |
| OR6K2_HUMAN | (Q8NGY2) | OR6K2 | Olfactory II fam 6/MOR103-105,107-119 | *Homo sapiens* (Human) |
| OR6K3_HUMAN | (Q8NGY3) | OR6K3 | Olfactory II fam 6/MOR103-105,107-119 | *Homo sapiens* (Human) |
| OR6K6_HUMAN | (Q8NGW6) | OR6K6 | Olfactory II fam 6/MOR103-105,107-119 | *Homo sapiens* (Human) |
| OR6M1_HUMAN | (Q8NGM8) | OR6M1 | Olfactory II fam 6/MOR103-105,107-119 | *Homo sapiens* (Human) |
| OR6N1_HUMAN | (Q8NGY5) | OR6N1 | Olfactory II fam 6/MOR103-105,107-119 | *Homo sapiens* (Human) |
| OR6N2_HUMAN | (Q8NGY6) | OR6N2 | Olfactory II fam 6/MOR103-105,107-119 | *Homo sapiens* (Human) |
| OR6P1_HUMAN | (Q8NGX9) | OR6P1 | Olfactory II fam 6/MOR103-105,107-119 | *Homo sapiens* (Human) |
| OR6Q1_HUMAN | (Q8NGQ2) | OR6Q1 | Olfactory II fam 6/MOR103-105,107-119 | *Homo sapiens* (Human) |
| OR6S1_HUMAN | (Q8NH40) | OR6S1 | Olfactory II fam 6/MOR103-105,107-119 | *Homo sapiens* (Human) |
| OR6T1_HUMAN | (Q8NGN1) | OR6T1 | Olfactory II fam 6/MOR103-105,107-119 | *Homo sapiens* (Human) |
| OR6V1_HUMAN | (Q8N148) | OR6V1 | Olfactory II fam 6/MOR103-105,107-119 | *Homo sapiens* (Human) |
| OR6X1_HUMAN | (Q8NH79) | OR6X1 | Olfactory II fam 6/MOR103-105,107-119 | *Homo sapiens* (Human) |
| OR6Y1_HUMAN | (Q8NGX8) | OR6Y1 | Olfactory II fam 6/MOR103-105,107-119 | *Homo sapiens* (Human) |
| OR7A2_HUMAN | (Q8NGA2) | OR7A2 | Olfactory II fam 7/MOR139-155 | *Homo sapiens* (Human) |
| OR7A5_HUMAN | (Q15622) | OR7A5 | Olfactory II fam 7/MOR139-155 | *Homo sapiens* (Human) |
| OR7AA_HUMAN | (O76100) | OR7A10 | Olfactory II fam 7/MOR139-155 | *Homo sapiens* (Human) |
| OR7AH_HUMAN | (O14581) | OR7A17 | Olfactory II fam 7/MOR139-155 | *Homo sapiens* (Human) |
| OR7C1_HUMAN | (O76099) | OR7C1 | Olfactory II fam 7/MOR139-155 | *Homo sapiens* (Human) |
| OR7C2_HUMAN | (O60412) | OR7C2 | Olfactory II fam 7/MOR139-155 | *Homo sapiens* (Human) |
| OR7D2_HUMAN | (Q96RA2) | OR7D2 | Olfactory II fam 7/MOR139-155 | *Homo sapiens* (Human) |
| OR7D4_HUMAN | (Q8NG98) | OR7D4 | Olfactory II fam 7/MOR139-155 | *Homo sapiens* (Human) |
| OR7G1_HUMAN | (Q8NGA0) | OR7G1 | Olfactory II fam 7/MOR139-155 | *Homo sapiens* (Human) |
| OR7G2_HUMAN | (Q8NG99) | OR7G2 | Olfactory II fam 7/MOR139-155 | *Homo sapiens* (Human) |
| OR7G3_HUMAN | (Q8NG95) | OR7G3 | Olfactory II fam 7/MOR139-155 | *Homo sapiens* (Human) |
| OR8A1_HUMAN | (Q8NGG7) | OR8A1 | Olfactory II fam 8/MOR161-171 | *Homo sapiens* (Human) |
| OR8B2_HUMAN | (Q96RD0) | OR8B2 | Olfactory II fam 8/MOR161-171 | *Homo sapiens* (Human) |
| OR8B3_HUMAN | (Q8NGG8) | OR8B3 | Olfactory II fam 8/MOR161-171 | *Homo sapiens* (Human) |
| OR8B4_HUMAN | (Q96RC9) | OR8B4 | Olfactory II fam 8/MOR161-171 | *Homo sapiens* (Human) |
| OR8B8_HUMAN | (Q15620) | OR8B8 | Olfactory II fam 8/MOR161-171 | *Homo sapiens* (Human) |
| OR8BC_HUMAN | (Q8NGG6) | OR8B12 | Olfactory II fam 8/MOR161-171 | *Homo sapiens* (Human) |
| OR8D1_HUMAN | (Q8WZ84) | OR8D1 | Olfactory II fam 8/MOR161-171 | *Homo sapiens* (Human) |
| OR8D2_HUMAN | (Q9GZM6) | OR8D2 | Olfactory II fam 8/MOR161-171 | *Homo sapiens* (Human) |
| OR8D4_HUMAN | (Q8NGM9) | OR8D4 | Olfactory II fam 8/MOR161-171 | *Homo sapiens* (Human) |
| OR8G1_HUMAN | (Q15617) | OR8G1 | Olfactory II fam 8/MOR161-171 | *Homo sapiens* (Human) |
| OR8G2_HUMAN | (Q15614) | OR8G2 | Olfactory II fam 8/MOR161-171 | *Homo sapiens* (Human) |
| OR8G5_HUMAN | (Q8NG78) | OR8G5 | Olfactory II fam 8/MOR161-171 | *Homo sapiens* (Human) |
| OR8H1_HUMAN | (Q8NGG4) | OR8H1 | Olfactory II fam 8/MOR161-171 | *Homo sapiens* (Human) |
| OR8H2_HUMAN | (Q8N162) | OR8H2 | Olfactory II fam 8/MOR161-171 | *Homo sapiens* (Human) |
| OR8H3_HUMAN | (Q8N146) | OR8H3 | Olfactory II fam 8/MOR161-171 | *Homo sapiens* (Human) |
| OR8I2_HUMAN | (Q8N0Y5) | OR8I2 | Olfactory II fam 8/MOR161-171 | *Homo sapiens* (Human) |

TABLE D-continued

| | | | non-limiting list human GPCRs | |
|---|---|---|---|---|
| OR8J1_HUMAN | (Q8NGP2) | OR8J1 | Olfactory II fam 8/MOR161-171 | *Homo sapiens* (Human) |
| OR8J3_HUMAN | (Q8NGG0) | OR8J3 | Olfactory II fam 8/MOR161-171 | *Homo sapiens* (Human) |
| OR8K1_HUMAN | (Q8NGG5) | OR8K1 | Olfactory II fam 5/MOR172-224,249,254 | *Homo sapiens* (Human) |
| OR8K3_HUMAN | (Q8NH51) | OR8K3 | Olfactory II fam 8/MOR161-171 | *Homo sapiens* (Human) |
| OR8K5_HUMAN | (Q8NH50) | OR8K5 | Olfactory II fam 8/MOR161-171 | *Homo sapiens* (Human) |
| OR8S1_HUMAN | (Q8NH09) | OR8S1 | Olfactory unclassified class II | *Homo sapiens* (Human) |
| OR8U1_HUMAN | (Q8NH10) | OR8U1 | Olfactory II fam 8/MOR161-171 | *Homo sapiens* (Human) |
| OR9A2_HUMAN | (Q8NGT5) | OR9A2 | Olfactory II fam 9/MOR120 | *Homo sapiens* (Human) |
| OR9A4_HUMAN | (Q8NGU2) | OR9A4 | Olfactory II fam 9/MOR120 | *Homo sapiens* (Human) |
| OR9G1_HUMAN | (Q8NH87) | OR9G1 | Olfactory II fam 9/MOR120 | *Homo sapiens* (Human) |
| OR9G4_HUMAN | (Q8NGQ1) | OR9G4 | Olfactory II fam 9/MOR120 | *Homo sapiens* (Human) |
| OR9G5_HUMAN | (Q8NGQ0) | OR9G5 | Olfactory II fam 9/MOR120 | *Homo sapiens* (Human) |
| OR9I1_HUMAN | (Q8NGQ6) | OR9I1 | Olfactory II fam 9/MOR120 | *Homo sapiens* (Human) |
| OR9K2_HUMAN | (Q8NGE7) | OR9K2 | Olfactory II fam 9/MOR120 | *Homo sapiens* (Human) |
| OR9Q1_HUMAN | (Q8NGQ5) | OR9Q1 | Olfactory II fam 9/MOR120 | *Homo sapiens* (Human) |
| OR9Q2_HUMAN | (Q8NGE9) | OR9Q2 | Olfactory II fam 9/MOR120 | *Homo sapiens* (Human) |
| OX1R_HUMAN | (O43613) | HCRTR1 | Orexin | *Homo sapiens* (Human) |
| OX2R_HUMAN | (O43614) | HCRTR2 | Orexin | *Homo sapiens* (Human) |
| OXER1_HUMAN | (Q8TDS5) | OXER1 | Putative/unclassified Class A GPCRs | *Homo sapiens* (Human) |
| OXGR1_HUMAN | (Q96P68) | OXGR1 | Putative/unclassified Class A GPCRs | *Homo sapiens* (Human) |
| OXYR_HUMAN | (P30559) | OXTR | Oxytocin/mesotocin | *Homo sapiens* (Human) |
| P2RY1_HUMAN | (P47900) | P2RY1 | Purinoceptor P2RY1-4,6,11 GPR91 | *Homo sapiens* (Human) |
| P2RY2_HUMAN | (P41231) | P2RY2 | Purinoceptor P2RY1-4,6,11 GPR91 | *Homo sapiens* (Human) |
| P2RY4_HUMAN | (P51582) | P2RY4 | Purinoceptor P2RY1-4,6,11 GPR91 | *Homo sapiens* (Human) |
| P2RY5_HUMAN | (P43657) | P2RY5 | Purinoceptor P2RY5,8,9,10 GPR35,92,174 | *Homo sapiens* (Human) |
| P2RY6_HUMAN | (Q15077) | P2RY6 | Purinoceptor P2RY1-4,6,11 GPR91 | *Homo sapiens* (Human) |
| P2RY8_HUMAN | (Q86VZ1) | P2RY8 | Purinoceptor P2RY5,8,9,10 GPR35,92,174 | *Homo sapiens* (Human) |
| P2RY9_HUMAN | (Q99677) | GPR23 | Purinoceptor P2RY5,8,9,10 GPR35,92,174 | *Homo sapiens* (Human) |
| P2Y10_HUMAN | (O00398) | P2RY10 | Purinoceptor P2RY5,8,9,10 GPR35,92,174 | *Homo sapiens* (Human) |
| P2Y11_HUMAN | (Q96G91) | P2RY11 | Purinoceptor P2RY1-4,6,11 GPR91 | *Homo sapiens* (Human) |
| P2Y12_HUMAN | (Q9H244) | P2RY12 | Purinoceptor P2RY12-14 GPR87 (UDP-Glucose) | *Homo sapiens* (Human) |
| P2Y13_HUMAN | (Q9BPV8) | P2RY13 | Purinoceptor P2RY12-14 GPR87 (UDP-Glucose) | *Homo sapiens* (Human) |
| P2Y14_HUMAN | (Q15391) | P2RY14 | Purinoceptor P2RY12-14 GPR87 (UDP-Glucose) | *Homo sapiens* (Human) |
| P78470_HUMAN | (P78470) | | fragments | *Homo sapiens* (Human) |
| P78471_HUMAN | (P78471) | | fragments | *Homo sapiens* (Human) |
| PACR_HUMAN | (P41586) | ADCYAP1R1 | PACAP | *Homo sapiens* (Human) |
| PAR1_HUMAN | (P25116) | F2R | Thrombin | *Homo sapiens* (Human) |
| PAR2_HUMAN | (P55085) | F2RL1 | Proteinase-activated | *Homo sapiens* (Human) |
| PAR3_HUMAN | (O00254) | F2RL2 | Proteinase-activated | *Homo sapiens* (Human) |
| PAR4_HUMAN | (Q96RI0) | F2RL3 | Proteinase-activated | *Homo sapiens* (Human) |
| PD2R_HUMAN | (Q13258) | PTGDR | Prostaglandin E2/D2 subtype EP2 | *Homo sapiens* (Human) |
| PE2R1_HUMAN | (P34995) | PTGER1 | Prostaglandin E2 subtype EP1 | *Homo sapiens* (Human) |
| PE2R2_HUMAN | (P43116) | PTGER2 | Prostaglandin E2/D2 subtype EP2 | *Homo sapiens* (Human) |
| PE2R3_HUMAN | (P43115) | PTGER3 | Prostaglandin E2 subtype EP3 | *Homo sapiens* (Human) |
| PE2R4_HUMAN | (P35408) | PTGER4 | Prostaglandin E2 subtype EP4 | *Homo sapiens* (Human) |
| PF2R_HUMAN | (P43088) | PTGFR | Prostaglandin F2-alpha | *Homo sapiens* (Human) |
| PI2R_HUMAN | (P43119) | PTGIR | Prostacyclin | *Homo sapiens* (Human) |
| PKR1_HUMAN | (Q8TCW9) | PROKR1 | Prokineticin receptors | *Homo sapiens* (Human) |
| PKR2_HUMAN | (Q8NFJ6) | PROKR2 | Prokineticin receptors | *Homo sapiens* (Human) |
| PRLHR_HUMAN | (P49683) | PRLHR | Prolactin-releasing peptide (GPR10) | *Homo sapiens* (Human) |
| PSYR_HUMAN | (Q8IYL9) | GPR65 | Putative/unclassified Class A GPCRs | *Homo sapiens* (Human) |
| PTAFR_HUMAN | (P25105) | PTAFR | Platelet activating factor | *Homo sapiens* (Human) |
| PTHR1_HUMAN | (Q03431) | PTHR1 | Parathyroid hormone | *Homo sapiens* (Human) |
| PTHR2_HUMAN | (P49190) | PTHR2 | Parathyroid hormone | *Homo sapiens* (Human) |
| Q13027_HUMAN | (Q13027) | | fragments | *Homo sapiens* (Human) |
| Q13167_HUMAN | (Q13167) | DRD3 | Dopamine Vertebrate type 3 | *Homo sapiens* (Human) |
| Q14968_HUMAN | (Q14968) | | Putative/unclassified Class A GPCRs | *Homo sapiens* (Human) |
| Q15613_HUMAN | (Q15613) | tpcr110 | fragments | *Homo sapiens* (Human) |
| Q15616_HUMAN | (Q15616) | OR5E1P | fragments | *Homo sapiens* (Human) |
| Q15618_HUMAN | (Q15618) | OR7E18P | fragments | *Homo sapiens* (Human) |
| Q16144_HUMAN | (Q16144) | | CCK type B | *Homo sapiens* (Human) |
| Q16292_HUMAN | (Q16292) | | thrombin receptor fragments | *Homo sapiens* (Human) |
| Q16303_HUMAN | (Q16303) | | dopamine D4 receptor fragments | *Homo sapiens* (Human) |
| Q16503_HUMAN | (Q16503) | | fragments | *Homo sapiens* (Human) |
| Q2F3K1_HUMAN | (Q2F3K1) | CASR | fragments | *Homo sapiens* (Human) |
| Q2HIZ3_HUMAN | (Q2HIZ3) | OR10H3 | Olfactory II fam 10/MOR263-269 | *Homo sapiens* (Human) |
| Q2I7G5_HUMAN | (Q2I7G5) | EMR1 | EMR1 | *Homo sapiens* (Human) |
| Q2I8G2_HUMAN | (Q2I8G2) | ADRA2A | Alpha Adrenoceptors type 2 | *Homo sapiens* (Human) |
| Q2KHP3_HUMAN | (Q2KHP3) | PTGFR | Prostaglandin F2-alpha | *Homo sapiens* (Human) |
| Q2L7J7_HUMAN | (Q2L7J7) | ADORA2B | fragments | *Homo sapiens* (Human) |
| Q2M1L3_HUMAN | (Q2M1L3) | GPR133 | Putative/unclassified Class B GPCRs | *Homo sapiens* (Human) |
| Q2M1M6_HUMAN | (Q2M1M6) | OR10J1 | fragments | *Homo sapiens* (Human) |
| Q2M1M8_HUMAN | (Q2M1M8) | OR10J1 | Olfactory II fam 10/MOR263-269 | *Homo sapiens* (Human) |
| Q2M1T0_HUMAN | (Q2M1T0) | CASR | Extracellular calcium-sensing | *Homo sapiens* (Human) |

TABLE D-continued

| | | | non-limiting list human GPCRs | |
|---|---|---|---|---|
| Q2M1U3_HUMAN | (Q2M1U3) | PTHR1 | Parathyroid hormone | *Homo sapiens* (Human) |
| Q2M1V1_HUMAN | (Q2M1V1) | TAAR5 | Trace amine | *Homo sapiens* (Human) |
| Q2M1V7_HUMAN | (Q2M1V7) | MRGPRE | Mas proto-oncogene & Mas-related (MRGs) | *Homo sapiens* (Human) |
| Q2M1W5_HUMAN | (Q2M1W5) | TAAR1 | Trace amine | *Homo sapiens* (Human) |
| Q2M1Y3_HUMAN | (Q2M1Y3) | OR2H2 | Olfactory II fam 2/MOR256-262,270-285 | *Homo sapiens* (Human) |
| Q2M215_HUMAN | (Q2M215) | RXFP1 | LGR like (hormone receptors) | *Homo sapiens* (Human) |
| Q2M229_HUMAN | (Q2M229) | GLP1R | Glucagon | *Homo sapiens* (Human) |
| Q2M249_HUMAN | (Q2M249) | RHO | Rhodopsin Vertebrate type 1 | *Homo sapiens* (Human) |
| Q2M2D2_HUMAN | (Q2M2D2) | HTR5A | Serotonin type 5 | *Homo sapiens* (Human) |
| Q2M2E2_HUMAN | (Q2M2E2) | GPR26 | Putative/unclassified Class A GPCRs | *Homo sapiens* (Human) |
| Q2M339_HUMAN | (Q2M339) | TRHR | Thyrotropin-releasing hormone | *Homo sapiens* (Human) |
| Q2M369_HUMAN | (Q2M369) | GPR148 | Putative/unclassified Class A GPCRs | *Homo sapiens* (Human) |
| Q2M3C0_HUMAN | (Q2M3C0) | PROKR2 | Prokineticin receptors | *Homo sapiens* (Human) |
| Q2M3E2_HUMAN | (Q2M3E2) | VN1R4 | Vomeronasal receptors V1RL | *Homo sapiens* (Human) |
| Q2M3F7_HUMAN | (Q2M3F7) | GPR174 | Purinoceptor P2RY5,8,9,10 GPR35,92,174 | *Homo sapiens* (Human) |
| Q2M3L0_HUMAN | (Q2M3L0) | OR2S2 | Olfactory II fam 13/MOR253 | *Homo sapiens* (Human) |
| Q2M3M4_HUMAN | (Q2M3M4) | OR13A1 | Olfactory II fam 13/MOR253 | *Homo sapiens* (Human) |
| Q2M3M5_HUMAN | (Q2M3M5) | GCGR | Glucagon | *Homo sapiens* (Human) |
| Q2M3T5_HUMAN | (Q2M3T5) | OR2L2 | Olfactory II fam 2/MOR256-262,270-285 | *Homo sapiens* (Human) |
| Q2MZ38_HUMAN | (Q2MZ38) | GNRHR2 | fragments | *Homo sapiens* (Human) |
| Q2NKN6_HUMAN | (Q2NKN6) | BAI3 | Brain-specific angiogenesis inhibitor (BAI) | *Homo sapiens* (Human) |
| Q2NL85_HUMAN | (Q2NL85) | GPRC5C | Orphan GPRC5 | *Homo sapiens* (Human) |
| Q2PNZ0_HUMAN | (Q2PNZ0) | GPR115 | Putative/unclassified Class B GPCRs | *Homo sapiens* (Human) |
| Q2PNZ1_HUMAN | (Q2PNZ1) | GPR111 | Putative/unclassified Class B GPCRs | *Homo sapiens* (Human) |
| Q2TBC9_HUMAN | (Q2TBC9) | MAS1 | Mas proto-oncogene & Mas-related (MRGs) | *Homo sapiens* (Human) |
| Q2VPE4_HUMAN | (Q2VPE4) | | fragments | *Homo sapiens* (Human) |
| Q2YD84_HUMAN | (Q2YD84) | | C—X—C Chemokine type 5 | *Homo sapiens* (Human) |
| Q2YD89_HUMAN | (Q2YD89) | | Prostacyclin | *Homo sapiens* (Human) |
| Q2YDB9_HUMAN | (Q2YDB9) | | C-C Chemokine type 3 | *Homo sapiens* (Human) |
| Q2YEF8_HUMAN | (Q2YEF8) | | Interleukin-8 type A | *Homo sapiens* (Human) |
| Q2YEG4_HUMAN | (Q2YEG4) | | Interleukin-8 type A | *Homo sapiens* (Human) |
| Q2YEG5_HUMAN | (Q2YEG5) | | Interleukin-8 type A | *Homo sapiens* (Human) |
| Q2YEG7_HUMAN | (Q2YEG7) | | Interleukin-8 type A | *Homo sapiens* (Human) |
| Q2YEG8_HUMAN | (Q2YEG8) | | Interleukin-8 type A | *Homo sapiens* (Human) |
| Q32MN8_HUMAN | (Q32MN8) | GALR2 | Galanin | *Homo sapiens* (Human) |
| Q32VQ0_HUMAN | (Q32VQ0) | GPCRLTM7 | Olfactory II fam 4/MOR225-248 | *Homo sapiens* (Human) |
| Q38L21_HUMAN | (Q38L21) | CCR5 | C-C Chemokine type 5 | *Homo sapiens* (Human) |
| Q3C1V7_HUMAN | (Q3C1V7) | | fragments | *Homo sapiens* (Human) |
| Q3KNQ8_HUMAN | (Q3KNQ8) | CCR8 | C-C Chemokine type 8 | *Homo sapiens* (Human) |
| Q3KNR3_HUMAN | (Q3KNR3) | CCR8 | C-C Chemokine type 8 | *Homo sapiens* (Human) |
| Q3KNS9_HUMAN | (Q3KNS9) | GPR22 | GPR | *Homo sapiens* (Human) |
| Q3KNV3_HUMAN | (Q3KNV3) | GPRC5D | Orphan GPRC5 | *Homo sapiens* (Human) |
| Q3KP37_HUMAN | (Q3KP37) | CMKLR1 | Chemokine receptor-like 1 | *Homo sapiens* (Human) |
| Q3KPF5_HUMAN | (Q3KPF5) | P2RY5 | Purinoceptor P2RY5,8,9,10 GPR35,92,174 | *Homo sapiens* (Human) |
| Q3KRG8_HUMAN | (Q3KRG8) | CEACAM1 | fragments | *Homo sapiens* (Human) |
| Q3KU23_HUMAN | (Q3KU23) | | LGR like (hormone receptors) | *Homo sapiens* (Human) |
| Q3KU24_HUMAN | (Q3KU24) | | LGR like (hormone receptors) | *Homo sapiens* (Human) |
| Q3KU25_HUMAN | (Q3KU25) | | LGR like (hormone receptors) | *Homo sapiens* (Human) |
| Q3L3Q6_HUMAN | (Q3L3Q6) | CCR5 | C-C Chemokine type 5 | *Homo sapiens* (Human) |
| Q3MI45_HUMAN | (Q3MI45) | MC2R | fragments | *Homo sapiens* (Human) |
| Q3MIJ6_HUMAN | (Q3MIJ6) | MC4R | Melanocortin hormone | *Homo sapiens* (Human) |
| Q3MIL4_HUMAN | (Q3MIL4) | GPR15 | GPR | *Homo sapiens* (Human) |
| Q3MIS8_HUMAN | (Q3MIS8) | OR5P2 | Olfactory II fam 5/MOR172-224,249,254 | *Homo sapiens* (Human) |
| Q3MIV9_HUMAN | (Q3MIV9) | GRM8 | Metabotropic glutamate group III | *Homo sapiens* (Human) |
| Q3MJ87_HUMAN | (Q3MJ87) | PTGER4 | Prostaglandin E2 subtype EP4 | *Homo sapiens* (Human) |
| Q3MJB1_HUMAN | (Q3MJB1) | RXFP4 | Somatostatin- and angiogenin-like peptide | *Homo sapiens* (Human) |
| Q3MJC7_HUMAN | (Q3MJC7) | OR6A2 | Olfactory II fam 6/MOR103-105,107-119 | *Homo sapiens* (Human) |
| Q3MJD3_HUMAN | (Q3MJD3) | AVPR2 | Vasopressin type 2 | *Homo sapiens* (Human) |
| Q3S2J4_HUMAN | (Q3S2J4) | AVPR1 | Vasopressin type 1 | *Homo sapiens* (Human) |
| Q3SAH0_HUMAN | (Q3SAH0) | GPR34 | Putative/unclassified Class A GPCRs | *Homo sapiens* (Human) |
| Q3SAH2_HUMAN | (Q3SAH2) | GPR34 | Putative/unclassified Class A GPCRs | *Homo sapiens* (Human) |
| Q3ZAR0_HUMAN | (Q3ZAR0) | GPR50 | Melatonin | *Homo sapiens* (Human) |
| Q495D1_HUMAN | (Q495D1) | OR5F1 | Olfactory II fam 5/MOR172-224,249,254 | *Homo sapiens* (Human) |
| Q495H1_HUMAN | (Q495H1) | GPR120 | Putative/unclassified Class A GPCRs | *Homo sapiens* (Human) |
| Q495H7_HUMAN | (Q495H7) | GPR119 | Putative/unclassified Class A GPCRs | *Homo sapiens* (Human) |
| Q499G4_HUMAN | (Q499G4) | OPRK1 | Opioid type K | *Homo sapiens* (Human) |
| Q499H0_HUMAN | (Q499H0) | GPR64 | Putative/unclassified Class B GPCRs | *Homo sapiens* (Human) |
| Q4G0I6_HUMAN | (Q4G0I6) | HRH4 | Histamine type 4 | *Homo sapiens* (Human) |

TABLE D-continued

| non-limiting list human GPCRs | | | | |
|---|---|---|---|---|
| Q4G0K7_HUMAN | (Q4G0K7) | GPR116 | fragments | *Homo sapiens* (Human) |
| Q4G0Q6_HUMAN | (Q4G0Q6) | MGC72080 | fragments | *Homo sapiens* (Human) |
| Q4KKW2_HUMAN | (Q4KKW2) | PPYR1 | Neuropeptide Y type 4 | *Homo sapiens* (Human) |
| Q4KN04_HUMAN | (Q4KN04) | TAS2R8 | Taste receptors T2R | *Homo sapiens* (Human) |
| Q4KN27_HUMAN | (Q4KN27) | MC3R | Melanocortin hormone | *Homo sapiens* (Human) |
| Q4KN29_HUMAN | (Q4KN29) | TAS2R8 | Taste receptors T2R | *Homo sapiens* (Human) |
| Q4QRI5_HUMAN | (Q4QRI5) | TACR2 | Substance K (NK2) | *Homo sapiens* (Human) |
| Q4QRI9_HUMAN | (Q4QRI9) | HTR1F | fragments | *Homo sapiens* (Human) |
| Q4QRJ0_HUMAN | (Q4QRJ0) | DRD1 | Dopamine Vertebrate type 1 | *Homo sapiens* (Human) |
| Q4QRJ1_HUMAN | (Q4QRJ1) | CRHR1 | Corticotropin releasing factor | *Homo sapiens* (Human) |
| Q4QRJ3_HUMAN | (Q4QRJ3) | FSHR | Follicle stimulating hormone | *Homo sapiens* (Human) |
| Q4QRJ4_HUMAN | (Q4QRJ4) | CRHR2 | Corticotropin releasing factor | *Homo sapiens* (Human) |
| Q4V749_HUMAN | (Q4V749) | CCR10 | C-C Chemokine type 10 | *Homo sapiens* (Human) |
| Q4V9L2_HUMAN | (Q4V9L2) | MRGPRX1 | Mas proto-oncogene & Mas-related (MRGs) | *Homo sapiens* (Human) |
| Q4VAM0_HUMAN | (Q4VAM0) | LGR5 | LGR like (hormone receptors) | *Homo sapiens* (Human) |
| Q4VAM2_HUMAN | (Q4VAM2) | LGR5 | LGR like (hormone receptors) | *Homo sapiens* (Human) |
| Q4VAT1_HUMAN | (Q4VAT1) | GLP2R | fragments | *Homo sapiens* (Human) |
| Q4VAT2_HUMAN | (Q4VAT2) | GLP2R | fragments | *Homo sapiens* (Human) |
| Q4VAT3_HUMAN | (Q4VAT3) | GLP2R | Glucagon | *Homo sapiens* (Human) |
| Q4VAT4_HUMAN | (Q4VAT4) | GLP2R | fragments | *Homo sapiens* (Human) |
| Q4VAV7_HUMAN | (Q4VAV7) | | Neuropeptide Y type 4 | *Homo sapiens* (Human) |
| Q4VAY7_HUMAN | (Q4VAY7) | HTR1B | Serotonin type 1 | *Homo sapiens* (Human) |
| Q4VB06_HUMAN | (Q4VB06) | OR3A1 | Olfactory II fam 3/MOR255 | *Homo sapiens* (Human) |
| Q4VBB0_HUMAN | (Q4VBB0) | CCRL2 | C-C Chemokine other | *Homo sapiens* (Human) |
| Q4VBB4_HUMAN | (Q4VBB4) | GPR68 | GPR | *Homo sapiens* (Human) |
| Q4VBK6_HUMAN | (Q4VBK6) | CHRM2 | Musc. acetylcholine Vertebrate type 2 | *Homo sapiens* (Human) |
| Q4VBK7_HUMAN | (Q4VBK7) | CHRM4 | fragments | *Homo sapiens* (Human) |
| Q4VBK8_HUMAN | (Q4VBK8) | CNR2 | fragments | *Homo sapiens* (Human) |
| Q4VBL0_HUMAN | (Q4VBL0) | NMBR | Bombesin | *Homo sapiens* (Human) |
| Q4VBL2_HUMAN | (Q4VBL2) | CCR2 | C-C Chemokine type 2 | *Homo sapiens* (Human) |
| Q4VBL3_HUMAN | (Q4VBL3) | GPR31 | fragments | *Homo sapiens* (Human) |
| Q4VBL6_HUMAN | (Q4VBL6) | GPR52 | GPR | *Homo sapiens* (Human) |
| Q4VBL7_HUMAN | (Q4VBL7) | GALR1 | Galanin | *Homo sapiens* (Human) |
| Q4VBL8_HUMAN | (Q4VBL8) | TACR1 | fragments | *Homo sapiens* (Human) |
| Q4VBL9_HUMAN | (Q4VBL9) | TACR3 | fragments | *Homo sapiens* (Human) |
| Q4VBM3_HUMAN | (Q4VBM3) | CCR9 | fragments | *Homo sapiens* (Human) |
| Q4VBM7_HUMAN | (Q4VBM7) | ADRA1A | Alpha Adrenoceptors type 1 | *Homo sapiens* (Human) |
| Q4VBN0_HUMAN | (Q4VBN0) | GPR61 | fragments | *Homo sapiens* (Human) |
| Q4VBN1_HUMAN | (Q4VBN1) | GPR81 | fragments | *Homo sapiens* (Human) |
| Q4VBN3_HUMAN | (Q4VBN3) | GPR119 | Putative/unclassified Class A GPCRs | *Homo sapiens* (Human) |
| Q4VBN4_HUMAN | (Q4VBN4) | CCRL1 | fragments | *Homo sapiens* (Human) |
| Q4VBN5_HUMAN | (Q4VBN5) | GPR35 | fragments | *Homo sapiens* (Human) |
| Q4VBN6_HUMAN | (Q4VBN6) | F2RL2 | fragments | *Homo sapiens* (Human) |
| Q4VBN7_HUMAN | (Q4VBN7) | P2RY10 | Purinoceptor P2RY5,8,9,10 GPR35,92,174 | *Homo sapiens* (Human) |
| Q4VBP0_HUMAN | (Q4VBP0) | SSTR2 | Somatostatin type 2 | *Homo sapiens* (Human) |
| Q4VBP1_HUMAN | (Q4VBP1) | GIPR | fragments | *Homo sapiens* (Human) |
| Q4VWM1_HUMAN | (Q4VWM1) | OPRM1 | Opioid type M | *Homo sapiens* (Human) |
| Q4VWM2_HUMAN | (Q4VWM2) | OPRM1 | Opioid type M | *Homo sapiens* (Human) |
| Q4VWM3_HUMAN | (Q4VWM3) | OPRM1 | Opioid type M | *Homo sapiens* (Human) |
| Q4VWM4_HUMAN | (Q4VWM4) | OPRM1 | Opioid type M | *Homo sapiens* (Human) |
| Q4VWM6_HUMAN | (Q4VWM6) | OPRM1 | Opioid type M | *Homo sapiens* (Human) |
| Q4VWX6_HUMAN | (Q4VWX6) | OPRM | Opioid type M | *Homo sapiens* (Human) |
| Q4W594_HUMAN | (Q4W594) | ADRA2C | Alpha Adrenoceptors type 2 | *Homo sapiens* (Human) |
| Q4W5G7_HUMAN | (Q4W5G7) | NPY2R | Neuropeptide Y type 2 | *Homo sapiens* (Human) |
| Q4ZFV2_HUMAN | (Q4ZFV2) | GPR35 | Purinoceptor P2RY5,8,9,10 GPR35,92,174 | *Homo sapiens* (Human) |
| Q4ZIL0_HUMAN | (Q4ZIL0) | | fragments | *Homo sapiens* (Human) |
| Q502U7_HUMAN | (Q502U7) | GPR32 | Chemokine receptor-like 1 | *Homo sapiens* (Human) |
| Q502U9_HUMAN | (Q502U9) | GPR23 | Purinoceptor P2RY5,8,9,10 GPR35,92,174 | *Homo sapiens* (Human) |
| Q502V0_HUMAN | (Q502V0) | XCR1 | XC Chemokine | *Homo sapiens* (Human) |
| Q502V1_HUMAN | (Q502V1) | MC5R | Melanocortin hormone | *Homo sapiens* (Human) |
| Q502V2_HUMAN | (Q502V2) | RXFP3 | Somatostatin- and angiogenin-like peptide | *Homo sapiens* (Human) |
| Q502V7_HUMAN | (Q502V7) | TAS2R9 | Taste receptors T2R | *Homo sapiens* (Human) |
| Q502V9_HUMAN | (Q502V9) | MAS1L | Mas proto-oncogene & Mas-related (MRGs) | *Homo sapiens* (Human) |
| Q504X6_HUMAN | (Q504X6) | MC2R | Adrenocorticotropic hormone | *Homo sapiens* (Human) |
| Q506J9_HUMAN | (Q506J9) | | Cannabinoid | *Homo sapiens* (Human) |
| Q50KD4_HUMAN | (Q50KD4) | Hosa(Biaka)-T2R55 | fragments | *Homo sapiens* (Human) |
| Q50KD6_HUMAN | (Q50KD6) | Hosa(Adygei)-T2R55 | fragments | *Homo sapiens* (Human) |
| Q50KT0_HUMAN | (Q50KT0) | Hosa(Biaka)-T2R9 | fragments | *Homo sapiens* (Human) |
| Q50KT1_HUMAN | (Q50KT1) | Hosa(Japanese)-T2R9 | fragments | *Homo sapiens* (Human) |
| Q50KU1_HUMAN | (Q50KU1) | Hosa(Biaka)-T2R8 | fragments | *Homo sapiens* (Human) |
| Q50KU2_HUMAN | (Q50KU2) | Hosa(Japanese)-T2R8 | fragments | *Homo sapiens* (Human) |
| Q50KV5_HUMAN | (Q50KV5) | Hosa(Biaka)-T2R7 | fragments | *Homo sapiens* (Human) |
| Q50KV7_HUMAN | (Q50KV7) | Hosa(Adygei)-T2R7 | fragments | *Homo sapiens* (Human) |

TABLE D-continued

| | | | non-limiting list human GPCRs | |
|---|---|---|---|---|
| Q52LG8_HUMAN | (Q52LG8) | PTGER2 | Prostaglandin E2/D2 subtype EP2 | *Homo sapiens* (Human) |
| Q52M04_HUMAN | (Q52M04) | GIPR | Gastric inhibitory peptide | *Homo sapiens* (Human) |
| Q52M68_HUMAN | (Q52M68) | F2RL2 | Proteinase-activated | *Homo sapiens* (Human) |
| Q52R92_HUMAN | (Q52R92) | | fragments | *Homo sapiens* (Human) |
| Q52R93_HUMAN | (Q52R93) | | fragments | *Homo sapiens* (Human) |
| Q52R94_HUMAN | (Q52R94) | | fragments | *Homo sapiens* (Human) |
| Q53EM0_HUMAN | (Q53EM0) | | fragments | *Homo sapiens* (Human) |
| Q53EZ5_HUMAN | (Q53EZ5) | | fragments | *Homo sapiens* (Human) |
| Q53F99_HUMAN | (Q53F99) | | fragments | *Homo sapiens* (Human) |
| Q53FA0_HUMAN | (Q53FA0) | | fragments | *Homo sapiens* (Human) |
| Q53FA1_HUMAN | (Q53FA1) | | fragments | *Homo sapiens* (Human) |
| Q53GA6_HUMAN | (Q53GA6) | | fragments | *Homo sapiens* (Human) |
| Q53GM2_HUMAN | (Q53GM2) | | fragments | *Homo sapiens* (Human) |
| Q53GP0_HUMAN | (Q53GP0) | | fragments | *Homo sapiens* (Human) |
| Q53PC4_HUMAN | (Q53PC4) | IL8RB | Interleukin-8 type B | *Homo sapiens* (Human) |
| Q53QQ5_HUMAN | (Q53QQ5) | NTSR2 | fragments | *Homo sapiens* (Human) |
| Q53QT9_HUMAN | (Q53QT9) | GPR73 | Prokineticin receptors | *Homo sapiens* (Human) |
| Q53R18_HUMAN | (Q53R18) | IL8RA | Interleukin-8 type A | *Homo sapiens* (Human) |
| Q53R22_HUMAN | (Q53R22) | FZD5 | frizzled Group A (Fz 1&2&4&5&7-9) | *Homo sapiens* (Human) |
| Q53RU7_HUMAN | (Q53RU7) | GPR39 | fragments | *Homo sapiens* (Human) |
| Q53RV4_HUMAN | (Q53RV4) | tmp_locus_35 | RDC1 | *Homo sapiens* (Human) |
| Q53S49_HUMAN | (Q53S49) | LHCGR | fragments | *Homo sapiens* (Human) |
| Q53S59_HUMAN | (Q53S59) | FZD7 | frizzled Group A (Fz 1&2&4&5&7-9) | *Homo sapiens* (Human) |
| Q53S69_HUMAN | (Q53S69) | CXCR4 | C—X—C Chemokine type 4 | *Homo sapiens* (Human) |
| Q53SF6_HUMAN | (Q53SF6) | PTHR2 | fragments | *Homo sapiens* (Human) |
| Q53T00_HUMAN | (Q53T00) | SCTR | Secretin | *Homo sapiens* (Human) |
| Q53T35_HUMAN | (Q53T35) | PTHR2 | fragments | *Homo sapiens* (Human) |
| Q53TA5_HUMAN | (Q53TA5) | GPR113 | Putative/unclassified Class B GPCRs | *Homo sapiens* (Human) |
| Q53TI1_HUMAN | (Q53TI1) | HTR2B | Serotonin type 2 | *Homo sapiens* (Human) |
| Q53TQ2_HUMAN | (Q53TQ2) | TACR1 | fragments | *Homo sapiens* (Human) |
| Q53TR1_HUMAN | (Q53TR1) | TACR1 | fragments | *Homo sapiens* (Human) |
| Q53TS5_HUMAN | (Q53TS5) | CALCRL | fragments | *Homo sapiens* (Human) |
| Q53XJ8_HUMAN | (Q53XJ8) | F2RL1 | Proteinase-activated | *Homo sapiens* (Human) |
| Q53XV0_HUMAN | (Q53XV0) | | Thrombin | *Homo sapiens* (Human) |
| Q53XV5_HUMAN | (Q53XV5) | | Leukotriene B4 receptor BLT1 | *Homo sapiens* (Human) |
| Q53XZ3_HUMAN | (Q53XZ3) | | Musc. acetylcholine Vertebrate type 1 | *Homo sapiens* (Human) |
| Q53Y09_HUMAN | (Q53Y09) | | Vasoactive intestinal polypeptide | *Homo sapiens* (Human) |
| Q53YA1_HUMAN | (Q53YA1) | CCBP2 | C-C Chemokine type X | *Homo sapiens* (Human) |
| Q53YJ4_HUMAN | (Q53YJ4) | GALR3 | Galanin | *Homo sapiens* (Human) |
| Q53YY0_HUMAN | (Q53YY0) | AGTR1 | Angiotensin type 1 | *Homo sapiens* (Human) |
| Q53ZR7_HUMAN | (Q53ZR7) | SSTR3 | Somatostatin type 3 | *Homo sapiens* (Human) |
| Q541E0_HUMAN | (Q541E0) | | Somatostatin type 5 | *Homo sapiens* (Human) |
| Q546Q1_HUMAN | (Q546Q1) | HTR4 | Serotonin type | *Homo sapiens* (Human) |
| Q548M6_HUMAN | (Q548M6) | HRH3 | Histamine type 3 | *Homo sapiens* (Human) |
| Q548Y0_HUMAN | (Q548Y0) | HCRTR2 | Orexin | *Homo sapiens* (Human) |
| Q549E0_HUMAN | (Q549E0) | CCR9 | C-C Chemokine type 9 | *Homo sapiens* (Human) |
| Q57Z87_HUMAN | (Q57Z87) | NTSR2 | fragments | *Homo sapiens* (Human) |
| Q59EH9_HUMAN | (Q59EH9) | | fragments | *Homo sapiens* (Human) |
| Q59ER8_HUMAN | (Q59ER8) | | fragments | *Homo sapiens* (Human) |
| Q59ES7_HUMAN | (Q59ES7) | | fragments | *Homo sapiens* (Human) |
| Q59FC0_HUMAN | (Q59FC0) | | fragments | *Homo sapiens* (Human) |
| Q59FW2_HUMAN | (Q59FW2) | | fragments | *Homo sapiens* (Human) |
| Q59G39_HUMAN | (Q59G39) | | fragments | *Homo sapiens* (Human) |
| Q59G72_HUMAN | (Q59G72) | | fragments | *Homo sapiens* (Human) |
| Q59G95_HUMAN | (Q59G95) | | fragments | *Homo sapiens* (Human) |
| Q59GA2_HUMAN | (Q59GA2) | | fragments | *Homo sapiens* (Human) |
| Q59GB1_HUMAN | (Q59GB1) | | fragments | *Homo sapiens* (Human) |
| Q59GE5_HUMAN | (Q59GE5) | glutamate receptor homolog | fragments | *Homo sapiens* (Human) |
| Q59GI0_HUMAN | (Q59GI0) | | fragments | *Homo sapiens* (Human) |
| Q59GL3_HUMAN | (Q59GL3) | | fragments | *Homo sapiens* (Human) |
| Q59GP3_HUMAN | (Q59GP3) | | fragments | *Homo sapiens* (Human) |
| Q59H16_HUMAN | (Q59H16) | | fragments | *Homo sapiens* (Human) |
| Q59HC2_HUMAN | (Q59HC2) | | fragments | *Homo sapiens* (Human) |
| Q59HG8_HUMAN | (Q59HG8) | | fragments | *Homo sapiens* (Human) |
| Q5CZ57_HUMAN | (Q5CZ57) | EP3-I | Prostaglandin E2 subtype EP3 | *Homo sapiens* (Human) |
| Q5CZ59_HUMAN | (Q5CZ59) | EP3e | Prostaglandin E2 subtype EP3 | *Homo sapiens* (Human) |
| Q5CZ60_HUMAN | (Q5CZ60) | EP3f | Prostaglandin E2 subtype EP3 | *Homo sapiens* (Human) |
| Q5CZ61_HUMAN | (Q5CZ61) | EP3-VI | Prostaglandin E2 subtype EP3 | *Homo sapiens* (Human) |
| Q5CZ62_HUMAN | (Q5CZ62) | EP3-V | Prostaglandin E2 subtype EP3 | *Homo sapiens* (Human) |
| Q5CZ63_HUMAN | (Q5CZ63) | EP3-IV | Prostaglandin E2 subtype EP3 | *Homo sapiens* (Human) |
| Q5CZ64_HUMAN | (Q5CZ64) | EP3-III | Prostaglandin E2 subtype EP3 | *Homo sapiens* (Human) |
| Q5EGP2_HUMAN | (Q5EGP2) | GPR112 | Putative/unclassified Class B GPCRs | *Homo sapiens* (Human) |
| Q5EKM8_HUMAN | (Q5EKM8) | CCR5 | C-C Chemokine type 5 | *Homo sapiens* (Human) |
| Q5EKM9_HUMAN | (Q5EKM9) | CCR5 | C-C Chemokine type 5 | *Homo sapiens* (Human) |
| Q5EKN0_HUMAN | (Q5EKN0) | CCR5 | C-C Chemokine type 5 | *Homo sapiens* (Human) |
| Q5HYM4_HUMAN | (Q5HYM4) | DKFZp686H1993 | fragments | *Homo sapiens* (Human) |
| Q5HYQ4_HUMAN | (Q5HYQ4) | GPR173 | SREB | *Homo sapiens* (Human) |
| Q5IFH6_HUMAN | (Q5IFH6) | GPR24 | Melanin-concentrating hormone receptors | *Homo sapiens* (Human) |

TABLE D-continued

| | | | non-limiting list human GPCRs | |
|---|---|---|---|---|
| Q5IFI4_HUMAN | (Q5IFI4) | GPR24 | Melanin-concentrating hormone receptors | *Homo sapiens* (Human) |
| Q5ISU3_HUMAN | (Q5ISU3) | PPYR1 | Neuropeptide Y type 4 | *Homo sapiens* (Human) |
| Q5INZ1_HUMAN | (Q5JNZ1) | DAQB-117O11.7-001 | fragments | *Homo sapiens* (Human) |
| Q5JPQ2_HUMAN | (Q5JPQ2) | GPR64 | Putative/unclassified Class B GPCRs | *Homo sapiens* (Human) |
| Q5JPQ3_HUMAN | (Q5JPQ3) | GPR64 | Putative/unclassified Class B GPCRs | *Homo sapiens* (Human) |
| Q5JPQ4_HUMAN | (Q5JPQ4) | GPR64 | Putative/unclassified Class B GPCRs | *Homo sapiens* (Human) |
| Q5JPQ5_HUMAN | (Q5JPQ5) | GPR64 | Putative/unclassified Class B GPCRs | *Homo sapiens* (Human) |
| Q5JPQ6_HUMAN | (Q5JPQ6) | GPR64 | Putative/unclassified Class B GPCRs | *Homo sapiens* (Human) |
| Q5JQT0_HUMAN | (Q5JQT0) | RP11-978I15.6 | Olfactory II fam 5/MOR172-224,249,254 | *Homo sapiens* (Human) |
| Q5JRH7_HUMAN | (Q5JRH7) | CNR2 | Cannabinoid | *Homo sapiens* (Human) |
| Q5JSM8_HUMAN | (Q5JSM8) | GPR101 | Putative/unclassified Class A GPCRs | *Homo sapiens* (Human) |
| Q5JU89_HUMAN | (Q5JU89) | GPR112 | fragments | *Homo sapiens* (Human) |
| Q5JUH7_HUMAN | (Q5JUH7) | EBI2 | EBV-induced | *Homo sapiens* (Human) |
| Q5JUH9_HUMAN | (Q5JUH9) | GPR18 | fragments | *Homo sapiens* (Human) |
| Q5JVI7_HUMAN | (Q5JVI7) | PTGFR | Prostaglandin F2-alpha | *Homo sapiens* (Human) |
| Q5JVK3_HUMAN | (Q5JVK3) | GPR112 | fragments | *Homo sapiens* (Human) |
| Q5JVL5_HUMAN | (Q5JVL5) | CNR1 | Cannabinoid | *Homo sapiens* (Human) |
| Q5KSY4_HUMAN | (Q5KSY4) | CCR5 | fragments | *Homo sapiens* (Human) |
| Q5KU14_HUMAN | (Q5KU14) | KPG_013 | Putative/unclassified Class A GPCRs | *Homo sapiens* (Human) |
| Q5KU17_HUMAN | (Q5KU17) | KPG_011 | Cysteinyl leukotriene | *Homo sapiens* (Human) |
| Q5KU18_HUMAN | (Q5KU18) | KPG_010 | Purinoceptor P2RY5,8,9,10 GPR35,92,174 | *Homo sapiens* (Human) |
| Q5KU19_HUMAN | (Q5KU19) | KPG_009 | Putative/unclassified Class B GPCRs | *Homo sapiens* (Human) |
| Q5KU20_HUMAN | (Q5KU20) | KPG_008 | Putative/unclassified Class B GPCRs | *Homo sapiens* (Human) |
| Q5KU21_HUMAN | (Q5KU21) | KPG_007 | Purinoceptor P2RY5,8,9,10 GPR35,92,174 | *Homo sapiens* (Human) |
| Q5KU22_HUMAN | (Q5KU22) | KPG_006 | Putative/unclassified Class B GPCRs | *Homo sapiens* (Human) |
| Q5KU27_HUMAN | (Q5KU27) | KPG_005 | Putative/unclassified Class A GPCRs | *Homo sapiens* (Human) |
| Q5KU28_HUMAN | (Q5KU28) | KPG_004 | Leukotriene B4 receptor BLT2 | *Homo sapiens* (Human) |
| Q5KU34_HUMAN | (Q5KU34) | KPG_003 | ETL receptors | *Homo sapiens* (Human) |
| Q5KU35_HUMAN | (Q5KU35) | KPG_002 | Purinoceptor P2RY12-14 GPR87 (UDP-Glucose) | *Homo sapiens* (Human) |
| Q5QIN9_HUMAN | (Q5QIN9) | CCR5 | C-C Chemokine type 5 | *Homo sapiens* (Human) |
| Q5QIP0_HUMAN | (Q5QIP0) | CCR5 | C-C Chemokine type 5 | *Homo sapiens* (Human) |
| Q5QIP1_HUMAN | (Q5QIP1) | CCR5 | C-C Chemokine type 5 | *Homo sapiens* (Human) |
| Q5RJ87_HUMAN | (Q5RJ87) | DAQB-36F16.7-002 | fragments | *Homo sapiens* (Human) |
| Q5S4P5_HUMAN | (Q5S4P5) | POGR | Olfactory I fam 51-52/MOR1-42 | *Homo sapiens* (Human) |
| Q5SQD8_HUMAN | (Q5SQD8) | EDG3 | Sphingosine 1-phosphate Edg-3 | *Homo sapiens* (Human) |
| Q5SQI9_HUMAN | (Q5SQI9) | XXbac-BCX92J3.1-001 | Olfactory II fam 5/MOR172-224,249,254 | *Homo sapiens* (Human) |
| Q5ST16_HUMAN | (Q5ST16) | DAQB-304F3.2-001 | Olfactory II fam 11/MOR106,121-122 | *Homo sapiens* (Human) |
| Q5ST27_HUMAN | (Q5ST27) | XXbac-BCX147D4.2-001 | Olfactory II fam 5/MOR172-224,249,254 | *Homo sapiens* (Human) |
| Q5ST39_HUMAN | (Q5ST39) | OR2J2 | Olfactory II fam 2/MOR256-262,270-285 | *Homo sapiens* (Human) |
| Q5STL4_HUMAN | (Q5STL4) | GABBR1 | fragments | *Homo sapiens* (Human) |
| Q5STL7_HUMAN | (Q5STL7) | GABBR1 | fragments | *Homo sapiens* (Human) |
| Q5SUJ6_HUMAN | (Q5SUJ6) | XXbac-BPG171B11.5-001 | Olfactory II fam 2/MOR256-262,270-285 | *Homo sapiens* (Human) |
| Q5SUJ7_HUMAN | (Q5SUJ7) | XXbac-BPG171B11.3-001 | Olfactory II fam 2/MOR256-262,270-285 | *Homo sapiens* (Human) |
| Q5SUJ8_HUMAN | (Q5SUJ8) | GABBR1 | GABA-B subtype 1 | *Homo sapiens* (Human) |
| Q5SUJ9_HUMAN | (Q5SUJ9) | GABBR1 | GABA-B subtype 1 | *Homo sapiens* (Human) |
| Q5SUK1_HUMAN | (Q5SUK1) | OR2H2 | Olfactory II fam 2/MOR256-262,270-285 | *Homo sapiens* (Human) |
| Q5SUL3_HUMAN | (Q5SUL3) | GABBR1 | GABA-B subtype 1 | *Homo sapiens* (Human) |
| Q5SUN5_HUMAN | (Q5SUN5) | MAS1L | Mas proto-oncogene & Mas-related (MRGs) | *Homo sapiens* (Human) |
| Q5SUN6_HUMAN | (Q5SUN6) | DAQB-12N14.4-001 | Olfactory II fam 2/MOR256-262,270-285 | *Homo sapiens* (Human) |
| Q5SUN7_HUMAN | (Q5SUN7) | XXbac-BPG13B8.1-001 | Olfactory II fam 10/MOR263-269 | *Homo sapiens* (Human) |
| Q5SUN9_HUMAN | (Q5SUN9) | XXbac-BPG13B8.6-001 | Olfactory II fam 12/MOR250 | *Homo sapiens* (Human) |
| Q5SWW2_HUMAN | (Q5SWW2) | ELTD1 | fragments | *Homo sapiens* (Human) |
| Q5SWW3_HUMAN | (Q5SWW3) | ELTD1 | ETL receptors | *Homo sapiens* (Human) |
| Q5SXP7_HUMAN | (Q5SXP7) | RP11-294K24.1-001 | GPR37/endothelin B-like | *Homo sapiens* (Human) |
| Q5SY22_HUMAN | (Q5SY22) | TAS1R1 | fragments | *Homo sapiens* (Human) |
| Q5SY23_HUMAN | (Q5SY23) | TAS1R1 | fragments | *Homo sapiens* (Human) |
| Q5SY24_HUMAN | (Q5SY24) | TAS1R1 | fragments | *Homo sapiens* (Human) |
| Q5T234_HUMAN | (Q5T234) | GPR123 | Putative/unclassified Class B GPCRs | *Homo sapiens* (Human) |
| Q5T261_HUMAN | (Q5T261) | EDG2 | fragments | *Homo sapiens* (Human) |
| Q5T2X9_HUMAN | (Q5T2X9) | PPYR1 | fragments | *Homo sapiens* (Human) |
| Q5T2Y7_HUMAN | (Q5T2Y7) | CELSR2 | Cadherin EGF LAG (CELSR) | *Homo sapiens* (Human) |
| Q5T5Y4_HUMAN | (Q5T5Y4) | ADRB1 | Beta Adrenoceptors type 1 | *Homo sapiens* (Human) |
| Q5T6D8_HUMAN | (Q5T6D8) | GPR147 | fragments | *Homo sapiens* (Human) |
| Q5T6K0_HUMAN | (Q5T6K0) | BAI2 | Brain-specific angiogenesis inhibitor (BAI) | *Homo sapiens* (Human) |
| Q5T7Z3_HUMAN | (Q5T7Z3) | RP11-64P14.4-001 | Olfactory II fam 1/MOR125-138,156 | *Homo sapiens* (Human) |
| Q5T8C0_HUMAN | (Q5T8C0) | HTR2A | Serotonin type 2 | *Homo sapiens* (Human) |

TABLE D-continued non-limiting list human GPCRs

| | | | | |
|---|---|---|---|---|
| Q5T8P3_HUMAN | (Q5T8P3) | GPR12 | GPR | *Homo sapiens* (Human) |
| Q5T9D2_HUMAN | (Q5T9D2) | LPHN2 | fragments | *Homo sapiens* (Human) |
| Q5TBX0_HUMAN | (Q5TBX0) | OPRM1 | Opioid type M | *Homo sapiens* (Human) |
| Q5TF06_HUMAN | (Q5TF06) | RP3-365O12.1-001 | Putative/unclassified Class B GPCRs | *Homo sapiens* (Human) |
| Q5TGK2_HUMAN | (Q5TGK2) | GPR161 | Putative/unclassified Class A GPCRs | *Homo sapiens* (Human) |
| Q5TGN7_HUMAN | (Q5TGN7) | GPR126 | Putative/unclassified Class B GPCRs | *Homo sapiens* (Human) |
| Q5TGZ1_HUMAN | (Q5TGZ1) | HTR6 | Serotonin type 6 | *Homo sapiens* (Human) |
| Q5TH86_HUMAN | (Q5TH86) | PTGER3 | Prostaglandin E2 subtype EP3 | *Homo sapiens* (Human) |
| Q5TH88_HUMAN | (Q5TH88) | PTGER3 | Prostaglandin E2 subtype EP3 | *Homo sapiens* (Human) |
| Q5U003_HUMAN | (Q5U003) | | C-C Chemokine type 1 | *Homo sapiens* (Human) |
| Q5U0H0_HUMAN | (Q5U0H0) | | Chemokine receptor-like 1 | *Homo sapiens* (Human) |
| Q5U5U4_HUMAN | (Q5U5U4) | PTGER1 | Prostaglandin E2 subtype EP1 | *Homo sapiens* (Human) |
| Q5VSV1_HUMAN | (Q5VSV1) | RP11-180D21.2-001 | Olfactory II fam 10/MOR263-269 | *Homo sapiens* (Human) |
| Q5VT13_HUMAN | (Q5VT13) | GPR82 | Putative/unclassified Class A GPCRs | *Homo sapiens* (Human) |
| Q5VT14_HUMAN | (Q5VT14) | GPR34 | Putative/unclassified Class A GPCRs | *Homo sapiens* (Human) |
| Q5VT23_HUMAN | (Q5VT23) | RP11-34P13.6-001 | Olfactory II fam 4/MOR225-248 | *Homo sapiens* (Human) |
| Q5VTM0_HUMAN | (Q5VTM0) | SLC31A2 | Orexin | *Homo sapiens* (Human) |
| Q5VTV7_HUMAN | (Q5VTV7) | GPR145 | Melanin-concentrating hormone receptors | *Homo sapiens* (Human) |
| Q5VUF8_HUMAN | (Q5VUF8) | HTR2C | Serotonin type 2 | *Homo sapiens* (Human) |
| Q5VUF9_HUMAN | (Q5VUF9) | HTR2C | fragments | *Homo sapiens* (Human) |
| Q5VUK8_HUMAN | (Q5VUK8) | NMBR | Bombesin | *Homo sapiens* (Human) |
| Q5VX01_HUMAN | (Q5VX01) | HTR7 | Serotonin type 7 | *Homo sapiens* (Human) |
| Q5VX02_HUMAN | (Q5VX02) | HTR7 | Serotonin type 7 | *Homo sapiens* (Human) |
| Q5VX03_HUMAN | (Q5VX03) | HTR7 | Serotonin type 7 | *Homo sapiens* (Human) |
| Q5VX04_HUMAN | (Q5VX04) | HTR7 | Serotonin type 7 | *Homo sapiens* (Human) |
| Q5VX75_HUMAN | (Q5VX75) | LPHN2 | Latrophilin type 2 | *Homo sapiens* (Human) |
| Q5VX77_HUMAN | (Q5VX77) | LPHN2 | Latrophilin type 2 | *Homo sapiens* (Human) |
| Q5VX78_HUMAN | (Q5VX78) | LPHN2 | Latrophilin type 2 | *Homo sapiens* (Human) |
| Q5VX79_HUMAN | (Q5VX79) | LPHN2 | Latrophilin type 2 | *Homo sapiens* (Human) |
| Q5VX80_HUMAN | (Q5VX80) | LPHN2 | Latrophilin type 2 | *Homo sapiens* (Human) |
| Q5VX81_HUMAN | (Q5VX81) | LPHN2 | Latrophilin type 2 | *Homo sapiens* (Human) |
| Q5VX82_HUMAN | (Q5VX82) | LPHN2 | Latrophilin type 2 | *Homo sapiens* (Human) |
| Q5VX83_HUMAN | (Q5VX83) | LPHN2 | Latrophilin type 2 | *Homo sapiens* (Human) |
| Q5VXR2_HUMAN | (Q5VXR2) | ADRA1D | Alpha Adrenoceptors type 1 | *Homo sapiens* (Human) |
| Q5VXY3_HUMAN | (Q5VXY3) | CHRM3 | fragments | *Homo sapiens* (Human) |
| Q5VY37_HUMAN | (Q5VY37) | BAI3 | Brain-specific angiogenesis inhibitor (BAI) | *Homo sapiens* (Human) |
| Q5VZX0_HUMAN | (Q5VZX0) | EDG2 | Lysophosphatidic acid Edg-2 | *Homo sapiens* (Human) |
| Q5W0G9_HUMAN | (Q5W0G9) | EDNRB | Endothelin | *Homo sapiens* (Human) |
| Q5W0N7_HUMAN | (Q5W0N7) | RP11-432E15.1 | LGR like (hormone receptors) | *Homo sapiens* (Human) |
| Q5Y190_HUMAN | (Q5Y190) | RESDA1 | Cadherin EGF LAG (CELSR) | *Homo sapiens* (Human) |
| Q5ZGL8_HUMAN | (Q5ZGL8) | HCTR-6 | fragments | *Homo sapiens* (Human) |
| Q5ZGX3_HUMAN | (Q5ZGX3) | 5HT1A | Serotonin type 1 | *Homo sapiens* (Human) |
| Q63ZY2_HUMAN | (Q63ZY2) | GPR30 | Chemokine receptor-like 2 | *Homo sapiens* (Human) |
| Q645Y1_HUMAN | (Q645Y1) | TAS2R7 | Taste receptors T2R | *Homo sapiens* (Human) |
| Q659U6_HUMAN | (Q659U6) | HCTR-5 | fragments | *Homo sapiens* (Human) |
| Q66K38_HUMAN | (Q66K38) | MC1R | Melanocyte stimulating hormone | *Homo sapiens* (Human) |
| Q66X57_HUMAN | (Q66X57) | | Olfactory I fam 51-52/MOR1-42 | *Homo sapiens* (Human) |
| Q684M0_HUMAN | (Q684M0) | HTR4 | Serotonin type 4 | *Homo sapiens* (Human) |
| Q68CR4_HUMAN | (Q68CR4) | DKFZp781I1948 | Rhodopsin Vertebrate type 2 | *Homo sapiens* (Human) |
| Q68DM8_HUMAN | (Q68DM8) | DKFZp686O088 | Bradykinin | *Homo sapiens* (Human) |
| Q6B0G7_HUMAN | (Q6B0G7) | CNR2 | Cannabinoid | *Homo sapiens* (Human) |
| Q6DHZ4_HUMAN | (Q6DHZ4) | GPR126 | Putative/unclassified Class B GPCRs | *Homo sapiens* (Human) |
| Q6DJW7_HUMAN | (Q6DJW7) | OR6W1P | fragments | *Homo sapiens* (Human) |
| Q6DKN4_HUMAN | (Q6DKN4) | P2RY13 | fragments | *Homo sapiens* (Human) |
| Q6F3F5_HUMAN | (Q6F3F5) | DREG | Putative/unclassified Class B GPCRs | *Homo sapiens* (Human) |
| Q6F3F6_HUMAN | (Q6F3F6) | GPR126 | Putative/unclassified Class B GPCRs | *Homo sapiens* (Human) |
| Q6F3F7_HUMAN | (Q6F3F7) | DREG | Putative/unclassified Class B GPCRs | *Homo sapiens* (Human) |
| Q6F3F8_HUMAN | (Q6F3F8) | DREG | Putative/unclassified Class B GPCRs | *Homo sapiens* (Human) |
| Q6FGM5_HUMAN | (Q6FGM5) | OPRL1 | Opioid type X | *Homo sapiens* (Human) |
| Q6FH06_HUMAN | (Q6FH06) | PPYR1 | fragments | *Homo sapiens* (Human) |
| Q6FH34_HUMAN | (Q6FH34) | DRD1 | fragments | *Homo sapiens* (Human) |
| Q6FHI8_HUMAN | (Q6FHI8) | GPR35 | Purinoceptor P2RY5,8,9,10 GPR35,92,174 | *Homo sapiens* (Human) |
| Q6FHK3_HUMAN | (Q6FHK3) | ADORA1 | fragments | *Homo sapiens* (Human) |
| Q6FHL1_HUMAN | (Q6FHL1) | GPR30 | Chemokine receptor-like 2 | *Homo sapiens* (Human) |
| Q6FHU6_HUMAN | (Q6FHU6) | GPR30 | fragments | *Homo sapiens* (Human) |
| Q6GMT1_HUMAN | (Q6GMT1) | OPN3 | fragments | *Homo sapiens* (Human) |
| Q6GMT4_HUMAN | (Q6GMT4) | ADRB2 | Beta Adrenoceptors type 2 | *Homo sapiens* (Human) |
| Q6GPG7_HUMAN | (Q6GPG7) | EDG2 | Lysophosphatidic acid Edg-2 | *Homo sapiens* (Human) |
| Q6GTR7_HUMAN | (Q6GTR7) | NPY5R | Neuropeptide Y type 5 | *Homo sapiens* (Human) |
| Q6I939_HUMAN | (Q6I939) | OR17-219 | fragments | *Homo sapiens* (Human) |
| Q6I940_HUMAN | (Q6I940) | OR17-207 | fragments | *Homo sapiens* (Human) |
| Q6I941_HUMAN | (Q6I941) | OR17-82 | fragments | *Homo sapiens* (Human) |
| Q6IBH2_HUMAN | (Q6IBH2) | GPR19 | GPR | *Homo sapiens* (Human) |
| Q6IET8_HUMAN | (Q6IET8) | RP1-154J13.4-001 | Olfactory II fam 13/MOR253 | *Homo sapiens* (Human) |

TABLE D-continued non-limiting list human GPCRs

| | | | | |
|---|---|---|---|---|
| Q6IET9_HUMAN | (Q6IET9) | OR12D2 | Olfactory II fam 12/MOR250 | *Homo sapiens* (Human) |
| Q6IEU0_HUMAN | (Q6IEU0) | OR2W1 | Olfactory II fam 2/MOR256-262,270-285 | *Homo sapiens* (Human) |
| Q6IEU2_HUMAN | (Q6IEU2) | | Olfactory II fam 5/MOR172-224,249,254 | *Homo sapiens* (Human) |
| Q6IEV0_HUMAN | (Q6IEV0) | | Olfactory II fam 9/MOR120 | *Homo sapiens* (Human) |
| Q6IEV1_HUMAN | (Q6IEV1) | | Olfactory II fam 9/MOR120 | *Homo sapiens* (Human) |
| Q6IEV3_HUMAN | (Q6IEV3) | | Olfactory II fam 10/MOR263-269 | *Homo sapiens* (Human) |
| Q6IEW6_HUMAN | (Q6IEW6) | | Olfactory II fam 8/MOR161-171 | *Homo sapiens* (Human) |
| Q6IEW7_HUMAN | (Q6IEW7) | | Olfactory II fam 8/MOR161-171 | *Homo sapiens* (Human) |
| Q6IEX0_HUMAN | (Q6IEX0) | | Olfactory II fam 11/MOR106,121-122 | *Homo sapiens* (Human) |
| Q6IEX5_HUMAN | (Q6IEX5) | | Olfactory II fam 4/MOR225-248 | *Homo sapiens* (Human) |
| Q6IEY2_HUMAN | (Q6IEY2) | | Olfactory II fam 4/MOR225-248 | *Homo sapiens* (Human) |
| Q6IEY3_HUMAN | (Q6IEY3) | | Olfactory II fam 4/MOR225-248 | *Homo sapiens* (Human) |
| Q6IEZ1_HUMAN | (Q6IEZ1) | | Olfactory II fam 2/MOR256-262,270-285 | *Homo sapiens* (Human) |
| Q6IEZ2_HUMAN | (Q6IEZ2) | | Olfactory II fam 5/MOR172-224,249,254 | *Homo sapiens* (Human) |
| Q6IEZ4_HUMAN | (Q6IEZ4) | | Olfactory II fam 4/MOR225-248 | *Homo sapiens* (Human) |
| Q6IEZ6_HUMAN | (Q6IEZ6) | OR5BF1 | Olfactory II fam 5/MOR172-224,249,254 | *Homo sapiens* (Human) |
| Q6IF01_HUMAN | (Q6IF01) | | Olfactory II fam 6/MOR103-105,107-119 | *Homo sapiens* (Human) |
| Q6IF09_HUMAN | (Q6IF09) | | Olfactory II fam 11/MOR106,121-122 | *Homo sapiens* (Human) |
| Q6IF12_HUMAN | (Q6IF12) | | Olfactory II fam 4/MOR225-248 | *Homo sapiens* (Human) |
| Q6IF17_HUMAN | (Q6IF17) | RP11-112J3.12-001 | Olfactory II fam 1/MOR125-138,156 | *Homo sapiens* (Human) |
| Q6IF20_HUMAN | (Q6IF20) | | Olfactory II fam 13/MOR253 | *Homo sapiens* (Human) |
| Q6IF23_HUMAN | (Q6IF23) | OR12D3 | Olfactory II fam 12/MOR250 | *Homo sapiens* (Human) |
| Q6IF24_HUMAN | (Q6IF24) | OR2J2 | Olfactory II fam 2/MOR256-262,270-285 | *Homo sapiens* (Human) |
| Q6IF25_HUMAN | (Q6IF25) | DAQB-117O11.4-001 | Olfactory II fam 2/MOR256-262,270-285 | *Homo sapiens* (Human) |
| Q6IF31_HUMAN | (Q6IF31) | OR52A1 | Olfactory I fam 51-52 MOR1-42 | *Homo sapiens* (Human) |
| Q6IF34_HUMAN | (Q6IF34) | | Olfactory II fam 2/MOR256-262,270-285 | *Homo sapiens* (Human) |
| Q6IF35_HUMAN | (Q6IF35) | | Olfactory II fam 6/MOR103-105,107-119 | *Homo sapiens* (Human) |
| Q6IF36_HUMAN | (Q6IF36) | | Olfactory II fam 8/MOR161-171 | *Homo sapiens* (Human) |
| Q6IF40_HUMAN | (Q6IF40) | | Olfactory II fam 2/MOR256-262,270-285 | *Homo sapiens* (Human) |
| Q6IF41_HUMAN | (Q6IF41) | | Olfactory II fam 2/MOR256-262,270-285 | *Homo sapiens* (Human) |
| Q6IF43_HUMAN | (Q6IF43) | | Olfactory II fam 2/MOR256-262,270-285 | *Homo sapiens* (Human) |
| Q6IF44_HUMAN | (Q6IF44) | | Olfactory II fam 2/MOR256-262,270-285 | *Homo sapiens* (Human) |
| Q6IF46_HUMAN | (Q6IF46) | | Olfactory II fam 5/MOR172-224,249,254 | *Homo sapiens* (Human) |
| Q6IF50_HUMAN | (Q6IF50) | RP11-317C20.1-001 | Olfactory II fam 13/MOR253 | *Homo sapiens* (Human) |
| Q6IF51_HUMAN | (Q6IF51) | RP11-317C20.4-001 | Olfactory II fam 13/MOR253 | *Homo sapiens* (Human) |
| Q6IF52_HUMAN | (Q6IF52) | | Olfactory II fam 13/MOR253 | *Homo sapiens* (Human) |
| Q6IF53_HUMAN | (Q6IF53) | RP11-317C20.6-001 | Olfactory II fam 13/MOR253 | *Homo sapiens* (Human) |
| Q6IF54_HUMAN | (Q6IF54) | RP11-413C10.2-001 | Olfactory II fam 13/MOR253 | *Homo sapiens* (Human) |
| Q6IF55_HUMAN | (Q6IF55) | | Olfactory II fam 2/MOR256-262,270-285 | *Homo sapiens* (Human) |
| Q6IF56_HUMAN | (Q6IF56) | | Olfactory II fam 4/MOR225-248 | *Homo sapiens* (Human) |
| Q6IF57_HUMAN | (Q6IF57) | | Olfactory II fam 4/MOR225-248 | *Homo sapiens* (Human) |
| Q6IF58_HUMAN | (Q6IF58) | | Olfactory II fam 10/MOR263-269 | *Homo sapiens* (Human) |
| Q6IF59_HUMAN | (Q6IF59) | | Olfactory II fam 10/MOR263-269 | *Homo sapiens* (Human) |
| Q6IF60_HUMAN | (Q6IF60) | | Olfactory II fam 5/MOR172-224,249,254 | *Homo sapiens* (Human) |
| Q6IF61_HUMAN | (Q6IF61) | | Olfactory II fam 5/MOR172-224,249,254 | *Homo sapiens* (Human) |
| Q6IF62_HUMAN | (Q6IF62) | | Olfactory II fam 9/MOR120 | *Homo sapiens* (Human) |
| Q6IF65_HUMAN | (Q6IF65) | | Olfactory II fam 5/MOR172-224,249,254 | *Homo sapiens* (Human) |
| Q6IF66_HUMAN | (Q6IF66) | | Olfactory II fam 5/MOR172-224,249,254 | *Homo sapiens* (Human) |
| Q6IF67_HUMAN | (Q6IF67) | | Olfactory II fam 5/MOR172-224,249,254 | *Homo sapiens* (Human) |
| Q6IF68_HUMAN | (Q6IF68) | | Olfactory II fam 5/MOR172-224,249,254 | *Homo sapiens* (Human) |
| Q6IF69_HUMAN | (Q6IF69) | | Olfactory II fam 5/MOR172-224,249,254 | *Homo sapiens* (Human) |
| Q6IF70_HUMAN | (Q6IF70) | | Olfactory II fam 6/MOR103-105,107-119 | *Homo sapiens* (Human) |
| Q6IF71_HUMAN | (Q6IF71) | | Olfactory II fam 9/MOR120 | *Homo sapiens* (Human) |
| Q6IF72_HUMAN | (Q6IF72) | | Olfactory II fam 4/MOR225-248 | *Homo sapiens* (Human) |
| Q6IF73_HUMAN | (Q6IF73) | | Olfactory II fam 4/MOR225-248 | *Homo sapiens* (Human) |
| Q6IF74_HUMAN | (Q6IF74) | | Olfactory II fam 4/MOR225-248 | *Homo sapiens* (Human) |
| Q6IF77_HUMAN | (Q6IF77) | | Olfactory I fam 51-52/MOR1-42 | *Homo sapiens* (Human) |
| Q6IF78_HUMAN | (Q6IF78) | | Olfactory I fam 51-52/MOR1-42 | *Homo sapiens* (Human) |
| Q6IF79_HUMAN | (Q6IF79) | | Olfactory I fam 51-52/MOR1-42 | *Homo sapiens* (Human) |
| Q6IF85_HUMAN | (Q6IF85) | | Olfactory II fam 5/MOR172-224,249,254 | *Homo sapiens* (Human) |
| Q6IF86_HUMAN | (Q6IF86) | | Olfactory II fam 13/MOR253 | *Homo sapiens* (Human) |
| Q6IF87_HUMAN | (Q6IF87) | | Olfactory II fam 5/MOR172-224,249,254 | *Homo sapiens* (Human) |
| Q6IF88_HUMAN | (Q6IF88) | | Olfactory II fam 5/MOR172-224,249,254 | *Homo sapiens* (Human) |
| Q6IF89_HUMAN | (Q6IF89) | OR2B6 | Olfactory II fam 2/MOR256-262,270-285 | *Homo sapiens* (Human) |
| Q6IF91_HUMAN | (Q6IF91) | | Olfactory I fam 51-52/MOR1-42 | *Homo sapiens* (Human) |
| Q6IF93_HUMAN | (Q6IF93) | | Olfactory I fam 51-52/MOR1-42 | *Homo sapiens* (Human) |
| Q6IF94_HUMAN | (Q6IF94) | | Olfactory I fam 51-52/MOR1-42 | *Homo sapiens* (Human) |
| Q6IF95_HUMAN | (Q6IF95) | | Olfactory II fam 4/MOR225-248 | *Homo sapiens* (Human) |
| Q6IF96_HUMAN | (Q6IF96) | | Olfactory II fam 5/MOR172-224,249,254 | *Homo sapiens* (Human) |
| Q6IFA1_HUMAN | (Q6IFA1) | | Olfactory II fam 2/MOR256-262,270-285 | *Homo sapiens* (Human) |
| Q6IFA2_HUMAN | (Q6IFA2) | | Olfactory II fam 4/MOR225-248 | *Homo sapiens* (Human) |
| Q6IFA3_HUMAN | (Q6IFA3) | | Olfactory II fam 4/MOR225-248 | *Homo sapiens* (Human) |
| Q6IFA4_HUMAN | (Q6IFA4) | | Olfactory II fam 4/MOR225-248 | *Homo sapiens* (Human) |
| Q6IFA5_HUMAN | (Q6IFA5) | | Olfactory II fam 4/MOR225-248 | *Homo sapiens* (Human) |
| Q6IFA7_HUMAN | (Q6IFA7) | | Olfactory II fam 4/MOR225-248 | *Homo sapiens* (Human) |

TABLE D-continued non-limiting list human GPCRs

| | | | | |
|---|---|---|---|---|
| Q6IFA8_HUMAN | (Q6IFA8) | | Olfactory II fam 10/MOR263-269 | *Homo sapiens* (Human) |
| Q6IFA9_HUMAN | (Q6IFA9) | | Olfactory II fam 1/MOR125-138,156 | *Homo sapiens* (Human) |
| Q6IFB0_HUMAN | (Q6IFB0) | | Olfactory II fam 1/MOR125-138,156 | *Homo sapiens* (Human) |
| Q6IFB4_HUMAN | (Q6IFB4) | | Olfactory II fam 4/MOR225-248 | *Homo sapiens* (Human) |
| Q6IFB5_HUMAN | (Q6IFB5) | | Olfactory II fam 8/MOR161-171 | *Homo sapiens* (Human) |
| Q6IFB6_HUMAN | (Q6IFB6) | | Olfactory II fam 8/MOR161-171 | *Homo sapiens* (Human) |
| Q6IFB7_HUMAN | (Q6IFB7) | | Olfactory II fam 8/MOR161-171 | *Homo sapiens* (Human) |
| Q6IFB8_HUMAN | (Q6IFB8) | | Olfactory II fam 5/MOR172-224,249,254 | *Homo sapiens* (Human) |
| Q6IFB9_HUMAN | (Q6IFB9) | | Olfactory II fam 5/MOR172-224,249,254 | *Homo sapiens* (Human) |
| Q6IFC0_HUMAN | (Q6IFC0) | | Olfactory II fam 8/MOR161-171 | *Homo sapiens* (Human) |
| Q6IFC1_HUMAN | (Q6IFC1) | | Olfactory II fam 8/MOR161-171 | *Homo sapiens* (Human) |
| Q6IFC2_HUMAN | (Q6IFC2) | | Olfactory II fam 8/MOR161-171 | *Homo sapiens* (Human) |
| Q6IFC3_HUMAN | (Q6IFC3) | | Olfactory II fam 8/MOR161-171 | *Homo sapiens* (Human) |
| Q6IFC4_HUMAN | (Q6IFC4) | | Olfactory II fam 8/MOR161-171 | *Homo sapiens* (Human) |
| Q6IFC5_HUMAN | (Q6IFC5) | | Olfactory II fam 8/MOR161-171 | *Homo sapiens* (Human) |
| Q6IFC7_HUMAN | (Q6IFC7) | | Olfactory II fam 5/MOR172-224,249,254 | *Homo sapiens* (Human) |
| Q6IFC8_HUMAN | (Q6IFC8) | | Olfactory II fam 5/MOR172-224,249,254 | *Homo sapiens* (Human) |
| Q6IFC9_HUMAN | (Q6IFC9) | | Olfactory II fam 5/MOR172-224,249,254 | *Homo sapiens* (Human) |
| Q6IFD0_HUMAN | (Q6IFD0) | | Olfactory II fam 5/MOR172-224,249,254 | *Homo sapiens* (Human) |
| Q6IFD1_HUMAN | (Q6IFD1) | | fragments | *Homo sapiens* (Human) |
| Q6IFD3_HUMAN | (Q6IFD3) | | Olfactory II fam 5/MOR172-224,249,254 | *Homo sapiens* (Human) |
| Q6IFD4_HUMAN | (Q6IFD4) | | Olfactory II fam 5/MOR172-224,249,254 | *Homo sapiens* (Human) |
| Q6IFD5_HUMAN | (Q6IFD5) | | Olfactory II fam 10/MOR263-269 | *Homo sapiens* (Human) |
| Q6IFD6_HUMAN | (Q6IFD6) | | Olfactory II fam 9/MOR120 | *Homo sapiens* (Human) |
| Q6IFD7_HUMAN | (Q6IFD7) | | Olfactory I fam 51-52/MOR1-42 | *Homo sapiens* (Human) |
| Q6IFD9_HUMAN | (Q6IFD9) | | Olfactory II fam 10/MOR263-269 | *Homo sapiens* (Human) |
| Q6IFE0_HUMAN | (Q6IFE0) | | Olfactory II fam 5/MOR172-224,249,254 | *Homo sapiens* (Human) |
| Q6IFE1_HUMAN | (Q6IFE1) | | Olfactory II fam 5/MOR172-224,249,254 | *Homo sapiens* (Human) |
| Q6IFE4_HUMAN | (Q6IFE4) | | Olfactory I fam 51-52/MOR1-42 | *Homo sapiens* (Human) |
| Q6IFE5_HUMAN | (Q6IFE5) | | Olfactory I fam 51-52/MOR1-42 | *Homo sapiens* (Human) |
| Q6IFE7_HUMAN | (Q6IFE7) | | Olfactory II fam 6/MOR103-105,107-119 | *Homo sapiens* (Human) |
| Q6IFE8_HUMAN | (Q6IFE8) | | Olfactory II fam 10/MOR263-269 | *Homo sapiens* (Human) |
| Q6IFE9_HUMAN | (Q6IFE9) | | Olfactory II fam 8/MOR161-171 | *Homo sapiens* (Human) |
| Q6IFF2_HUMAN | (Q6IFF2) | | Olfactory II fam 5/MOR172-224,249,254 | *Homo sapiens* (Human) |
| Q6IFF4_HUMAN | (Q6IFF4) | | Olfactory II fam 5/MOR172-224,249,254 | *Homo sapiens* (Human) |
| Q6IFF6_HUMAN | (Q6IFF6) | | Olfactory I fam 51-52/MOR1-42 | *Homo sapiens* (Human) |
| Q6IFF7_HUMAN | (Q6IFF7) | | Olfactory I fam 51-52/MOR1-42 | *Homo sapiens* (Human) |
| Q6IFF8_HUMAN | (Q6IFF8) | | Olfactory I fam 51-52/MOR1-42 | *Homo sapiens* (Human) |
| Q6IFF9_HUMAN | (Q6IFF9) | | Olfactory I fam 51-52/MOR1-42 | *Homo sapiens* (Human) |
| Q6IFG0_HUMAN | (Q6IFG0) | | Olfactory I fam 51-52/MOR1-42 | *Homo sapiens* (Human) |
| Q6IFG2_HUMAN | (Q6IFG2) | | Olfactory I fam 51-52/MOR1-42 | *Homo sapiens* (Human) |
| Q6IFG3_HUMAN | (Q6IFG3) | | Olfactory II fam 1/MOR125-138,156 | *Homo sapiens* (Human) |
| Q6IFG4_HUMAN | (Q6IFG4) | | Olfactory II fam 10/MOR263-269 | *Homo sapiens* (Human) |
| Q6IFG5_HUMAN | (Q6IFG5) | | Olfactory II fam 1/MOR125-138,156 | *Homo sapiens* (Human) |
| Q6IFG6_HUMAN | (Q6IFG6) | | Olfactory II fam 10/MOR263-269 | *Homo sapiens* (Human) |
| Q6IFG7_HUMAN | (Q6IFG7) | | Olfactory II fam 2/MOR256-262,270-285 | *Homo sapiens* (Human) |
| Q6IFG8_HUMAN | (Q6IFG8) | | Olfactory II fam 2/MOR256-262,270-285 | *Homo sapiens* (Human) |
| Q6IFG9_HUMAN | (Q6IFG9) | | Olfactory II fam 10/MOR263-269 | *Homo sapiens* (Human) |
| Q6IFH0_HUMAN | (Q6IFH0) | | Olfactory II fam 9/MOR120 | *Homo sapiens* (Human) |
| Q6IFH1_HUMAN | (Q6IFH1) | | Olfactory II fam 6/MOR103-105,107-119 | *Homo sapiens* (Human) |
| Q6IFH2_HUMAN | (Q6IFH2) | OR10J5 | Olfactory II fam 10/MOR263-269 | *Homo sapiens* (Human) |
| Q6IFH6_HUMAN | (Q6IFH6) | | Olfactory I fam 51-52/MOR1-42 | *Homo sapiens* (Human) |
| Q6IFH7_HUMAN | (Q6IFH7) | | Olfactory I fam 51-52/MOR1-42 | *Homo sapiens* (Human) |
| Q6IFH8_HUMAN | (Q6IFH8) | | Olfactory I fam 51-52/MOR1-42 | *Homo sapiens* (Human) |
| Q6IFH9_HUMAN | (Q6IFH9) | | Olfactory I fam 51-52/MOR1-42 | *Homo sapiens* (Human) |
| Q6IFI0_HUMAN | (Q6IFI0) | | Olfactory I fam 51-52/MOR1-42 | *Homo sapiens* (Human) |
| Q6IFI1_HUMAN | (Q6IFI1) | | Olfactory I fam 51-52/MOR1-42 | *Homo sapiens* (Human) |
| Q6IFI2_HUMAN | (Q6IFI2) | | Olfactory I fam 51-52/MOR1-42 | *Homo sapiens* (Human) |
| Q6IFI3_HUMAN | (Q6IFI3) | | Olfactory I fam 51-52/MOR1-42 | *Homo sapiens* (Human) |
| Q6IFI4_HUMAN | (Q6IFI4) | | Olfactory II fam 9/MOR120 | *Homo sapiens* (Human) |
| Q6IFI5_HUMAN | (Q6IFI5) | | Olfactory II fam 13/MOR253 | *Homo sapiens* (Human) |
| Q6IFI7_HUMAN | (Q6IFI7) | | Olfactory I fam 51-52/MOR1-42 | *Homo sapiens* (Human) |
| Q6IFI8_HUMAN | (Q6IFI8) | | Olfactory II fam 2/MOR256-262,270-285 | *Homo sapiens* (Human) |
| Q6IFI9_HUMAN | (Q6IFI9) | | Olfactory II fam 1/MOR125-138,156 | *Homo sapiens* (Human) |
| Q6IFJ0_HUMAN | (Q6IFJ0) | | Olfactory II fam 10/MOR263-269 | *Homo sapiens* (Human) |
| Q6IFJ2_HUMAN | (Q6IFJ2) | | Olfactory II fam 10/MOR263-269 | *Homo sapiens* (Human) |
| Q6IFJ3_HUMAN | (Q6IFJ3) | | Olfactory II fam 1/MOR125-138,156 | *Homo sapiens* (Human) |
| Q6IFJ4_HUMAN | (Q6IFJ4) | | Olfactory II fam 7/MOR139-155 | *Homo sapiens* (Human) |
| Q6IFJ5_HUMAN | (Q6IFJ5) | | Olfactory II fam 7/MOR139-155 | *Homo sapiens* (Human) |
| Q6IFJ6_HUMAN | (Q6IFJ6) | | Olfactory II fam 7/MOR139-155 | *Homo sapiens* (Human) |
| Q6IFJ7_HUMAN | (Q6IFJ7) | | Olfactory II fam 7/MOR139-155 | *Homo sapiens* (Human) |
| Q6IFJ8_HUMAN | (Q6IFJ8) | | Olfactory I fam 51-52/MOR1-42 | *Homo sapiens* (Human) |
| Q6IFJ9_HUMAN | (Q6IFJ9) | | Olfactory II fam 6/MOR103-105,107-119 | *Homo sapiens* (Human) |
| Q6IFK1_HUMAN | (Q6IFK1) | | Olfactory II fam 6/MOR103-105,107-119 | *Homo sapiens* (Human) |
| Q6IFK4_HUMAN | (Q6IFK4) | | Olfactory I fam 51-52/MOR1-42 | *Homo sapiens* (Human) |
| Q6IFK5_HUMAN | (Q6IFK5) | | Olfactory I fam 51-52/MOR1-42 | *Homo sapiens* (Human) |
| Q6IFK7_HUMAN | (Q6IFK7) | | Olfactory I fam 51-52/MOR1-42 | *Homo sapiens* (Human) |
| Q6IFK8_HUMAN | (Q6IFK8) | | Olfactory I fam 51-52/MOR1-42 | *Homo sapiens* (Human) |

TABLE D-continued

| | | | non-limiting list human GPCRs | |
|---|---|---|---|---|
| Q6IFK9_HUMAN | (Q6IFK9) | | Olfactory I fam 51-52/MOR1-42 | Homo sapiens (Human) |
| Q6IFL0_HUMAN | (Q6IFL0) | | Olfactory I fam 51-52/MOR1-42 | Homo sapiens (Human) |
| Q6IFL1_HUMAN | (Q6IFL1) | RP11-413C10.1-001 | Olfactory II fam 13/MOR253 | Homo sapiens (Human) |
| Q6IFL2_HUMAN | (Q6IFL2) | RP11-413C10.9-001 | Olfactory II fam 13/MOR253 | Homo sapiens (Human) |
| Q6IFL7_HUMAN | (Q6IFL7) | | Olfactory II fam 1/MOR125-138,156 | Homo sapiens (Human) |
| Q6IFL8_HUMAN | (Q6IFL8) | OR1D2 | Olfactory II fam 1/MOR125-138,156 | Homo sapiens (Human) |
| Q6IFL9_HUMAN | (Q6IFL9) | | Olfactory II fam 1/MOR125-138,156 | Homo sapiens (Human) |
| Q6IFM2_HUMAN | (Q6IFM2) | | Olfactory II fam 1/MOR125-138,156 | Homo sapiens (Human) |
| Q6IFM3_HUMAN | (Q6IFM3) | OR3A2 | Olfactory II fam 3/MOR255 | Homo sapiens (Human) |
| Q6IFM4_HUMAN | (Q6IFM4) | OR3A1 | Olfactory II fam 3/MOR255 | Homo sapiens (Human) |
| Q6IFM5_HUMAN | (Q6IFM5) | | Olfactory II fam 1/MOR125-138,156 | Homo sapiens (Human) |
| Q6IFM6_HUMAN | (Q6IFM6) | OR3A3 | Olfactory II fam 3/MOR255 | Homo sapiens (Human) |
| Q6IFM7_HUMAN | (Q6IFM7) | | Olfactory II fam 1/MOR125-138,156 | Homo sapiens (Human) |
| Q6IFM8_HUMAN | (Q6IFM8) | | Olfactory II fam 1/MOR125-138,156 | Homo sapiens (Human) |
| Q6IFM9_HUMAN | (Q6IFM9) | | Olfactory II fam 5/MOR172-224,249,254 | Homo sapiens (Human) |
| Q6IFN0_HUMAN | (Q6IFN0) | | Olfactory II fam 1/MOR125-138,156 | Homo sapiens (Human) |
| Q6IFN2_HUMAN | (Q6IFN2) | | Olfactory II fam 1/MOR125-138,156 | Homo sapiens (Human) |
| Q6IFN5_HUMAN | (Q6IFN5) | | Olfactory II fam 7/MOR139-155 | Homo sapiens (Human) |
| Q6IFN7_HUMAN | (Q6IFN7) | | Olfactory II fam 2/MOR256-262,270-285 | Homo sapiens (Human) |
| Q6IFP1_HUMAN | (Q6IFP1) | OR7A5 | Olfactory II fam 7/MOR139-155 | Homo sapiens (Human) |
| Q6IFP2_HUMAN | (Q6IFP2) | | Olfactory II fam 7/MOR139-155 | Homo sapiens (Human) |
| Q6IFP3_HUMAN | (Q6IFP3) | | Olfactory II fam 4/MOR225-248 | Homo sapiens (Human) |
| Q6IFP4_HUMAN | (Q6IFP4) | | Olfactory II fam 2/MOR256-262,270-285 | Homo sapiens (Human) |
| Q6IFP6_HUMAN | (Q6IFP6) | | Olfactory II fam 6/MOR103-105,107-119 | Homo sapiens (Human) |
| Q6IFP7_HUMAN | (Q6IFP7) | OR2F1 | Olfactory II fam 2/MOR256-262,270-285 | Homo sapiens (Human) |
| Q6IFP9_HUMAN | (Q6IFP9) | | Olfactory II fam 7/MOR139-155 | Homo sapiens (Human) |
| Q6IFQ0_HUMAN | (Q6IFQ0) | | Olfactory II fam 10/MOR263-269 | Homo sapiens (Human) |
| Q6IFQ1_HUMAN | (Q6IFQ1) | OR10H2 | Olfactory II fam 10/MOR263-269 | Homo sapiens (Human) |
| Q6IFQ2_HUMAN | (Q6IFQ2) | | Olfactory II fam 10/MOR263-269 | Homo sapiens (Human) |
| Q6IFQ5_HUMAN | (Q6IFQ5) | DAQB-304F3.1-001 | Olfactory II fam 10/MOR263-269 | Homo sapiens (Human) |
| Q6IFQ6_HUMAN | (Q6IFQ6) | OR7A17 | Olfactory II fam 7/MOR139-155 | Homo sapiens (Human) |
| Q6IFQ7_HUMAN | (Q6IFQ7) | | Olfactory II fam 8/MOR161-171 | Homo sapiens (Human) |
| Q6IFQ8_HUMAN | (Q6IFQ8) | | Olfactory II fam 8/MOR161-171 | Homo sapiens (Human) |
| Q6IFR0_HUMAN | (Q6IFR0) | | Olfactory II fam 8/MOR161-171 | Homo sapiens (Human) |
| Q6IFR1_HUMAN | (Q6IFR1) | | Olfactory II fam 10/MOR263-269 | Homo sapiens (Human) |
| Q6IFR2_HUMAN | (Q6IFR2) | OR6N2 | Olfactory II fam 6/MOR103-105,107-119 | Homo sapiens (Human) |
| Q6IFR3_HUMAN | (Q6IFR3) | | Olfactory II fam 6/MOR103-105,107-119 | Homo sapiens (Human) |
| Q6IFR4_HUMAN | (Q6IFR4) | | Olfactory II fam 6/MOR103-105,107-119 | Homo sapiens (Human) |
| Q6IFR5_HUMAN | (Q6IFR5) | | Olfactory II fam 6/MOR103-105,107-119 | Homo sapiens (Human) |
| Q6IFR6_HUMAN | (Q6IFR6) | OR6K2 | Olfactory II fam 6/MOR103-105,107-119 | Homo sapiens (Human) |
| Q6IFR7_HUMAN | (Q6IFR7) | | Olfactory II fam 10/MOR263-269 | Homo sapiens (Human) |
| Q6IFS1_HUMAN | (Q6IFS1) | | Olfactory II fam 10/MOR263-269 | Homo sapiens (Human) |
| Q6IFS2_HUMAN | (Q6IFS2) | OR10K1 | Olfactory II fam 10/MOR263-269 | Homo sapiens (Human) |
| Q6IN95_HUMAN | (Q6IN95) | IL8RA | Interleukin-8 type A | Homo sapiens (Human) |
| Q6IPX0_HUMAN | (Q6IPX0) | CCRL2 | C-C Chemokine other | Homo sapiens (Human) |
| Q6ISR6_HUMAN | (Q6ISR6) | OR6W1P | fragments | Homo sapiens (Human) |
| Q6ISR8_HUMAN | (Q6ISR8) | GHSR | Growth hormone secretagogue | Homo sapiens (Human) |
| Q6J164_HUMAN | (Q6J164) | GRM5 | Metabotropic glutamate group I | Homo sapiens (Human) |
| Q6KH09_HUMAN | (Q6KH09) | OR5D4 | fragments | Homo sapiens (Human) |
| Q6L5J4_HUMAN | (Q6L5J4) | | Fmet-leu-phe | Homo sapiens (Human) |
| Q6LAJ3_HUMAN | (Q6LAJ3) | | gamrh Adrenomedullin (G10D) | Homo sapiens (Human) |
| Q6LD06_HUMAN | (Q6LD06) | ADRA1C | fragments | Homo sapiens (Human) |
| Q6LDH7_HUMAN | (Q6LDH7) | DRD2 | fragments | Homo sapiens (Human) |
| Q6LEE7_HUMAN | (Q6LEE7) | CMKLR1 | fragments | Homo sapiens (Human) |
| Q6N055_HUMAN | (Q6N055) | DKFZp686O11112 | fragments | Homo sapiens (Human) |
| Q6N0A5_HUMAN | (Q6N0A5) | DKFZp686I13174 | frizzled Group B (Fz 3 & 6) | Homo sapiens (Human) |
| Q6NSL8_HUMAN | (Q6NSL8) | FZD10 | frizzled Group A (Fz 1&2&4&5&7-9) | Homo sapiens (Human) |
| Q6NSP5_HUMAN | (Q6NSP5) | GPR23 | Purinoceptor P2RY5,8,9,10 GPR35,92,174 | Homo sapiens (Human) |
| Q6NSY0_HUMAN | (Q6NSY0) | CNR2 | Cannabinoid | Homo sapiens (Human) |
| Q6NTA9_HUMAN | (Q6NTA9) | OR1A1 | Olfactory II fam 1/MOR125-138,156 | Homo sapiens (Human) |
| Q6NTB3_HUMAN | (Q6NTB3) | OR2C1 | Olfactory II fam 2/MOR256-262,270-285 | Homo sapiens (Human) |
| Q6NTB5_HUMAN | (Q6NTB5) | OR5V1 | fragments | Homo sapiens (Human) |
| Q6NTC7_HUMAN | (Q6NTC7) | NPBWR1 | GPR | Homo sapiens (Human) |
| Q6NTD7_HUMAN | (Q6NTD7) | OR51B4 | Olfactory I fam 51-52/MOR1-42 | Homo sapiens (Human) |
| Q6NTI7_HUMAN | (Q6NTI7) | GPR143 | Ocular albinism proteins | Homo sapiens (Human) |
| Q6NUM3_HUMAN | (Q6NUM3) | CHRM5 | Muse. acetylcholine Vertebrate type 5 | Homo sapiens (Human) |
| Q6NUP5_HUMAN | (Q6NUP5) | AGTR1 | Angiotensin type 1 | Homo sapiens (Human) |
| Q6NWM4_HUMAN | (Q6NWM4) | GPR4 | GPR | Homo sapiens (Human) |
| Q6NWM5_HUMAN | (Q6NWM5) | GPR21 | GPR | Homo sapiens (Human) |
| Q6NWQ5_HUMAN | (Q6NWQ5) | NPBWR2 | GPR | Homo sapiens (Human) |
| Q6NWQ6_HUMAN | (Q6NWQ6) | NPBWR2 | GPR | Homo sapiens (Human) |
| Q6NWQ8_HUMAN | (Q6NWQ8) | GPR77 | C5a anaphylatoxin | Homo sapiens (Human) |
| Q6NWQ9_HUMAN | (Q6NWQ9) | GPR77 | C5a anaphylatoxin | Homo sapiens (Human) |
| Q6NWR0_HUMAN | (Q6NWR0) | GPR77 | C5a anaphylatoxin | Homo sapiens (Human) |
| Q6NWR3_HUMAN | (Q6NWR3) | GPR83 | Neuropeptide Y other | Homo sapiens (Human) |

TABLE D-continued

| | | | non-limiting list human GPCRs | |
|---|---|---|---|---|
| Q6NWR4_HUMAN | (Q6NWR4) | GPR83 | Neuropeptide Y other | *Homo sapiens* (Human) |
| Q6NWR5_HUMAN | (Q6NWR5) | GPR68 | fragments | *Homo sapiens* (Human) |
| Q6NWR6_HUMAN | (Q6NWR6) | GPR68 | fragments | *Homo sapiens* (Human) |
| Q6NWR7_HUMAN | (Q6NWR7) | GPR63 | GPR45 like | *Homo sapiens* (Human) |
| Q6NWR8_HUMAN | (Q6NWR8) | GPR63 | GPR45 like | *Homo sapiens* (Human) |
| Q6NWR9_HUMAN | (Q6NWR9) | GPR63 | GPR45 like | *Homo sapiens* (Human) |
| Q6NWS6_HUMAN | (Q6NWS6) | GPR12 | fragments | *Homo sapiens* (Human) |
| Q6NWS7_HUMAN | (Q6NWS7) | GPR12 | fragments | *Homo sapiens* (Human) |
| Q6NWS8_HUMAN | (Q6NWS8) | GPR12 | fragments | *Homo sapiens* (Human) |
| Q6NXU6_HUMAN | (Q6NXU6) | GPR45 | GPR45 like | *Homo sapiens* (Human) |
| Q6P2M6_HUMAN | (Q6P2M6) | VIPR1 | Vasoactive intestinal polypeptide | *Homo sapiens* (Human) |
| Q6P4D8_HUMAN | (Q6P4D8) | | fragments | *Homo sapiens* (Human) |
| Q6P523_HUMAN | (Q6P523) | HTR2B | Serotonin type 2 | *Homo sapiens* (Human) |
| Q6P5R4_HUMAN | (Q6P5R4) | MGC72080 | fragments | *Homo sapiens* (Human) |
| Q6P5W7_HUMAN | (Q6P5W7) | OPN3 | fragments | *Homo sapiens* (Human) |
| Q6P7P0_HUMAN | (Q6P7P0) | C10orf97 | fragments | *Homo sapiens* (Human) |
| Q6P9E5_HUMAN | (Q6P9E5) | HRH1 | Histamine type 1 | *Homo sapiens* (Human) |
| Q6PK25_HUMAN | (Q6PK25) | LOC441453 | fragments | *Homo sapiens* (Human) |
| Q6RKA2_HUMAN | (Q6RKA2) | ADCYAP1R1 | fragments | *Homo sapiens* (Human) |
| Q6RKA3_HUMAN | (Q6RKA3) | ADCYAP1R1 | fragments | *Homo sapiens* (Human) |
| Q6RYQ6_HUMAN | (Q6RYQ6) | PTGFR | Prostaglandin F2-alpha | *Homo sapiens* (Human) |
| Q6S991_HUMAN | (Q6S991) | ADCYAP1R1 | fragments | *Homo sapiens* (Human) |
| Q6S992_HUMAN | (Q6S992) | ADCYAP1R1 | fragments | *Homo sapiens* (Human) |
| Q6SL56_HUMAN | (Q6SL56) | CHRM2 | fragments | *Homo sapiens* (Human) |
| Q6TTN3_HUMAN | (Q6TTN3) | PTGER3 | Prostaglandin E2 subtype EP3 | *Homo sapiens* (Human) |
| Q6UPP1_HUMAN | (Q6UPP1) | OPRM1 | Opioid type M | *Homo sapiens* (Human) |
| Q6UQ80_HUMAN | (Q6UQ80) | OPRM1 | Opioid type M | *Homo sapiens* (Human) |
| Q6UR92_HUMAN | (Q6UR92) | MC1R | Melanocyte stimulating hormone | *Homo sapiens* (Human) |
| Q6UR93_HUMAN | (Q6UR93) | MC1R | Melanocyte stimulating hormone | *Homo sapiens* (Human) |
| Q6UR94_HUMAN | (Q6UR94) | MC1R | Melanocyte stimulating hormone | *Homo sapiens* (Human) |
| Q6UR95_HUMAN | (Q6UR95) | MC1R | Melanocyte stimulating hormone | *Homo sapiens* (Human) |
| Q6UR96_HUMAN | (Q6UR96) | MC1R | Melanocyte stimulating hormone | *Homo sapiens* (Human) |
| Q6UR97_HUMAN | (Q6UR97) | MC1R | Melanocyte stimulating hormone | *Homo sapiens* (Human) |
| Q6UR98_HUMAN | (Q6UR98) | MC1R | Melanocyte stimulating hormone | *Homo sapiens* (Human) |
| Q6UR99_HUMAN | (Q6UR99) | MC1R | Melanocyte stimulating hormone | *Homo sapiens* (Human) |
| Q6URA0_HUMAN | (Q6URA0) | MC1R | Melanocyte stimulating hormone | *Homo sapiens* (Human) |
| Q6UVH2_HUMAN | (Q6UVH2) | ATGR2 | fragments | *Homo sapiens* (Human) |
| Q6UXT6_HUMAN | (Q6UXT6) | UNQ9373 | Olfactory II fam 5/MOR172-224,249,254 | *Homo sapiens* (Human) |
| Q6XGY1_HUMAN | (Q6XGY1) | | fragments | *Homo sapiens* (Human) |
| Q6ZMH0_HUMAN | (Q6ZMH0) | | Putative/unclassified Class B GPCRs | *Homo sapiens* (Human) |
| Q6ZMH4_HUMAN | (Q6ZMH4) | | Putative/unclassified Class B GPCRs | *Homo sapiens* (Human) |
| Q6ZMI9_HUMAN | (Q6ZMI9) | ETL | receptors | *Homo sapiens* (Human) |
| Q6ZMN0_HUMAN | (Q6ZMN0) | | | *Homo sapiens* (Human) |
| Q6ZMN6_HUMAN | (Q6ZMN6) | EMR1 | Olfactory II fam 13/MOR253 | *Homo sapiens* (Human) |
| Q6ZMP1_HUMAN | (Q6ZMP1) | | Putative/unclassified Class B GPCRs | *Homo sapiens* (Human) |
| Q6ZMP9_HUMAN | (Q6ZMP9) | | Purinoceptor P2RY5,8,9,10 GPR35,92,174 | *Homo sapiens* (Human) |
| Q6ZMQ2_HUMAN | (Q6ZMQ2) | | Metabotropic glutamate group III | *Homo sapiens* (Human) |
| Q6ZN22_HUMAN | (Q6ZN22) | | Vasoactive intestinal polypeptide | *Homo sapiens* (Human) |
| Q6ZPB0_HUMAN | (Q6ZPB0) | | fragments | *Homo sapiens* (Human) |
| Q6ZS44_HUMAN | (Q6ZS44) | | fragments | *Homo sapiens* (Human) |
| Q6ZTE9_HUMAN | (Q6ZTE9) | | fragments | *Homo sapiens* (Human) |
| Q6ZW62_HUMAN | (Q6ZW62) | | fragments | *Homo sapiens* (Human) |
| Q711G2_HUMAN | (Q711G2) | P2Y2-like | Putative/unclassified Class A GPCRs | *Homo sapiens* (Human) |
| Q712M9_HUMAN | (Q712M9) | htr4 | Serotonin type 4 | *Homo sapiens* (Human) |
| Q71U75_HUMAN | (Q71U75) | | Taste receptors T2R | *Homo sapiens* (Human) |
| Q71V90_HUMAN | (Q71V90) | OPRM1 | fragments | *Homo sapiens* (Human) |
| Q75LH0_HUMAN | (Q75LH0) | HTR5A | fragments | *Homo sapiens* (Human) |
| Q76E76_HUMAN | (Q76E76) | DRD4 | fragments | *Homo sapiens* (Human) |
| Q76L88_HUMAN | (Q76L88) | GPCR | Putative/unclassified Class A GPCRs | *Homo sapiens* (Human) |
| Q7KYP5_HUMAN | (Q7KYP5) | | fragments | *Homo sapiens* (Human) |
| Q7KYZ9_HUMAN | (Q7KYZ9) | alpha 1c-adrenoceptor subtype | fragments | *Homo sapiens* (Human) |
| Q7KZS6_HUMAN | (Q7KZS6) | | Melanocyte stimulating hormone | *Homo sapiens* (Human) |
| Q7L853_HUMAN | (Q7L853) | EDG1 | fragments | *Homo sapiens* (Human) |
| Q7M4L8_HUMAN | (Q7M4L8) | | Melanocyte stimulating hormone | *Homo sapiens* (Human) |
| Q7Z3W3_HUMAN | (Q7Z3W3) | DKFZp686N1782 | Proteinase-activated | *Homo sapiens* (Human) |
| Q7Z580_HUMAN | (Q7Z580) | HTR2B | fragments | *Homo sapiens* (Human) |
| Q7Z581_HUMAN | (Q7Z581) | GPR50 | fragments | *Homo sapiens* (Human) |
| Q7Z582_HUMAN | (Q7Z582) | GPR50 | fragments | *Homo sapiens* (Human) |
| Q7Z5R9_HUMAN | (Q7Z5R9) | | Histamine type 2 | *Homo sapiens* (Human) |
| Q7Z7I1_HUMAN | (Q7Z7I1) | CCBP2 | C-C Chemokine type X | *Homo sapiens* (Human) |
| Q7Z7Q5_HUMAN | (Q7Z7Q5) | DRD4 | fragments | *Homo sapiens* (Human) |
| Q86SE3_HUMAN | (Q86SE3) | | fragments | *Homo sapiens* (Human) |
| Q86SF1_HUMAN | (Q86SF1) | | fragments | *Homo sapiens* (Human) |
| Q86SF3_HUMAN | (Q86SF3) | | fragments | *Homo sapiens* (Human) |
| Q86SF4_HUMAN | (Q86SF4) | | fragments | *Homo sapiens* (Human) |
| Q86SG0_HUMAN | (Q86SG0) | | fragments | *Homo sapiens* (Human) |
| Q86SG8_HUMAN | (Q86SG8) | | fragments | *Homo sapiens* (Human) |

TABLE D-continued non-limiting list human GPCRs

| | | | | |
|---|---|---|---|---|
| Q86SG9_HUMAN | (Q86SG9) | | fragments | *Homo sapiens* (Human) |
| Q86SH1_HUMAN | (Q86SH1) | | fragments | *Homo sapiens* (Human) |
| Q86SH3_HUMAN | (Q86SH3) | | fragments | *Homo sapiens* (Human) |
| Q86SI3_HUMAN | (Q86SI3) | | fragments | *Homo sapiens* (Human) |
| Q86SI5_HUMAN | (Q86SI5) | | fragments | *Homo sapiens* (Human) |
| Q86SI8_HUMAN | (Q86SI8) | | fragments | *Homo sapiens* (Human) |
| Q86SJ4_HUMAN | (Q86SJ4) | | fragments | *Homo sapiens* (Human) |
| Q86SM2_HUMAN | (Q86SM2) | | fragments | *Homo sapiens* (Human) |
| Q86SP4_HUMAN | (Q86SP4) | | fragments | *Homo sapiens* (Human) |
| Q86UG6_HUMAN | (Q86UG6) | | fragments | *Homo sapiens* (Human) |
| Q86UG7_HUMAN | (Q86UG7) | | fragments | *Homo sapiens* (Human) |
| Q86UG8_HUMAN | (Q86UG8) | | fragments | *Homo sapiens* (Human) |
| Q86UG9_HUMAN | (Q86UG9) | | fragments | *Homo sapiens* (Human) |
| Q86UH0_HUMAN | (Q86UH0) | | fragments | *Homo sapiens* (Human) |
| Q86UK4_HUMAN | (Q86UK4) | PTC | Taste receptors T2R | *Homo sapiens* (Human) |
| Q86UN1_HUMAN | (Q86UN1) | HTR5A | fragments | *Homo sapiens* (Human) |
| Q86UN7_HUMAN | (Q86UN7) | CASR | fragments | *Homo sapiens* (Human) |
| Q86UZ8_HUMAN | (Q86UZ8) | FZD2 | fragments | *Homo sapiens* (Human) |
| Q86V80_HUMAN | (Q86V80) | | Opioid type M | *Homo sapiens* (Human) |
| Q86XI5_HUMAN | (Q86XI5) | GLP2R | fragments | *Homo sapiens* (Human) |
| Q86YF2_HUMAN | (Q86YF2) | | fragments | *Homo sapiens* (Human) |
| Q86YG3_HUMAN | (Q86YG3) | | fragments | *Homo sapiens* (Human) |
| Q86YG9_HUMAN | (Q86YG9) | | fragments | *Homo sapiens* (Human) |
| Q86YW1_HUMAN | (Q86YW1) | MC1R | Melanocyte stimulating hormone | *Homo sapiens* (Human) |
| Q8IU63_HUMAN | (Q8IU63) | 6M1-16 | fragments | *Homo sapiens* (Human) |
| Q8IV06_HUMAN | (Q8IV06) | GPR171 | Putative/unclassified Class A GPCRs | *Homo sapiens* (Human) |
| Q8IV17_HUMAN | (Q8IV17) | SCTR | Secretin | *Homo sapiens* (Human) |
| Q8IV19_HUMAN | (Q8IV19) | CYSLTR1 | Cysteinyl leukotriene | *Homo sapiens* (Human) |
| Q8IV68_HUMAN | (Q8IV68) | LOC442421 | fragments | *Homo sapiens* (Human) |
| Q8IVW0_HUMAN | (Q8IVW0) | CHRM5 | Musc. acetylcholine Vertebrate type 5 | *Homo sapiens* (Human) |
| Q8IW08_HUMAN | (Q8IW08) | GABBR1 | GABA-B subtype 1 | *Homo sapiens* (Human) |
| Q8IWP3_HUMAN | (Q8IWP3) | | Opioid type K | *Homo sapiens* (Human) |
| Q8IWW3_HUMAN | (Q8IWW3) | OPRM | Opioid type M | *Homo sapiens* (Human) |
| Q8IWW4_HUMAN | (Q8IWW4) | OPRM | Opioid type M | *Homo sapiens* (Human) |
| Q8IXA4_HUMAN | (Q8IXA4) | GPR126 | Putative/unclassified Class B GPCRs | *Homo sapiens* (Human) |
| Q8IXB0_HUMAN | (Q8IXB0) | | Opioid type X | *Homo sapiens* (Human) |
| Q8IXD9_HUMAN | (Q8IXD9) | | fragments | *Homo sapiens* (Human) |
| Q8IXE0_HUMAN | (Q8IXE0) | OR11H13P | fragments | *Homo sapiens* (Human) |
| Q8IXE2_HUMAN | (Q8IXE2) | | Putative/unclassified Class A GPCRs | *Homo sapiens* (Human) |
| Q8IXE4_HUMAN | (Q8IXE4) | | Putative/unclassified Class B GPCRs | *Homo sapiens* (Human) |
| Q8IXE5_HUMAN | (Q8IXE5) | | Putative/unclassified Class A GPCRs | *Homo sapiens* (Human) |
| Q8IXE7_HUMAN | (Q8IXE7) | | fragments | *Homo sapiens* (Human) |
| Q8IXH9_HUMAN | (Q8IXH9) | HTR4B | Serotonin type 4 | *Homo sapiens* (Human) |
| Q8N0W0_HUMAN | (Q8N0W0) | | fragments | *Homo sapiens* (Human) |
| Q8N0W1_HUMAN | (Q8N0W1) | | fragments | *Homo sapiens* (Human) |
| Q8N0X1_HUMAN | (Q8N0X1) | | fragments | *Homo sapiens* (Human) |
| Q8N0Y1_HUMAN | (Q8N0Y1) | | Olfactory II fam 8/MOR161-171 | *Homo sapiens* (Human) |
| Q8N0Z0_HUMAN | (Q8N0Z0) | | fragments | *Homo sapiens* (Human) |
| Q8N164_HUMAN | (Q8N164) | | fragments | *Homo sapiens* (Human) |
| Q8N2R3_HUMAN | (Q8N2R3) | | fragments | *Homo sapiens* (Human) |
| Q8N537_HUMAN | (Q8N537) | LGR4 | LGR like (hormone receptors) | *Homo sapiens* (Human) |
| Q8N5S7_HUMAN | (Q8N5S7) | GPR | | *Homo sapiens* (Human) |
| Q8N6T6_HUMAN | (Q8N6T6) | IL8RA | Interleukin-8 type A | *Homo sapiens* (Human) |
| Q8N7J6_HUMAN | (Q8N7J6) | | Putative/unclassified Class A GPCRs | *Homo sapiens* (Human) |
| Q8NCH4_HUMAN | (Q8NCH4) | | fragments | *Homo sapiens* (Human) |
| Q8NEI9_HUMAN | (Q8NEI9) | OR7E91P | fragments | *Homo sapiens* (Human) |
| Q8NEN2_HUMAN | (Q8NEN2) | GPR85 | SREB | *Homo sapiens* (Human) |
| Q8NG71_HUMAN | (Q8NG71) | | Corticotropin releasing factor | *Homo sapiens* (Human) |
| Q8NG73_HUMAN | (Q8NG73) | | fragments | *Homo sapiens* (Human) |
| Q8NG79_HUMAN | (Q8NG79) | | Olfactory unclassified class II | *Homo sapiens* (Human) |
| Q8NG87_HUMAN | (Q8NG87) | | fragments | *Homo sapiens* (Human) |
| Q8NG89_HUMAN | (Q8NG89) | OR7E86P | fragments | *Homo sapiens* (Human) |
| Q8NG90_HUMAN | (Q8NG90) | | fragments | *Homo sapiens* (Human) |
| Q8NG91_HUMAN | (Q8NG91) | | fragments | *Homo sapiens* (Human) |
| Q8NGA3_HUMAN | (Q8NGA3) | | fragments | *Homo sapiens* (Human) |
| Q8NGA4_HUMAN | (Q8NGA4) | | Chemokine receptor-like 1 | *Homo sapiens* (Human) |
| Q8NGA9_HUMAN | (Q8NGA9) | | Putative/unclassified Class B GPCRs | *Homo sapiens* (Human) |
| Q8NGB0_HUMAN | (Q8NGB0) | GPR142 | Putative/unclassified Class A GPCRs | *Homo sapiens* (Human) |
| Q8NGB5_HUMAN | (Q8NGB5) | | fragments | *Homo sapiens* (Human) |
| Q8NGC8_HUMAN | (Q8NGC8) | | fragments | *Homo sapiens* (Human) |
| Q8NGD6_HUMAN | (Q8NGD6) | | Olfactory II fam 4/MOR225-248 | *Homo sapiens* (Human) |
| Q8NGD7_HUMAN | (Q8NGD7) | | fragments | *Homo sapiens* (Human) |
| Q8NGD8_HUMAN | (Q8NGD8) | | fragments | *Homo sapiens* (Human) |
| Q8NGE6_HUMAN | (Q8NGE6) | | fragments | *Homo sapiens* (Human) |
| Q8NGF2_HUMAN | (Q8NGF2) | | Olfactory I fam 51-52/MOR1-42 | *Homo sapiens* (Human) |
| Q8NGG1_HUMAN | (Q8NGG1) | | fragments | *Homo sapiens* (Human) |
| Q8NGG9_HUMAN | (Q8NGG9) | | Olfactory II fam 8/MOR161-171 | *Homo sapiens* (Human) |
| Q8NGH0_HUMAN | (Q8NGH0) | | Olfactory II fam 8/MOR161-171 | *Homo sapiens* (Human) |

TABLE D-continued non-limiting list human GPCRs

| | | | | |
|---|---|---|---|---|
| Q8NGH1_HUMAN | (Q8NGH1) | | Olfactory II fam 8/MOR161-171 | *Homo sapiens* (Human) |
| Q8NGH2_HUMAN | (Q8NGH2) | | Olfactory II fam 8/MOR161-171 | *Homo sapiens* (Human) |
| Q8NGH4_HUMAN | (Q8NGH4) | | Olfactory II fam 2/MOR256-262,270-285 | *Homo sapiens* (Human) |
| Q8NGI5_HUMAN | (Q8NGI5) | | fragments | *Homo sapiens* (Human) |
| Q8NGK8_HUMAN | (Q8NGK8) | | fragments | *Homo sapiens* (Human) |
| Q8NGL5_HUMAN | (Q8NGL5) | | Olfactory II fam 5/MOR172-224,249,254 | *Homo sapiens* (Human) |
| Q8NGM0_HUMAN | (Q8NGM0) | | Olfactory II fam 4/MOR225-248 | *Homo sapiens* (Human) |
| Q8NGM3_HUMAN | (Q8NGM3) | OR5E1P | fragments | *Homo sapiens* (Human) |
| Q8NGM4_HUMAN | (Q8NGM4) | | Olfactory II fam 10/MOR263-269 | *Homo sapiens* (Human) |
| Q8NGM5_HUMAN | (Q8NGM5) | | Dopamine Vertebrate type 4 | *Homo sapiens* (Human) |
| Q8NGM6_HUMAN | (Q8NGM6) | | fragments | *Homo sapiens* (Human) |
| Q8NGM7_HUMAN | (Q8NGM7) | | Olfactory I fam 51-52/MOR1-42 | *Homo sapiens* (Human) |
| Q8NGN9_HUMAN | (Q8NGN9) | | Olfactory II fam 4/MOR225-248 | *Homo sapiens* (Human) |
| Q8NGP1_HUMAN | (Q8NGP1) | | fragments | *Homo sapiens* (Human) |
| Q8NGP5_HUMAN | (Q8NGP5) | | fragments | *Homo sapiens* (Human) |
| Q8NGP7_HUMAN | (Q8NGP7) | | fragments | *Homo sapiens* (Human) |
| Q8NGQ7_HUMAN | (Q8NGQ7) | | fragments | *Homo sapiens* (Human) |
| Q8NGQ8_HUMAN | (Q8NGQ8) | | Substance K (NK2) | *Homo sapiens* (Human) |
| Q8NGT3_HUMAN | (Q8NGT3) | | fragments | *Homo sapiens* (Human) |
| Q8NGT4_HUMAN | (Q8NGT4) | | fragments | *Homo sapiens* (Human) |
| Q8NGU0_HUMAN | (Q8NGU0) | | Olfactory II fam 2/MOR256-262,270-285 | *Homo sapiens* (Human) |
| Q8NGU1_HUMAN | (Q8NGU1) | | fragments | *Homo sapiens* (Human) |
| Q8NGU3_HUMAN | (Q8NGU3) | | Putative/unclassified Class A GPCRs | *Homo sapiens* (Human) |
| Q8NGU6_HUMAN | (Q8NGU6) | OR2J4P | fragments | *Homo sapiens* (Human) |
| Q8NGU7_HUMAN | (Q8NGU7) | | fragments | *Homo sapiens* (Human) |
| Q8NGV4_HUMAN | (Q8NGV4) | | Olfactory II fam 13/MOR253 | *Homo sapiens* (Human) |
| Q8NGV8_HUMAN | (Q8NGV8) | | fragments | *Homo sapiens* (Human) |
| Q8NGV9_HUMAN | (Q8NGV9) | | calcium-sensing like other | *Homo sapiens* (Human) |
| Q8NGW2_HUMAN | (Q8NGW2) | DRD5P1 | fragments | *Homo sapiens* (Human) |
| Q8NGW3_HUMAN | (Q8NGW3) | | fragments | *Homo sapiens* (Human) |
| Q8NGW5_HUMAN | (Q8NGW5) | | fragments | *Homo sapiens* (Human) |
| Q8NGW8_HUMAN | (Q8NGW8) | | Brain-specific angiogenesis inhibitor (BAI) | *Homo sapiens* (Human) |
| Q8NGX4_HUMAN | (Q8NGX4) | OR10K2 | fragments | *Homo sapiens* (Human) |
| Q8NGX7_HUMAN | (Q8NGX7) | OR10R3P | fragments | *Homo sapiens* (Human) |
| Q8NGY4_HUMAN | (Q8NGY4) | | Olfactory II fam 6/MOR103-105,107-119 | *Homo sapiens* (Human) |
| Q8NGY8_HUMAN | (Q8NGY8) | | fragments | *Homo sapiens* (Human) |
| Q8NH06_HUMAN | (Q8NH06) | | fragments | *Homo sapiens* (Human) |
| Q8NH07_HUMAN | (Q8NH07) | | Olfactory II fam 11/MOR106,121-122 | *Homo sapiens* (Human) |
| Q8NH08_HUMAN | (Q8NH08) | | Olfactory unclassified class II | *Homo sapiens* (Human) |
| Q8NH11_HUMAN | (Q8NH11) | | Olfactory II fam 8/MOR161-171 | *Homo sapiens* (Human) |
| Q8NH13_HUMAN | (Q8NH13) | | Brain-specific angiogenesis inhibitor (BAI) | *Homo sapiens* (Human) |
| Q8NH14_HUMAN | (Q8NH14) | | Olfactory unclassified class II | *Homo sapiens* (Human) |
| Q8NH17_HUMAN | (Q8NH17) | | fragments | *Homo sapiens* (Human) |
| Q8NH20_HUMAN | (Q8NH20) | | fragments | *Homo sapiens* (Human) |
| Q8NH22_HUMAN | (Q8NH22) | DRD5P2 | fragments | *Homo sapiens* (Human) |
| Q8NH23_HUMAN | (Q8NH23) | | fragments | *Homo sapiens* (Human) |
| Q8NH24_HUMAN | (Q8NH24) | | fragments | *Homo sapiens* (Human) |
| Q8NH25_HUMAN | (Q8NH25) | | fragments | *Homo sapiens* (Human) |
| Q8NH27_HUMAN | (Q8NH27) | | fragments | *Homo sapiens* (Human) |
| Q8NH28_HUMAN | (Q8NH28) | | C—X—C Chemokine type 4 | *Homo sapiens* (Human) |
| Q8NH29_HUMAN | (Q8NH29) | | fragments | *Homo sapiens* (Human) |
| Q8NH32_HUMAN | (Q8NH32) | | fragments | *Homo sapiens* (Human) |
| Q8NH33_HUMAN | (Q8NH33) | | fragments | *Homo sapiens* (Human) |
| Q8NH36_HUMAN | (Q8NH36) | | Olfactory II fam 10/MOR263-269 | *Homo sapiens* (Human) |
| Q8NH38_HUMAN | (Q8NH38) | | fragments | *Homo sapiens* (Human) |
| Q8NH44_HUMAN | (Q8NH44) | | Olfactory unclassified class II | *Homo sapiens* (Human) |
| Q8NH45_HUMAN | (Q8NH45) | | fragments | *Homo sapiens* (Human) |
| Q8NH46_HUMAN | (Q8NH46) | | fragments | *Homo sapiens* (Human) |
| Q8NH47_HUMAN | (Q8NH47) | | fragments | *Homo sapiens* (Human) |
| Q8NH52_HUMAN | (Q8NH52) | | fragments | *Homo sapiens* (Human) |
| Q8NH58_HUMAN | (Q8NH58) | | fragments | *Homo sapiens* (Human) |
| Q8NH62_HUMAN | (Q8NH62) | | fragments | *Homo sapiens* (Human) |
| Q8NH65_HUMAN | (Q8NH65) | | fragments | *Homo sapiens* (Human) |
| Q8NH66_HUMAN | (Q8NH66) | | Olfactory I fam 51-52/MOR1-42 | *Homo sapiens* (Human) |
| Q8NH68_HUMAN | (Q8NH68) | | Olfactory I fam 51-52/MOR1-42 | *Homo sapiens* (Human) |
| Q8NH71_HUMAN | (Q8NH71) | | fragments | *Homo sapiens* (Human) |
| Q8NH75_HUMAN | (Q8NH75) | | fragments | *Homo sapiens* (Human) |
| Q8NH77_HUMAN | (Q8NH77) | | Olfactory I fam 51-52/MOR1-42 | *Homo sapiens* (Human) |
| Q8NH78_HUMAN | (Q8NH78) | OR52W1 | Olfactory I fam 51-52/MOR1-42 | *Homo sapiens* (Human) |
| Q8NH80_HUMAN | (Q8NH80) | | Olfactory II fam 10/MOR263-269 | *Homo sapiens* (Human) |
| Q8NH82_HUMAN | (Q8NH82) | | fragments | *Homo sapiens* (Human) |
| Q8NH84_HUMAN | (Q8NH84) | | Olfactory II fam 4/MOR225-248 | *Homo sapiens* (Human) |
| Q8NH86_HUMAN | (Q8NH86) | | Olfactory II fam 5/MOR172-224,249,254 | *Homo sapiens* (Human) |
| Q8NH88_HUMAN | (Q8NH88) | | fragments | *Homo sapiens* (Human) |
| Q8NH91_HUMAN | (Q8NH91) | | Olfactory II fam 5/MOR172-224,249,254 | *Homo sapiens* (Human) |
| Q8NH95_HUMAN | (Q8NH95) | | Olfactory II fam 13/MOR253 | *Homo sapiens* (Human) |
| Q8NH96_HUMAN | (Q8NH96) | | fragments | *Homo sapiens* (Human) |
| Q8NH97_HUMAN | (Q8NH97) | | fragments | *Homo sapiens* (Human) |

TABLE D-continued

| | | | non-limiting list human GPCRs | |
|---|---|---|---|---|
| Q8NH98_HUMAN | (Q8NH98) | | fragments | *Homo sapiens* (Human) |
| Q8NH99_HUMAN | (Q8NH99) | | Olfactory II fam 7/MOR139-155 | *Homo sapiens* (Human) |
| Q8NHA0_HUMAN | (Q8NHA0) | | Olfactory II fam 7/MOR139-155 | *Homo sapiens* (Human) |
| Q8NHA1_HUMAN | (Q8NHA1) | | Olfactory II fam 7/MOR139-155 | *Homo sapiens* (Human) |
| Q8NHA2_HUMAN | (Q8NHA2) | | Olfactory II fam 2/MOR256-262,270-285 | *Homo sapiens* (Human) |
| Q8NHA5_HUMAN | (Q8NHA5) | | GABA-B subtype 1 | *Homo sapiens* (Human) |
| Q8NHA6_HUMAN | (Q8NHA6) | | Olfactory II fam 2/MOR256-262,270-285 | *Homo sapiens* (Human) |
| Q8NHA7_HUMAN | (Q8NHA7) | | Olfactory II fam 12/MOR250 | *Homo sapiens* (Human) |
| Q8NHA9_HUMAN | (Q8NHA9) | | Metabotropic glutamate group III | *Homo sapiens* (Human) |
| Q8NHB0_HUMAN | (Q8NHB0) | | fragments | *Homo sapiens* (Human) |
| Q8NHB1_HUMAN | (Q8NHB1) | OR2V1 | fragments | *Homo sapiens* (Human) |
| Q8NHB3_HUMAN | (Q8NHB3) | | fragments | *Homo sapiens* (Human) |
| Q8NHB4_HUMAN | (Q8NHB4) | | Parathyroid hormone | *Homo sapiens* (Human) |
| Q8NHB5_HUMAN | (Q8NHB5) | | Olfactory II fam 7/MOR139-155 | *Homo sapiens* (Human) |
| Q8NHB6_HUMAN | (Q8NHB6) | OR5H14 | fragments | *Homo sapiens* (Human) |
| Q8NHB9_HUMAN | (Q8NHB9) | OR7E85P | fragments | *Homo sapiens* (Human) |
| Q8NHC0_HUMAN | (Q8NHC0) | | fragments | *Homo sapiens* (Human) |
| Q8NHC1_HUMAN | (Q8NHC1) | | Olfactory II fam 7/MOR139-155 | *Homo sapiens* (Human) |
| Q8NHC2_HUMAN | (Q8NHC2) | | fragments | *Homo sapiens* (Human) |
| Q8NHC3_HUMAN | (Q8NHC3) | | fragments | *Homo sapiens* (Human) |
| Q8NHD6_HUMAN | (Q8NHD6) | | fragments | *Homo sapiens* (Human) |
| Q8NI49_HUMAN | (Q8NI49) | HRH3 | fragments | *Homo sapiens* (Human) |
| Q8NI50_HUMAN | (Q8NI50) | HRH3 | fragments | *Homo sapiens* (Human) |
| Q8TAM0_HUMAN | (Q8TAM0) | GPR62 | Putative/unclassified Class A GPCRs | *Homo sapiens* (Human) |
| Q8TAN2_HUMAN | (Q8TAN2) | FZD9 | frizzled Group A (Fz 1&2&4&5&7-9) | *Homo sapiens* (Human) |
| Q8TBK4_HUMAN | (Q8TBK4) | AGTR1 | Angiotensin type 1 | *Homo sapiens* (Human) |
| Q8TD34_HUMAN | (Q8TD34) | OPRL1 | Opioid type X | *Homo sapiens* (Human) |
| Q8TDP5_HUMAN | (Q8TDP5) | CCR3 | fragments | *Homo sapiens* (Human) |
| Q8TDP6_HUMAN | (Q8TDP6) | CCR3 | fragments | *Homo sapiens* (Human) |
| Q8TDP8_HUMAN | (Q8TDP8) | CCR3 | fragments | *Homo sapiens* (Human) |
| Q8TDS9_HUMAN | (Q8TDS9) | GPCR | Putative/unclassified other | *Homo sapiens* (Human) |
| Q8TDT0_HUMAN | (Q8TDT0) | GPCR | Putative/unclassified other | *Homo sapiens* (Human) |
| Q8TDT1_HUMAN | (Q8TDT1) | GPCR | fragments | *Homo sapiens* (Human) |
| Q8TDT4_HUMAN | (Q8TDT4) | GPCR | Putative/unclassified Class B GPCRs | *Homo sapiens* (Human) |
| Q8TDT7_HUMAN | (Q8TDT7) | GPCR | Putative/unclassified other | *Homo sapiens* (Human) |
| Q8TDT8_HUMAN | (Q8TDT8) | GPCR | frizzled Group A (Fz 1&2&4&5&7-9) | *Homo sapiens* (Human) |
| Q8TDT9_HUMAN | (Q8TDT9) | GPCR | frizzled Group B (Fz 3 & 6) | *Homo sapiens* (Human) |
| Q8TDU0_HUMAN | (Q8TDU0) | GPCR | Putative/unclassified other | *Homo sapiens* (Human) |
| Q8TDU1_HUMAN | (Q8TDU1) | GPCR | calcium-sensing like other | *Homo sapiens* (Human) |
| Q8TDU5_HUMAN | (Q8TDU5) | GPCR | fragments | *Homo sapiens* (Human) |
| Q8TDV1_HUMAN | (Q8TDV1) | GPCR | fragments | *Homo sapiens* (Human) |
| Q8TDV3_HUMAN | (Q8TDV3) | GPCR | fragments | *Homo sapiens* (Human) |
| Q8TEV7_HUMAN | (Q8TEV7) | MTNR1B | fragments | *Homo sapiens* (Human) |
| Q8WUR8_HUMAN | (Q8WUR8) | | fragments | *Homo sapiens* (Human) |
| Q8WW42_HUMAN | (Q8WW42) | | fragments | *Homo sapiens* (Human) |
| Q8WXR5_HUMAN | (Q8WXR5) | CRHR1 | fragments | *Homo sapiens* (Human) |
| Q8WXR6_HUMAN | (Q8WXR6) | CRHR1 | fragments | *Homo sapiens* (Human) |
| Q8WXR7_HUMAN | (Q8WXR7) | CRHR1 | fragments | *Homo sapiens* (Human) |
| Q8WXR9_HUMAN | (Q8WXR9) | FZD6 | frizzled Group B (Fz 3 & 6) | *Homo sapiens* (Human) |
| Q8WXV1_HUMAN | (Q8WXV1) | | fragments | *Homo sapiens* (Human) |
| Q8WXV2_HUMAN | (Q8WXV2) | | fragments | *Homo sapiens* (Human) |
| Q8WXZ9_HUMAN | (Q8WXZ9) | HRH3 | Histamine type 3 | *Homo sapiens* (Human) |
| Q8WY00_HUMAN | (Q8WY00) | HRH3 | fragments | *Homo sapiens* (Human) |
| Q8WY01_HUMAN | (Q8WY01) | HRH3 | Histamine type 3 | *Homo sapiens* (Human) |
| Q8WZ72_HUMAN | (Q8WZ72) | MTNR1A | fragments | *Homo sapiens* (Human) |
| Q8WZ85_HUMAN | (Q8WZ85) | PJCG2 | fragments | *Homo sapiens* (Human) |
| Q8WZ86_HUMAN | (Q8WZ86) | JCG4 | fragments | *Homo sapiens* (Human) |
| Q8WZ87_HUMAN | (Q8WZ87) | PJCG1 | fragments | *Homo sapiens* (Human) |
| Q8WZA6_HUMAN | (Q8WZA6) | OR17-210 | fragments | *Homo sapiens* (Human) |
| Q92492_HUMAN | (Q92492) | CCKBR | CCK type B | *Homo sapiens* (Human) |
| Q93003_HUMAN | (Q93003) | hA2aR | fragments | *Homo sapiens* (Human) |
| Q96CD9_HUMAN | (Q96CD9) | OR7E91P | fragments | *Homo sapiens* (Human) |
| Q96EC3_HUMAN | (Q96EC3) | ADRB2 | fragments | *Homo sapiens* (Human) |
| Q96HT6_HUMAN | (Q96HT6) | | fragments | *Homo sapiens* (Human) |
| Q96KE0_HUMAN | (Q96KE0) | | fragments | *Homo sapiens* (Human) |
| Q96KP5_HUMAN | (Q96KP5) | CCR11 | C-C Chemokine other | *Homo sapiens* (Human) |
| Q96LC6_HUMAN | (Q96LC6) | CCKBR | CCK type B | *Homo sapiens* (Human) |
| Q96LD9_HUMAN | (Q96LD9) | | Histamine type 4 | *Homo sapiens* (Human) |
| Q96N54_HUMAN | (Q96N54) | OR7E5P | fragments | *Homo sapiens* (Human) |
| Q96R43_HUMAN | (Q96R43) | | fragments | *Homo sapiens* (Human) |
| Q96R54_HUMAN | (Q96R54) | | fragments | *Homo sapiens* (Human) |
| Q96RE8_HUMAN | (Q96RE8) | ADRA1A | Alpha Adrenoceptors type 1 | *Homo sapiens* (Human) |
| Q96RG8_HUMAN | (Q96RG8) | CHRM4 | Musc. acetylcholine Vertebrate type 4 | *Homo sapiens* (Human) |
| Q96RG9_HUMAN | (Q96RG9) | CHRM3 | fragments | *Homo sapiens* (Human) |
| Q96RH0_HUMAN | (Q96RH0) | CHRM2 | Musc. acetylcholine Vertebrate type 2 | *Homo sapiens* (Human) |
| Q96RH1_HUMAN | (Q96RH1) | CHRM1 | Musc. acetylcholine Vertebrate type 1 | *Homo sapiens* (Human) |
| Q96T96_HUMAN | (Q96T96) | CCR3 | fragments | *Homo sapiens* (Human) |
| Q99412_HUMAN | (Q99412) | 5-HT7 | fragments | *Homo sapiens* (Human) |

TABLE D-continued

| | | | non-limiting list human GPCRs | |
|---|---|---|---|---|
| Q99463_HUMAN | (Q99463) | NPY6R | Neuropeptide Y type 6/7 | *Homo sapiens* (Human) |
| Q99586_HUMAN | (Q99586) | | dopamine D4 receptor fragments | *Homo sapiens* (Human) |
| Q99587_HUMAN | (Q99587) | | dopamine D4 receptor fragments | *Homo sapiens* (Human) |
| Q99642_HUMAN | (Q99642) | | fragments | *Homo sapiens* (Human) |
| Q99997_HUMAN | (Q99997) | | fragments | *Homo sapiens* (Human) |
| Q9BSP0_HUMAN | (Q9BSP0) | | fragments | *Homo sapiens* (Human) |
| Q9BXA0_HUMAN | (Q9BXA0) | | C—X—C Chemokine type 4 | *Homo sapiens* (Human) |
| Q9BXX6_HUMAN | (Q9BXX6) | DRD3 | fragments | *Homo sapiens* (Human) |
| Q9BY61_HUMAN | (Q9BY61) | | fragments | *Homo sapiens* (Human) |
| Q9BYT4_HUMAN | (Q9BYT4) | | fragments | *Homo sapiens* (Human) |
| Q9BYX5_HUMAN | (Q9BYX5) | CCR8 | C-C Chemokine type 8 | *Homo sapiens* (Human) |
| Q9BYY6_HUMAN | (Q9BYY6) | CNR1 | fragments | *Homo sapiens* (Human) |
| Q9BYZ0_HUMAN | (Q9BYZ0) | ADRB2 | fragments | *Homo sapiens* (Human) |
| Q9BZC5_HUMAN | (Q9BZC5) | FKSG35 | fragments | *Homo sapiens* (Human) |
| Q9H011_HUMAN | (Q9H011) | GIR | fragments | *Homo sapiens* (Human) |
| Q9H208_HUMAN | (Q9H208) | | fragments | *Homo sapiens* (Human) |
| Q9H2C6_HUMAN | (Q9H2C6) | | Olfactory I fam 51-52/MOR1-42 | *Homo sapiens* (Human) |
| Q9H2C7_HUMAN | (Q9H2C7) | | Olfactory I fam 51-52/MOR1-42 | *Homo sapiens* (Human) |
| Q9H2L2_HUMAN | (Q9H2L2) | | Putative/unclassified Class A GPCRs | *Homo sapiens* (Human) |
| Q9H342_HUMAN | (Q9H342) | | Olfactory I fam 51-52/MOR1-42 | *Homo sapiens* (Human) |
| Q9H345_HUMAN | (Q9H345) | | Olfactory I fam 51-52/MOR1-42 | *Homo sapiens* (Human) |
| Q9H573_HUMAN | (Q9H573) | OPRM1 | Opioid type M | *Homo sapiens* (Human) |
| Q9H7M4_HUMAN | (Q9H7M4) | FLJ00046 | fragments | *Homo sapiens* (Human) |
| Q9H7Q2_HUMAN | (Q9H7Q2) | FLJ00015 | fragments | *Homo sapiens* (Human) |
| Q9HB44_HUMAN | (Q9HB44) | | fragments | *Homo sapiens* (Human) |
| Q9HB45_HUMAN | (Q9HB45) | | Growth hormone-releasing hormone | *Homo sapiens* (Human) |
| Q9HBV6_HUMAN | (Q9HBV6) | HCRTR1 | Orexin | *Homo sapiens* (Human) |
| Q9HD50_HUMAN | (Q9HD50) | | fragments | *Homo sapiens* (Human) |
| Q9NRB8_HUMAN | (Q9NRB8) | | Lysophosphatidic acid Edg-7 | *Homo sapiens* (Human) |
| Q9NSC9_HUMAN | (Q9NSC9) | OR51A1P | fragments | *Homo sapiens* (Human) |
| Q9NSM3_HUMAN | (Q9NSM3) | DKFZp434B1272 | fragments | *Homo sapiens* (Human) |
| Q9NYK7_HUMAN | (Q9NYK7) | | CCK type B | *Homo sapiens* (Human) |
| Q9NYN8_HUMAN | (Q9NYN8) | CHEDG1 | Sphingosine 1-phosphate Edg-1 | *Homo sapiens* (Human) |
| Q9NZP3_HUMAN | (Q9NZP3) | HSA12 | fragments | *Homo sapiens* (Human) |
| Q9NZP4_HUMAN | (Q9NZP4) | HSA10 | fragments | *Homo sapiens* (Human) |
| Q9P1R1_HUMAN | (Q9P1R1) | OR7E35P | fragments | *Homo sapiens* (Human) |
| Q9P1T4_HUMAN | (Q9P1T4) | CCR5 | fragments | *Homo sapiens* (Human) |
| Q9P1T5_HUMAN | (Q9P1T5) | CCR5 | fragments | *Homo sapiens* (Human) |
| Q9P1V4_HUMAN | (Q9P1V4) | | fragments | *Homo sapiens* (Human) |
| Q9P2Q4_HUMAN | (Q9P2Q4) | HTR1F | fragments | *Homo sapiens* (Human) |
| Q9P2Q9_HUMAN | (Q9P2Q9) | HTR2A | fragments | *Homo sapiens* (Human) |
| Q9UBJ7_HUMAN | (Q9UBJ7) | CCR5 | fragments | *Homo sapiens* (Human) |
| Q9UBT9_HUMAN | (Q9UBT9) | CCR5 | fragments | *Homo sapiens* (Human) |
| Q9UCW0_HUMAN | (Q9UCW0) | | fragments | *Homo sapiens* (Human) |
| Q9UD23_HUMAN | (Q9UD23) | | Endothelin | *Homo sapiens* (Human) |
| Q9UD67_HUMAN | (Q9UD67) | | fragments | *Homo sapiens* (Human) |
| Q9UDD7_HUMAN | (Q9UDD7) | | fragments | *Homo sapiens* (Human) |
| Q9UDD8_HUMAN | (Q9UDD8) | | fragments | *Homo sapiens* (Human) |
| Q9UDD9_HUMAN | (Q9UDD9) | | fragments | *Homo sapiens* (Human) |
| Q9UDE6_HUMAN | (Q9UDE6) | | Substance K (NK2) | *Homo sapiens* (Human) |
| Q9UEB1_HUMAN | (Q9UEB1) | | fragments | *Homo sapiens* (Human) |
| Q9UJ48_HUMAN | (Q9UJ48) | LPHH1 | fragments | *Homo sapiens* (Human) |
| Q9UJ49_HUMAN | (Q9UJ49) | LPHH1 | fragments | *Homo sapiens* (Human) |
| Q9UJ50_HUMAN | (Q9UJ50) | LPHH1 | fragments | *Homo sapiens* (Human) |
| Q9UJ51_HUMAN | (Q9UJ51) | LPHH1 | fragments | *Homo sapiens* (Human) |
| Q9UJ52_HUMAN | (Q9UJ52) | LPHH1 | fragments | *Homo sapiens* (Human) |
| Q9UL14_HUMAN | (Q9UL14) | OR17-1 | fragments | *Homo sapiens* (Human) |
| Q9UM77_HUMAN | (Q9UM77) | OR1E3P | fragments | *Homo sapiens* (Human) |
| Q9UN23_HUMAN | (Q9UN23) | CCR5 | fragments | *Homo sapiens* (Human) |
| Q9UN24_HUMAN | (Q9UN24) | CCR5 | fragments | *Homo sapiens* (Human) |
| Q9UN25_HUMAN | (Q9UN25) | CCR5 | fragments | *Homo sapiens* (Human) |
| Q9UN26_HUMAN | (Q9UN26) | CCR5 | fragments | *Homo sapiens* (Human) |
| Q9UN27_HUMAN | (Q9UN27) | CCR5 | fragments | *Homo sapiens* (Human) |
| Q9UN28_HUMAN | (Q9UN28) | CCR5 | fragments | *Homo sapiens* (Human) |
| Q9UPG0_HUMAN | (Q9UPG0) | CRAM-B | C-C Chemokine other | *Homo sapiens* (Human) |
| Q9UPJ0_HUMAN | (Q9UPJ0) | | fragments | *Homo sapiens* (Human) |
| Q9UPJ1_HUMAN | (Q9UPJ1) | | fragments | *Homo sapiens* (Human) |
| Q9UQQ6_HUMAN | (Q9UQQ6) | CCR9 | C-C Chemokine type 9 | *Homo sapiens* (Human) |
| Q9UQS0_HUMAN | (Q9UQS0) | | fragments | *Homo sapiens* (Human) |
| QRFPR_HUMAN | (Q96P65) | GPR103 | Orexigenic neuropeptide QRFP | *Homo sapiens* (Human) |
| RAI3_HUMAN | (Q8NFJ5) | GPRC5A | Orphan GPRC5 | *Homo sapiens* (Human) |
| RDC1_HUMAN | (P25106) | CMKOR1 | RDC1 | *Homo sapiens* (Human) |
| RGR_HUMAN | (P47804) | RGR | Rhodopsin Other | *Homo sapiens* (Human) |
| RL3R1_HUMAN | (Q9NSD7) | RXFP3 | Somatostatin- and angiogenin-like peptide | *Homo sapiens* (Human) |
| RL3R2_HUMAN | (Q8TDU9) | RXFP4 | Somatostatin- and angiogenin-like peptide | *Homo sapiens* (Human) |
| RXFP1_HUMAN | (Q9HBX9) | RXFP1 | LGR like (hormone receptors) | *Homo sapiens* (Human) |

TABLE D-continued non-limiting list human GPCRs

| SCTR_HUMAN | (P47872) | SCTR | Secretin | *Homo sapiens* (Human) |
|---|---|---|---|---|
| SMO_HUMAN | (Q99835) | SMO | Smoothened | *Homo sapiens* (Human) |
| SNSR2_HUMAN | (Q8TDE0) | SNSR2 | Mas proto-oncogene & Mas-related (MRGs) | *Homo sapiens* (Human) |
| SNSR3_HUMAN | (Q8TDD9) | SNSR3 | Mas proto-oncogene & Mas-related (MRGs) | *Homo sapiens* (Human) |
| SNSR5_HUMAN | (Q8TDD7) | SNSR5 | Mas proto-oncogene & Mas-related (MRGs) | *Homo sapiens* (Human) |
| SPR1_HUMAN | (Q15743) | GPR68 | GPR | *Homo sapiens* (Human) |
| SSR1_HUMAN | (P30872) | SSTR1 | Somatostatin type 1 | *Homo sapiens* (Human) |
| SSR2_HUMAN | (P30874) | SSTR2 | Somatostatin type 2 | *Homo sapiens* (Human) |
| SSR3_HUMAN | (P32745) | SSTR3 | Somatostatin type 3 | *Homo sapiens* (Human) |
| SSR4_HUMAN | (P31391) | SSTR4 | Somatostatin type 4 | *Homo sapiens* (Human) |
| SSR5_HUMAN | (P35346) | SSTR5 | Somatostatin type 5 | *Homo sapiens* (Human) |
| SUCR1_HUMAN | (Q9BXA5) | SUCNR1 | Purinoceptor P2RY1-4,6,11 GPR91 | *Homo sapiens* (Human) |
| T2R10_HUMAN | (Q9NYW0) | TAS2R10 | Taste receptors T2R | *Homo sapiens* (Human) |
| T2R12_HUMAN | (P59531) | TAS2R12 | Taste receptors T2R | *Homo sapiens* (Human) |
| T2R13_HUMAN | (Q9NYV9) | TAS2R13 | Taste receptors T2R | *Homo sapiens* (Human) |
| T2R14_HUMAN | (Q9NYV8) | TAS2R14 | Taste receptors T2R | *Homo sapiens* (Human) |
| T2R16_HUMAN | (Q9NYV7) | TAS2R16 | Taste receptors T2R | *Homo sapiens* (Human) |
| T2R38_HUMAN | (P59533) | TAS2R38 | Taste receptors T2R | *Homo sapiens* (Human) |
| T2R39_HUMAN | (P59534) | TAS2R39 | Taste receptors T2R | *Homo sapiens* (Human) |
| T2R40_HUMAN | (P59535) | TAS2R40 | Taste receptors T2R | *Homo sapiens* (Human) |
| T2R41_HUMAN | (P59536) | TAS2R41 | Taste receptors T2R | *Homo sapiens* (Human) |
| T2R43_HUMAN | (P59537) | TAS2R43 | Taste receptors T2R | *Homo sapiens* (Human) |
| T2R44_HUMAN | (P59538) | TAS2R44 | Taste receptors T2R | *Homo sapiens* (Human) |
| T2R45_HUMAN | (P59539) | TAS2R45 | Taste receptors T2R | *Homo sapiens* (Human) |
| T2R46_HUMAN | (P59540) | TAS2R46 | Taste receptors T2R | *Homo sapiens* (Human) |
| T2R47_HUMAN | (P59541) | TAS2R47 | Taste receptors T2R | *Homo sapiens* (Human) |
| T2R48_HUMAN | (P59542) | TAS2R48 | Taste receptors T2R | *Homo sapiens* (Human) |
| T2R49_HUMAN | (P59543) | TAS2R49 | Taste receptors T2R | *Homo sapiens* (Human) |
| T2R50_HUMAN | (P59544) | TAS2R50 | Taste receptors T2R | *Homo sapiens* (Human) |
| T2R55_HUMAN | (Q7RTR8) | TAS2R55 | Taste receptors T2R | *Homo sapiens* (Human) |
| T2R60_HUMAN | (P59551) | TAS2R60 | Taste receptors T2R | *Homo sapiens* (Human) |
| TA2R1_HUMAN | (Q9NYW7) | TAS2R1 | Taste receptors T2R | *Homo sapiens* (Human) |
| TA2R3_HUMAN | (Q9NYW6) | TAS2R3 | Taste receptors T2R | *Homo sapiens* (Human) |
| TA2R4_HUMAN | (Q9NYW5) | TAS2R4 | Taste receptors T2R | *Homo sapiens* (Human) |
| TA2R5_HUMAN | (Q9NYW4) | TAS2R5 | Taste receptors T2R | *Homo sapiens* (Human) |
| TA2R7_HUMAN | (Q9NYW3) | TAS2R7 | Taste receptors T2R | *Homo sapiens* (Human) |
| TA2R8_HUMAN | (Q9NYW2) | TAS2R8 | Taste receptors T2R | *Homo sapiens* (Human) |
| TA2R9_HUMAN | (Q9NYW1) | TAS2R9 | Taste receptors T2R | *Homo sapiens* (Human) |
| TA2R_HUMAN | (P21731) | TBXA2R | Thromboxane | *Homo sapiens* (Human) |
| TAAR1_HUMAN | (Q96RJ0) | TAAR1 | Trace amine | *Homo sapiens* (Human) |
| TAAR2_HUMAN | (Q9P1P5) | TAAR2 | Trace amine | *Homo sapiens* (Human) |
| TAAR3_HUMAN | (Q9P1P4) | TAAR3 | Trace amine | *Homo sapiens* (Human) |
| TAAR5_HUMAN | (O14804) | TAAR5 | Trace amine | *Homo sapiens* (Human) |
| TAAR6_HUMAN | (Q96RI8) | TAAR6 | Trace amine | *Homo sapiens* (Human) |
| TAAR8_HUMAN | (Q969N4) | TAAR8 | Trace amine | *Homo sapiens* (Human) |
| TAAR9_HUMAN | (Q96RI9) | TAAR9 | Trace amine | *Homo sapiens* (Human) |
| TRFR_HUMAN | (P34981) | TRHR | Thyrotropin-releasing hormone | *Homo sapiens* (Human) |
| TS1R1_HUMAN | (Q7RTX1) | TAS1R1 | Taste receptors (T1R) | *Homo sapiens* (Human) |
| TS1R2_HUMAN | (Q8TE23) | TAS1R2 | Taste receptors (T1R) | *Homo sapiens* (Human) |
| TS1R3_HUMAN | (Q7RTX0) | TAS1R3 | Taste receptors (T1R) | *Homo sapiens* (Human) |
| TSHR_HUMAN | (P16473) | TSHR | Thyrotropin | *Homo sapiens* (Human) |
| UR2R_HUMAN | (Q9UKP6) | UTS2R | Urotensin II | *Homo sapiens* (Human) |
| V1AR_HUMAN | (P37288) | AVPR1A | Vasopressin type 1 | *Homo sapiens* (Human) |
| V1BR_HUMAN | (P47901) | AVPR1B | Vasopressin type 1 | *Homo sapiens* (Human) |
| V2R_HUMAN | (P30518) | AVPR2 | Vasopressin type 2 | *Homo sapiens* (Human) |
| VIPR1_HUMAN | (P32241) | VIPR1 | Vasoactive intestinal polypeptide | *Homo sapiens* (Human) |
| VIPR2_HUMAN | (P41587) | VIPR2 | Vasoactive intestinal polypeptide | *Homo sapiens* (Human) |
| VN1R1_HUMAN | (Q9GZP7) | VN1R1 | Vomeronasal receptors V1RL | *Homo sapiens* (Human) |
| VN1R2_HUMAN | (Q8NFZ6) | VN1R2 | Vomeronasal receptors V1RL | *Homo sapiens* (Human) |
| VN1R3_HUMAN | (Q9BXE9) | VN1R3 | Vomeronasal receptors V1RL | *Homo sapiens* (Human) |
| VN1R4_HUMAN | (Q7Z5H5) | VN1R4 | Vomeronasal receptors V1RL | *Homo sapiens* (Human) |
| VN1R5_HUMAN | (Q7Z5H4) | VN1R5 | Vomeronasal receptors others | *Homo sapiens* (Human) |
| XCR1_HUMAN | (P46094) | XCR1 | XC Chemokine | *Homo sapiens* (Human) |

Those skilled in the art will recognize, or be able to ascertain using no more than routine experimentation, many equivalents to the specific embodiments of the invention described herein. Such equivalents are intended to be encompassed by the following aspects.

All references disclosed herein are incorporated by reference in their entirety for the purpose and information indicated in the specification.

Preferred Aspects:
1. Amino acid sequence, e.g. single variable domain, that is directed against and/or that specifically binds to a GPCR and has antagonistic properties on said GPCR, preferably only antagonistic properties, i.e. no agonistic properties.
2. Amino acid sequence, e.g. single variable domain, that is directed against and/or that specifically binds to a GPCR and has antagonistic or inverse agonstic properties on said GPCR, preferably inverse agonstic properties.

3. Amino acid sequence, e.g. single variable domain, that is directed against and/or that specifically binds to a GPCR and has inverse agonistic properties on said GPCR, preferably can reduce activity, measured e.g. by IP accumulation, to 90% or more of the basal activity, preferably 80% or more of the basal activity, more preferably 70% of the basal activity or more, even more preferably 60% or more of the basal activity, most preferred 50% or more of the basal activity.

4. Amino acid sequence, e.g. single variable domain, that is directed against and/or that a) specifically binds to a GPCR; and b) fully inhibits ligand-dependent activation of said GPCR, wherein the ligand is present in a concentration of 100 nM or less, more preferably 30 nM or less.

5. Amino acid sequence, e.g. single variable domain, that is directed against and/or that a) specifically binds to a GPCR; and b) fully inhibits ligand-dependent activation of said GPCR, wherein the ligand is present in a concentration of 100 nM or less, more preferably 30 nM or less; and c) provides no activation of said GPCR.

6. Amino acid sequence, e.g. single variable domain, according to any of the above aspects; and b) that is obtainable by a method that comprises at least the steps of:
   i. immunizing a Camelid with whole cells that are alive and overexpress the desired extracellular part, region, domain, loop or other extracellular epitope(s) of said GPCR, e.g. human CXCR4 and/or human CXCR7, on their surface in their native confirmation; and
   ii. selecting for binding for the desired extracellular part, region, domain, loop or other extracellular epitope(s) using cell membranes preparation of different (other than the one used in immunization) cell types overexpressing said GPCR, e.g. human CXCR4 and/or human CXCR7; and optionally
   iii. washing only mildly with a buffer such as PBS without detergents.

7. Amino acid sequence according to aspect 6, wherein the Camelid is a Llama.

8. Amino acid sequence according to aspect 6 or 7, wherein the selecting is done in 2 rounds and wherein cell membrane preparations of 2 different cell types are used.

9. Amino acid sequence according to any previous aspects, that is in essentially isolated form.

10. Amino acid sequence according to any previous aspects, for administration to a subject, wherein said amino acid sequence does not naturally occur in said subject.

11. Amino acid sequence according to any of the preceding aspects, that can specifically bind to a GPCR with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

12. Amino acid sequence according to any of the preceding aspects, that can specifically bind to a GPCR with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

13. Amino acid sequence according to any of the preceding aspects, that can specifically bind to a GPCR with a rate of dissociation ($k_{off}$-rate) between 1 $s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

14. Amino acid sequence according to any of the preceding aspects, that can specifically bind to a GPCR with an affinity less than 500 nM, preferably less than 200 nM, more preferably less than 10 nM, such as less than 500 μM.

15. Amino acid sequence according to any of the preceding aspects, that is a naturally occurring amino acid sequence (from any suitable species) or a synthetic or semi-synthetic amino acid sequence.

16. Amino acid sequence according to any of the preceding aspects, that comprises an immunoglobulin fold or that under suitable conditions is capable of forming an immunoglobulin fold.

17. Amino acid sequence according to any of the preceding aspects, that essentially consists of 4 framework regions (FR1 to FR4 respectively) and 3 complementarity determining regions (CDR1 to CDR3 respectively).

18. Amino acid sequence according to any of the preceding aspects, that is an immunoglobulin sequence.

19. Amino acid sequence according to any of the preceding aspects, that is a naturally occurring immunoglobulin sequence (from any suitable species) or a synthetic or semi-synthetic immunoglobulin sequence.

20. Amino acid sequence according to any of the preceding aspects that is a humanized immunoglobulin sequence, a camelized immunoglobulin sequence or an immunoglobulin sequence that has been obtained by techniques such as affinity maturation.

21. Amino acid sequence according to any of the preceding aspects, that essentially consists of a light chain variable domain sequence (e.g. a $V_L$-sequence); or of a heavy chain variable domain sequence (e.g. a $V_H$-sequence).

22. Amino acid sequence according to any of the preceding aspects, that essentially consists of a heavy chain variable domain sequence that is derived from a conventional four-chain antibody or that essentially consist of a heavy chain variable domain sequence that is derived from heavy chain antibody.

23. Amino acid sequence according to any of the preceding aspects, that essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody™ (including but not limited to a $V_{HH}$ sequence).

24. Amino acid sequence according to any of the preceding aspects, that essentially consists of a Nanobody™

25. Amino acid sequence according to any of the preceding aspects, that essentially consists of a Nanobody™ that has 80% amino acid identity with at least one of the amino acid sequences of SEQ ID NO's: 1 to 22, in which for the purposes of determining the degree of amino acid identity, the amino acid residues that form the CDR sequences are disregarded; and in which: preferably one or more of the amino acid residues at positions 11, 37, 44, 45, 47, 83, 84, 103, 104 and 108 according to the Kabat numbering are chosen from the Hallmark residues mentioned in Table A-3.

26. Amino acid sequence according to any of the preceding aspects, that essentially consists of a Nanobody™ that has 80% amino acid identity with at least one of the amino acid sequences of SEQ ID NO's: 238 to 253, more preferably 238 to 239, in which for the purposes of determining the degree of amino acid identity, the amino acid residues that form the CDR sequences are disregarded; and in which: preferably one or more of the amino acid residues at positions 11, 37, 44, 45, 47, 83, 84, 103, 104 and 108 according to the Kabat numbering are chosen from the Hallmark residues mentioned in Table A-3.

27. Amino acid sequence according to any of the preceding aspects, that essentially consists of a humanized Nanobody™.
28. Amino acid sequence according to any of the preceding aspects, that in addition to the at least one binding site for binding against a GPCR, contain one or more further binding sites for binding against other antigens, proteins or targets.
29. A single variable domain that specifically binds to at least one member of CXCR4.
30. The single variable domain according to aspect 29, wherein the member of CXCR4 is human CXCR4.
31. The single variable domain according to aspect 29, wherein the single variable domain additionally blocks the interaction between at least one member of the group consisting of CXCR4, e.g. human CXCR4, with at least one single variable domain with sequences having SEQ ID NO: 238 to 253, more preferably 238 to 239.
32. The single variable domain according to aspect 29, wherein the single variable domain is selected from the group consisting of a) single variable domains with sequences having SEQ ID NO: 238 to 253, more preferably 238 to 239; and b) single variable domains with 80% sequence identity to at least one sequence selected from the group consisting of single variable domains with sequences having SEQ ID NO: 238 to 253, more preferably 238 to 239.
33. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 10 amino acid residues are replaced by naturally occurring amino acids and wherein said replaced amino acids are located within the framework regions.
34. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 8 amino acid residues are replaced by naturally occurring amino acids and wherein said replaced amino acids are located within the framework regions.
35. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 5 amino acid residues are replaced by naturally occurring amino acids and wherein said replaced amino acids are located within the framework regions.
36. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 3 amino acid residues are replaced by naturally occurring amino acids and wherein said replaced amino acids are located within the framework regions.
37. The single variable domain according to aspect 29, wherein the single variable domain is selected from the group consisting of a) single variable domains with sequences having SEQ ID NO: 238 to 253, more preferably 238 to 239; and b) single variable domains with 80% sequence identity to at least one sequences selected from the group consisting of sequences having SEQ ID NO: 238 to 253, more preferably 238 to 239; and wherein said selected single variable domain from group a) and b) binds to at least one member of the GPCR receptors with a dissociation constant ($K_D$) of $10^{-7}$ to $10^{12}$ moles/liter or less.
38. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 10 amino acid residues are replaced by naturally occurring amino acids and wherein said replaced amino acids are located within the framework regions; and wherein said selected single variable domain from group a) and b) binds to at least one member of the GPCR receptors with a dissociation constant ($K_D$) of $10^{-7}$ to $10^{-12}$ moles/liter or less.
39. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 8 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-7}$ to $10^{-12}$ moles/liter or less.
40. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 5 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-7}$ to $10^{-12}$ moles/liter or less.
41. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 3 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-7}$ to $10^{-12}$ moles/liter or less.
42. The single variable domain according to aspect 29, wherein the single variable domain is selected from the group consisting of a) single variable domains with sequences having SEQ ID NO: 238 to 253, more preferably 238 to 239; and b) single variable domains with 80% sequence identity to at least one sequences selected from the group consisting of sequences having SEQ ID NO: 238 to 253, more preferably 238 to 239; and wherein said selected single variable domain from group a) and b) binds to members of the Notch signalling pathway with a dissociation constant ($K_D$) of $10^{-8}$ to $10^{-12}$ moles/liter or less.

43. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 10 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-8}$ to $10^{-12}$ moles/liter or less.

44. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 8 amino acid residues are replaced by naturally occurring amino acids and wherein said replaced amino acids are located within the framework regions; and wherein said selected single variable domain from group a) and b) binds to at least one member of the GPCR receptors with a dissociation constant ($K_D$) of $10^{-8}$ to $10^{-12}$ moles/liter or less.

45. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 5 amino acid residues are replaced by naturally occurring amino acids and wherein said replaced amino acids are located within the framework regions; and wherein said selected single variable domain from group a) and b) binds to at least one member of the GPCR receptors with a dissociation constant ($K_D$) of $10^{-8}$ to $10^{-12}$ moles/liter or less.

46. The single variable domain according to aspect 29, wherein the single variable domain is selected from the group consisting of a) single variable domains with sequences having SEQ ID NO: 238 to 253, more preferably 238 to 239; and b) single variable domains with sequences having SEQ ID NO: 238 to 253, more preferably 238 to 239, wherein up to 3 amino acid residues are replaced by naturally occurring amino acids and wherein said replaced amino acids are located within the framework regions; and wherein said selected single variable domain from group a) and b) binds to at least one member of the GPCR receptors with a dissociation constant ($K_D$) of $10^{-8}$ to $10^{-12}$ moles/liter or less.

47. A single variable domain that specifically binds to at least one member of CXCR7.

48. The single variable domain according to aspect 29, wherein the member of CXCR7 is human CXCR7.

49. Compound or construct, that a) comprises or essentially consists of one or more amino acid sequences according to any of aspects 1 to 29; or b) that comprises or essentially consists of one or more single variable domains according to any of aspects 30 to 48; and optionally further comprises one or more other groups, residues, moieties or binding units, optionally linked via one or more linkers.

50. Compound or construct according to aspect 49, in which said one or more other groups, residues, moieties or binding units are amino acid sequences.

51. Compound or construct according to aspect 50 in which said one or more linkers, if present, are one or more amino acid sequences.

52. Compound or construct according to any of aspects 49 to 51, in which said one or more other groups, residues, moieties or binding units are immunoglobulin sequences.

53. Compound or construct according to any of aspects 49 to 52, in which said one or more other groups, residues, moieties or binding units are chosen from the group consisting of single domain antibodies.

54. Compound or construct according to any of aspects 49 to 53, in which said one or more other groups, residues, moieties or binding units are Nanobodies.

55. Compound or construct according to any of aspects 49 to 54, which is a multivalent construct such as e.g. SEQ ID NO: 261 to 266, preferably SEQ ID NO: 263, 264 and functional equivalents such as e.g. a compound or construct with a) 80% identity to SEQ ID NO: 261 to 266 and b) fully inhibits ligand-dependent activation of said GPCR, wherein the ligand is present in a concentration of 100 nM or less, more preferably 30 nM or less; or in case the GPCR has basal activity is a full antagonist or preferably reduces activity to 90% or more basal activity, more preferably to 80% or more basal activity, even more preferably to 70% or more basal activity, even more preferably to 60% or more basal activity.

56. Compound or construct according to any of aspects 49 to 55, which is a multispecific construct.

57. Compound or construct according to any of aspects 49 to 56, which has an increased half-life, compared to the corresponding amino acid sequence or single variable domains according to any of aspects 1 to 48 per se.

58. Compound or construct according to aspect 57, in which said one or more other groups, residues, moieties or binding units provide the compound or construct with increased half-life, compared to the corresponding amino acid sequence or single variable domains according to any of aspects 1 to 48 per se.

59. Compound or construct according to aspect 58, in which said one or more other groups, residues, moieties or binding units that provide the compound or construct with increased half-life is chosen from the group consisting of serum proteins or fragments thereof, binding units that can bind to serum proteins, an Fc portion, and small proteins or peptides that can bind to serum proteins.

60. Compound or construct according to aspect 58 or 59, in which said one or more other groups, residues, moieties or binding units that provide the compound or construct with increased half-life is chosen from the group consisting of human serum albumin or fragments thereof.

61. Compound or construct according to aspect 60, in which said one or more other groups, residues, moieties or binding units that provides the compound or construct with increased half-life are chosen from the group consisting of binding units that can bind to serum albumin (such as human serum albumin) or a serum immunoglobulin (such as IgG).

62. Compound or construct according to aspect 61, in which said one or more other groups, residues, moieties or binding units that provides the compound or construct with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum albumin (such as human serum albumin) or a serum immunoglobulin (such as IgG).

63. Compound or construct according to any of aspects 57 to 62, that has a serum half-life that is at least 1.5 times, preferably at least 2 times, such as at least 5 times, for example at least 10 times or more than 20 times, greater than the half-life of the corresponding amino acid sequence of amino acid sequence or single variable domain according to any of aspects 1 to 48 per se.

64. Compound or construct according to any of aspects 57 to 62, that has a serum half-life that is increased with more than 1 hours, preferably more than 2 hours, more preferably more than 6 hours, such as more than 12 hours, or even more than 24, 48 or 72 hours, compared to the corresponding amino acid sequence or single variable domain according to any of aspects 1 to 48 per se.

65. Compound or construct according to any of aspects 57 to 64, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

66. Monovalent construct, comprising or essentially consisting of one amino acid sequence or single variable domain according to any of aspects 1 to 48.

67. Monovalent construct according to aspect 66, in which said amino acid sequence of the invention is chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

68. Nucleic acid or nucleotide sequence, that encodes an amino acid sequence or single variable domain according to any of aspects 1 to 48, a compound or construct according to any of aspects 49 to 65, or a monovalent construct according to any of aspects 66 to 67.

69. Nucleic acid or nucleotide sequence according to aspect 68, that is in the form of a genetic construct.

70. Host or host cell that expresses, or that under suitable circumstances is capable of expressing, an amino acid sequence or single variable domain according to any of aspects 1 to 48, a compound or construct according to any of aspects 49 to 65, or a monovalent construct according to any of aspects 66 to 67; and/or that comprises a nucleic acid or nucleotide sequence according to aspect 68 to 69.

71. Method for producing an amino acid sequence or single variable domain according to any of aspects 1 to 48, a compound or construct according to any of aspects 49 to 65, or a monovalent construct according to any of aspects 66 to 67, said method at least comprising the steps of:
a) expressing, in a suitable host cell or host organism or in another suitable expression system, a nucleic acid or nucleotide sequence according to aspect 68, or a genetic construct according to aspect 69; optionally followed by:
b) isolating and/or purifying the amino acid sequence or single variable domain according to any of aspects 1 to 48, the compound or construct according to any of aspects 49 to 65, or a monovalent construct according to any of aspects 66 to 67.

72. Method for producing an amino acid sequence or single variable domain according to any of aspects 1 to 48, a compound or construct according to any of aspects 49 to 65, or a monovalent construct according to any of aspects 66 to 67, said method at least comprising the steps of:
a) cultivating and/or maintaining a host or host cell according to aspect 70 under conditions that are such that said host or host cell expresses and/or produces at least one an amino acid sequence or single variable domain according to any of aspects 1 to 48, a compound or construct according to any of aspects 49 to 65, or a monovalent construct according to any of aspects 66 to 67; optionally followed by:
b) isolating and/or purifying the amino acid sequence or single variable domain according to any of aspects 1 to 48, a compound or construct according to any of aspects 49 to 65, or a monovalent construct according to any of aspects 66 to 67.

73. Composition, comprising at least one amino acid sequence or single variable domain according to any of aspects 1 to 48, a compound or construct according to any of aspects 49 to 65, or a monovalent construct according to any of aspects 66 to 67.

74. Composition according to aspect 73, which is a pharmaceutical composition.

75. Composition according to aspect 74 that further comprises at least one pharmaceutically acceptable carrier, diluent or excipient and/or adjuvant, and that optionally comprises one or more further pharmaceutically active polypeptides and/or compounds.

76. Method for the prevention and/or treatment of at least one GPCR-related disease or disorder, said method comprising administering, to a subject in need thereof, a pharmaceutically active amount of at least one amino acid sequence or single variable domain according to any of aspects 1 to 48, compound or construct according to any of aspects 49 to 65, monovalent construct according to any of aspects 66 to 67, or composition according to aspect 74 or 75.

77. Method for the prevention and/or treatment of at least one disease or disorder that is associated with a GPCR, with its biological or pharmacological activity, and/or with the biological pathways or signalling in which a GPCR is involved, said method comprising administering, to a subject in need thereof, a pharmaceutically active amount of at least one amino acid sequence or single variable domain according to any of aspects 1 to 48, compound or construct according to any of aspects 49 to 65, monovalent construct according to any of aspects 66 to 67, or composition according to aspect 74 or 75.

78. Method for the prevention and/or treatment of at least one disease or disorder that can be prevented and/or treated by administering, to a subject in need thereof, an amino acid sequence or single variable domain according to any of aspects 1 to 48, compound or construct according to any of aspects 49 to 65, monovalent construct according to any of aspects 66 to 67, said method comprising administering, to a subject in need thereof, a pharmaceutically active amount of at least one amino acid sequence or single variable domain according to any of aspects 1 to 48, compound or construct according to any of aspects 49 to 65, monovalent construct according to any of aspects 66 to 67, or composition according to aspect 76 or 77.

79. Method for immunotherapy, said method comprising administering, to a subject in need thereof, a pharmaceutically active amount of at least one amino acid sequence or single variable domain according to any of aspects 1 to 48, compound or construct according to any of aspects 49 to 65, monovalent construct according to any of aspects 66 to 67, or composition according to aspect 72 or 73.

80. Use of an amino acid sequence or single variable domain according to any of aspects 1 to 48, compound or construct according to any of aspects 49 to 65, monovalent construct according to any of aspects 66 to 67 in the preparation of a pharmaceutical composition for prevention and/or treatment of at least one GPCR-related disease or disorder.

81. Method of generating amino acid sequence or single variable domain according to any of aspects 1 to 48, at least one building block of compound or construct according to any of aspects 49 to 65, at least one building block of monovalent construct according to any of aspects 66 to 67, comprising at least the steps of:
   a) immunizing a Camelid, preferably Llama, with whole cells that are alive and overexpress the desired extracellular part, region, domain, loop or other extracellular epitope(s) of said GPCR, e.g. human CXCR4 and/or human CXCR7, on their surface in their native confirmation; and
   b) selecting for binding for the desired extracellular part, region, domain, loop or other extracellular epitope(s) using cell membranes preparation of different (other than the one used in immunization) cell types overexpressing said GPCR, e.g. human CXCR4 and/or human CXCR7; and optionally
   c) washing only mildly with a buffer such as PBS without detergents.

82. Method of screening to identify an amino acid sequence, e.g. a single variable domain, that is directed against a GPCR, e.g. human CXCR4 and/or human CXCR7, comprising the step of contacting any of the amino acid sequences or single variable domains according to any of aspects 1 to 48, any of the compounds or constructs according to any of aspects 49 to 65, any of the monovalent constructs according to any of aspects 66 to 67 with said GPCR.

83. Construct comprising i) a first ligand directed to or having affinity for an epitope that upon binding is capable to provoke an inverse agonistic or inverse antagonistic effect; and ii) a second ligand directed to or having affinity for an epitope that upon binding is capable to provoke an antagonistic effect.

84. Construct according to aspects 83; wherein at least one of the ligand is an immunoglobulin sequence.

85. Construct according to aspects 83 or 84; wherein at least one of the ligand is a dAb or a Nanobody, preferably a Nanobody.

86. Construct according to aspects 83 to 85; wherein both ligands are immunoglobulin sequences.

87. Construct according to aspects 83 to 86; wherein both ligands are dAbs or Nanobodies, preferably Nanobodies.

88. Construct according to aspects 83 to 87, wherein the construct is a polypeptide.

The invention claimed is:

1. Polypeptide that comprises at least one Nanobody that specifically binds human CXCR4 (SEQ ID NO: 254) and optionally at least one Nanobody that specifically binds to a serum protein, wherein the at least one Nanobody that specifically binds human CXCR4 essentially consists of 4 framework regions (FR1 to FR4, respectively) and 3 complementarity determining regions (CDR1 to CDR3, respectively), in which CDR1 is:
the amino acid sequence of SEQ ID NO: 142;
and
CDR2 is
the amino acid sequence of SEQ ID NO: 174;
and
CDR3 is
the amino acid sequence of SEQ ID NO: 206;
in which
CDR1 is the amino acid sequence of SEQ ID NO: 143;
and
CDR2 is the amino acid sequence of SEQ ID NO: 175;
and
CDR3 is the amino acid sequence of SEQ ID NO: 207.

2. Polypeptide of claim 1; wherein the polypeptide comprises two Nanobodies that specifically bind human CXCR4 and wherein the two Nanobodies that specifically bind human CXCR4 each essentially consists of 4 framework regions (FR1 to FR4, respectively) and 3 complementarity determining regions (CDR1 to CDR3, respectively), in which CDR1
the amino acid sequence of SEQ ID NO: 142;
and
CDR2 is
the amino acid sequence of SEQ ID NO: 174;
and
CDR3 is
the amino acid sequence of SEQ ID NO: 206;
or
in which
CDR1 is the amino acid sequence of SEQ ID NO: 143;
and
CDR2 is the amino acid sequence of SEQ ID NO: 175;
and
CDR3 is the amino acid sequence of SEQ ID NO: 207.

3. Polypeptide of claim 2;
wherein one Nanobody that specifically binds human CXCR4 essentially consists of 4 framework regions (FR1 to FR4, respectively) and 3 complementarity determining regions (CDR1 to CDR3, respectively), in which CDR1 is
the amino acid sequence of SEQ ID NO: 142;
and
CDR2 is
the amino acid sequence of SEQ ID NO: 174;
and
CDR3 is
the amino acid sequence of SEQ ID NO: 206;
wherein another Nanobody that specifically binds human CXCR4 essentially consists of 4 framework regions (FR1 to FR4, respectively) and 3 complementarity determining regions (CDR1 to CDR3, respectively), in which CDR1 is
the amino acid sequence of SEQ ID NO: 143;
and
CDR2 is
the amino acid sequence of SEQ ID NO: 175;
and
CDR3 is
the amino acid sequence of SEQ ID NO: 207.

4. Nanobody that essentially consists of 4 framework regions (FR1 to FR4, respectively) and 3 complementarity determining regions (CDR1 to CDR3, respectively), in which CDR1 is
the amino acid sequence of SEQ ID NO: 142;
and
CDR2 is
the amino acid sequence of SEQ ID NO: 174;
and
CDR3 is
the amino acid sequence of SEQ ID NO: 206;
in which
CDR1 is the amino acid sequence of SEQ ID NO: 143;
and
CDR2 is the amino acid sequence of SEQ ID NO: 175;
and
CDR3 is the amino acid sequence of SEQ ID NO: 207.

5. Polypeptide of claim 1 wherein the Nanobodies are selected from the group consisting of Nanobodies represented by the amino acid sequences of SEQ ID NO's 238 to 239.

6. Polypeptide of claim 1, wherein the polypeptide is selected from the group consisting of polypeptides represented by the amino acid sequences of SEQ ID NO's 261 to 264, preferably SEQ ID NO's 263 to 264.

7. Nanobody of claim 4 selected from the group consisting of Nanobodies represented by the amino acid sequences of SEQ ID NO's 238 to 239.

8. Pharmaceutical composition comprising a polypeptide according to claim 1.

9. Pharmaceutical composition according to claim 8 that further comprises at least one pharmaceutically acceptable carrier, diluent or excipient and/or adjuvant, and that optionally comprises one or more further pharmaceutically active polypeptides and/or compounds.

10. Pharmaceutical composition comprising a Nanobody according to claim 4.

11. Pharmaceutical composition according to claim 10 that further comprises at least one pharmaceutically acceptable carrier, diluent or excipient and/or adjuvant, and that optionally comprises one or more further pharmaceutically active polypeptides and/or compounds.

12. Polypeptide of claim 6, wherein the polypeptide is selected from the group consisting of polypeptides represented by the amino acid sequences of SEQ ID NOs: 263 to 264.

* * * * *

UNITED STATES PATENT AND TRADEMARK OFFICE
CERTIFICATE OF CORRECTION

PATENT NO. : 9,212,226 B2
APPLICATION NO. : 12/992982
DATED : December 15, 2015
INVENTOR(S) : Christophe Blanchetot et al.

It is certified that error appears in the above-identified patent and that said Letters Patent is hereby corrected as shown below:

In the Claims:

Claim 1, column 373, line 24, should read:

1. Polypeptide that comprises at least one Nanobody that specifically binds human CXCR4 (SEQ ID NO: 254) and optionally at least one Nanobody that specifically binds to a serum protein, wherein the at least one Nanobody that specifically binds human CXCR4 essentially consists of 4 framework regions (FR1 to FR4, respectively) and 3 complementarity determining regions (CDR1 to CDR3, respectively), in which CDR1 is:

the amino acid sequence of SEQ ID NO: 142;

and

CDR2 is the amino acid sequence of SEQ ID NO: 174;

and

CDR3 is the amino acid sequence of SEQ ID NO: 206;

or in which

CDR1 is the amino acid sequence of SEQ ID NO: 143;

and

CDR2 is the amino acid sequence of SEQ ID NO: 175;

and

CDR3 is the amino acid sequence of SEQ ID NO: 207.

Signed and Sealed this
Fifth Day of July, 2016

Michelle K. Lee
*Director of the United States Patent and Trademark Office*

CERTIFICATE OF CORRECTION (continued)
U.S. Pat. No. 9,212,226 B2

Claim 2, column 373, line 45, should read:

2. Polypeptide of claim 1; wherein the polypeptide comprises two Nanobodies that specifically bind human CXCR4 and wherein the two Nanobodies that specifically bind human CXCR4 each essentially consists of 4 framework regions (FR1 to FR4, respectively) and 3 complementarity determining regions (CDR1 to CDR3, respectively), in which CDR1 is >  the amino acid sequence of SEQ ID NO: 142;
>  and
>  CDR2 is
>  the amino acid sequence of SEQ ID NO: 174;
>  and
>  CDR3 is
>  the amino acid sequence of SEQ ID NO: 206;
>  or in which >  CDR1 is the amino acid sequence of SEQ ID NO: 143;
>  and
>  CDR2 is the amino acid sequence of SEQ ID NO: 175;
>  and
>  CDR3 is the amino acid sequence of SEQ ID NO: 207.

Claim 4, column 374, line 57, should read:

4. Nanobody that essentially consists of 4 framework regions (FR1 to FR4, respectively) and 3 complementarity determining regions (CDR1 to CDR3, respectively), in which CDR1 is >  the amino acid sequence of SEQ ID NO: 142;
>  and
>  CDR2 is
>  the amino acid sequence of SEQ ID NO: 174;
>  and
>  CDR3 is
>  the amino acid sequence of SEQ ID NO: 206;
>  or in which >  CDR1 is the amino acid sequence of SEQ ID NO: 143;
>  and

CERTIFICATE OF CORRECTION (continued)
U.S. Pat. No. 9,212,226 B2

CDR2 is the amino acid sequence of SEQ ID NO: 175; and

CDR3 is the amino acid sequence of SEQ ID NO: 207.